US012680083B2

(12) United States Patent
Hanna et al.

(10) Patent No.: US 12,680,083 B2
(45) Date of Patent: *Jul. 14, 2026

(54) MEDIA FOR CULTURING NAIVE HUMAN PLURIPOTENT STEM CELLS

(71) Applicant: Yeda Research and Development Co. Ltd., Rehovot (IL)

(72) Inventors: Yaqub Hanna, Tel Aviv-Jaffa (IL); Noa Novershtern, Rehovot (IL); Yoach Rais, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/433,553

(22) Filed: Feb. 6, 2024

(65) Prior Publication Data

US 2024/0318144 A1 Sep. 26, 2024

Related U.S. Application Data

(63) Continuation of application No. 15/500,163, filed as application No. PCT/IL2015/050785 on Jul. 30, 2015, now Pat. No. 11,920,164.

(60) Provisional application No. 62/167,469, filed on May 28, 2015, provisional application No. 62/030,792, filed on Jul. 30, 2014.

(51) Int. Cl.
*C12N 5/0735* (2010.01)
*C12N 5/00* (2006.01)
*C12N 5/074* (2010.01)

(52) U.S. Cl.
CPC ......... *C12N 5/0696* (2013.01); *C12N 5/0037* (2013.01); *C12N 5/0606* (2013.01); *C12N 2500/38* (2013.01); *C12N 2500/90* (2013.01); *C12N 2501/01* (2013.01); *C12N 2501/115* (2013.01); *C12N 2501/125* (2013.01); *C12N 2501/15* (2013.01); *C12N 2501/155* (2013.01); *C12N 2501/16* (2013.01); *C12N 2501/235* (2013.01); *C12N 2501/415* (2013.01); *C12N 2501/50* (2013.01); *C12N 2501/60* (2013.01); *C12N 2501/71* (2013.01); *C12N 2501/72* (2013.01); *C12N 2501/727* (2013.01); *C12N 2501/73* (2013.01); *C12N 2501/999* (2013.01); *C12N 2506/00* (2013.01)

(58) Field of Classification Search
None
See application file for complete search history.

(56) References Cited

U.S. PATENT DOCUMENTS

| | | | |
|---|---|---|---|
| 6,090,622 A | 7/2000 | Gearhart et al. | |
| 10,920,164 B2 | 2/2021 | Klein et al. | |
| 10,920,192 B2 | 2/2021 | Hanna et al. | |
| 2006/0194315 A1 | 8/2006 | Condie et al. | |
| 2011/0076678 A1 | 3/2011 | Jaenisch et al. | |
| 2011/0088107 A1 | 4/2011 | Hanna et al. | |
| 2013/0273649 A1 | 10/2013 | Wu et al. | |
| 2014/0315301 A1 | 10/2014 | Hanna et al. | |
| 2016/0257928 A1 | 9/2016 | Nakauchi et al. | |
| 2017/0275593 A1 | 9/2017 | Hanna et al. | |
| 2021/0253998 A1 | 8/2021 | Hanna et al. | |

FOREIGN PATENT DOCUMENTS

| | | |
|---|---|---|
| CN | 102317442 | 1/2012 |
| GB | 2436737 | 10/2007 |
| WO | WO 98/43679 | 10/1998 |
| WO | WO 2009/101084 | 8/2009 |
| WO | WO 2010/077955 | 7/2010 |
| WO | WO 2014/174470 | 10/2014 |
| WO | WO 2016/016894 | 2/2016 |
| WO | WO 2016/079146 | 5/2016 |

OTHER PUBLICATIONS

Gafni et al Nature, 504(7479):282-6, (Year: 2013).*
Kim et al Nat Communication. 4: 2403, 1-11 (Year: 2013).*
Shimizu et al Stem Cells, 30, 1394-1404 (Year: 2012).*
Xu et al PNAS, 107 (18), 8129-8134 (Year: 2010).*
Huang et al Cell Research 19:1127-1138 (Year: 2009).*
Rajendran et al J. Biol. Chem. 288, 24351-24362 (Year: 2013).*
Dutta et al Stem Cells 29, 618-628 (Year: 2010).*
Bayerl et al. Cell Stem Cell 28, 1549-1565 (Year: 2021).*
Interview Summary Dated Mar. 27, 2024 from the US Patent and Trademark Office Re. U.S. Appl. No. 17/117,157. (2 pages).
Advisory Action Before the Filing of An Appeal Brief Dated Mar. 1, 2018 From the US Patent and Trademark Office Re. U.S. Appl. No. 14/259,997. (8 pages).
Advisory Action Before the Filing of An Appeal Brief Dated Jul. 23, 2015 From the US Patent and Trademark Office Re. U.S. Appl. No. 14/259,997.
Advisory Action Dated Jul. 13, 2022 from US Patent and Trademark Office Re. U.S. Appl. No. 15/500,163. (7 pages).
Advisory Action Dated Jul. 2, 2020 from the US Patent and Trademark Office Re. U.S. Appl. No. 14/259,997. (8 pages).
Applicant-Initiated Interview Summary Dated Jan. 11, 2017 From the US Patent and Trademark Office Re. U.S. Appl. No. 14/259,997. (3 pages).
Communication Pursuant to Article 94(3) EPC Dated Aug. 2, 2018 From the European Patent Office Re. Application No. 15759548.9 (5 Pages).
Communication Pursuant to Article 94(3) EPC Dated Jan. 5, 2022 From the European Patent Office Re. Application No. 15759548.9. (3 Pages).
Communication Pursuant to Article 94(3) EPC Dated Jun. 5, 2019 From the European Patent Office Re. Application No. 15759548.9 (6 Pages).

(Continued)

*Primary Examiner* — Anoop K Singh

(57) ABSTRACT

A culture medium is disclosed which comprises STAT3 activator, an ERK1/2 inhibitor and an Axin stabilizer, and optionally also a PKC inhibitor. Cell cultures comprising same and uses thereof are also disclosed.

11 Claims, 28 Drawing Sheets
(28 of 28 Drawing Sheet(s) Filed in Color)

Specification includes a Sequence Listing.

(56)                    References Cited

OTHER PUBLICATIONS

Communication Pursuant to Article 94(3) EPC Dated Oct. 5, 2020 From the European Patent Office Re. Application No. 15759548.9. (4 Pages).
Communication Pursuant to Article 94(3) EPC Dated Nov. 10, 2017 From the European Patent Office Re. Application No. 15759548.9 (3 Pages).
Communication Pursuant to Article 94(3) EPC Dated Mar. 19, 2020 From the European Patent Office Re. Application No. 15759548.9 (5 Pages).
Communication Pursuant to Article 94(3) EPC Dated May 20, 2019 From the European Patent Office Re. Application No. 14727237.1. (3 Pages).
Communication Pursuant to Article 94(3) EPC Dated Feb. 22, 2021 From the European Patent Office Re. Application No. 15759548.9. (3 Pages).
Communication Pursuant to Article 94(3) EPC Dated Jul. 24, 2018 From the European Patent Office Re. Application No. 14727237.1. (4 Pages).
Communication Pursuant to Article 94(3) EPC Dated Oct. 25, 2016 From the European Patent Office Re. Application No. 14727237.1. (5 Pages).
Communication Pursuant to Article 94(3) EPC Dated Oct. 26, 2017 From the European Patent Office Re. Application No. 14727237.1. (4 Pages).
Communication Relating to the Results of the Partial International Search Dated Nov. 11, 2015 From the International Searching Authority Re. Application No. PCT/IL2015/050785.
Communication Relating to the Results of the Partial International Search Dated Jul. 30, 2014 From the International Searching Authority Re. Application No. PCT/IB2014/060954.
Decision of Rejection Dated Apr. 8, 2022 From the State Intellectual Property Office of the People's Republic of China Re. Application No. 201580052710.1 totether with English Summary and Claims. (12 Pages).
Declaration Yaqub Hanna Under 37 CFR 1.132 Dated Jan. 23, 2017 in The U.S. Patent and Trademark Office Re. U.S. Appl. No. 14/259,997.
English Translation Dated May 7, 2022 of Decision of Rejetion Dated Apr. 8, 2022 From the State Intellectual Property Office of the People's Republic of China Re. Application No. 201580052710.1 totether with English Summary and Claims. (12 Pages).
Final Official Action Dated Apr. 1, 2020 from the US Patent and Trademark Office Re. U.S. Appl. No. 14/259,997. (12 pages).
Final Official Action Dated Feb. 14, 2022 from US Patent and Trademark Office Re. U.S. Appl. No. 15/500,163. (20 pages).
Final Official Action Dated Sep. 24, 2020 from the US Patent and Trademark Office Re. U.S. Appl. No. 15/500,163. (25 pages).
International Preliminary Report on Patentability Dated Nov. 5, 2015 From the International Bureau of WIPO Re. Application No. PCT/IB2014/060954.
International Preliminary Report on Patentability Dated Feb. 9, 2017 From the International Bureau of WIPO Re. Application No. PCT/IL2015/050785. (11 Pages).
International Search Report and the Written Opinion Dated Oct. 7, 2014 From the International Searching Authority Re. Application No. PCT/IB2014/060954.
International Search Report and the Written Opinion Dated Jan. 12, 2016 From the International Searching Authority Re. Application No. PCT/IL2015/050785.
Interview Summary Dated Jun. 15, 2023 from the US Patent and Trademark Office Re. U.S. Appl. No. 17/117,157. (2 pages).
Notice of Allowance Dated Aug. 19, 2020 from the US Patent and Trademark Office Re. U.S. Appl. No. 14/259,997. (11 pages).
Notice of Allowance Dated Oct. 19, 2023 together with Interview Summary Dated Oct. 9, 2023 from the US Patent and Trademark Office Re. U.S. Appl. No. 15/500,163. (9 pages).

Notice of Reasons for Refusal Dated Mar. 27, 2018 From the Japan Patent Office Re. Application No. 2016-509588 and Its Translation Into English. (7 Pages).
Notification of Office Action and Search Report Dated May 8, 2021 From the State Intellectual Property Office of the People's Republic of China Re. Application No. 201580052710.1 (13 Pages).
Notification of Office Action and Search Report Dated Oct. 12, 2020 From the National Intellectual Property Administration of the People's Republic of China Re. Application No. 201580052710.1. (19 Pages).
Notification of Office Action and Search Report Dated Apr. 17, 2018 From the State Intellectual Property Office of the People's Republic of China Re. Application No. 201480035892.7 and Its Translation Into English. (38 Pages).
Notification of Office Action Dated Nov. 18, 2021 From the State Intellectual Property Office of the People's Republic of China Re. Application No. 201580052710.1 together with an English Summary. (13 Pages).
Office Action Dated Aug. 3, 2017 From the Israel Patent Office Re. Application No. 241930. (2 Pages).
Office Action Dated Apr. 13, 2016 From the Israel Patent Office Re. Application No. 241930.
Office Action Dated Jan. 23, 2017 From the Israel Patent Office Re. Application No. 241930. (2 Pages).
Office Action Dated May 23, 2019 From the Israel Patent Office Re. Application No. 241930 and Its Translation Into English. (7 Pages).
Office Action Dated Jul. 28, 2020 From the Israel Patent Office Re. Application No. 250340. (3 Pages).
Office Action Dated Mar. 28, 2018 From the Israel Patent Office Re. Application No. 241930. (2 Pages).
Office Action Dated Mar. 28, 2019 From the Israel Patent Office Re. Application No. 250340 and Its Translation Into English. (6 Pages).
Official Action Dated Feb. 1, 2016 From the US Patent and Trademark Office Re. U.S. Appl. No. 14/259,997.
Official Action Dated Aug. 3, 2023 from the US Patent and Trademark Office Re. U.S. Appl. No. 17/117,157. (48 pages).
Official Action Dated May 5, 2015 From the US Patent and Trademark Office Re. U.S. Appl. No. 14/259,997.
Official Action Dated Jul. 7, 2023 from the US Patent and Trademark Office Re. U.S. Appl. No. 15/500,163. (16 pages).
Official Action Dated Jan. 8, 2019 From the US Patent and Trademark Office Re. U.S. Appl. No. 15/500,163. (45 pages).
Official Action Dated May 10, 2017 From the US Patent and Trademark Office Re. U.S. Appl. No. 14/259,997. (18 pages).
Official Action Dated Jun. 15, 2021 from the US Patent and Trademark Office Re. U.S. Appl. No. 15/500,163. (19 pages).
Official Action Dated Sep. 16, 2016 From the US Patent and Trademark Office Re. U.S. Appl. No. 14/259,997.
Official Action Dated May 18, 2018 From the US Patent and Trademark Office Re. U.S. Appl. No. 14/259,997. (20 pages).
Official Action Dated Mar. 20, 2020 from the US Patent and Trademark Office Re. U.S. Appl. No. 15/500,163. (26 pages).
Official Action Dated Dec. 21, 2023 from the US Patent and Trademark Office Re. U.S. Appl. No. 17/117,157. (17 pages).
Official Action Dated Aug. 22, 2019 From the US Patent and Trademark Office Re. U.S. Appl. No. 14/259,997. (24 pages).
Official Action Dated Jul. 25, 2019 From the US Patent and Trademark Office Re. U.S. Appl. No. 15/500,163. (25 pages).
Official Action Dated Sep. 26, 2014 From the US Patent and Trademark Office Re. U.S. Appl. No. 14/259,997.
Official Action Dated Nov. 27, 2017 From the US Patent and Trademark Office Re. U.S. Appl. No. 14/259,997. (15 pages).
Official Action Dated Dec. 31, 2018 From the US Patent and Trademark Office Re. U.S. Appl. No. 14/259,997. (19 pages).
Official Action Dated Dec. 8, 2022 together with Interview Summary from the US Patent and Trademark Office Re. U.S. Appl. No. 15/500,163. (21 pages).
Restriction Official Action Dated Jul. 2, 2018 From the US Patent and Trademark Office Re. U.S. Appl. No. 15/500,163. (8 pages).
Restriction Official Action Dated Jun. 5, 2014 From the US Patent and Trademark Office Re. U.S. Appl. No. 14/259,997.
Restriction Official Action Dated Apr. 14, 2023 from the US Patent and Trademark Office Re. U.S. Appl. No. 17/117,157. (6 pages).

(56) References Cited

OTHER PUBLICATIONS

Translation Dated Dec. 9, 2020 of Notification of Office Action and Search Report Dated Oct. 12, 2020 From the National Intellectual Property Administration of the People's Republic of China Re. Application No. 201580052710.1. (25 Pages).

Translation Dated Jun. 10, 2021 of Notification of Office Action and Search Report Dated May 8, 2021 From the State Intellectual Property Office of the People's Republic of China Re. Application No. 201580052710.1 (19 Pages).

Translation Dated Nov. 23, 2021 of Notification of Office Action Dated Nov. 18, 2021 From the State Intellectual Property Office of the People's Republic of China Re. Application No. 201580052710.1. (18 Pages).

Ahn et al. "Production of Human CD59-Transgenic Pigs by Embryonic Germ Cell Nuclear Transfer", Biochemical and Biophysical Research Communications, XP027356570, 400(4): 667-672, Available Online Sep. 8, 2010.

Ang et al. "Wdr5 Mediates Self-Renewal and Reprogramming Via the Embryonic Stem Cell Core Transcriptional Network", Cell, 145: 183-197, Apr. 15, 2011.

Aulicino et al. "Temporal Perturbation of the Wnt Signaling Pathway in the Control of Cell Reprogramming Is Modulated by TCF1", Stem Cell Reports 2(5):707-720, May 6, 2014.

Bayerl et al. "Principles of Signaling Pathway Modulation for Enhancing Human Naive Pluripotency Induction", Stem Cell, 28(9): 1549-1565.e12, Sep. 2, 2021.

Bendall et al. "IGF and FGF Cooperatively Establish the Regulatory Stem Cell Niche of Pluripotent Human Cells In Vitro", Nature, 448(7157): 1015-1023, Aug. 30, 2007.

Bermejo-Alvarez et al. "Solving the 'X' in Embryos and Stem Cells", Stem Cells and Development, XP055128368, 21(8): 1215-1224, May 20, 2012.

Betschinger et al. "Exit From Pluripotency Is Gated by Intracellular Redistribution of the bHLH Transcription Factor Tfe3", Cell, 153(2): 335-347, Apr. 11, 2013.

Cerdan et al. "Novel Roles for Notch, Wnt and Hedgehog in Hematopoiesis Derived From Human Pluripotent Stem Cells", The International Journal of Developmental Biology, 54(6-7): 955-964, Published Online Mar. 15, 2010.

Claveria et al. "Myc-Driven Endogenous Cell Competition in the Early Mammalian Embryo", Nature, 500(7460): 39-44, Aug. 1, 2013.

Daheron et al. "LIF/STAT3 Signaling Fails to Maintain Self-Renewal of Human Embryonic Stem Cells", Stem Cells 22(5): 770-778, Sep. 2004.

De Los Angeles et al. "Accessing Naive Human Pluripotency", Current Opinion in Genetics & Development, XP028493568, 22(3): 272-282, Mar. 29, 2012.

De Vooght et al. "Management of Gene Promoter Mutations in Molecular Diagnostics", Clinical Chemistry, 55(4): 698-708, 2009.

Dejosez et al. "Safeguards for Cell Cooperation in Mouse Embryogenesis Shown by Genome-Wide Cheater Screen", Science, 341: 1511-1514, Sep. 27, 2013.

Dhanak et al. "Development and Classes of Epigenetic Drug for Cancer", Biochemical and Biophysical Research Communications, 455(1-2): 58-69, Published Online Jul. 10, 2014.

Dutta "Signaling Pathways Dictating Pluripotency in Embryonic Stem Cells", The International Journal of Developmental Biology, XP055224613, 57(9-10): 667-675, Nov. 4, 2013.

Dutta et al. "Self-Renewal Versus Lineage Commitment of Embryonic Stem Cells: Protein Kinase C Signaling Shifts the Balance", Stem Cells, 29(4): 618-628, Published Online Feb. 3, 2011.

Eguizabal et al. "Generation of Primordial Germ Cells From Pluripotent Stem Cells", Differentiation, XP026601254, 78(2-3): 116-123, Sep. 1, 2009. Fig.1, 2.

Ezashi et al. "Low O2 Tensions and the Prevention of Differentiation of hES Cells", Proc. Natl. Acad. Sci. USA, PNAS, 102(13): 4783-4788, Mar. 29, 2005.

Fang et al. "Generation of Naive Induced Pluripotent Stem Cells from Rhesus Monkey Fibroblasts", Cell Stem Cell, 15: 488-496, Oct. 2, 2014.

Gafni et al. "Derivation of Novel Human Ground State Naive Pluripotent Stem Cells", Nature 504:282-286, Oct. 30, 2013.

Gafni et al. "Derivation of Novel Human Ground State Naive Pluripotent Stem Cells", Nature, XP055128176, 504(7479): 282-286, Dec. 12, 2013.

Gao et al. "The BMP Inhibitor Coco Reactivates Breast Cancer Cells at Lung Metastatic Sites", Cell, 150(4): 764-779, Aug. 17, 2012.

Gauthaman et al. "Effect of ROCK Inhibitor Y-27632 on Normal and Variant Human Embryonic Stem Cells (hESCs) In Vitro: Its Benefits in hESC Expansion", Stem Cell Reviews and Reports, 6(1): 86-95, Published Online Dec. 15, 2009.

Gerstein et al. "What Is A Gene, Post-ENCODE? History and Updated Definition", Genome Research, 17: 669-681, 2007.

Gnanapragasam et al. "P66Alpha-MBD2 Coiled-Coil Interaction and Recruitment of Mi-2 Are Critical for Globin Gene Silencing by the MBD2-NuRD Complex", Proc. Natl. Acad. Sci. USA, PNAS, 108(18): 7487-7492, May 3, 2011.

Griffin et al. "RAPGEF5 Regulates Nuclear Translocation of b-Catenin", Developmental Cell 44: 1-13, 2018.

Hanna "Curriculum Vitae for Jacob H. Hanna," 18 pages, Apr. 2017.

Hanna "The STATs on Naive iPSC Reprogramming", Cell Stem Cell, 7: 274-276, Sep. 3, 2010.

Hanna et al. "Direct Cell Reprogramming Is A Stochastic Process Amenable to Acceleration", Nature, 462(7273): 595-601, Dec. 3, 2009.

Hanna et al. "Human Embryonic Stem Cells With Biological and Epigenetic Characteristics Similar to Those of Mouse ESCs", PNAS, 10(20): 9222-9227, May 4, 2010.

Hanna et al. "Human Embryonic Stem Cells With Biological and Epigenetic Characteristics Similar to Those of Mouse ESCs", Proc. Natl. Acad. Sci. USA, PNAS, XP055054545, 107(20): 9222-9227, May 18, 2010. p. 9224-9225.

Hanna et al. "Metastable Pluripotent States in NOD Mouse Derived ES Cells", Cell Stem Cell, 4(6): 513-524, Jun. 5, 2009.

Hanna et al. "Pluripotency and Cellular Reprogramming: Facts, Hypotheses, Unresolved Issues", Cell, XP055074652, 143(4): 508-525, Nov. 12, 2010.

Hanna et al. "Supporting Information", Proc. Nat. Acad. Sci., PNAS, USA, vol. 107: pp. 1-10, 2010.

Hao et al. "WNT/Beta-Catenin Pathway Up-Regulates Stat3 and Converges on LIF to Prevent Differentiation of Mouse Embryonic Stem Cells", Developmental Biology, XP027332417, 290(1): 81-91, Available Online Dec. 5, 2005. Abstract, p. 86, Fig.2, p. 89, 1-h Col., Para 1, Fig.5.

Hayashi et al. "Reconstitution of the Mouse Germ Cell Specification Pathway in Culture by Pluripotent Stem Cells", Cell, XP028383021, 146(4): 519-532, Aug. 19, 2011. p. 531, Fig.6.

Hirai et al. "Regulation of Embryonic Stem Cell Self-Renewal and Pluripotency by Leukaemia Inhibitory Factor", Biochemical Journal, 438: 11-23, 2011.

Huang et al. "More Synergetic Cooperation of Yamanaka Factors in Induced Pluripotent Stem Cells Than in Embryonic Stem Cells", Cell Research, 19: 1127-1138, 2009.

Huangfu et al. "Induction of Pluripotent Stem Cells From Primary Human Fibroblasts With Only Oct4 and Sox2", Nature Biotechnology, 26(11): 1269-1275, Advance Online Publication Oct. 12, 2008.

Humphrey et al. "Maintenance of Pluripotency in Human Embryonic Stem Cells Is STAT3 Independent", Stem Cells, 22(4): 522-530, Jul. 2004.

Johnson et al. "The Two Faces of Hippo: Targeting the Hippo Pathway for Regenerative Medicine and Cancer Treatment", Nature Reviews Drug Discovery, 13(1): 63-79, Published Online Dec. 13, 2013.

Kaji et al. "The NuRD Component Mbd3 Is Required for Pluripotency of Embryonic Stem Cells", Nature Cell Biology, 8(3): 285-292, Published Online Feb. 5, 2006.

Katoh "Network of WNT and Other Regualtory Signaling Cascades in Pluripotent Stem Cells and Cancer Stem Cells", Current Pharmaceutical Biotechnology, 12(2): 160-170, Feb. 1, 2011.

(56)        References Cited

OTHER PUBLICATIONS

Kawakami et al. "XIST Unmethylated DNA Fragments in Male-Derived Plasma as A Tumour Marker for Testicular Cancer", The Lancet, 363: 40-42, Jan. 3, 2004.
Kee et al. "Human DAZL, DAZ and BOULE Genes Modulate Primordial Germ Cell and Haploid Gamete Formation", Nature, 462(7270): 222-225, Nov. 12, 2009.
Kim et al. "Modulation of Beta-Catenin Function Maintains Mouse Epiblast Stem Cell and Human Embryonic Stem Cell Self-Renewal", Nature Communications, 4(2403): 1-11, Aug. 29, 2013.
Lai et al. "Cancer Biology and NuRD: A Multifaceted Chromatin Remodelling Complex", Nature Reviews Cancer, 11: 588-596, Aug. 2011.
Larsen et al. "The Chromatin-Remodeling Factor CHD4 Coordinates Signaling and Repair After DNA Damage", The Journal of Cell Biology, 190(3): 731-740, Aug. 30, 2010.
Lengner et al. "Derivation of Pre-X Inactivation Human Embryonic Stem Cells Under Physiological Oxygen Concentrations", Cell, XP055075377, 141(5): 872-883, May 1, 2010. Figs.2, 3.
Li et al. "Calcineurin-NFAT Signaling Critically Regulates Early Lineage Specification in Mouse Embryonic Stem Cells and Embryos", Cell Stem Cell, 8: 46-58, Jan. 7, 2011.
Library of Medicine "What Is A Gene?", Genetics Home Reference, National Library of Medicine, Database [Online], 2 Pages, Apr. 28, 2015.
Lin et al. "Toward Directed Reprogramming Through Exogenous Factors", Current Opinion in Genetics & Development, XP055224607, 23(5): 519-525, Available Online Aug. 8, 2013. Abstract, p. 519, r-h Col., Para 4—p. 520, 1-h Col., Para 1, Fig.1.
Liu et al. "Generation of Induced Pluripotent Stem Cells from Adult Rhesus Monkey Fibroblasts", Cell Stem Cell, 3(6), 587-590, Dec. 4, 2008.
Ludwig et al. "Derivation of Human Embryonic Stem Cells in Defined Conditions", Nature Biotechnology, 24(2): 185-187, Feb. 2006 and Supplementary Material.
Ludwig et al. "Feeder-Independent Culture of Human Embryonic Stem Cells", Nature Methods, 3(8): 637-646, Aug. 2006.
Luo et al. "NuRD Blocks Reprogramming of Mouse Somatic Cells Into Pluripotent Stem Cells", Stem Cells, 31(7): 1278-1286, Epub Ahead of Print Mar. 26, 2013. Abstract, p. 1279, 1-h Col., Last Para, p. 1282, r-h Col., Last Para—p. 1283, 1-h Col., Para 1.
Mansour et al. "The H3K27 Demethylase Utx Regulates Somatic and Germ Cell Epigenetic Reprogramming", Nature, 488: 409413, Aug. 16, 2012.
Medvedev et al. "Epigenetics of Pluripotent Cells", Acta Naturae, XP055236451, 4(4): 28-46, Oct. 2012. Abstract, p. 34, r-h Col., Para 2, p. 40, 1-h Col., Para 1.
Mitalipov et al. "Isolation and Characterization of Novel Rhesus Monkey Embryonic Stem Cell Lines", Stem Cells, 24(10): 2177-2186, Oct. 2006.
Murayama et al. "Successful Reprogramming of Epiblast Stem Cells by Blocking Nuclear Localization of ?-Catenin", Stem Cell Reports 4(1):103-113, Jan. 13, 2015.
Okamoto et al. "Eutherian Mammals Use Diverse Strategies to Initiate X-Chromosome Inactivation During Development", Nature, 472: 370-374, Apr. 21, 2011.
Onder et al. "Chromatin-Modifying Enzymes as Modulators of Reprogramming", Nature, 483: 598-602, Mar. 29, 2012.
Orkin et al. "Chromatin Connections to Pluripotency and Cellular Reprogramming", Cell, 145: 835-850, Jun. 10, 2011.
Park et al. "Derivation of Primordial Germ Cells From Human Embryonic and Induced Pluripotent Stem Cells Is Significantly Improved by Coculture With Human Fetal Gonadal Cells", Stem Cells, XP002730074, 27(4): 783-795, 2009.
Polo et al. "A Molecular Roadmap of Reprogramming Somatic Cells Into iPS Cells", Cell, 151: 1617-1632, Dec. 21, 2012.
Rajendran et al. "Inhibition of Protein Kinase C Signaling Maintains Rat Embryonic Stem Cell Pluripotency", Journal of Biological Chemistry 288(34): 24351-24362, Aug. 23, 2013.

Shimizu et al. "Dual Inhibition of Src and GSK3 Maintains Mouse Embryonic Stem Cells, Whose Differentiation Is Mechanically Regulated by Scr Signalling", Stem Cells, 30: 1394-1404, 2012.
Silva et al. "X-Chromosome Inactivation and Epigenetic Fluidity in Human Embryonic Stem Cells", Proc. Natl. Acad. Sci. USA, 105(12): 4820-4825, Mar. 25, 2008.
Song et al. "Formation of Mouse Chimeras From Early Embryonic Pluripotent Stem Cell", Acta Genetica Sinica, 20(6): 499-503, 1993. English Abstract.
Takahashi et al. "Induction of Pluripotent Stem Cells From Mouse Embryonic and Adult Fibroblast Cultures by Defined Factors", Cell, 126: 663-676, Aug. 25, 2006.
Takao et al. "Beta-Catenin Up-Regulates Nanog Expression Through Interaction With Oct-3/4 in Embryonic Stem Cells", Biochemical and Biophysical Research Communications, 353(3): 699-705, Available Online Dec. 20, 2006.
Tesar et al. "New Cell Lines From Mouse Epiblast Share Defining Features With Human Embryonic Stem Cells", Nature, 448: 196-199, Jul. 12, 2007.
ThermoFisher "Technical Resources, 12634, Advanced D-MEM/F-12", ThermoFisher Scientific, 3 Pages, 2016.
Theunissen et al. "Systematic Identification of Culture Conditions for Induction and Maintenance of Naive Human Pluripotency", Cell, 15: 471-487, Oct. 2, 2014.
Thomson et al. "Embryonic Stem Cell Lines Derived from Human Blastocysts", Science, 282: 1145-1147, Nov. 6, 1998.
Thomson et al. "Isolation of a Primate Embryonic Stem Cell Line," Proceedings of the National Academy of Sciences of the United States of America, 92: 7844-7848, 1995.
Thomson et al. "Pluripotent Cell Lines Derived from Common Marmoset (Callithrix jacchus) Blastocysts," Biology of Reproduction 55: 254-259, 1996.
Tomoda et al. "Derivation Conditions Impact X-Inactivation Status in Female Human Induced Pluripotent Stem Cells", Cell Stem Cell, 11: 91-99, Jul. 6, 2012.
Tsuneyoshi et al. "Guards at the Gate to Embryonic Stem Cell Differentiation", Cell, 153: 281-283, Apr. 11, 2013.
U.S. National Library of Medicine "Genetics Home Reference: Your Guide to Understanding Genetic Conditions", U.S. National Library of Medicine, Handbook, 1 P., Apr. 20, 2015.
Van der Jeught et al. "Application of Small Molecules Favoring Naive Pluripotency During Human Embryonic Stem Cell Derivation", Cellular Reprogramming, XP055224755, 17(3): 170-180, Jun. 2015. Abstract, p. 174, r-h Col., Para 3.
Vasques et al. "XIST Repression in the Absence of DNMT1 and DNMT3B", DNA Research, 12: 373-378, Published Online Jan. 11, 2006.
Vedadi et al. "A Chemical Probe Selectively Inhibits G9a and GLP Methyltransferase Activity in Cells", Nature Chemical Biology, 7(8): 566-574, Published Online Jul. 10, 2011.
Verfaillie et al. "Stem Cells: Hype and Reality", American Society of Hematology Education Program Book, 2002(1): 369-391, 2002.
Ware et al. "Derivation of Naive Human Embryonic Stem Cells", Proc. Natl. Acad. Sci. USA, PNAS, XP002727154, 111(12): 4484-4489, Mar. 25, 2014.
Xu et al. "C-Jun NH2-Terminal Kinase Is Required for Lineage-Specific Differentiation But Not Stem Cell Self-Renewal", Molecular and Cellular Biology, 3096): 1329-1340, May 30, 2010.
Xu et al. "NANOG Is a Direct Target of TGFbeta/Activin-Mediated SMAD Signaling in Human ESCs", Cell Stem Cell 3(2): 196-206, Aug. 7, 2008.
Xu et al. "Proliferation Rate of Somatic Cells Affects Reprogramming Efficiency", The Journal of Biological Chemistry, 288(14): 9767-9778, Apr. 5, 2013.
Ying et al. "Induction of Primordial Germ Cells From Pluripotent Epiblast", Reviews in Stem and Progenitor Cells, The Scientific World Journal, XP009097195, 2: 801-810, Mar. 26, 2002.
Yoshida et al. "Hypoxia Enhances the Generation of Induced Pluripotent Stem Cells", Cell Stem Cell, 5: 237-241, Sep. 4, 2009.
Zhang et al. "Small Molecules, Big Roles—The Chemical Manipulation of Stem Cell Fate and Somatic Cell Reprogramming", Journal of Cell Science, XP055112620, 125(23): 5609-5620, Dec. 1, 2012.

(56)                References Cited

OTHER PUBLICATIONS

Zhou et al. "Generation of Induced Pluripotent Stem Cells Using Recombinant Proteins", Cell Stem Cell, 4(5): 381-384, May 8, 2009.

Zhou et al. "Two Vital Transcriptional Factors Oct-4 and Nanog to Keep the Pluripotency and Self-Renewal of Stem Cells and Related Regulation Network", Hereditas, 30(5): 529-536, May 2008. English Abstract.

Zhu et al. "Mbd3, A Component of NuRD/Mi-2 Complex, Helps Maintain Pluripotency of Mouse Embryonic Stem Cells by Repressing Trophectoderm Differentiation", PLoS One, 4(11): e7684-1-e7684-11, Nov. 3, 2009.

Official Action Dated Jun. 21, 2024 together with Interview Summary Dated Jun. 5, 2024 from the US Patent and Trademark Office Re. U.S. Appl. No. 17/117,157. (19 Pages).

Kook et al. "Fibroblast Growth Factor-4 Enhances Proliferation of Mouse Embryonic Stem Cells via Activation of C-Jun Signaling", PloS one, 8(8):e71641-1-e71641-11, Aug. 13, 2013.

Xu et al. "Revealing a Core Signaling Regulatory Mechanism for Pluripotent Stem Cell Survival and Self-Renewal by Small Molecules", Proceedings of the National Academy of Sciences, 107(18):8129-8134, May 4, 2010.

Interview Summary Dated Sep. 12, 2024 from the US Patent and Trademark Office Re. U.S. Appl. No. 17/117,157. (3 pages).

Notice of Allowance Dated Mar. 24, 2025 together with Interview Summary Dated Feb. 14, 2025 from the US Patent and Trademark Office Re. U.S. Appl. No. 17/117,157. (16 pages).

Notification of Reexamination Dated Nov. 14, 2025 From the National Intellectual Property Administration of the People's Republic of China Re. Application No. 201580052710.1 and its Machine Translation into English. (17 Pages).

Decision of Reexamination Dated Jan. 28, 2026 From the State Intellectual Property Office of the People's Republic of China Re. Application No. 201580052710.1 with English Translation. (36 Pages).

* cited by examiner

Extended and Defined/Xeno Free WIS-NHSM
Human Naive Pluripotency
by Cell Signaling Modulation

FIG. 8

Condition 41: WIS-NHSM

LIF (20ng/ml)
ERK1/2i (PD0325901 1μM)
AXINs (IWR1 5μM)
PKCi (Go6983 2μM)

------

Condition 42: WIS-NHSM

LIF (20ng/ml)
ERK1/2i (PD0325901 1μM)
AXINs (IWR1 5μM)
PKCi (Go6983 2μM)

------

L-ascorbic acid (50μg/ml)

dition 43: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)

Condition 44: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)

Condition 45: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
ROCKi (Y27632 2μM)

Condition 46: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
ROCKi (Y27632 2μM)
SRCi (CGP77675 1.5μM)

Condition 47: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
P38i (BIRB796 1μM)

Condition 48: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
ROCKi (Y27632 2μM)
P38i (BIRB796 1μM)

Condition 49: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
SRCi (CGP77675 1.5μM)

Condition 50: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
ROCKi (Y27632 2μM)
RAFi (SB590885 0.5μM)

Condition 51: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
RAFi- SB590885 0.5μM

Condition 52: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
ROCKi (Y27632 2μM)
P38i (BIRB796 0.1μM)

Condition 53: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
SRCi (CGP77675 1.5μM)
RAFi (SB590885 0.5μM)

Condition 54: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
ROCKi (Y27632 2μM)
RAFi (SB590885 0.5μM)
SRCi (CGP77675 1.5μM)

Condition 55: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
RAFi- SB590885 0.5μM
P38i (BIRB796 0.1μM)

Condition 56: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
ROCKi (Y27632 2μM)
P38i (BIRB796 0.1μM)
SRCi (CGP77675 1.5μM)

Condition 57: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
SRCi (CGP77675 1.5μM)
RAFi (SB590885 0.5μM)
+BMPi (LDN-193189 0.2μM)

Condition 58: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
ROCKi (Y27632 2μM)
RAFi (SB590885 0.5μM)
SRCi (CGP77675 1.5μM)
+BMPi (LDN-193189 0.2μM)

Condition 59: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
RAFi- SB590885 0.5μM
P38i (BIRB796 0.1μM)
+BMPi (LDN-193189 0.2μM)

Condition 60: WIS-NHSM

LIF (20ng/ml)
ERK1/2i (PD0325901 1μM)
AXINs (IWR1 5μM)
PKCi (Go6983 2μM)

------

GSK3βi (CHIR99021 1.5μM)
L-ascorbic acid (50μg/ml)
ROCKi (Y27632 2μM)
P38i (BIRB796 0.1μM)
SRCi (CGP77675 1.5μM)
+BMPi (LDN-193189 0.2μM)

FIG. 9

Condition 61: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
SRCi (CGP77675
1.5μM)+BMP4 (5ng/ml)

Condition 62: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
ROCKi (Y27632 2μM)
RAFi (SB590885 0.5μM)
SRCi (CGP77675 1.5μM)
+BMP4 (5ng/ml)

Condition 63: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
RAFi- SB590885 0.5μM
P38i (BIRB796 0.1μM)
+BMP4 (5ng/ml)

Condition 64: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
ROCKi (Y27632 2μM)
P38i (BIRB796 0.1μM)
SRCi (CGP77675 1.5μM)
+BMP4 (5ng/ml)

Condition 65: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
ROCKi (Y27632 2μM)
+BMP4 (5ng/ml)

Condition 66: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
+BMP4 (5ng/ml)

Condition 67: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
ROCKi (Y27632 2μM)
+BMP4 (5ng/ml)

Condition 68: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
P38i (BIRB796 0.1μM)
ROCKi (Y27632 2μM)
+BMP4 (5ng/ml)

Condition 69: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
ROCKi (Y27632 2μM)
+BMPi (LDN-193189 0.2μM)

Condition 70: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
+BMPi (LDN-193189 0.2μM)

Condition 71: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
ROCKi (Y27632 2μM)
SRCi (CGP77675 1.5μM)
+BMPi (LDN-193189 0.2μM)

Condition 72: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
ROCKi (Y27632 2μM)
P38i (BIRB796 0.1μM)
+BMPi (LDN-193189 0.2μM)

Condition 73: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
ROCKi (Y27632 2μM)
FGFRi (PD173074 0.1μM)

Condition 74: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
FGFRi (PD173074 0.1μM)

Condition 75: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
ROCKi (Y27632 2μM)
SRCi (CGP77675 1.5μM)
FGFRi (PD173074 0.1μM)

Condition 76: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
ROCKi (Y27632 2μM)
P38i (BIRB796 0.1μM)
FGFRi (PD173074 0.1μM)

Condition 77: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
SRCi (CGP77675 1.5μM)
FGFRi (PD173074 0.1μM)

Condition 78: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
ROCKi (Y27632 2μM)
P38i (BIRB796 0.1μM)
FGFRi (PD173074 0.1μM)

Condition 79: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
P38i (BIRB796 0.1μM)
FGFRi (PD173074 0.1μM)

Condition 80: WIS-NHSM

LIF (20ng/ml)
ERK1/2i (PD0325901 1μM)
AXINs (IWR1 5μM)
PKCi (Go6983 2μM)
------
GSK3βi (CHIR99021 1.5μM)
L-ascorbic acid (50μg/ml)
SRCi (CGP77675 1.5μM)
FGFRi (PD173074 0.1μM)
P38i (BIRB796 1μM)

FIG. 10

Condition 81: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
SRCi (CGP77675 1.5μM)
RAFi (SB590885 0.5μM)
+Activin A (20ng/ml)

Condition 82: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
ROCKi (Y27632 2μM)
RAFi (SB590885 0.5μM)
SRCi (CGP77675 1.5μM)
+Activin A (20ng/ml)

Condition 83: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
RAFi- SB590885 0.5μM
P38i (BIRB796 0.1μM)
+Activin A (20ng/ml)

Condition 84: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
ROCKi (Y27632 2μM)
P38i (BIRB796 0.1μM)
SRCi (CGP77675 1.5μM)
+Activin A (20ng/ml)

Condition 85: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
ROCKi (Y27632 2μM)
+Activin A (20ng/ml)

Condition 86: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
+Activin A (20ng/ml)

Condition 87: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
ROCKi (Y27632 2μM)
+Activin A (20ng/ml)

Condition 88: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
P38i (BIRB796 0.1μM)
ROCKi (Y27632 2μM)
+Activin A (20ng/ml)

Condition 89: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
ROCKi (Y27632 2μM)
TGFRi (SB431542 2μM)

Condition 90: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
TGFRi (SB431542 2μM)

Condition 91: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
ROCKi (Y27632 2μM)
SRCi (CGP77675 1.5μM)
TGFRi (SB431542 2μM)

Condition 92: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
ROCKi (Y27632 2μM)
P38i (BIRB796 0.1μM)
TGFRi (SB431542 2μM)

Condition 93: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
ROCKi (Y27632 2μM)
FGFRi (PD173074 0.1μM)
TGFRi (SB431542 2μM)

Condition 74: WIS-NHSM 9

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
FGFRi (PD173074 0.1μM)
TGFRi (SB431542 2μM)

Condition 95: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
ROCKi (Y27632 2μM)
FGFRi (PD173074 0.1μM)
TGFRi (SB431542 2μM)
SRCi (CGP77675 1.5μM)

Condition 96: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
ROCKi (Y27632 2μM)
P38i (BIRB796 0.1μM)
FGFRi (PD173074 0.1μM)
TGFRi (SB431542 2μM)

Condition 97: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
SRCi (CGP77675 1.5μM)
FGFRi (PD173074 0.1μM)
TGFRi (SB431542 2μM)

Condition 98: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
ROCKi (Y27632 2μM)
RAFi (SB590885 0.5μM)
FGFRi (PD173074 0.1μM)
TGFRi (SB431542 2μM)

Condition 99: WIS-NHSM

LIF (20ng/ml)
ERK1/2i (PD0325901 1μM)
AXINs (IWR1 5μM)
PKCi (Go6983 2μM)
-------
GSK3βi (CHIR99021 1.5μM)
L-ascorbic acid (50μg/ml)
SRCi (CGP77675 1.5μM)
FGFRi (PD173074 0.1μM)
TGFRi (SB431542 2μM)
P38i (BIRB796 0.1μM)

FIG. 11

Condition 100: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)

Condition 101: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
ROCKi (Y27632 2µM)

Condition 102: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
P38i (BIRB796 2µM)

Condition 103: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
ROCKi (Y27632 2µM)
P38i (BIRB796 2µM)

Condition 104: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
P38i (BIRB796 2µM)
JNKi (SP600125 5µM)

Condition 105: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
ROCKi (Y27632 2µM)
P38i (BIRB796 2µM)
JNKi (SP600125 5µM)

Condition 106: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
P38i (BIRB796 2µM)
ERK5i (BIX02189 5µM)

Condition 107: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
ROCKi (Y27632 2µM)
P38i (BIRB796 2µM)
ERK5i (BIX02189 5µM)

Condition 108: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
TGFRi (SB431542 2µM)

Condition 109: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
ROCKi (Y27632 2µM)
TGFRi (SB431542 2µM)

Condition 110: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
FGFRi (PD173074 0.1µM)

Condition 111: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
ROCKi (Y27632 2µM)
FGFRi (PD173074 0.1µM)

Condition 112: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
P38i (BIRB796 2µM)
TGFRi (SB431542 2µM)

Condition 113: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
ROCKi (Y27632 2µM)
P38i (BIRB796 2µM)
TGFRi (SB431542 2µM)

Condition 114: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
P38i (BIRB796 2µM)
FGFRi (PD173074 0.1µM)

Condition 115: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
ROCKi (Y27632 2µM)
P38i (BIRB796 2µM)
FGFRi (PD173074 0.1µM)

Condition 116: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
LSDi (TCP 5µM)

Condition 117: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
ROCKi (Y27632 2µM)
LSDi (TCP 5µM)

Condition 118: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
P38i (BIRB796 2µM)
LSDi (TCP 5µM)

Condition 119: WIS-NHSM

LIF (20ng/ml)
ERK1/2i (PD0325901 1µM)
AXINs (IWR1 5µM)
PKCi (Go6983 4µM)
------
GSK3βi (CHIR99021 3µM)
L-ascorbic acid (50µg/ml)
ROCKi (Y27632 2µM)
P38i (BIRB796 2µM)
LSDi (TCP 5µM)

FIG. 12

Condition 120: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
Forskolin 5µM

Condition 121: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
ROCKi (Y27632 2µM)
Forskolin 5µM

Condition 122: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
P38i (BIRB796 2µM)
Forskolin 5µM

Condition 123: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
ROCKi (Y27632 2µM)
P38i (BIRB796 2µM)
Forskolin 5µM

Condition 124: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
DOT1Li (SGC0946 5µM)

Condition 125: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
ROCKi (Y27632 2µM)
DOT1Li (SGC0946 5µM)

Condition 126: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
P38i (BIRB796 2µM)
DOT1Li (SGC0946 5µM)

Condition 127: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
ROCKi (Y27632 2µM)
P38i (BIRB796 2µM)
DOT1Li (SGC0946 5µM)

Condition 128: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
P38i (BIRB796 2µM)
JNKi (SP600125 5µM)
ERK5i (BIX02189 5µM)

Condition 129: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
ROCKi (Y27632 2µM)
P38i (BIRB796 2µM)
JNKi (SP600125 5µM)
ERK5i (BIX02189 5µM)

Condition 130: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
ERK5i (BIX02189 5µM)

Condition 131: WIS-NHSM

LIF (20ng/ml)
ERK1/2i (PD0325901 1µM)
AXINs (IWR1 5µM)
PKCi (Go6983 4µM)
-------
GSK3βi (CHIR99021 3µM)
L-ascorbic acid (50µg/ml)
ROCKi (Y27632 2µM)
ERK5i (BIX02189 5µM)

WIBR3-deltaPEOCT4-GFP

WIS-NHSM conditions 100-131 as described in Example 5

● Methylated    ○ Unmethylated
XIST promoter
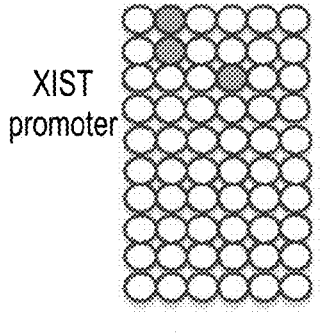
Naive
LIS1
hESC
(Male 46XY)
XIST promoter
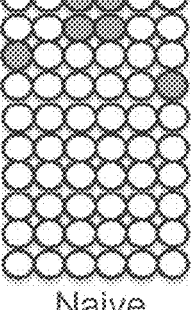
Naive
WIBR3
hESC
(Female
46XX)
FIG. 17A
XIST promoter
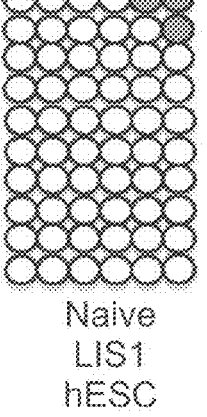
Naive
LIS1
hESC
(Male 46XY)
XIST promoter
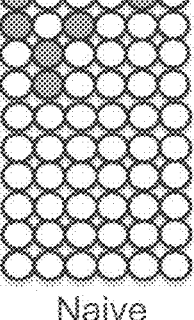
Naive
WIBR3
hESC
(Female
46XX)
FIG. 17B
XIST promoter
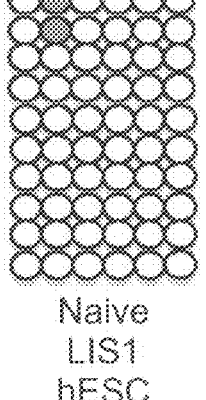
Naive
LIS1
hESC
(Male 46XY)
XIST promoter
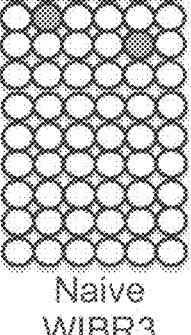
Naive
WIBR3
hESC
(Female
46XX)
FIG. 17C

 Methylated ○ Unmethylated
XIST promoter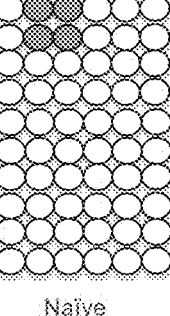
Naïve
LIS1
hESC
(Male 46XY)
XIST promoter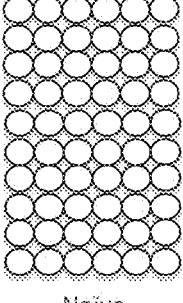
Naïve
WIBR3
hESC
(Female 46XX)
FIG. 17D
XIST promoter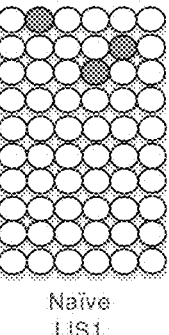
Naïve
LIS1
hESC
(Male 46XY)
XIST promoter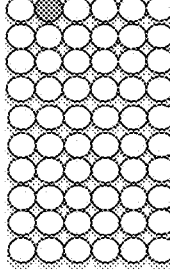
Naïve
WIBR3
hESC
(Female 46XX)
FIG. 17E
XIST promoter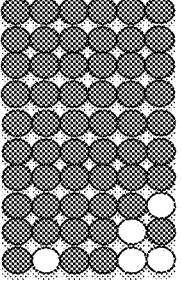
Primed LIS1
hESC
(male 46XY)
XIST promoter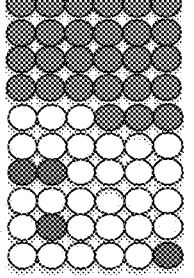
Primed WIBR3
hESC
(Female 46XX)
FIG. 17F

FIG. 18

Extended and Defined/Xeno Free WIS-NHSM
Human Naïve Pluripotency
by Cell Signaling Modulation ENHANCED Human
Naïve
WIS-NHSM
conditions 1) STAT3 activator (LIF 20ng/ml)
2) ERK1/2i (PD0325901 1μM)
3) Axin stabilizers (AXINs): IWR1 (2.5-5μM)
4) PKCi (Go6983 0.5-5μM)

Supplementary Ingredients
for Base Growth Media

N2 supplement
B27 supplement

Primary signaling regulating components

Secondary optional signaling optimizing components

ROCK inhibitors
ROCKi (Y27632 1-10μM)
Blebbistatin (0.25-5μM)

SRC inhibitors
SRCi (CGP 77675 0.25-1.5μM)

L-Ascorbic Acid
(50μg/ml)

PKA agonist
Forskolin (5-10μM)

YAP/TAZ Inhibitor
Verteporfin (VP) (2-5μM)

Morphogen inhibitors
NOTCHi (DBZ 0.2μM)
SHHi (RU- SKI43 3μM)
TGFβRi (SB431542 2μM)
BMPi (LDN193189 0.2μM)
FGF Inhibitor(s) (PD173074, 0.1μM)

MAPK Inhibitors
JNKi (SP600125 5μM)
ERK5i (BIX02189 5μM)
BRAFi (SB590885 0.25- 0.5μM)
p38i (BIRB796 0.1 - 2μM)

GSK3 inhibitor
(CHIR99021 0.6-3μM)

LSD1 inhibitor
Tranylcypromine -TCP (5-
10μM)

G9a/GLP Inhibitor
BIX01294 (0.25-0.5μM)
UNC 0638 (0.05-0.25μM)

PI3K boosters
(activators)
IGF1 (10ng/ml)
IGF2 (10ng/ml)
SCF (20ng/ml)
FGF2 (0.1-8ng/ml)

TGFbeta cytokines
(SMAD activators)
Activin A (2-20ng/ml)
TGFβ1 (1-10ng/ml)
BMP4 (5-10ng/ml)

DOT1L inhibitor
SGC0946 (0.5μM)

FIG. 19

Condition 132: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
P38i (BIRB796 0.25μM)
G9ai BIX01294 0.5μM)
ROCKi (Y27632 2μM)

Condition 133: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
P38i (BIRB796 0.25μM)
G9ai BIX01294 0.5μM)

Condition 134: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
SRCi (CGP77675 0.5μM)
P38i (BIRB796 0.25μM)
G9ai BIX01294 0.5μM)
ROCKi (Y27632 2μM)

Condition 135: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
P38i (BIRB796 0.25μM)
ROCKi (Y27632 2μM)

Condition 136: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
G9ai BIX01294 0.5μM)
ROCKi (Y27632 2μM)

Condition 137: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
G9ai BIX01294 0.5μM)

Condition 138: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
SRCi (CGP77675 0.5μM)
G9ai BIX01294 0.5μM)
ROCKi (Y27632 2μM)

Condition 139: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
ROCKi (Y27632 2μM)

Condition 140: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
P38i (BIRB796 0.25μM)
G9ai BIX01294 0.5μM)
ROCKi (Y27632 2μM)
RAFi (SB590885 0.25μM)

Condition 141: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
P38i (BIRB796 0.25μM)
G9ai BIX01294 0.5μM)
RAFi (SB590885 0.25μM)

Condition 142: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
SRCi (CGP77675 0.5μM)
P38i (BIRB796 0.25μM)
G9ai BIX01294 0.5μM)
ROCKi (Y27632 2μM)
RAFi (SB590885 0.25μM)

Condition 143: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
P38i (BIRB796 0.25μM)
ROCKi (Y27632 2μM)
RAFi (SB590885 0.25μM)

Condition 144: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
P38i (BIRB796 0.25μM)
G9ai BIX01294 0.5μM)
ROCKi (Y27632 2μM)
SCF (20ng/ml)

Condition 145: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
P38i (BIRB796 0.25μM)
G9ai BIX01294 0.5μM)
SCF (10ng/ml)

Condition 146: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
SRCi (CGP77675 0.5μM)
P38i (BIRB796 0.25μM)
G9ai BIX01294 0.5μM)
ROCKi (Y27632 2μM)
SCF (10ng/ml)

Condition 147: WIS-NHSM

LIF (20ng/ml)
ERK1/2i (PD0325901 1μM)
AXINs (IWR1 5μM)
PKCi (Go6983 2μM)
-------
JNKi (SP600125 5μM)
GSK3βi (CHIR99021 1.5μM)
L-ascorbic acid (50μg/ml)
SRCi (CGP77675 0.5μM)
P38i (BIRB796 0.25μM)
ROCKi (Y27632 2μM)
SCF (10ng/ml)

● Methylated          ○ Unmethylated

XIST promoter

Naïve LIS1
hESC (Male 46XY)

XIST promoter

Naïve WIBR3
hESC (Female 46XX)

XIST promoter

Naïve LIS1
hESC (Male 46XY)

XIST promoter

Naïve WIBR3
hESC (Female 46XX)

FIG. 23A
LIS38 WT:  ATGCTGTCCCCGGACGATATTGAACAATGGTTCACTGAAG (SEQ ID NO:134)
Crispr_C2: ATGCTGTCCCCGTGAGCCACCGTGCC-----------CACTGAAG (SEQ ID NO:135)
FIG. 23B
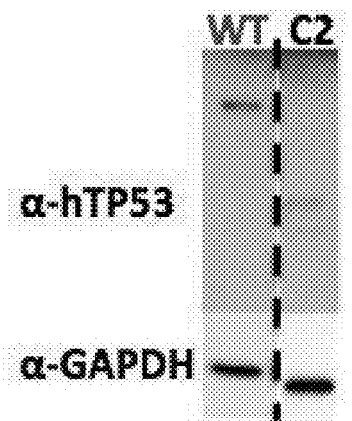
FIG. 23C
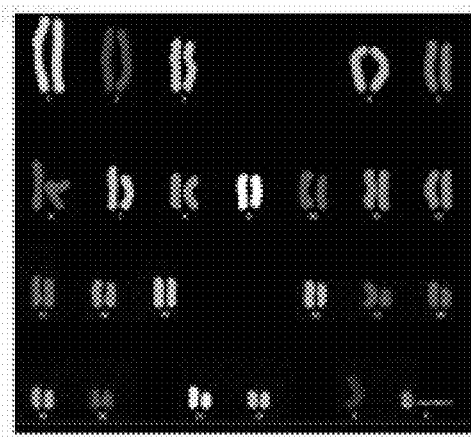
FIG. 23D
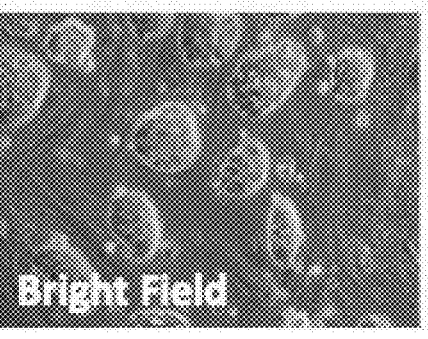
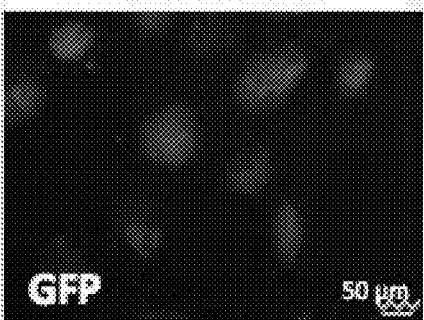

Non-injected Embryo

Injected Embryo

Primed WIBR3 hESC
(In mTESR™ conditions)

MFI Control - MFI sample = -2

Naive WIBR3 hESC
condition #136

MFI Control - MFI sample = 314

Naive WIBR3 hESC
Naive Condition 138

MFI Control - MFI sample = 350

FIG. 26A
Targeting strategy for making ESRRB-mCherry
Knock-in reporter human PSC line
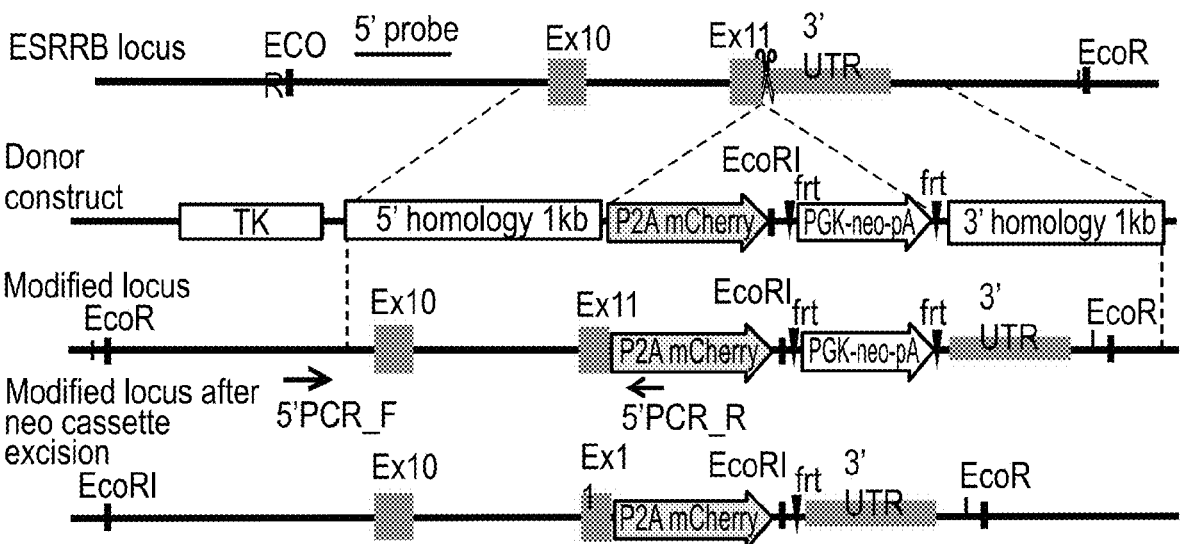
FIG. 26B
FIG. 26C
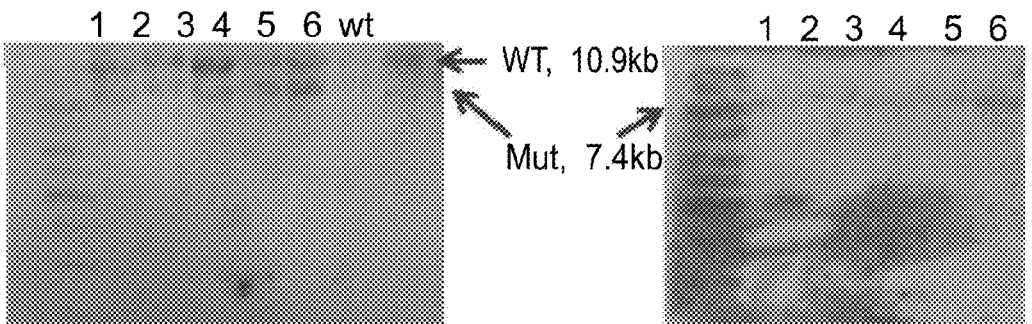
SB: EcoRI, 5' ext probe
SB: EcoRI, aCherry probe Naive WIBR3 (no reporter allele)
in condition #136

Naive WIBR3 (no reporter allele)
in condition #136 - BIX01294

Naive WIBR3 ESRRB-mCherry knock-in
in condition #136

Naive WIBR3 ESRRB-mCherry knock-in
in condition #136 - BIX01294

Naive WIBR3 ESRRB-mCherry knock-in
in condition #136 ++ ACTIVIN A

SEQUENCE LISTING

```
Sequence total quantity: 222
SEQ ID NO: 1              moltype = DNA  length = 30
FEATURE                   Location/Qualifiers
misc_feature              1..30
                          note = Single strand DNA oligonucleotide
source                    1..30
                          mol_type = other DNA
                          organism = synthetic construct
SEQUENCE: 1
ggtaccggat actcaggcca ggcccagaaa                                        30

SEQ ID NO: 2              moltype = DNA  length = 25
FEATURE                   Location/Qualifiers
misc_feature              1..25
                          note = Single strand DNA oligonucleotide
source                    1..25
                          mol_type = other DNA
```

```
                        organism = synthetic construct
SEQUENCE: 2
ctcgagtcca cagacctctg gcact                                              25

SEQ ID NO: 3           moltype = DNA   length = 35
FEATURE                Location/Qualifiers
misc_feature           1..35
                       note = Single strand DNA oligonucleotide
source                 1..35
                       mol_type = other DNA
                       organism = synthetic construct
SEQUENCE: 3
ggtacccatt gagtccaaat cctctttact aggtg                                   35

SEQ ID NO: 4           moltype = DNA   length = 25
FEATURE                Location/Qualifiers
misc_feature           1..25
                       note = Single strand DNA oligonucleotide
source                 1..25
                       mol_type = other DNA
                       organism = synthetic construct
SEQUENCE: 4
ctcgagctga ggctcatgct gctgg                                              25

SEQ ID NO: 5           moltype = AA   length = 605
FEATURE                Location/Qualifiers
source                 1..605
                       mol_type = protein
                       organism = Homo sapiens
SEQUENCE: 5
MAEDWLDCPA LGPGWKRREV FRKSGATCGR SDTYYQSPTG DRIRSKVELT RYLGPACDLT    60
LFDFKQGILC YPAPKAHPVA VASKKRKKPS RPAKTRKRQV GPQSGEVRKE APRDETKADT   120
DTAPASFPAP GCCENCGISF SGDGTQRQRL KTLCKDCRAQ RIAFNREQRM FKRVGCGECA   180
ACQVTEDCGA CSTCLLQLPH DVASGLFCKC ERRRCLRIVE RSRGCGVCRG CQTQEDCGHC   240
PICLRPPRPG LRRQWKCVQR RCLRGKHARR KGGCDSKMAA RRRPGAQPLP PPPPSQSPEP   300
TEPHPRALAP SPPAEFIYYC VDEDELQPYT NRRQNRKCGA CAACLRRMDC GRCDFCCDKP   360
KFGGSNQKRQ KCRWRQCLQF AMKRLLPSVW SESEDGAGSP PPYRRRKRPS SARRHHLGPT   420
LKPTLATRTA QPDHTQAPTK QEAGGGFVLP PPGTDLVFLR EGASSPVQVP GPVAASTEAL   480
LQEAQCSGLS WVVALPQVKQ EKADTQDEWT PGTAVLTSPV LVPGCPSKAV DPGLPSVKQE   540
PPDPEEDKEE NKDDSASKLA PEEEAGGAGT PVITEIFSLG GTRFRDTAVW LPRSKDLKKP   600
GARKQ                                                                  605

SEQ ID NO: 6           moltype = AA   length = 411
FEATURE                Location/Qualifiers
source                 1..411
                       mol_type = protein
                       organism = Homo sapiens
SEQUENCE: 6
MRAHPGGGRC CPEQEEGESA AGGSGAGGDS AIEQGGQGSA LAPSPVSGVR REGARGGGRG    60
RGRWKQAGRG GGVCGRGRGR GRGRGRGRGR GRGRGRPPSG GSGLGGDGGG CGGGGSGGGG   120
APRREPVPFP SGSAGPGPRG PRATESGKRM DCPALPPGWK KEEVIRKSGL SAGKSDVYYF   180
SPSGKKFRSK PQLARYLGNT VDLSSFDFRT GKMMPSKLQK NKQRLRNDPL NQNKGKPDLN   240
TTLPIRQTAS IFKQPVTKVT NHPSNKVKSD PQRMNEQPRQ LFWEKRLQGL SASDVTEQII   300
KTMELPKGLQ GVGPGSNDET LLSAVASALH TSSAPITGQV SAAVEKNPAV WLNTSQPLCK   360
AFIVTDEDIR KQEERVQQVR KKLEEALMAD ILSRAADTEE MDIEMDSGDE A             411

SEQ ID NO: 7           moltype = AA   length = 291
FEATURE                Location/Qualifiers
source                 1..291
                       mol_type = protein
                       organism = Homo sapiens
SEQUENCE: 7
MERKRWECPA LPQGWEREEV PRRSGLSAGH RDVFYYSPSG KKFRSKPQLA RYLGGSMDLS    60
TFDFRTGKML MSKMNKSRQR VRYDSSNQVK GKPDLNTALP VRQTASIFKQ PVTKITNHPS   120
NKVKSDPQKA VDQPRQLFWE KKLSGLNAFD IAEELVKTMD LPKGLQGVGP GCTDETLLSA   180
IASALHTSTM PITGQLSAAV EKNPGVWLNT TQPLCKAFMV TDEDIRKQEE LVQQVRKRLE   240
EALMADMLAH VEELARDGEA PLDKACAEDD DEEDEEEEEE EPDPDPEMEH V             291

SEQ ID NO: 8           moltype = AA   length = 580
FEATURE                Location/Qualifiers
source                 1..580
                       mol_type = protein
                       organism = Homo sapiens
SEQUENCE: 8
MGTTGLESLS LGDRGAAPTV TSSERLVPDP PNDLRKEDVA MELERVGEDE EQMMIKRSSE    60
CNPLLQEPIA SAQFGATAGT ECRKSVPCGW ERVVKQRLFG KTAGRFDVYF ISPQGLKFRS   120
KSSLANYLHK NGETSLKPED FDFTVLSKRG IKSRYKDCSM AALTSHLQNQ SNNSNWNLRT   180
RSKCKKDVFM PPSSSSELQE SRGLSNFTST HLLLKEDEGV DDVNFRKVRK PKGKVTILKG   240
IPIKKTKKGC RKSCSGFVQS DSKRESVCNK ADAESEPVAQ KSQLDRTVCI SDAGACGETL   300
```

```
SVTSEENSLV KKKERSLSSG SNFCSEQKTS GIINKFCSAK DSEHNEKYED TFLESEEIGT  360
KVEVVERKEH LHTDILKRGS EMDNNCSPTR KDFTGEKIFQ EDTIPRTQIE RRKTSLYFSS  420
KYNKEALSPP RRKAFKKWTP PRSPPFNLVQE TLFHDPWKLL IATIFLNRTS GKMAIPVLWK  480
FLEKYPSAEV ARTADWRDVS ELLKPLGLYD LRAKTIVKFS DEYLTKQWKY PIELHGIGKY  540
GNDSYRIFCV NEWKQVHPED HKLNKYHDWL WENHEKLSLS                        580

SEQ ID NO: 9           moltype = AA  length = 360
FEATURE                Location/Qualifiers
source                 1..360
                       mol_type = protein
                       organism = Homo sapiens
SEQUENCE: 9
MAGHLASDFA FSPPPGGGGD GPGGPEPGWV DPRTWLSFQG PPGGPGIGPG VGPGSEVWGI   60
PPCPPPPYEFC GGMAYCGPQV GVGLVPQGGL ETSQPEGEAG VGVESNSDGA SPEPCTVTPG  120
AVKLEKEKLE QNPEESQDIK ALQKELEQFA KLLKQKRITL GYTQADVGLT LGVLFGKVFS  180
QTTICRFEAL QLSFKNMCKL RPLLQKWVEE ADNNENLQEI CKAETLVQAR KRKRTSIENR  240
VRGNLENLFL QCPKPTLQQI SHIAQQLGLE KDVVRVWFCN RRQKGKRSSS DYAQREDFEA  300
AGSPFSGGPV SFPLAPGPHF GTPGYGSPHF TALYSSVPFP EGEAFPPVSV TTLGSPMHSN  360

SEQ ID NO: 10          moltype = AA  length = 317
FEATURE                Location/Qualifiers
source                 1..317
                       mol_type = protein
                       organism = Homo sapiens
SEQUENCE: 10
MYNMMETELK PPGPQQTSGG GGGNSTAAAA GGNQKNSPDR VKRPMNAFMV WSRGQRRKMA   60
QENPKMHNSE ISKRLGAEWK LLSETEKRPF IDEAKRLRAL HMKEHPDYKY RPRRKTKTLM  120
KKDKYTLPGG LLAPGGNSMA SGVGVGAGLG AGVNQRMDSY AHMNGWSNGS YSMMQDQLGY  180
PQHPGLNAHG AAQMQPMHRY DVSALQYNSM TSSQTYMNGS PTYSMSYSQQ GTPGMALGSM  240
GSVVKSEASS SPPVVTSSSH SRAPCQAGDL RDMISMYLPG AEVPEPAAPS RLHMSQHYQS  300
GPVPGTAING TLPLSHM                                                  317

SEQ ID NO: 11          moltype = AA  length = 1912
FEATURE                Location/Qualifiers
source                 1..1912
                       mol_type = protein
                       organism = Homo sapiens
SEQUENCE: 11
MASGLGSPSP CSAGSEEEDM DALLNNSLPP PHPENEEDPE EDLSETETPK LKKKKKPKKP   60
RDPKIPKSKR QKKERMLLCR QLGDSSGEGP EFVEEEEEVA LRSDSEGSDY TPGKKKKKKL  120
GPKKEKKSKS KRKEEEEEED DDDDSKEPKS SAQLLEDWGM EDIDHVFSEE DYRTLTNYKA  180
FSQFVRPLIA AKNPKIAVSK MMMVLGAKWR EFSTNNPFKG SSGASVAAAA AAAVAVVESM  240
VTATEVAPPP PPVEVPIRKA KTKEGKGPNA RRKPKGSPRV PDAKKPKPKK VAPLKIKLGG  300
FGSKRKRSSS EDDDLDVESD FDDASINSYS VSDGSTSRSS RSRKKLRTTK KKKKGEEEVT  360
AVDGYETDHQ DYCEVCQQGG EIILCDTCPR AYHMVCLDPD MEKAPEGKWS CPHCEKEGIQ  420
WEAKEDNSEG EEILEEVGGD LEEEDDHHME FCRVCKDGGE LLCCDTCPSS YHIHCLNPPL  480
PEIPNGEWLC PRCTCPALKG KVQKILIWKW GQPPSPTPVP RPPDADPNTP SPKPLEGRPE  540
RQFFVKWQGM SYWHCSWVSE LQLELHCQVM FRNYQRKNDM DEPPSGDFGG DEEKSRKRKN  600
KDPKFAEMEE RFYRYGIKPE WMMIHRILNH SVDKKGHVHY LIKWRDLPYD QASWESEDVE  660
IQDYDLFKQS YWNHRELMRG EEGRPGKKLK KVKLRKLERP PETPTVDPTV KYERQPEYLD  720
ATGGTLHPYQ MEGLNWLRFS WAQGTDTILA DEMGLGKTVQ TAVFLYSLYK EGHSKGPFLV  780
SAPLSTIINW EREFEMWAPD MYVVTYVGDK DSRAIIRENE FSFEDNAIRG GKKASRMKKE  840
ASVKFHVLLT SYELITIDMA ILGSIDWACL IVDEAHRLKN NQSKFFRVLN GYSLQHKLLL  900
TGTPLQNNLE ELFHLLNFLT PERFHNLEGF LEEFADIAKE DQIKKLHDML GPHMLRRLKA  960
DVFKNMPSKT ELIVRVELSP MQKKYYKYIL TRNFEALNAR GGGNQVSLLN VVMDLKKCCN 1020
HPYLFPVAAM EAPKMPNGMY DGSALIRASG KLLLLQKMLK NLKEGGHRVL IFSQMTKMLD 1080
LLEDFLEHEG YKYERIDGGI TGNMRQEAID RFNAPGAQQF CFLLSTRAGG LGINLATADT 1140
VIIYDSDWNP HNDIQAFSRA HRIGQNKKVM IYRFVTRASV EERITQVAKK KMMLTHLVVR 1200
PGLGSKTGSM SKQELDDILK FGTEELFKDE ATDGGGDNKE GEDSSVIHYD DKAIERLLDR 1260
NQDETEDTEL QGMNEYLSSF KVAQYVVREE EMGEEEEVER EIIKQEESVD PDYWEKLLRH 1320
HYEQQQEDLA RNLGKGKRIR KQVNYNDGSQ EDRDWQDDQS DNQSDYSVAS EEGDEDFDER 1380
SEAPRRPSRK GLRNDKDKPL PPLLARVGGN IEVLGFNARQ RKAFLNAIMR YGMPPQDAFT 1440
TQWLVRDLRG KSEKEFKAYV SLFMRHLCEP GADGAETFAD GVPREGLSRQ HVLTRIGVMS 1500
LIRKKVQEFE HVNGRWSMPE LAEVEENKKM SQPGSPSPKT PTPSTPGDTQ PNTPAPVPPA 1560
EDGIKIEENS LKEEESIEGE KEVKSTAPET AIECTQAPAP ASEDEKVVVE PPEGEEKVEK 1620
AEVKERTEEP METEPKGAAD VEKVEEKSAI DLTPIVVEDK EEKKEEEEKK EVMLQNGETP 1680
KDLNDEKQKK NIKQRFMFNI ADGGFTELHS LWQNEERAAT VTKKTYEIWH RRHDYWLLAG 1740
IINHGYARWQ DIQNDPRYAI LNEPFKGEMN RGNFLEIKNK FLARRFKLLE QALVIEEQLR 1800
RAAYLNMSED PSHPSMALNT RFAEVECLAE SHQHLSKESM AGNKPANAVL HKVLKQLEEL 1860
LSDMKADVTR LPATIARIPP VAVRLQMSER NILSRLANRA PEPTPQQVAQ QQ           1912

SEQ ID NO: 12          moltype = AA  length = 305
FEATURE                Location/Qualifiers
source                 1..305
                       mol_type = protein
                       organism = Homo sapiens
SEQUENCE: 12
MSVDPACPQS LPCFEASDCK ESSPMPVICG PEENYPSLQM SSAEMPHTET VSPLPSSMDL   60
LIQDSPDSST SPKGKQPTSA EKSVAKKEDK VPVKKQKTRT VFSSTQLCVL NDRFQRQKYL  120
```

```
SLQQMQELSN ILNLSYKQVK TWFQNQRMKS KRWQKNNWPK NSNGVTQKAS APTYPSLYSS      180
YHQGCLVNPT GNLPMWSNQT WNNSTWSNQT QNIQSWSNHS WNTQTWCTQS WNNQAWNSPF      240
YNCGEESLQS CMQFQPNSPA SDLEAALEAA GEGLNVIQQT TRYFSTPQTM DLFLNYSMNM      300
QPEDV                                                                 305

SEQ ID NO: 13              moltype = AA  length = 424
FEATURE                    Location/Qualifiers
source                     1..424
                           mol_type = protein
                           organism = Homo sapiens
SEQUENCE: 13
MADKEAFDDA VEERVINEEY KIWKKNTPFL YDLVMTHALE WPSLTAQWLP DVTRPEGKDF       60
SIHRLVLGTH TSDEQNHLVI ASVQLPNDDA QFDASHYDSE KGEFGGFGSV SGKIEIEIKI      120
NHEGEVNRAR YMPQNPCIIA TKTPSSDVLV FDYTKHPSKP DPSGECNPDL RLRGHQKEGY      180
GLSWNPNLSG HLLSASDDHT ICLWDISAVP KEGKVVDAKT IFTGHTAVVE DVSWHLLHES      240
LFGSVADDQK LMIWDTRSNN TSKPSHSVDA HTAEVNCLSF NPYSEFILAT GSADKTVALW      300
DLRNLKLKLH SFESHKDEIF QVQWSPHNET ILASSGTDRR LNVWDLSKIG EEQSPEDAED      360
GPPELLFIHG GHTAKISDFS WNPNEPWVIC SVSEDNIMQV WQMAENIYND EDPEGSVDPE      420
GQGS                                                                  424

SEQ ID NO: 14              moltype = AA  length = 1792
FEATURE                    Location/Qualifiers
source                     1..1792
                           mol_type = protein
                           organism = Homo sapiens
SEQUENCE: 14
MSCVHYKFSS KLNYDTVTFD GLHISLCDLK KQIMGREKLK AADCDLQITN AQTKEEYTDD       60
NALIPKNSSV IVRRIPIGGV KSTSKTYVIS RTEPAMATTK AIDDSSASIS LAQLTKTANL      120
AEANASEEDK IKAMMSQSGH EYDPINYMKK PLGPPPPSYT CFRCGKPGHY IKNCPTNGDK      180
NFESGPRIKK STGIPRSFMM EVKDPNMKGA MLTNTGKYAI PTIDAEAYAI GKKEKPPFLP      240
EEPSSSSEED DPIPDELLCL ICKDIMTDAV VIPCCGNSYC DECIRTALLE SDEHTCPTCH      300
QNDVSPDALI ANKFLRQAVN NFKNETGYTK RLRKQLPPPP PPIPPPRPLI QRNLQPLMRS      360
PISRQQDPLM IPVTSSSTHP APSISSLTSN QSSLAPPVSG NPSSAPAPVP DITATVSISV      420
HSEKSDGPFR DSDNKILPAA ALASEHSKGT SSIAITALME EKGYQVPVLG TPSLLGQSLL      480
HGQLIPTTGP VRINTARPGG GRPGWEHSNK LGYLVSPPQQ IRRGERSCYR SINRGRHHSE      540
RSQRTQGPSL PATPVFVPVP PPPLYPPPPH TLPLPPGVPP PQFSPQFPPG QPPPAGYSVP      600
PPGFPPAPAN LSTPWVSSGV QTAHSNTIPT TQAPPLSREE FYREQRRLKE EEKKKSKLDE      660
FTNDFAKELM EYKKIQKERR RSFSRSKSPY SGSSYSRSSY TYSKSRSGST RSRSYSRSFS      720
RSHSRSYSRS PPYPRRGRGK SRNYRSRSRS HGYHRSRSRS PPYRRYHSRS RSPQAFRGQS      780
PNKRNVPQGE TEREYFNRYR EVPPPYDMKA YYGRSVDFRD PFEKERYREW ERKYREWYEK      840
YYKGYAAGAQ PRPSANRENF SPERFLPLNI RNSPFTRGRR EDYVGGQSHR SRNIGSNYPE      900
KLSARDGHNQ KDNTKSKEKE SENAPGDGKG NKHKKHRKRR KGEESEGFLN PELLETSRKS      960
REPTGVEENK TDSLFVLPSR DDATPVRDEP MDAESITFKS VSEKDKRERD KPKAKGDKTK     1020
RKNDGSAVSK KENIVKPAKG PQEKVDGERE RSPRSEPPIK KAKEETPKTD NTKSSSSSQK     1080
DEKITGTPRK AHSKSAKEHQ ETKPVKEEKV KKDYSKDVKS EKLTTKEEKA KKPNEKNKPL     1140
DNKGEKRKRK TEEKGVDKDF ESSSMKISKL EVTEIVKPSP KRKMEPDTEK MDRTPEKDKI     1200
SLSAPAKKIK LNRETGKKIG STENISNTKE PSEKLESTSS KVKQEKVKGK VRRKVTGTEG     1260
SSSTLVDYTS TSSTGGSPVR KSEEKTDTKR TVIKTMEEYN NDNTAPAEDV IIMIQVPQSK     1320
WDKDDFESEE EDVKSTQPIS SVGKPASVIK NVSTKPSNIV KYPEKESEPS EKIQKFTKDV     1380
SHEIIQHEVK SSKNSASSEK GKTKDRDYSV LEKENPEKRK NSTQPEKESN LDRLNEQGNF     1440
KSLSQSSKEA RTSDKHDSTR ASSNKDFTPN RDKKTDYDTR EYSSSKRRDE KNELTRRKDS     1500
PSRNKDSASG QKNKPREERD LPKKGTGDSK KSNSSPSRDR KPHDHKATYD TKRPNEETKS     1560
VDKNPCKDRE KHVLEARNNK ESSGNKLLYI LNPPETQVEK EQITGQIDKS TVKPKPQLSH     1620
SSRLSSDLTR ETDEAAFEPD YNESDSESNV SVKEEESSGN ISKDLKDKIV EKAKESLDTA     1680
AVVQVGISRN QSHSSPSVSP SRSHSPSGSQ TRSHSSSASS AESQDSKKKK KKKEKKKHKK     1740
HKKHKKHKKH AGTEVELEKS QKHKHKKKKS KKNKDKEKEK EKDDQKVKSV TV             1792

SEQ ID NO: 15              moltype = AA  length = 469
FEATURE                    Location/Qualifiers
source                     1..469
                           mol_type = protein
                           organism = Homo sapiens
SEQUENCE: 15
MAAEAGVVGA GASPDGDWRD QACGLLLHVH LSSRLGRAAP VRTGRHLRTV FEDTVEERVI       60
NEEYKIWKKN TPFLYDLVMT HALQWPSLTV QWLPEVTKPE GKDYALHWLV LGTHTSDEQN      120
HLVVARVHIP NDDAQFDASH CDSDKGEFGG FGSVTGKIEC EIKINHEGEV NRARYMPQNP      180
HIIATKTPSS DVLVFDYTKH PAKPDPSGEC NPDLRLRGHQ KEGYGLSWNS NLSGHLLSAS      240
DDHTVCLWDI NAGPKEGKIV DAKAIFTGHS AVVEDVAWHL LHESLFGSVA DDQKLMIWDT      300
RSNTTSKPSH LVDAHTAEVN CLSFNPYSEF ILATGSADKT VALWDLRNLK LKLHTFESHK      360
DEIFQVHWSP HNETILASSG TDRRLNVWDL SKIGEEQSAE DAEDGPPELL FIHGGHTAKI      420
SDFSWNPNEP WVICSVSEDN IMQIWQMAEN IYNDEESDVT TSELEGQGS                 469

SEQ ID NO: 16              moltype = AA  length = 482
FEATURE                    Location/Qualifiers
source                     1..482
                           mol_type = protein
                           organism = Homo sapiens
SEQUENCE: 16
MAQTQGTRRK VCYYYDGDVG NYYYGQGHPM KPHRIRMTHN LLLNYGLYRK MEIYRPHKAN       60
```

```
AEEMTKYHSD DYIKFLRSIR PDNMSEYSKQ MQRFNVGEDC PVFDGLFEFC QLSTGGSVAS  120
AVKLNKQQTD IAVNWAGGLH HAKKSEASGF CYVNDIVLAI LELLKYHQRV LYIDIDIHHG  180
DGVEEAFYTT DRVMTVSFHK YGEYFPGTGD LRDIGAGKGK YYAVNYPLRD GIDDESYEAI  240
FKPVMSKVME MFQPSAVVLQ CGSDSLSGDR LGCFNLTIKG HAKCVEFVKS FNLPMLMLGG  300
GGYTIRNVAR CWTYETAVAL DTEIPNELPY NDYFEYFGPD FKLHISPSNM TNQNTNEYLE  360
KIKQRLFENL RMLPHAPGVQ MQAIPEDAIP EESGDEDEDD PDKRISICSS DKRIACEEEF  420
SDSEEEGEGG RKNSSNFKKA KRVKTEDEKE KDPEEKKEVT EEEKTKEEKP EAKGVKEEVK  480
LA                                                                 482

SEQ ID NO: 17          moltype = AA  length = 488
FEATURE                Location/Qualifiers
source                 1..488
                       mol_type = protein
                       organism = Homo sapiens
SEQUENCE: 17
MAYSQGGGKK KVCYYYDGDI GNYYYGQGHP MKPHRIRMTH NLLLNYGLYR KMEIYRPHKA  60
TAEEMTKYHS DEYIKFLRSI RPDNMSEYSK QMQRFNVGED CPVFDGLFEF CQLSTGGSVA  120
GAVKLNRQQT DMAVNWAGGL HHAKKSEASG FCYVNDIVLA ILELLKYHQR VLYIDIDIHH  180
GDGVEEAFYT TDRVMTVSFH KYGEYFPGTG DLRDIGAGKG KYYAVNFPMR DGIDDESYGQ  240
IFKPIISKVM EMYQPSAVVL QCGADSLSGD RLGCFNLTVK GHAKCVEVVK TFNLPLLMLG  300
GGGYTIRNVA RCWTYETAVA LDCEIPNELP YNDYFEYFGP DFKLHISPSN MTNQNTPEYM  360
EKIKQRLFEN LRMLPHAPGV QMQAIPEDAV HEDSGDEDGE DPDKRISIRA SDKRIACDEE  420
FSDSEDEGEG GRRNVADHKK GAKKARIEED KKETEDKKTD VKEEDKSKDN SGEKTDTKGT  480
KSEQLSNP                                                           488

SEQ ID NO: 18          moltype = AA  length = 430
FEATURE                Location/Qualifiers
source                 1..430
                       mol_type = protein
                       organism = Homo sapiens
SEQUENCE: 18
MAANMYRVGD YVYFENSSSN PYLIRRIEEL NKTANGNVEA KVVCFYRRRD ISSTLIALAD  60
KHATLSVCYK AGPGADNGEE GEIEEEMENP EMVDLPEKLK HQLRHRELFL SRQLESLPAT  120
HIRGKCSVTL LNETESLKSY LEREDFFFYS LVYDPQQKTL LADKGEIRVG NRYQADITDL  180
LKEGEEDGRD QSRLETQVWE AHNPLTDKQI DQFLVVARSV GTFARALDCS SSVRQPSLHM  240
SAAAASRDIT LFHAMDTLHK NIYDISKAIS ALVPQGGPVL CRDEMEEWSA SEANLFEEAL  300
EKYGKDFTDI QQDFLPWKSL TSIIEYYYMW KTTDRYVQQK RLKAAEAESK LKQVYIPNYN  360
KPNPNQISVN NVKAGVVNGT GAPGQSPGAG RACESCYMSS LRILLDILEE IWWLENANPV  420
RWREARTKPQ                                                         430

SEQ ID NO: 19          moltype = AA  length = 668
FEATURE                Location/Qualifiers
source                 1..668
                       mol_type = protein
                       organism = Homo sapiens
SEQUENCE: 19
MAANMYRVGD YVYFENSSSN PYLVRRIEEL NKTANGNVEA KVVCLFRRRD ISSSLNSLAD  60
SNAREFEEES KQPGVSEQQR HQLKHRELFL SRQFESLPAT HIRGKCSVTL LNETDILSQY  120
LEKEDCFFYS LVFDPVQKTL LADQGEIRVG CKYQAEIPDR LVEGESDNRN QQKMEMKVWD  180
PDNPLTDRQI DQFLVVARAV GTFARALDCS SSIRQPSLHM SAAAASRDIT LFHAMDTLQR  240
NGYDLAKAMS TLVPQGGPVL CRDEMEEWSA SEAMLFEEAL EKYGKDFNDI RQDFLPWKSL  300
ASIVQFYYMW KTTDRYIQQK RLKAAEADSK LKQVYIPTYT KPNPNQIISV GSKPGMNGAG  360
FQKGLTCESC HTTQSAQWYA WGPPNMQCRL CASCWIYWKK YGGLKTPTQL EGATRGTTEP  420
HSRGHLSRPE AQSLSPYTTS ANRAKLLAKN RQTFLLQTTK LTRLARRMCR DLLQPRRAAR  480
RPYAPINANA IKAECSIRLP KAAKTPLKIH PLVRLPLATI VKDLVAQAPL KPKTPRGTKT  540
PINRNQLSQN RGLGGIMVKR AYETMAGAGV PFSANGRPLA SGIRSSSQPA AKRQKLNPAD  600
APNPVVFVAT KDTRALRKAL THLEMRRAAR RPNLPLKVKP TLIAVRPPVP LPAPSHPAST  660
NEPIVLED                                                           668

SEQ ID NO: 20          moltype = DNA  length = 19296
FEATURE                Location/Qualifiers
source                 1..19296
                       mol_type = genomic DNA
                       organism = Homo sapiens
SEQUENCE: 20
ccttcagttc ttaaagcgct gcaattcgct gctgcagcca tatttcttac tctctcgggg  60
ctggaagctt cctgactgaa gatctctctg cacttggggt tctttctaga acattttcta  120
gtcccccaac accctttatg gcgtatttct ttaaaaaaat cacctaaatt ccataaaata  180
tttttttaaa ttctatactt tctcctagtg tcttcttgac acgtcctcca tattttttta  240
aagaaagtat ttggaatatt ttgaggcaat ttttaatatt taaggaattt ttctttggaa  300
tcattttttgg ttgacatctc tgtttttttgt ggatcagttt tttactcttc cactctcttt  360
tctatatttt gcccatcggg gctgcggata cctggtttta ttatttttttc tttgcccaac  420
ggggccgtgg atacctgcct tttaattctt ttttattcgc ccatcggggc cgcggatacc  480
tgcttttat tttttttttcc ttagcccatc ggggtatcgg atacctgctg attccctcc  540
cctctgaacc cccaacactc tggcccatcg gggtgacgga tatctgcttt ttaaaaattt  600
tcttttttttg gcccatcggg gcttcggata cctgcttttt tttttttttat ttttccttgc  660
ccatcggggc ctcggatacc tgctttaatt tttgtttttc tggcccatcg gggccgcgga  720
tacctgcttt gattttttttt tttcatcgcc catcggtgct ttttatggat gaaaaaaatgt  780
tggttttgtg ggttgttgca ctctctggaa tatctacact ttttttttgct gctgatcatt  840
```

-continued

```
tggtggtgtg tgagtgtacc taccgctttg gcagagaatg actctgcagt taagctaagg     900
gcgtgttcag attgtggagg aaaagtggcc gccattttag acttgccgca taactcggct     960
tagggctagt cgtttgtgct aagttaaact agggaggcaa gatggatgat agcaggtcag    1020
gcagaggaag tcatgtgcat tgcatgagct aaacctatct gaatgaattg atttggggct    1080
tgttaggagc tttgcgtgat tgttgtatcg ggaggcagta agaatcatct tttatcagta    1140
caagggacta gttaaaaatg gaaggttagg aaagactaag gtgcagggct taaaatggcg    1200
attttgacat tgcggcattg ctcagcatgg cgggctgtgc tttgttaggt tgtccaaaat    1260
ggcggatcca gttctgtcgc agtgttcaag tggcgggaag gccacatcat gatgggcgag    1320
gctttgttaa gtggttagca tggtggtgga catgtgcggt cacacaggaa aagatggcgg    1380
ctgaaggtct tgccgcagtg taaaacatgg cgggcctctt tgtctttgct gtgtgctttt    1440
cgtgttgggt tttgccgcag ggacaatatg gcaggcgttg tcatatgtat atcatggctt    1500
ttgtcacgtg gacatcatgg cgggcttgcc gcattgttaa agatggcggg ttttgccgcc    1560
tagtgccacg cagagcggga gaaaaggtgg gatggacagt gctggattgc tgcataaccc    1620
aaccaattag aaatgggggt ggaattgatc acagccaatt agagcagaag atggaattag    1680
actgatgaca cactgtccag ctactcagcg aagacctggg tgaattagca tggcacttcg    1740
cagctgtctt tagccagtca ggagaaagaa gtggaggggc cacgtgtatg tctcccagtg    1800
ggcggtacac caggtgtttt caaggtcttt tcaaggacat ttagcctttc cacctctgtc    1860
ccctcttatt tgtcccctcc tgtccagtgc tgcctcttgc agtgctggat atctggctgt    1920
gtggtctgaa cctccctcca ttcctctgta ttggtgcctc acctaaggct aagtatacct    1980
cccccccac ccccaacccc ccccaactcc ccacccccac cccccacccc ccacctcccc     2040
accccccctac ccccctaccc ccctacccccc ctctggtctg ccctgcactg cactgttgcc    2100
atgggcagtg ctccaggcct gcttgggtgtg gacatggtgg tgagccgtgg caaggaccag    2160
aatggatcac agatgatcgt tggccaacag gtggcagaag aggaattcct gccttcctca    2220
agaggaacac ctaccccttg gctaatgctg gggtcggatt ttgatttata tttatctttt    2280
ggatgtcagt catacagtct gattttgtgg tttgctagtg tttgaattta agtcttaagt    2340
gactattata gaaatgtatt aagaggcttt atttgtagaa ttcactttaa ttacatttaa    2400
tgagttttg ttttgagttc cttaaaattc cttaaagttt ttagcttctc attacaaatt     2460
ccttaacctt ttttttggcag tagatagtca aagtcaaatc atttctaatg ttttaaaaat    2520
gtgctggtca ttttctttga aattgactta actattttcc tttgaagagt ctgtagcaca    2580
gaaacagtaa aaaatttaac ttcatgacct aatgtaaaaa agagtgtttg aaggtttaca    2640
caggtccagg ccttgctttg ttcccatcct tgatgctgca ctaattgact aatcacctac    2700
ttatcagaca ggaaacttga attgctgtgg tctggtgtcc tctattcaga cttattatat    2760
tggagtattt caatttttcg ttgtatcctg cctgcctagc atccagttcc tccccagccc    2820
tgctcccagc aaaccctag tctagcccca gccctactcc cacccccgcc cagccctgcc     2880
ccagccccag tcccctaacc ccccagccct agcccagtc ccagtcctag ttcctcagtc     2940
ccgcccagct tctctcgaaa gtcactctaa tttttcattga ttcagtgctc aaaataagtt    3000
gtccattgct tatcctatta tactgggata ttccgtttac ccttggcatt gctgatcttc    3060
agtactgact ccttgaccat tttcagttaa tgcatacaat cccatttgtc tgtgatctca    3120
ggacaaagaa tttccttact cggtacgttg aagttaggga atgtcaattg agagctttct    3180
atcagagcat tattgcccac aatttgagtt acttatcatt ttctcgatcc cctgcccttta   3240
aaggagaaac catttctctg tcattgcttc tgtagtcaca gtcccaattt tgagtagtga    3300
tcttttcttg tgtactgtgt tggccaccta aaactctttg cattgagtaa aattctaatt    3360
gccaataatc ctacccattg gattagacag cactctgaac cccatttgca ttcagcaggg    3420
ggtcgcagac aacccgtctt ttgttggaca gttaaaatgc tcagtcccaa ttgtcatagc    3480
tttgcctatt aaacaaaggc accctactgc gcttttttgct gtgcttctgg agaatcctgc    3540
tgttcttgga caattaaaga acaaagtagt aattgctaat tgtctcaccc attaatcatg    3600
aagactacca gtcgcccttg catttgcctt gaggcagcgc tgctacctg agatttaaga    3660
gtttcttaaa ttattgagta aaatcccaat tatccatagt tctgttagtt acactatggc    3720
ctttgcaaac atctttgcat aacagcagtg ggactgactc attcttagag ccccttccct    3780
tggaatatta atggatacaa tagtaattat tcatggttct gcgtaacaga gaagacccac    3840
ttatgtgtat gcctttatca ttgctcctag atagtgtgaa ctacctacca ccttgcatta    3900
atatgtaaaa cactaattgc ccatagtccc actcattagt ctaggatgtc ctctttgcca    3960
ttgctgctga gttctgacta cccaagtttc cttctcttaa acagttgata tgcataattg    4020
catatattca tggttctgtg caataaaaat ggattctcac cccatcccac cttctgtggg    4080
atgttgctaa cgagtgcaga ttattcaata acagctcttg aacagttaat ttgcacagtt    4140
gcaattgtcc agagtcctgt ccattagaaa gggactctgt atcctatttg cacgctacaa    4200
tgtgggctga tcacccaagg actcttcttg tgcattgatg ttcataattg tatttgtcca    4260
cgatcttgtg cactaaccct tccactccct ttgtattcca gcaggggacc cttactactc    4320
aagacctctg tactaggaca gtttatgtgc acaatcctaa ttgattagaa ctgagtcttt    4380
tatatcaagg tccctgcatc atctttgctt tacatcaaga gggtgctggt tacctaatgc    4440
ccctcctcca gaaattattg atgtgcaaaa tgcaatttcc ctatctgctg ttagtctggg    4500
gtctcatccc ctcatattcc ttttgtctta cagcaggggg tacttgggac tgttaatgcg    4560
cataattgca attatggtct tttccattaa attaagatcc caactgctca caccctctta    4620
gcattacagt agagggtgct aatcacaagg acatttcttt tgtactgtta atgtgctact   4680
tgcatttgtc cctcttcctg tgcactaaag accccactca cttccctagt gttcagcagt    4740
ggatgacctc tagtcaagac cttttgcacta ggatagttaa tgtgaaccat ggcaactgat   4800
cacaacaatg tctttcagat cagatccatt ttatcctcct tgttttacag caagggatat    4860
taattaccta tgttacctt ccctgggact atgaatgtgc aaaattccaa tgttcatggt     4920
ctctcccttt aaacctatat tctaccccctt ttacattata gaaaagggatg ctggaaaccc   4980
agagtccttc tcttgggact cttaatgtgt atttctaatt atccatgact cttaatgtgc    5040
atattttcaa ttgcctaatt gatttcaatt gtctaagaca tttcaaatgt ctaattgatt    5100
agaactgagt cttttatatc aagctaatat ctagctttta tatcaagcta atatcttgac    5160
ttctcagcat catagaaggg ggtactgatt tcctaaagtc tttcttgaat ttctattatg    5220
caaaattgcc ctgaggccgg gtgtggtggc tcacacctgt aatcccagca ctttgggagg    5280
ctgaggtggg aagatccctt actgccagga gtttgagacc agcctggcca acattaaaaa    5340
aaaaaaaaag taagacaatt gccctggaat cccatccccc tcacacctcc ttggcaaagc    5400
agcaggagtg ctaactagct agtgcttctt ctcttatact gcttaaatgc gcataattag    5460
cagtagttga tgtgcccca tgttagagta gaatcccgct tccttgctcc atttgcatta    5520
ctgcaggagc ttctaactag cctgaattca ctctcttgga ctgttaatgt gcatacttat    5580
```

-continued

```
atttgctgct gtactttttt accatgtaag gacccaccc actgtattta catcccagct   5640
ggaagtacct actacttaag acccttagac tagtaaagtt agcgtgcata atcttaggtg   5700
ttatatacac atttttcagtt gcatacagtt gtgccttta tcaggactcc tgtacttatc   5760
aaaagcagaga gtgctaatca atattaagcc cttctcttcg aactgtagat ggcatgtaat   5820
tgcagttgtc aatggtcctt caattagact tgggtttctg acctatcaca ccctctttgc   5880
tttattgcat ggggtactat tcacttaagg cccctttctc aaactgttaa tgtgcctaat   5940
gacaattaca tcagtatcct tcctttgaa ggacagcatg gttggtgaca cctaaggccc    6000
catttcttgg cctcccaata tgtgtgattg tatttgtcga ggttgctatg cactagagaa    6060
ggaaagtgct cccctcatcc ccactttcc cttccagcag gaagtgccca ccccataaga    6120
ccctttatt tggagagtct aggtgcacaa ttgtaagtga ccacaagcat gcatcttgga    6180
catttatgtg cgtaatcgca cactgctcat tccatgtgaa taaggtccta ctctccgacc    6240
cctttgcaa tacagaaggg ttgctgataa cgcagtcccc ttttcttggc atgttgtgtg    6300
tgattataat cgtctgggat cctatgcact agaaaaggag ggtcctctcc acatacctca    6360
gtctcacctt tcccttccag cagggagtgc ccactccata agactctcac atttggacag    6420
tcaaggtgcg taattgttaa gtgaacacaa ccatgcacct tagacatgga tttgcataac    6480
tacacacagc tcaacctatc tgaataaaat cctactctca gaccccttt gcagtacagc    6540
aggggtgctg atcaccaagg cccttttttcc tggcctggta tgcgtgtgat tatgtttgtc    6600
ccggttcctg tgtattagac atggaagcct ccctgccac actccacccc caatcttcct    6660
ttcccttccg gcagggagtg ccctctccat aagacgctta cgtttggaca atcaaggtgc    6720
acagttgtaa gtgaccacag gcatacacct tggacattaa tgtgcataac cactttgccc    6780
attccatctg aataaggtcc tactctcaga ccccttttgc agtacagcag gggtgctgat    6840
caccaaggcc cctttttcttg gcctgttatg tgcgtgatta tatttgtctg ggttcctgtg    6900
tattagacaa ggaagccttc cccccgcccc caccccact cccagtcttc ctttcccttc    6960
cagcagggag tgcccctcc ataagatcat tacatttgga caatcaaggt gcacaattat    7020
aagtgaccac agccatgcac cttggacatt attggacatt aatgtgcgta actgcacatg    7080
gcccatccca tctgaataag gtcctactcc cagatgcct ttgcagtaca gcaggggtac    7140
tgaatcacca aggcccttttt tcttggcctg ttatgtgtgt gattatattt atcccagttt    7200
ctgtgtaata gacatgaaag cctccccctgc cacacccac ctccaatctt cctttccctt    7260
ccaccaggga gtgtccactc catataccct tacatttgga caatcaaggt gcacaattgt    7320
aagtgacgat aggcactcac cttggacatg aatgtgcata actgcacatg gcccatccca    7380
tctgaataag gtcctactct cagacccttt ttgcagtaca gcaggggtgc tgatcaccaa    7440
ggcccctttt cctggcctgt tatgtgtgtg attatatttg ttccagttcc tgtgtaatag    7500
acatggaagc ctcccctgcc acactccacc cccaatcttc cttttcccttc tggcaggaag    7560
tacccgctcc ataagaccct tacatttgga cagtcaaggt gcacaattgt atgtgaccac    7620
aaccatgcac cttggacata aatgtgtgta actgcacatg gcccatccca tctgaataag    7680
gtcctactct cagacccctt ttgcagtaca gtaggtgtgc tgataaccaa ggcccctctt    7740
cctgggctgt taacgtatgt gattatattt gtctggggttc cagtgtataa gacatggaag    7800
cctcccctgc cccaccccac cctcaatctt cctttcccctt ctggcaggga gtgccagctc    7860
cataagaacc ttacatttgg acagtcaagg tgcacaatcc taagtgaccg cagccatgca    7920
ccttggtcaa taatgtgtgt aactgcacac ggcctatctc atctgaataa ggccttactc    7980
tcagacccct tttgcagtac agcaggggtg ctgataacca aggcccattt tcctggcctg    8040
ttatgtgtgt gattatattt gtccaggttt ctgtgtacta gacaaggaag cctcctctgc    8100
cccatcccat ctacgcataa tctttctttt cctcccagca gggagtgtgc actccataag    8160
acccttacat ttggacaatc aaggtgcaca attgtaagtg accacaacca tgcatcttgg    8220
aaatttatgt gcataactgc acatggctta tcctatttga ataaagtcct actctcagac    8280
cccctttgca gtatagctgg ggtgctgatc actgaggcct cttttgcttgg cttgtctata    8340
ttcttgtgta ctagataagg gcaccttctc atggactccc tttgctttc aacaaggagt    8400
acccactact ttttaagatt cttatatttg tccaaagtac atggtttttaa ttgaccacaa    8460
caatgtccct tggacattaa tgtatgtaat caccacatgg ttcatcctaa ttaaacaaag    8520
ttctaccttc tcaccctcca tttgcagtat accaggggttg ctgacccccct aagtcccctt    8580
ttcttggctt gttgacatgc ataattgcat ttatgttggt tcttgtgccc tagacaagga    8640
tgccccacct ctttttcaata gtgggtgccc actccttatg atctttacat ttgaacagtt    8700
aatgtgaata attgcagttg tccacaaccc tatcacttct aggaccatta tacctctttt    8760
gcattactgt ggggtatact gtttccctcc aaggcccctt ctggtggact atcaacatat    8820
aattgaaatt ttcttttgtc tttgtcagta gattaaggtc atacccatc acctttcctt    8880
tgtagtacaa cagggtgtcc tgatcaacca aagtcctgtt gtttttggact gttaatatgt    8940
gcaattacat ttgctcctga tctgtgcact agataaggat cctacctact ttcttagtgt    9000
ttttagcagg tagtgcccac tactcaagac tgtcacttgg aatgttcatg tgcacaaact    9060
caattctcta agcatgttcc tgtaccacct ttgctttaga gcagggggat gatattcact    9120
aagtgcccct tcttttggac ttaatatgca ttaatgcaat tgtccacctc ttcttttaga    9180
ctaagagttg atctccacat attccccttg catcaggggc atgttaatta tgaatgaacc    9240
cttttctttt aatattaatg tcataattgt atttgtggac ctgtgtagga gaaaaagacc    9300
ctatgttcct cccattaccc tttggattgc tgctgagaag tgttaactac tcataatctc    9360
agctcttgga caattaatag cattaataac aattatcaag ggcactgatc attagataag    9420
actcctgctt cctcgttgct tacatcgggg gtactgaccc actaaggccc cttgtactgt    9480
taatgtgaat atttgcaatt atatatgtct ccttctggta gagtgggata ttatgccta    9540
gtatccccctt tgcattactg caggggctgc tgactactca aaacttctcc tgggactgtt    9600
aataggcaca atggcagtta tcaatggttt tctccctccc tgaccttgtt aagcaagcgc    9660
cccaccccac ccttagtttc ccatggcata ataagtata agcattggag tattccatgc    9720
acttgtctat caaacagtgg tccatactcc caacccttttt gcattgcgcc agtgtgtaaa    9780
atcacaggta gccatggtgt catgcttat atacgaagtc ttccctctct ctgccccttg    9840
tgtgcccttg gcccctttttt acagactatt gctcacaatc tcaggtgtcc atatttgcag    9900
ctattaggta agattgtgct gtctccctct tcccttccct ctgccctgcc ccttttgcct    9960
ctttgctggg taatgttgac cagacaaggc cctttctcgtt ggacttaaac aattctcagt    10020
tgcactttcc ttggtcccac ccattataca tgaaccccctc tacttccttt cgcattgctt    10080
ctgagtatgc tgactaccca aagccccttc tgtgttatta ataaacacag tactgattgt    10140
cccatttttc agcccatcag tccaagatct ccctaccact ttggtgtgtt ggtgcagtgt    10200
tgactatgaa aagcaggcct gaactaggtg gataagcctt cactcatttt ctttcattta    10260
ttaatgatcc tagtttcaat tattgtcaga ttctggggac aagaaccatt cttgcccacc    10320
```

-continued

```
tgtgttactg ctttactgtg caaaatactg aaggcaagtc agacccaggg agctggattg 10380
ccatccttta ttttgtgttt ccagtgtaca ctataaaatt gtctccccag gaaggaaggt 10440
tggcactttc tctgcattct tctttccaga gcagattgcc tggttaagaa tctcttgttg 10500
tccccttgt atattgttat tgtaaagtgc caaatgccag gatacagcca gaaaaattgc 10560
ttattattat taaaaaaatt tttttaagaa agacatctgg attgtagggt ggactcgata 10620
acctggtcat tattttttg aagccaaaat atccatttat actatgtacc tggtgaccag 10680
tgtctctcat tttaactgag ggtggtgggt ctgtggatag aacactgact cttgctattt 10740
taatatcaaa gatattctag agtggaactc ttaagaccag tatctttgtg tgggctttac 10800
cagcattcac ttttagaaaa actacctaaa ttttataatc ctttaatttc ttcatctgga 10860
gcacctgccc ctacttattt caagaagatt gcagtaaaac gattaaatga gggaacatat 10920
gcagaggtgc ttttaaaaag catatgccac ctttttttatt aattattata taaaatgaag 10980
catttaatta tagtaataat ttgaagtagt ttgaagtacc acactgaggt gaggacttaa 11040
aaatgataag acgagttccc tattttataa gaaaaataag ccaaaattaa atattcttt 11100
ggatataaat ttcaacagtg agatagctgc ctagtggaaa tgaataatat cccagccact 11160
agtgtacagg gtgtttgtg gcacaggatt atgtaatatg gaactgctca agcaaataac 11220
tagtcatcac aacagcagtt ctttgtaata actgaaaaag aatattgttt ctcggagaag 11280
gatgtcaaaa gatcggccca gctcagggag cagtttgccc tactagctcc tcggacagct 11340
gtaaagaaga gtctctggct ctttagaata ctgatcccat tgaagatacc acgctgcatg 11400
tgtccttagt agtcatgtct ccttaggctc ctcttggaca ttctgagcat gtgagacctg 11460
aggactgcaa acagctataa gaggctccaa attaatcata tctttccctt tgagaatctg 11520
gccaagctcc agctaatcta cttggatggg ttgccagcta tctggagaaa aagatcttcc 11580
tcagaagaat aggcttgttg ttttacagtg ttagtgatcc attccctttg acgatcccta 11640
ggtgagatg gggcatgagg atcctccagg ggaaaagctc actaccactg ggcaacaacc 11700
ctaggtcagg aggttctgtc aagatactttt cctggtccca gataggaaga taaagtctca 11760
aaaacaacca ccacacgtca agctcttcat tgttcctatc tgccaaatca ttatacttcc 11820
tacaagcagt gcagagagct gagtcttcag caggtccaag aaatttgaac acactgaagg 11880
aagtcagcct tcccacctga agatcaacat gcctggcact ctagcacttg aggatagctg 11940
aatgaatgtg tatttctttg tctctttctt tcttgtcttt gctctttgtt ctctatctaa 12000
agtgtgtctt acccatttcc atgtttctct tgctaatttc tttcgtgtgt gccttttgcct 12060
cattttctct ttttgttcac aagagtggtc tgtgtcttgt cttagacata tctctcattt 12120
ttcattttgt tgctatttct ctttgctctc ctagatgtgg ctcttctttc acgctttatt 12180
tcatgtctcc tttttgggtc acatgctgtg tgctttttgt cctttttcttg ttctgtctac 12240
ctctcctttc tctgcctacc tctctttttct cttttgtgaac tgtgattatt tgttacccct 12300
tccccttctc gttcgtttta aatttcacct tttttctgag ttggcctcc tttctgctgt 12360
ttctactttt tatctcacat ttctcatttc tgcatttcct ttctgcctct cttgggctat 12420
tctctctctc ctcccctgcg tgcctcagca tctcttgctg tttgtgatttt tctatttcag 12480
tattaatctc tgttggcttg tatttgttct ctgcttcttc cctttctact cacctttgag 12540
tatttcagcc tcttcatgaa tctatctccc tctctttgat ttcatgtaat ctctccttaa 12600
atatttcttt gcatatgtgg gcaagtgtac gtgtgtgtgt gtcatgtgtg gcagagggcc 12660
ttcctaaccc ctgcctgata ggtgcagaac gtcggctatc agagcaagca ttgtggagcg 12720
gttccttatg ccaggctgcc atgtgagatg atccaagacc aaaacaaggc cctagactgc 12780
agtaaaaccc agaactcaag tagggcagaa ggtggaaggc tcatatggat agaaggccca 12840
aagtataaga cagatggttt gagacttgag acccgaggac taagatggaa agcccatgtt 12900
ccaagataga tagaagcctc aggcctgaaa ccaacaaaag cctcaagagc caagaaaaca 12960
gagggtggcc tgaattggac cgaaggcctg agttggatgg aagtctcaag gcttgagtta 13020
gaagtcttaa gacctgggac aggacacatg gaaggcctaa gaactgagac ttgtgacaca 13080
aggccaacga cctaagatta gcccagggtt gtagctgaga gacctacaac ccaaggatgg 13140
aaggcccctg tcacaaagcc tacctagatg gatagaggac ccaagcgaaa aaggtatctc 13200
aagactaacg gccggaatct ggaggcccat gacccagaac ccaggaagga tagaagcttg 13260
aagacctggg gaaatcccaa gatgagaacc ctaaacccta cctcttttct attgtttaca 13320
cttcttactc ttagatattt ccagttctcc tgtttatctt taagcctgat tcttttgaga 13380
tgtacttttt gatgttgccg gttacctta gattgacagt attatgcctg ggccagtctt 13440
gagccagctt taaatcacag ctttttaccta tttgttaggc tatagtgttt tgtaaacttc 13500
tgtttctatt cacatcttct ccacttgaga gagacaccaa aatccagtca gtatctaatc 13560
tggcttttgt taacttccct caggagcaga cattcatata ggtgatactg tatttcagtc 13620
ctttcttttg accccagaag ccctagactg agaagataaa atggtcaggt tgttggggaa 13680
aaaaaagtgc caggctctct agagaaaaat gtgaagagat gctccaggcc aatgagaaga 13740
attagacaag aaatacacag atgtgccaga cttctgagaa gcacctgcca gcaacagctt 13800
ccttctttga gcttaggtga gcaggattct ggggtttggg atttctagtg atggttatgg 13860
aaagggtgac tgtgcctggg acaaagcgag gtcccaaggg gacagcctga actccctgct 13920
catagtagtg gccaaataat ttggtggact gtgccaacgc tactcctggg tttaataccc 13980
atctctaggc ttaaagatga gagaacctgg gactgttgag catgtttaat actttccttg 14040
atttttttct tcctgtttat gtgggaagtt gatttaaatg actgataatg tgtatgaaag 14100
cactgtaaaa cataagagaa aaaccaatta gtgtattggc aatcatgcag ttaacatttg 14160
aaagtgcagt gtaaattgtg aagcattatg taaatcaggg gtccacagtt tttctgtaag 14220
gggtcaaatc ataaatactt tagactgtgg gccatatggt ttctgttaca tatttgttt 14280
ttaaacaacg tttttataag gtcaaaatca ttcttagttt ttgagccaat tggatttggc 14340
ctgctgttca tagcttacca cccctgatg tattatttgt tattcagaga aaatttctga 14400
atactactag tttccttttc tgtgcctgtc cctgtgctag gcactaaaaa tgcaatgatt 14460
attgatatct aggtgacctg aaaaaaaata gtgaatgtgc tttgtaaact gtaaagcact 14520
tgtattctac tgtgataagc gttgtggata caaagaaagg agcaagcata aaaaagtgct 14580
ctttcaaaag gatatagtac tatgcagaca caaggaattg tttgataaat gaataaatta 14640
tatgtatatt tgaggccaat ttgtgtttgc tgctctggta attttgagta aaaatgcagt 14700
attccaggta tcagaaacga aaacacatgg aaactgcttt taacttttaa aatatactga 14760
aaacataagg gactaagctt gttgtggtca cctataatgt gccagatacc atgctgggtg 14820
ctagagctac caaaggggga aaagtattct catagaacaa aaaatttcag aaaggtgcat 14880
attaaagtgc tttgtaaact aaagcatgat acaaatgtca atgggctaca tatttatgaa 14940
tgaatgaatg gatgaatgaa tattaagtgc ctccttacata ccagctattt tgggtactgt 15000
aaaatacaag attaattctc ctatgtaata agaggaaagt ttatcctcta tactattcag 15060
```

-continued

```
atgtaaggaa tgatatattg cttaatttta aacaatcaag actttactgg tgaggttaag   15120
ttaaattatt actgatacat tttttccaggt aaccaggaaa gagctagtat gaggaaatga   15180
agtaatagat gtgagatcca gaccgaaagt cacttaattc agcttgcgaa tgtgctttct   15240
aaaattataaa gcacttgtaa atgaaaaatt tgatgctttc tgtatgaata aaactttctg   15300
taagctaggt attgtctcta caaaattctc attgtatagt taaaccacag tgagaagggt   15360
tctataagta gttatacaaa ccaagggttt aaatacctgt taaatagatc aattttgatt   15420
gcctactatg tgaactcact gttaaaggca ctgaaaattt atcatatttc atttagccac   15480
agccaaaaat aaggcaatac ctatgttagc attttgtgaa ctctaaggca ccatataaat   15540
gtaactgttg attttctcac ttggtgctgg gtactaggtt tataaaattg tatgatagtt   15600
attatattgt gcaaataaag taggaaaatt tgaataacaa tgattatctt ttgaatacgc   15660
atacgcaagg gattggttgt ctgaagaatg ccactatagt agttatctat tgtgtgccaa   15720
tctcattgct aggcattggg gatgcaaaga taaaccatct ttattgtgtc ttgggtagca   15780
gaagaaaata tgtgtaaaat caatttataa tttgtaaact gccacccata tataagctat   15840
atctgctgaa tgatcattga ttactcttat ccttagagat aacaactggg ggcacaaaca   15900
tttattatca ttattgaacc tacaacagag atctatgtgt agatttacaa agcctacagt   15960
tctatacaga taggaatgaa ctattggctt actgaatggt gattactttc tgtggggctc   16020
ggaactacat gccctaggat ataaaaatga tgttatcatt atagagtgct cacagaagga   16080
aatgaagtaa tataggtgtg agatccagac caaaagtcat ttaacaagtt tattcagtga   16140
tgaaaacatg ggacaaatgg actaatataa ggcagtgtac taagctgagt agagagataa   16200
agtcctgtcc agaagataca tgcttcctgg cctgattgag gagatggaaa atttttgcaa   16260
aaaacaaggt gttgtggtct tccatccagt ttcttaagtg ctgatgataa aagtgaatta   16320
gacccacctt gacctggcct acagaagtaa aggagtaaaa ataaatgcct caggcgtgct   16380
ttttgattca tttgataaac aaagcatctt ttatgtggaa tataccattc tgggtcctga   16440
ggataagaga gatgagggca ttagatcact gacagctgaa gatagaagaa catctttggt   16500
ttgattgttt aaataaatatt tcaatgccta ttctctgcaa ggtactatgt ttcgtaaatt   16560
aaataggtct ggcccagaag acccactcaa ttgcctttga gattaaaaaa aaaaaaaaaa   16620
agaaagaaaa atgcaagttt ctttcaaaat aaagagacat ttttcctagt ttcaggaatc   16680
ccccaaatca cttcctcatt ggcttagttt aaagccagga gactgataaa agggctcagg   16740
gtttgttctt taattcatta actaaacatt ctgctttat tacagttaaa tggttcaaga   16800
tgtaacaact agttttaaag gtatttgctc attggtctgg cttagagaca ggaagacata   16860
tgagcaataa aaaaaagatt cttttgcatt taccaattta gtaaaaattt attaaaactg   16920
aataaagtgc tgttcttaag tgcttgaaag acgtaaacca aagtgcactt tatctcattt   16980
atcttatggt ggaaacacag gaacaaattc tctaagagac tgtgtttctt tagttgagaa   17040
gaaacttcat tgagtagctg tgatatgttc gatactaagg aaaaactaaa cagatcacct   17100
ttgacatgcg ttgtagagtg ggaataagag agggctttt attttttcgt tcatacgagt   17160
attgatgaag atgatactaa atgctaaatg aaatatatct gctccaaaag gcatttattc   17220
tgacttggag atgcaacaaa aacacaaaaa tggaatgaag tgatactctt catcaaacag   17280
aagtgactgt tatctcaacc attttgttaa atcctaaaca gaaaacaaaa aaatcatga   17340
cgaaaagaca cttgcttatt aattggcttg gaaagtagaa tataggagaa aggttactgt   17400
ttatttttt tcatgtattc attcattcta caaatatatt cgggtgccaa taggtacttg   17460
gtataaggtt tttggcccca gagacatggg aaaaaaatgc atgccttccc agagaatgcc   17520
taatactttc cttttggctt gttttcttgt taggggcatg gcttagtccc taaataacat   17580
tgtgtgggtt aattcctact ccgtatctct tctaccactc tggccactac gataagcagg   17640
tagctgggtt ttgtagtgag cttgctcctt aagttacagg aactctcctt ataatagaca   17700
cttcattttc ctagtccatc cctcatgaaa aatgactgac cactgctggg cagcaggagg   17760
gatgatgacc aactaattcc caaaccccag tctcattggt accagccttg gggaaccacc   17820
tacacttgag ccacaattgg tttttgaagtg catttacaag gtttgtctat tttcagttct   17880
ttactttta catgctgaca catacataca ctgcctaaat agatctcttt cagaaacaat   17940
cctcagataa cgcatagcaa aatggagatg gagacatgt ttctcatgca acagcttctc   18000
taattatacc ttagaaatgt tctcctttt atcatcaaat ctgctcaaga agggcttttt   18060
atagtagaat aatatcagtg gatgaaaaca gcttaacatt ttaccatgct taagttttaa   18120
gaataaaata aaaattggaa ataattggcc aaaattgaaa ggaaaaattt ttttaaaatt   18180
tctctaaatg taggcctggc tgggctttga ccttttccgt ttttaaatca ctcacagagg   18240
gtgggacagg aggaagagtg aaggaaaagg tcaaacctgt tttaagggca acctgccttt   18300
gttctgaatt ggtcttaaga acattaccag ctccaggttt aaattgttca gtttcatgca   18360
gttccaatag ctgatcattg ttgagatgag gacaaaatcc tttgtcctca ctagtttgct   18420
ttacattttt gaaaagtatt attttttgtcc aagtgcttat caactaaacc ttgtgttagg   18480
taagaatgga atttattaag tgaatcagtg tgacccttct tgtcataaga ttatcttaaa   18540
gctgaagcca aaatatgctt caaaagaaga ggactttatt gttcattgta gttcatacat   18600
tcaaagcatc tgaactgtag tttctatagc aagccaatta catccataag tggagaagga   18660
aatagataaa tgtcaaagta tgattggtgg agggagcaag gttgaagata atctggggtt   18720
gaaattttct agttttcatt ctgtacattt ttagttagac atcagatttg aaatattaat   18780
gtttaccttt caatgtgtgg tatcagctgg actcagtaac accccttct tcagctgggg   18840
atggggaatg gattattgga aaatggaaag aagaaagtaa ctaaaagcct tcctttcaca   18900
gtttctggca tcactaccac tactgattaa acaagaataa gagaacattt tatcatcatc   18960
tgctttattc acataaatga agttgtgatg aataaatctg cttttatgca gacacaagga   19020
attaagtggc ttcgtcattg tccttctacc tcaaagataa tttattccaa aagctaagat   19080
aaatggaaga ctcttgaact tgtgaactga tgtgaaatgc agaatctctt ttgagtcttt   19140
gctgtttgga agattgaaaa atattgttca gcatgggtgg ccaccagaaa gtaatcttaa   19200
gccatctaga tgtcacaatt gaaacaaact ggggagttgg ttgctattgt aaaataaaat   19260
atactgtttt gaaaactttg aaaaaaaaaa aaaaaa                            19296
```

```
SEQ ID NO: 21          moltype = DNA  length = 25
FEATURE                Location/Qualifiers
misc_feature           1..25
                       note = Single strand DNA oligonucleotide
source                 1..25
                       mol_type = other DNA
                       organism = synthetic construct
```

```
SEQUENCE: 21
tgttttttg tttattgggg ttgtg                                                 25

SEQ ID NO: 22            moltype = DNA   length = 24
FEATURE                  Location/Qualifiers
misc_feature             1..24
                         note = Single strand DNA oligonucleotide
source                   1..24
                         mol_type = other DNA
                         organism = synthetic construct
SEQUENCE: 22
taaattttaa attaattaaa ttat                                                 24

SEQ ID NO: 23            moltype = DNA   length = 29
FEATURE                  Location/Qualifiers
misc_feature             1..29
                         note = Single strand DNA oligonucleotide
source                   1..29
                         mol_type = other DNA
                         organism = synthetic construct
SEQUENCE: 23
tgttttagaa agaattttaa gtgtagaga                                            29

SEQ ID NO: 24            moltype = DNA   length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 24
agggagcagt ttgccctact                                                      20

SEQ ID NO: 25            moltype = DNA   length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 25
cacatgcagc gtggtatctt                                                      20

SEQ ID NO: 26            moltype = DNA   length = 8199
FEATURE                  Location/Qualifiers
source                   1..8199
                         mol_type = genomic DNA
                         organism = Homo sapiens
SEQUENCE: 26
ttgccctact agctcctcgg acagctgtaa agaagagtct ctggctcttt agaatactgt   60
aagtactact tcgtagctat taagtaatct ttttcctatt ctattttctt tctcttagat   120
gccacctata gaaaagtcag agggtccagt aagtttcttt ccttcttccc acctcatctg   180
caatatatat atatagagag agaaatagat acatacatac atgcataaat acacatatgt   240
gagttaacca gcagaactgt agaattaata ttgtggaccc agctctatgc taggttacac   300
tgataacctg ggtaggaatg atatcatcct atataatttc attcctgaga tgattttatc   360
gttgaggagc taatgtgagc acatttgaaa taactttaga aaataataag tgctgttttg   420
tgtgaatcat aagtagtagt tttaggaagg gaacccacaa ggatttgaag ttgatagaat   480
aaacttaagg aagtgggttt gctttttctc tttaagccaa gataggatta atattgcagc   540
catctggata gtccagttgg tttatttaa tttcatttgt tttttacctc ttttggagcc   600
atggaaagag atgaaaggga tagagcatag ccattgtgtt tggctatttg cgaaggttgg   660
caaattagtg attgctaaat ctcataagct tgagtatttt aaagttcaga gattgagggc   720
ataaatctaa tacttcggct ccttccacaa ttttactaca tttctgccca agaacagatg   780
accatggata atgcatatcg tagatacttt ttaagtttgg aacctttttg ccaagagggt   840
agtggagaag tgaagtcaaa accttgacct tccttgccta ccttatgctg tagtttatat   900
accttctttc ctcccacctt tcgtaaagct aaaagaagct tagcctcctt aatgtttcc   960
agctgacaaa atattgttta acataacatt cgaaactttt tttctggtgc acattcatgc   1020
atcacagcag gagcaacaag aaccatataa gtgaactggc ttcacttata gcccgtttta   1080
attcatatcc atatttcctc agggcttgtt tccatgcctc ccagccccac tccatatgct   1140
taacaacatt gtctggctga ctgagggtta tatacatcat ggtcttgaac cttcttggaa   1200
acatggtctg tgccattgtt tctcaaaccc aagtaatgct tcatgatgaa acaccttcta   1260
aaggaacaaa attttctgag atcctaaaaa aatgtgtttt gaggaacact gacttaacaa   1320
agatatttga aatgtaaata tgttttccaa tttcacgttg tctttgtcaa agatgtgttt   1380
tatataactt atgtagaact tggggatcca ttagaatata ttcacaaatc cccagggtta   1440
tcaccccaat ttgagaaacc ctggtctatg cttatgaaat cttctattgg taattaaatt   1500
gtcattcatt gtcaacatac aattataatt attattggaa tttgtttaa atgaatgaat   1560
ttggagtgga ttctgtacct taagtcaaga ggaaggatgg cttgatttta ggtggattga   1620
ttatactaga tagcatccaa aggtgaatct tgaagctgta tttaaattca ttgcttgaaa   1680
taatttccac cctaagaaa aatctctagc aattgtaaaa agggatgctc tggaaatgtg   1740
ggcatcttca aaatagagat aattcttgtg ttagttcaac aaatattatt gtaccaggtg   1800
```

-continued

```
ctggaataaa tagcaaaacc aaagacagga tttatatcaa ggaatttgct ttcttatgga      1860
ggatgcagaa ggaaatcatt atggttttgg gcagaaatgc ttagacttta gtcctggctc      1920
tgagtttggt tcagatcacc atcaatctga ccatctcgag actgctagtg aaataagata      1980
ggggcttata tcaaatacct aaatccctga aaatgacatt ttgtgatttg gaaaattttc      2040
aaaagtctaa tgaaggaaac tttttggca tttctttaaa tgattattgt catttctttt      2100
ctgacttttc cctttataaa accttaacat gtaggattgg aggaagtttt ctgaccattt      2160
tctcatatcc tctttcagct ttatctttct gtaacttcca tttctctagc cacctccta      2220
aattacagaa gactgtgaga cccagggctg ctgtgattag gcattcataa tttctttttca      2280
gggtgtttgt gccctgatta tcaaatgtac agcttgaagg gagtcatgt cttaaagtaa      2340
tgaattaaga gttgacctt gttgactgct aaaatattct tatatgtgaa agcatcctgg      2400
aaaaatacgt taccagctta aagagaaaga aactaatgat tatatctgaa ctgagctaat      2460
gcctcttctc ttcccccaaa ccttatcagt ttggatggca aagagtaatg atgtgtcagt      2520
taaacagagc taatgccttc ctctgccttg tcttaaagac tggattggga gaaaattgat      2580
attctcacta ccatattttg ggctgtaggc aagtagcatt ttacacaggt ttccttcaaa      2640
aatccaactc aagttggagc tcatgtattt aagacatagc tggcctgctg aatttaacaa      2700
gttaaacttc agtggccatg tacagttata tatcactata tatatgtgta ttaggctgtc      2760
gagttggtca tgttttttgtt ggtgacttag gctttacttg atagctcttc cttgacctt      2820
ccaaattgag tactgataca tggagcttgg gcttcttctg catcttatac aaatgagttt      2880
ggtaaagaag cctctccttt actgttttga tgtttatatt agaaataact tttgattatt      2940
ttttttcatg ttaggatgag aaactgaaac aaaatgtaaa tttgaccggt gctagacttc      3000
ttaaattatg ggtagactta aagtattatt ttccttaacc aattagaatg ctagtcttct      3060
agtgttcccg gaaacatgag aggttatgca gtagacccaa gcaataccct cttattacat      3120
aatcaagtgc gtataagaat ttaaaaatag ggatatgact ggaacatcac tgtactttac      3180
caggtcccat tataaaatta tctatgttac tttacccata gctttgaaaa ctagtggcat      3240
agtatatttt atagtatgct gttagtgtga ttggcattga acagtgatgg gatataatca      3300
ctctacaatc tatatgttat taaagtttc cagccttata gatctcctt gactgaaaat      3360
tagctactaa cttacgactt attttttaca gcagattgac taggtctttc caggaaatct      3420
gttgatgtac aaaaacaaag tttaattgct aatgttttt taaaaaataa ctttttgata      3480
ttacggatac ctggttattt gggccttgta tattttaaca tcaaaattac ctattataaa      3540
tccatataaa cagaaaagaa agagagtaag tctttagatc agatctgcaa acaatgatgg      3600
tacgtactgt agaaaaatct ggaacataga cttaccagtt cttaggttcc attttgcttg      3660
cttttaaaa actgtgtctt ataagtcttc agcaactggt tgggagattt ttagaaaaaa      3720
taacctttta atgttagaac agtgtagaga tttacagaat gattctgaag atagagtttc      3780
tgtgtacttc acacccagtt tttcccagtg ttaacatttt acattagttt ggtacatttg      3840
tcacaacaaa ccaatattga tacattatta ttaactagag tccatatttt attcagattt      3900
ccttagtttt tccttaatgt tcttttgtgt ttccaggatc ccattgaaga taccacgctg      3960
catgtgtcct tagtagtcat gtctccttag gctcctcttg gtaatgacag tttctcagac      4020
tctttgtttt tgatgaactt cacagttttg aggactaatg gtccagtatt ctatagaatg      4080
tctctctatt ggaatttgtc tgatgttctt ctcatgacta gattgggttt atgagtgttt      4140
aggaggaaga ccacaaaggt agagtgccat tcttatcact tatcaagagt acatactatc      4200
aacatgactt atcactgttt atgttatcct taatcacctg tctgaggtac tatttgtcag      4260
gtttctccag cgtaaaatta gtctttattt ctccatttcc ctactatact gttcacatag      4320
gaagtcacta tgtgcagcca gcacttaagg aatgggaaat taccttccac ctcattgagg      4380
gcagagtatt tacataaatt atttggaatt cttttgcaca ggatgtcttt tctccacaat      4440
gtattgtgtt tattcagtca tttatatcag tatgatctca gggatatttt atactctggg      4500
ttataataca gtattacttt attctgttgt tcaaattgtt ccagctttgg ccattgggag      4560
gtctttcatt tggctttgat ataacccccat gaatgtgggt tttttgtttg agcactttct      4620
tatttttgga actacaacat gcttcagact catttgcata tctcctgcct ggacctaaaa      4680
tgatgtattt ctgcaaggag ccttgatact tttattggga gagtaatatt agaaatcaag      4740
aagtgaatgc taggtgcgct cattactact ggagtgtcat tccttcaaga cctttttcagt      4800
tgacaagagc aaggagatat atatttgcat tctaacgtgt gtatatgcac atagctataa      4860
atatatataa ccatctgtat ctatattaaa ctaaatgtgt ttatacctac gtctccaact      4920
ctaatcattg ccacatggat cattatagtc tcacctcctt gcttatctgt tacctcccat      4980
ttctacagtg agaaacctgg cttggttggg aaatttttct gttaatatta cggtagtgag      5040
tgtttgacat ttgcttctat ggttaagttt agggagagtt tagctgtagg gtattcttga      5100
aactagaaat gaccccttctg ccctaaatgt ttctgccagt tttgaaacgt aaaataggtt      5160
gcagaaacaa actttatctt aagaaccaga atttacttca atccacattt tgacattgat      5220
tttcagatta aattattctg atatcgccag gtaagctgtt ccttgggtat gcatttcttc      5280
tttccgtttt tttctaagag ctaaaggacc ctgagaacac tggaggtggg aaaggaaggg      5340
aaaggcatgt tcacacgtgg gataggaaag gttcatttac tgacctccag ctagccttcc      5400
aaagtgccta tttaagaccc aaggagtaga tgtcttcctt ggcaattgta acccaaatat      5460
aattttttaac ctttcaattt tagtcaagaa agttggtgtg ctgttacaaa aagtgccctg      5520
attaacagca ttgtcatgtg cattgcatat taatcagcaa tttaaaataa catgaaatta      5580
tgttgagtat aatttttaata tttatatta gatattagtt tgagacagtg tttctcaagt      5640
ctgtataata agtttgatag tagggaggtt ttctctcaag aaaagaatta ttcagtgtgc      5700
acctacataa tcactgctta gattctacaa ttaatatttt gctatatttg attaaacgtt      5760
ttctgtaaaa gaaaaatatt attatgtact atttaggttt atgggaataa ttgttaagtt      5820
aaagtgtatg aacaaacctg gaatgaaatc tgtttgccta catctataat acaactataa      5880
aacatagcag atgtacaaat tagtagttaa tagataacta aaatgcaaat atggcactac      5940
tattatagta ttatagtttc ttttgagtgg cgtgtctgta atatcacatg ctgtgttgat      6000
gcacttcacc aaactgctgt tttcaaactg cttttaaatcc tgccattata gcacatagca      6060
atgctatttc actttcattt ggcacaaaac acatttatat attgtttgct tctcttcttt      6120
tctgtaatcc ccaggcaaca aaactagaac atttgccact aatctggcaa cgtggtccta      6180
tattatgaag tagtcatata gctgatctaa actatcctta cagtgaaatg agagtattgt      6240
gaaagttttg tagaaagctc cccatatgtc ctgagaatct atgcacagac cccacagtta      6300
aaagacctt gaattgtggg aagacatggg tttaagtatc acttggttac cttctatttg      6360
tgtaacattg aggtagtttc atcttctggg ttcccagttt ccttagagaa tgaaaatgtt      6420
gaattatgtg attttttttt tttttgaga cggagttttg ctctttcgcc caggctggag      6480
tgaagtagca cgatctcgac tcactgcaac ctccttcccc catgatcaag caattctcct      6540
```

-continued

```
gcctcagcct cccaagtagc tgggattaca ggcacccgcc ccccacccc cgccccagc      6600
taatgtttgt atttttagta cagatggagt tttgccgtgt tggccaggct ggtctcgaac   6660
ttctgacctc aggtgatcca ctcgccttgg cctcccaaag tgctaggatt acaggcatga   6720
gccactgcgc ctggcctatg tgattattaa tatcacgtct agctgtgaca attctgtctg   6780
atgctggagt atttgaacca gatggctggc tgtgccactc agttattctc tccataagac   6840
tttgatattt tgttggtctg caagatgacg gattctcaaa attcttgtca gtgaatattg   6900
aaccctagtg aaatgtatgg ttctgtatca gttccaaaat gtaaccactt tctctagcct   6960
tagattccca gttccaaaat gtaaccattt tctctagcct tagattcccg ttaagggaaa   7020
gggaatgctc tttgagtatg tcatcaccat agtaacaggc aaaactagag ggctttgatg   7080
ctaaagcaag atactccata aatatgctta agaagacttg gggagactgg aatagttgtt   7140
ccctttaga tgccagtgta taaatgaatt tgagctagga tccgtttatt taaaatttct    7200
ttaggtgtat ttgcttgcat atggagtgca catttactct cattaatgga gttttaggaa   7260
gcagtagagt aaatgcataa acatgtatga accgccatgt ttaactggaa gcctgcattt   7320
ggaagtcaag tatctaatct tagattaaat taggatgggg aaggatgttg gcaagagatt   7380
ttgaagcttg ttctgcttat attgagaaca tcatagaaca gtttggcctt tttaaagcta   7440
gagaatagtg ttgaataagt gatgttccat atattcctgt ttgacattga cataaaggtt   7500
tcctcatgat acagtaatcc ctgatcaggg atctggaagc ctgtattcat ttaaggtact   7560
caggtttaac atactgggtg cttttcacac catactatac agtaccatgc aaagtgcttt   7620
caagactgca aatttggctt agatcccctt tagtgagctc ctatgctata gtaaaggtag   7680
atagccaatt attaaaaaca gtcaagacaa ttgcacctct aagcagtagt agcagttgcc   7740
acaccacctt gaatcttgaa gtattttcag caacaggatg accattagcc acaaatttag   7800
tgtcagccct taaggtcggt attggtttga cccatatttt catgtagttc tttttcttca   7860
cttgtctaat cttcccgtgt actgccaggg cttgtcatta gaggactttta gggagaccaa   7920
gcaggctaga aagtagagac aggagatacc tatgtctaat gcttcagttt atacttccta   7980
ggttttttc attggggttt ttgtaactct tttggtatcc taccggtgct ttggtagcct    8040
actgaaccct gtctttcttc ttaaggacat tctgagcatg tgagacctga ggactgcaaa   8100
cagctataag aggctccaaa ttaatcatat cttttccttt gagaatctgg ccaagctcca   8160
gctaatctac ttggatgggt tgccagctat ctggagaaa                          8199
```

| SEQ ID NO: 27 | moltype = DNA   length = 3578 |
| FEATURE | Location/Qualifiers |
| source | 1..3578 |
| | mol_type = genomic DNA |
| | organism = Homo sapiens |

```
SEQUENCE: 27
aatttcacct ttttctgag tctggcctcc tttctgctgt ttctacttt tatctcacat     60
ttctcatttc tgcatttcct ttctgcctct cttgggctat tctctctct ctcccctgcg    120
tgcctcagca tctcttgctg tttgtgattt tctatttcag tattaatctc tgttggcttg   180
tatttgttct ctgcttcttc cctttctact caccttttgag tatttcagcc tcttcatgaa   240
tctatctccc tctctttgat ttcatgtaat ctctccttaa atatttcttt gcatatgtgt    300
gcaagtgtac gtgtgtgtgt gtcatgtgtg gcagagggggc ttcctaaccc ctgcctgata   360
ggtgcagaac gtcggctatc agagcaagca ttgtggagcg gttccttatg ccaggctgcc    420
atgtgagatg atccaagacc aaaacaaggc cctagactgc agtaaaaccc agaactcaag    480
tagggcagaa ggtggaaggc tcatatggat agaaggccca aagtataaga cagatggttt   540
gagacttgag acccgaggac taagatggaa agcccatgtt ccaagataga tagaagcctc    600
aggcctgaaa ccaacaaaag cctcaagagc caagaaaaca gagggtggcc tgaattggac    660
cgaaggcctg agttggatgg aagtctcaag gcttgagtta gaagtcttaa gacctgggac   720
aggacacatg gaaggcctaa gaactgagac ttgtgcaca aggccaacga cctaagatta    780
gcccagggtt gtagctggaa gacctacaac ccaaggatgg aaggccctg tcacaaagcc     840
tacctagatg gatagaggac ccaagcgaaa aaggtatctc aagactaacg gccggaatct    900
ggaggcccat gacccagaac ccaggaagga tagaagcttg aagacctggg gaaatcccaa    960
gatgagaacc ctaaacccta cctcttttct attgtttaca cttcttactc ttagatattt   1020
ccagttctcc tgtttatctt taagcctgat tcttttgaga tgtactttt gatgttgccg    1080
gttacccttta gattgacagt attatgcctg ggccagtctt gagccagctt taaatcacag   1140
cttttaccta tttgttaggc tatagtgttt tgtaaacttc tgtttctatt cacatcttct   1200
ccacttgaga gagacaccaa aatccagtca gtatctaatc tggctttttgt taacttccct   1260
caggagcaga cattcatata ggtgatactg tatttcagtc ctttcttttg accccagaag   1320
ccctagactg agaagataaa atggtcaggt tgttggggaa aaaaagtgc caggctctct    1380
agagaaaaat gtgaagagat gctccaggcc aatgagaaga attagacaag aaatacacag   1440
atgtgccaga cttctgagaa gcacctgcca gcaacagctt ccttctttga gcttaggtga   1500
gcaggattct ggggtttggg atttctagtg atggttatgg aaagggtgac tgtgcctggg   1560
acaaagcgag gtcccaaggg gacagcctga actccctgct catagtagtg gccaaataat   1620
ttggtggact gtgccaacgc tactcctggg tttaatacccc atctctaggc ttaaagatga   1680
gagaacctgg gactgttgag catgtgtaat acttttcttt atttttttct tcctgtttat   1740
gtgggaagtt gatttaaatg actgataatg tgtatgaaag cactgtaaaa cataagagaa   1800
aaaccaatta gtgtattggc aatcatgcag ttaacatttg aaagtgcagt gtaaattgtg   1860
aagcattatg taaatcaggg gtccacagtt tttctgtaag gggtcaaatc ataaatactt   1920
tagactgtgg gccatatggt ttctgttaca tatttgtttt ttaaacaacg tttttataag   1980
gtcaaaatca ttcttagttt ttgagccaat tggatttggc ctgctgttca tagcttacca   2040
ccccctgatg tattatttgt tattcagaga aaatttctga atactactag ttttcctttc   2100
tgtgcctgtc cctgtgctag gcactaaaaa tgcaatgatt attgatatct aggtgacctg    2160
aaaaaaaata gtgaatgtgc tttgtaaact gtaaagcact tgtattctac tgtgataagc    2220
gttgtggata caaagaaagg agcaagcata aaaagtgct ctttcaaaag gatatagtac    2280
tatgcagaca caaggaattg tttgataaat gaataaatta tatgtatatt tgaggccaat   2340
ttgtgtttgc tgctctggta attttgagta aaaatgcagt attccaggta tcagaaacga   2400
aaacacatgg aaactgcttt taaactttaa aatatactga aaacataagg gactaagctt   2460
gttgtggtca cctataatgt gccagatacc atgctgggtg ctagagctac caaaggggga   2520
aaagtattct catagaacaa aaaatttcag aaaggtgcat attaaagtgc tttgtaaact   2580
aaagcatgat acaaatgtca atgggctaca tatttatgaa tgaatgaatg gatgaatgaa   2640
```

```
tattaagtgc ctcttacata ccagctattt tgggtactgt aaaatacaag attaattctc   2700
ctatgtaata agaggaaagt ttatcctcta tactattcag atgtaaggaa tgatatattg   2760
cttaatttta aacaatcaag actttactgg tgaggttaag ttaaattatt actgatacat   2820
ttttccaggt aaccaggaaa gagctagtat gaggaaatga agtaatagat gtgagatcca   2880
gaccgaaagt cacttaattc agcttgcgaa tgtgctttct aaattataaa gcacttgtaa   2940
atgaaaaatt tgatgctttc tgtatgaata aaactttctg taagctaggt attgtctcta   3000
caaaattctc attgtatagt taaaccacag tgagaagggt tctataagta gttatacaaa   3060
ccaagggttt aaatacctgt taaatagatc aattttgatt gcctactatg tgaactcact   3120
gttaaaggca ctgaaaattt atcatatttc atttagccac agccaaaaat aaggcaatac   3180
ctatgttagc attttgtgaa ctctcaaggca ccatataaat gtaactgttg attttctcac   3240
ttggtgctgg gtactaggtt tataaaattg tatgatagtt attatattgt gcaaataaag   3300
taggaaaatt tgaataacaa tgattatctt ttgaatacgc atacgcaagg gattggttgt   3360
ctgaagaatg ccactatagt agttatctat tgtgtgccaa tctcattgct aggcattggg   3420
gatgcaaaga taaaccatct ttattgtgtc ttgggtagca gagaaaata tgtgtaaaat   3480
caatttataa tttgtaaact gccacccata tataagctat atctgctgaa tgatcattga   3540
ttactcttat ccttagagat aacaactggg ggcacaaa                           3578
```

SEQ ID NO: 28               moltype = AA  length = 390
FEATURE                     Location/Qualifiers
source                      1..390
                            mol_type = protein
                            organism = Homo sapiens
SEQUENCE: 28
```
MPPSGLRLLP LLLPLLWLLV LTPGRPAAGL STCKTIDMEL VKRKRIEAIR GQILSKLRLA   60
SPPSQGEVPP GPLPEAVLAL YNSTRDRVAG ESAEPEPEPE ADYYAKEVTR VLMVETHNEI   120
YDKFKQSTHS IYMFFNTSEL REAVPEPVLL SRAELRLLRL KLKVEQHVEL YQKYSNNSWR   180
YLSNRLLAPS DSPEWLSFDV TGVVRQWLSR GGEIEGFRLS AHCSCDSRDN TLQVDINGFT   240
TGRRGDLATI HGMNRPFLLL MATPLERAQH LQSSRHRRAL DTNYCFSSTE KNCCVRQLYI   300
DFRKDLGWKW IHEPKGYHAN FCLGPCPYIW SLDTQYSKVL ALYNQHNPGA SAAPCCVPQA   360
LEPLPIVYYV GRKPKVEQLS NMIVRSCKCS                                     390
```

SEQ ID NO: 29               moltype = AA  length = 288
FEATURE                     Location/Qualifiers
source                      1..288
                            mol_type = protein
                            organism = Homo sapiens
SEQUENCE: 29
```
MVGVGGGDVE DVTPRPGGCQ ISGRGARGCN GIPGAAAWEA ALPRRRPRRH PSVNPRSRAA   60
GSPRTRGRRT EERPSGSRLG DRGRGRALPG GRLGGRGRGR APERVGGRGR GRGTAAPRAA   120
PAARGSRPGP AGTMAAGSIT TLPALPEDGG SGAFPPGHFK DPKRLYCKNG GFFLRIHPDG   180
RVDGVREKSD PHIKLQLQAE ERGVVSIKGV CANRYLAMKE DGRLLASKCV TDECFFFERL   240
ESNNYNTYRS RKYTSWYVAL KRTGQYKLGS KTGPGQKAIL FLPMSAKS                 288
```

SEQ ID NO: 30               moltype = DNA  length = 3808
FEATURE                     Location/Qualifiers
source                      1..3808
                            mol_type = genomic DNA
                            organism = Homo sapiens
SEQUENCE: 30
```
cttcctggac tggggatccc ggctaaatat agctgtttct gtcttacaac acaggctcca   60
gtatataaat caggcaaatt ccccatttga gcatgaacct ctgaaaactg ccggcatctg   120
aggtttcctc caaggccctc tgaagtgcag cccataatga aggtcttggc ggcagtacac   180
agcccagggg gagccgttcc ccaacaacct ggacaagcta tgtggcccca acgtgacgga   240
cttcccgccc ttccacgcca acggcacgga gaaggccaag ctggtggagc tgtaccgcat   300
agtcgtgtac cttggcacct ccctgggcaa catcacccgg gaccagaaga tcctcaaccc   360
cagtgccctc agcctccaca gcaagctcaa cgccaccgcc gacatcctgc gaggcctcct   420
tagcaacgtg ctgtgccgcc tgtgcagcaa gtaccacgtg ggccatgtgg acgtgaccta   480
cggccctgac acctcgggta aggatgtctt ccagaagaag aagctggggct gtcaactcct   540
ggggaagtat aagcagatca tcgccgtgtt ggcccaggcc ttctagcagg aggtcttgaa   600
gtgtgctgtg aaccgaggga tctcaggagt tgggtccaga tgtggggggcc tgtccaaggg   660
tggctggggc ccaggggcatc gctaaaccca aatggggggct gctggcagac cccgagggtg   720
cctggccagt ccactccact ctgggctggg ctgtgatgaa gctgagcaga gtggaaactt   780
ccatagggag ggagctagaa gaaggtgccc cttcctctgg gagattgtgg actggggagc   840
gtggggctgga cttctgcctc tacttgtccc tttggcccct tgctcacttt gtgcagtgaa   900
caaactacac aagtcatcta caagagccct gaccacactg tgagacagca gggcccaggg   960
gagtggacca gccccagca aattatcacc atctgtgcct ttgctgcccc ttaggttggg   1020
acttaggtgg gccagagggg ctaggatccc aaaggactcc ttgtcccta gaagtttgat   1080
gagtggaaga tagagagggg cctctgggat ggaaggctgt cttcttttga ggatgatcag   1140
agaacttggg cataggaaca atctggcaga agtttccaga aggaggtcac ttggcattca   1200
ggctcttggg gaggcagaga agccaccttc aggcctggga aggaagacac tgggaggagg   1260
agaggcctgg aaagctttgg taggttcttc gttctcttcc ccgtgatctt ccctgcagcc   1320
tgggatggcc agggtctgat ggctggacct gcagcagggg tttgtggagg tgggtagggc   1380
aggggcaggt tgctaagtca ggtgcagagg ttctgaggga cccaggctct tcctctgggt   1440
aaaggtctgt aagaaggggc tggggtagct cagagtagca gctcacatct gggcctttgg   1500
gaggccttgt gaggtcacac agaggtactt gaggggggact ggaggccgtc tctggtcccc   1560
agggcaaggg aacagcagaa cttagggtca gggtctcagg gaaccctgag ctccaagcgt   1620
gctgtgcgtc tgacctggca tgatttctat ttattatgat atcctattta tattaactta   1680
ttggtgcttt cagtggccaa gttaattccc ctttccctgg tccctactca acaaaatatg   1740
atgatggctc ccgacacaag cgccagggcc agggcttagc agggcctggt ctggaagtcg   1800
```

-continued

```
acaatgttac aagtggaata agccttacgg gtgaagctca gagaagg0gtc ggatctgaga  1860
gaatggggag gcctgagtgg gagtgggggg ccttgctcca cccccccca tccctactg   1920
tgacttgctt tagggtgtca gggtccaggc tgcagggget gggccaattt gtggagaggc  1980
cgggtgcctt tctgtcttga ttccaggggg ctggttcaca ctgttcttgg gcgccccagc  2040
attgtgttgt gaggcgcact gttcctggca gatattgtgc ccctggagc agtgggcaag  2100
acagtccttg tggcccacc tgtccttgtt tctgtgtccc catgctgcct ctgaaatagc  2160
gccctggaac aaccctgccc ctgcacccag catgctccga cacagcaggg aagctcctcc  2220
tgtggcccgg acaccatag acggtgcggg gggcctggct gggccagacc ccaggaaggt  2280
ggggtagact gggggggatca gctgcccatt gctcccaaga ggaggagagg gaggctgcag  2340
atgcctggga ctcagaccag gaagctgtgg gccctcctgc tccacccca tcccactccc  2400
acccatgtct gggctcccag gcagggaacc cgatctcttc ctttgtgctg gggccaggcg  2460
agtggagaaa cgccctccag tctgagagca ggggagggaa ggaggcagca gagttgggc  2520
agctgctcag agcagtgttc tggcttcttc tcaaaccctg agcgggctgc cggcctccaa  2580
gttcctccga caagatgatg gtactaatta tggtactttt cactcacttt gcacctttcc  2640
ctgtcgctct ctaagcactt tacctggatg gcgcgtgggc agtgtgcagg caggtcctga  2700
ggcctggggt tggggtggag ggtgcggccc ggagttgtcc atctgtccat cccaacagca  2760
agacgaggat gtggctgttg agatgtgggc cacactcacc cttgtccagg atgcagggac  2820
tgccttctcc ttcctgcttc atccggctta gcttggggct ggctgcattc ccccaggatg  2880
ggcttcgaga aagacaaact tgtctggaaa ccagagttgc tgattccacc cggggggccc  2940
ggctgactcg cccatcacct catctccctg tggacttggg agctctgtgc caggcccacc  3000
ttgcggccct ggctctgagt cgctctccca cccagcctgg acttggcccc atgggaccca  3060
tcctcagtgc tccctccaga tcccgtccgg cagcttggcg tccaccctgc acagcatcac  3120
tgaatcacag agcctttgcg tgaaacagct ctgccaggcc gggagctggg tttctcttcc  3180
cttttttatct gctggtgtgg accacacctg ggcctggccg gaggaagaga gagtttacca  3240
agagagatgt ctccgggccc ttatttatta tttaaacatt tttttaaaaa gcactgctag  3300
tttacttgtc tctcctcccc atcgtcccca tcgtcctcct tgtccctgac ttggggcact  3360
tccaccctga cccagccagt ccagctctgc cttgccggct ctccagagta gacatagtgt  3420
gtggggttgg agctctggca cccggggagg tagcatttcc ctgcagatgg tacagatgtt  3480
cctgccttag agtcatctct agttccccac ctcaatcccg gcatccagcc ttcagtcccg  3540
cccacgtgct agctccgtgg gcccaccgtg cggccttaga ggtttccctc cttcctttcc  3600
actgaaaagc acatggcctt gggtgacaaa ttcctctttg atgaatgtac cctgtgggga  3660
tgtttcatac tgacagatta ttttttattta ttcaatgtca tatttaaaat atttattttt  3720
tataccaaat gaatactttt ttttttaaga aaaaaagag aaatgaataa agaatctact  3780
cttggctggc aaaaaaaaaa aaaaaaaa                                      3808
```

```
SEQ ID NO: 31           moltype = DNA   length = 2217
FEATURE                 Location/Qualifiers
source                  1..2217
                        mol_type = genomic DNA
                        organism = Homo sapiens
SEQUENCE: 31
cccgccgcc gccgcccttc gcgccctggg ccatctccct cccacctccc tccgcggagc   60
agccagacag cgagggcccc ggccggggac aggggggacg ccccgtccgg ggcaccccc   120
cggctctgag ccgcccgcgg ggccggcctc ggcccggagc ggaggaagga gtcgccgagg  180
agcagcctga ggccccagag tctgagacga gccgccgccg ccccgccac tgcgggggagg   240
aggggagga ggagcgggag gagggacgag ctggtcggga gaagaggaaa aaaacttttg    300
agacttttcc gttgccgctg ggagccggag gcgcggggac ctcttggcgc gacgctgccc    360
cgcgaggagg caggacttgg ggaccccaga ccgcctccct ttgccgccgg ggacgcttgc    420
tccctccctg cccctacac ggcgtccctc aggcgccccc attccggacc agccctcggg    480
agtcgccgac ccgcctccc gcaaagactt ttccccagac ctcgggcgca cccctgcac    540
gccgccttca tccccggcct gtctcctgag cccccgcgca tcctagaccc tttctcctcc    600
aggagacgga tctctctccg acctgccaca gatcccctat tcaagaccac ccaccttctg    660
gtaccagatc gcgcccatct aggttatttc cgtgggatac tgagacaccc ccggtccaag    720
cctcccctcc accactgcgc ccttctccct gaggacctca gctttccctc gaggccctcc    780
tacctttgc cgggagaccc ccagcccctg caggggcggg gcctccccac cacaccagcc    840
ctgttcgcgc tctcggcagt gccggggggc gccgcctccc ccatgccgcc ctccgggctg    900
cggctgctgc cgctgctgct accgctgctg tggctactgg tgctgacgcc tggccggccg    960
gccgcgggac tatccacctg caagactatc gacatggagc tggtgaagcg gaagcgcatc   1020
gaggccatcc gcggccagat cctgtccaag ctgcggctcg ccagccccc gagccagggg   1080
gaggtgccgc ccggcccgct gcccgaggcc gtgctcgccc tgtacaacag caccgccgac   1140
cgggtggccg gggagagtgc agaaccggag cccgagcctg aggccgacta ctacgccaag   1200
gaggtcaccc gcgtgctaat ggtggaaacc cacaacgaaa tctatgacaa gttcaagcag   1260
agtacacaca gcatatatat gttcttcaac acatcagagc tccgagaagc ggtacctgaa   1320
cccgtgttgc tctcccgggc agagctgcgt ctgctgaggc tcaagttaaa agtggagcag   1380
cacgtggagc tgtaccagaa atacagcaac aattcctggc gatacctcag caaccggctg   1440
ctggcacca gcgactcgcc agagtggtta tcttttgatg tcaccggagt tgtgcggcag   1500
tggttgagcc gtggaggga aattgagggc tttcgcctta gcgccactg ctcctgtgac    1560
agcagggata acacactgca agtggacatc aacgggttca ctaccggccg ccgaggtgac   1620
ctggcacca ttcatggcat gaaccggcct ttcctgcttc tcatggccac ccgcgctggag  1680
agggcccagc atctgcaaag ctcccggcac cgccgagccc tggacaccaa ctattgcttc   1740
agctccacgg agaagaactg ctgcgtgcgg cagctgtaca ttgacttccg caaggacctc   1800
ggctggaagt ggatccacga gcccaagggc taccatgcca acttctgcct cgggccctgc   1860
ccctacattt ggagcctgga cacgcagtac agcaaggtcc tggccctgta caaccagcat   1920
aacccggggcg cctcggcggc gccgtgctgc gtgccgcagg cgctggagcc gctgcccatc   1980
gtgtactacg tgggccgcaa gcccaaggtg gagcagctgt ccaacatgat cgtgcgctcc   2040
tgcaagtgca gctgaggtcc cgccccgccc cgccccgccc cggcaggcc ggccccacccc   2100
cgccccgccc ccgctgcctt gcccatgggg gctgtattta aggacacccg tgcccccaagc   2160
ccacctgggg ccccattaaa gatggagaga ggactgcgga aaaaaaaaaaa aaaaaaa      2217
```

-continued

```
SEQ ID NO: 32          moltype = DNA   length = 6774
FEATURE                Location/Qualifiers
source                 1..6774
                       mol_type = genomic DNA
                       organism = Homo sapiens
SEQUENCE: 32
cggccccaga aaacccgagc gagtagggggg cggcgcgcag gagggaggag aactgggggc    60
gcgggaggct ggtgggtgtg gggggtggag atgtagaaga tgtgacgccg cggcccggcg   120
ggtgccagat tagcggacgc ggtgcccgcg gttgcaacgg gatcccgggc gctgcagctt   180
gggaggcggc tctccccagg cggcgtccgc ggagacaccc atccgtgaac cccaggtccc   240
gggccgccgg ctcgccgcgc accaggggcc ggcggacaga agagcggccg agcggctcga   300
ggctggggga ccgcgggcgc ggccgcgcgc tgccgggcgg gaggctgggg ggccggggcc   360
ggggccgtgc cccggagcgg gtcggaggcc ggggccgggg ccggggacg gcggctcccc    420
gcgcggctcc agcggctcgg ggatcccggc cgggccccgc agggaccatg gcagccggga   480
gcatcaccac gctgcccgcc ttgcccgagg atggcggcag cggcgccttc ccgcccggcc   540
acttcaagga ccccaagcgg ctgtactgca aaaacgggg cttcttcctg cgcatccacc    600
ccgacggccg agttgacggg gtccgggaga agagcgaccc tcacatcaag ctacaacttc   660
aagcagaaga gagaggagtt gtgtctatca aaggagtgtg tgctaaccgt tacctggcta   720
tgaaggaaga tggaagatta ctggcttcta aatgtgttac ggatgagtgt ttctttttg    780
aacgattgga atctaataac tacaatactt accggtcaag gaaatacacc agttggtatg   840
tggcactgaa acgaactggg cagtataaac ttggatccaa aacaggacct gggcagaaag   900
ctatacttt tcttccaatg tctgctaaga gctgatttta atggccacat ctaatctcat   960
ttcacatgaa agaagaagta tatttagaa atttgttaat gagagtaaaa gaaaatat    1020
gtgtatagct cagtttggat aattggtcaa acaattttt atccagtagt aaaatatgta   1080
accattgtcc cagtaaagaa aaataacaaa agttgtaaaa tgtatattct cccttttata   1140
ttgcatctgc tgttacccag tgaagcttac ctagagcaat gatctttttc acgcatttgc   1200
tttattcgaa aagaggcttt taaaatgtgc atgtttagaa acaaaatttc ttcatggaaa   1260
tcatatacat tagaaaatca cagtcagatg tttaatcaat ccaaaatgtc cactatttct   1320
tatgtcattc gttagtctac atgtttctaa acatataaat gtgaatttaa tcaattcctt   1380
tcatagtttt ataattctct ggcagttcct tatgatagag tttataaaac agtcctgtgt   1440
aaactgctgg aagttcttcc acagtcaggt caatttttgtc aaaccttct ctgtacccat   1500
acagcagcag cctagcaact ctgctggtga tgggagttgt attttcagtc ttcgccaggt   1560
cattgagatc catccactca catcttaagc attcttcctg gcaaaaattt atggtgaatg   1620
aatatggctt taggcggcag atgatataca tatctgactt cccaaaagct ccaggatttg   1680
tgtgctgttg ccgaatactc aggacggacc tgaattctga ttttataccca gtctcttcaa   1740
aaacttctcg aaccgctgtg tctcctacgt aaaaaaagag atgtacaaat caataataat   1800
tacacttta gaaactgtat catcaaagat tttcagttaa agtagcatta tgtaaaggct   1860
caaaacatta ccctaacaaa gtaaagtttt caatacaaat tctttgcctt gtggatatca   1920
agaaatccca aaatattttc ttaccactgt aaattcaaga agcttttgaa atgctgaata   1980
tttctttggc tgctacttgg aggcttatct acctgtacat ttttggggtc agctcttttt   2040
aacttcttgc tgctcttttt cccaaaaggt aaaaatatag attgaaaagt taaaacattt   2100
tgcatggctg cagttccttt gtttcttgag ataagattcc aaagaactta gattcatttc   2160
ttcaacaccg aaatgctgga ggtgtttgat cagtttcaa gaacttgga atataaataa   2220
ttttataatt caacaaaggt tttcacattt tataaggttg attttcaat aaatgcaaa   2280
tttgtgtggc aggattttta ttgccattaa catatttttg tggctgcttt ttctacacat   2340
ccagatggtc cctctaactg ggctttctct aatttttgtga tgttctgtca ttgtctccca   2400
aagtatttag gagaagccct ttaaaaagct gccttcctct accactttgc tggaaagctt   2460
cacaattgtc acagacaaag attttttgttc caatactcgt tttgcctcta ttttttcttgt   2520
ttgtcaaata gtaaatgata tttgcccttg cagtaattct actggtgaaa aacatgcaaa   2580
gaagaggaag tcacagaaac atgtctcaat tcccatgtgc tgtgactgta gactgtctta   2640
ccatagactg tcttacccat cccctggata tgctcttgtt ttttccctct aatagctatg   2700
gaaagatgca tagaaagagt ataatgtttt aaaacataag gcattcgtct gccattttc    2760
aattacatgc tgacttccct tacaattgag atttgcccat aggttaaaca tggttagaaa   2820
caactgaaag cataaaagaa aaatctaggc cgggtgcagt ggctcatgcc tatattcct    2880
gcacttttggg aggccaaagc aggaggatcg cttgagccca ggagttcaag accaacctgg   2940
tgaaaccccg tctctacaaa aaaacacaaa aaatagccag gcatggtggc gtgtacatgt   3000
ggtctcagat acttgggagg ctgaggtggg agggttgatc acttgaggct gagaggtcaa   3060
ggttgcagtg agccataatc gtgccactgc agtccagcct aggcaacaga gtgagactttt   3120
gtctcaaaaa aagagaaatt ttccttaata agaaaagtaa tttttactct gatgtgcaat   3180
acatttgtta ttaaatttat tatttaagat ggtagcacta gtcttaaatt gtataaaata   3240
tcccctaaca tgtttaaatg tccatttttta ttcattatgc tttgaaaaat aattatgggg   3300
aaatacatgt ttgttattaa atttattatt aaagatagta gcactagtct taaatttgat   3360
ataacatctc ctaacttgtt taaatgtcca ttttttattct ttatgtttga aaataaatta   3420
tggggatcct atttagctct tagtaccact aatcaaaagt tcggcatgta gctcatgatc   3480
tatgctgttt ctatgtcgtg gaagcaccgg atggggtag tgagcaaatc tgccctgctc   3540
agcagtcacc atagcagctg actgaaaatc agcactgcct gagtagtttt gatcagttta   3600
acttgaatca ctaactgact gaaaattgaa tgggcaaata agtgcttttg tctccagagt   3660
atgcgggaaa cccttccacc tcaagatgga tatttcttcc ccaaggattt caagatgaat   3720
tgaaatttt aatcaagata gtgtgcttta ttctgttgta tttttttatta ttttaatata   3780
ctgtaagcca aactgaaata acatttgctg ttttataggt ttgaagaaca taggaaaaac   3840
taagaggttt tgttttttatt tttgctgatg aagagatatg tttaaatatg ttgtattgtt   3900
ttgtttagtt acaggacaat aatgaaatgg agtttatatt tgttatttct attttgttat   3960
atttaataat agaattagat tgaaataaaa tataatggga aataatctgc agaatgtggg   4020
ttttcctggt gtttccctct gactctagtg cactgatgat ctctgataag gctcagctgc   4080
tttatagttc tctggctaat gcagcagata ctcttcctgc cagtggtaat acgatttttt   4140
aagaaggcag tttgtcaatt ttaatcttgt ggatacctttt atactcttag ggtattattt   4200
tatacaaaag ccttgaggat tgcattctat tttctatatg accctcttga tatttaaaaa   4260
acactatgga taacaattct tcatttacct agtattatga aagaatgaag gagttcaaac   4320
aaatgtgttt cccagttaac tagggtttac tgtttgagcc aatataaatg tttaactgtt   4380
```

```
tgtgatggca gtattcctaa agtacattgc atgtttttcct aaatacagag tttaaataat 4440
ttcagtaatt cttagatgat tcagcttcat cattaagaat atctttttgtt ttatgttgag 4500
ttagaaatgc cttcatatag acatagtctt tcagacctct actgtcagtt ttcatttcta 4560
gctgctttca gggtttttatg aatttttcagg caaagcttta atttatacta agcttaggaa 4620
gtatggctaa tgccaacggc agttttttttc ttcttaattc cacatgactg aggcatatat 4680
gatctctggg taggtgagtt gttgtgacaa ccacaagcac ttttttttttt tttaaagaaa 4740
aaaaggtagt gaattttttaa tcatctggac tttaagaagg attctggagt atacttaggc 4800
ctgaaattat atatatttgg cttggaaatg tgttttttctt caattacatc tacaagtaag 4860
tacagctgaa attcagagga cccataagag ttcacatgaa aaaaatcaat ttatttgaaa 4920
aggcaagatg caggagagag gaagccttgc aaacctgcag actgctttttt gcccaatata 4980
gattgggtaa ggctgcaaaa cataagctta attagctcac atgctctgct ctcacgtggc 5040
accagtggat agtgtgagag aattaggctg tagaacaaat ggccttctct ttcagcattc 5100
acaccactac aaaatcatct tttatatcaa cagaagaata agcataaact aagcaaaagg 5160
tcaataagta cctgaaacca agattggcta gagatatatc ttaatgcaat ccattttctg 5220
atggattgtt acgagttggc tatataatgt atgtatggta ttttgatttg tgtaaaagtt 5280
ttaaaaatca agctttaagt acatggacat ttttaaataa aatatttaaa gacaatttag 5340
aaaattgcct taatatcatt gttggctaaa tagaataggg gacatgcata ttaaggaaaa 5400
ggtcatggag aaataatatt ggtatcaaac aaatacattg attgtcatg atacacattg 5460
aatttgatcc aatagtttaa ggaataggta ggaaaatttg gtttctattt ttcgatttcc 5520
tgtaaatcag tgacataaat aattcttagc ttatttttata tttccttgtc ttaaatactg 5580
agctcagtaa gttgtgttag gggattattt ctcagttgag acttttcttat atgacatttt 5640
actatgtttt gacttcctga ctattaaaaa taaatagtag atacaatttt cataaagtga 5700
agaattatat aatcactgct ttataactga cttttattata tttatttcaa agttcattta 5760
aaggctacta ttcatcctct gtgatggaat ggtcaggaat ttgttttctc atagtttaat 5820
tccaacaaca atattagtcg tatccaaaat aacctttaat gctaaacttt actgatgtat 5880
atccaaagct tctcatttttc agacagatta atccagaagc agtcataaac agaagaaatg 5940
gtggtatgtt cctaatgata ttatttctac taatggaata aactgtaata ttagaaatta 6000
tgctgctaat tatatcagct ctgaggtaat ttctgaaatg ttcagactca gtcggaacaa 6060
attggaaaat ttaaattttt attcttagct ataaagcaag aaagtaaaca cattaatttc 6120
ctcaacattt ttaagccaat taaaaatata aaagatacac accaatatct tcttcaggct 6180
ctgacaggcc tcctggaaac ttccacatat ttttcaactg cagtataaag tcagaaaata 6240
aagttaacat aactttcact aacacacaca tatgtagatt tcacaaaatc cacctataat 6300
tggtcaaagt ggttgagaat atattttttta gtaattgcat gcaaaatttt tctagcttcc 6360
atcctttctc cctcgtttct tcttttttttg ggggagctgg taactgatga aatctttccc 6420
caccttttct cttcaggaaa tataagtggt tttgtttggt taacgtgata cattctgtat 6480
gaatgaaaca ttggagggaa acatctactg aatttctgta atttaaaata ttttgctgct 6540
agttaactat gaacagatag aagaatctta cagatgctgc tataaataag tagaaaatat 6600
aaatttcatc actaaaatat gctattttttaa aatctatttc ctatattgta tttctaatca 6660
gatgtattac tcttattatt tctattgtat gtgttaatga ttttatgtaa aaatgtaatt 6720
gctttttcatg agtagtatga ataaaattga ttagtttgtg ttttcttgtc tccc 6774

SEQ ID NO: 33         moltype = AA  length = 379
FEATURE               Location/Qualifiers
source                1..379
                      mol_type = protein
                      organism = Homo sapiens
SEQUENCE: 33
MAAAAAQGGG GGEPRRTEGV GPGVPGEVEM VKGQPFDVGP RYTQLQYIGE GAYGMVSSAY   60
DHVRKTRVAI KKISPFEHQT YCQRTLREIQ ILLRFRHENV IGIRDILRAS TLEAMRDVYI  120
VQDLMETDLY KLLKSQQLSN DHICYFLYQI LRGLKYIHSA NVLHRDLKPS NLLINTTCDL  180
KICDFGLARI ADPEHDHTGF LTEYVATRWY RAPEIMLNSK GYTKSIDIWS VGCILAEMLS  240
NRPIFPGKHY LDQLNHILGI LGSPSQEDLN CIINMKARNY LQSLPSKTKV AWAKLFPKSD  300
SKALDLLDRM LTFNPNKRIT VEEALAHPYL EQYYDPTDEP VAEEPFTFAM ELDDLPKERL  360
KELIFQETAR FQPGVLEAP                                                379

SEQ ID NO: 34         moltype = AA  length = 357
FEATURE               Location/Qualifiers
source                1..357
                      mol_type = protein
                      organism = Homo sapiens
SEQUENCE: 34
MAAAAAQGGG GGEPRRTEGV GPGVPGEVEM VKGQPFDVGP RYTQLQYIGE GAYGMVSSAY   60
DHVRKTRVAI KKISPFEHQT YCQRTLREIQ ILLRFRHENV IGIRDILRAS TLEAMRDVYI  120
VQDLMETDLY KLLKSQQLSN DHICYFLYQI LRGLKYIHSA NVLHRDLKPS NLLINTTCDL  180
KICDFGLARI ADPEHDHTGF LTEYVATRWY RAPEIMLNSK GYTKSIDIWS VGCILAEMLS  240
NRPIFPGKHY LDQLNHILGI LGSPSQEDLN CIINMKARNY LQSLPSKTKV AWAKLFPKSD  300
SKALDLLDRM LTFNPNKRIT VEEALAHPYL EQYYDPTDEV GQSPAAVGLG AGEQGGT      357

SEQ ID NO: 35         moltype = AA  length = 335
FEATURE               Location/Qualifiers
source                1..335
                      mol_type = protein
                      organism = Homo sapiens
SEQUENCE: 35
MAAAAAQGGG GGEPRRTEGV GPGVPGEVEM VKGQPFDVGP RYTQLQYIGE GAYGMVSSAY   60
DHVRKTRVAI KKISPFEHQT YCQRTLREIQ ILLRFRHENV IGIRDILRAS TLEAMRDVYI  120
VQDLMETDLY KLLKSQQLSN DHICYFLYQI LRGLKYIHSA NVLHRDLKPS NLLINTTCDL  180
KICDFGLARI ADPEHDHTGF LTEYVATRWY RAPEIMLNSK GYTKSIDIWS VGCILAEMLS  240
NRPIFPGKHY LDQLNHILAL DLLDRMLTFN PNKRITVEEA LAHPYLEQYY DPTDEPVAEE  300
```

```
PFTFAMELDD LPKERLKELI FQETARFQPG VLEAP                                    335

SEQ ID NO: 36          moltype = AA  length = 366
FEATURE                Location/Qualifiers
source                 1..366
                       mol_type = protein
                       organism = Homo sapiens
SEQUENCE: 36
PRRTEGVGPG VPGEVEMVKG QPFDVGPRYT QLQYIGEGAY GMVSSAYDHV RKTRVAIKKI        60
SPFEHQTYCQ RTLREIQILL RFRHENVIGI RDILRASTLE AMRDVYIVQD LMETDLYKLL        120
KSQQLSNDHI CYFLYQILRG LKYIHSANVL HRDLKPSNLL INTTCDLKIC DFGLARIADP        180
EHDHTGFLTE YVATRWYRAP EIMLNSKGYT KSIDIWSVGC ILAEMLSNRP IFPGKHYLDQ        240
LNHILGILGS PSQEDLNCII NMKARNYLQS LPSKTKVAWA KLFPKSDSKA LDLLDRMLTF        300
NPNKRITVEE ALAHPYLEQY YDPTDEPVAE EPFTFAMELD DLPKERLKEL IFQETARFQP        360
GVLEAP                                                                   366

SEQ ID NO: 37          moltype = AA  length = 360
FEATURE                Location/Qualifiers
source                 1..360
                       mol_type = protein
                       organism = Homo sapiens
SEQUENCE: 37
MAAAAAAGAG PEMVRGQVFD VGPRYTNLSY IGEGAYGMVC SAYDNVNKVR VAIKKISPFE        60
HQTYCQRTLR EIKILLRFRH ENIIGINDII RAPTIEQMKD VYIVQDLMET DLYKLLKTQH        120
LSNDHICYFL YQILRGLKYI HSANVLHRDL KPSNLLLNTT CDLKICDFGL ARVADPDHDH        180
TGFLTEYVAT RWYRAPEIML NSKGYTKSID IWSVGCILAE MLSNRPIFPG KHYLDQLNHI        240
LGILGSPSQE DLNCIINLKA RNYLLSLPHK NKVPWNRLFP NADSKALDLL DKMLTFNPHK        300
RIEVEQALAH PYLEQYYDPS DEPIAEAPFK FDMELDDLPK EKLKELIFEE TARFQPGYRS        360

SEQ ID NO: 38          moltype = AA  length = 360
FEATURE                Location/Qualifiers
source                 1..360
                       mol_type = protein
                       organism = Homo sapiens
SEQUENCE: 38
MAAAAAAGAG PEMVRGQVFD VGPRYTNLSY IGEGAYGMVC SAYDNVNKVR VAIKKISPFE        60
HQTYCQRTLR EIKILLRFRH ENIIGINDII RAPTIEQMKD VYIVQDLMET DLYKLLKTQH        120
LSNDHICYFL YQILRGLKYI HSANVLHRDL KPSNLLLNTT CDLKICDFGL ARVADPDHDH        180
TGFLTEYVAT RWYRAPEIML NSKGYTKSID IWSVGCILAE MLSNRPIFPG KHYLDQLNHI        240
LGILGSPSQE DLNCIINLKA RNYLLSLPHK NKVPWNRLFP NADSKALDLL DKMLTFNPHK        300
RIEVEQALAH PYLEQYYDPS DEPIAEAPFK FDMELDDLPK EKLKELIFEE TARFQPGYRS        360

SEQ ID NO: 39          moltype = AA  length = 360
FEATURE                Location/Qualifiers
source                 1..360
                       mol_type = protein
                       organism = Homo sapiens
SEQUENCE: 39
MSQERPTFYR QELNKTIWEV PERYQNLSPV GSGAYGSVCA AFDTKTGLRV AVKKLSRPFQ        60
SIIHAKRTYR ELRLLKHMKH ENVIGLLDVF TPARSLEEFN DVYLVTHLMG ADLNNIVKCQ        120
KLTDDHVQFL IYQILRGLKY IHSADIIHRD LKPSNLAVNE DCELKILDFG LARHTDDEMT        180
GYVATRWYRA PEIMLNWMHY NQTVDIWSVG CIMAELLTGR TLFPGTDHIN QLQQIMRLTG        240
TPPAYLINRM PSHEARNYIQ SLTQMPKMNF ANVFIGANPL AVDLLEKMLV LDSDKRITAA        300
QALAHAYFAQ YHDPDDEPVA DPYDQSFESR DLLIDEWKSL TYDEVISFVP PPLDQEEMES        360

SEQ ID NO: 40          moltype = AA  length = 360
FEATURE                Location/Qualifiers
source                 1..360
                       mol_type = protein
                       organism = Homo sapiens
SEQUENCE: 40
MSQERPTFYR QELNKTIWEV PERYQNLSPV GSGAYGSVCA AFDTKTGLRV AVKKLSRPFQ        60
SIIHAKRTYR ELRLLKHMKH ENVIGLLDVF TPARSLEEFN DVYLVTHLMG ADLNNIVKCQ        120
KLTDDHVQFL IYQILRGLKY IHSADIIHRD LKPSNLAVNE DCELKILDFG LARHTDDEMT        180
GYVATRWYRA PEIMLNWMHY NQTVDIWSVG CIMAELLTGR TLFPGTDHID QLKLILRLVG        240
TPGAELLKKI SSESARNYIQ SLTQMPKMNF ANVFIGANPL AVDLLEKMLV LDSDKRITAA        300
QALAHAYFAQ YHDPDDEPVA DPYDQSFESR DLLIDEWKSL TYDEVISFVP PPLDQEEMES        360

SEQ ID NO: 41          moltype = AA  length = 297
FEATURE                Location/Qualifiers
source                 1..297
                       mol_type = protein
                       organism = Homo sapiens
SEQUENCE: 41
MSQERPTFYR QELNKTIWEV PERYQNLSPV GSGAYGSVCA AFDTKTGLRV AVKKLSRPFQ        60
SIIHAKRTYR ELRLLKHMKH ENVIGLLDVF TPARSLEEFN DVYLVTHLMG ADLNNIVKCQ        120
KLTDDHVQFL IYQILRGLKY IHSADIIHRD LKPSNLAVNE DCELKILDFG LARHTDDEMT        180
GYVATRWYRA PEIMLNWMHY NQTVDIWSVG CIMAELLTGR TLFPGTDHID QLKLILRLVG        240
TPGAELLKKI SSESARNYIQ SLTQMPKMNF ANVFIGANPL GKLTIYPHLM DIELVMI          297
```

-continued

```
SEQ ID NO: 42            moltype = AA   length = 307
FEATURE                  Location/Qualifiers
source                   1..307
                         mol_type = protein
                         organism = Homo sapiens
SEQUENCE: 42
MSQERPTFYR QELNKTIWEV PERYQNLSPV GSGAYGSVCA AFDTKTGLRV AVKKLSRPFQ     60
SIIHAKRTYR ELRLLKHMKH ENVIGLLDVF TPARSLEEFN DVYLVTHLMG ADLNNIVKCQ    120
KLTDDHVQFL IYQILRGLKY IHSADIIHRD LKPSNLAVNE DCELKILDFG LARHTDDEMT    180
GYVATRWYRA PEIMLNWMHY NQTVDIWSVG CIMAELLTGR TLFPGTDHID QLKLILRLVG    240
TPGAELLKKI SSESLSTCWR RCLYWTQIRE LQRPKPLHMP TLLSTTILMM NQWPILMISP    300
LKAGTSL                                                             307

SEQ ID NO: 43            moltype = AA   length = 364
FEATURE                  Location/Qualifiers
source                   1..364
                         mol_type = protein
                         organism = Homo sapiens
SEQUENCE: 43
MSGPRAGFYR QELNKTVWEV PQRLQGLRPV GSGAYGSVCS AYDARLRQKV AVKKLSRPFQ     60
SLIHARRTYR ELRLLKHLKH ENVIGLLDVF TPATSIEDFS EVYLVTTLMG ADLNNIVKCQ    120
ALSDEHVQFL VYQLLRGLKY IHSAGIIHRD LKPSNVAVNE DCELRILDFG LARQADEEMT    180
GYVATRWYRA PEIMLNWMHY NQTVDIWSVG CIMAELLQGK ALFPGSDYID QLKRIMEVVG    240
TPSPEVLAKI SSEHARTYIQ SLPPMPQKDL SSIFRGANPL AIDLLGRMLV LDSDQRVSAA    300
EALAHAYFSQ YHDPEDEPEA EPYDESVEAK ERTLEEWKEL TYQEVLSFKP PEPPKPPGSL    360
EIEQ                                                                364

SEQ ID NO: 44            moltype = AA   length = 367
FEATURE                  Location/Qualifiers
source                   1..367
                         mol_type = protein
                         organism = Homo sapiens
SEQUENCE: 44
MSSPPPARSG FYRQEVTKTA WEVRAVYRDL QPVGSGAYGA VCSAVDGRTG AKVAIKKLYR     60
PFQSELFAKR AYRELRLLKH MRHENVIGLL DVFTPDETLD DFTDFYLVMP FMGTDLGKLM    120
KHEKLGEDRI QFLVYQMLKG LRYIHAAGII HRDLKPGNLA VNEDCELKIL DFGLARQADS    180
EMTGYVVTRW YRAPEVILNW MRYTQTVDIW SVGCIMAEMI TGKTLFKGSD HLDQLKEIMK    240
VTGTPPAEFV QRLQSDEAKN YMKGLPELEK KDFASILTNA SPLAVNLLEK MLVLDAEQRV    300
TAGEALAHPY FESLHDTEDE PQVQKYDDSF DDVDRTLDEW KRVTYKEVLS FKPPRQLGAR    360
VSKETPL                                                             367

SEQ ID NO: 45            moltype = AA   length = 365
FEATURE                  Location/Qualifiers
source                   1..365
                         mol_type = protein
                         organism = Homo sapiens
SEQUENCE: 45
MSLIRKKGFY KQDVNKTAWE LPKTYVSPTH VGSGAYGSVC SAIDKRSGEK VAIKKLSRPF     60
QSEIFAKRAY RELLLLKHMQ HENVIGLLDV FTPASSLRNF YDFYLVMPFM QTDLQKIMGM    120
EFSEEKIQYL VYQMLKGLKY IHSAGVVHRD LKPGNLAVNE DCELKILDFG LARHADAEMT    180
GYVVTRWYRA PEVILSWMHY NQTVDIWSVG CIMAEMLTGK TLFKGKDYLD QLTQILKVTG    240
VPGTEFVQKL NDKAAKSYIQ SLPQTPRKDF TQLFPRASPQ AADLLEKMLE LDVDKRLTAA    300
QALTHPFFEP FRDPEEETEA QQPFDDSLEH EKLTVDEWKQ HIYKEIVNFS PIARKDSRRR    360
SGMKL                                                               365

SEQ ID NO: 46            moltype = AA   length = 427
FEATURE                  Location/Qualifiers
source                   1..427
                         mol_type = protein
                         organism = Homo sapiens
SEQUENCE: 46
MSRSKRDNNF YSVEIGDSTF TVLKRYQNLK PIGSGAQGIV CAAYDAILER NVAIKKLSRP     60
FQNQTHAKRA YRELVLMKCV NHKNIIGLLN VFTPQKSLEE FQDVIYVMEL MDANLCQVIQ    120
MELDHERMSY LLYQMLCGIK HLHSAGIIHR DLKPSNIVVK SDCTLKILDF GLARTAGTSF    180
MMTPYVVTRY YRAPEVILGM GYKENVDLWS VGCIMGEMVC HKILFPGRDY IDQWNKVIEQ    240
LGTPCPEFMK KLQPTVRTYV ENRPKYAGYS FEKLFPDVLF PADSEHNKLK ASQARDLLSK    300
MLVIDASKRI SVDEALQHPY INVWYDPSEA EAPPPKIPDK QLDEREHTIE EWKELIYKEV    360
MDLEERTKNG VIRGQPSPLG AAVINGSQHP SSSSSVNDVS SMSTDPTLAS DTDSSLEAAA    420
GPLGCCR                                                             427

SEQ ID NO: 47            moltype = AA   length = 427
FEATURE                  Location/Qualifiers
source                   1..427
                         mol_type = protein
                         organism = Homo sapiens
SEQUENCE: 47
MSRSKRDNNF YSVEIGDSTF TVLKRYQNLK PIGSGAQGIV CAAYDAILER NVAIKKLSRP     60
FQNQTHAKRA YRELVLMKCV NHKNIIGLLN VFTPQKSLEE FQDVYIVMEL MDANLCQVIQ    120
```

```
MELDHERMSY LLYQMLCGIK HLHSAGIIHR DLKPSNIVVK SDCTLKILDF GLARTAGTSF 180
MMTPYVVTRY YRAPEVILGM GYKENVDIWS VGCIMGEMIK GGVLFPGTDH IDQWNKVIEQ 240
LGTPCPEFMK KLQPTVRTYV ENRPKYAGYS FEKLFPDVLF PADSEHNKLK ASQARDLLSK 300
MLVIDASKRI SVDEALQHPY INVWYDPSEA EAPPPKIPDK QLDEREHTIE EWKELIYKEV 360
MDLEERTKNG VIRGQPSPLG AAVINGSQHP SSSSSVNDVS SMSTDPTLAS DTDSSLEAAA 420
GPLGCCR                                                            427

SEQ ID NO: 48          moltype = AA  length = 384
FEATURE                Location/Qualifiers
source                 1..384
                       mol_type = protein
                       organism = Homo sapiens
SEQUENCE: 48
MSRSKRDNNF YSVEIGDSTF TVLKRYQNLK PIGSGAQGIV CAAYDAILER NVAIKKLSRP 60
FQNQTHAKRA YRELVLMKCV NHKNIIGLLN VFTPQKSLEE FQDVYIVMEL MDANLCQVIQ 120
MELDHERMSY LLYQMLCGIK HLHSAGIIHR DLKPSNIVVK SDCTLKILDF GLARTAGTSF 180
MMTPYVVTRY YRAPEVILGM GYKENVDIWS VGCIMGEMIK GGVLFPGTDH IDQWNKVIEQ 240
LGTPCPEFMK KLQPTVRTYV ENRPKYAGYS FEKLFPDVLF PADSEHNKLK ASQARDLLSK 300
MLVIDASKRI SVDEALQHPY INVWYDPSEA EAPPPKIPDK QLDEREHTIE EWKELIYKEV 360
MDLEERTKNG VIRGQPSPLA QVQQ                                          384

SEQ ID NO: 49          moltype = AA  length = 384
FEATURE                Location/Qualifiers
source                 1..384
                       mol_type = protein
                       organism = Homo sapiens
SEQUENCE: 49
MSRSKRDNNF YSVEIGDSTF TVLKRYQNLK PIGSGAQGIV CAAYDAILER NVAIKKLSRP 60
FQNQTHAKRA YRELVLMKCV NHKNIIGLLN VFTPQKSLEE FQDVYIVMEL MDANLCQVIQ 120
MELDHERMSY LLYQMLCGIK HLHSAGIIHR DLKPSNIVVK SDCTLKILDF GLARTAGTSF 180
MMTPYVVTRY YRAPEVILGM GYKENVDLWS VGCIMGEMVC HKILFPGRDY IDQWNKVIEQ 240
LGTPCPEFMK KLQPTVRTYV ENRPKYAGYS FEKLFPDVLF PADSEHNKLK ASQARDLLSK 300
MLVIDASKRI SVDEALQHPY INVWYDPSEA EAPPPKIPDK QLDEREHTIE EWKELIYKEV 360
MDLEERTKNG VIRGQPSPLA QVQQ                                          384

SEQ ID NO: 50          moltype = AA  length = 1354
FEATURE                Location/Qualifiers
source                 1..1354
                       mol_type = protein
                       organism = Homo sapiens
SEQUENCE: 50
MSTGDSFETR FEKMDNLLRD PKSEVNSDCL LDGLDALVYD LDFPALRKNK NIDNFLSRYK 60
DTINKIRDLR MKAEDYEVVK VIGRGAFGEV QLVRHKSTRK VYAMKLLSKF EMIKRSDSAF 120
FWEERDIMAF ANSPWVVQLF YAFQDDRYLY MVMEYMPGGD LVNLMSNYDV PEKWARFYTA 180
EVVLALDAIH SMGFIHRDVK PDNMLLDKSG HLKLADFGTC MKMNKEGMVR CDTAVGTPDY 240
ISPEVLKSQG GDGYYGRECD WWSVGVFLYE MLVGDTPFYA DSLVGTYSKI MNHKNSLTFP 300
DDNDISKEAK NLICAFLTDR EVRLGRNGVE EIKRHLFFKN DQWAWETLRD TVAPVVPDLS 360
SDIDTSNFDD LEEDKGEEET FPIPKAFVGN QLPFVGFTYY SNRRYLSSAN PNDNRTSSNA 420
DKSLQESLQK TIYKLEEQLH NEMQLKDEME QKCRTSNIKL DKIMKELDEE GNQRRNLEST 480
VSQIEKEKML LQHRINEYQR KAEQENEKRR NVENEVSTLK DQLEDLKKVS QNSQLANEKL 540
SQLQKQLEEA NDLLRTESDT AVRLRKSHTE MSKSISQLES LNRELQERNR ILENSKSQTD 600
KDYYQLQAIL EAERRDRGHD SEMIGDLQAR ITSLQEEVKH LKHNLEKVEG ERKEAQDMLN 660
HSEKEKNNLE IDLNYKLKSL QQRLEQEVNE HKVTKARLTD KHQSIEEAKS VAMCEMEKKL 720
KEEREAREKA ENRVVQIEKQ CSMLDVDLKQ SQQKLEHLTG NKERMEDEVK NLTLQLEQES 780
NKRLLLQNEL KTQAFEADNL KGLEKQMKQE INTLLEAKRL LEFELAQLTK QYRGNEGQMR 840
ELQDQLEAEQ YFSTLYKTQV KELKEEIEEK NRENLKKIQE LQNEKETLAT QLDLAETKAE 900
SEQLARGLLE EQYFELTQES KKAASRNRQE ITDKDHTVSR LEEANSMLTK DIEILRRENE 960
ELTEKMKKAE EEYKLEKEEE ISNLKAAFEK NINTERTLKT QAVNKLAEIM NRKDFKIDRK 1020
KANTQDLRKK EKENRKLQLE LNQEREKFNQ MVVKHQKELN DMQAQLVEEC AHRNELQMQL 1080
ASKESDIEQL RAKLLDLSDS TSVASFPSAD ETDGNLPESR IEGWLSVPNR GNIKRYGWKK 1140
QYVVVSSKKI LFYNDEQDKE QSNPSMVLDI DKLFHVRPVT QGDVYRAETE EIPKIFQILY 1200
ANEGECRKDV EMEPVQQAEK TNFQNHKGHE FIPTLYHFPA NCDACAKPLW HVFKPPPALE 1260
CRRCHVKCHR DHLDKKEDLI CPCKVSYDVT SARDMLLLAC SQDEQKKWVT HLVKKIPKNP 1320
PSGFVRASPR TLSTRSTANQ SFRKVVKNTS GKTS                              1354

SEQ ID NO: 51          moltype = AA  length = 1388
FEATURE                Location/Qualifiers
source                 1..1388
                       mol_type = protein
                       organism = Homo sapiens
SEQUENCE: 51
MSRPPPTGKM PGAPETAPGD GAGASRQRKL EALIRDPRSP INVESLLDGL NSLVLDLDFP 60
ALRKNKNIDN FLNRYEKIVK KIRGLQMKAE DYDVVKVIGR GAFGEVQLVR HKASQKVYAM 120
KLLSKFEMIK RSDSAFFWEE RDIMAFANSP WVVQLFYAFQ DDRYLYMVME YMPGGDLVNL 180
MSNYDVPEKW AKFYTAEVVL ALDAIHSMGL IHRDVKPDNM LLDKHGHLKL ADFGTCMKMD 240
ETGMVHCDTA VGTPDYISPE VLKSQGGDGF YGRECDWWSV GVFLYEMLVG DTPFYADSLV 300
GTYSKIMDHK NSLCFPEDAE ISKHAKNLIC AFLTDREVRL GRNGVEEIRQ HPFFKNDQWH 360
WDNIRETAAP VVPELSSDID SSNFDDIEDD KGDVETFPIP KAFVGNQLPF IGFTYYRENL 420
LLSDSPSCRE TDSIQSRKNE ESQEIQKKLY TLEEHLSNEM QAKEELEQKC KSVNTRLEKT 480
```

```
AKELEEEITL RKSVESALRQ LEREKALLQH KNAEYQRKAD HEADKKRNLE NDVNSLKDQL   540
EDLKKRNQNS QISTEKVNQL QRQLDETNAL LRTESDTAAR LRKTQAESSK QIQQLESNNR   600
DLQDKNCLLE TAKLKLEKEF INLQSALESE RRDRTHGSEI INDLQGRICG LEEDLKNGKI   660
LLAKVELEKR QLQERFTDLE KEKSNMEIDM TYQLKVIQQS LEQEEAEHKA TKARLADKNK   720
IYESIEEAKS EAMKEMEKKL LEERTLKQKV ENLLLEAEKR CSLLDCDLKQ SQQKINELLK   780
QKDVLNEDVR NLTLKIEQET QKRCLTQNDL KMQTQQVNTL KMSEKQLKQE NNHLMEMKMN   840
LEKQNAELRK ERQDADGQMK ELQDQLEAEQ YFSTLYKTQV RELKEECEEK TKLGKELQQK   900
KQELQDERDS LAAQLEITLT KADSEQLARS IAEEQYSDLE KEKIMKELEI KEMMARHKQE   960
LTEKDATIAS LEETNRTLTS DVANLANEKE ELNNKLKDVQ EQLSRLKDEE ISAAAIKAQF  1020
EKQLLTERTL KTQAVNKLAE IMNRKEPVKR GNDTDVRRKE KENRKLHMEL KSEREKLTQQ  1080
MIKYQKELNE MQAQIAEESQ IRIELQMTLD SKDSDIEQLR SQLQALHIGL DSSSIGSGPG  1140
DAEADDGFPE SRLEGWLSLP VRNNTKKFGW VKKYVIVSSK KILFYDSEQD KEQSNPYMVL  1200
DIDKLFHVRP VTQTDVYRAD AKEIPRIFQI LYANEGESKK EQEFPVEPVG EKSNYICHKG  1260
HEFIPTLYHF PTNCEACMKP LWHMFKPPPA LECRRCHIKC HKDHMDKKEE IIAPCKVYYD  1320
ISTAKNLLLL ANSTEEQQKW VSRLVKKIPK KPPAPDPFAR SSPRTSMKIQ QNQSIRRPSR  1380
QLAPNKPS                                                          1388

SEQ ID NO: 52          moltype = RNA   length = 25
FEATURE                Location/Qualifiers
misc_feature           1..25
                       note = SiRNA oligonucleotide
source                 1..25
                       mol_type = other RNA
                       organism = synthetic construct
SEQUENCE: 52
aggtcaaggg caagcccgac ctgaa                                        25

SEQ ID NO: 53          moltype = RNA   length = 25
FEATURE                Location/Qualifiers
misc_feature           1..25
                       note = SiRNA oligonucleotide
source                 1..25
                       mol_type = other RNA
                       organism = synthetic construct
SEQUENCE: 53
ttcaggtcgg gcttgccctt gacct                                        25

SEQ ID NO: 54          moltype = AA   length = 360
FEATURE                Location/Qualifiers
source                 1..360
                       mol_type = protein
                       organism = Homo sapiens
SEQUENCE: 54
MAGHLASDFA FSPPPGGGGD GPGGPEPGWV DPRTWLSFQG PPGGPGIGPG VGPGSEVWGI   60
PPCPPPYEFC GGMAYCGPQV GVGLVPQGGL ETSQPEGEAG VGVESNSDGA SPEPCTVTPG  120
AVKLEKEKLE QNPEESQDIK ALQKELEQFA KLLKQKRITL GYTQADVGLT LGVLFGKVFS  180
QTTICRFEAL QLSFKNMCKL RPLLQKWVEE ADNNENLQEI CKAETLVQAR KRKRTSIENR  240
VRGNLENLFL QCPKPTLQQI SHIAQQLGLE KDVVRVWFCN RRQKGKRSSS DYAQREDFEA  300
AGSPFSGGPV SFPLAPGPHF GTPGYGSPHF TALYSSVPFP EGEAFPPVSV TTLGSPMHSN  360

SEQ ID NO: 55          moltype = DNA   length = 1411
FEATURE                Location/Qualifiers
source                 1..1411
                       mol_type = genomic DNA
                       organism = Homo sapiens
SEQUENCE: 55
ccttcgcaag ccctcatttc accaggcccc cggcttgggg cgccttcctt ccccatggcg   60
ggacacctgg cttcggattt cgccttctcg cccctccag gtggtggagg tgatgggcca  120
gggggggccgg agccgggctg ggttgatcct cggacctggc taagcttcca aggccctcct  180
ggagggccag gaatcgggcc gggggttggg ccaggctcta aggtgtgggg gattcccca   240
tgccccccgc cgtatgagtt ctgtgggggg atggcgtact gtgggcccca ggttggagtg   300
gggctagtgc cccaaggcgg cttggagacc tctcagcctg agggcgaagc aggagtcggg   360
gtggagagca actccgatgg ggcctccccg gagccctgca ccgtcacccc tggtgccgtg   420
aagctggaga aggagaagct ggagcaaaac ccggaggagt cccaggacat caaagctctg   480
cagaaagaac tcgagcaatt tgccaagctc ctgaagcaga agaggatcac cctgggatat   540
acacaggccg atgtggggct caccctgggg gttctatttg gaaaggtatt cagccaaacg   600
accatctgcc gctttgaggc tctgcagctt agcttcaaga acatgtgtaa gctgcggccc   660
ttgctgcaga agtgggtgga ggaagctgac aacaatgaaa atcttcagga gatatgcaaa   720
gcagaaaccc tcgtgcaggc ccgaaagaga agcgaacca gtatcgagaa ccgagtgaga   780
ggcaacctgg agaatttgtt cctgcagtgc ccgaaaccca cactgcagca gatcagccac   840
atcgcccagc agcttgggct cgagaaggat gtggtccgag tgtggttctg taaccggcgc   900
cagaagggca agcgatcaag cagcgactat gcacaacgag aggattttga ggctgctggg   960
tctcctttct caggggggacc agtgtccttt cctctggccc cagggcccca ttttggtacc  1020
ccaggctatg ggagccctca cttcactgca ctgtactcct cggtcccttt cctgagggg  1080
gaagcctttc ccctgtctct cgtcaccact ctgggcctctc ccatgcattc aaactgaggt  1140
gcctgccctt ctaggaatgg gggacagggg gaggggagga gctagggaaa gaaaacctgg  1200
agtttgtgcc agggtttttg ggattaagtt cttcattcac taaggaagga attgggaaca  1260
caaagggtgg gggcaggggga gtttgggggca actggttgga gggaaggtga agttcaatga  1320
tgctcttgat tttaatccca catcatgtat cacttttttc ttaaataaag aagcctggga  1380
```

-continued

```
cacagtagat agacacactt aaaaaaaaaa a                                    1411

SEQ ID NO: 56          moltype = AA   length = 317
FEATURE                Location/Qualifiers
source                 1..317
                       mol_type = protein
                       organism = Homo sapiens
SEQUENCE: 56
MYNMMETELK PPGPQQTSGG GGGNSTAAAA GGNQKNSPDR VKRPMNAFMV WSRGQRRKMA   60
QENPKMHNSE ISKRLGAEWK LLSETEKRPF IDEAKRLRAL HMKEHPDYKY RPRRKTKTLM   120
KKDKYTLPGG LLAPGGNSMA SGVGVGAGLG AGVNQRMDSY AHMNGWSNGS YSMMQDQLGY   180
PQHPGLNAHG AAQMQPMHRY DVSALQYNSM TSSQTYMNGS PTYSMSYSQQ GTPGMALGSM   240
GSVVKSEASS SPPVVTSSSH SRAPCQAGDL RDMISMYLPG AEVPEPAAPS RLHMSQHYQS   300
GPVPGTAING TLPLSHM                                                   317

SEQ ID NO: 57          moltype = DNA   length = 2520
FEATURE                Location/Qualifiers
source                 1..2520
                       mol_type = genomic DNA
                       organism = Homo sapiens
SEQUENCE: 57
ggatggttgt ctattaactt gttcaaaaaa gtatcaggag ttgtcaaggc agagaagaga   60
gtgtttgcaa aagggggaaa gtagtttgct gcctctttaa gactaggact gagagaaaga   120
agaggagaga gaaagaaagg gagagaagtt tgagccccag gcttaagcct ttccaaaaaa   180
taataataac aatcatcggc ggcggcagga tcggccagag gaggagggaa gcgctttttt   240
tgatcctgat tccagtttgc ctctctcttt ttttcccca aattattctt cgcctgattt   300
tcctcgcgga gccctgcgct cccgacaccc ccgcccgcct ccctcctcc tctcccccg   360
cccgcgggcc ccccaaagtc ccggccgggc cgagggtcgg cggccgccgg cgggccgggc   420
ccgcgcacag cgcccgcatg tacaacatga tggagacgga gctgaagccg ccgggccgc   480
agcaaacttc ggggggcggc ggcggcaact ccaccgccgg ccgggccggc ggcaaccaga   540
aaaacagccc ggaccgcgtc aagcggccca tgaatgcctt catggtgtgg tcccgcgggc   600
agcggcgcaa gatggcccag gagaacccca agatgcacaa ctcggagatc agcaagcgcc   660
tgggcgccga gtggaaactt ttgtcggaga cggagaagcg gccgttcatc gacgaggcta   720
agcggctgcg agcgctgcac atgaaggagc acccggatta taaataccgg cccggcggg   780
aaaccaagac gctcatgaag aaggataagt acacgctgcc cggcgggctg ctggcccccg   840
gcggcaatag catggcgagc ggggtcgggg tgggcgccgg cctggcgcg ggcgtgaacc   900
agcgcatgga cagttacgcg cacatgaacg gctggagcaa cggcagctac agcatgatgc   960
aggaccagct gggctacccg cagcacccgg gcctcaatgc gcacggcgca gcgcagatgc   1020
agcccatgca ccgctacgac gtgagcgccc tgcagtacaa ctccatgacc agctcgcaga   1080
cctacatgaa cggctcgccc acctacagca tgtcctactc gcagcaggc accctggca   1140
tggctcttgg ctccatgggt tcggtggtca agtccgaggc cagctccagc ccccctgtgg   1200
ttacctcttc ctcccactcc agggcgcct gccaggccgg ggacctccgg gacatgatca   1260
gcatgtatct ccccggcgcg gaggtgccgg aacccgccgc ccccagcaga cttcacatgt   1320
cccagcacta ccagagcggc ccggtgcccg gcacggccat taacggcaca ctgcccctct   1380
cacacatgtg agggccggac agcgaactgg aggggggaga aattttcaaa gaaaaacgag   1440
ggaaatggga ggggtgcaaa agaggagagt aagaaacagc atggagaaaa cccggtacgc   1500
tcaaaaagaa aaaggaaaaa aaaaaatccc atcacccaca gcaaatgaca gctgcaaaag   1560
agaacaccaa tcccatccac actcacgcaa aaaccgcgat gccgacaaga aaactttat   1620
gagagagatc ctggacttct tttttgggga ctattttgt acagagaaaa cctggggagg   1680
gtggggaggg cgggggaatg gaccttgtat agatctggag gaaagaaagc tacgaaaaac   1740
tttttaaaag ttctagtggt acggtaggag ctttgcagga agtttgcaaa agtctttacc   1800
aataatattt agagctagtc tccaagcgac gaaaaaaatg ttttaatatt tgcaagcaac   1860
ttttgtacag tatttatcga gataaacatg gcaatcaaaa tgtccattgt ttataagctg   1920
agaatttgcc aatattttc aaggagaggc ttcttgctga attttgattc tgcagctgaa   1980
atttaggaca gttgcaaacg tgaaaagaag aaaattattc aaatttgaac attttaattg   2040
tttaaaaatt gtacaaaagg aaaaaattag aataagtact ggcgaaccat ctctgtggtc   2100
ttgtttaaaa agggcaaaag ttttagactg tactaaattt tataacttac tgttaaaagc   2160
aaaaatggcc atgcaggttg acaccgttgg taatttataa tagcttttgt tcgatcccaa   2220
ctttccattt tgttcagata aaaaaaacca tgaaattact gtgtttgaaa tattttctta   2280
tggtttgtaa tatttctgta aatttattgt gatatttttaa ggttttcccc ccttttattt   2340
ccgtagttgt atttttaaaag attcggctct gtattatttg aatcagtctg ccagaatcc   2400
atgtatatat ttgaactaat atcatcctta taacaggtac attttcaact taagttttta   2460
ctccattatg cacagtttga gataaataaa tttttgaaat atggacactg aaaaaaaaaa   2520

SEQ ID NO: 58          moltype = AA   length = 479
FEATURE                Location/Qualifiers
source                 1..479
                       mol_type = protein
                       organism = Homo sapiens
SEQUENCE: 58
MRQPPGESDM AVSDALLPSF STFASGPAGR EKTLRQAGAP NNRWREELSH MKRLPPVLPG   60
RPYDLAAATV ATDLESGGAG AACGGSNLAP LPRRETEEFN DLLDLDFILS NSLTHPPESV   120
AATVSSSASA SSSSSPSSSG PASAPSTCSF TYPIRAGNDP GVAPGGTGGG LLYGRESAPP   180
PTAPFNLADI NDVSPSGGFV AELLRPELDP VYIPPQQPQP PGGGLMGKFV LKASLSAPGS   240
EYGSPSVISV SKGSPDGSHP VVVAPYNGGP PRTCPKIKQE AVSSCTHLGA GPPLSNGHRP   300
AAHDFPLGRQ LPSRTTPTLG LEEVLSSRDC HPALPLPPGF HPHPGPNYPS FLPDQMQPQV   360
PPLHYQELMP PGSCMPEEPK PKRGRRSWPR KRTATHTCDY AGCGKTYTKS SHLKAHLRTH   420
TGEKPYHCDW DGCGWKFARS DELTRHYRKH TGHRPFQCQK CDRAFSRSDH LALHMKRHF   479
```

```
SEQ ID NO: 59         moltype = DNA   length = 2949
FEATURE               Location/Qualifiers
source                1..2949
                      mol_type = genomic DNA
                      organism = Homo sapiens
SEQUENCE: 59
agtttcccga ccagagagaa cgaacgtgtc tgcgggcgcg cggggagcag aggcggtggc   60
gggcggcggc ggcaccggga gccgccgagt gaccctcccc cgcccctctg gcccccacc   120
ctcccacccg cccgtggccc gcgcccatgg ccgcgcgcgc tccacacaac tcaccggagt   180
ccgcgccttg cgccgccgac cagttcgcag ctccgcgcca cggcagccag tctcacctgg   240
cggcaccgcc cgcccaccgc cccggccaca gccctgcgc ccacggcagc actcgaggcg   300
accgcgacag tggtggggga cgctgctgag tggaagagag cgcagccgg ccaccggacc   360
tacttactcg ccttgctgat tgtctatttt tgcgtttaca acttttctaa gaacttttgt   420
atacaaagga actttttaaa aaagacgctt ccaagttata tttaatccaa agaagaagga   480
tctcggccaa tttgggggttt tgggtttttgg cttcgtttct tctcttcgtt gactttgggg   540
ttcaggtgcc ccagctgctt cgggctgccg aggaccttct gggcccccac attaatgagg   600
cagccacctg gcgagtctga catggctgtc agcgacgcgc tgctcccatc tttctccacg   660
ttcgcgtctg gcccggcggg aagggagaag acactgcgtc aagcaggtgc cccgaataac   720
cgctggcggg aggagctctc ccacatgaag cgacttcccc cagtgcttcc cggccgcccc   780
tatgacctgg cggcggcgac cgtggccaca gacctggaga gcggcggagc cggtgcggct   840
tgcggcggta gcaacctggc gccctacct cggagagaga ccgaggagtt caacgatctc   900
ctggaccgg actttattct ctccaattcg ctgacccatc ctccggagtc agtggccgcc   960
accgtgtcct cgtcagcgtc agcctcctct tcgtcgtcgc cgtcgagcag cggccctgcc   1020
agcgcgccct ccacctgcag cttcacctat ccgatccggg ccgggaacga cccgggcgtg   1080
gcgccgggcg gcacgggcgg aggcctcctc tatggcaggg agtccgctcc ccctccgacg   1140
gctcccttca acctggcgga catcaacgac gtgagccct cgggcggctt cgtggccgag   1200
ctcctgcggc cagaattgga cccggtgtac attccgccgc agcagccgca gccgccaggt   1260
ggcgggctga tgggcaagtt cgtgctgaag gcgtcgctga gcgccctgg cagcgagtac   1320
ggcagccgt cggtcatcag cgtcagcaaa ggcagccctg acggcagcca cccggtggtg   1380
gtggcgccct acaacggcgg gccgccgcgc acgtgcccca agatcaagca ggaggcggtc   1440
tcttcgtgca cccacttggg cgctggaccc cctctcagca atggccaccg gccggctgca   1500
cacgacttcc ccctggggcg gcagctcccc agcaggacta ccccgaccct gggtcttgag   1560
gaagtgctga gcagcaggga ctgtcaccct gccctgccgc ttcctcccgg cttccatccc   1620
cacccggggc ccaattaccc atccttcctg cccgatcaga tgcagccgca agtcccgccg   1680
ctccattacc aagagctcat gccacccggt tcctgcatgc cagaggagcc caagccaaag   1740
aggggaagac gatcgtggcc ccggaaaagg accgccaccc acacttgtga ttacgcgggc   1800
tgcggcaaaa cctacacaaa gagttcccat ctcaaggcac acctgcgaac ccacacaggt   1860
gagaaacctt accactgtga ctgggacggc tgtggatgga aattcgcccg ctcagatgaa   1920
ctgaccaggc actaccgtaa acacacgggg caccgcccgt tccagtgcca aaaatgcgac   1980
cgagcatttt ccaggtcgga ccacctcgcc ttacacatga agaggcattt ttaaatccca   2040
gacagtggat atgacccaca ctgccagaag agaattcagt atttttttact tttcacactg   2100
tcttcccgat gagggaagga gcccagccag aaagcactac aatcatggtc aagttcccaa   2160
ctgagtcatc ttgtgagtgg ataatcagga aaaatgagga atccaaaaga caaaaatcaa   2220
agaacagatg gggtctgtga ctggatcttc tatcattcca attctaaatc cgacttgaat   2280
attcctggac ttacaaaatg ccaaggggggt gactggaagt tgtggatatc agggtataaa   2340
ttatatccgt gagttggggg agggaagacc agaattccct tgaattgtgt attgatgcaa   2400
tataagcata aaagatcacc ttgtattctc tttaccttct aaaagccatt attatgatgt   2460
tagaagaaga ggaagaaatt caggtacaga aaacatgttt aaatagccta aatgatggta   2520
cttggtgagt cttggttcta aaggtaccaa acaaggaagc caaagttttc aaaactgctgc   2580
atactttgac aaggaaaatc tatatttgtc ttccgatcaa catttatgac ctaagtcagg   2640
taatatacct ggtttacttc tttagcattt ttatgcagac agtctgttat gcactgtggt   2700
ttcagatgtg caataatttg tacaatggtt tattcccaag tatgccttaa gcagaacaaa   2760
tgtgtttttc tatatagttc cttgccttaa taaatatgta atataaattt aagcaaacgt   2820
ctattttgta tatttgtaaa ctacaaagta aaatgaacat tttgtggagt ttgtattttg   2880
catactcaag gtgagaatta agtttttaaat aaacctataa tatttttatct gaaaaaaaaaa   2940
aaaaaaaaa                                                            2949

SEQ ID NO: 60         moltype = AA   length = 454
FEATURE               Location/Qualifiers
source                1..454
                      mol_type = protein
                      organism = Homo sapiens
SEQUENCE: 60
MDFFRVVENQ QPPATMPLNV SFTNRNYDLD YDSVQPYFYC DEEENFYQQQ QQSELQPPAP   60
SEDIWKKFEL LPTPPLSPSR RSGLCSPSYV AVTPFSLRGD NDGGGGSFST ADQLEMVTEL   120
LGGDMVNQSF ICDPDDETFI KNIIIQDCMW SGFSAAAKLV SEKLASYQAA RKDSGSPNPA   180
RGHSVCSTSS LYLQDLSAAA SECIDPSVVF PYPLNDSSSP KSCASQDSSA FSPSSDSLLS   240
STESSPQGSP EPLVLHEETP PTTSSDSEEE QEDEEEIDVV SVEKRQAPGK RSESGSPSAG   300
GHSKPPHSPL VLKRCHVSTH QHNYAAPPST RKDYPAAKRV KLDSVRVLRQ ISNNRKCTSP   360
RSSDTEENVK RRTHNVLERQ RRNELKRSFF ALRDQIPELE NNEKAPKVVI LKKATAYILS   420
VQAEEQKLIS EEDLLRKRRE QLKHKLEQLR NSCA                                454

SEQ ID NO: 61         moltype = DNA   length = 2379
FEATURE               Location/Qualifiers
source                1..2379
                      mol_type = genomic DNA
                      organism = Homo sapiens
SEQUENCE: 61
gaccccgag ctgtgctgct cgcggccgcc accgccgggc cccggccgtc cctggctccc     60
```

```
ctcctgcctc gagaagggca gggcttctca gaggcttggc gggaaaaaga acggagggag  120
ggatcgcgct gagtataaaa gccggttttc ggggctttat ctaactcgct gtagtaattc  180
cagcgagagg cagagggagc gagcgggcgg ccggctaggg tggaagagcc gggcgagcag  240
agctgcgctg cgggcgtcct gggaagggag atccggagcg aatagggggc ttcgcctctg  300
gcccagccct cccgctgatc ccccagccag cggtccgcaa cccttgccgc atccacgaaa  360
ctttgcccat agcagcgggc gggcactttg cactggaact tacaacaccc gagcaaggac  420
gcgactctcc cgacgcgggg aggctattct gcccatttgg ggacacttcc ccgccgctgc  480
caggacccgc ttctctgaaa ggctctcctt gcagctgctt agacgctgga ttttttttcgg  540
gtagtggaaa accagcagcc tcccgcgacg atgcccctca acgttagctt caccaacagg  600
aactatgacc tcgactacga ctcggtgcag ccgtatttct actgcgacga ggaggagaac  660
ttctaccagc agcagcagca gagcgagctg cagcccccgg cgcccagcga ggatatctgg  720
aagaaattcg agctgctgcc caccccgccc ctgtccccta gccgccgctc cgggctctgc  780
tcgccctcct acgttgcggt cacacccttc tccttcgggg agacaacga cggcggtggc  840
gggagcttct ccacggccga ccagctggag atggtgaccg agctgctgga ggagacatg  900
gtgaaccaga gtttcatctg cgacccggac gacgagacct tcatcaaaaa catcatcatc  960
caggactgta tgtggagcgg cttctcggcc gccgccaagc tcgtctcaga gaagctggcc  1020
tcctaccagg ctgcgcgcaa agacagcggc agcccgaacc ccgccgcgg ccacagcgtc  1080
tgctccacct ccagcttgta cctgcaggat ctgagcgccg cccgcctcaga gtgcatcgac  1140
ccctcggtgg tcttcccta ccctctcaac gacagcagct cgcccaagtc ctgcgcctcg  1200
caagactcca gcgccttctc tccgtcctcg gattctctgc tctcctcgac ggagtcctcc  1260
ccgcagggca gcccccgagcc cctggtgctc catgaggaga caccgcccac caccagcagc  1320
gactctgagg aggaacaaga agatgaggaa gaaatcgatt ttgtttctgt ggaaaagagg  1380
caggctcctg gcaaaaggtc agagtctgga tcaccttctg ctggaggcca cagcaaacct  1440
cctcacagcc cactggtcct caagaggtgc cacgtctcca cacatcagca caactacgca  1500
gcgcctcct ccactcggaa ggactatcct gctgccaaga gggtcaagtt ggacagtgtc  1560
agagtcctga gacagatcag caacaaccga aaatgcacca gcccccaggtc ctcggacacc  1620
gaggagaatg tcaagaggcg aacacacaac gtcttggagc gccagaggag gaacgagcta  1680
aaacggagct ttttttgccct gcgtgaccag atcccggagt tggaaaacaa tgaaaaggcc  1740
cccaaggtag ttatccttaa aaaagccaca gcatacatcc tgtccgtcca agcagaggag  1800
caaaagctca tttctgaaga ggacttgttg cggaaacgac gagaacagtt gaaacacaaa  1860
cttgaacagc tacggaactc ttgtgcgtaa ggaaaagtaa ggaaaacgat tccttctaac  1920
agaaatgtcc tgagcaatca cctatgaact tgtttcaaat gcatgatcaa atgcaacctc  1980
acaaccttgg ctgagtcttg agactgaaag atttagccat aatgtaaact gcctcaaatt  2040
ggacttttggg cataaaagaa ctttttttatg cttaccatct ttttttttttc tttaacagat  2100
ttgtatttaa gaattgtttt taaaaaattt taagatttac acaatgtttc tctgtaaata  2160
ttgccattaa atgtaaataa ctttaataaa acgtttatag cagttacaca gaatttcaat  2220
cctagtatat agtacctagt attataggta ctataaaccc taatttttt tatttaagta  2280
catttttgctt tttaaagttg atttttttct attgtttta gaaaaaataa aataactggc  2340
aaatatatca ttgagccaaa tcttaaaaaa aaaaaaaaa                           2379
```

```
SEQ ID NO: 62            moltype = DNA  length = 5489
FEATURE                  Location/Qualifiers
misc_feature             1..5489
                         note = OSKM expression cassette:
                         OCT4-F2A-KLF4-IRES-SOX2-E2A SEQUENCE
source                   1..5489
                         mol_type = other DNA
                         organism = synthetic construct
SEQUENCE: 62
atggctggac acctggcttc agacttcgcc ttctcacccc caccaggtgg gggtgatggg   60
tcagcagggc tggagccggg ctgggtggat cctcgaacct ggctaagctt ccaagggcct  120
ccaggtgggc ctggaatcgg accaggctca gaggtattgg ggatctcccc atgtccgccc  180
gcatacgagt tctgcggagg gatggcatac tgtggacctc aggttggact gggcctagtc  240
ccccaagttg gcgtggagac tttgcagcct gagggccagg caggagcacg agtggaaagc  300
aactcagagg gaacctcctc tgagccctgt gccgaccgcc ccaatgccgt gaagttggag  360
aaggtggaac caactcccga ggagtcccag gacatgaaag ccctgcagaa ggagctagaa  420
cagtttgcca agctgctgaa gcagaagagg atcaccttgg ggtacaccca ggccgacgtg  480
gggctcaccg tgggcgttct ctttggaaag gtgttcagcc agaccaccat ctgtcgcttc  540
gaggccttgc agctcagcct taagaacatg tgtaagctgc ggcccctgct ggagaagtgg  600
gtggaggaag ccgacaacaa tgagaacctt caggagatat gcaaatcgga gaccctggtg  660
caggcccgga agagaaagcg aactagcatt gagaaccgtg tgaggtggag tctggagacc  720
atgtttctga gtgcccgaa gccctcccta cagcagatca ctcacatcgc caatcagctt  780
gggctagaga aggatgtggt tcgagtatgg ttctgtaacc ggcgcagaa gggcaaaaga  840
tcaagtattg agtattccca acgagaagag tatgaggcca tttcccaggc tttggaaagc  900
ggggctgtat cctttcctct gccccaggt ccccactttg gcaccccagg ctatggaagc  960
ccccacttca ccacactcta ctcagtccct tttcctgagg gcgaggcctt tccctctgtt  1020
cccgtcactc tctctgggctc tcccatgcat tcaaacggaa gtggcgtgaa acagactttg  1080
aattttgacc ttctcaagtt ggcggggagac gtggagtcca acccagggcc catggctgtc  1140
agcgacgctc tgctcccgtc cttctccacg ttcgcgtccg gcccggcgg aagggagaag  1200
acactgcgtc cagcaggtgc cccgactaac cgttggcgtg aggaactctc tcacatgaag  1260
cgacttcccc cacttcccgg ccgcccctac gacctggcgg cgacggtggc cacagacctg  1320
gagagtggcg gagctggtgc agcttgcagc agtaacaacc cggccctcct agcccggagg  1380
gagaccgagg agttcaacga cctcctggac ctagacttta tccttccaa ctcgctaacc  1440
caccaggaat cctggtccgt caccgtgacc acctcggcgt cagcttcatc ctcgtcttcc  1500
ccagcgagca gcggccctgc cagcgcgccc tccacctgca gcttcagcta tccgatccgg  1560
gccggggtg accggggcgt ggctgccagc aacacaggtg gagggctcct ctacagccga  1620
gaatctgcgc cacctccac ggcccccttc aacctggcgg acatcaatga cgtgagcccc  1680
tcgggcggct tcgtggctga gctcctgcgg ccggagttgg acccagtata cattccgcca  1740
cagcagcctc agccgccagg tggcgggctg atgggcaagt ttgtgctgaa ggcgtctctg  1800
```

-continued

```
accacccctg gcagcgagta cagcagccct tcggtcatca gtgttagcaa aggaagccca    1860
gacggcagcc accccgtggt agtggcgccc tacagcggtg gccgccgcg catgtgcccc    1920
aagattaagc aagaggcggt cccgtcctgc acggtcagcc ggtccctaga ggcccatttg    1980
agcgctggac cccagctcag caacggccac cggcccaaca cacacgactt cccctgggg    2040
cggcagctcc ccaccaggac tacccctaca ctgagtcccg aggaactgct gaacagcagg    2100
gactgtcacc ctggcctgcc tcttccccca ggattccatc cccatccggg gcccaactac    2160
cctcctttcc tgccagacca gatgcagtca caagtccct ctctccatta tcaagagctc    2220
atgccaccgg gttcctgcct gccagaggag cccaagccaa agaggggaag aaggtcgtgg    2280
ccccggaaaa gaacagccac ccacacttgt gactatgcag gctgtggcaa aacctatacc    2340
aagagttctc atctcaaggc acacctgcga actcacacag gcgagaaacc ttaccactgt    2400
gactgggacg gctgtgggtg gaaattcgcc cgctccgatg aactgaccag gcactaccgc    2460
aaacacacag ggcaccggcc ctttcagtgc cagaagtgtg acagggcctt ttccaggtcg    2520
gaccaccttg ccttacacat gaagaggcac tttttaaagat ccctcccccc ccctaacgt    2580
tactggccga agccgcttgg aataaggccg gtgtgcgttt gtctatatgt tattttccac    2640
catattgccg tcttttggca atgtgagggc ccggaaacct ggccctgtct tcttgacgag    2700
cattcctagg ggtctttccc ctctcgccaa aggaatgcaa ggtctgttga atgtcgtgaa    2760
ggaagcagtt cctctggaag cttcttgaag acaaacaacg tctgtagcga ccctttgcag    2820
gcagcggaac cccccacctg gcgacaggtg cctctgcggc caaaagccac gtgtataaga    2880
tacacctgca aaggcggcac aaccccagtg ccacgttgtg agttggatag ttgtggaaag    2940
agtcaaatgg ctctcctcaa gcgtattcaa caaggggctg aaggatgccc agaaggtacc    3000
ccattgtatg ggatctgatc tggggcctcg gtgcacatgc tttacatgtg tttagtcgag    3060
gttaaaaaaa cgtctaggcc ccccgaacca cggggacgtg gttttccttt gaaaaacacg    3120
atgataatat ggccacacat atgatgtata acatgatgga gacggagctg aagccgccgg    3180
gcccgcagca agcttcgggg ggcggcggcg gaggaggcaa cgccacggcg gcggcgaccg    3240
gcggcaacca gaagaacagc ccggaccgcg tcaagaggcc catgaacgcc ttcatggtat    3300
ggtcccgggg gcagcggcgt aagatggccc aggagaaccc caagatgcac aactcggaga    3360
tcagcaagcg cctgggcgcg gagtggaaac ttttgtccga gaccgagaag cggccgttca    3420
tcgacgaggc caagcggctg cgcgctctgc acatgaagga gcacccggat tataaatacc    3480
ggccgcggcg gaaaaccaag acgctcatga agaaggataa gtacacgctt cccggaggct    3540
tgctggcccc cggcgggaac agcatggcga gcggggttgg ggtggggcgc ggcctggtg    3600
cgggcgtgaa ccagcgcatg gacagctacg cgcacatgaa cggctggagc aacggcagct    3660
acagcatgat gcaggagcag ctgggctacc cgcagcaccc gggcctcaac gctcacggcg    3720
cggcacagat gcaaccgatg caccgctacg acgtcagcgc cctgcagtac aactccatga    3780
ccagctcgca gacctacatg aacggctcgc ccacctacag catgtcctac tcgcagcagg    3840
gcacccccgg tatggcgctg ggctccatgg gctctgtggt caagtccgag gccagctcca    3900
gccccccgt ggttacctct tcctcccact ccagggcgcc ctgccaggcc ggggacctcc    3960
gggacatgat cagcatgtac ctccccgcg ccgaggtgcc ggagcccgct gcgcccagta    4020
gactgcacat ggcccagcac taccagagcg gcccggtgcc cggcacggcc attaacggca    4080
cactgccccct gtcgcacatg ggtagtgggc aatgtactaa ctacgctttg ttgaaactcg    4140
ctggcgatgt tgaaagtaac cccggtccta tgccctcaa cgtgaacttc accaacagga    4200
actatgacct cgactacgac tccgtacagc cctatttcat ctgcgacgag gaagagaatt    4260
tctatcacca gcaacagcag agcgagctgc agccgcccgc gcccagtgag gatatctgga    4320
agaaattcga gctgcttccc accccgcccc tgtccccgag ccgctctgct gggctctgct    4380
ctccatccta tgttgcggtc gctacgtcct tctccccaag ggaagacgat gacggcggcg    4440
gtggcaactt ctccaccgcc gatcagctgg agatgatgac cgagttactt ggaggagaca    4500
tggtgaacca gagcttcatc tgcgatcctg acgacgagac cttcatcaag aacatcatca    4560
tccaggactg tatgtggagc ggtttctcag ccgctgccaa gctggtctcg gagaagtcg    4620
cctcctacca ggctgcgcgc aaagacagca ccagcctgag ccccgcccgc gggcacagcg    4680
tctgctccac ctccagcctg tacctgcagg acctcaccgc cgccgcgtcc gagtgcattg    4740
acccctcagt ggtctttccc tacccgctca acgacagcag ctcgcccaaa tcctgtacct    4800
cgtccgattc cacggccttc tctccttcct cggactcgct gctgcctccc gagtcctcc    4860
cacgggccag ccctgagccc ctagtgctgc atgaggagac accgccccacc accagcagcg    4920
actctgaaga agagcaagaa gatgaggaag aaattgatgt ggtgtctgtg gagaagaggc    4980
aaacccctgc caagaggtcg gagtcgggct catctccatc ccgaggccac agcaaacctc    5040
cgcacagccc actggtcctc aagaggtgcc acgtctccac tcaccagcac aactacgccg    5100
cacccccctc cacaaggaag gactatccag ctgccaagag ggccaagttg gacagtggca    5160
gggtcctgaa gcagatcagc aacaaccgca agtgctccag ccccaggtcc tcagacacgg    5220
aggaaaacga caagaggcgg acacacaacg tcttggaacg tcagaggagg aacgagctga    5280
agcgcagctt ttttgccctg cgtgaccaga tccctgaatt ggaaaacaac gaaaaggccc    5340
ccaaggtagt gatcctcaaa aaagccaccg cctacatcct gtccattcaa gcagcagac    5400
acaagctcac ctctgaaaag gacttattga ggaaacgacg agaacagttg aaacacaaac    5460
tcgaacagct tcgaaactct ggtgcataa                                      5489
```

SEQ ID NO: 63            moltype = DNA  length = 58
FEATURE                  Location/Qualifiers
misc_feature             1..58
                         note = Single strand DNA oligonucleotide
source                   1..58
                         mol_type = other DNA
                         organism = synthetic construct
SEQUENCE: 63
ccggctaagt ggattgagtg cctttctcga gaaaggcact caatccactt agtttttg      58

SEQ ID NO: 64            moltype = DNA  length = 58
FEATURE                  Location/Qualifiers
misc_feature             1..58
                         note = Single strand DNA oligonucleotide
source                   1..58
                         mol_type = other DNA
```

-continued

```
                        organism = synthetic construct
SEQUENCE: 64
aattcaaaaa ctaagtggat tgagtgcctt tctcgagaaa ggcactcaat ccacttag      58

SEQ ID NO: 65           moltype = DNA   length = 58
FEATURE                 Location/Qualifiers
misc_feature            1..58
                        note = Single strand DNA oligonucleotide
source                  1..58
                        mol_type = other DNA
                        organism = synthetic construct
SEQUENCE: 65
ccgggcgcta tgattcttcc aaccactcga gtggttggaa gaatcatagc gctttttg      58

SEQ ID NO: 66           moltype = DNA   length = 58
FEATURE                 Location/Qualifiers
misc_feature            1..58
                        note = Single strand DNA oligonucleotide
source                  1..58
                        mol_type = other DNA
                        organism = synthetic construct
SEQUENCE: 66
aattcaaaaa gcgctatgat tcttccaacc actcgagtgg ttggaagaat catagcgc      58

SEQ ID NO: 67           moltype = DNA   length = 26
FEATURE                 Location/Qualifiers
misc_feature            1..26
                        note = Single strand DNA oligonucleotide
source                  1..26
                        mol_type = other DNA
                        organism = synthetic construct
SEQUENCE: 67
acaactaacc taaaccaaat tataca                                         26

SEQ ID NO: 68           moltype = DNA   length = 25
FEATURE                 Location/Qualifiers
misc_feature            1..25
                        note = Single strand DNA oligonucleotide
source                  1..25
                        mol_type = other DNA
                        organism = synthetic construct
SEQUENCE: 68
tgtttttttg tttatcgggg tcgcg                                          25

SEQ ID NO: 69           moltype = DNA   length = 28
FEATURE                 Location/Qualifiers
misc_feature            1..28
                        note = Single strand DNA oligonucleotide
source                  1..28
                        mol_type = other DNA
                        organism = synthetic construct
SEQUENCE: 69
cgaattatac gacaaatcta aaataacg                                       28

SEQ ID NO: 70           moltype = DNA   length = 203
FEATURE                 Location/Qualifiers
misc_feature            1..203
                        note = 203bp amplicon covering human XIST transcription
                         start site
source                  1..203
                        mol_type = other DNA
                        organism = synthetic construct
SEQUENCE: 70
gggtaaattt tgaaccaacc aaatcacaaa gatgtccggc tttcaatctt ctaggccacg    60
cctcttatgc tctctccgcc ctcagccccc ccttcagttc ttaaagcgct gcaattcgct    120
gctgcagcca tatttcttac tctctcgggg ctggaagctt cctgactgaa gatctgttct    180
agaaagaacc ccaagtgcag aga                                            203

SEQ ID NO: 71           moltype = DNA   length = 1902
FEATURE                 Location/Qualifiers
source                  1..1902
                        mol_type = genomic DNA
                        organism = Homo sapiens
SEQUENCE: 71
atgaccgaag aagcatgccg aacacggagt cagaaacgag cgcttgaacg ggacccaaca    60
gaggacgatg tggagagcaa gaaaataaaa atggagagag gattgttggc ttcagattta    120
aacactgacg gagacatgag ggtgacacct gagccgggac caggtccaac ccaaggattg    180
ctgagggcaa cagaggccac ggccatggcc atgggcagag cgaagggct ggtgggcgat     240
gggcccgtgg acatgcgcac ctcacacagt gacatgaagt ccgagaggag acccccctca    300
```

```
cctgacgtga ttgtgctctc cgacaacgag cagccctcga gcccgagagt gaatgggctg    360
accacggtgg ccttgaagga gactagcacc gaggccctca tgaaaagcag tcctgaagaa    420
cgagaaagga tgatcaagca gctgaaggaa gaattgaggt tagaagaagc aaaactcgtg    480
ttgttgaaaa agttgcggca gagtcaaata caaaaggaag ccaccgccca gaagcccaca    540
ggttctgttg ggagcaccgt gaccacccct cccccgcttg ttcggggcac tcagaacatt    600
cctgctggca agccatcact ccagacctct tcagctcgga tgcccggcag tgtcataccc    660
ccgcccctgg tccgaggtgg gcagcaggcg tcctcgaagc tggggccaca ggcgagctca    720
caggtcgtca tgccccact cgtcaggggg gctcagcaaa tccacagcat taggcaacat    780
tccagcacag ggccaccgcc cctcctcctg gcccccggg cgtcggtgcc cagtgtgcag    840
attcagggac agaggatcat ccagcagggc ctcatccgcg tcgccaatgt tcccaacacc    900
agcctgctcg tcaacatccc acagcccacc ccagcatcac tgaaggggac aacagccacc    960
tccgctcagg ccaactccac ccccactagt gtggcctctg tggtcacctc tgccgagtct   1020
ccagcaagcc gacaggcggc cgccaagctg gcgctgcgca aacgctgga gaagacgcta   1080
ctcgagatcc ccccacccaa gccccagcc ccagagatga acttcctgcc cagcgccgcc   1140
aacaacgagt tcatctacct ggtcggcctg gaggaggtgg tgcagaacct actggagaca   1200
caaggcagga tgtcggccgc cactgtgctg tcccggggagc cctacatgtg tgcacagtgc   1260
aagacggact tcacgtgccg ctggcgggag gagaagagcg gcgccatcat gtgtgagaac   1320
tgcatgacaa ccaaccagaa gaaggcgctc aaggtggagc acaccagccg gtcgaaggcc   1380
gcctttgtga aggcgctgca gcaggaacag gagattgagc agcggctcct gcagcagggc   1440
acggcccctg cacaggccaa ggccgagccc accgctgccc cacaccccgt gctgaagcag   1500
gtcataaaac cccggcgtaa gttggcgttc cgctcaggag aggcccgcga ctggagtaac   1560
ggggctgtgc tacaggcctc cagccagctg tcccggggtt cggccacgac gccccgaggt   1620
gtcctgcaca cgttcagtcc gtcacccaaa ctgcagaact cagcctcggc cacagccctg   1680
gtcagcagga ccggcagaca ttctgagaga accgtgagcg ccggcaaggg cagcgccacc   1740
tccaactgga agaagacgcc cctcagcaca ggcgggaccc ttgcgtttgt cagcccaagc   1800
ctggcggtgc acaagagctc ctcggccgtg gaccgccagc gagagtacct cctggacatg   1860
atcccacccc gctccatccc ccagtcagcc acgtggaaat ag                       1902

SEQ ID NO: 72           moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 72
cagggctgaa gagaagatgg                                                   20

SEQ ID NO: 73           moltype = DNA  length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 73
acaggaggtg ggaatctga                                                    19

SEQ ID NO: 74           moltype = DNA  length = 30
FEATURE                 Location/Qualifiers
misc_feature            1..30
                        note = Single strand DNA oligonucleotide
source                  1..30
                        mol_type = other DNA
                        organism = synthetic construct
SEQUENCE: 74
ggtaccggat actcaggcca ggcccagaaa                                        30

SEQ ID NO: 75           moltype = DNA  length = 25
FEATURE                 Location/Qualifiers
misc_feature            1..25
                        note = Single strand DNA oligonucleotide
source                  1..25
                        mol_type = other DNA
                        organism = synthetic construct
SEQUENCE: 75
ctcgagtcca cagacctctg gcact                                             25

SEQ ID NO: 76           moltype = DNA  length = 35
FEATURE                 Location/Qualifiers
misc_feature            1..35
                        note = Single strand DNA oligonucleotide
source                  1..35
                        mol_type = other DNA
                        organism = synthetic construct
SEQUENCE: 76
ggtacccatt gagtccaaat cctctttact aggtg                                  35

SEQ ID NO: 77           moltype = DNA  length = 25
```

-continued

```
FEATURE              Location/Qualifiers
misc_feature         1..25
                     note = Single strand DNA oligonucleotide
source               1..25
                     mol_type = other DNA
                     organism = synthetic construct
SEQUENCE: 77
ctcgagctga ggctcatgct gctgg                                          25

SEQ ID NO: 78        moltype = DNA   length = 20
FEATURE              Location/Qualifiers
misc_feature         1..20
                     note = Single strand DNA oligonucleotide
source               1..20
                     mol_type = other DNA
                     organism = synthetic construct
SEQUENCE: 78
agggagcagt ttgccctact                                                20

SEQ ID NO: 79        moltype = DNA   length = 20
FEATURE              Location/Qualifiers
misc_feature         1..20
                     note = Single strand DNA oligonucleotide
source               1..20
                     mol_type = other DNA
                     organism = synthetic construct
SEQUENCE: 79
cacatgcagc gtggtatctt                                                20

SEQ ID NO: 80        moltype = DNA   length = 20
FEATURE              Location/Qualifiers
misc_feature         1..20
                     note = Single strand DNA oligonucleotide
source               1..20
                     mol_type = other DNA
                     organism = synthetic construct
SEQUENCE: 80
agtgattctc ctgcctcagc                                                20

SEQ ID NO: 81        moltype = DNA   length = 20
FEATURE              Location/Qualifiers
misc_feature         1..20
                     note = Single strand DNA oligonucleotide
source               1..20
                     mol_type = other DNA
                     organism = synthetic construct
SEQUENCE: 81
cttctgcttc aggagcttgg                                                20

SEQ ID NO: 82        moltype = DNA   length = 20
FEATURE              Location/Qualifiers
misc_feature         1..20
                     note = Single strand DNA oligonucleotide
source               1..20
                     mol_type = other DNA
                     organism = synthetic construct
SEQUENCE: 82
ggaatgggag gacaggattt                                                20

SEQ ID NO: 83        moltype = DNA   length = 20
FEATURE              Location/Qualifiers
misc_feature         1..20
                     note = Single strand DNA oligonucleotide
source               1..20
                     mol_type = other DNA
                     organism = synthetic construct
SEQUENCE: 83
aacagccgga gcagaagata                                                20

SEQ ID NO: 84        moltype = DNA   length = 20
FEATURE              Location/Qualifiers
misc_feature         1..20
                     note = Single strand DNA oligonucleotide
source               1..20
                     mol_type = other DNA
                     organism = synthetic construct
SEQUENCE: 84
aaggatgttg aacgggcaga                                                20
```

```
SEQ ID NO: 85           moltype = DNA   length = 18
FEATURE                 Location/Qualifiers
misc_feature            1..18
                        note = Single strand DNA oligonucleotide
source                  1..18
                        mol_type = other DNA
                        organism = synthetic construct
SEQUENCE: 85
tccgttggaa ctgatgga                                                18

SEQ ID NO: 86           moltype = DNA   length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 86
tgacactggc aaaacaatgc a                                            21

SEQ ID NO: 87           moltype = DNA   length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 87
ggtcctttc accagcaagc t                                             21

SEQ ID NO: 88           moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 88
cgccaccaaa ctgagatgat                                              20

SEQ ID NO: 89           moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 89
cacattgtag tgggcagtgg                                              20

SEQ ID NO: 90           moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 90
cagtcgctac atcaccatcc                                              20

SEQ ID NO: 91           moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 91
tttcctctcc tttgctctgc                                              20

SEQ ID NO: 92           moltype = DNA   length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 92
aactcaagaa ggcggatgg                                               19
```

-continued

```
SEQ ID NO: 93          moltype = DNA   length = 19
FEATURE                Location/Qualifiers
misc_feature           1..19
                       note = Single strand DNA oligonucleotide
source                 1..19
                       mol_type = other DNA
                       organism = synthetic construct
SEQUENCE: 93
cggtgcgtcc tttaatcct                                              19

SEQ ID NO: 94          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 94
cgcctcggct acaacaacta                                             20

SEQ ID NO: 95          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 95
cgcctcggct acaacaacta                                             20

SEQ ID NO: 96          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 96
aaacgtgctg ctctacgaca                                             20

SEQ ID NO: 97          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 97
tagtcgatga cgtgctggag                                             20

SEQ ID NO: 98          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 98
ctacagcgcg tcatcgacta                                             20

SEQ ID NO: 99          moltype = DNA   length = 21
FEATURE                Location/Qualifiers
misc_feature           1..21
                       note = Single strand DNA oligonucleotide
source                 1..21
                       mol_type = other DNA
                       organism = synthetic construct
SEQUENCE: 99
tcgttggaga tgacaagttc c                                           21

SEQ ID NO: 100         moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 100
```

```
gcgctccgag aatttaaaga                                                     20

SEQ ID NO: 101          moltype = DNA   length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 101
gtcgctgctg ttagcgaag                                                      19

SEQ ID NO: 102          moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 102
gatttgtggg cctgaagaaa                                                     20

SEQ ID NO: 103          moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 103
cagatccatg gaggaaggaa                                                     20

SEQ ID NO: 104          moltype = DNA   length = 19
FEATURE                 Location/Qualifiers
misc_feature            1..19
                        note = Single strand DNA oligonucleotide
source                  1..19
                        mol_type = other DNA
                        organism = synthetic construct
SEQUENCE: 104
agctgctgga gctcgtctt                                                      19

SEQ ID NO: 105          moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 105
cgcctgttct ggaaccatac                                                     20

SEQ ID NO: 106          moltype = DNA   length = 24
FEATURE                 Location/Qualifiers
misc_feature            1..24
                        note = Single strand DNA oligonucleotide
source                  1..24
                        mol_type = other DNA
                        organism = synthetic construct
SEQUENCE: 106
taaattttaa attaattaaa ttat                                                24

SEQ ID NO: 107          moltype = DNA   length = 29
FEATURE                 Location/Qualifiers
misc_feature            1..29
                        note = Single strand DNA oligonucleotide
source                  1..29
                        mol_type = other DNA
                        organism = synthetic construct
SEQUENCE: 107
tgttttagaa agaattttaa gtgtagaga                                           29

SEQ ID NO: 108          moltype = DNA   length = 2457
FEATURE                 Location/Qualifiers
misc_feature            1..37
                        note = 1st exon
misc_feature            531..536
                        note = Premature polyA signal
misc_feature            1033..1038
```

```
                             note = Premature polyA signal
misc_feature                 1051..1056
                             note = Premature polyA signal
misc_feature                 1569..1574
                             note = Premature polyA signal
misc_feature                 1669..2457
                             note = 2nd exon
misc_feature                 1712..1714
                             note = Putative translation start site
source                       1..2457
                             mol_type = genomic DNA
                             organism = Homo sapiens
SEQUENCE: 108
accgtcgggg acccccaagc tccgtcctcc gcttcctgct ctctttatcc cgccccccgct   60
ccttctgggc caacgccgcc agtgactatt cccagggatc cctcagagct gaggacgccg   120
cggccgcatc cccatttggg accttgcccc gactccgacc tccggatctc cagctccacc   180
aaacctcgaa gccaccatcc gccccaaac tgccgctgcg ccaggctttc ggaggggagt   240
cgtggcaaca gccattagga tgcactaagc agggcacttc ctgagcccaa ggacaccgag   300
gggcattcac tgagtgaatg gggatgtgct gctaataact aacactaatt gaccacctgc   360
cgtgtgccca tcctcttcga acatgcaact tccttgttcc ttatcttgtt actgtctctt   420
tctctctgcc agaatccaat cctcacaagg gcagggactg gggtctgttt tgttaactgc   480
catatcacaa tgcctggcac gaaggaagat tcttgaatta atgaatggag attaaattat   540
aatttaaaag cctggcatga actgagcacc ttctgcatgc ttatcacccg ctactgacat   600
atagttcact tttttttttt tttttttttt gagacggagt tttgctctta tctcccaggc   660
tggagtgcaa gtggtgtgat ctcagctcac tgcaacctcc gcctcccggg ttcaagcgat   720
tcttctgcct cagcctcccg agtagctggg attacaggcg tccaccacca ctcctggcta   780
attttttttgt gtttttatta gagacagggt ttcgcaatgt tgggcaggct ggtctcgaac   840
tcctgacctc aggtgatcca cccgactcgg cctccaaagt gctgggatta caggcgtgag   900
ccattgtgcc ccgccccctt tttaacctag tttgttgtct ctcaccccga ccagaatata   960
accttcatga gggctacagt ttgttgtcta tttattgccc aactccatgt ccttgccaca   1020
cagtaggttc ccaataaatg tatgttgaat aattaataaa gactacattc taatgataat   1080
ggctaacaga ccacgtgatt tacatattta tttggtttat tatattatct gcctctgcct   1140
tttagaacat aaaccttctg ggggtgggaa tgttgggtcc ctactgtctg gcaggcactg   1200
tgctgggcta gggttcaatg gtgaccaaaa ccggcaaaat cctgccctcc ctctgtcatg   1260
gggaggaact gctaatgggc atgggggattc ttttctgggt gaggaaaatg ttctaaaatt   1320
tacttatggt gatagttgca caacttcgtg aatatgctaa aacccgttaa attggacact   1380
agctggctga acttgatggg atgtaaatta catctcaata aagctgtttg ggaaatccag   1440
ccttcacagt tgttgattcg cgtgaggagg gaaggagaga tggggggacg tgggacaggg   1500
agaaaacaac ataaatcata tatatatagc atgcaaattg gaaggtgatc agcacacaat   1560
aggcattcaa taaatgttga aataatgaca ccccactgtc tccttgccct caaatggtct   1620
cccctaacgt atccctgtt gtcttgcttc ttctcttccc acttgcagag cctgctgccc   1680
acgtctcttc cctgagctgc ctgctggggt catggagctg ccaacaaagc ctggcacctt   1740
cgacctgggc ctggccacat ggagcccttc cttccagggg gaaacccacc ggctcaggc   1800
acgccgcagg gatgttggca ggcagctgcc tgagtacaag gctgtggtgg tgggcgccag   1860
tggcgtgggc aagagtgcgc tgaccatcca gctgaaccac cagtgcttcg tggaggacca   1920
cgaccccacc atccaggatt cctactggaa ggagttgacc ctggacagtg gggactgcat   1980
tctgaatgtg ctggacacag cagggcaggc catcataggg ccctgcgtga ccagtgcct   2040
ggctgtctgt gatggtgtgc tgggcgtctt cgctctcgat gacccctcgt ctctgatcca   2100
gctgcagcag atatgggcca cctggggccc tcaccccgcc cagcccttg tcctcgtggg   2160
caacaagtgt gaccttgtga ccactgctgg agatgctcat gccgctgctg cagccctcgc   2220
acacagctgg ggggcccact tcgtggagac ctcggccaaa acacggcaag gcgtggagga   2280
ggcctttttcc ctgctggtcc atgagatcca gagggtccag gaggccatgg cgaaggagcc   2340
catggcaagg tcctgtaggg agaagacccg gcaccagaag gccacctgcc actgtggctg   2400
ctctgtggcc tgaaggtctt ggccaagaaa tgtagacctt tccccaggcc agggtga    2457

SEQ ID NO: 109             moltype = DNA  length = 826
FEATURE                    Location/Qualifiers
misc_feature               81..83
                           note = Putative translation start site
source                     1..826
                           mol_type = genomic DNA
                           organism = Homo sapiens
SEQUENCE: 109
accgtcgggg accccaagc tccgtcctcc gcttcctagc ctgctgccca cgtctcttcc   60
ctgagctgcc tgctggggtc atggagctgc caacaaagcc tggcaccttc gacctgggcc   120
tggccacatg gagcccttcc ttcagggggg aaacccaccg gctcaggca cgccgcaggg   180
atgttggcag gcagctgcct gagtacaagg ctgtggtggt gggcgccagt ggcgtgggca   240
agagtgcgct gaccatccag ctgaaccacc agtgcttcgt ggaggaccac gacccacca   300
tccaggattc ctactggaag gagttgaccc tggacacagc agggcaggc atccataggg   360
tggacacagc agggcaggcc atccataggg ccctgcgtga ccagtgcctg ctgtctgtg   420
atggtgtgct gggcgtcttc gctctcgatg accccctcgtc tctgatccag ctgcagcaga   480
tatgggccac ctggggccct caccccgccc agccccttgt cctcgtgggc aacaagtgtg   540
accttgtgac cactgctgga gatgctcatg ccgctgctgc agccctcgca cacagctggg   600
gggcccactt cgtggaagacc tcggccaaaa cacggcaagg cgtggaggag gcctttttcc   660
tgctggtcca tgagatccag agggtccagg aggccatggc gaaggagccc atggcaaggt   720
cctgtaggga agacccggg caccagaagg ccacctgcc ctgtggctgc tctgtggcct   780
gaaggtcttg gccaagaaat gtagaccttt ccccaggcca gggtga             826

SEQ ID NO: 110             moltype = DNA  length = 7979
```

-continued

```
FEATURE            Location/Qualifiers
misc_feature       1..7979
                   note = reverse tetracycline transactivator (M2rtTA) - vector
source             1..7979
                   mol_type = other DNA
                   organism = synthetic construct
SEQUENCE: 110
cgataatcaa cctctggatt acaaaatttg tgaaagattg actggtattc ttaactatgt    60
tgctcctttt acgctatgtg gatacgctgc tttaatgcct ttgtatcatg ctattgcttc   120
ccgtatggct ttcattttct cctccttgta taaatcctgg ttgctgtctc tttatgagga   180
gttgtggccc gttgtcaggc aacgtggcgt ggtgtgcact gtgtttgctg acgcaacccc   240
cactggttgg ggcattgcca ccacctgtca gctcctttcc gggactttcg ctttccccct   300
ccctattgcc acggcggaac tcatcgccgc ctgccttgcc cgctgctgga caggggctcg   360
gctgttgggc actgacaatt ccgtggtgtt gtcggggaaa tcatcgtcct ttccttggct   420
gctcgcctgt gttgccacct ggattctgcg cgggacgtcc ttctgctacg tcccttcggc   480
cctcaatcca gcggaccttc cttccgcgcg cctgctgccg gctctgcggc ctcttccgcg   540
tcttcgcctt cgccctcaga cgagtcggat ctccctttgg gccgcctccc cgcatcgata   600
ccgtcgacct cgagacctag aaaaacatgg agcaatcaca agtagcaata cagcagctac   660
caatgctgat tgtgcctggc tagaagcaca agaggaggag gaggtgtggtt ttccagtcac   720
acctcaggta cctttaagac caatgactta caaggcagct gtagatctta gccacttttt   780
aaaagaaaag gggggactgg aagggctaat tcactcccaa cgaagacaag atatccttga   840
tctgtggatc taccacacac aaggctactt ccctgattgg cagaactaca caccagggcc   900
agggatcaga tatccactga cctttggatg tgctacaag ctagtaccag ttgagcaaga   960
gaaggtagaa gaagccaatg aaggagagaa cacccgcttg ttcacccctg tgagcctgca  1020
tgggatggat gacccggaga gagaagtatt agagtggagg tttgacagcc gcctagcatt  1080
tcatcacatg gcccgagagc tgcatccgga ctgtactgag tctctctggt tagaccagat  1140
ctgagcctgg gagctctctg gctaactagg gaacccactg cttaagcctc aataaagctt  1200
gccttgagtg cttcaagtag tgtgtgcccg tctgttgtgt gactctggta actagagatc  1260
cctcagaccc ttttagtcag tgtggaaaat ctctagcagg gcccgtttaa acccgctgat  1320
cagcctcgac tgtgccttct agttgccagc catctgttgt ttgcccctcc ccgtgcctt  1380
ccttgaccct ggaaggtgcc actcccactg tcctttccta ataaaatgag gaaattgcat  1440
cgcattgtct gagtaggtgt cattctattc tggggggtgg ggtggggcag gacagcaagg  1500
gggaggattg ggaagacaat agcaggcatg tgagcaaaag gccagcaaaa ggccaggaac  1560
cgtaaaaagg ccgcgttgct ggcgtttttc cataggctcc gcccccctga cgagcatcac  1620
aaaaatcgac gctcaagtca gaggtggcga aacccgacag gactataaag ataccaggcg  1680
tttccccctg gaagctccct cgtgcgctct cctgttccga ccctgccgct taccggatac  1740
ctgtccgcct ttctcccttc gggaagcgtg gcgctttctc atagctcacg ctgtaggtat  1800
ctcagttcgg tgtaggtcgt tcgctccaag ctgggctgtg tgcacgaacc ccccgttcag  1860
cccgaccgct gcgccttatc cggtaactat cgtcttgagt ccaacccggt aagacacgac  1920
ttatcgccac tggcagcagc cactggtaac aggattagca gagcgaggta tgtaggcggt  1980
gctacagagt tcttgaagtg gtggcctaac tacggctaca ctagaagaac agtatttggt  2040
atctgcgctc tgctgaagcc agttaccttc ggaaaaagag ttggtagctc ttgatccggc  2100
aaacaaacca ccgctggtag cggtggtttt tttgtttgca agcagcagat tacgcgcaga  2160
aaaaaaggat ctcaagaaga tcctttgatc ttttctacgg ggtctgacgc tcagtggaac  2220
gaaaactcac gttaagggat tttggtcatg agattatcaa aaaggatctt cacctagatc  2280
cttttaaatt aaaaatgaag ttttaaatca atctaaagta tatatgagta aacttggtct  2340
gacagttacc aatgcttaat cagtgaggca cctatctcag cgatctgtct atttcgttca  2400
tccatagttg cctgactccc cgtcgtgtag ataactacga tacgggaggg cttaccatct  2460
ggccccagtg ctgcaatgat accgcgagac ccacgctcac cggctccaga tttatcagca  2520
ataaaccagc cagccggaag ggccgagcgc agaagtggtc ctgcaacttt atccgcctcc  2580
atccagtcta ttaattgttg ccgggaagct agagtaagta gttcgccagt taatagtttg  2640
cgcaacgttg ttgccattgc tacaggcatc gtggtgtcac gctcgtcgtt ggtatggct  2700
tcattcagct ccggttccca acgatcaagg cgagttacat gatcccccat gttgtgcaaa  2760
aaagcggtta gctccttcgg tcctccgatc gttgtcagaa gtaagttggc cgcagtgtta  2820
tcactcatgg ttatggcagc actgcataat tctcttactg tcatgccatc cgtaagatgc  2880
ttttctgtga ctggtgagta ctcaaccaag tcattctgag aatagtgtat gcggcgaccg  2940
agttgctctt gcccggcgtc aatacgggat aataccgcgc cacatagcag aactttaaaa  3000
gtgctcatca ttggaaaacg ttcttcgggg cgaaaactct caaggatctt accgctgttg  3060
agatccagtt cgatgtaacc cactcgtgca cccaactgat cttcagcatc ttttactttc  3120
accagcgttt ctgggtgagc aaaaacagga aggcaaaatg ccgcaaaaaa gggaataagg  3180
gcgcacggga atgttgaat actcatactc ttcctttttc aatattattg aagcatttat  3240
cagggttatt gtctcatgag cggatacata tttgaatgta tttagaaaaa taaacaaata  3300
ggggttccgc gcacatttcc ccgaaaagtg ccacctgacg tcgacggatc gggagatctc  3360
ccgatcccct atggtgcact ctcagtacaa tctgctctga tgccgcatag ttaagccagt  3420
atctgctccc tgcttgtgtg ttggaggtcg ctgagtagtg cgcgagcaaa atttaagcta  3480
caacaaggca aggcttgacc gacaattgca tgaagaatct gcttagggtt aggcgttttg  3540
cgctgcttcg cgatgtacgg gccagatata cgcgttgaca ttgattattg actagttatt  3600
aatagtaatc aattacgggg tcattagttc atagcccata tatggagttc cgcgttacat  3660
aacttacggt aaatggcccg cctggctgac cgcccaacga cccccgccca ttgacgtcaa  3720
taatgacgta tgttcccata gtaacgccaa tagggacttt ccattgacgt caatgggtgg  3780
agtatttacg gtaaactgcc cacttggcag tacatcaagt gtatcatatg ccaagtacgc  3840
ccctattga cgtcaatgac ggtaaatggc ccgcctggca ttatgcccag tacatgacct  3900
tatgggactt tcctacttgg cagtacatct acgtattagt catcgctatt accatggtga  3960
tgcggttttg gcagtacatc aatgggcgtg gatagcggtt tgactcacgg ggatttccaa  4020
gtctccaccc cattgacgtc aatgggagtt tgttttggca ccaaaatcaa cgggactttc  4080
caaaatgtcg taacaactcc gccccattga cgcaaatggg cggtaggcgt gtacggtggg  4140
aggtctatat aagcagcgcg ttttgcctgt actgggtctc tctggttaga ccagatctga  4200
gcctgggagc tctctggcta actagggaac ccactgctta agcctcaata aagcttgcct  4260
tgagtgcttc aagtagtgtg tgcccgtctg ttgtgtgact ctggtaacta gagatccctc  4320
```

```
agaccctttt agtcagtgtg gaaaatctct agcagtggcg cccgaacagg gacttgaaag  4380
cgaaagggaa accagaggag ctctctcgac gcaggactcg gcttgctgaa gcgcgcacgg  4440
caagaggcga ggggcggcga ctggtgagta cgccaaaaat tttgactagc ggaggctaga  4500
aggagagaga tgggtgcgag agcgtcagta ttaagcgggg gagaattaga tcgcgatggg  4560
aaaaaattcg gttaaggcca gggggaaaga aaaaatataa attaaaacat atagtatggg  4620
caagcaggga gctagaacga ttcgcagtta atcctggcct gttagaaaca tcagaaggct  4680
gtagacaaat actgggacag ctacaaccat cccttcagac aggatcagaa gaacttagat  4740
cattatataa tacagtagca accctctatt gtgtgcatca aaggatagag ataaaagaca  4800
ccaaggaagc tttagacaag atagaggaag agcaaaacaa aagtaagacc accgcacagc  4860
aagcggccgc tgatcttcag acctggagga ggagatatga gggacaattg gagaagtgaa  4920
ttatataaat ataaagtagt aaaaattgaa ccattaggag tagcacccac caaggcaaag  4980
agaagagtgg tgcagagaga aaaaagagca gtgggaatag gagctttgtt ccttgggttc  5040
ttgggagcag caggaagcac tatgggcgca gcgtcaatga cgctgacggt acaggccaga  5100
caattattgt ctggtatagt gcagcagcag aacaatttgc tgagggctat tgaggcgcaa  5160
cagcatctgt tgcaactcac agtctgtggc atcaagcagc tccaggcaag aatcctggct  5220
gtggaaagat acctaaagga tcaacagctc ctggggattt ggggttgctc tggaaaactc  5280
atttgcacca ctgctgtgcc ttggaatgct agttggagta taaatctct ggaacagatt  5340
tggaatcaca cgacctggat ggagtggac agagaaatta acaattacac aagcttaata  5400
cactccttaa ttgaagaatc gcaaaaccag caagaaaaga atgaacaaga attattggaa  5460
ttagataaat gggcaagttt gtggaattgg tttaacataa caaattggct gtggtatata  5520
aaattattca taatgatagt aggaggcttg gtaggtttaa gaatagtttt tgctgtactt  5580
tctatagtga atagagttag gcagggatat tcaccattat cgtttcagac ccacctccca  5640
accccgaggg gacccgacag gcccgaagga atagaagaag aaggtggaga gagagacaga  5700
gacagatcca ttcgattagt gaacggatcg gcactgcgtg cgccaattct gcagacaaat  5760
ggcagtattc atccacaatt ttaaaagaaa aggggggatt ggggggtaca gtgcagggga  5820
aagaatagta gacataatag caacagacat acaaactaaa gaattacaaa aacaaattac  5880
aaaaattcaa aattttcggg tttattacag ggacagcaga gatccagttt ggttaattaa  5940
cccgtgtcgg ctccagatct ggcctccgcg ccgggttttg gcgcctcccg cgggcgcccc  6000
cctcctcacg gcgagcgctg ccacgtcaga cgaagggcgc agcgagcgtc ctgatccttc  6060
cgcccgacg ctcaggacag cggcccgctg ctcataagac tcggccttag aaccccagta  6120
tcagcagaag gacattttag gacgggactt gggtgactct agggcactgg ttttctttcc  6180
agagagcgga acaggcgagg aaaagtagtc ccttctcggc gattctgcgg agggatctcc  6240
gtggggcggt gaacgccgat gattatataa ggacgcgccg ggtgtggcac agctagttcc  6300
gtcgcagccg ggatttgggt cgcggttctt gtttgtggat cgctgtgatc gtcacttggt  6360
gagtacgggg ctgctgggct ggccggggct ttcgtggccg ccgggccgct cggtgggacg  6420
gaagcgtgtg gagagaccgc caagggcgtg agtctgggtc cgcgagcaag gttgccctga  6480
actgggggtt ggggggagcg cagcaaaatg gcggctgttc ccgagtcttg aatggaagac  6540
gcttgtgagg cgggctgtga ggtcgttgaa acaaggtggg gggcatggtg ggcggcaaga  6600
acccaaggtc ttgaggcctt cgctaatgcg gaaagctct tattcgggtg agatgggctg  6660
gggcaccatc tggggaccct gacgtgaagt ttgtcactga ctggagaact cggtttgtcg  6720
tctgttgcgg gggcggcagt tatggcggtg ccgttgggca gtgcaccgt acctttggga  6780
gcgcgcgccc tcgtcgtgtc gtgacgtcac ccgttctgtt ggcttataat gcagggtggg  6840
gccacctgcc ggtaggtgtg cggtaggctt ttctccgtcg caggacgcag ggttcgggcc  6900
tagggtaggc tctcctgaat cgacaggcgc cggacctctg gtgaggggag ggataagtga  6960
ggcgtcagtt tctttggtcg gttttatgta cctatcttct taagtagctg aagctccggt  7020
tttgaactat gcgctcgggg ttggcgagtg tgttttgtga agtttttag gcacctttg  7080
aaatgtaatc atttgggtca atatgtaatt ttcagtgtta gactagtaaa ttgtccgcta  7140
aattctggcc gttttttggct tttttgttag acgaagcttg ggcccgggaa ttaattcacc  7200
atgtctagac tggacaagag caaagtcata aacggcgctc tggaattact caatggagtc  7260
ggtatcgaag gcctgacgac aaggaaactc gctcaaaagc tgggagttga gcagcctacc  7320
ctgtactggc acgtgaagaa caagcggggcc ctgctcgatg ccctgccaat cgagatgctg  7380
gacaggcatc atacccactt ctgcccctg gaaggcgagt catggcaaga ctttctgcgg  7440
aacaacgcca agtcattccg ctgtgctctc ctctcacatc gcgacggggc taaagtgcat  7500
ctcggcaccc gcccaacaga gaaacagtac gaaaccctgg aaaatcagct cgcgttcctg  7560
tgtcagcaag gcttctccct ggagaacgca ctgtacgctc tgtccgccgt gggccacttt  7620
acactgggct gcgtattgga ggaacaggag catcaagtag caaaagagga aagagagaca  7680
cctaccaccg attctatgcc cccacttctg agacaagcaa ttgagctgtt cgaccggcag  7740
ggagccgaac ctgccttcct tttcggcctg gaactaatca tatgtggcct ggagaaacag  7800
ctaaagtgcg aaagcggcgg gccggccgac gcccttgacg attttgactt agacatgctc  7860
ccagccgatg cccttgacga ctttgacctt gatatgctgc ctgctgacgc tcttgacgat  7920
tttgaccttg acatgctccc cgggtaacta gtaaggatc aattcgatat caagcttat  7979
```

SEQ ID NO: 111        moltype = DNA  length = 1201
FEATURE               Location/Qualifiers
source                1..1201
                      mol_type = genomic DNA
                      organism = Homo sapiens
SEQUENCE: 111

```
aatattagag tctcaacccc caataaatat aggactggag atgtctgagg ctcattctgc  60
cctcgagccc accgggaacg aaagagaagc tctatctccc ctccaggagc ccagctatga  120
actccttctc cacaagcgcc ttcggtccag ttgccttctc cctgggggctg ctcctggtgt  180
tgcctgctgc cttccctgcc ccagtacccc caggagaaga ttccaaagat gtagccgccc  240
cacacagaca gccactcacc tcttcagaac gaattgacaa acaaattcgg tacatcctcg  300
acggcatctc agccctgaga aaggagacat gtaacaagag taacatgtgt gaaagcagca  360
aagaggcact ggcagaaaac aacctgaacc ttccaaagat ggctgaaaaa gatggatgct  420
tccaatctgg attcaatgag gagacttgcc tggtgaaaat catcactggt cttttggagt  480
ttgaggtata cctagagtac ctccagaaca gatttgagag tagtgaggaa caagccagag  540
ctgtgcagat gagtacaaaa gtcctgatcc agttcctgca gaaaaaggca aagaatctag  600
atgcaataac caccccctgac ccaaccacaa atgccagcct gctgacgaag ctgcaggcac  660
```

-continued

```
agaaccagtg gctgcaggac atgacaactc atctcattct gcgcagcttt aaggagttcc    720
tgcagtccag cctgagggct cttcggcaaa tgtagcatgg gcacctcaga ttgttgttgt    780
taatgggcat tccttcttct ggtcagaaac ctgtccactg ggcacagaac ttatgttgtt    840
ctctatggag aactaaaagt atgagcgtta ggacactatt ttaattattt ttaatttatt    900
aatatttaaa tatgtgaagc tgagttaatt tatgtaagtc atatttatat ttttaagaag    960
taccacttga aacattttat gtattagttt tgaaataata atggaaagtg gctatgcagt   1020
ttgaatatcc tttgtttcag agccagatca tttcttggaa agtgtaggct tacctcaaat   1080
aaatggctaa cttatacata ttttttaaga aatatttata ttgtatttat ataatgtata   1140
aatggttttt ataccaataa atggcatttt aaaaaattca gcaaaaaaa aaaaaaaaa    1200
a                                                                  1201

SEQ ID NO: 112          moltype = DNA  length = 1902
FEATURE                 Location/Qualifiers
source                  1..1902
                        mol_type = genomic DNA
                        organism = Homo sapiens
SEQUENCE: 112
atgaccgaag aagcatgccg aacacggagt cagaaacgag cgcttgaacg ggacccaaca    60
gaggacgatg tggagagcaa gaaaataaaa atggagagag gattgttggc ttcagattta   120
aacactgacg gagacatgag ggtgacacct gagccgggag caggtccaac ccaaggattg   180
ctgagggcaa cagaggccac ggccatggcc atgggcagag cgaagggct ggtgggcgat    240
gggcccgtgg acatgcgcac ctcacacagt gacatgaagt gaccccctca                300
cctgacgtga ttgtgctctc cgacaacgag cagccctcga gcccgagagt gaatgggctg    360
accacggtgg ccttgaagga gactagcacc gaggccctca tgaaaagcag tcctgaagaa    420
cgagaaagga tgatcaagca gctgaaggaa gaattgaggt tagaagaagc aaaactcgtg    480
ttgttgaaaa agttgcggca gagtcaaata caaaaggaag ccaccgccca gaagcccaca    540
ggttctgttg ggagcaccgt gaccacccct ccccgcttg ttcggggcac tcagaacatt     600
cctgctggca agccatcact ccagacctct tcagctcgga tgcccggcag tgtcataccc    660
ccgcccctgg tccgaggtgg gcagcaggcg tcctcgaagc tggggccaca ggcgagctca    720
caggtcgtca tgcccccact cgtcagggg gctcagcaaa tccacagcat taggcaacat     780
tccagcacag ggccaccgcc cctcctcctg gcccccgggg cgtcggtgcc cagtgtgcag    840
attcagggac agaggatcat ccagcagggc ctcatccgcg tcgccaatgt tcccaacacc    900
agcctgctcg tcaacatccc acagcccacc ccagcatcac tgaaggggac aacagccacc    960
tccgctcagg ccaactccac ccccactagt gtggcctctg tggtcacctc tgccgagtct   1020
ccagcaagcc gacaggcggc cgccaagctg cgcctgcgca aacagctgga gaagacgcta   1080
ctcgagatcc ccccacccaa gcccccagcc ccagagatga acttcctgcc cagcgccgcc   1140
aacaacgagt tcatctacct ggtcggcctg gaggaggtgg tgcagaacct actggagaca   1200
caaggcagga tgtcggccgc cactgtgctg tcccgggagc cctacatgtg tgcacagtgc   1260
aagacggact tcacgtgccg ctggccggag gagaagacgg gcgccatcat gtgtgagaac   1320
tgcatgacaa ccaaccagaa gaaggcgctc aaggtggagc acaccagccg gctgaaggcc   1380
gcctttgtga aggcgctgca gcaggaacag gagattgagc agcggctcct gcagcagggc   1440
acggcccctg cacaggccaa ggccgagccc accgctgccc cacacccgt gctgaagcag     1500
gtcataaaac cccggcgtaa gttggcgttc cgctcaggag aggccgcga tggagtaac     1560
ggggctgtgc tacaggcctc cagccagctg tcccgggggtt cggccacgac gcccgaggt    1620
gtcctgcaca cgttcagtcc gtcacccaaa ctgcagaact cagcctcggc cacagccctg   1680
gtcagcagga ccggcagaca ttctgagaga accgtgagcg ccggcaaggg cagcgccacc   1740
tccaactgga agaagacgcc cctcacacaa ggcgggaccc ttgcgtttgt cagcccaagc   1800
ctggcggtgc acaagagctc ctcggccgtg gaccgccagc gagagtacct cctggacatg   1860
atcccacccc gctccatccc ccagtcagcc acgtggaaat ag                      1902

SEQ ID NO: 113          moltype = DNA  length = 123
FEATURE                 Location/Qualifiers
misc_feature            1..123
                        note = P66 alpha coiled-coil domain coding sequence
source                  1..123
                        mol_type = genomic DNA
                        organism = Homo sapiens
SEQUENCE: 113
cctgaagaac gagaaaggat gatcaagcag ctgaaggaag aattgaggtt agaagaagca    60
aaactcgtgt tgttgaaaaa gttgcggcag agtcaaatac aaaaggaagc caccgcccag   120
aag                                                                 123

SEQ ID NO: 114          moltype = AA  length = 41
FEATURE                 Location/Qualifiers
REGION                  1..41
                        note = MISC_FEATURE - P66 alpha coiled-coil domain
source                  1..41
                        mol_type = protein
                        organism = Homo sapiens
SEQUENCE: 114
PEERERMIKQ LKEELRLEEA KLVLLKKLRQ SQIQKEATAQ K                         41

SEQ ID NO: 115          moltype = DNA  length = 30
FEATURE                 Location/Qualifiers
misc_feature            1..30
                        note = Single strand DNA oligonucleotide
source                  1..30
                        mol_type = other DNA
                        organism = synthetic construct
```

```
SEQUENCE: 115
aaaaaaaccg gtcctgaaga acgagaaagg                                                30

SEQ ID NO: 116          moltype = DNA  length = 27
FEATURE                 Location/Qualifiers
misc_feature            1..27
                        note = Single strand DNA oligonucleotide
source                  1..27
                        mol_type = other DNA
                        organism = synthetic construct
SEQUENCE: 116
aaaaaactta agcttctggg cggtggc                                                   27

SEQ ID NO: 117          moltype = AA  length = 426
FEATURE                 Location/Qualifiers
source                  1..426
                        mol_type = protein
                        organism = Homo sapiens
SEQUENCE: 117
MPLLWLRGFL LASCWIIVRS SPTPGSEGHS AAPDCPSCAL AALPKDVPNS QPEMVEAVKK     60
HILNMLHLKK RPDVTQPVPK AALLNAIRKL HVGKVGENGY VEIEDDIGRR AEMNELMEQT    120
SEIITPAESG TARKTLHFEI SKEGSDLSVV ERAEVWLFLK VPKANRTRTK VTIRLFQQQK    180
HPQGSLDTGE EAEEVGLKGE RSELLLSEKV VDARKSTWHV FPVSSSIQRL LDQGKSSLDV    240
RIACEQCQES GASLVLLGKK KKKEEEGEGK KKGGGEGGAG ADEEKEQSHR PFLMLQARQS    300
EDHPHRRRRR GLECDGKVNI CCKKQFFVSF KDIGWNDWII APSGYHANYC EGECPSHIAG    360
TSGSSLSFHS TVINHYRMRG HSPFANLKSC CVPTKLRPMS MLYYDDGQNI IKKDIQNMIV    420
EECGCS                                                                         426

SEQ ID NO: 118          moltype = AA  length = 232
FEATURE                 Location/Qualifiers
source                  1..232
                        mol_type = protein
                        organism = Homo sapiens
SEQUENCE: 118
MERCPSLGVT LYALVVVLGL RATPAGGQHY LHIRPAPSDN LPLVDLIEHP DPIFDPKEKD     60
LNETLLRSLL GGHYDPGFMA TSPPEDRPGG GGGAAGGAED LAELDQLLRQ RPSGAMPSEI    120
KGLEFSEGLA QGKKQRLSKK LRRKLQMWLW SQTFCPVLYA WNDLGSRFWP RYVKVGSCFS    180
KRSCSVPEGM VCKPSKSVHL TVLRWRCQRR GGQRCGWIPI QYPIISECKC SC                    232

SEQ ID NO: 119          moltype = AA  length = 88
FEATURE                 Location/Qualifiers
source                  1..88
                        mol_type = protein
                        organism = Homo sapiens
SEQUENCE: 119
MKVLAAVHSP GGAVPQQPGQ AMWPQRDGLP ALPRQRHGEG QAGGAVPHSR VPWHLPGQHH     60
PGPEDPQPQC PQPPQQAQRH RRHPARPP                                                  88

SEQ ID NO: 120          moltype = AA  length = 212
FEATURE                 Location/Qualifiers
source                  1..212
                        mol_type = protein
                        organism = Homo sapiens
SEQUENCE: 120
MNSFSTSAFG PVAFSLGLLL VLPAAFPAPV PPGEDSKDVA APHRQPLTSS ERIDKQIRYI     60
LDGISALRKE TCNKSNMCES SKEALAENNL NLPKMAEKDG CFQSGFNEET CLVKIITGLL    120
EFEVYLEYLQ NRFESSEEQA RAVQMSTKVL IQFLQKKAKN LDAITTPDPT TNASLLTKLQ    180
AQNQWLQDMT THLILRSFKE FLQSSLRALR QM                                            212

SEQ ID NO: 121          moltype = AA  length = 433
FEATURE                 Location/Qualifiers
source                  1..433
                        mol_type = protein
                        organism = Homo sapiens
SEQUENCE: 121
MSGRPRTTSF AESCKPVQQP SAFGSMKVSR DKDGSKVTTV VATPGQGPDR PQEVSYTDTK     60
VIGNGSFGVV YQAKLCDSGE LVAIKKVLQD KRFKNRELQI MRKLDHCNIV RLRYFFYSSG    120
EKKDEVYLNL VLDYVPETVY RVARHYSRAK QTLPVIYVKL YMYQLFRSLA YIHSFGICHR    180
DIKPQNLLLD PDTAVLKLCD FGSAKQLVRG EPNVSYICSR YYRAPELIFG ATDYTSSIDV    240
WSAGCVLAEL LLGQPIFPGD SGVDQLVEII KVLGTPTREQ IREMNPNYTE FKFPQIKAHP    300
WTKDSSGTGH FTSGVRVFRP RTPPEAIALC SRLLEYTPTA RLTPLEACAH SFFDELRDPN    360
VKLPNGRDTP ALFNFTTQEL SSNPPLATIL IPPHARIQAA ASTPTNATAA SDANTGDRGQ    420
TNNAASASAS NST                                                                 433

SEQ ID NO: 122          moltype = AA  length = 420
FEATURE                 Location/Qualifiers
source                  1..420
                        mol_type = protein
                        organism = Homo sapiens
```

```
SEQUENCE: 122
MSGRPRTTSF AESCKPVQQP SAFGSMKVSR DKDGSKVTTV VATPGQGPDR PQEVSYTDTK   60
VIGNGSFGVV YQAKLCDSGE LVAIKKVLQD KRFKNRELQI MRKLDHCNIV RLRYFFYSSG  120
EKKDEVYLNL VLDYVPETVY RVARHYSRAK QTLPVIYVKL YMYQLFRSLA YIHSFGICHR  180
DIKPQNLLLD PDTAVLKLCD FGSAKQLVRG EPNVSYICSR YYRAPELIFG ATDYTSSIDV  240
WSAGCVLAEL LLGQPIFPGD SGVDQLVEII KVLGTPTREQ IREMNPNYTE FKFPQIKAHP  300
WTKVFRPRTP PEAIALCSRL LEYTPTARLT PLEACAHSFF DELRDPNVKL PNGRDTPALF  360
NFTTQELSSN PPLATILIPP HARIQAAAST PTNATAASDA NTGDRGQTNN AASASASNST  420

SEQ ID NO: 123        moltype = DNA  length = 2175
FEATURE                Location/Qualifiers
source                 1..2175
                       mol_type = genomic DNA
                       organism = Homo sapiens
SEQUENCE: 123
agtacagtat aaaacttcac agtgccaata ccatgaagag gagctcagac agctcttacc   60
acatgataca agagccggct ggtggaagag tggggaccag aaagagaatt tgctgaagag  120
gagaaggaaa aaaaaaacac caaaaaaaaa aataaaaaaa tccacacaca caaaaaaacc  180
tgcgcgtgag gggggaggaa aagcagggcc ttttaaaaag gcaatcacaa caactttttgc  240
tgccaggatg cccttgcttt ggctgagagg atttctgttg gcaagttgct ggattatagt  300
gaggagttcc cccaccccag gatccgaggg gcacagcgcg gcccccgact gtccgtcctg  360
tgcgctggcc gccctcccaa aggatgtacc caactctcag ccagagatgg tggaggccgt  420
caagaagcac attttaaaca tgctgcactt gaagaagaga cccgatgtca cccagccggt  480
acccaaggcg gcgcttctga acgcgatcag aaagcttcat gtgggcaaag tcggggagaa  540
cgggtatgtg gagatagagg atgacattgg aaggagggca gaaatgaatg aacttatgga  600
gcagacctcg gagatcatca cgtttgccga gtcaggaaca gccaggaaga cgctgcactt  660
cgagatttcc aaggaaggca gtgacctgtc agtggtggag cgtgcagaag tctggctctt  720
cctaaaagtc cccaaggcca acaggaccag gaccaaagtc accatccgcc tcttccagca  780
gcagaagcac ccgcagggca gcttggacac aggggaaagg gccgaggaag tgggcttaaa  840
gggggagagg agtgaactgt tgctctctga aaaagtagta gacgctcgga agagcacctg  900
gcatgtcttc cctgtctcca gcagcatcca gcggttgctg gaccagggca agagctccct  960
ggacgttcgg attgcctgtg agcagtgcca ggagagtggc gccagcttgg ttctcctggg  1020
caagaagaag aagaaagaag aggaggggga agggaaaaag aagggcggag gtgaaggtgg  1080
ggcaggagca gatgaggaaa aggagcagtc gcacagacct ttcctcatgc tgcaggcccg  1140
gcagtctgaa gaccaccctc atcgccggcg tcggcggggc ttggagtgtg atggcaaggt  1200
caacatctgc tgtaagaaac agttctttgt cagtttcaag gacatcggct ggaatgactg  1260
gatcattgct ccctctggct atcatgccaa ctactgcgag ggtgagtgcc cgagccatat  1320
agcaggcacg tccgggtcct cactgtcctt ccactcaaca gtcatcaacc actaccgcat  1380
gcggggccat agcccctttg ccaacctcaa atcgtgctgt gtgcccacca agctgagacc  1440
catgtccatg ttgtactatg atgatggtca aaacatcatc aaaaaggaca ttcagaacat  1500
gatcgtggag gagtgtgggt gctcatagag ttgcccagcc caggggggaaa gggagcaaga  1560
gttgtccaga gaagacagtg gcaaatgaa gaaattttta aggtttctga gttaaccaga  1620
aaaatagaaa ttaaaaacaa aacaaaaaaa aaaacaaaaa taaattaaaa  1680
acaaaacctg atgaaacaga tgaaggaaga tgtggaaaaa atccttagcc agggctcaga  1740
gatgaagcag tgaaagagac aggaattggg agggaaaggg agaatggtgt acccttatt  1800
tcttctgaaa tcacactgat gacatcagtt gtttaaacgg ggtattgtcc tttcccccct  1860
tgaggttcc ttgtgagcct tgaatcaacc aatctagtct gcagtagtgt ggactagaac  1920
aacccaaata gcatctagaa agccatgagt ttgaaagggc ccatcacagg cactttccta  1980
cccaattacc caggtcataa ggtatgtctg tgtgacactt atctctgtgt atatcagcat  2040
acacacacac acacacacac acacacacac acacaggcat ttccacacat tacatatata  2100
cacatactgg taaaagaaca atcgtgtgca ggtggtcaca cttccttttt ctgtaccact  2160
tttgcaacaa aacaa                                                  2175

SEQ ID NO: 124        moltype = DNA  length = 3029
FEATURE                Location/Qualifiers
source                 1..3029
                       mol_type = genomic DNA
                       organism = Homo sapiens
SEQUENCE: 124
ccgcagagag gtgtggtcag ggacatttcc cctggccggg agcccatgga gcactgtcct   60
cagagatgcg caggttaggc tcactgtcta ggccaggccc accttagtca ctgtggactg  120
gcaatggaag ctcttcctgg acacacctgc cctagccctc accctggggt ggaagagaaa  180
tgagcttggc ttgcaactca gaccattcca cggaggcatc ctcccttcc tgggctggtg  240
aataaaagtt tcctgaggtc aaggacttcc ttttccctgc caaatggtg tccagaactt  300
tgaggccaga ggtgatccag tgatttggga gctgcaggtc acacaggctg ctcagagggc  360
tgctgaacag gatgtcctcg gacgacaggc acctgggctc cagctgcggc tccttcatca  420
agactgagcc gtccagcccg tcctcgggca tcgatgccct cagccaccac agccccagtg  480
gctcgtccga cgccagcggc ggctttggcc tggccctggg cacccacgcc aacggtctgg  540
actcgccacc catgtttgca ggcgccgggc tgggaggcac cccatgccgc aagagctacg  600
aggactgtgc cagcggcatc atggaggact cggccatcaa gtgcgagtac atgctcaacg  660
ccatccccaa gcgcctgtgc ctcgtgtgcg ggacattgc ctctggctac cactacggcg  720
tggcctcctg cgaggcttgc aaggccttct tcaaggagca tatccaaggg aacattgagt  780
acagctgccc ggccaccaac gagtgcgaga tcacccaacg gaggcgcaag tcctgccagg  840
cctgccgctt catgaaatgc ctcaaagtgg ggatgctgaa gaggtatgtc cgccttgatc  900
gagtcgcgtg aggccgtcag aaatacaagc gacggctgga ctcagagagc agcccatacc  960
tgagcttaca aatttctcca cctgctaaaa agccattgac caagattgtc tcatacctac  1020
tggtggctga gccggacaag ctctatgcca tgcctccccc tggtatgcct gagggggaca  1080
tcaaggcccct gaccactctc tgtgacctgg cagaccgaga gcttgtggtc atcattggct  1140
gggccaagca catcccaggc ttctcaagcc tctccctggg ggaccagatg agcctgctgc  1200
```

-continued

```
agagtgcctg gatggaaatc ctcatcctgg gcatcgtgta ccgctcgctg ccctatgacg   1260
acaagctggt gtacgctgag gactacatca tggatgagga gcactcccgc ctcgcggggc   1320
tgctggagct ctaccgggcc atcctgcagc tggtacgcag gtacaagaag ctcaaggtgg   1380
agaaggagga gtttgtgacg ctcaaggccc tggccctcgc caactccgat tccatgtaca   1440
tcgaggatct agaggctgtc cagaagctgc aggacctgct gcacgaggca ctgcaggact   1500
acgagctgag ccagcgccat gaggagccct ggaggacggg caagctgctg ctgacactgc   1560
cgctgctgcg gcagacggcc gccaaggcg tgcagcactt ctatagcgtc aaactgcagg   1620
gcaaagtgcc catgcacaaa ctcttcctgg agatgctgga ggccaaggtt ggccaagagc   1680
agcttagagg atctcccaag gatgaaagaa tgtcaagcca tgatggaaaa tgccccttcc   1740
aatcagctgc cttcacaagc agggatcaga gcaactcccc ggggatcccc aatccacgcc   1800
cttctagtcc aaccccctc aatgagagag gcaggcagat ctcacccagc actaggacac   1860
caggaggcca gggaaagcat ctctggctca ccatgtaaca tctggcttgg agcaagtggg   1920
tgttctgcac accaggcagc tgcacctcac tggatcagt gttgctgcga gtgacctcac   1980
ttcagagccc ctctagcaga gtggggcgga agtcctgagtg gttggtgtcc atgaggtgga   2040
agctgctttt atacttaaaa ctcagatcac aacaggaaat gtgtcagtaa caatggaact   2100
ccatccaatg ggaaagttcc tggtactgaa ggggtccatt ggacactcag aaaagaagtt   2160
cagggggccaa cttcttagct ggaatcctgg ccagatgagg accctctccg gggaagggag   2220
aggactgact tagtggaagg tggtgaagtg aggagagttt aggggaacct tcccccaggtg   2280
gaacagatct caagtttacc ctaaacctgc catttctgga aaatctgtaa agaggaaaca   2340
gcctgtctca gctgtactct catgatacag gtcatttgaa atgaaccaag aaataaaaca   2400
tgaaaatcca accatggaga aggtggtatg gctgggtttt gtttggtccc cttgtcctta   2460
tacgttctaa agtttccaga ctggctttgt cactttgtca actcgtcatg tgtgaaaacc   2520
aatctttgca tatagggaac ttcctcgggc cacactttaa gaaccaagta agaggctctc   2580
aagactccag cagagtcggg aggccatggc agcgccttag aggagctgga acctgcaccc   2640
acctgtgtcg gtggggggggg cctcctttcc ccatagactc tgccctccct ctgtgcagat   2700
ggaagtggca ggggagggtg accagcttgt gacaagaagc ctgaagggtc cagagtccat   2760
gctcacggaa cagcaccaaa gaaaagcact atgtggaaag attgttttat tttctaataa   2820
tgataatatg gctggaatgg cttcttaaga tgtatatatt ttttaaaatg gcagttcccc   2880
attgcagcat cacctacttg tatgtctttc tgcctctgta tatgttctcc cagaaacccc   2940
catgtaaatc aaatgcccta ggatgcttcc atcctggtcc catgtatctg gaatctaata   3000
aataaggaaa ggaaaaaaaa aaaaaaaa                                        3029
```

```
SEQ ID NO: 125          moltype = AA  length = 508
FEATURE                 Location/Qualifiers
source                  1..508
                        mol_type = protein
                        organism = Homo sapiens
SEQUENCE: 125
MSSDDRHLGS SCGSFIKTEP SSPSSGIDAL SHHSPSGSSD ASGGFGLALG THANGLDSPP   60
MFAGAGLGGT PCRKSYEDCA SGIMEDSAIK CEYMLNAIPK RLCLVCGDIA SGYHYGVASC   120
EACKAFFKRT IQGNIEYSCP ATNECEITKR RRKSCQACRF MKCLKVGMLK EGVRLDRVRG   180
GRQKYKRRLD SESSPYLSLQ ISPPAKKPLT KIVSYLLVAE PDKLYAMPPP GMPEGDIKAL   240
TTLCDLADRE LVVIIGWAKH IPGFSSLSLG DQMSLLQSAW MEILILGIVY RSLPYDDKLV   300
YAEDYIMDEE HSRLAGLLEL YRAILQLVRR YKKLKVEKEE FVTLKALALA NSDSMYIEDL   360
EAVQKLQDLL HEALQDYELS QRHEEPWRTG KLLLTLPLLR QTAAKAVQHF YSVKLQGKVP   420
MHKLFLEMLE AKVGQEQLRG SPKDERMSSH DGKCPFQSAA FTSRDQSNSP GIPNPRPSSP   480
TPLNERGRQI SPSTRTPGGQ GKHLWLTM                                       508
```

```
SEQ ID NO: 126          moltype = AA  length = 355
FEATURE                 Location/Qualifiers
source                  1..355
                        mol_type = protein
                        organism = Homo sapiens
SEQUENCE: 126
MALSEPILPS FSTFASPCRE RGLQERWPRA EPESGGTDDD LNSVLDFILS MGLDGLGAEA   60
APEPPPPPPP PAFYYPEPGA PPPYSAPAGG LVSELLRPEL DAPLGPALHG RFLLAPPGRL   120
VKAEPPEADG GGGYGCAPGL TRGPRGLKRE GAPGPAASCM RGPGGRPPPP PDTPPLSPDG   180
PARLPAPGPR ASFPPPFGGP GFGAPGPGLH YAPPAPPAFG LFDDAAAAAA ALGLAPPAAR   240
GLLTPPASPL ELLEAKPKRG RRSWPRKRTA THTCSYAGCG KTYTKSSHLK AHLRTHTGEK   300
PYHCNWDGCG WKFARSDELT RHYRKHTGHR PFQCHLCDRA FSRSDHLALH MKRHM         355
```

```
SEQ ID NO: 127          moltype = DNA  length = 1655
FEATURE                 Location/Qualifiers
source                  1..1655
                        mol_type = genomic DNA
                        organism = Homo sapiens
SEQUENCE: 127
gcccgcccgc gccccgacca gcccggcctc gggcagccac tcaccggtgt ccccgtccgc   60
gtccttcctc cccgggtccc ggccatggcc ctgagtgaac ccatcctgcc gtccttctcc   120
actttcgcca gcccgtgccg cgagcgcggc ctgcaggagc gctggccgcg cgccgaaccc   180
gagtccggcg gcaccgacga cgacctcaac agcgtgctgg acttcatcct gtccatgggg   240
ctggatggcc tgggcgccga ggcgcccccg agccgccgc cgcgcccccc gccgcctgcg   300
ttctattacc ccgaacccgg cgcgcccccg ccctacagcg ccccgcgggg tggcctggtg   360
tctgagctgc tgcgacccga gctggatgcg ccgctgggcc cggcactgca cggccgcttt   420
ctgctggcgc cgcccggccg cctggtcaag gccgagcccc ctgaagcgga cggcggcggc   480
ggctacggct gcgcccccgg gctgacccgt ggaccgcgcg gcctcaagcg cgagggcgcc   540
ccgggcccgg cggcttcgtg catgcgaggt cccgggggcc gccccccgcc gccgcccgac   600
acaccgccgc tcagccccga cggccccgcg cgcctgcccg cgcccggtcc gcgcgcctcc   660
ttcccgccgc ctttcggtgg ccctggtttc ggcgcgcccg ggcccggcct gcattacgcg   720
```

-continued

```
ccgcctgcgc ccccagcctt cggtctcttc gacgacgcgg ccgccgccgc ggcagccctg      780
ggcctggcgc cccccgccgc ccgcggtctc ctcacgccgc ctgcgtcccc gctggagctg      840
ctggaggcca agccaaagcg cggccgccgc tcttggcccc gcaaacgcac cgccactcac      900
acctgcagct acgcgggctg cggcaagacc tacaccaaga gttcgcatct gaaggcgcat      960
ctgcgcacgc acacaggtga gaagccctac cactgcaagt gggacggctg cggctggaag     1020
tttgcgcgct cagacgagct cacgcgccac taccgaaagc acacgggcca ccggccattc     1080
cagtgccatc tgtgcgatcg tgccttctcg cgctccgatc acctggcgct gcacatgaaa     1140
cggcacatgt agccgggacg ccccccgccca cctgcgcgcg gccgtggcgg gtcccacgcg     1200
ccgggcgcgg cccctcccca aactgtgact ggtatttatt ggacccagag aaccgggccg     1260
ggcacagcgt ggctacagag ggtctccctc gatgacgacg acgacgacgc caccacccca     1320
gcccccgtct gtgactgaag gcccggtggg aaaagaccac gatcctcctc gacgagtttt     1380
gttttcaaa atggtgcaat aatttaagtg gcatcttctc tcccaccggg tctacactag      1440
aggatcgagg cttgtgatgc cttgtgagaa ataagggcct taatttgtac tgtctgcggc     1500
atttttata atattgtata tagtgactga caaatattgt attactgtac atagagagac     1560
aggtgggcat tttttgggcta cctggttcgt ttttataaga ttttgctggg ttggtttttt     1620
ttttaattaa aaagtttttgc atcttttaaa aaaaa                                1655
```

SEQ ID NO: 128          moltype = AA   length = 723
FEATURE                 Location/Qualifiers
source                  1..723
                        mol_type = protein
                        organism = Homo sapiens
SEQUENCE: 128
```
MSLSMRDPVI PGTSMAYHPF LPHRAPDFAM SAVLGHQPPF FPALTLPPNG AAALSLPGAL      60
AKPIMDQLVG AAETGIPFSS LGPQAHLRPL KTMEPEEEVE DDPKVHLEAK ELWDQFHKRG     120
TEMVITKSGR RMFPPPKVRC SGLDKKAKYI LLMDIIAADD CRYKFHNSRW MVAGKADPEM     180
PKRMYIHPDS PATGEQWMSK VVTFHKLKLT NNISDKHGFT ILNSMHKYQP RFHIVRANDI     240
LKLPYSTFRT YLFPETEFIA VTAYQNDKIT QLKIDNNPFA KGFRDTGNGR REKRKQLTLQ     300
SMRVFDERHK KENGTSDESS SEQAAFNCFA QASSPAASTV GTSNLKDLCP SEGESDAEAE     360
SKEEHGPEAC DAAKISTTTS EEPCRDKGSP AVKAHLFAAE RPRDSGRLDK ASPDSRHSPA     420
TISSSTRGLG AEERRSPVRE GTAPAKVEEA RALPGKEAFA PLTVQTDAAA AHLAQGPLPG     480
LGFAPGLAGQ QFFNGHPLFL HPSQFAMGGA FSSMAAAGMG PLLATVSGAS TGVSGLDSTA     540
MASAAAAQGL SGASAATLPF HLQQHVLASQ GLAMSPFGSL FPYPYTYMAA AAAASSAAAS     600
SSVHRHPFLN LNTMRPRLRY SPYSIPVPVP DGSSLLTTAL PSMAAAAGPL DGKVAALAAS     660
PASVAVDSGS ELNSRSSTLS SSSMSLSPKL CAEKEAATSE LQSIQRLVSG LEAKPDRSRS     720
ASP                                                                  723
```

SEQ ID NO: 129          moltype = AA   length = 743
FEATURE                 Location/Qualifiers
source                  1..743
                        mol_type = protein
                        organism = Homo sapiens
SEQUENCE: 129
```
MSLSMRDPVI PGTSMAYHPF LPHRAPDFAM SAVLGHQPPF FPALTLPPNG AAALSLPGAL      60
AKPIMDQLVG AAETGIPFSS LGPQAHLRPL KTMEPEEEVE DDPKVHLEAK ELWDQFHKRG     120
TEMVITKSGR RMFPPPKVRC SGLDKKAKYI LLMDIIAADD CRYKFHNSRW MVAGKADPEM     180
PKRMYIHPDS PATGEQWMSK VVTFHKLKLT NNISDKHGFT LAFPSDHATW QGNYSFGTQT     240
ILNSMHKYQP RFHIVRANDI LKLPYSTFRT YLFPETEFIA VTAYQNDKIT QLKIDNNPFA     300
KGFRDTGNGR REKRKQLTLQ SMRVFDERHK KENGTSDESS SEQAAFNCFA QASSPAASTV     360
GTSNLKDLCP SEGESDAEAE SKEEHGPEAC DAAKISTTTS EEPCRDKGSP AVKAHLFAAE     420
RPRDSGRLDK ASPDSRHSPA TISSSTRGLG AEERRSPVRE GTAPAKVEEA RALPGKEAFA     480
PLTVQTDAAA AHLAQGPLPG LGFAPGLAGQ QFFNGHPLFL HPSQFAMGGA FSSMAAAGMG     540
PLLATVSGAS TGVSGLDSTA MASAAAAQGL SGASAATLPF HLQQHVLASQ GLAMSPFGSL     600
FPYPYTYMAA AAAASSAAAS SSVHRHPFLN LNTMRPRLRY SPYSIPVPVP DGSSLLTTAL     660
PSMAAAAGPL DGKVAALAAS PASVAVDSGS ELNSRSSTLS SSSMSLSPKL CAEKEAATSE     720
LQSIQRLVSG LEAKPDRSRS ASP                                            743
```

SEQ ID NO: 130          moltype = DNA   length = 4754
FEATURE                 Location/Qualifiers
source                  1..4754
                        mol_type = genomic DNA
                        organism = Homo sapiens
SEQUENCE: 130
```
gaattctaga ggcggcggag ggtggcgagg agctctcgct ttctctcgct ccctccctct      60
ccgactccgt ctctctctct ctctctctct ctccctcc tctctttccc tctgttccat      120
ttttccccc tctaaatcct ccctgccctg cgcgcctgga cacagattta ggaagcgaat      180
tcgctcacgt tttaggacaa ggaagagaga gaggcacggg agaagagccc agcaagattt      240
ggattgaaac cgagacaccc tccggaggct cggagcagag gaaggaggag gagggcggcg      300
aacggaagcc agtttgcaat tcaagttttg atagcgctgg tagaaggggg tttaaatcag      360
atttttttt ttttaaagga gagagacttt ttccgctctc tcgctccctg ttaaagccgg      420
gtctagcaca gctgcagacg ccaccagcga gaaagaggga gaggaagaca gatagggggc      480
gggggaagaa gaaaagaaa ggtaaaaagt cttctaggag aacctttcac atttgcaaca      540
aaagacctag gggctggaga gagattcctg ggacgcaggg ctggagtgtc tatttcgagc      600
tcagcggcag ggctcggggcg cgagtcgaga ccctgctcgc tcctctcgct tctgaaaccg      660
acgttcagga gcggctttt aaaaacgcaa ggcacaagga cggtcacccg cgcgactatg      720
tttgctgatt tttcgccttg ccctctttaa aagcggcctc ccattctcca aaagacactt      780
cccctcctcc ctttgaagtg cattagttgt gatttctgcc tccttttctt ttttctttct      840
tttttgtttt gcttttttcc ccctttttgaa ttatgtgctg ctgttaaaca acaacaaaaa      900
aacaacaaaa cacagcagct gcggacttgt ccccggctgg agcccagcgc cccgcctgga      960
```

-continued

```
gtggatgagc ctctccatga gagatccggt cattcctggg acaagcatgg cctaccatcc   1020
gttcctacct caccgggcgc cggacttcgc catgagcgcg gtgctgggtc accagccgcc   1080
gttcttcccc gcgctgacgc tgcctcccaa cggcgcggcg gcgctctcgc tgccgggcgc   1140
cctggccaag ccgatcatgg atcaattggt gggggcggcc gagaccggca tcccgttctc   1200
ctccctgggg ccccaggcgc atctgaggcc tttgaagacc atggagcccg aagaagaggt   1260
ggaggacgac cccaaggtgc acctggaggc taaagaactt tgggatcagt ttcacaagcg   1320
gggcaccgag atggtcatta ccaagtcggc aaggcgaatg tttcctccat ttaaagtgag   1380
atgttctggg ctgataaaa aagccaaata cattttattg atggacatta tagctgctga   1440
tgactgtcgt tataaatttc acaattctcg gtggatggtg gctggtaagg ccgacccga   1500
aatgccaaag aggatgtaca ttcacccgga cagccccgct actggggaac agtggatgtc   1560
caaagtcgtc actttccaca aactgaaact caccaacaac atttcagaca aacatggatt   1620
tactatattg aactccatgc acaaatacca gccccggttc cacattgtaa gagccaatga   1680
catcttgaaa ctcccttata gtacatttcg gacatacttg ttccccgaaa ctgaattcat   1740
cgctgtgact gcataccaga atgataagat aacccagtta aaaatagaca acaacccttt   1800
tgcaaaaggt ttccgggaca ctggaaatgg ccgaagagaa aaaagaaaac agctcaccct   1860
gcagtccatg agggtgtttg atgaaagaca caaaaaggag aatgggacct ctgatgagtc   1920
ctccagtgaa caagcagctt tcaactgctt cgcccaggct tcttctccag ccgcctccac   1980
tgtagggaca tcgaacctca aagatttatg tcccagcgag ggtgagagcg acgccgaggc   2040
cgagagcaaa gaggagcatg gccccgaggc ctgcgacgcg gccaagatct ccaccaccac   2100
gtcggaggag ccctgccgtg acaagggcag ccccgcggtc aaggctacc ttttcgctgc   2160
tgagcggccc cgggacagcg ggcggctgga caaagcgtcg cccgactcac gccatagccc   2220
cgccaccatc tcgtccagca ctcgcgggcct gggcgcggcg gagcgcagga gcccggttcg   2280
cgagggcaca gcgccggcca aggtggaaga ggcgcgcgcg ctcccgggca aggaggcctt   2340
cgcgccgctc acggtgcaga cggacgcggc cgccgcgcac ctggcccagg gcccctgcc   2400
tggcctcggc ttcgccccgg gcctggcggg ccaacagttc ttcaacgggc acccgctctt   2460
cctgcacccc agccagtttg ccatgggggg cgccttctcc agcatggcgg ccgctggcat   2520
gggtccctc ctggccacgg tttctggggc ctccaccggt gtctcgggcc tggattccac   2580
ggccatggcc tctgccgctg cggcgcaggg actgtccggg gcgtccgcgg ccaccctgcc   2640
cttccacctc cagcagcacg tcctggcct tcagggcctg gccatgtccc ctttcggaag   2700
cctgttccct taccccctaca cgtacatggc cgcagcgggcg gccgcctcct ctgcggcagc   2760
ctccagctcg gtgcaccgcc accccttcct caatctgaac accatgcgcc cgcggctgcg   2820
ctacagcccc tactccatcc cggtgccggt cccggacggc agcagtctgc tcaccaccgc   2880
cctgccctcc atggcggcgg ccgcgggggcc cctggacggc aaagtcgccg ccctggccgc   2940
cagcccggcc tcggtggcag tggactcggg ctctgacctc aacagccgct cctccacgct   3000
ctcctccagc tccatgtcct tgtcgcccaa actctgcgcg gagaagagag cggccaccag   3060
cgaactgcag agcatccagc ggttggttag cggcttggaa gccaagccgg acaggtcccg   3120
cagcgcgtcc ccgtagaccc gtcccagaca cgtcttttca ttccagtcca gttcaggctg   3180
ccgtgcactt tgtcggatat aaaataaacc acgggcccgc catggcgtta gcccttcctt   3240
ttgcagttgc gtctgggaag gggccccgga ctccctcgga agaatgtgct agagacagcc   3300
cctgtcttct tggcgtggtt tatatgtccg ggatctggat cagattctgg gggctcagaa   3360
acgtcggttg cattgagcta ctgggggtag gagttccaac atttatgtcc agagcaactt   3420
ccagcaaggc tggtctgggt ctctgcccac caggcgggga ggtgttcaaa gacatctccc   3480
tcagtgcgga tttatatata tatttttcct tcactgtcgtc aagtggaaac aaaaacaaaa   3540
tctttcaaaa aaaaaatcgg gacaagtgaa cacattaaca tgattctgtt tgtgcagatt   3600
aaaaactttta tagggacttg cattatcggt tctcaataaa ttactgagca gctttgtttg   3660
gggagggaag tccctaccat ccttgtttag tctatattaa gaaaatctgt gtcttttaa   3720
tattcttgtg atgtttttcag agccgctgta ggtctcttct tgcatgtcca cagtaatgta   3780
tttgtggttt ttatttttgaa cgcttgcttt tagagagaaa acaatatagc ccctaccct   3840
tttcccaatc ctttgccctc aaatcagtga cccaagggag gggggattt aaagggaagg   3900
agtgggcaaa acacataaaa tgaatttatt atatctaagc tctgtagcag gattcatgtc   3960
gttctttgac agttctttct ctttcctgta tatgcaataa caaggtttta aaaaaataat   4020
aaagaagtga gactattaga caaagtattt atgtaattat ttgataactc ttgtaaatag   4080
gtggaatatg aatgcttgga aaattaaact ttaatttatt gacattgtac atagctctgt   4140
gtaaataaa ttgcaactgt caggttttgt gttcttgttt tcctttagtt gggtttattt   4200
ccaggtcaca gaattgctgt taacactaga aaacacactt cctgcaccaa caccaatacc   4260
ctttcaaaag agttgtctgc aacatttttg ttttcttttt taatgtccaa aagtggggga   4320
aagtgctatt tcctattttc accaaaattg gggaaggagt gccactttcc agctccactt   4380
caaattcctt aaaatataac tgagattgct gtggggaggg aggagggcag aggctgcggt   4440
ttgacttttt aatttttctt ttgttatttg tatttgctag tctctgattt cctcaaaacg   4500
aagtggaatt tactactgtt gtcagtatcg gtgtttttgaa ttggtgcctg cctatagaga   4560
tatattcaca gttcaaaagt caggtgctga gagatggttt aaagacaaat tcatgaaggt   4620
atattttgtg ttatagttgt tgatgagttc tttggttttc tgtattttc ccctctctt   4680
taaaacatca ctgaaatttc aataaatttt tattgaaatg tctaaaaaaa aaaaaaaaa   4740
aaaaaaaaaa aaaa   4754
```

```
SEQ ID NO: 131         moltype = DNA   length = 4814
FEATURE                Location/Qualifiers
source                 1..4814
                       mol_type = genomic DNA
                       organism = Homo sapiens
SEQUENCE: 131
gaattctaga ggcggcggag ggtggcgagg agctctcgct ttctctcgct ccctccctct   60
ccgactccgt ctctctctct ctctctctct ctccctccc tctctttccc tctgttccat   120
tttttccccc tctaaatcct ccctgccctg cgcgcctgga cacagattta ggaagcgaat   180
tcgctcacgt tttaggacaa ggaagagaga gaggcacggg agaagagccc agcaagattt   240
ggattgaaac cgagacaccc tccggaggct cggagcagag gaaggaggag gagggcggcg   300
aacggaagca gtttgcaat tcaagttttg atagcgctgg tagaaggggg tttaaatcag   360
attttttttt ttttaaagga gagagacttt ttccgctctc tcgctccctg ttaaagccgg   420
gtctagcaca gctgcagacg ccaccagcga gaaagaggga gaggaagaca gatagggggc   480
```

```
gggggaagaa gaaaaagaaa ggtaaaaagt cttctaggag aacctttcac atttgcaaca    540
aaagacctag gggctggaga gagattcctg ggacgcaggg ctggagtgtc tatttcgagc    600
tcagcggcag ggctcgggcg cgagtcgaga ccctgctcgc tcctctcgct tctgaaaccg    660
acgttcagga gcggcttttt aaaaacgcaa ggcacaagga cggtcacccg cgcgactatg    720
tttgctgatt tttcgccttg ccctctttaa aagcggcctc ccattctcca aaagacactt    780
cccctcctcc ctttgaagtg cattagttgt gatttctgcc tccttttctt ttttctttct    840
tttttgtttt gcttttttccc cccttttttgaa ttatgtgctg ctgttaaaca acaacaaaaa    900
aacaacaaaa cacagcagct gcggacttgt ccccggctgg agcccagcgc cccgcctgga    960
gtggatgagc ctctccatga gagatccggt cattcctggg acaagcatgg cctaccatcc   1020
gttcctacct caccgggcgc cggacttcgc catgagcgcg gtgctgggtc accagccgcc   1080
gttcttcccc gcgctgacgc tgcctcccaa cggcgcggcg gcgctctcgc tgccgggcgc   1140
cctggccaag ccgatcatgg atcaattggt gggggcggcc gagaccggca tcccgttctc   1200
ctccctgggg ccccaggcgc atctgaggcc tttgaagacc atggagcccg aagaagaggt   1260
ggaggacgac cccaaggtgc acctggaggc taaagaactt tgggatcagt ttcacaagcg   1320
gggcaccgag atggtcatta ccaagtcggg aaggcgaatg tttcctccat ttaaagtgag   1380
atgttctggg ctggataaaa aagccaaata cattttattg atggacatta tagctgctga   1440
tgactgtcgt tataaatttc acaattctcg gtggatggtg gctggtaagg ccgaccccga   1500
aatgccaaag aggatgtaca ttcacccgga cagccccgct actggggaac agtggatgtc   1560
caaagtcgtc actttccaca aactgaaact caccaacaac atttcagaca aacatggatt   1620
tactttggcc ttcccaagtg atcacgctac gtggcagggg aattatagtt ttggtactca   1680
gactatattg aactccatgc acaaataccca gccccggttc cacattgtaa gagccaatga   1740
catcttgaaa ctccccttata gtacatttcg gacatacttg ttccccgaaa ctgaattcat   1800
cgctgtgact gcataccaga atgataagat aacccagtta aaaatagaaca acaacccttt   1860
tgcaaaaggt ttccgggaca ctggaaatgg ccgaagagaa aaaagaaaac agctcaccct   1920
gcagtccatg agggtgtttg atgaaagaca caaaaaggag aatgggacct ctgatgagtc   1980
ctccagtgaa caagcagctt tcaactgctt cgcccaggct tcttctccag ccgcctccaa   2040
tgtagggaca tcgaacctca aagatttatg tcccagcgag ggtgagacgg acgccgaggc   2100
cgagagcaaa gaggagcatg gccccgaggc ctgcgacgcg gccaagatct ccaccaccac   2160
gtcggaggag ccctgccgtg acaagggcag ccccgcggtc aaggctcacc ttttcgctgc   2220
tgagcggccc cgggacagcg ggcggctgga caaagcgcc cccgactcac gccatagccc   2280
cgccaccatc tcgtccagca ctcgcgcct gggcgcggag gagcgcagga gcccggttcg   2340
cgagggcaca gcgccggcca aggtggaaga ggcgcgcgcg ctcccgggca aggaggcctt   2400
cgcgccgctc acggtgcaga cggacgcggc cgccgcgcac ctggcccagg gcccctgcc   2460
tggcctcggc ttcgccccgg gcctggcggg ccaacagttc ttcaacgggc accgctctt   2520
cctgcacccc agccagtttg ccatggggggg cgccttctcc agcatggccg ccgctggcat   2580
gggtcccctc ctggccacgg tttctgggc ctccaccggt gtctcgggcc tggattccac   2640
ggccatggcc tctgccgctg cggcgcaggg actgtccggg gcgtccgcgg ccaccctgcc   2700
cttccacctc cagcagcacg tcctggcctc tcagggcctg gccatgtccc ctttcggaag   2760
cctgttccct tacccctaca cgtacatggc cgcagcgggc gccgcctcct ctgcggcagc   2820
ctccagctcg gtgcaccgcc acccccttcct caatctgaac accatgcgcc gcgggctgcg   2880
ctacagcccc tactccatcc cggtgccggt cccggacggc agcagtctgc tcaccaccgc   2940
cctgcctctc atggcggcgg ccgcgggcc cctggacggc aaagtcgccg ccctggccgc   3000
cagcccggcc tcggtggcag tggactcggg ctctgaactc aacagccgct cctccacgct   3060
ctcctccagc tccatgtcct tgtcgcccaa actctgcgcg gagaaagagg cggccaccag   3120
cgaactgcag agcatccagc ggttggttag cggcttggaa gccaagccgg acaggtcccg   3180
cagcgcgtcc ccgtagaccc gtcccagaca cgtctttca ttccagtcca gttcaggctg   3240
ccgtgcactt tgtcggatat aaaataaacc acgggcccgc catggcgtta gcccttcctt   3300
ttgcagttgc gtctgggaag gggcccggga ctccctcgag agaatgtgct agagacagcc   3360
cctgtcttct tggcgtggtt tatatgtccg ggatctggat cagattctgg gggctcagaa   3420
acgtcggttg cattgagcta ctggggggtag gagttccaac atttatgtcc agagcaactt   3480
ccagcaaggc tggtctgggt ctctgcccac caggcgggga ggtgttcaaa gacatctccc   3540
tcagtgcgga tttatatata tatttttcct tcactgtgtc aagtggaaac aaaaacaaaa   3600
tctttcaaaa aaaaaatcgg gacaagtgaa cacattaaca tgattctgtt tgtgcagatt   3660
aaaaacttta tagggacttg cattatcggt tctcaataaa ttactgagca gctttgtttg   3720
gggagggaag tccctaccat ccttgtttag tctatattaa gaaaatctgt gtctttttaa   3780
tattcttgtg atgttttcag agccgctgta ggtctcttct tgcatgtcca cagtaatgta   3840
tttgtggttt ttattttgaa cgcttgcttt tagagagaaa acaatatagc cccctaccct   3900
tttcccaatc ctttgccctc aaatcagtga cccaagggag ggggggattt aaagggaagg   3960
agtgggcaaa acacataaaa tgaatttatt atatctaagc tctgtagcag gattcatgtc   4020
gttctttgac agttctttct ctttcctgta tatgcaataa caaggtttta aaaaaataat   4080
aaagaagtga gactattaga caaagtattt atgtaattat ttgataactc ttgtaaatag   4140
gtggaatatg aatgcttgga aaattaaact ttaatttatt gacattgtac atagctctgt   4200
gtaaataga ttgcaactgt caggttttgt gttcttgttt tcctttagtt gggtttattt   4260
ccaggtcaca gaattgctgt taacactaga aaacacactt cctgcaccaa caccaatacc   4320
ctttcaaaag agttgtctgc aacattttttg ttttcttttt taatgtccaa aagtgggggga   4380
aagtgctatt tcctattttc accaaaattg gggaaggagt gccactttcc agctccactt   4440
caaattcctt aaaatataac tgagattgct gtggggaggg aggagggcag aggctgcggt   4500
ttgactttt aattttttctt ttgttatttg tatttgctag tctctgattt cctcaaaacg   4560
aagtggaatt tactactgtt gtcagtatcg gtgttttgaa ttggtgcctg cctatagaga   4620
tatattcaca gttcaaaagt caggtgctga gagatggttt aaagacaaat tcatgaaggt   4680
atattttgtg ttatagttgt tgatgagttc tttggttttc tgtatttttc cccctctctt   4740
taaaacatca ctgaaatttc aataaatttt tattgaaatg tctaaaaaaa aaaaaaaaaa   4800
aaaaaaaaaa aaaa                                                     4814
```

```
SEQ ID NO: 132       moltype = AA  length = 233
FEATURE              Location/Qualifiers
source               1..233
                     mol_type = protein
                     organism = Homo sapiens
```

```
SEQUENCE: 132
MELPTKPGTF DLGLATWSPS FQGETHRAQA RRRDVGRQLP EYKAVVVGAS GVGKSALTIQ   60
LNHQCFVEDH DPTIQDSYWK ELTLDSGDCI LNVLDTAGQA IHRALRDQCL AVCDGVLGVF  120
ALDDPSSLIQ LQQIWATWGP HPAQPLVLVG NKCDLVTTAG DAHAAAAALA HSWGAHFVET  180
SAKTRQGVEE AFSLLVHEIQ RVQEAMAKEP MARSCREKTR HQKATCHCGC SVA         233

SEQ ID NO: 133              moltype = DNA   length = 826
FEATURE                     Location/Qualifiers
source                      1..826
                            mol_type = genomic DNA
                            organism = Homo sapiens
SEQUENCE: 133
agagcgtccc agcgcgcccg cctccccacg gacacagagc ctgctgccca cgtctcttcc   60
ctgagctgcc tgctggggtc atggagctgc caacaaagcc tggcaccttc gacctgggcc  120
tggccacatg gagcccttcc ttccaggggg aaacccaccg ggctcaggca cgccgcaggg  180
atgttggcag gcagctgcct gagtacaagg ctgtggtggt gggcgccagt ggcgtgggca  240
agagtgcgct gaccatccag ctgaaccacc agtgcttcgt ggaggaccac gaccccacca  300
tccaggattc ctactggaag gagttgaccc tggacagtgg gactgcatt ctgaatgtgc   360
tggacacagc agggcaggcc atccataggg ccctgcgtga ccagtgcctg gctgtctgtg  420
atggtgtgct gggcgtcttc gctctcgatg acccctcgtc tctgatccag ctgcagcaga  480
tatgggccac ctggggccct caccccgccc agcccttgt cctcgtgggc aacaagtgtg   540
accttgtgac cactgctgga gatgctcatg ccgctgctgc agccctcgca cacagctggg  600
gggcccactt cgtggagacc tcggccaaaa cacggcaagg cgtggaggag gccttttccc  660
tgctggtcca tgagatccag agggtccagg aggccatggc gaaggagccc atggcaaggt  720
cctgtaggga aagacccgg caccagaagg ccacctgcca ctgtggctgc tctgtggcct   780
gaaggtcttg gccaagaaat gtagacccttt ccccaggcca gggtga              826

SEQ ID NO: 134              moltype = AA   length = 536
FEATURE                     Location/Qualifiers
source                      1..536
                            mol_type = protein
                            organism = Homo sapiens
SEQUENCE: 134
MGSNKSKPKD ASQRRRSLEP AENVHGAGGG AFPASQTPSK PASADGHRGP SAAFAPAAAE   60
PKLFGGFNSS DTVTSPQRAG PLAGGVTTFV ALYDYESRTE TDLSFKKGER LQIVNNTEGD  120
WWLAHSLSTG QTGYIPSNYV APSDSIQAEE WYFGKITRRE SERLLLNAEN PRGTFLVRES  180
ETTKGAYCLS VSDFDNAKGL NVKHYKIRKL DSGGFYITSR TQFNSLQQLV AYYSKHADGL  240
CHRLTTVCPT SKPQTQGLAK DAWEIPRESL RLEVKLGQGC FGEVWMGTWN GTTRVAIKTL  300
KPGTMSPEAF LQEAQVMKKL RHEKLVQLYA VVSEEPIYIV TEYMSKGSLL DFLKGETGKY  360
LRLPQLVDMA AQIASGMAYV ERMNYVHRDL RAANILVGEN LVCKVADFGL ARLIEDNEYT  420
ARQGAKFPIK WTAPEAALYG RFTIKSDVWS FGILLTELTT KGRVPYPGMV NREVLDQVER  480
GYRMPCPPEC PESLHDLMCQ CWRKEPEERP TFEYLQAFLE DYFTSTEPQY QPGENL      536

SEQ ID NO: 135              moltype = DNA   length = 4131
FEATURE                     Location/Qualifiers
source                      1..4131
                            mol_type = genomic DNA
                            organism = Homo sapiens
SEQUENCE: 135
caaacaagtg cggccatttc accagcccag gctggcttct gctgttgact ggctgtggca   60
cctcagcag cccctttccc ctctagcctc agtttatcac cgcaagagct accattcatc   120
tagcacaacc tgaccatcct cacactggtc agttccaacc ttcccaggaa tcttctgtgg  180
ccatgttcac tccggtttta cagaacagag aacagaagct cagagaagtg aagcaacttg  240
cccagctatg agagacagag ccaggatttg aaaccagatg aggacgctga ggcccagaga  300
gggaaagcca cttgcctagg gacacacagc ggggagaggt ggagcagggc ctctatttcg  360
agaccctga ctccacacct ggtgtttgtg ccaagacccc aggctgcctc ccaggtcctc   420
tgggacagcc cctgccttct accaggacca tgggtagcaa caagagcaag cccaaggatg  480
ccagccagcg gcgccgcagc ctggagcccg ccgagaacgt gcacggcgct ggcgggggcg  540
ctttccccgc ctcgcagacc cccagcaagc cagcctcggc cgacgggcac cgcggccca   600
gcgcggcctt cgcccccgcg ccgcgccagc ccaagctgtt cggaggcttc aactcctcgg  660
acaccgtcac ctccccgcag agggcgggcc cgctggccgg tggagtgacc accttttgtgg  720
ccctctatga ctatgagtct aggacggaga cagacctgtc cttcaagaaa ggcgagcggc  780
tccagattgt caacaacaca gagggagact ggtggctggc ccactcgctc agcacaggac  840
agacaggcta tatccccagc aactacgtgg cgccctccga ctccatccag gctgaggagt  900
ggtattttgg caagatcacc agacgggagt cagagcggtt actgctcaat gcagagaacc  960
cgagagggac cttcctcgtg cgagaaagtg agaccacgaa aggtgcctac tgcctctcag 1020
tgtctgactt cgacaacgcc aagggcctca acgtgaagca ctacaagatc cgcaagctgg 1080
acagcggcgg cttctacatc acctcccgca cccagttcaa cagcctgcag cagctggtgg 1140
cctactactc caaacacgct gatggcctgt gccaccgtct gaccaccgt tgccccacgt 1200
ccaagccgca gactcagggc ctggccaagg atgcctggga gatccctcgg gagtcgctgc 1260
ggctggaggt caagctgggc cagggctgct ttggcgaggt gtggatgggg acctggaacg 1320
gtaccaccag ggtggccatc aaaacctga agcctggcac gatgtctcca gaggccttcc 1380
tgcaggaggc ccaggtcatg aagaagctga ggcatgagaa gctggtgcag ttgtatgctg 1440
tggtttcaga ggagcccatt tacatcgtca cggagtacat gagcaagggg agtttgctgg 1500
actttctcaa gggggagaca ggcaagtacc tgcggctgcc tcagctggtg gacatggctg 1560
ctcagatcgc ctcaggcatg gcgtacgtgg agcggatgaa ctacgtccac cgggaccttc 1620
gtgcagccaa catcctggtg ggagagaacc tggtgtgcaa agtggccgac tttgggctgg 1680
ctcggctcat tgaagacaat gagtacacgc gcggcaagg tgccaaattc cccatcaagt 1740
ggacggctcc agaagctgcc ctctatggcc gcttcaccat caagtcggac gtgtggtcct 1800
```

-continued

```
tcgggatcct gctgactgag ctcaccacaa agggacgggt gccctaccct gggatggtga  1860
accgcgaggt gctggaccag gtggagcggg gctaccggat gccctgcccg ccggagtgtc  1920
ccgagtccct gcacgacctc atgtgccagt gctggcggaa ggagcctgag gagcggccca  1980
ccttcgagta cctgcaggcc ttcctggagg actacttcac gtccaccgag ccccagtacc  2040
agcccgggga gaacctctag gcacaggcgg gcccagaccg gcttctcggc ttggatcctg  2100
ggctgggtgg cccctgtctc ggggcttgcc ccactctgcc tgcctgctgt tggtcctctc  2160
tctgtggggc tgaattgcca ggggcgaggc ccttcctctt tggtggcatg gaaggggctt  2220
ctggacctag ggtggcctga gagggcggtg ggtatgcgag accagcacgg tgactctgtc  2280
cagctcccgc tgtggccgca cgcctctccc tgcactccct cctggagctc tgtgggtctc  2340
tggaagagga accaggagaa gggctggggc cggggctggg ggtgcccttt tccagcctca  2400
gcctactccg ctcactgaac tccttcccca cttctgtgcc accccggtc tatgtcgaga  2460
gctggccaaa gagcctttcc aaagaggagc gatgggcccc tggccccgcc tgcctgccac  2520
cctgcccctt gccatccatt ctggaaacac ctgtaggcag aggctgccga gacagaccct  2580
ctgccgctgc ttccaggctg ggcagcacaa ggccttgcct ggcctgatga tggtgggtgg  2640
gtgggatgag tacccctca aaccctgccc tccttagacc tgaggggaccc ttcgagatca  2700
tcacttcctt gcccccattt cacccatggg gagacagttg agagcgggga tgtgacatgc  2760
ccaaggccac ggagcagttc agagtggagg cgggcttgga acccggtgct ccctctgtca  2820
tcctcaggaa ccaacaattc tcggaggca tcatggaaag actgggacag cccaggaaac  2880
aaggggtctg aggatgcatt cgagatggca gattcccact gccgctgccc gctcagccca  2940
gctgttggga acagcatgga ggcagatgtg gggctgagct ggggaatcag ggtaaaaggt  3000
gcaggtgtgg agagagaggc ttcaatcggc ttgtgggtga tgtttgacct tcagagccag  3060
ccggctatga aagggagcga gcccctcggc tctggaggca atcaagcaga catagaagag  3120
ccaagagtcc aggaggccct ggtcctggcc tccttccccg tactttgtcc cgtggcattt  3180
caattcctgg ccctgttctc ctccccaagt cggcaccctt taactcatga ggagggaaaa  3240
gagtgcctaa gcgggggtga aagaggacgt gttacccact gccatgcacc aggactggct  3300
gtgtaacctt gggtggcccc tgctgtctct ctgggctgca gagtctgccc cacatgtggc  3360
catggcctct gcaactgctc agctctggtc caggccctgt ggcaggacac acatggtgag  3420
cctagccctg ggacatcagg agactgggct ctggctctgt tcggcctttg ggtgtgtggt  3480
ggattctccc tgggcctcag tgtgcccatc tgtaaagggg cagctgacag tttgtggcat  3540
cttgccaagg gtccctgtgt gtgtgtatgt gtgtgccatgt gtgcgtgtct ccatgtgcgt  3600
ccatatttaa catgtaaaaa tgtccccccc gctccgtccc ccaaacatgt tgtacatttc  3660
accatggccc cctcatcata gcaataacat tcccactgcc aggggttctt gagccagcca  3720
ggccctgcca gtggggaagg aggccaagca gtgcctgcct atgaaatttc aacttttcct  3780
ttcatacgtc tttattaccc aagtcttctc ccgtccattc cagtcaaatc tgggctcact  3840
cacccagcg agctctcaaa tccctctcca actgcctaag gccctttgtg taaggtgtct  3900
taatactgtc ctttttttttt ttttaacagt gttttgtaga tttcagatga ctatgcagag  3960
gcctggggga ccctggctc tgggccgggc ctggggctcc gaaattccaa ggcccagact  4020
tgcggggggt ggggggggtat ccagaattgg ttgtaaatac tttgcatatt gtctgattaa  4080
acacaaacag acctcagaat ctgatcaaca gttaaaaaaa aaaaaaaaa a  4131
```

```
SEQ ID NO: 136        moltype = DNA  length = 4056
FEATURE               Location/Qualifiers
source                1..4056
                      mol_type = genomic DNA
                      organism = Homo sapiens
SEQUENCE: 136
ggcccggaat ccattccggc ctgggagccg gagcggccag gccgccgtct gcccgtcccg  60
ctggacgtcc cgcggtccgc cctcccgtgc gtccgtctgc cggtgagccc gcccgcccgc  120
cggcccagaa cagagaacag aagctcagag aagtgaagca acttgcccag ctatgagaga  180
cagagccagg atttgaaacc agatgaggac gctgaggccc agagagggaa agccacttgc  240
ctaggacac acagcgggga gaggtggagc agggcctcta tttcgagacc cctgactcca  300
cacctggtgt ttgtgccaag accccaggct gcctccagg tcctctggga cagcccctgc  360
cttctaccag gaccatgggt agcaacaaga gcaagcccaa ggatgccagc cagcggcgcc  420
gcagcctgga gcccgccgag aacgtgcacg gcgctggcgg gggcgctttc cccgcctcgc  480
agaccccag caagccagcc tcggccgacg gccaccgcgg ccccagcgcg gccttcgcgc  540
ccgcggccgc cgagcccaag ctgttcggag gcttcaactc ctcggacacc gtcacctccc  600
cgcagagggc gggcccgctg gccggtggag tgaccacctt tgtggccctc tatgactatg  660
agtctaggac ggagacagac ctgtccttca agaaaggcga gcggctccag attgtcaaca  720
acacagaggg agactggtgg ctggcccact cgctcagcac aggacagaca ggctacatcc  780
ccagcaacta cgtggcgccc tccgactcca tccaggctga ggagtggtat tttggcaaga  840
tcaccagacg ggagtcagag cggttactgc tcaatgcaga gaacccgaga gggaccttcc  900
tcgtgcgaga aagtgagacc acgaaaggtg cctactgcct ctcagtgtct gacttcgaca  960
acgccaaggg cctcaacgtg aagcactaca agatccgcaa gctggacagc ggcggcttct  1020
acatcacctc ccgcacccag ttcaacagcc tgcagcagct ggtggcctac tactccaaac  1080
acgccgatgg cctgtgccac cgcctcacca ccgtgtgccc cacgtccaag ccgcagactc  1140
agggcctggc caaggatgcc tgggagatcc ctcgggagtc gctgcggctg gaggtcaagc  1200
tgggccaggg ctgctttggc gaggtgtgga tgggacctg gaacggtacc accagggtgg  1260
ccatcaaaac cctgaagcct ggcacgatgt ctccagaggc cttcctgcag gaggcccagg  1320
tcatgaagaa gctgaggcat gagaagctgg tgcagttgta tgctgtggtt tcagaggagc  1380
ccatttacat cgtcacggag tacatgagca aggggagttt gctggacttt ctcaaggggg  1440
agacaggcaa gtacctgcgg ctgcctcagc tggtggacat ggctgctcag atcgcctcag  1500
gcatggcgta cgtggagcgg atgaactacg tccaccggga ccttcgtgca gccaacatcc  1560
tggtgggaga gaacctggtg tgcaaagtgg ccgactttgg gctggctcgg ctcattgaag  1620
acaatgagta cacggcgcag caaggtgcca aattcccat caagtggacg gctccagaag  1680
ctgccctcta tggccgcttc accatcaagt cggacgtgtg gtccttcggg atcctgctga  1740
ctgagctcac cacaaaggga cgggtgcct accctgggat ggtgaaccgc gaggtgctgg  1800
accaggtgga gcgggggctac cggatgccct gcccgccgga gtgtcccgag tcctgcacg  1860
acctcatgtg ccagtgctgg cggaaggagc ctgaggagcg gcccaccttc gagtacctgc  1920
aggccttcct ggaggactac ttcacgtcca ccgagcccca gtaccagccc ggggagaacc  1980
```

-continued

```
tctaggcaca ggcgggccca gaccggcttc tcggcttgga tcctgggctg ggtggcccct  2040
gtctcggggc ttgccccact ctgcctgcct gctgttggtc ctctctctgt ggggctgaat  2100
tgccagggrc gaggccctc ctctttggtg gcatggaagg ggcttctgga cctagggtgg  2160
cctgagaggg cggtggggtat gcgagaccag cacggtgact ctgtccagct cccgctgtgg  2220
ccgcacgcct ctccctgcac tccctcctgg agctctgtgg gtctctggaa gaggaaccag  2280
gagaagggct ggggccgggg ctgagggtgc ccttttccag cctcagccta ctccgctcac  2340
tgaactcctt ccccacttct gtgccacccc cggtctatgt cgagagctgg ccaaagagcc  2400
tttccaaaga ggagcgatgg gccctggcc ccgcctgcct gccaccctgc cccttgccat  2460
ccattctgga aacacctgta ggcagaggct gccgagacag accctctgcc gctgcttcca  2520
ggctgggcag cacaaggcct tgcctggcct gatgatggtg ggtgggtggg atgagtaccc  2580
cctcaaaccc tgccctcctt agacctgagg gaccccttcga gatcatcact tccttgcccc  2640
catttcaccc atggggagac agttgagagc ggggatgtga catgcccaag gccacggagc  2700
agttcagagt ggaggcgggc ttggaacccg gtgctccctc tgtcatcctc aggaaccaac  2760
aattcgtcgg aggcatcatg gaaagactgg gacagcccag gaaacaaggg gtctgaggat  2820
gcattcgaga tggcagattc ccactgccgc tgcccgctca gcccagctgt tgggaacagc  2880
atggaggcag atgtggggct gagctgggga atcagggtaa aagtgcagg tgtggagaga  2940
gaggcttcaa tcggcttgtg ggtgatgtt gaccttcaga gccagccggc tatgaaaggg  3000
agcgagcccc tcggctctgg aggcaatcaa gcagacatag aagagccaag agtccaggag  3060
gccctggtcc tggcctcctt ccccgtactt tgtcccgtgg catttcaatt cctggccctg  3120
ttctcctccc caagtcggca ccctttaact catgaggagg gaaaagagtg cctaagcggg  3180
ggtgaaagag gacgtgttac ccactgccat gcaccaggac tggctgtgta accttgggtg  3240
gccctgctg tctctctggg ctgcagagtc tgccccacat ggggcatgg cctctgcaac  3300
tgctcagctc tggtccaggc cctgtggcag gacacacatg gtgagcctag ccctgggaca  3360
tcaggagact gggctctggc tctgttcggc ctttgggtgt gtggtggatt ctccctgggc  3420
ctcagtgtgc ccatctgtaa aggggcagct gacagtttgt ggcatcttgc caagggtccc  3480
tgtgtgtgtg tatgtgtgcg tgtctccatg tgtctccata tttaacatgt  3540
aaaaatgtcc cccccgctcc gtcccccaaa catgttgtac atttcaccat ggcccctca  3600
tcatagcaat aacattccca ctgccagggg ttcttgagcc agccaggccc tgccagtggg  3660
gaaggaggcc aagcagtgcc tgcctatgaa atttcaactt ttcctttcat acgtctttat  3720
tacccaagtc ttctcccgtc cattccagtc aaatctgggc tcactcaccc cagcgagctc  3780
tcaaatccct ctccaactgc ctaaggcct ttgtgtaagg tgtcttaata ctgtcctttt  3840
ttttttttta acagtgtttt gtagatttca gatgactatg cagaggcctg ggggacccct  3900
ggctctgggc cgggcctggg gctccgaaat tccaaggccc agacttgcgg ggggtggggg  3960
ggtatccaga attggttgta aatactttgc atattgtctg attaaacaca aacagacctc  4020
agaatctgat caacagttaa aaaaaaaaaa aaaaaa                              4056
```

```
SEQ ID NO: 137              moltype = AA  length = 358
FEATURE                     Location/Qualifiers
source                      1..358
                            mol_type = protein
                            organism = Homo sapiens
SEQUENCE: 137
MGLSRKSSDA SACSSSEISD SFVKEFLAKA KEDFLKKWEN PTQNNAGLED FERKKTLGTG  60
SFGRVMLVKH KATEQYYAMK ILDKQKVVKL KQIEHTLNEK RILQAVNFPF LVRLEYAFKD  120
NSNLYMVMEY VPGGEMFSHL RRIGRFSEPH ARFYAAQIVL TFEYLHSLDL IYRDLKPENL  180
LIDHQGYIQV TDFGFAKRVK GRTWTLCGTP EYLAPEIILS KGYNKAVDWW ALGVLIYEMA  240
AGYPPFFADQ PIQIYEKIVS GKVRFPSHFS SDLKDLLRNL LQVDLTKRFG NLKNGVSDIK  300
THKWFATTDW IAIYQRKVEA PFIPKFRGSG DTSNFDDYEE EDIRVSITEK CAKEFGEF    358
```

```
SEQ ID NO: 138              moltype = AA  length = 339
FEATURE                     Location/Qualifiers
source                      1..339
                            mol_type = protein
                            organism = Homo sapiens
SEQUENCE: 138
MGLLKEFLAK AKEDFLKKWE NPTQNNAGLE DFERKKTLGT GSFGRVMLVK HKATEQYYAM  60
KILDKQKVVK LKQIEHTLNE KRILQAVNFP FLVRLEYAFK DNSNLYMVME YVPGGEMFSH  120
LRRIGRFSEP HARFYAAQIV LTFEYLHSLD LIYRDLKPEN LLIDHQGYIQ VTDFGFAKRV  180
KGRTWTLCGT PEYLAPEIIL SKGYNKAVDW WALGVLIYEM AAGYPPFFAD QPIQIYEKIV  240
SGKVRFPSHF SSDLKDLLRN LLQVDLTKRF GNLKNGVSDI KTHKWFATTD WIAIYQRKVE  300
APFIPKFRGS GDTSNFDDYE EEDIRVSITE KCAKEFGEF                         339
```

```
SEQ ID NO: 139              moltype = AA  length = 355
FEATURE                     Location/Qualifiers
source                      1..355
                            mol_type = protein
                            organism = Homo sapiens
SEQUENCE: 139
MGLSRKSSDA SACSSSEISV KEFLAKAKED FLKKWENPTQ NNAGLEDFER KKTLGTGSFG  60
RVMLVKHKAT EQYYAMKILD KQKVVKLKQI EHTLNEKRIL QAVNFPFLVR LEYAFKDNSN  120
LYMVMEYVPG GEMFSHLRRI GRFSEPHARF YAAQIVLTFE YLHSLDLIYR DLKPENLLID  180
HQGYIQVTDF GFAKRVKGRT WTLCGTPEYL APEIILSKGY NKAVDWWALG VLIYEMAAGY  240
PPFFADQPIQ IYEKIVSGKV RFPSHFSSDL KDLLRNLLQV DLTKRFGNLK NGVSDIKTHK  300
WFATTDWIAI YQRKVEAPFI PKFRGSGDTS NFDDYEEEDI RVSITEKCAK EFGEF       355
```

```
SEQ ID NO: 140              moltype = AA  length = 357
FEATURE                     Location/Qualifiers
source                      1..357
                            mol_type = protein
```

```
                             organism = Homo sapiens
SEQUENCE: 140
MSARKSSDAS ACSSSEISDS FVKEFLAKAK EDFLKKWENP TQNNAGLEDF ERKKTLGTGS    60
FGRVMLVKHK ATEQYYAMKI LDKQKVVKLK QIEHTLNEKR ILQAVNFPFL VRLEYAFKDN   120
SNLYMVMEYV PGGEMFSHLR RIGRFSEPHA RFYAAQIVLT FEYLHSLDLI YRDLKPENLL   180
IDHQGYIQVT DFGFAKRVKG RTWTLCGTPE YLAPEIILSK GYNKAVDWWA LGVLIYEMAA   240
GYPPFFADQP IQIYEKIVSG KVRFPSHFSS DLKDLLRNLL QVDLTKRFGN LKNGVSDIKT   300
HKWFATTDWI AIYQRKVEAP FIPKFRGSGD TSNFDDYEEE DIRVSITEKC AKEFGEF      357

SEQ ID NO: 141           moltype = AA   length = 321
FEATURE                  Location/Qualifiers
source                   1..321
                         mol_type = protein
                         organism = Homo sapiens
SEQUENCE: 141
MSARKSSDAS ACSSSEISVK EFLAKAKEDF LKKWENPTQN NAGLEDFERK KTLGTGSFGR    60
VMLVKHKATE QYYAMKILDK QKDNSNLYMV MEYVPGGEMF SHLRRIGRFS EPHARFYAAQ   120
IVLTFEYLHS LDLIYRDLKP ENLLIDHQGY IQVTDFGFAK RVKGRTWTLC GTPEYLAPEI   180
ILSKGYNKAV DWWALGVLIY EMAAGYPPFF ADQPIQIYEK IVSGKVRFPS HFSSDLKDLL   240
RNLLQVDLTK RFGNLKNGVS DIKTHKWFAT TDWIAIYQRK VEAPFIPKFR GSGDTSNFDD   300
YEEEDIRVSI TEKCAKEFGE F                                            321

SEQ ID NO: 142           moltype = AA   length = 338
FEATURE                  Location/Qualifiers
source                   1..338
                         mol_type = protein
                         organism = Homo sapiens
SEQUENCE: 142
MLLLSSSISL YKDRNEARLI SSQNNAGLED FERKKTLGTG SFGRVMLVKH KATEQYYAMK    60
ILDKQKVVKL KQIEHTLNEK RILQAVNFPF LVRLEYAFKD NSNLYMVMEY VPGGEMFSHL   120
RRIGRFSEPH ARFYAAQIVL TFEYLHSLDL IYRDLKPENL LIDHQGYIQV TDFGFAKRVK   180
GRTWTLCGTP EYLAPEIILS KGYNKAVDWW ALGVLIYEMA AGYPPFFADQ PIQIYEKIVS   240
GKVRFPSHFS SDLKDLLRNL LQVDLTKRFG NLKNGVSDIK THKWFATTDW IAIYQRKVEA   300
PFIPKFRGSG DTSNFDDYEE EDIRVSITEK CAKEFGEF                          338

SEQ ID NO: 143           moltype = AA   length = 351
FEATURE                  Location/Qualifiers
source                   1..351
                         mol_type = protein
                         organism = Homo sapiens
SEQUENCE: 143
MGNAATAKKG SEVESVKEFL AKAKEDFLKK WENPTQNNAG LEDFERKKTL GTGSFGRVML    60
VKHKATEQYY AMKILDKQKV VKLKQIEHTL NEKRILQAVN FPFLVRLEYA FKDNSNLYMV   120
MEYVPGGEMF SHLRRIGRFS EPHARFYAAQ IVLTFEYLHS LDLIYRDLKP ENLLIDHQGY   180
IQVTDFGFAK RVKGRTWTLC GTPEYLAPEI ILSKGYNKAV DWWALGVLIY EMAAGYPPFF   240
ADQPIQIYEK IVSGKVRFPS HFSSDLKDLL RNLLQVDLTK RFGNLKNGVS DIKTHKWFAT   300
TDWIAIYQRK VEAPFIPKFR GSGDTSNFDD YEEEDIRVSI TEKCAKEFGE F            351

SEQ ID NO: 144           moltype = AA   length = 398
FEATURE                  Location/Qualifiers
source                   1..398
                         mol_type = protein
                         organism = Homo sapiens
SEQUENCE: 144
MAAYREPPCN QYTGTTTALQ KLEGFASRLF HRHSKGTAHD QKTALENDSL HFSEHTALWD    60
RSMKEFLAKA KEDFLKKWEN PTQNNAGLED FERKKTLGTG SFGRVMLVKH KATEQYYAMK   120
ILDKQKVVKL KQIEHTLNEK RILQAVNFPF LVRLEYAFKD NSNLYMVMEY VPGGEMFSHL   180
RRIGRFSEPH ARFYAAQIVL TFEYLHSLDL IYRDLKPENL LIDHQGYIQV TDFGFAKRVK   240
GRTWTLCGTP EYLAPEIILS KGYNKAVDWW ALGVLIYEMA AGYPPFFADQ PIQIYEKIVS   300
GKVRFPSHFS SDLKDLLRNL LQVDLTKRFG NLKNGVSDIK THKWFATTDW IAIYQRKVEA   360
PFIPKFRGSG DTSNFDDYEE EDIRVSITEK CAKEFGEF                          398

SEQ ID NO: 145           moltype = AA   length = 257
FEATURE                  Location/Qualifiers
source                   1..257
                         mol_type = protein
                         organism = Homo sapiens
SEQUENCE: 145
MGNAATAKKG SEVESVKEFL AKAKEDFLKK WENPTQNNAG LEDFERKKTL GTGSFGRVML    60
VKHKATEQYY AMKILDKQKV VKLKQIEHTL NEKRILQAVN FPFLVRLEYA FKDNSNLYMV   120
MEYVPGGEMF SHLRRIGRFS EPHARFYAAQ IVLTFEYLHS LDLIYRDLKP ENLLIDHQGY   180
IQVTDFGFAK RVKGRTWTLC GTPEYLAPEI ILSKGYNKAV DWWALGVLIY EMAAGYPPFF   240
ADQPIQIYEK IVSGKNF                                                 257

SEQ ID NO: 146           moltype = AA   length = 351
FEATURE                  Location/Qualifiers
source                   1..351
                         mol_type = protein
                         organism = Homo sapiens
```

```
SEQUENCE: 146
MGNAAAAKKG SEQESVKEFL AKAKEDFLKK WESPAQNTAH LDQFERIKTL GTGSFGRVML  60
VKHKETGNHY AMKILDKQKV VKLKQIEHTL NEKRILQAVN FPFLVKLEFS FKDNSNLYMV  120
MEYVPGGEMF SHLRRIGRFS EPHARFYAAQ IVLTFEYLHS LDLIYRDLKP ENLLIDQQGY  180
IQVTDFGFAK RVKGRTWTLC GTPEYLAPEI ILSKGYNKAV DWWALGVLIY EMAAGYPPFF  240
ADQPIQIYEK IVSGKVRFPS HFSSDLKDLL RNLLQVDLTK RFGNLKNGVN DIKNHKWFAT  300
TDWIAIYQRK VEAPFIPKFK GPGDTSNFDD YEEEEIRVSI NEKCGKEFSE F          351

SEQ ID NO: 147            moltype = AA  length = 343
FEATURE                   Location/Qualifiers
source                    1..343
                          mol_type = protein
                          organism = Homo sapiens
SEQUENCE: 147
MASNSSDVKE FLAKAKEDFL KKWESPAQNT AHLDQFERIK TLGTGSFGRV MLVKHKETGN  60
HYAMKILDKQ KVVKLKQIEH TLNEKRILQA VNFPFLVKLE FSFKDNSNLY MVMEYVPGGE  120
MFSHLRRIGR FSEPHARFYA AQIVLTFEYL HSLDLIYRDL KPENLLIDQQ GYIQVTDFGF  180
AKRVKGRTWT LCGTPEYLAP EIILSKGYNK AVDWWALGVL IYEMAAGYPP FFADQPIQIY  240
EKIVSGKVRF PSHFSSDLKD LLRNLLQVDL TKRFGNLKNG VNDIKNHKWF ATTDWIAIYQ  300
RKVEAPFIPK FKGPGDTSNF DDYEEEEIRV SINEKCGKEF SEF                    343

SEQ ID NO: 148            moltype = AA  length = 408
FEATURE                   Location/Qualifiers
source                    1..408
                          mol_type = protein
                          organism = Homo sapiens
SEQUENCE: 148
MIPGNRMLMV VLLCQVLLGG ASHASLIPET GKKKVAEIQG HAGGRRSGQS HELLRDFEAT  60
LLQMFGLRRR PQPSKSAVIP DYMRDLYRLQ SGEEEEEQIH STGLEYPERP ASRANTVRSF  120
HHEEHLENIP GTSENSAFRF LFNLSSIPEN EVISSAELKL FREQVDQGPD WERGFHRINI  180
YEVMKPPAEV VPGHLITRLL DTRLVHHNVT RWETFDVSPA VLRWTREKQP NYGLAIEVTH  240
LHQTRTHQGQ HVRISRSLPQ GSGNWAQLRP LLVTFGHDGR GHALTRRRRA KRSPKHHSQR  300
ARKKNKNCRR HSLYVDFSDV GWNDWIVAPP GYQAFYCHGD CPFPLADHLN STNHAIVQTL  360
VNSVNSSIPK ACCVPTELSA ISMLYLDEYD KVVLKNYQEM VVEGCGCR               408

SEQ ID NO: 149            moltype = AA  length = 1537
FEATURE                   Location/Qualifiers
source                    1..1537
                          mol_type = protein
                          organism = Homo sapiens
SEQUENCE: 149
MGEKLELRLK SPVGAEPAVY PWPLPVYDKH HDAAHEIIET IRWVCEEIPD LKLAMENYVL  60
IDYDTKSFES MQRLCDKYNR AIDSIHQLWK GTTQPMKLNT RPSTGLLRHI LQQVYNHSVT  120
DPEKLNNYEP FSPEVYGETS FDLVAQMIDE IKMTDDDLFV DLGSGVGQVV LQVAAATNCK  180
HHYGVEKADI PAKYAETMDR EFRKWMKWYG KKHAEYTLER GDFLSEEWRE RIANTSVIFV  240
NNFAFGPEVD HQLKERFANM KEGGRIVSSK PFAPLNFRIN SRNLSDIGTI MRVVELSPLK  300
GSVSWTGKPV SYYLHTIDRT ILENYFSSLK NPKLREEQEA ARRQQRESK SNAATPTKGP  360
EGKVAGPADA PMDSGAEEEK AGAATVKKPS PSKARKKKLN KKGRKMAGRK RGRPKKMNTA  420
NPERKPKKNQ TALDALHAQT VSQTAASSPQ DAYRSPHSPF YQLPPSVQRH SPNPLLVAPT  480
PPALQKLLES FKIQYLQFLA YTKTPQYKAS LQELLGQEKE KNAQLLGAAQ QLLSHCQAQK  540
EEIRRLFQQK LDELGVKALT YNDLIQAQKE ISAHNQQLRE QSEQLEQDNR ALRGQSLQL  600
KARCEELQLD WATLSLEKLL KEKQALKSQI SEKQRHCLEL QISIVELEKS QRQQELLQLK  660
SCVPPDDALS LHLRGKGALG RELEPDASRL HLELDCTKFS LPHLSSMSPE LSMNGQAAGY  720
ELCGVLSRPS SKQNTPQYLA SPLDQEVVPC TPSHVGRPRL EKLSGLAAPD YTRLSPAKIV  780
LRRHLSQDHT VPGRPAASEL HSRAEHTKEN GLPYQSPSVP GSMKLSPQDP RPLSPGALQL  840
AGEKSSEKGL RERAYGSSGE LITSLPISIP LSTVQPNKLP VSIPLASVVL PSRAERARST  900
PSPVLQPRDP SSTLEKQIGA NAHGAGSRSL ALAPAGFSYA GSVAISGALA GSPASLTPGA  960
EPATLDESSS SGSLFATVGS RSSTPQHPLL LAQPRNSLPA SPAHQLSSSP RLGGAAQGPL  1020
PEASKGDLPS DSGFSDPESE AKRRIVFTIT TGAGSAKQSP SSKHSPLTAS ARGDCVPSHG  1080
QDSRRRGRRK RASAGTPSLS AGVSPKRRAL PSVAGLFTQP SGSPLNLNSM VSNINQPLEI  1140
TAISSPETSL KSSPVPYQDH DQPPVLKKER PLSQTNGAHY SPLTSDEEPG SEDEPSSARI  1200
ERKIATISLE SKSPPKTLEN GGGLAGRKPA PAGEPVNSSK WKSTFSPISD IGLAKSADSP  1260
LQASSALSQN SLFTFRPALE EPSADAKLAA HPRKGFPQSL SGADGLSPGT NPANGCTPGG  1320
GLAADLSLHS FSDGASLPHK GPEAAGLSSP LSFPSQRGKE GSDANPFLSK RQLDGLAGLK  1380
GEGSRGKEAG EGGLPLCGPT DKTPLLSGKA AKARDREVDL KNGHNLFISA AAVPPGSLLS  1440
GPGLAPAASS AGGAASSAQT HRSFLGPFPP GPQFALGPMS LQANLGSVAG SSVLQSLFSS  1500
VPAAAGLVHV SSAATRLTNS HAMGSFSGVA GGTVGGN                          1537

SEQ ID NO: 150            moltype = AA  length = 634
FEATURE                   Location/Qualifiers
source                    1..634
                          mol_type = protein
                          organism = Homo sapiens
SEQUENCE: 150
MTEEACRTRS QKRALERDPT EDDVESKKIK MERGLLASDL NTDGDMRVTP EPGAGPTQGL  60
LRATEATAMA MGRGEGLVGD GPVDMRTSHS DMKSERRPPS PDVIVLSDNE QPSSPRVNGL  120
TTVALKETST EALMKSSPEE RERMIKQLKE ELRLEEAKLV LLKKLRQSQI QKEATAQKPT  180
GSVGSTVTTP PPLVRGTQNI PAGKPSLQTS SARMPGSVIP PPLVRGGQQA SSKLGPQASS  240
QVVMPPPLVRG AQQIHSIRQH SSTGPPPLLL APRASVPSVQ IQGQRIIQQG LIRVANVPNT  300
```

```
SLLVNIPQPT PASLKGTTAT SAQANSTPTS VASVVTSAES PASRQAAAKL ALRKQLEKTL   360
LEIPPPKPPA PEMNFLPSAA NNEFIYLVGL EEVVQNLLET QAGRMSAATV LSREPYMCAQ   420
CKTDFTCRWR EEKSGAIMCE NCMTTNQKKA LKVEHTSRLK AAFVKALQQE QEIEQRLLQQ   480
GTAPAQAKAE PTAAPHPVLK QVIKPRRKLA FRSGEARDWS NGAVLQASSQ LSRGSATTPR   540
GVLHTFSPSP KLQNSASATA LVSRTGRHSE RTVSAGKGSA TSNWKKTPLS TGGTLAFVSP   600
SLAVHKSSSA VDRQREYLLD MIPPRSIPQS ATWK                               634

SEQ ID NO: 151          moltype = DNA   length = 5386
FEATURE                 Location/Qualifiers
source                  1..5386
                        mol_type = genomic DNA
                        organism = Homo sapiens
SEQUENCE: 151
ttcagaatga ccgaagaagc atgccgaaca cggagtcaga aacgagcgct tgaacgggac    60
ccaacagagg acgatgtgga gagcaagaaa ataaaaatgg agagaggatt gttggcttca   120
gatttaaaca ctgacggaga catgagggtg acacctgagc cgggagcagg tccaacccaa   180
ggattgctga gggcaacaga ggccacggcc atggccatgg gcagaggcga agggctggtg   240
ggcgatgggc ccgtggacat gcgcacctca cacagtgaca tgaagtccga gaggagaccc   300
ccctcacctg acgtgattgt gctctccgac aacgagcagc cctcgagccc gagagtgaat   360
gggctgacca cggtggcctt gaaggagact agcaccgagg ccctcatgaa aagcagtcct   420
gaagaacgag aaaggatgat caagcagctg aaggaagaat tgaggttaga agaagcaaaa   480
ctcgtgttgt tgaaaaagtt gcggcagagt caaatacaaa aggaagccac cgcccagaag   540
cccacaggtt ctgttgggag caccgtgacc accctcccc cgcttgttcg gggcactcag   600
aacattcctg ctggcaagcc atcactccag acctcttcag ctcggatgcc cggcagtgtc   660
ataccccgc ccctggtccg aggtgggcag caggcgtcct cgaagctggg gccacaggcg    720
agctcacagg tcgtcatgcc cccactcgtc agggggggctc agcaaatcca cagcattagg   780
caacattcca gcacagggcc accgcccctc ctcctggccc cccgggcgtc ggtgcccagt   840
gtgcagattc agggacagag gatcatccag cagggcctca tccgcgtcgc caatgttccc   900
aacaccagcc tgctcgtcaa catcccacag cccacccag catcactgaa ggggacaaca   960
gccacctccg ctcaggccaa ctccacccc actagtgtgg cctctgtggt cacctctgcc  1020
gagtctccag caagccgaca ggcggccgcc aagctggcgc tgcgcaaaca gctggagaag  1080
acgctactcg agatccccc acccaagccc cagccccag agatgaactt cctgcccagc   1140
gccgccaaca acgagttcat ctacctggtc ggcctggagg aggtggtgca gaacctactg  1200
gagacacaag caggcaggat gtcggccgca actgtgctgt ccgggagcc ctacatgtgt   1260
gcacagtgca agacggactt cacgtgccgc tggcgggagg agaagagcgg cgccatcatg  1320
tgtgagaact gcatgacaac caaccagaag aaggcgctca aggtggagca caccagccgg  1380
ctgaaggccg cctttgtgaa ggcgctgcag caggaacagg agattgagca gcggctcctg  1440
cagcagggca cggcccctgc acaggccaag gccgagccca ccgctgcccc acaccccgtg  1500
ctgaagcagg tcataaaacc ccggcgtaag ttggcgttcc gctcaggaga ggccgccgac  1560
tggagtaacg gggctgtgct acaggcctcc agccagctgt cccgggggttc ggccacgacg  1620
ccccgaggtg tcctgcacac gttcagtccg tcacccaaac tgcagaactc agcctcggcc  1680
acagccctgg tcagcaggac cggcagacat tctgagagaa ccgtgagcgc cggcaagggc  1740
agcgccacct ccaactggaa gaagacgccc ctcagcacag gtggcacce tgcgtttgtc  1800
agcccaagcc tggcggtgca caagagctcc tcggccgtgg accgccagcg agagtacctc  1860
ctggacatga tcccacccg ctccatcccc cagtcagcca cgtggaaata gtgcgagcca  1920
ggccccgtgg aagacgggct ccctcctccc ccacctggcc cctggtctag aaggaccac  1980
tgcaccaccc tccgctggct cgggaagaca ccgtgcccgc cccaagagca agcaccggcc  2040
atgctgcaga ggcaagacct caattcttgg ctgcaaagtt tcatcagggc tagggggctg  2100
gtgccgcctc ataggcagac gaggatcatc gctggggggac cttttcccgtg ggctttcttc  2160
ctttctctct ttgcctttag tttgcccgac accagcagaa aagtggacct tgggggctgg   2220
ttctgctcct ggcccccttg ttcagccct gccggcacac gggcggctca ccctggacac  2280
tgtgatgcgc atgggcaagg ccagcgcccg gggcttctga accgagcggg gtgtttcatt  2340
tttttgcttt tccctgtctt aggctcccag tctttgactg ccttcccatg gcgatctata  2400
agttgaaaga tttttttttt ttttaatcac ctcatgatga tggagttaaa agtaaaccgt  2460
gcagacctg gggtccctgt tgtacgctgc atcatcccgc tggccctgtg ccctggaggg   2520
tgggcggctc atggtgccac agccctggc agggacggcc ggcccgcccc cgtgactgac  2580
tgacagatgc agggatggcc gaggcagccc tcgctccagc tgaacgcctc cattgctgct  2640
tgttctggag accccgccc ccgcaccttc cagacttagc agaagaacaa actgaagaac   2700
agacccagcc agagaagcag ggattccaga agctgcccat taagggagaa ggagaggatc  2760
cggtcggcag cagccctgag cagaaagctg gagggggggac tgtcgcgggg ttttctgtt   2820
gtggtttatt ttattaaatt ttttccttttt ttctattcat ttcgatggac gcaatcttaa  2880
gccaccctgg ccttgctcct gggaggtgag cgtgcacagg tgtgtgcagg tcaggaggtg  2940
ccgtccaggt gtgcggcgag ccgctgcgca cagatgtcag gatttccgtt tgggtctagt  3000
ttagaacctg tccttaaacc taggggttgc tgtcaggatt tgctttcaga ctttttttc   3060
ttttgtaatt ccctttagag tctacaaaaa tgttttttaaa aggatcaggt ctgcttttag   3120
tttcattttt gtttctttcc cgtcccactc tttaaaaact ggttccgtga ggaaaggcag  3180
aagccgttcc gtgtctcttg caggctgggc cggcttcatg ccagtgcgag ggcgtcccgt  3240
gcccacgtac atacgtatgt ctccatgagt tctgggctcc actggtttcca attgagctcc  3300
agcctggtt ttcctaccca tgcagttagg gactttaatt taattttttt tttgtagggc   3360
caccgccttc aaaacacaact gctacaacat tctaataaag gctcatttaa ccccccaggct  3420
cctgtcgtgt gaatatcctc agtctgtagg aaactttttt tgacacagca tagaagacct   3480
agttttggaa aacattatct aatttttttgt tgtgcaaatc cccaaatttc tcactaattt  3540
ttgtttttttt gtgcataact tggatgggct gaaggaggtg aggacagatt ggggaagggt  3600
ggcttttcatt ccaagatcca gggatttggg gaaaaggaag gaatttgatg ttttttgggg  3660
tgggagggga gggtgtgttt tttacaccaa aaaaaaaaaa aaaaatcaag agtatgcaag  3720
catttctatt cctcgcattt ttctgtgtgc ctggcaaata aatacctgtc tcctacgacc  3780
ctgagctgtt agcctctct gttccatgac aggggccaga tcttccagct cctcccagaa   3840
ggagcaccca ggctggcttc ttcccactga aagccctccc cagcgaacca acctcagttc  3900
tatgcagtgg ctggggatca ggcatccaga ccgaagtcac ctctgcctgc tccagcttgg  3960
```

```
gtcagctggg tctgaccagg gggccagatc cgagccgcac ctgccggccc ccagccccag   4020
ctccagctcc tgacctctcc cagcctggcc tggctgttcc tccagggctg atggctgtca   4080
acccatcctt gtgagttcat atggactgct gcccctcgaa agggagaggg tcggccccat   4140
gtccccaggg agcattccat cagggacaac gtacatactg tgatgtaaac ttttttttttt  4200
tcccccaggg gggcaaaagt gtgagatgcc ttaatctttc cttcatttct gctgtctcga   4260
acactctagc ccattatttc ctttcagttc cttgcagcat aacctctacg ataagcccca   4320
agcgggttgt tgtattatga cgtttatgat gttccaggtg aaggcattat taagtacctc   4380
tctgggtgtg gggtttggac gcaccaggat agctattgat taatgttaag ggtgttctac   4440
ccacagcaaa gcacaccctc ttaaaccagg cactgcctgg gtcctggtcc cgagagccct   4500
accaggatca ggttcctgca agccgtcaga atgtgggagc ccccagccca actgattgta   4560
actgtccctt gttacctgtg acatgaacct ccaacagcac ctggaaacgg ttccctctgt   4620
cagctgctct gtagacaggg ctggggagat ctcagagttc acacctcgcc tgttgtaggg   4680
gaggttgggg gtagggtttg gaatggccaa gtgcccttgg aacctcccac agctatggcc   4740
gtcctgacct catcccagga actctacggt gaccaggaac cacccctctg acgaggtctg   4800
tagcggcccc tctcagagtg gaacagccca cagtgctagt tgtgcctggt cttacctgta   4860
ctccacggac ctcggtgaag caaaagcttc agggcagagg gaatgaggca acccagtggc   4920
agccccgctg ggccccgtgg ctcctgctct cctattggac gtagaggcag gggagagact   4980
tctctataca aatattctca tcacagaagg gatgatcctt gctgctctgc cgtagggttt   5040
ttgatgctga gctatgctgc acatgacgtt aacctaaaga acttggactg agcttttaaa   5100
aaaggacagc aaacaatttt ataatcctta aagtgtaata gacggttaca ctagtgcagg   5160
gtattgggga ggctctttgg gtgtggaggc tgtcacttgt atttattgtg actctaaatc   5220
tttgatagta aaacaaatgt aaaaagaaat gtttgccacc agatgggaat agaagttcca   5280
ataagcaggc tggaatgggg ggctatacgt tgtatcacga ggaagtttta gactctgaag   5340
gataataaat ggatgatgtg tcaactgaa aaaaaaaaaa aaaaaa             5386
```

```
SEQ ID NO: 152          moltype = AA  length = 633
FEATURE                 Location/Qualifiers
source                  1..633
                        mol_type = protein
                        organism = Homo sapiens
SEQUENCE: 152
MTEEACRTRS QKRALERDPT EDDVESKKIK MERGLLASDL NTDGDMRVTP EPGAGPTQGL   60
LRATEATAMA MGRGEGLVGD GPVDMRTSHS DMKSERRPPS PDVIVLSDNE QPSSPRVNGL   120
TTVALKETST EALMKSSPEE RERMIKQLKE ELRLEEAKLV LLKKLRQSQI QKEATAQKPT   180
GSVGSTVTTP PPLVRGTQNI PAGKPSLQTS SARMPGSVIP PPLVRGGQQA SSKLGPQASS   240
QVVMPPLVRG AQQIHSIRQH SSTGPPPLLL APRASVPSVQ IQGQRIIQQG LIRVANVPNT   300
SLLVNIPQPT PASLKGTTAT SAQANSTPTS VASVVTSAES PASRQAAAKL ALRKQLEKTL   360
LEIPPPKPPA PEMNFLPSAA NNEFIYLVGL EEVVQNLLET QGRMSAATVL SREPYMCAQC   420
KTDFTCRWRE EKSGAIMCEN CMTTNQKKAL KVEHTSRLKA AFVKALQQEQ EIEQRLLQQG   480
TAPAQAKAEP TAAPHPVLKQ VIKPRRKLAF RSGEARDWSN GAVLQASSQL SRGSATTPRG   540
VLHTFSPSPK LQNSASATAL VSRTGRHSER TVSAGKGSAT SNWKKTPLST GGTLAFVSPS   600
LAVHKSSSAV DRQREYLLDM IPPRSIPQSA TWK                                633
```

```
SEQ ID NO: 153          moltype = DNA  length = 5689
FEATURE                 Location/Qualifiers
source                  1..5689
                        mol_type = genomic DNA
                        organism = Homo sapiens
SEQUENCE: 153
gggcaatttc agtgtgagac tgagccgcga gactgagctg cggctccgag cgctgcgcgg   60
cggctcctcc cgcccagggt cagcgccccg gcgcgcgcac ggcgcacccc ggcgcccgag   120
cgcgccccgc gccgcccgcg cagtcggtcg gtcggtcgtc tgtcctgtcg ccgctgccgc   180
cgccgccaca gcgcgccgcg cgggcgccac ctgagggagt cgcctccgcg ggacgccaca   240
agacctgacc ggactgcgcc gcccgaggcc gtcggccgcc gtcagcgagg gcgccgagca   300
acttcgttca gaatgaccga agaagcatgc cgaacacggt ctcagaaacg agcgcttgaa   360
cgggacccaa cagaggacga tgtggagagc aagaaaataa aaatggagag aggattgttg   420
gcttcagatt taaacactga cggagacatg agggtgacac ctgagccggg agcaggtcca   480
acccaaggat tgctgagggc aacagaggcc acggccatgg ccatgggcag aggcgaaggg   540
ctggtgggcg atgggcccgt ggacatgcgc acctcacaca gtgacatgaa gtccgagagg   600
agacccccct cacctgacgt gattgtgctc tccgacaacg agcagccctc gagcccgaga   660
gtgaatgggc tgaccacggt ggccttgaag gagactagca ccgaggccct catgaaaagc   720
agtcctgaag aacgagaaag gatgatcaag cagctgaagg aagaattgag gttagaagaa   780
gcaaaactcg tgttgttgaa aaagttgcgg cagagtcaaa tacaaaagga agccaccgcc   840
cagaagcaca caggttctgt tgggagcacc gtgaccaccc ctccccccgt tgttcgggga   900
actcagaaca ttcctgctgg caagccatca ctccagaccc cttcagctcg gatgcccggc   960
agtgtcatac ccccgcccct ggtccgaggt gggcagcagg cgtcctcgaa gctggggcca   1020
caggcgagct cacaggtcgt catgcccca ctcgtcaggg gggctcagca aatccacagc   1080
attaggcaac attccagcac agggcaccg ccctcctcc tggcccccg ggcgtcggtg   1140
cccagtgtgc agattcaggg acagaggatc atccagcagg gcctcatccg gctcgccaat   1200
gttcccaaca ccagcctgct cgtcaacatc ccacagccca ccccagcatc actgaagggg   1260
acaacagcca cctccgctca ggccaactcc acccccacta gtgtggcctc tgtggtcacc   1320
tctgccgagt ctccagcaag ccgacaggcg ccgccaagc tggcgctgcg caaacagctg   1380
gagaagacgc tactcgagat ccccccaccc aagccccag ccccagagat gaacttcctg   1440
cccagcgcag ccaacaacga gttcatctac ctggtcgggc tggaggaggt ggtgcagaac   1500
ctactggaga cacaaggcag gatgtcggcc gccactgtgc tgtcccggga gcctacatg   1560
tgtgcacagt gcaagacgga cttcacgtgc cgctggcggg aggagaagag cggcgccatc   1620
atgtgtgaga actgcatgac aaccaaccag aagaaggcgc tcaaggtgga gcacaccagc   1680
cggctgaagg ccgcctttgt gaaggcgctg cagcaggaac aggagattga gcagcggctc   1740
ctgcagcagg gcacggcccc tgcacaggcc aaggccgagc ccaccgctgc cccacacccc   1800
```

```
gtgctgaagc aggtcataaa acccggcgt aagttggcgt tccgctcagg agaggcccgc   1860
gactggagta acggggctgt gctacaggcc tccagccagc tgtcccgggg ttcggccacg   1920
acgccccgag gtgtcctgca cacgttcagt ccgtcaccca aactgcagaa ctcagcctcg   1980
gccacagccc tggtcagcag gaccggcaga cattctgaga gaaccgtgag cgccggcaag   2040
ggcagcgcca cctccaactg gaagaagacg cccctcagca caggcgggac ccttgcgttt   2100
gtcagcccaa gcctggccgt gcacaagagc tcctcggccg tggaccgcca gcgagagtac   2160
ctcctggaca tgatcccacc ccgctccatc ccccagtcag ccacgtggaa atagtgcgag   2220
ccaggccccg tggaagacgg gctccctcct cccccacctg gccctggtc tagaaggacc     2280
cactgcacca ccctccgctg gctcgggaag acaccgtgcc cgccccaaga gcaagcaccg   2340
gccatgctgc agaggcaaga cctcaattct tggctgcaaa gtttcatcag ggctagggg     2400
ctggtgccgc ctcataggca gacgaggatc atcgctgggg gacctttccc gtgggctttc   2460
ttcctttctc tctttgcctt tagtttgccc gacaccagca gaaagtggaa ccttgggggc   2520
tggttctgct cctggccccc ttgttcagcc cctgccggca cacgggcggc tcaccctgga   2580
cactgtgatg cgcatgggca aggccagcgc ccggggcttc tgaaccgagc ggggtgtttc   2640
atttttttgc ttttccctgt cttaggctcc cagtctttga ctgccttccc atggcgatct   2700
ataagttgaa agatttttt tttttttaat cacctcatga tgatggagtt aaaagtaaac    2760
cgtgcagacc ctggggtccc tgttgtacgc tgcatcatcc cgctggccct gtgccctgga   2820
gggtgggcgg ctcatggtgc cacagcccct ggcagggacg gccggcccgc ccccgtgact   2880
gactgacaga tgcagggatg gccgaggcag ccctcgctcc agctgaacgc ctccattgct   2940
gcttgttctg gagacccccg cccccgcacc ttccagactt agcagaagaa caaactgaag   3000
aacagaccca gccagagaag cagggattcc agaagctgcc cattaaggga gaaggagagg   3060
atccggtcgg cagcagccct gagcagaaag ctggaggggg gactgtcgcg gggtttttct   3120
gttgtggttt attttattaa atttttttcct tttttctatt catttcgatg gacgcaatct   3180
taagccaccc tggccttgct cctgggaggg gagcgtgcac aggtgtgtgc aggtcaggag   3240
gtgccgtcca ggtgtgcggc gagccgctgc gcacagatgt caggatttcc gtttgggtct   3300
agtttagaac ctgtccttaa acctaggggt tgctgtcagg atttgctttc agactttttt   3360
tttttttgta attcccttta gagtctacaa aaatgttttt aaaaggatca ggtctgcttt   3420
tagtttcatt tttgtttctt tcccgtccca ctctttaaaa actggttccg tgaggaaagg   3480
cagaagccgt tccgtgtctc ttgcaggctg ggccggcttc atgccagtgc gagggcgtcc   3540
cgtgcccacg tacatacgta tgtctccatg agttctgggc tccactggtt ccaattgagc   3600
tccagccctg gtttcctac ccatgcagtt agggactta atttaatttt tttttgtag     3660
ggccaccgcc ttcaaacaca actgctacaa cattctaata aaggctcatt taaccccag     3720
gctcctgtcg tgtgaatatc ctcagtctgt aggaaacttt ttttgacaca gcatagaaga   3780
cctagttttg gaaaacatta tctaattttt tgttgtgcaa atccccaaat ttctcactaa   3840
tttttgtttt tttgtgcata acttggatgg gctgaaggag gtgaggacag attggggaag   3900
ggtggctttc attccaagat ccagggattt ggggaaaagg aaggaatttg atgtttttg    3960
gggtgggagg ggagggtgtg tttttttacac caaaaaaaaa aaaaaaaatc aagagtatgc   4020
aagcatttct attcctcgca ttttttctgtg tgcctggcaa ataaatacct gtctcctacg   4080
accctgagct gttagccctc tctgttccat gacaggggcc agatcttcca gctcctccca   4140
gaaggagcac ccaggctggc ttcttcccac tgaaagccct ccccagcgaa ccaacctcag   4200
ttctatgcag tggctgggga tcaggcatcc agaccgaagt cacctctgcc tgctccagct   4260
tgggtcagct gggtctgacc aggggccag atccgagccg cacctgccgg cccccagccc   4320
cagctccagc tcctgacctc tcccagcctg gcctggctgt cctccaggg ctgatggctg    4380
tcaacccatc cttgtgagtt catatggact gctgcccctc gaaagggaga gggtcggccc   4440
catgtcccca gggagcattc catcagggac aacgtacata ctgtgatgta aacttttttt   4500
ttttcccccc aggggggcaaa agtgtgagat gccttaatct ttccttcatt tctgctgtct   4560
cgaacactct agcccattat ttcctttcag ttccttgcag cataacctct acgataagcc   4620
ccaagcgggt tgttgtatta tgacgtttat gatgttccag gtgaaggcat tattaagtac   4680
ctctctgggt gtggggtttg gacgcaccag gatagctatt gattaatgtt aagggtgttc   4740
tacccacagc aaagcacacc ctcttaaacc aggcactgcc tgggtcctgg tcccgagagc   4800
cctaccagga tcaggttcct gcaagccgtc agaatgtggg agcccccagc ccaactgatt   4860
gtaactgtcc cctgttacct gtgacatgaa cctccaacag cacctggaaa cggttccctc   4920
tgtcagctgc tctgtagaca gggctgggga gatctcagag ttcacacctc gcctgttgta   4980
ggggaggttg ggggtagggt ttggaatggc caagtgccct tggaacctcc cacagctatg   5040
gccgtcctga cctcatccca ggaactctac ggtgaccagg aaccacccct ctgacgaggt   5100
ctgtagcggc ccttctcaga gtggaacagc ccacagtgct agttgtgcct ggtcttacct   5160
gtactccacg gacctcggtg aagcaaaagc ttcagggcag agggaatgag gcaacccagt   5220
ggcagccccg ctgggccccg tggctcctgc tctcctattg gacgtagagg caggggagag   5280
acttctctat acaaatattc tcatcacaga agggatgatc cttgctgctc tgccgtaggg   5340
tttttgatgc tgagctatgc tgcacatgac gttaacctaa agaacttgga ctgagctttt   5400
aaaaaaggac agcaaacaat tttataatcc ttaaagtgta atagacggtt acactagtgc   5460
agggtattgg ggaggctctt tgggtgtgga ggctgtcact tgtatttatt gtgactctaa   5520
atctttgata gtaaaacaaa tgtaaaaaga aatgtttgcc accagatggg aatagaagtt   5580
ccaataagca ggctggaatg ggtggctata cgttgtatca cgaggaagtt ttagactctg   5640
aaggataata aatggatgat gtgtcaactg gaaaaaaaaa aaaaaaaaa                5689
```

```
SEQ ID NO: 154           moltype = AA  length = 389
FEATURE                  Location/Qualifiers
source                   1..389
                         mol_type = protein
                         organism = Homo sapiens
SEQUENCE: 154
MYGRPQAEME QEAGELSRWQ AAHQAAQDNE NSAPILNMSS SSGSSGVHTS WNQGLPSIQH    60
FPHSAEMLGS PLVSVEAPGQ NVNEGGPQFS MPLPERGMSY CPQATLTPSR MIYCQRMSPP   120
QQEMTIFSGP QLMPVGEPNI PRVARPFGGN LRMPPNGLPV SASTGIPIMS HTGNPPVPYP   180
GLSTVPSDET LLGPTVPSTE AQAVLPSMAQ MLPPQDAHDL GMPPAESQSL LVLGSQDSLV   240
SQPDSQEGPF LPEQPGPAPQ TVEKNSRPQE GTGRRGSSEA RPYCCNYENC GKAYTKRSHL   300
VSHQRKHTGE RPYSCNWESC SWSFFRSDEL RRHMRVHTRY RPYKCDQCSR EFMRSDHLKQ   360
HQKTHRPGPS DPQANNNNGE QDSPPAAGP                                     389
```

-continued

```
SEQ ID NO: 155              moltype = DNA  length = 3131
FEATURE                     Location/Qualifiers
source                      1..3131
                            mol_type = genomic DNA
                            organism = Homo sapiens
SEQUENCE: 155
gccgtggtgg ctggttccct gtctcttcag tagagagtct agaccccacc cagtcttcat    60
gtacggccga ccgcaggctg agatggaaca ggaggctggg gagctgagcc ggtggcaggc   120
ggcgcaccag gctgcccagg ataacgagaa ctcagcgccc atcttgaaca tgtcttcatc   180
ttctggaagc tctggagtgc acacctcttg gaaccaaggc ctaccaagca ttcagcactt   240
tcctcacagc gcagagatgc tggggtcccc tttggtgtct gttgaggcgc cggggcagaa   300
tgtgaatgaa gggggccac agttcagtat gccactgcct gagcgtggta tgagctactg   360
cccccaagcg actctcactc cttcccggat gatttactgt cagagaatgt ctccccctca   420
gcaagagatg acgattttca gtgggcccca actaatgccc gtaggagagc ccaatattcc   480
aagggtagcc aggcccttcg gtgggaatct aaggatgccc cccaatgggc tgccagtctc   540
ggcttccact ggaatcccaa taatgtccca cactgggaac cctccagtgc cttaccctgg   600
cctctcgaca gtaccttctg acgaaacatt gttgggccgc actgtgcctt ccactgaggc   660
ccaggcagtg ctcccctcca tggctcagat gttgcccccg caagatgccc atgaccttgg   720
gatgcccca gctgagtccc agtcattgct ggttttagga tctcaggact ctcttgtcag   780
tcagccagac tctcaagaag gcccatttct accagagcag cccggacctg ctccacagac   840
agtagagaag aactccaggc ctcaggaagg gactggtaga aggggctcct cagaggcaag   900
gccttactgc tgcaactacg agaactgcgg aaaagcttat accaaacgct cccacctcgt   960
gagccaccag cgcaagcaca caggtgagag gccatattct tgcaactggg aaagttgttc  1020
atggtctttc ttccgttctg atgagcttag acgacatatg cgggtacaca ccagatatcg  1080
accatataaa tgtgatcagt gcagccggga gttcatgagg tctgaccatc tcaagcaaca  1140
ccagaagact catcggccgg gaccctcaga cccacaggcc aacaacaaca atggagagca  1200
ggacagtcct cctgctgctg gtccttaggt gaatgaagaa ggaagaggat tccaggctga  1260
gagcactgga cgtggcaact gttcagagga gaggcagtct tcaagttcta cattcattca  1320
gaaaaatgtt ttttgagcct acaatactga gcgcaacaag gctgtggaga cccatggtga  1380
ggagcatgga gttaactaaa ggatgtgtca gggaagaaag acttctcaag gaggtgcctc  1440
catcagaccc aaaggactca tggggggctag ctgcacctca catttcttgg acatataccg  1500
ttggacatgt ctatcttctg gaaactatgg catggacagt aaggattcag aagtgcatga  1560
aggcaccctg cctctgcaga gcagaaagat catagacaac atttatgaat gtgcccagtg  1620
ctgccaagaa gagaagccgg tcctctgcag gctcaagcct atctgggcct ctggggaagc  1680
cccacagcct tggctgtgcc tgccctgcc ctctcacccc taccctgacc ttgtcctact  1740
tcactgcctt tgtctgtgtt actagtggcc ccagtatacc tgggatggac atccaggtgc  1800
ccttcatcca agctcctatg tgaggggaat ggacattatt aaaagaacag gggcagaagt  1860
ggctcattta tgacccattc actagcccca gggattgaag tcttgggtac tcaaagtgtc  1920
tttctaccag ggcaccagat cccttccatg gagcaggtca tctcgggttc actgggccag  1980
ggatggtctc tgttccccag cccacctggc tcacacacag cctcatgggt agggtcagca  2040
aaccagatgg cttgttgttg gaatgtagga tgagaggcct gcttggtgac ctagcatttt  2100
caccaagaag tggacgtgga gaggaccaga gtgatcaaga gtgtatgatg tgcactacaa  2160
tggtgggcaa aacaggctcc tgctcttgtg gaggtcacaa tctagcggag aaaggatgtt  2220
actagaagta cacaaattgg gcccggcgcg atggctcacg cctgtaatcc cagcactttt  2280
ggaggccgag gcaggcggat catttgaggt tagagattcg agaccagccg ggccaacatg  2340
gtgaaacccc atctctacaa aaaatacaaa aattagcctg gcatatgggc ggtaccgtaa  2400
tcctagctac tcgggagact gacgggagaa tcgcttgaac ccaggaggcg gaggttgcag  2460
tgagctcaga tctcaccatt gcactccagc ctgggcgact gagcgagact ctatctcaaa  2520
acaatcaaaa caaaaaagac ctgtggactc tagtagattt tgaatcctgc ctctgccatt  2580
tcctggctat gaggtgtctt gagaaattta cttgtcactc ttgcttctga tagtaaaggg  2640
gatggtgcga tagattcaag atggagagat aaggttaagt gttttctttg gctgcaacat  2700
ggagattaga ttagagcaag gatgtaaggg agaggaaggg acatagcagt atttcaggtg  2760
agagtcaagg tggcttttggc tagggtgtga gagtggaggt agggagaagt aggaaagtga  2820
tagttaactg gatttgttag gtgagggtga ggccaagggt gacttccagg ttcctgactt  2880
gtgttataag taacacagaa gaagaatgga tgaacttgat tcgtttttcca ttgattgtga  2940
tatctatcat acctgcaaaa aatattttgt atatatccaa tttaataata aatgcactca  3000
tgttaggaag gtcaaaaaaa aggaaaaaag aaaaataata aaaaataata aaaatcctta  3060
ggataacttg aggccaggag tttgagacca gtgtgacctt gtctctgtaa aaaataaaat  3120
taaaagaaaa a                                                       3131

SEQ ID NO: 156              moltype = AA  length = 273
FEATURE                     Location/Qualifiers
source                      1..273
                            mol_type = protein
                            organism = Homo sapiens
SEQUENCE: 156
MKKTQTWILT CIYLQLLLFN PLVKTEGICR NRVTNNVKDV TKLVANLPKD YMITLKYVPG    60
MDVLPSHCWI SEMVVQLSDS LTDLLDKFSN ISEGLSNYSI IDKLVNIVDD LVECVKENSS   120
KDLKKSFKSP EPRLFTPEEF FRIFNRSIDA FKDFVVASET SDCVVSSTLS PEKDSRVSVT   180
KPFMLPPVAA SSLRNDSSSS NRKAKNPPGD SSLHWAAMAL PALFSLIIGF AFGALYWKKR   240
QPSLTRAVEN IQINEEDNEI SMLQEKEREF QEV                                273

SEQ ID NO: 157              moltype = DNA  length = 5460
FEATURE                     Location/Qualifiers
source                      1..5460
                            mol_type = genomic DNA
                            organism = Homo sapiens
SEQUENCE: 157
```

```
gggcttcgct cgccgcctcg cgccgagact agaagcgctg cgggaagcag ggacagtgga  60
gagggcgctg cgctcgggct acccaatgcg tggactatct gccgccgctg ttcgtgcaat  120
atgctggagc tccagaacag ctaaacggag tcgccacacc actgtttgtg ctggatcgca  180
gcgctgcctt tccttatgaa gaagacacaa acttggattc tcacttgcat ttatcttcag  240
ctgctcctat ttaatcctct cgtcaaaact gaagggatct gcaggaatcg tgtgactaat  300
aatgtaaaag acgtcactaa attggtggca aatcttccaa aagactacat gataaccctc  360
aaatatgtcc ccgggatgga tgttttgcca agtcattgtt ggataagcga gatggtagta  420
caattgtcag acagcttgac tgatcttctg gacaagtttt caaatatttc tgaaggcttg  480
agtaattatt ccatcataga caaacttgtg aatatagtgg atgaccttgt ggagtgcgtg  540
aaagaaaact catctaagga tctaaaaaaa tcattcaaga gcccagaacc caggctcttt  600
actcctgaag aattctttag aatttttaat agatccattg atgccttcaa ggactttgta  660
gtggcatctc aaactagtga ttgtgtggtt tcttcaacat taagtcctga gaaagattcc  720
agagtcagtg tcacaaaacc atttatgtta cccctgttg cagccagctc ccttaggaat  780
gacagcagta gcagtaatag gaaggccaaa aatcccctg agactccag cctacactgg  840
gcagccatgg cattgccagc attgttttct cttataattg gctttgcttt tggagcctta  900
tactggaaga agagacagcc aagtcttaca agggcagttg aaaatataca aattaatgaa  960
gaggataatg agataagtat gttgcaagag aaagagagag agtttcaaga agtgtaattg  1020
tggcttgtat caacactgtt actttcgtac attggctggt aacagttcat gtttgcttca  1080
taaatgaagc agctttaaac aaaattcatat tctgtctgga gtgacagacc acatctttat  1140
ctgttcttgc tacccatgac tttatatgga tgattcagaa attggaacag aatgttttac  1200
tgtgaaactg gcactgaatt aatcatctat aaagaagaac ttgcatggag caggactcta  1260
ttttaaggac tgcgggactt gggtctcatt tagaacttgc agctgatgtt ggaagagaaa  1320
gcacgtgtct cagactgcat gtaccatttg catggctcca gaaatgtcta aatgctgaaa  1380
aaacacctag ctttattctt cagatacaaa ctgcagcctg tagttatcct ggtctctgca  1440
agtagatttc agcttggata gtgagggtaa caatttttct caaagggatc tggaaaaaat  1500
gtttaaaact cagtagtgtc agccactgta cagtgtagaa agcagtggga actgtgattg  1560
gatttggcaa catgtcagct ttatagttgc cgattagtga tatgggtctg atttcgatct  1620
cttcctgatg taaaccatgc tcacccatat cccactatac aaatgcaaat ggttgcctgg  1680
ttccatttat gcaagggagc cagtactgaa ttatgccttg gcagagggga gactccaaaa  1740
gagtcatcgc aggaagaagt taagaacact gaacatcaga acagtctgcc aagaaggaca  1800
ttggcatcct gggaaagtcc gccttttccc ttgaccacta tagggtgtat aaatcgtgtt  1860
tgcaaaatgt gttatgatgt gtttatattc taaaactatt acagagctat gtaaagggac  1920
ttaggagaaa atgctgaatg taagatggtc ccatttcaat ttccaccatg ggagagccta  1980
aaaataaatt atgacattta gtatctaagg ttagaaaacc acgcccacat gctaatatgg  2040
gtgttgaaaa ctaggttact tataatgcaa ggaatcagga aactttagtt atttatagta  2100
taatcaccat tatctgttta aaggatccat ttagttaaaa tcgggcactc tatattcatt  2160
aaggtttatg aattaaaaag aaagctttat gtagttatgc atgtcagttt gctatttaaa  2220
atgtgtgaca gtgtttgtca tattaagagt gaatttggca ggaattccca agatggacat  2280
tgtgctttta aactagaact tgtaagacat tatgtgaata tcccttgcca atttttttta  2340
taataagaaa acatctgact aaagtcaaag aatgatttct tatggtttat tttgatgaaa  2400
gttcttttaa catgtcttga atgtacacat aaaggaatcc aaagctttcc attctaactt  2460
aatctttgtg ataacattat tgccatgttc tacaaccgta agatgacagt tttcaatgta  2520
gtgacacaaa agggcatgaa aaactaactg ctagctttcc tttcatttca aaagtccaaa  2580
aatttctagt atatttggat tttagcttct gttcaaagca aatccagatg caactccagt  2640
aagtggcctt tgctcttttt tgtaccaaag agcccagatg attcctacag tccctttctt  2700
ctctaacatg ctgtggttcc ttaaaatatga gtaatttctc taagatataa cccaggtgct  2760
ttgagaagct gcattaaggt gttcaggccc tcagatatca catggtacac ttgattagta  2820
ataaaaccag agatcaattt aaattgctga taggtcctgt ctcagtgtgt ggcattgact  2880
gttttcagga aaatagatac agattaatat gagttatgcg tgtaggttgt gtatagattg  2940
agaagataga tacttctcaa tctagtagtt tgatttattt aaccaatggt ttcagtttgc  3000
ttgagcatat gaaaatcctg cttaatgtgc ttaagagtat aataaatgtg tactttttgc  3060
ctcaaaccta gtagctgggt tttaacactc atggacatgg tcttaatcaa tggagttaaa  3120
taaacaaatt cagcaagtta ttaaatctga catggtagga gaggggagat gtgtcctgct  3180
tattaaatgt gttggtccat tgaaagttac atggattgcc aattttttaaa acactaaagt  3240
tgaataaaat gcatgaacaa tagaaaaatg ctgaacatta ttttggatgc tagctgcttg  3300
gacattaact gtgttatttc tgctttgaga tgaaaatata tatttatctt tgcttatttt  3360
atcccagatg tgttctgaat atccttcttc ataaatcatg gaaaactcac tgctgagata  3420
gtaaccatg aaatcgcctt ttcagttggt gccatgtatc tgacagttcc atcttggaag  3480
gtttcaaaat taccttttaa aatgatctca gaagtctgta gattctcaat gatactgaaa  3540
gctttgcacc tctttggtag aaaccaggtc tatttagaaa atggctttat gataaatgtt  3600
gcctcctgag tgataatgaa gtgttcctgg atattgtatt gtaatttaat gtgcttacca  3660
cactgccaca ttttaatgag tcagagaaaa attaatttt cttcaataca ataatagaac  3720
aagtagccta ttctcttaaa aagtatgtga aaagaaaatt atgaaaaaat atgcatacct  3780
aatgaagtat tggttttagt aagaattaaa tacatttcat tgagctttaa agtactttgg  3840
agaaactttg gggcacgttt tcctactcta attcaactaa agttataaat aaagagaaaa  3900
actcattcag aaatcatgga tttttaaaaat attttactgc agccaagttt tcatttcaaa  3960
atgtaatttc agtttggagc ttttaggcat tatgtatatt taaaaaatat attcttcaaa  4020
aatgcatttt ggcatggtgg gatggatgtt gcaaaagata tccggagcct ccagtctgtc  4080
attaactgat atggtaaatc acctctcttc tttgggtctc aatttttat ttatctatat  4140
ggtaaactca gagatcactc cttagggggtg agtcctattg caatatgacc gacaaagaag  4200
acaaaatagc attgaaacta acccatacaa aatatccaac tctggattct gtgaataagt  4260
atcttgacca taaaaagtca ttgctgttct tgtttctaat gtaaatagtg tccattagta  4320
aaagtgaaat tcagtcttaa gtagggtgaa ttggatcacc atttacacaa gagatggctt  4380
tttcctttgc ttgaataaac atttggatc acctccaaag aatgaaaacc agtagtacgt  4440
tttagtcata ttagtcagga tgagaaacta taagatgtgt gtaacatttg gaaatgcacc  4500
aaagtgagcg tttaaatctt ctcattttat tgaaaactaa gagcagaaaa tgtaaaatgc  4560
tcatgaaggt tttgaatgcc aaaagatatt ttagaatcaa tttataaagg ggtaattcat  4620
taattacact ttaaaattgg aaagtgggat aagaaatcta aagtaaacca gcttatcttt  4680
gaaacaatat tattttgaaa ttggctttaa aataaaacca ttcagattga aattctaatt  4740
```

```
agctcatttg tggagtttga tcacacaatt cataatgttg ctgctttcca ttaactagtc   4800
ttgaaatgcc tttgtttgta aaaataaaat aatggtactt tcatttata acaaggtgtt    4860
tttttcaaga aataatccat gctaaaatgg atatttgtga tcctgaaatg tttactaagc   4920
attgtaaatt tatttataac tgccatctcc aactacatcc ttatgatgtt tttaacaata   4980
aaattaaaac aactgttaaa ctaaaaacca caccgttttc cagtacttga tctctgagct   5040
acaatactca ctaaatataa ttttccaatc aaaatattct attctatatt ctaagggtta   5100
atatgtgatt atagtgtcca cttgccacca ttttttttaaa tcaatggact tgaaaagtat  5160
taatttagat ggatgcgcag atataccctc agttcagtca tagattggag tttgcatata   5220
ataatgtaaa tgtatgtcga cactattcta aatagttcta ttatgactga aatttaatta   5280
aataaaaaag gttgtaaaat gtgatgtgta tgtgtatata ctgtatgtgt acttttttaaa 5340
ataggtgtat gtcccaaccc ttttttatac aggtttgaat ttaaaattac atgatatata   5400
catatacttt attgttctaa ataaagaatt ttatgcactc tcaaaaaaaa aaaaaaaaa    5460

SEQ ID NO: 158          moltype = AA  length = 245
FEATURE                 Location/Qualifiers
source                  1..245
                        mol_type = protein
                        organism = Homo sapiens
SEQUENCE: 158
MKKTQTWILT CIYLQLLLFN PLVKTEGICR NRVTNNVKDV TKLVANLPKD YMITLKYVPG   60
MDVLPSHCWI SEMVVQLSDS LTDLLDKFSN ISEGLSNYSI IDKLVNIVDD LVECVKENSS   120
KDLKKSFKSP EPRLFTPEEF FRIFNRSIDA FKDFVVASET SDCVVSSTLS PEKGKAKNPP   180
GDSSLHWAAM ALPALFSLII GFAFGALYWK KRQPSLTRAV ENIQINEEDN EISMLQEKER   240
EFQEV                                                               245

SEQ ID NO: 159          moltype = DNA  length = 5376
FEATURE                 Location/Qualifiers
source                  1..5376
                        mol_type = genomic DNA
                        organism = Homo sapiens
SEQUENCE: 159
gggcttcgct cgccgcctcg cgccgagact agaagcgctg cgggaagcag ggacagtgga   60
gagggcgctg cgctcgggct acccaatgcg tggactatct gccgccgctg ttcgtgcaat   120
atgctggagc tccagaacag ctaaacggag tcgccacacc actgtttgtg ctggatcgca   180
gcgctgcctt tccttatgaa gaagcacaa acttggattc tcacttgcat ttatcttcag    240
ctgctcctat ttaatcctct cgtcaaaact gaagggatct gcaggaatcg tgtgactaat   300
aatgtaaaag acgtcactaa attggtggca aatcttccaa aagactacat gataaccctc   360
aaatatgtcc ccgggatgga tgttttgcca agtcattgtt ggataagcga gatggtagta   420
caattgtcag acagcttgac tgatcttctg gacaagtttt caaatatttc tgaaggcttg   480
agtaattatt ccatcataga caaacttgtg aatatagtgg atgaccttgt ggagtgcgtg   540
aaagaaaact catctaagga tctaaaaaaa tcattcaaga gcccagaacc caggctcttt   600
actcctgaag aattctttag aattttaat agatccattg atgccttcaa ggactttgta   660
gtggcatctg aaactagtga ttgtgtggtt tcttcaacat taagtcctga gaaagggaag   720
gccaaaaatc cccctggaga ctccagccta cactgggcag ccatggcatt gccagcattg   780
ttttctctta taattggctt tgcttttgga gccttatact ggaagaagag acagccaagt   840
cttacaaggg cagttgaaaa tatacaaatt aatgaagagg ataatgagat aagtatgttg   900
caagagaaag agagagagtt tcaagaagtg taattgtgat ttgtatcaac actgttactt   960
tcgtacattg gctggtaaca gttcatgttt gcttcataaa tgaagcagct ttaaacaaat   1020
tcatattctg tctggagtga cagaccacat ctttatctgt tcttgctacc catgacttta   1080
tatggatgat tcagaaattg gaacagaatg tttttactgtg aaactggcac tgaattaatc  1140
atctataaag aagaacttgc atggagcagg actctatttt aaggactgcg ggacttgggt   1200
ctcatttaga acttgcagct gatgttggaa gagagaaagcac gtgtctcaga ctgcatgtac 1260
catttgcatg gctccagaaa tgtctaaatg ctgaaaaaac acctagcttt attcttcaga   1320
tacaaactgc agcctgtagt tatcctggtc tctgcaagta gatttcagct tggatagtga   1380
gggtaacaat ttttctcaaa gggatctgga aaaaatgttt aaaactcagt agtgtcagcc   1440
actgtacagt gtagaaagca gtgggaactg tgattggatt tggcaacatg tcagcttat    1500
agttgccgat tagtgatatg ggtctgattt cgatctcttc ctgatgtaaa ccatgctcac   1560
ccatatccca ctatacaaat gcaaatggtt gcctggttcc atttatgcaa gggagccagt   1620
actgaattat gccttggcag aggggagact ccaaaagagt catcgcagga agaagttaag  1680
aacactgaac atcagaacag tctgccaaga aggacatggg catcctggga agtccgcct    1740
tttcccttga ccactatagg gtgtataaat cgtgtttgca aaatgtgtta tgatgtgttt   1800
atattctaaa actattacag agctatgtaa agggacttag gagaaaatgc tgaatgtaag   1860
atggtcccat ttcaatttcc accatgggag agcctaaaaa taaattatga catttagtat   1920
ctaaggttag aaaaccacgc ccacatgcta atatgggtgt tgaaaactag gttacttata   1980
atgcaaggaa tcaggaaact ttagttattt atagtataat caccattatc tgtttaaagg   2040
atccatttag ttaaaatcgg gcactctata ttcattaagg tttatgaatt aaaaagaaag   2100
ctttatgtag ttatgcatgt cagtttgcta tttaaaatgt gtgacagtgt ttgtcatatt   2160
aagagtgaat ttggcaggaa ttcccaagat ggacattgtg ctttttaaact agaacttgtt  2220
agacattatg tgaatatccc ttgccaattt tttttataat aagaaaaacat ctgactaaag  2280
tcaaagaatg atttcttatg gtttattttg atgaaagttc ttttaacatg tcttgaatgt   2340
acacataaag gaatccaaag ctttccattc taacttaatc tttgtgataa cattattgcc   2400
atgttctaca accgtaagat gacagttttc aatgtagtga cacaaaaggg catgaaaaac   2460
taactgctag ctttccttc atttcaaaag tccaagaatt tctagtatat ttggattta    2520
gcttctgttc aaagcaaatc cagatgcaac tccagtaagt ggcctttgct cttttttga    2580
ccaaagagcc cagatgattc ctacagtccc tttcttctct aacatgctgt ggttccttaa   2640
atatgagtaa tttctctaag atataaccca ggtgcttga gaagctgcat taaggtgttc    2700
aggccctcag atatcacatg gtacacttga ttagtaataa aaccagagat caatttaaat   2760
tgctgatagg tcctgtctca gtgtgtggca ttgactgttt tcaggaaaat agatacagat   2820
taatatgagt tatgcgtgta ggttgtgtat agattgagaa gatagatact tctcaatcta   2880
```

```
gtagtttgat ttatttaacc aatggtttca gtttgcttga gcatatgaaa atcctgctta   2940
atgtgcttaa gagtataata aatgtgtact tttgtcctca aacctagtag ctgggtttta   3000
acactcatgg acatggtctt aatcaatgga gttaaataaa caaattcagc aagttattaa   3060
atctgacatg gtaggagagg ggagatgtgt cctgcttatt aaatgtgttg gtccattgaa   3120
agttacatgg attgccaatt tttaaaacac taaagttgaa taaaatgcat gaacaataga   3180
aaaatgctga acattatttt ggatgctagc tgcttggaca ttaactgtgt tatttctgct   3240
ttgagatgaa aatatatatt tatctttgct tattttatcc cagatgtgtt ctgaatatcc   3300
ttcttcataa atcatggaaa actcactgct gagatagtaa accatgaaat cgcctttca    3360
gttggtgcca tgtatctgac agttccatct tggaaggttt caaaattacc ttttaaaagt   3420
atctcagaag tctgtagatt ctcaatgata ctgaaagctt tgcacctctt tggtagaaac   3480
caggtctatt tagaaaatgg ctttatgata aatgttgcct cctgagtgat aatgaagtgt   3540
tcctggatat tgtattgtaa tttaatgtgc ttaccacact gccacatttt aatgagtcag   3600
agaaaaatta attttttcttc aatacaataa tagaacaagt agcctattct cttaaaaagt   3660
atgtgaaaag aaaattatga aaaaaatgc atacctaatg aagtattggt tttagtaaga   3720
attaaataca tttcattgag ctttaaagta ctttggagaa actttggggc acgttttcct   3780
actctaattc aactaaagtt ataaataaag agaaaaactc attcagaaat catggatttt   3840
aaaaatattt tactgcagcc aagttttcat ttcaaaatgt aatttcagtt tggagctttt   3900
aggcattatg tatatttaaa aaatatattc ttcaaaaatg catttttggca tggtggggatg   3960
gatgttgcaa aagatatccg gagcctccag tctgtcatta actgatatgg taaatcacct   4020
ctcttctttg ggtctcaatt tttttatttat ctatatggta aactcagaga tcactcctta   4080
ggggtgagtc ctattgcaat atgaccgaca aagaagacaa aatagcattg aaactaaccc   4140
atacaaaata tccaactctg gattctgtga ataagtatct tgaccataaa aagtcattgc   4200
tgttcttgtt tctaatgtaa atagtgtcca ttagtaaaag tgaaattcag tcttaagtag   4260
ggtgaattgg atcaccattt acacaagaga tggcttttttc ctttgcttga ataaacatttt  4320
tggatcacct ccaaagaatg aaaaccagta gtacgttttaa gtcatattag tcaggatgag   4380
aaactataag atgtgtgtaa catttggaaa tgcaccaaag tgagcgttta aatcttctca   4440
ttttattgaa aactaagagc agaaaatgta aaatgctcat gaaggttttg aatgccaaaa   4500
gatattttag aatcaattta taaaggggta attcattaat tacactttaa aattggaaag   4560
tgggataaga aatctaaagt aaaccagctt atctttgaaa caatattatt ttgaaattgg   4620
ctttaaaata aaaccattca gattgaaatt ctaattagct catttgtgga gtttgatcac   4680
acaattcata atgttgctgc tttccattaa ctagtcttga aatgcctttg tttgtaaaaa   4740
taaaataatg gtactttcat tttataacaa ggtgtttttt tcaagaaata atccatgcta   4800
aaatggatat ttgtgatcct gaaatgttta ctaagcattg taaatttatt tataactgcc   4860
atctccaact acatccttat gatgttttta acaataaaat taaaacaact gttaaactaa   4920
aaaccacacc gttttccagt acttgatctc tgagctacaa tactcactaa atataatttt   4980
ccaatcaaaa tattctattc tatattctaa gggttaatat gtgattatag tgtccacttg   5040
ccaccatttt tttaaatcaa tggacttgaa aagtattaat ttagatggat gcgcagatat   5100
accctcagtt cagtcataga ttggagtttg catataataa tgtaaatgta tgtcgacact   5160
attctaaaata gttctattat gactgaaatt taattaaata aaaaaggttg taaaatgtga   5220
tgtgtatgtg tatatactgt atgtgtactt tttaaaatag gtgtatgtcc caaccctttt   5280
ttatacaggt ttgaatttaa aattacatga tatatacata tactttattg ttctaaataa   5340
agaattttat gcactctcaa aaaaaaaaaa aaaaaa                             5376
```

```
SEQ ID NO: 160          moltype = AA   length = 153
FEATURE                 Location/Qualifiers
source                  1..153
                        mol_type = protein
                        organism = Homo sapiens
SEQUENCE: 160
MGKISSLPTQ LFKCCFCDFL KVKMHTMSSS HLFYLALCLL TFTSSATAGP ETLCGAELVD   60
ALQFVCGDRG FYFNKPTGYG SSSRRAPQTG IVDECCFRSC DLRRLEMYCA PLKPAKSARS   120
VRAQRHTDMP KTQKEVHLKN ASRGSAGNKN YRM                                153

SEQ ID NO: 161          moltype = DNA   length = 7321
FEATURE                 Location/Qualifiers
source                  1..7321
                        mol_type = genomic DNA
                        organism = Homo sapiens
SEQUENCE: 161
ttttgtagat aaatgtgagg attttctcta aatccctctt ctgtttgcta aatctcactg   60
tcactgctaa attcagagca gatagagcct gcgcaatgga ataaagtcct caaaattgaa   120
atgtgacatt gctctcaaca tctcccatct ctctggattt cttttttgctt cattattcct   180
gctaaccaat tcattttcag actttgtact tcagaagcaa tgggaaaaat cagcagtctt   240
ccaacccaat tatttaagtg ctgcttttgt gatttcttga aggtgaagat gcacaccatg   300
tcctcctcgc atctcttcta cctggcgctg tgcctgctca ccttcaccag ctctgccacg   360
gctggaccgg agacgctctg cggggctgag ctggtggatg ctcttcagtt cgtgtgtgga   420
gacagggggct tttatttcaa caagcccaca gggtatggct ccagcagtcg gagggcgcct   480
cagacaggca tcgtggatga gtgctgcttc cggagctgtg atctaaggag gctggagatg   540
tattgcgcac ccctcaagcc tgccaagtca gctcgctctg tccgtgccca gcgccacacc   600
gacatgccca gacccagaa ggaagtacat ttgaagaacg caagtagagg gagtgcagga   660
aacaagaact acaggatgta ggaagaccct cctgaggagt gaagagtgac atgccaccgc   720
aggatccttt gctctgcacg agttacctgt taaactttgg aacacctacc aaaaaataag   780
tttgataaca tttaaaagat gggcgtttcc cccaatgaaa tacacaagta aacattccaa   840
cattgtcttt aggagtgatt tgcaccttgc aaaaatggtc ctggagttgg tagattgctg   900
ttgatctttt atcaataatg ttctatagaa aagaaaaaa aaatatatat atatatatat   960
cttagtccct gcctctcaag agccacaaat gcatgggtgt tgtatagatc cagttgcact   1020
aaattcctct ctgaatcttg gctgctggag ccattcattc agcaaccttg tctaagtggt   1080
ttatgaattg tttccttatt tgcacttctt tctacacaac tcgggctgtt tgttttacag   1140
tgtctgataa tcttgttagt ctatacccac cacctccctt cataaccttt atatttgccg   1200
```

-continued

```
aatttggcct cctcaaaagc agcagcaagt cgtcaagaag cacaccaatt ctaacccaca   1260
agattccatc tgtggcattt gtaccaaata taagttggat gcattttatt ttagacacaa   1320
agctttattt ttccacatca tgcttacaaa aaagaataat gcaaatagtt gcaactttga   1380
ggccaatcat ttttaggcat atgtttttaaa catagaaagt ttcttcaact caaaagagtt   1440
ccttcaaatg atgagttaat gtgcaaccta attagtaact ttcctctttt tatttttttcc  1500
atatagagca ctatgtaaat ttagcatatc aattatacag gatatatcaa acagtatgta   1560
aaactctgtt ttttagtata atggtgctat ttttgtagttt gttatatgaa agagtctggc   1620
caaaacggta atacgtgaaa gcaaaacaat aggggaagcc tggagccaaa gatgacacaa   1680
ggggaagggt actgaaaaca ccatccattt gggaaagaag gcaaagtccc cccagttatg   1740
ccttccaaga ggaacttcag acacaaaagt ccactgatgc aaattggact ggcgagtcca   1800
gagaggaaac tgtggaatgg aaaaagcaga aggctaggaa ttttagcagt cctggtttct   1860
ttttctcatg gaagaaatga acatctgcca gctgtgtcat ggactcacca ctgtgtgacc   1920
ttgggcaagt cacttcacct ctctgtgcct cagtttcctc atctgcaaaa tgggggcaat   1980
atgtcatcta cctacctcaa aggggtggta taaggtttaa aaagataaag attcagattt   2040
ttttaccct gggttgctgt aagggtgcaa catcagggcg cttgagttgc tgagatgcaa    2100
ggaattctat aaataaccca ttcatagcat agctagagat tggtgaattg aatgctcctg   2160
acatctcagt tcttgtcagt gaagctatcc aaataactgg ccaactagtt gttaaaagct   2220
aacagctcaa tctcttaaaa cacttttcaa aatatgtggg aagcatttga ttttcaattt   2280
gattttgaat tctgcatttg gttttatgaa tacaaagata agtgaaaaga gagaaaggaa   2340
aagaaaaagg agaaaaacaa agagatttct accagtgaaa ggggaattaa ttactctttg   2400
ttagcactca ctgactcttc tatgcagtta ctacatatct agtaaaacct cgtttaatac   2460
tataaataat attctattca ttttgaaaaa cacaatgatt ccttctttttc taggcaatat   2520
aaggaaagtg atccaaaatt tgaaatatta aaataatatc taataaaaag tcacaaagtt   2580
atcttcttta acaaacttta ctcttattct tagctgtata tacatttttt taaaagtttg   2640
ttaaaatatg cttgactaga gtttccagtt gaaaggcaaa aacttccatc acaacaagaa   2700
atttcccatg cctgctcaga agggtagccc ctagctctct gtgaatgtgt tttatccatt   2760
caactgaaaa ttggtatcaa gaaagtccac tggttagtgt actagtccat catagcctag   2820
aaaatgatcc ctatctgcag atcaagattt tctcattaga acaatgaatt atccagcatt   2880
cagatctttc tagtcacctt agaacttttt ggttaaaagt acccaggctt gattatttca   2940
tgcaaattct atattttaca ttcttggaaa gtctatatga aaaacaaaaa taacatcttc   3000
agtttttctc ccactgggtc acctcaagga tcagaggcca ggaaaaaaaa aaaaagact    3060
ccctggatct ctgaatatat gcaaaaagaa ggccccattt agtggagcca gcaatcctgt   3120
tcagtcaaca agtattttaa ctctcagtcc aacattattt gaattgagca cctcaagcat   3180
gcttagcaat gttctaatca ctatggacag atgtaaaaga aactatacat cattttttgcc  3240
ctctgcctgt tttccagaca tacaggttct gtggaataag atactggact cctcttccca   3300
agatggcact tctttttatt tcttgtcccc agtgtgtacc ttttaaaatt attccctctc   3360
aacaaaactt tataggcagt cttctgcaga cttaacgtgt tttctgtcat agttagatgt   3420
gataattcta agagtgtcta tgacttattt ccttcactta attctatcca cagtcaaaaa   3480
tcccccaagg aggaaagctg aaagatgcac tgccatatta tctttcttaa ctttttccaa   3540
cacataatcc tctccaactg gattataaat aaattgaaaa taactcatta taccaattca   3600
ctattttatt ttttaatgaa ttaaaactag aaaacaaatt gatgcaaacc ctggaagtca   3660
gttgattact atatactaca gcagaatgac tcagatttca tagaaaggag caaccaaaat   3720
gtcacaaccc aaaactttac aagctttgct tcagaattag attgctttat aattcttgaa   3780
tgaggcaatt tcaagatatt tgtaaaagaa cagtaaacat tggtaagaat gagctttcaa   3840
ctcataggct tatttccaat ttaattgacc atactggata cttaggtcaa atttctgttc   3900
tctcttcccc aaataaatatt aaagtattat ttgaacttttt taagatgagg cagttcccct  3960
gaaaaagtta atgcagctct ccatcagaat ccactctttt agggatatga aaatctctta   4020
acacccaccc tacatacaca gacacacaca cacacacaca cacacacaca cacacacaca   4080
ttcaccctaa ggatccaatg gaatactgaa aagaaatcac ttccttgaaa attttattaa   4140
aaaacaaaca aacaaacaaa aagcctgtcc acccttgaga atccttcctc tccttggaac   4200
gtcaatgttt gtgtagatga aaccatctca tgctctgtgg ctccagggtt tctgttacta   4260
ttttatgcac ttgggagaag gcttagaata aaagatgtag cacattttgc tttcccattt   4320
attgtttggc cagctatgcc aatgtggtgc tattgtttct ttaagaaagt acttgactaa   4380
aaaaaaaaga aaaaagaaa aaaagaaag catagacata ttttttttaaa gtataaaaac   4440
aacaattcta tagatagatg gcttaataaa atagcattag gtctatctag ccaccaccac   4500
ctttcaactt tttatcactc acaagtagtg tactgttcac caaattgtga atttgggggt   4560
gcaggggcag gagttggaaa ttttttaaag ttagaaggct ccattgtttt gttggctctc   4620
aaacttagca aaattagcaa tatattatcc aatcttctga acttgatcaa gagcatggag   4680
aataaacgcg ggaaaaaaga tcttataggc aaatagaaga atttaaaaga taagtaagtt   4740
ccttattgat ttttgtgcac tctgctctaa aacagatatt cagcaagtgg agaaaataag   4800
aacaaagaga aaaaatacat agatttacct gcaaaaaata gcttctgcca aatccccctt   4860
gggtattctt tggcatttac tggtttatag aagacattct cccttcaccc agacatctca   4920
aagagcagta gctctcatga aaagcaatca ctgatctcat ttgggaaatg ttggaaagta   4980
tttccttatg agatgggggt tatctactga taaagaaaga atttatgaga aattgttgaa   5040
agagatggct aacaatctgt gaagattttt tgtttcttgt ttttgttttt ttttttttt    5100
tactttatac agtctttatg aatttcttaa tgttcaaaat gacttggttc ttttcttctt   5160
ttttatatc agaatgagga ataataagtt aaacccacat agactcttta aaactatagg   5220
ctagatagaa atgtatgttt gacttgttga agctataatc agactatttta aaatgttttg   5280
ctattttttaa tcttaaaaga ttgtgctaat ttattagagc agaacctgtt tggctctcct   5340
cagaagaaag aatctttcca ttcaaatcac atggctttcc accaatattt tcaaaagata   5400
aatctgattt atgcaatggc atcatttatt ttaaaacaga agaattgtga aagtttatgc   5460
ccctcccttg caaagaccat aaagtccaga tctggtaggg gggcaacaac aaaaggaaaa   5520
tgttgttgat tcttggtttt ggattttgtt ttgttttcaa tgctagtgtt taatcctgta   5580
gtacatatt gcttattgct attttaatat tttataagac cttcctgtta ggtattagaa   5640
agtgatacat agatatcttt tttgtgtaat ttctatttaa aaaagagaga agactgtcag   5700
aagctttaag tgcatatggt acaggataaa gatatcaatt taaataacca attcctatct   5760
ggaacaatgc ttttgttttt taaagaaacc tctcacagat aagacagagg cccagggat    5820
ttttgaagct gtctttattc tgcccccatc ccaacccagc cctattatt ttagtatctg    5880
cctcagaatt ttatagaggg ctgaccaagc tgaaactcta gaattaaagg aacctcactg   5940
```

-continued

```
aaaacatata tttcacgtgt tccctctttt ttttttttcct ttttgtgaga tggggtctcg  6000
cactgtcccc caggctggag tgcagtggca tgatctcggc tcactgcaac ctccacctcc  6060
tgggtttaag cgattctcct gcctcagcct cctgagtagc tgggattaca ggcacccacc  6120
actatgcccg gctaattttt tggattttta atagagacgg ggtttacca tgttggccag  6180
gttggtctca aactcctgac cttgtgattt gcccgcctca gcctcccaaa ttgctgggat  6240
tacaggcatg agccaccaca ccctgcccat gtgttccctc ttaatgtatg attacatgga  6300
tcttaaacat gatccttctc tcctcattct tcaactatct ttgatggggt ctttcaaggg  6360
gaaaaaaatc caagcttttt taaagtaaaa aaaaaaaaag agaggacaca aaaccaaatg  6420
ttactgctca actgaaatat gagttaagat ggagacagag tttctcctaa taaccggagc  6480
tgaattacct ttcactttca aaaacatgac cttccacaat ccttagaatc tgcctttttt  6540
tatattactg aggcctaaaa gtaaacatta ctcattttat tttgcccaaa atgcactgat  6600
gtaaagtagg aaaaataaaa acagagctct aaaatccctt tcaagccacc cattgacccc  6660
actcaccaac tcatagcaaa gtcacttctg ttaatccctt aatctgattt tgtttggata  6720
tttatcttgt acccgctgct aaacacactg caggagggac tctgaaacct caagctgtct  6780
acttacatct tttatctgtg tctgtgtatc atgaaaatgt ctattcaaaa tatcaaaacc  6840
tttcaaaatat cacgcagctt atattcagtt tacataaagg ccccaaatac catgtcagat  6900
cttttttggta aaagagttaa tgaactatga gaattgggat tacatcatgt attttgcctc  6960
atgtattttt atcacactta taggccaagt gtgataaata aacttacaga cactgaatta  7020
atttcccctg ctactttgaa accagaaaat aatgactggc cattcgttac atctgtctta  7080
gttgaaaagc atattttta ttaaattaat tctgattgta tttgaaatta ttattcaatt  7140
cacttatggc agaggaatat caatcctaat gacttctaaa aatgtaacta attgaatcat  7200
tatcttacat ttactgttta ataagcatat tttgaaaatg tatggctaga gtgtcataat  7260
aaaatggtat atctttcttt agtaattaca ttaaaattag tcatgtttga ttaattagtt  7320
c                                                                   7321

SEQ ID NO: 162        moltype = AA   length = 158
FEATURE              Location/Qualifiers
source               1..158
                     mol_type = protein
                     organism = Homo sapiens
SEQUENCE: 162
MGKISSLPTQ LFKCCFCDFL KVKMHTMSSS HLFYLALCLL TFTSSATAGP ETLCGAELVD   60
ALQFVCGDRG FYFNKPTGYG SSSRRAPQTG IVDECCFRSC DLRRLEMYCA PLKPAKSARS  120
VRAQRHTDMP KTQKYQPPST NKNTKSQRRK GSTFEERK                           158

SEQ ID NO: 163        moltype = DNA   length = 7370
FEATURE              Location/Qualifiers
source               1..7370
                     mol_type = genomic DNA
                     organism = Homo sapiens
SEQUENCE: 163
ttttgtagat aaatgtgagg attttctcta aatccctct ctgtttgcta aatctcactg    60
tcactgctaa attcagagca gatagagcct gcgcaatgga ataaagtcct caaaattgaa   120
atgtgacatt gctctcaaca tctcccatct ctctggattt ctttttgctt cattattcct   180
gctaaccaat tcattttcag actttgtact tcagaagcaa tgggaaaaat cagcagtctt   240
ccaacccaat tatttaagtg ctgcttttgt gatttcttga aggtgaagat gcacaccatg   300
tcctcctcgc atctctctcta cctggcgctg tgcctgctca cctcaccag ctctgccacg   360
gctggaccgg agacgctctg cggggctgag ctggtggatg ctcttcagtt cgtgtgtgga   420
gacaggggct tttatttcaa caagcccaca gggtatggct ccagcagtcg gagggcgcct   480
cagacaggca tcgtggatga gtgctgcttc cggagctgtg atctcaggag gctggagatg   540
tattgcgcac ccctcaagcc tgccaagtca gctcgctctg tccgtgccca gcgccacacc   600
gacatgccca agacccagaa gtatcagccc ccatctacca acaagaacac gaagtctcag   660
agaaggaaag gaagtacatt tgaagaacgc aagtagaggg agtgcaggaa acaagaacta   720
caggatgtag gaagaccctc ctgaggagtg aagagtgaca tgccaccgca ggatcctttg   780
ctctgcacga gttacctgtt aaactttgga acacctacca aaaaataagt ttgataacat   840
ttaaaagatg ggcgtttccc ccaatgaaat acacaagtaa acattccaac attgtcttta   900
ggagtgattt gcaccttgca aaaatggtcc tggagttggt agattgctgt tgatctttta   960
tcaataatgt tctatagaaa agaaaaaaaa aatatatata tatatatatc ttagtccctg  1020
cctctcaaga gccacaaatg catgggtgtt gtatagatcc agttgcacta aattcctctc  1080
tgaatcttgg ctgctggagc cattcattca gcaaccttgt ctaagtggtt tatgaattgc  1140
ttccttatttt gcacttcttt ctacacaact cgggctgttt gttttacagt gtctgataat  1200
cttgttagtc tatacccacc acctcccttc ataacctta tatttgccga atttggcctc  1260
ctcaaaagca gcagcaagtc gtcaagaagc acaccaattc taaccacaa gattccatct  1320
gtggcatttg taccaaatat aagttggatg catttattt tagacacaaa gcttttatttt  1380
tccacatcat gcttacaaaa aagaataatg caaatagttg caactttgag gccaatcatt  1440
tttaggcata tgtttaaac atagaaagtt tcttcaactc aaaagagttc cttcaaatga  1500
tgagttaatg tgcaacctaa ttagtaactt tcctcttttt atttttttcca tatagagcac  1560
tatgtaaatt tagcatatca attatacagg atatatcaaa cagtatgtaa aactctgttt  1620
tttagtataa tggtgctatt ttgtagtttg ttatatgaaa gagtctggcc aaaacggtaa  1680
tacgtgaaag caaaacaata gggggaagcct ggagccaaag atgacacaag gggaagggta  1740
ctgaaaacac catccatttg ggaaagaagg caaagtcccc ccagttatgc cttccaagag  1800
gaacttcaga cacaaaagtc cactgatgca aattggactg gcgagtccag agaggaaact  1860
gtggaatgga aaaagcagaa ggctaggaat tttagcagtc ctggtttctt tttctcatgg  1920
aagaaatgaa catctgccag ctgtgtcatg gactcaccac tgtgtgacct tgggcaagtc  1980
acttcacctc tctgtgcctc agtttcctca tctgcaaaat ggggggcaata tgtcatctac  2040
ctacctcaaa ggggtggtat aaggtttaaa aagataaaga ttcagatttt ttttaccctg  2100
ggttgctgta agggtgcaac atcagggcgc ttgagttgct gagatgcaag gaattctata  2160
aataaccccat tcatagcata gctagagatt ggtgaattga atgctcctga catctcagtt  2220
cttgtcagtg aagctatcca aataactggc caactagttg ttaaaagcta acagctcaat  2280
```

-continued

```
ctcttaaaac acttttcaaa atatgtggga agcatttgat tttcaatttg attttgaatt  2340
ctgcatttgg ttttatgaat acaaagataa gtgaaaagag agaaaggaaa agaaaaagga  2400
gaaaaacaaa gagatttcta ccagtgaaag gggaattaat tactctttgt tagcactcac  2460
tgactcttct atgcagttac tacatatcta gtaaaacctc gtttaatact ataaataata  2520
ttctattcat tttgaaaaac acaatgattc cttcttttct aggcaatata aggaaagtga  2580
tccaaaattt gaaatattaa aataatatct aataaaaagt cacaaagtta tcttctttaa  2640
caaactttac tcttattctt agctgtatat acatttttt aaaagtttgt taaaatatgc  2700
ttgactagag tttccagttg aaaggcaaaa acttccatca caacaagaaa tttcccatgc  2760
ctgctcagaa gggtagcccc tagctctctg tgaatgtgtt ttatccattc aactgaaaat  2820
tggtatcaag aaagtccact ggttagtgta ctagtccatc atagcctaga aaatgatccc  2880
tatctgcaga tcaagatttt ctcattagaa caatgaatta tccagcattc agatctttct  2940
agtcacctta gaactttttg gttaaaagta cccaggcttg attatttcat gcaaattcta  3000
tattttacat tcttggaaag tctatatgaa aaacaaaaat aacatcttca gtttttctcc  3060
cactgggtca cctcaaggat cagaggccag gaaaaaaaaa aaaaagactc cctggatctc  3120
tgaatatatg caaaaagaag gccccattta gtggagccag caatcctgtt cagtcaacaa  3180
gtattttaac tctcagtcca acattatttg aattgagcac ctcaagcatg cttagcaatg  3240
ttctaatcac tatggacaga tgtaaaagaa actatacatc attttgccc tctgcctgtt  3300
ttccagacat acaggttctg tggaataaga tactggactc ctcttcccaa gatggcactt  3360
ctttttattt cttgtcccca gtgtgtacct tttaaaatta ttccctctca acaaaacttt  3420
ataggcagtc ttctgcagac ttaacgtgtt ttctgtcata gttagatgtg ataattctaa  3480
gagtgtctat gacttatttc cttcacttaa ttctatccac agtcaaaaat cccccaagga  3540
ggaaagctga aagatgcact gccatattat cttcttaac tttttccaac acataatcct  3600
ctccaactgg attataaata aattgaaaat aactcattat accaattcac tattttattt  3660
tttaatgaat taaaactaga aaacaaattg atgcaaaccc tggaagtcag ttgattacta  3720
tatactacag cagaatgact cagatttcat agaaaggagc aaccaaaatg tcacaaccca  3780
aaactttaca agctttgctt cagaattaga ttgctttata attcttgaat gaggcaattt  3840
caagatattt gtaaaagaac agtaaacatt ggtaagaatg agctttcaac tcataggctt  3900
atttccaatt taattgacca tactggatac ttaggtcaaa tttctgttct ctcttcccca  3960
aataatatta aagtattatt tgaacttttt aagatgaggc agttccctg aaaaagttaa  4020
tgcagctctc catcagaatc cactcttcta gggatatgaa aatctcttaa caccacccct  4080
acatacacag acacacacac acacacacac acacacacac acacacacat tcaccctaag  4140
gatccaatgg aatactgaaa agaaatcact tccttgaaaa ttttattaaa aaacaaacaa  4200
acaaacaaaa agcctgtcca cccttgagaa tccttcctct ccttggaacg tcaatgtttg  4260
tgtagatgaa accatctcat gctctgtggc tccaggggtt ctgttactat tttatgcact  4320
tgggagaagg cttagaataa aagatgtagc acattttgct ttcccattta ttgtttggcc  4380
agctatgcca atgtggtgct attgtttctt taagaaagta cttgactaaa aaaaaaagaa  4440
aaaaagaaaa aaaagaaagc atagacatat ttttttaaag tataaaaaca acaattctat  4500
agatagatgg cttaataaaa tagcattagg tctatctagc caccaccacc tttcaacttt  4560
ttatcactca caagtagtgt actgttcacc aaattgtgaa tttgggggtg caggggcagg  4620
agttggaaat tttttaaagt tagaaggctc cattgtttg ttggctctca aacttagcaa  4680
aattagcaat atattatcca atcttctgaa cttgatcaag agcatggaga ataaacgcgg  4740
gaaaaaagat cttataggca aatagaagaa tttaaaagat aagtaagttc cttattgatt  4800
tttgtgcact ctgctctaaa acagatattc agcaagtgga gaaaataaga acaaagagaa  4860
aaaatacata gatttacctg caaaaaatag cttctgccaa atcccccttg ggtattcttt  4920
ggcatttact ggtttatga agacattctc ccttcaccca gacatctcaa agagcagtag  4980
ctctcatgaa aagcaatcac tgatctcatt tgggaaatgt tggaaagtat ttccttatga  5040
gatggggtt atctactgat aaagaaagaa tttatgagaa attgttgaaa gagatggcta  5100
acaatctgtg aagattttt gtttcttgtt tttgtttttt tttttttttt actttatacca  5160
gtctttatga atttcttaat gttcaaaatg acttggttct tttcttcttt ttttatatca  5220
gaatgaggaa taataagtta aacccacata gactctttaa aactataggc tagatagaaa  5280
tgtatgtttg acttgttgaa gctataatca gactatttaa aatgtttttgc tattttaat  5340
cttaaaagat tgtgctaatt tattagagca gaacctgttt ggctctcctc agaagaaaga  5400
atcttttccat tcaaatcaca tggctttcca ccaatatttt caaaagataa atctgattta  5460
tgcaatggca tcatttattt taaaacagaa gaattgtgaa agtttatgcc cctcccttgc  5520
aaagaccata aagtccagat ctggtagggg ggcaacaaca aaaggaaaat gttgttgatt  5580
cttggttttg gattttgttt tgttttcaat gctagtgttt aatcctgtag tacatatttg  5640
cttattgcta ttttaatatt ttataagacc ttcctgttag gtattagaaa gtgatacata  5700
gatatctttt ttgtgtaatt tctatttaaa aaagagagaa gactgtcaga agctttaagt  5760
gcatatggta caggataaag atatcaattt aaataaccaa ttcctatctg gaacaatgct  5820
tttgttttt aaagaaacct ctcacagata agacagaggc ccaggggatt tttgaagctg  5880
tctttattct gcccccatcc caacccagcc cttattattt tagtatctgc ctcagaattt  5940
tatagagggc tgaccaagct gaaactctag aattaaagga acctcactga aaacatatat  6000
ttcacgtgtt ccctctttt ttttttcctt tttgtgagat gggggtctcgc actgtccccc  6060
aggctgggaa gcagtggcat gatctcggct cactgcaacc tccacctcct gggtttaagc  6120
gattctcctg cctcagcctc ctgagtagct gggattacag gcaccacca ctatgcccgg  6180
ctaattttt ggattttaa tagagacggg gttttaccat gttggccagg ttggtctcaa  6240
actcctgacc ttgtgatttg cccgcctcag cctcccaaat tgctgggatt acaggcatga  6300
gccaccacac cctgcccatg tgttccctct taatgtatga ttacatggat cttaaacatg  6360
atccttctct cctcattctt caactatctt tgatgggggtc tttcaagggg aaaaaaatcc  6420
aagctttttt aaagtaaaaa aaaaaaaaga gaggacacaa aaccaaatgt tactgctcaa  6480
ctgaaatatg agttaagatg gagacagagt ttctcctaat aaccggagct gaattacctt  6540
tcactttcaa aaacatgacc ttccacaatc cttagaatct gccttttttt atattactga  6600
ggcctaaaag taaacattac tcattttatt ttgcccaaaa tgcactgatg taaagtagga  6660
aaaataaaaa cagagctcta aaatcccttt caagccaccc attgaccca ctcaccaact  6720
catagcaaag tcacttctgt taatcccttta atctgatttt gtttggatat ttatcttgta  6780
cccgctgcta aacacactgc aggagggact ctgaaacctc aagctgtcta cttacatctt  6840
ttatctgtgt ctgtgtatca tgaaaatgtc tattcaaaat atcaaaacct ttcaaaatatc  6900
acgcagctta tattcagttt acataaaggc cccaaataacc atgtcagatc tttttggtaa  6960
aagagttaat gaactatgag aattgggatt acatcatgta ttttgcctca tgtattttta  7020
```

-continued

```
tcacacttat aggccaagtg tgataaataa acttacagac actgaattaa tttccctgc    7080
tactttgaaa ccagaaaata atgactggcc attcgttaca tctgtcttag ttgaaaagca    7140
tattttttat taaattaatt ctgattgtat ttgaaattat tattcaattc acttatggca    7200
gaggaatatc aatcctaatg acttctaaaa atgtaactaa ttgaatcatt atcttacatt    7260
tactgtttaa taagcatatt ttgaaaatgt atggctagag tgtcataata aaatggtata    7320
tctttcttta gtaattacat taaaattagt catgtttgat taattagttc               7370

SEQ ID NO: 164            moltype = AA  length = 137
FEATURE                   Location/Qualifiers
source                    1..137
                          mol_type = protein
                          organism = Homo sapiens
SEQUENCE: 164
MITPTVKMHT MSSSHLFYLA LCLLTFTSSA TAGPETLCGA ELVDALQFVC GDRGFYFNKP    60
TGYGSSSRRA PQTGIVDECC FRSCDLRRLE MYCAPLKPAK SARSVRAQRH TDMPKTQKEV    120
HLKNASRGSA GNKNYRM                                                   137

SEQ ID NO: 165            moltype = DNA  length = 7204
FEATURE                   Location/Qualifiers
source                    1..7204
                          mol_type = genomic DNA
                          organism = Homo sapiens
SEQUENCE: 165
gcatacctgc ctgggtgtcc aaatgtaact agatgctttc acaaacccca cccacaaagc    60
agcacatgtt tttaagactt cagtttttcta ttcatcgg cctcataata cccaccctga    120
cctgctgtaa aagacctgga acaaacaaaa atgattacac ctacagtgaa gatgcacacc    180
atgtcctcct cgcatctctt ctacctggcg ctgtgcctgc tcaccttcac cagctctgcc    240
acggctggac cggagacgct ctgcggggct gagctggtgg atgctcttca gttcgtgtgt    300
ggagacaggg gcttttattt caacaagccc acagggtatg gctccagcag tcggagggcg    360
cctcagacag gcatcgtgga tgagtgctgc ttccggagct gtgatctaag gaggctggag    420
atgtattgcg caccCctcaa gcctgccaag tcagctcgct ctgtccgtgc ccagcgccac    480
accgacatgc ccaagaccca gaaggaagta catttgaaga acgcaagtag agggagtgca    540
ggaaacaaga actacaggat gtaggaagac cctcctgagg agtgaagagt gacatgccac    600
cgcaggatcc tttgctctgc acgagttacc tgttaaactt tggaacacct accaaaaaat    660
aagtttgata acatttaaaa gatgggcgtt tcccccaatg aaatacacaa gtaaacattc    720
caacattgtc tttaggagtg atttgcacct tgcaaaaatg gtcctggagt tggtagattg    780
ctgttgatct tttatcaata atgttctata gaaaagaaaa aaaaaatata tatatatata    840
tatcttagtc cctgcctctc aagagccaca aatgcatggg tgttgtatag atccagttgc    900
actaaattcc tctctgaatc ttggctgctg gagccattca ttcagcaacc ttgtctaagt    960
ggtttatgaa ttgtttcctt atttgcactt cttttctacac aactcgggct gtttgtttta    1020
cagtgtctga taatcttgtt agtctatacc caccacctcc cttcataacc tttatatttg    1080
ccgaatttgg cctcctcaaa agcagcagca agtcgtcaag aagcacacca attctaaccc    1140
acaagatcc atctgtggca tttgtaccaa atataagttg gatgcatttt attttagaca    1200
caaagcttta ttttccaca tcatgcttac aaaaaagaat aatgcaaata gttgcaactt    1260
tgaggccaat catttttagg catatgtttt aaacatagaa agtttcttca actcaaaaga    1320
gttccttcaa atgatgagtt aatgtgcaac ctaattagta actttcctct ttttattttt    1380
tccatataga gcactatgta aatttagcat atcaattata caggatatat caaacagtat    1440
gtaaaactct gttttttagt ataatggtgc tatttgtag tttgttatat gaaagagtct    1500
ggccaaaacg gtaatacgtg aaagcaaaac aataggggaa gcctggagcc aaagatgaca    1560
caaggggaag ggtactgaaa acaccatcca tttgggaaag aaggcaaagt cccccagtt    1620
atgccttcca agaggaactt cagacacaaa agtccactga tgcaaattgg actggcagtt    1680
ccagagagga aactgtggaa tggaaaaagc agaaggctag gaattttagc agtcctggtt    1740
tcttttttctc atggaagaaa tgaacatctg ccagctgtgt catggactca ccactgtgtg    1800
accttgggca agtcacttca cctctctgtg cctcagtttc ctcatctgca aaatgggggc    1860
aatatgtcat ctacctacct caaaggggtg gtataaggtt taaaaagata aagattcaga    1920
ttttttttac cctgggttgc tgtaagggtg caacatcagg gcgcttgagt tgctgagatg    1980
caaggaattc tataaataac ccattcatag catagctaga gattggtgaa ttgaatgctc    2040
ctgacatctc agttcttgtc agtgaagcta tccaaataac tggccaacta gttgttaaaa    2100
gctaacagct caatctctta aaacactttt caaaatatgt gggaagcatt tgattttcaa    2160
tttgatttg aattctgcat ttggttttat gaatacaaag ataagtgaaa gagagagaag    2220
gaaaagaaaa aggagaaaaa caaagagatt tctaccagtg aaaggggaat taattactct    2280
ttgttagcac tcactgactc ttctatgcag ttactacata tctagtaaaa cctcgtttaa    2340
tactataaat aatattctat tcattttgaa aaacacaatg attccttctt ttctaggcaa    2400
tataaggaaa gtgatccaaa atttgaaata ttaaaataat atctaataaa aagtcacaaa    2460
gttatcttct ttaacaaact ttactcttat tcttagctgt atatacattt ttttaaaagt    2520
ttgttaaaat atgcttgact agagtttcca gttgaaaggc aaaaacttcc atcacaacaa    2580
gaaatttccc atgcctgctc agaagggtag cccctagctc tctgtgaatg tgtttttatcc    2640
attcaactga aaattggtat caagaaagtc cactggttag tgtactagtc catcatagcc    2700
tagaaaatga tccctatctg cagatcaaga tttctcatt agaacaatga attatccagc    2760
attcagatct ttctagtcac cttagaactt tttggttaaa agtacccagg cttgattatt    2820
tcatgcaaat tctatatttt acattcttgg aaagtctata tgaaaaacaa aaataacatc    2880
ttcagtttt ctcccactgg gtcacctcaa ggatcagagg ccaggaaaaa aaaaaaaaag    2940
actccctgga tctctgaata tatgcaaaaa gaaggcccca tttagtggag ccagcaatcc    3000
tgttcagtca acaagtattt taactctcag tccaacatta tttgaattga gcacctcaag    3060
catgcttagc aatgttctaa tcactatgga cagatgtaaa agaaactata catcattttt    3120
gccctctgcc tgtttccag acatacaggt tctgtggaat aagatactgg actcctcttc    3180
ccaagatggc acttcttttt atttcttgtc cccagtgtgt accttttaaa attattccct    3240
ctcaacaaaa ctttataggc agtcttctgc agacttaacg tgtttctgt catagttaga    3300
tgtgataatt ctaagagtgt ctatgactta tttccttcac ttaattctat ccacagtcaa    3360
```

-continued

```
aaatccccca aggaggaaag ctgaaagatg cactgccata ttatctttct taacttttttc  3420
caacacataa tcctctccaa ctggattata aataaattga aaataactca ttataccaat   3480
tcactatttt attttttaat gaattaaaac tagaaaacaa attgatgcaa accctggaag   3540
tcagttgatt actatatact acagcagaat gactcagatt tcatagaaag gagcaaccaa   3600
aatgtcacaa cccaaaactt tacaagcttt gcttcagaat tagattgctt tataattctt   3660
gaatgaggca atttcaagat atttgtaaaa gaacagtaaa cattggtaag aatgagcttt   3720
caactcatag gcttatttcc aatttaattg accatactgg atacttaggt caaatttctg   3780
ttctctcttc cccaaataat attaaagtat tatttgaact ttttaagatg aggcagttcc   3840
cctgaaaaag ttaatgcagc tctccatcag aatccactct tctagggata tgaaaatctc   3900
ttaacaccca ccctacatac acagacacac acacacacac acacacacac acacacacac   3960
acattcaccc taaggatcca atggaatact gaaaagaaat cacttccttg aaaattttat   4020
taaaaaacaa acaaacaaac aaaaagcctg tccacccttg agaatccttc ctctccttgg   4080
aacgtcaatg tttgtgtaga tgaaaccatc tcatgctctg tggctccagg gtttctgtta   4140
ctattttatg cacttgggag aaggcttaga ataaaagatg tagcacattt tgctttccca   4200
tttattgttt ggccagctat gccaatgtgg tgctattgtt tctttaagaa agtacttgac   4260
taaaaaaaaa agaaaaaaag aaaaaaaaga aagcatagac atattttttt aaagtataaa   4320
aacaacaatt ctatagatag atggcttaat aaaatagcat taggtctatc tagccaccac   4380
caccttttcaa cttttttatca ctcacaagta gtgtactgtt caccaaattg tgaatttggg   4440
ggtgcagggg caggagttgg aaattttttta aagttagaag gctccattgt tttgttggct   4500
ctcaaactta gcaaaattag caatatatta tccaatcttc tgaacttgat caagagcatg   4560
gagaataaac gcgggaaaaa agatcttata ggcaaataga agaatttaaa agataagtaa   4620
gttccttatt gatttttgtg cactctgctc taaaacagat attcagcaag tggagaaaat   4680
aagaacaaag agaaaaaata catagattta cctgcaaaaa atagcttctg ccaaatcccc   4740
cttgggtatt cttttggcatt tactggttta tagaagacat tctcccttca cccagacatc   4800
tcaaagagca gtagctctca tgaaaagcaa tcactgatct catttgggaa atgttggaaa   4860
gtatttcctt atgagatggg ggttatctac tgataaagaa agaaatttatg agaaattgtt   4920
gaaagagatg gctaacaatc tgtgaagatt ttttgtttct tgttttttgtt ttttttttttt   4980
ttttactttta tacagtctttt atgaatttct taatgttcaa aatgacttgg ttctttttctt   5040
cttttttttat atcagaatga ggaataataa gttaaaccca catagactct ttaaaactat   5100
aggctagata gaaatgtatg tttgacttgt tgaagctata atcagactat ttaaaatgtt   5160
ttgctatttt taatcttaaa agattgtgct aatttattag agcagaacct gtttggctct   5220
cctcagaaga aagaatcttt ccattcaaat cacatggctt tccaccaata ttttcaaaag   5280
ataaatctga tttatgcaat ggcatcattt attttaaaac agaagaattg tgaaagttta   5340
tgcccctccc ttgcaaagac cataaagtcc agatctggta gggggggcac aacaaaagga   5400
aaatgttgtt gattcttggt tttggatttt gttttgtttt caatgctagt gtttaatcct   5460
gtagtacata tttgcttatt gctattttaa tattttataa gaccttcctg ttaggtatta   5520
gaaagtgata catagatatc ttttttgtgt aatttctatt taaaaaagag agaagactgt   5580
cagaagcttt aagtgcatat ggtacaggat aaagatatca atttaaataa ccaattccta   5640
tctggaacaa tgctttttgtt ttttaaagaa acctctcaca gataagacag aggcccaggg   5700
gatttttgaa gctgtcttta ttctgccccc atcccaaccc agcccttatt attttagtat   5760
ctgcctcaga attttataga gggctgacca agctgaaact ctagaattaa aggaacctca   5820
ctgaaaacat atatttcacg tgttccctct tttttttttt cctttttgtg agatgggggtc   5880
tcgcactgtc ccccaggctg gagtgcagtg gcatgatctc ggctcactgc aacctccacc   5940
tcctgggttt aagcgattct cctgcctcag cctcctgagt agctgggatt acaggcaccc   6000
accactatgc ccggctaatt ttttggatttt ttaatagaga cggggttttta ccatgttggc   6060
caggttggtc tcaaactcct gaccttgtga tttgcccgcc tcagcctccc aaattgctgg   6120
gattacaggc atgagccacc acaccctgcc catgtgttcc ctcttaatgt atgattacat   6180
ggatcttaaa catgatcctt ctctcctcat tcttcaacta tctttgatgg ggtctttcaa   6240
ggggaaaaaa atccaagctt ttttaaagta aaaaaaaaaa aagagaggac acaaaaccaa   6300
atgttactgc tcaactgaaa tatgagttaa gatggagaca gagtttctcc taataaccgg   6360
agctgaatta cctttcactt tcaaaaacat gacctttccac aatccttaga atctgccttt   6420
ttttatatta ctgaggccta aaagtaaaca ttactcattt tattttgccc aaaatgcact   6480
gatgtaaagt aggaaaaata aaaacagagc tctaaaatcc ctttcaagcc acccattgac   6540
cccactcacc aactcatagc aaagtcactt ctgttaatcc cttaatctga ttttgtttgg   6600
atatttatct tgtacccgct gctaaacaca ctgcaggagg gactctgaaa cctcaagctg   6660
tctacttaca tcttttatct gtgtctgtgt atcatgaaaa tgtctattca aaatatcaaa   6720
acctttcaaa tatcacgcag cttatattca gtttacataa aggccccaaa taccatgtca   6780
gatcttttg gtaaaagagt taatgaacta tgagaattgg gattacatca tgtatttgc    6840
ctcatgtatt tttatcacac ttataggcca agtgtgataa ataaacttac agacactgaa   6900
ttaatttccc ctgctacttt gaaaccagaa aataatgact ggccattcgt tacatctgtc   6960
ttagttgaaa agcatatttt ttattaaatt aattctgatt gtatttgaaa ttattattca   7020
attcacttat ggcagaggaa tatcaatcct aatgacttct aaaaatgtaa ctaattgaat   7080
cattatctta catttactgt ttaataagca tattttgaaa atgtatggct agagtgtcat   7140
aataaaatgg tatatctttc tttagtaatt acattaaaat tagtcatgtt tgattaatta   7200
gttc                                                                 7204
```

```
SEQ ID NO: 166          moltype = AA   length = 195
FEATURE                 Location/Qualifiers
source                  1..195
                        mol_type = protein
                        organism = Homo sapiens
SEQUENCE: 166
MGKISSLPTQ LFKCCFCDFL KVKMHTMSSS HLFYLALCLL TFTSSATAGP ETLCGAELVD  60
ALQFVCGDRG FYFNKPTGYG SSSRRAPQTG IVDECCFRSC DLRRLEMYCA PLKPAKSARS  120
VRAQRHTDMP KTQKYQPPST NKNTKSQRRK GWPKTHPGGE QKEGTEASLQ IRGKKKEQRR  180
EIGSRNAECR GKKGK                                                     195

SEQ ID NO: 167          moltype = DNA   length = 949
FEATURE                 Location/Qualifiers
```

```
source                  1..949
                        mol_type = genomic DNA
                        organism = Homo sapiens
SEQUENCE: 167
ttttgtagat aaatgtgagg attttctcta aatccctctt ctgtttgcta aatctcactg    60
tcactgctaa attcagagca gatagagcct gcgcaatgga ataaagtcct caaaattgaa   120
atgtgacatt gctctcaaca tctcccatct ctctggattt ctttttgctt cattattcct   180
gctaaccaat tcattttcag actttgtact tcagaagcaa tgggaaaaat cagcagtctt   240
ccaacccaat tatttaagtg ctgcttttgt gatttcttga aggtgaagat gcacaccatg   300
tcctcctcgc atctcttcta cctggcgctg tgcctgctca ccttcaccag ctctgccacg   360
gctggaccgg agacgctctg cgggggctgag ctggtggatg ctcttcagtt cgtgtgtgga   420
gacaggggct tttatttcaa caagcccaca gggtatggct ccagcagtcg gagggcgcct   480
cagacaggca tcgtggatga gtgctgcttc cggagctgtg atctaaggag gctggagatg   540
tattgcgcac ccctcaagcc tgccaagtca gctcgctctg tccgtgccca gcgccacacc   600
gacatgccca agacccagaa gtatcagccc ccatctacca acaagaacac gaagtctcag   660
agaaggaaag gttggccaaa gacacatcca ggaggggaac agaaggaggg gacagaagca   720
agtctgcaga tcagaggaaa gaagaaagag cagaggaggg agattggaag tagaaatgct   780
gaatgcagac gcaaaaaagg aaaatgaagg acaggaggat taaacagaca gaggcaagga   840
tgatgagaga ggagcagaca gcaagaatga aaagcagaaa atacaataga ggaaatgaag   900
aaaagtaggc ctgctggagc tagatgatga tgtgatggaa atagaagta               949
```

```
SEQ ID NO: 168          moltype = AA  length = 180
FEATURE                 Location/Qualifiers
source                  1..180
                        mol_type = protein
                        organism = Homo sapiens
SEQUENCE: 168
MGIPMGKSML VLLTFLAFAS CCIAAYRPSE TLCGGELVDT LQFVCGDRGF YFSRPASRVS    60
RRSRGIVEEC CFRSCDLALL ETYCATPAKS ERDVSTPPTV LPDNFPRYPV GKFFQYDTWK   120
QSTQRLRRGL PALLRARRGH VLAKELEAFR EAKRHRPLIA LPTQDPAHGG APPEMASNRK   180
```

```
SEQ ID NO: 169          moltype = DNA  length = 5188
FEATURE                 Location/Qualifiers
source                  1..5188
                        mol_type = genomic DNA
                        organism = Homo sapiens
SEQUENCE: 169
cgcctgtccc cctcccgagg cccgggctcg cgacggcaga gggctccgtc ggcccaaacc    60
gagctgggcg cccgcggtcc gggtgcagcc tccactccgg cccccagtca ccgcctcccc   120
cggcccctcg acgtggcgcc cttccctccg cttctctgtg ctccccgcgc ccctcttggc   180
gtctggcccc ggccccgct ctttctcccg caaccttccc ttcgctccct cccgtccccc   240
ccagctccta gcctccgact ccctcccccc ctcacgcccg ccctctcgcc ttcgccgaac   300
caaagtggat taattacacg cttttctgttt ctctccgtgc tgttctctcc cgctgtgcgc   360
ctgcccgcct ctcgctgtcc tctctcccccc tcgccctctc ttcggccccc ccctttcacg   420
ttcactctgt ctctcccact atctctgccc ccctctatcc ttgatacaac agctgacctc   480
atttcccgat accttttccc ccccgaaaag tacaacatct ggcccgcccc agcccgaaga   540
cagcccgtcc tccctggaca atcagacgaa ttctcccccc cccccaaaa aaaagccatc   600
cccccgctct gccccgtcgc acattcggcc cccgcgactc ggccagacg gcgctggcag   660
aggagtgtcc ggcaggaggg ccaacgcccg ctgttcggtt tgcgcacgc agcagggagg   720
tgggcggcag cgtcgccggc ttccagacac caatgggaat cccaatgggg aagtcgatgc   780
tggtgcttct caccttcttg gccttcgcct cgtgctgcat tgctgcttac cgccccagtg   840
agaccctgtg cggcgggggag ctggtggaca ccctccagtt cgtctgtggg gaccgcggct   900
tctacttcag caggcccgca agccgtgtga gccgtcgcag ccgtggcatc gttgaggagt   960
gctgtttccg cagctgtgac ctggccctcc tggagacgta ctgtgctacc cccgccaagt  1020
ccgagaggga cgtgtcgacc cctccgaccg tgcttccgga caacttcccc agatacccg   1080
tgggcaagtt cttccaatat gacacctgga agcagtccac ccagcgcctg cgcagggggcc  1140
tgcctgccct cctgcgtgcc cgccggggtc acgtgctcgc caaggagctc gaggcgttca  1200
gggaggccaa acgtcaccgt cccctgattg ctctacccac ccaagacccc gcccacgggg  1260
gcgcccccccc agagatggcc agcaatcgga agtgagcaaa actgccgcaa gtctgcagcc  1320
cggcgccacc atcctgcagc ctcctcctga ccacggacgt ttccatcagg ttccatcccg  1380
aaaatctctc ggttccacgt ccccctgggg cttctcctga cccagtcccc gtgcccgcc   1440
tccccgaaac aggctactct cctcggcccc ctccatcggg ctgaggaagc acagcagcat  1500
cttcaaacat gtacaaaatc gattggcttt aaacacctt cacataccct ccccccaaat  1560
tatcccaat tatcccaca cataaaaaat caaaacatta aactaacccc cttccccccc  1620
ccccacaaca accctcttaa aactaattgg cttttttagaa acaccccaca aaagctcaga  1680
aattggcttt aaaaaaaaca accaccaaaa aaaatcaatt ggctaaaaaa aaaaagtatt  1740
aaaaacgaat tggctgagaa acaattggca aaataaagga atttggcact ccccaccccc  1800
ctctttctct tctcccttgg actttgagtc aaattggcct ggacttgagt ccctgaacca  1860
gcaaagagaa aagaaggacc ccagaaatca caggtgggca cgtcgctgct accgccatct  1920
cccttctcac gggaattttc agggtaaact ggccatccga aaatagcaac aacccagact  1980
ggctcctcac tcccttttcc atcactaaaa atcacagagc agtcagaggg acccagtaag  2040
accaaaggag gggaggacag agcatgaaaa ccaaaatcca tgcaaatgaa atgtaattgg  2100
cacgaccctc acccccaaat cttacatctc aattcccatc ctaaaaagca ctcatacttt  2160
atgcatcccc gcagctacac acacacaaca cacgcacac cacacacaca acacagcaca  2220
cgagcacagc acacacacaa acgcacagca cacacagcac acagatgagc acacagcaca  2280
cacacaaacg cacagcacac acacgcacac acatgcacac acagcacaca aacgcacggc  2340
acacacacgc acacacatgc acacacagca cacacacaaa cgcacagcac acacaaacgc  2400
acagcacaca cgcacacaca gcacacacac gagcacacag cacacaaacg cacagcacac  2460
gcacacacat gcacacacag cacacacact agcacacagc acacacacaa agacacagca  2520
```

```
cacacatgca cacacagcac acacacgcga acacagcaca cacgaacaca gcacacacag   2580
cacacacaca aacacagcac acacatgcac acagcacacg cacacacagc acacacatga   2640
acacagcaca cagcacacac atgcacacac agcacacacg catgcacagc acacatgaac   2700
acagcacaca cacaaacaca cagcacacac atgcacacac agcacacaca ctcatgcgca   2760
gcacatacat gaacacagct cacagcacac aaacacgcag cacacacgtt gcacacgcaa   2820
gcacccacct gcacacacac atgcgcacac acacgcacac ccccacaaaa ttggatgaaa   2880
acaataagca tatctaagca actacgatat ctgtatggat caggccaaag tcccgctaag   2940
attctccaat gttttcatgg tctgagcccc gctcctgttc ccatctccac tgcccctcgg   3000
ccctgtctgt gccctgcctc tcagaggagg gggctcagat ggtgcggcct gagtgtgcgg   3060
ccggcggcat ttgggataca cccgtagggt gggcggggtg tgtcccaggc ctaattccat   3120
ctttccacca tgacagagat gcccttgtga ggctggcctc cttggcgcct gtccccacgg   3180
cccccgcagc gtgagccacg atgctcccca taccccaccc attcccgata caccttactt   3240
actgtgtgtt ggcccagcca gagtgaggaa ggagtttggc cacattggag atggcggtag   3300
ctgagcagac atgcccccac gagtagcctg actccctggt gtgctcctgg aaggaagatc   3360
ttggggaccc ccccaccgga gcacacctag ggatcatctt tgcccgtctc ctggggaccc   3420
cccaagaaat gtggagtcct cggggggccgt gcactgatgc ggggagtgtg ggaagtctgg   3480
cggttggagg ggtgggtggg gggcagtggg ggctgggcgg ggggagttct ggggtaggaa   3540
gtggtcccgg gagattttgg atggaaaagt caggaggatt gacagcagac ttgcagaatt   3600
acatagagaa attaggaacc cccaaatttc atgtcaattg atctattccc cctctttgtt   3660
tcttggggca tttttccttt ttttttttt tttgttttt ttttacccct ccttagcttt   3720
atgcgctcag aaaccaaatt aaaccccccc cccatgtaac aggggggcag tgacaaaagc   3780
aagaacgcac gaagccagcc tggagaccac cacgtcctgc ccccgccat ttatcgccct   3840
gattggattt tgttttcat ctgtccctgt tgcttgggtt gagttgaggg tggagcctcc   3900
tgggggggcac tggccactga gcccccttgg agaagtcaga ggggagtgga gaaggccact   3960
gtccggcctg gcttctgggg acagtggctg gtccccagaa gtcctgaggg cggagggggg   4020
ggttgggcag ggtctcctca ggtgtcagga gggtgctcgg aggccacagg agggggagag   4080
tggctggcct gaggctggcc ggagggggaag gggctagcag gtgtgtaaac agagggttcc   4140
atcaggctgg ggcagggtgg ccgccttccg cacacttgag gaaccctccc ctctccctcg   4200
gtgacatctt gcccgcccct cagcaccctg ccttgtctcc aggaggtccg aagctctgtg   4260
ggacctcttg ggggcaaggt ggggtgaggc cggggagtag ggaggtcagg cgggtctgag   4320
cccacagagc aggagagctg ccaggtctgc ccatcgacca ggttgcttgg gcccggagc    4380
ccacgggtct ggtgatgcca tagcagccac caccgcggcg cctagggctg cggcagggac    4440
tcggcctctg ggaggtttac ctcgcccca cttgtgcccc cagctcagcc ccctgcacg     4500
cagcccgact agcagtctag aggcctgagg cttctgggtc ctggtgacgg ggctggcatg    4560
accccggggg tcgtccatgc cagtccgcct cagtcgcaga gggtccctcg gcaagcgccc    4620
tgtgagtggg ccattcggaa cattggacag aagcccaaag agccaaattg tcacaattgt    4680
ggaacccaca ttggcctgag atccaaaacg cttcgaggca ccccaaatta cctgcccatt    4740
cgtcaggaca cccacccacc cagtgttata ttctgcctcg ccggagtggg tgttcccggg    4800
ggcacttgcc gaccagcccc ttgcgtcccc aggtttgcag ctctccctg ggccactaac     4860
catcctggcc cgggctgcct gtctgacctc cgtgcctagt cgtggctctc catcttgtct    4920
cctccccgtg tccccaatgt cttcagtggg gggcccctc ttgggtcccc tcctctgcca     4980
tcacctgaag accccccacgc caaacactga atgtcacctg tgcctgccgc ctcggtccac   5040
cttgcggccc gtgtttgact caactcaact cctttaacgc taatatttcc ggcaaaatcc    5100
catgcttggg ttttgtcttt aaccttgtaa cgcttgcaat cccaataaag cattaaaagt   5160
catgatcttc aaaaaaaaaa aaaaaaaa                                      5188
```

```
SEQ ID NO: 170          moltype = AA   length = 180
FEATURE                 Location/Qualifiers
source                  1..180
                        mol_type = protein
                        organism = Homo sapiens
SEQUENCE: 170
MGIPMGKSML VLLTFLAFAS CCIAAYRPSE TLCGGELVDT LQFVCGDRGF YFSRPASRVS   60
RRSRGIVEEC CFRSCDLALL ETYCATPAKS ERDVSTPPTV LPDNFPRYPV GKFFQYDTWK   120
QSTQRLRRGL PALLRARRGH VLAKELEAFR EAKRHRPLIA LPTQDPAHGG APPEMASNRK   180
```

```
SEQ ID NO: 171          moltype = DNA   length = 5162
FEATURE                 Location/Qualifiers
source                  1..5162
                        mol_type = genomic DNA
                        organism = Homo sapiens
SEQUENCE: 171
ccgctaatgt accatgccct ggtgctggaa agtgcctgag ccagctgccc cagcggcctc   60
agcactacca agttggcaca aagctcccca aattcggagg ggctcaggga aacgagtgga   120
ggggatgagg aggtgagggg taaacccatc atttcagttg gcatttgagc aggtgccatg   180
ctcagcggag atgaggctct cccatctgta ggggccgtat taacatgcac actctaaaag   240
tgcccttcgt ttctccagcc tcagctttgt ccctctcctc ctccacgtca acctggccag   300
agggtctgga cgccacagcc agggcacccc ctgctttggt ggtgactgct aatattggcc   360
aggccggcgg atcatcgtcc ggcagtttc ggcagagagc cttgggcacc agtgactccc     420
cggtcctctt tatccactgt ccaggagctg cggggactgc gcaggacta gagtacaggg     480
gccgaagagt caccaccgag cttgtgtggg aggaggtgga ttccagcccc cagccccagg    540
gctctgaatc gctgccagct cagccccctg cccagcctgc cccacagcct gagccccagc   600
aggccagaga gcccagtcct gaggtgagct gctgtggcct gtggcccagg cgaccccagc   660
gctcccagaa ctgaggctgg cagccagccc cagcctcagc ccaactgcg aggcagagag     720
acaccaatgg gaatcccaat gggggaagtcg atgctggtgc ttctcacctt cttggccttc   780
gcctcgtgct gcattgctgc ttaccgcccc agtgagaccc tgtgcggcgg ggagctggtg   840
gacaccctcc agttcgtctg tggggaccgc ggcttctact tcagcaggcc cgcaagccgt   900
gtgagccgtc gcagccgtgg catcgttgag gagtgctgtt tccgcagctg tgacctggcc   960
ctcctggaga cgtactgtgc tacccccgcc aagtccgaga gggacgtgtc gaccccctccg   1020
```

```
accgtgcttc cggacaactt ccccagatac cccgtgggca agttcttcca atatgacacc    1080
tggaagcagt ccacccagcg cctgcgcagg ggcctgcctg ccctcctgcg tgcccgccgg    1140
ggtcacgtgc tcgccaagga gctcgaggcg ttcagggagg ccaaacgtca ccgtcccctg    1200
attgctctac ccacccaaga ccccgcccac gggggcgccc ccccagagat ggccagcaat    1260
cggaagtgag caaaactgcc gcaagtctgc agcccggcgc caccatcctg cagcctcctc    1320
ctgaccacgg acgtttccat caggttccat cccgaaaatc tctcggttcc acgtcccct    1380
ggggcttctc ctgacccagt ccccgtgccc cgcctccccg aaacaggcta ctctcctcgg    1440
cccccctccat cgggctgagg aagcacagca gcatcttcaa acatgtacaa aatcgattgg    1500
ctttaaacac ccttcacata ccctcccccc aaattatccc caattatccc cacacataaa    1560
aaatcaaaac attaaactaa cccccttccc cccccccac aacaaccctc ttaaaactaa    1620
ttggcttttt agaaacaccc cacaaaagct cagaaattgg ctttaaaaaa aacaaccacc    1680
aaaaaaaatc aattggctaa aaaaaaaaag tattaaaaac gaattggctg agaaacaatt    1740
ggcaaaataa aggaatttgg cactccccac cccctcttt ctcttctccc ttggactttg    1800
agtcaaattg gcctggactt gagtccctga accagcaaag agaaaagaag gaccccagaa    1860
atcacaggtg ggcacgtcgc tgctaccgcc atctcccttc tcacgggaat tttcagggta    1920
aactggccat ccgaaaatag caacaaccca gactggctcc tcactccctt ttccatcact    1980
aaaaatcaca gagcagtcag agggacccag taagaccaaa ggaggggagg acagagcatg    2040
aaaaccaaaa tccatgcaaa tgaaatgtaa ttggcacgac cctcaccccc aaatcttaca    2100
tctcaattcc catcctaaaa agcactcata ctttatgcat ccccgcagct acacacacac    2160
aacacacagc acacgcatga acacagcaca cacacgagca cagcacacac acaaacgcac    2220
agcacacaca gcacacagat gagcacacag cacacacaca aacgcacagc acacacacgc    2280
acacacatgc acacacagca cacaaacgca cggcacacac acgcacacac atgcacacac    2340
agcacacaca caaacgcaca gcacacacaa acgcacagca cacacgcaca cacagcacac    2400
acacgagcac acagcacaca aacgcacagc acacgcacac acatgcacac acagcacaca    2460
cactagcaca cagcacacac acaaagacac agcacacaca tgcacacaca gcacacacac    2520
gcgaacacag cacacacgaa cacagcacac acagcacaca acaaacaca gcacacacat    2580
gcacacagca cacgcacaca cagcacacac atgaacacag cacacagcac acacatgcac    2640
acacagcaca cacgcatgca cagcacacat gaacacagca cacacaaa cacacagcac    2700
acacatgcac acacagcaca cacactcatg cgcagcacat acatgaacac agctcacagc    2760
acacaaacac gcagcacaca cgttgcacac gcaagcaccc acctgcacac acacatgcac    2820
acacacgc acacccccac aaaattggat gaaaacaata agcatatcta agcaactacg    2880
atatctgtat ggatcaggcc aaagtcccgc taagattctc caatgttttc atggtctgag    2940
ccccgctcct gttcccatct ccactgcccc tcggccctgt ctgtgccctg cctctcagag    3000
gagggggctc agatggtgcg gcctgagtgt gcggccggcg gcatttggga tacacccgta    3060
gggtgggcgg ggtgtgtccc aggcctaatt ccatctttcc accatgacag agatgccctt    3120
gtgaggctgg cctccttggc gcctgtcccc acggcccccg cagcgtgagc cacgatgctc    3180
cccataccccc acccattccc gatacacctt acttactgtg tgttggccca gccagagtga    3240
ggaaggagtt tggccacatt ggagatggcg gtagctgagc agacatgccc ccacgagtag    3300
cctgactccc tggtgtgctc ctggaaggaa gatcttgggg accccccac cggagcacac    3360
ctagggatca tctttgcccg tctcctgggg accccccaag aaatgtggag tcctcggggg    3420
ccgtgcactg atgcggggag tgtgggaagt ctggcggttg gaggggtggg tgggggcag    3480
tggggggctgg gcggggggag ttctgggta ggaagtggtc ccgggagatt ttggatggaa    3540
aagtcaggag gattgacagc agacttgcag aattacatag agaaattagg aacccccaaa    3600
tttcatgtca attgatctat tccccctctt tgtttcttgg ggcattttc cttttttttt    3660
tttttttgtt tttttttac ccctccttag ctttatgcgc tcagaaacca aattaaaccc    3720
cccccccatg taacaggggg gcagtgacaa aagcaagaac gcacgaagcc agcctggaga    3780
ccaccacgtc ctgcccccg ccatttatcg ccctgattyg attttgtttt tcatctgtcc    3840
ctgttgcttg ggttgagttg agggtggagc ctcctggggg gcactggcca ctgagccccc    3900
ttggagaagt cagaggggag tggagaaggc cactgtccgg cctggcttct ggggacagtg    3960
gctggtcccc agaagtcctg agggcggagg gggggggttgg gcagggtctc ctcaggtgtc    4020
aggaggggtgc tcggaggcca caggaggggg ctcctggctg gcctgaggct ggcgggaagg    4080
gaagggggcta gcaggtgtgt aaacagaggg ttccatcagg ctggggcagg gtggccgcct    4140
tccgcacact tgaggaaccc tcccctctcc ctcggtgaca tcttgcccgc ccctcagcac    4200
cctgccttgt ctccaggagg tccgaagctc tgtgggacct cttgggggca aggtgggggtg    4260
aggccgggga gtaggaggt caggcgggtc tgagcccaca gagcaggaga gctgccaggt    4320
ctgcccatcg accaggttgc ttgggccccg gagcccacgg gtctggtgat gccatagcag    4380
ccaccaccgc ggcgcctagg gctgcggcag ggactcggcc tctgggaggt ttacctcgcc    4440
cccacttgtg cccccagctc agcccccctg cacgcagccc gactagcagt ctagaggcct    4500
gaggcttctg ggtcctggtg acggggctgg catgaccccg ggggtcgtcc atgccagtcc    4560
gcctcagtcg cagagggtcc ctcggcaagc gccctgtgag tgggccattc ggaacattgg    4620
acagaagccc aaagagccaa attgtcacaa ttgtggaacc cacattggcc tgagatccaa    4680
aacgcttcga ggcaccccaa attacctgcc cattcgtcag acacccacc cacccagtgt    4740
tatattctgc ctcgccggag tgggtgttcc cggggggcact tgccgaccag cccccttgcgt    4800
cccaggtttt gcagctctcc cctgggccac taaccatccc gagccgggct gcctgtctga    4860
cctccgtgcc tagtcgtggc tctccatctt gtctcctccc cgtgtcccca atgtcttcag    4920
tggggggccc cctcttgggt cccctcctct gccatcacct gaagaccccc acgccaaaca    4980
ctgaatgtca cctgtgcctg ccgcctcggt ccaccttgcg gcccgtgttt gactcaactc    5040
aactcctta acgctaatat ttccggcaaa atcccatgct tgggttttgt ctttaaccttt    5100
gtaacgcttg caatcccaat aaagcattaa aagtcatgat cttcaaaaaa aaaaaaaaa    5160
aa                                                                    5162
```

SEQ ID NO: 172          moltype = AA  length = 236
FEATURE                 Location/Qualifiers
source                  1..236
                        mol_type = protein
                        organism = Homo sapiens
SEQUENCE: 172
MVSPDPQIIV VAPETELASM QVQRTEDGVT IIQIFWVGRK GELLRRTPVS SAMQTPMGIP    60
MGKSMLVLLT FLAFASCCIA AYRPSETLCG GELVDTLQFV CGDRGFYFSR PASRVSRRSR    120

-continued

```
GIVEECCFRS CDLALLETYC ATPAKSERDV STPPTVLPDN FPRYPVGKFF QYDTWKQSTQ    180
RLRRGLPALL RARRGHVLAK ELEAFREAKR HRPLIALPTQ DPAHGGAPPE MASNRK       236

SEQ ID NO: 173          moltype = DNA  length = 4875
FEATURE                 Location/Qualifiers
source                  1..4875
                        mol_type = genomic DNA
                        organism = Homo sapiens
SEQUENCE: 173
acacacttgg gtcggccgcg cgccctcagg acgtggacag ggagggcttc cccgtgtcca    60
ggaaagcgac cgggcattgc ccccagtctc ccccaaattt gggcattgtc cccgggtctt    120
ccaacggact gggcgttgct cccggacact gaggactggc cccggggtct cgctcacctt    180
cagcagcgtc caccgcctgc cacagagcgt tcgatcgctc gctgcctgag ctcctggtgc    240
gcccgcggac gcagcctcca gcttcgcgga gatggtttcc ccagaccccc aaattatcgt    300
ggtggccccc gagaccgaac tcgcgtctat gcaagtccaa cgcactgagg acggggtaac    360
cattatccaa atattttggg tgggccgcaa aggcgagcta cttagacgca ccccggtgag    420
ctcggccatg cagacaccaa tgggaatccc aatggggaag tcgatgctgg tgcttctcac    480
cttcttggcc ttcgcctcgt gctgcattgc tgcttaccgc ccagtgaga ccctgtgcgg    540
cggggagctg gtgtgacaccc tccagttcgt ctgtggggac cgcggcttct acttcagcag    600
gccccgcaagc cgtgtgagcc gtcgcagccg tggcatcgtt gaggagtgct gtttccgcag    660
ctgtgacctg gccctcctgg agacgtactg tgctacccccc gccaagtccg agagggacgt    720
gtcgacccct ccgaccgtgc ttccggacaa cttcccccaga taccccgtgg gcaagttctt    780
ccaatatgac acctggaagc agtccaccca gcgcctgcgc aggggcctgc ctgccctcct    840
gcgtgccccgc cgggggtcacg tgctcgccaa ggagctcgag gcgttcaggg aggccaaacg    900
tcaccgtccc ctgattgctc tacccaccca agaccccgcc cacgggggcg ccccccccaga    960
gatggccagc aatcggaagt gagcaaaact gccgcaagtc tgcagcccgg cgccaccatc    1020
ctgcagcctc ctcctgacca cggacgtttc catcaggttc catcccgaaa atctctcggt    1080
tccacgtccc cctggggctt ctcctgaccc agtcccgtg ccccgcctcc ccgaaacagg    1140
ctactctcct cggccccctc catcgggctg aggaagcaca gcagcatctt caaacatgta    1200
caaaatcgat tggctttaaa caccctcac ataccctccc cccaaattat cccccaattat    1260
ccccacacat aaaaaatcaa aacattaaac taaccccctt cccccccccc cacaacaacc    1320
ctcttaaaac taattggctt tttagaaaca ccccacaaaa gctcagaaat tggctttaaa    1380
aaaaacaacc accaaaaaaa atcaattggc taaaaaaaaa aagtattaaa aacgaattgg    1440
ctgagaaaca attggcaaaa taaaggaatt tggcactccc caccccccct tttctcttct    1500
cccttggact ttgagtcaaa ttggcctgga cttgagtccc tgaaccagca aagagaaaag    1560
aaggacccca gaaatcacag gtgggcacgt cgctgctacc gccatctccc ttctcacggg    1620
aattttcagg gtaaactggc catccgaaaa tagcaacaac ccagactggc tcctcactcc    1680
cttttccatc actaaaaatc acagagcagt cagagggacc cagtaagacc aaaggagggg    1740
aggacagagc atgaaaacca aaatccatgc aaatgaaatg taattggcac gaccctcacc    1800
cccaaatctt acatctcaat tcccatccta aaaagcactc atactttatg catccccgca    1860
gctacacaca cacaacacac agcacacgca tgaacacagc acacacacga gcacagcaca    1920
cacacaaacg cacagcacac acagcacaca gatgagcaca cagcacacac acaaacgcac    1980
agcacacaca cgcacacaca tgcacacaca gcacacacaa gcacggcaca cacacgcaca    2040
cacatgcaca cacagcacac acacaaacgc acagcacaca caaacgcaca gcacacacgc    2100
acacacagca cacacgagag cacacagcac acaaacgcac agcacgcca cacacatgca    2160
cacacagcac acacactagc acacagcaca cacacaaaga cacagcacac acatgcacac    2220
acagcacaca cacgcgaaca cagcacacac gaacacacac acagcacaca acacacaaac    2280
acagcacaca catgcacaca gcacacgcac acacagcaca cacatgaaca cagcacacag    2340
cacacacatg cacacacagc acacacgcat gcacagcaca catgaacaca gcacacacac    2400
aaacacacag cacacacatg cacacacagc acacacactc atgcgcagca catacatgaa    2460
cacagctcac agcacacaaa cacgcagcac acacgttgca cacgcaagca cccacctgca    2520
cacacacatg cgcacacaca cgcacacccc cacaaaattg gatgaaaaca ataagcatat    2580
ctaagcaact acgatatctg tatggatcag gccaaagtcc cgctaagatt ctccaatgtt    2640
ttcatggtct gagccccgct cctgttccca tctccactgc ccctcggccc tgtctgtgcc    2700
ctgcctctca gaggaggggg ctcagatggt gcggcctgag tgtgcggccg gcggcatttg    2760
ggatacaccc gtagggtggg cggggtgtgt cccaggccta attccatctt tccaccatga    2820
cagagatgcc cttgtgaggc tggcctcctt ggcgcctgtc cccacggccc ccgcagcgtg    2880
agccacgatg ctccccatac cccacccatt cccgatacac cttacttact gtgtgttggc    2940
ccagccagag tgaggaagga gtttggccac attggagatg gcggtagctg agcagacatg    3000
cccccacgag tagcctgact ccctggtgtg ctcctggaag gaagatcttg gggacccccc    3060
caccggagca cacctaggga tcatctttgc ccgtctcctg gggaccccccc aagaaatgtg    3120
gagtcctcgg gggccgtgca ctgatgcggg gagtgtggga agtctggcgg ttggagggggt    3180
gggtggggggg cagtgggggggc tgggcggggg gagttctggg gtaggaagtg gtcccgggag    3240
attttggatg gaaaagtcag gaggattgac agcagacttg agaattaca tagagaaatt    3300
aggaaccccc aaatttcatg tcaattgatc tattcccccct ctttgtttct tggggcattt    3360
ttcctttttt tttttttttt gtttttttttt tacccctcct tagctttatg cgctcagaaa    3420
ccaaattaaa ccccccccccc atgtaacagg ggggcagtga caaaagcaag aacgcacgaa    3480
gccagcctgg agaccaccac gtcctgcccc ccgccattta tcgccctgat tggattttgt    3540
ttttcatctg tccctgttgc ttgggttgag ttgagggtgg agcctcctgg ggggcactgg    3600
ccactgagcc cccttggaga agtcagaggg gagtggagaa ggccactgtc cggcctggct    3660
tctgggggaca gtggctggtc cccagaagtc ctgagggcgg aggggggggt tgggcagggt    3720
ctcctcaggt gtcaggaggg tgctcggagg ccacaggagg gggctcctgg ctggcctgag    3780
gctggccgga ggggaagggg ctagcaggtg tgtaaacaga gggttccatc aggctggggc    3840
agggtggccg ccttccgcac acttgaggaa ccctccctc tccctcggtg acatcctgga    3900
cgccctcag caccctgcct tgtctccagg aggtccgaag ctctgtggga cctcttgggg    3960
gcaaggtggg gtgaggccgg ggagtaggga ggtcaggcgg gtctgagccc acagagcagg    4020
agagctgccg ggtctgccca tcgaccaggt tgcttgggcc ccgagcccca cgggtctggt    4080
gatgccatag cagccaccac cgcggcgcct aggggctgcgg cagggactcg gcctctggga    4140
ggtttacctc gcccccactt gtgcccccag ctcagccccc ctgcacgcag cccgactagc    4200
```

-continued

```
agtctagagg cctgaggctt ctgggtcctg gtgacggggc tggcatgacc ccggggggtcg   4260
tccatgccag tccgcctcag tcgcagaggg tccctcggca agcgccctgt gagtgggcca   4320
ttcggaacat tggacagaag cccaaagagc caaattgtca caattgtgga acccacattg   4380
gcctgagatc caaaacgctt cgaggcaccc caaattacct gcccattcgt caggacaccc   4440
acccacccag tgttatattc tgcctcgccg gagtggggtgt tcccgggggc acttgccgac   4500
cagccccttg cgtccccagg tttgcagctc tcccctgggc cactaaccat cctggcccgg   4560
gctgcctgtc tgacctccgt gcctagtcgt ggctctccat cttgtctcct ccccgtgtcc   4620
ccaatgtctt cagtgggggg cccctcttg ggtcccctcc tctgccatca cctgaagacc   4680
cccacgccaa acactgaatg tcacctgtgc ctgccgcctc ggtccacctt gcggcccgtg   4740
tttgactcaa ctcaactcct ttaacgctaa tatttccggc aaaatcccat gcttgggttt   4800
tgtctttaac cttgtaacgc ttgcaatccc aataaagcat taaaagtcat gatcttcaaa   4860
aaaaaaaaaa aaaaa                                                    4875

SEQ ID NO: 174         moltype = AA  length = 180
FEATURE                Location/Qualifiers
source                 1..180
                       mol_type = protein
                       organism = Homo sapiens
SEQUENCE: 174
MGIPMGKSML VLLTFLAFAS CCIAAYRPSE TLCGGELVDT LQFVCGDRGF YFSRPASRVS   60
RRSRGIVEEC CFRSCDLALL ETYCATPAKS ERDVSTPPTV LPDNFPRYPV GKFFQYDTWK   120
QSTQRLRRGL PALLRARRGH VLAKELEAFR EAKRHRPLIA LPTQDPAHGG APPEMASNRK   180

SEQ ID NO: 175         moltype = DNA  length = 4539
FEATURE                Location/Qualifiers
source                 1..4539
                       mol_type = genomic DNA
                       organism = Homo sapiens
SEQUENCE: 175
aaactggaca ttagcttctc ctgtgaaaga gacttccagc ttcctcctcc tcctcttcct   60
cctcctcctc ctgccccagc gagccttctg ctgagctaca ccaatgggaa tcccaatggg   120
gaagtcgatg ctggtgcttc tcaccttctt ggccttcgcc tcgtgctgca ttgctgctta   180
ccgccccagt gagaccctgt gcggcgggga gctggtggac accctccagt tcgtctgtgg   240
ggaccgcggc ttctacttca gcaggcccgc aagccgtgtg agccgtcgca gccgtggcat   300
cgttgaggag tgctgtttcc gcagctgtga cctggccctc ctggagacgt actgtgctac   360
ccccgccaag tccgagaggg acgtgtcgac ccctccgacc gtgcttccgg acaacttccc   420
cagataccc gtgggcaagt tcttccaata tgacacctgg aagcagtcca cccagcgcct   480
gcgcagggc ctgcctgccc tcctgcgtgc ccgccggggt cacgtgctcg ccaaggagct   540
cgaggcgttc agggaggcca aacgtcaccg tcccctgatt gctctaccca cccaagaccc   600
cgcccacggg ggcgccccc cagagatggc cagcaatcgg aagtgagcaa aactgccgca   660
agtctgcagc ccggcgccac catcctgcag cctcctcctg accacggacg tttccatcag   720
gttccatccc gaaaatctct cggttccacg tcccctctggg gcttctcctg acccagtccc   780
cgtgcccgac ctccccgaaa caggctactc tcctcggcc cctccatcgg gctgaggaag   840
cacagcagca tcttcaaaca tgtacaaaat cgattggctt taaacaccct tcacatcccc   900
tccccccaaa ttatccccaa ttatccccac acataaaaaa tcaaaacatt aaactaaccc   960
ccttccccc cccccacaac aaccctctta aaactaattg gctttttaga aacaccccac   1020
aaaagctcag aaattggctt taaaaaaaac aaccaccaaa aaaaatcaat tggctaaaaa   1080
aaaaaagtat taaaaacgaa ttggctgaga aacaattggc aaaataaagg aatttggcac   1140
tccccacccc cctctttctc ttctcccttg gactttgagt caaattggcc tggacttgag   1200
tccctgaacc agcaaagaga aaagaaggac cccagaaatc acaggtgggc acgtcgctgc   1260
taccgccatc tcccttctca cgggaatttt cagggtaaac tggccatccg aaaatagcaa   1320
caacccagac tggctcctca ctcccttttc catcactaaa aatcacagag cagtcagagg   1380
gacccagtaa gaccaaagga ggggaggaca gagcatgaaa accaaaatcc atgcaaatga   1440
aatgtaattg gcacgaccct cacccccaaa tcttacatct caattcccat cctaaaaagc   1500
actcatactt tatgcatccc cgcagctaca cacacacaac acacagcaca cgcatgaaca   1560
cagcacacac acgagcacag cacacacaca aacgcacagc acacacagca cacagatgag   1620
cacacagcac acacacaaac gcacagcaca cacgcaca cacatgcaca cacagcacac   1680
aaacgcacgg cacacacacg cacacacatg cacacacagc acacacacaa acgcacagca   1740
cacacaaacg cacagcacac acgcacacac agcacacaca cgagcacaca gcacacaaac   1800
gcacagcaca cgcacacaca tgcacacaca gcacacacac tagcacacag cacacacaca   1860
aagacacagc acacacatgc acacacagca cacacgcg aacacagcac acacgaacac   1920
agcacacaca gcacacacac aaacacagca cacacatgca cacagcacac gcacacacag   1980
cacacacatg aacacagcac acagcacaca catgcacaca cagcacacac gcatgcacag   2040
cacacatgaa cacagcacac acacaaacac acagcacaca catgcacaca cagcacacac   2100
actcatcgc agcacataca tgaacacagc tcacagcaca caaacacgca gcacacacgt   2160
tgcacacgca agcacccacc tgcacacaca catgcgcaca cacgcacac ccccacaaa   2220
attggatgaa aacaataagc atatctaagc aactacgata tctgtatgga tcaggccaaa   2280
gtcccgctaa gattctccaa tgttttcatg gtctgagccc cgctcctgtt cccatctcca   2340
ctgcccctcg ggcctgtctg tgccctgcct ctcagaggag ggggctcaga tggtgcggcc   2400
tgagtgtgcg gccggcggca tttgggatac acccgtaggg tgggcggggt gtgtcccagg   2460
cctaattcca tctttccacc atgacagaga tgccttgtg aggctggcct ccttggcgcc   2520
tgtccccacg gcccccgcag cgtgagccac gatgctcccc ataccccacc cattcccgat   2580
acaccttact tactgtgtgt tggcccagcc agagtgagga aggagtttgg ccacattgga   2640
gatgcgggta gctgagcaga catgccccca cgagtagcct gactccctgg tgtgctcctg   2700
gaaggaagat cttggggacc cccccaccgg agcacaccta gggatcatct ttgcccgtct   2760
cctgggacc ccccaagaaa tgtggagtcc tcggggggccg tgcactgatg cggggagtgt   2820
gggaagtctg gcggttggag gggtgggtgg ggggcagtgg gggctggggcg gggggagttc   2880
tggggtagga agtggtcccg ggagattttg gatggaaaag tcaggaggat tgacagcaga   2940
cttgcagaat tacatagaga aattaggaac ccccaaattt catgtcaatt gatctattcc   3000
```

```
ccctctttgt ttcttggggc attttttcctt tttttttttt ttttgttttt tttttacccc  3060
tccttagctt tatgcgctca gaaaccaaat taaaccccc ccccatgtaa caggggggca  3120
gtgacaaaag caagaacgca cgaagccagc ctggagacca ccacgtcctg ccccccgcca  3180
tttatcgccc tgattggatt ttgttttca tctgtccctg ttgcttgggt tgagttgagg  3240
gtggagcctc ctggggggca ctggccactg agcccccttg gagaagtcag aggggagtgg  3300
agaaggccac tgtccggcct ggcttctggg gacagtggct ggtccccaga agtcctgagg  3360
gcggagggg gggttgggca gggtctcctc aggtgtcagg agggtgctcg gaggccacag  3420
gaggggggctc ctggctggcc tgaggctggc cggaggggaa ggggctagca ggtgtgtaaa  3480
cagagggttc catcaggctg gggcagggtg gccgccttcc gcacacttga ggaaccctcc  3540
cctctccctc ggtgacatct tgcccgcccc tcagcacct gccttgtctc caggaggtcc  3600
gaagctctgt gggacctctt gggggcaagg tggggtgagg ccggggagta gggaggtcag  3660
gcgggtctga gcccacagag caggagagct gccaggtctg cccatcgacc aggttgcttg  3720
ggccccggag cccacgggtc tggtgatgcc atagcagcca ccaccgcggc gcctagggct  3780
gcggcaggga ctcggcctct gggaggttta cctcgcccc acttgtgccc ccagctcagc  3840
ccccctgcac gcagcccgac tagcagtcta gaggcctgag gcttctgggt cctggtgacg  3900
gggctggcat gaccccgggg gtcgtccatg ccagtccgcc tcagtcgcag agggtccctc  3960
ggcaagcgcc ctgtgagtgg gccattcgga acattggaca gaagcccaaa gagccaaatt  4020
gtcacaattg tggaacccac attggcctga gatccaaaac gcttcgaggc accccaaatt  4080
acctgcccat tcgtcaggac acccacccac ccagtgttat attctgcctc gccggagtgg  4140
gtgttcccgg gggcacttgc cgaccagccc cttgcgtccc caggtttgca gctctcccct  4200
gggccactaa ccatcctggc ccgggctgcc tgtctgacct ccgtgcctag tcgtggctct  4260
ccatcttgtc tcctccccgt gtcccaatg tcttcagtgg gggcccct cttgggtccc  4320
ctcctctgcc atcacctgaa gacccccacg ccaaacactg aatgtcacct gtgcctgccg  4380
cctcggtcca ccttgcggcc cgtgtttgac tcaactcaac tcctttaacg ctaatatttc  4440
cggcaaaatc ccatgcttgg gttttgtctt taaccttgta acgcttgcaa tcccaataaa  4500
gcattaaaag tcatgatctt caaaaaaaaa aaaaaaaa                            4539
```

SEQ ID NO: 176       moltype = AA  length = 180
FEATURE            Location/Qualifiers
source             1..180
                mol_type = protein
                organism = Homo sapiens
SEQUENCE: 176

```
MGIPMGKSML VLLTFLAFAS CCIAAYRPSE TLCGGELVDT LQFVCGDRGF YFSRPASRVS  60
RRSRGIVEEC CFRSCDLALL ETYCATPAKS ERDVSTPPTV LPDNFPRYPV GKFFQYDTWK  120
QSTQRLRRGL PALLRARRGH VLAKELEAFR EAKRHRPLIA LPTQDPAHGG APPEMASNRK  180
```

SEQ ID NO: 177       moltype = DNA  length = 4710
FEATURE            Location/Qualifiers
source             1..4710
                mol_type = genomic DNA
                organism = Homo sapiens
SEQUENCE: 177

```
acacacttgg gtcggccgcg cgccctcagg acgtggacag ggagggcttc cccgtgtcca  60
ggaaagcgac cgggcattgc ccccagtctc ccccaaattt gggcattgtc cccgggtctt  120
ccaacggact gggcgttgct cccggacact gaggactggc cccggggtct cgctcacctt  180
cagcagcgtc caccgcctgc cacagagcgt tcgatcgctc gctgcctgag ctcctggtgc  240
gcccgcggac gcagcctcca gcttcgcgac accaatggga atcccaatgg ggaagtcgat  300
gctggtgctt ctcaccttct tggccttcgc ctcgtgctgc attgctgctt accgccccag  360
tgagaccctg tgcggcgggg agctggtgga caccctccag ttcgtctgtg gggaccgcgg  420
cttctacttc agcaggcccg caagccgtgt gagccgtggca tcgttgagga  480
gtgctgtttc cgcagctgtg acctggccct cctggagacg tactgtgcta ccccccgccaa  540
gtccgagagg gacgtgtcga cccctccgac cgtgcttccg gacaacttcc ccagataccc  600
cgtgggcaag ttcttccaat atgacacctg gaagcagtcc acccagcgcc tgcgcagggg  660
cctgcctgcc ctcctgcgtg cccgccgggg tcacgtgctc gccaaggagc tcgaggcgtt  720
cagggaggcc aaacgtcacc gtcccctgat tgctctaccc acccaagacc ccgcccacgg  780
gggcgccccc ccagagatgg ccagcaatcg gaagtgagca aaactgccgc aagtctgcag  840
cccggcgcca ccatcctgca gcctcctcct gaccacggac gtttccatca ggttccatcc  900
cgaaaatctc tcggttccac gtcccctgg ggcttctcct gacccagtcc ccgtgcccg  960
cctccccgaa acaggctact ctcctcggcc ccctccatcg ggctgaggaa gcacagcagc  1020
atcttcaaac atgtacaaaa tcgattggct ttaaacaccc ttcacatacc ctcccccaa  1080
attatcccca attatcccca cacataaaaa atcaaaacat taaactaacc cccttcccc  1140
cccccacaa caaccctctt aaaactaatt ggcttttag aaacaccca caaaagctca  1200
gaaattggct ttaaaaaaaa caaccaccaa aaaaaatgaa ttggctaaaa aaaaaagta  1260
ttaaaaacga attggctgag aaacaattgg caaaataaag gaatttggca ctcccacccc  1320
ccctctttct cttctcccctt ggactttgag tcaaattggc ctggacttga gtccctgaac  1380
cagcaaagag aaaagaagga ccccagaaat cacaggtggg cacgtcgctg ctaccgccat  1440
ctccctcctc acgggaattt tcagggtaaa ctggccatcc gaaaatagca acaacccaga  1500
ctggctcctc actccctttt ccatcactaa aaatcacaga gcagtcagag ggacccagta  1560
agaccaaagg aggggaggac agagcatgaa aaccaaaatc catgcaaatg aaatgtaatt  1620
ggcacgaccc tcaccccaa atcttacatc tcaattccca tcctaaaaag cactcatact  1680
ttatgcatcc ccgcagctac acacacacaa cacacagcac acgcatgaac acagcacaca  1740
cacgagcaca gcacacacac aaacgcacag cacacacagc acacagatga gcacacagca  1800
cacacacaaa cgcacacaca cgcacacac acacatgcac acaacaagta caaacgcacg  1860
gcacacacac gcacacacat gcacacacag cacacacaca aacgcacagc acacacaaac  1920
gcacagcaca cacgcacaca cagcacacac acgagcacac agcacacaaa cgcacagcac  1980
acgcacacac atgcacacac agcacacaca ctagcacaca gcacacacac aaagacacag  2040
cacacacatg cacacacagc acacacacgc gaacacagca cacgaacaca cagcacacac  2100
agcacacaca caaacacagc acacacatgc acacagcaca cgcacacaca gcacacacat  2160
```

```
gaacacagca cacagcacac acatgcacac acagcacaca cgcatgcaca gcacacatga  2220
acacagcaca cacacaaaca cacagcacac acatgcacac acagcacaca cactcatgcg  2280
cagcacatac atgaacacag ctcacagcac acaaacacgc agcacacacg ttgcacacgc  2340
aagcacccac ctgcacacac acatgcgcac acacacgcac acccccacaa aattggatga  2400
aaacaataag catatctaag caactacgat atctgtatgg atcaggccaa agtcccgcta  2460
agattctcca atgtttttcat ggtctgagcc ccgctcctgt tcccatctcc actgccctc  2520
ggccctgtct gtgccctgcc tctcagagga gggggctcag atggtgcggc ctgagtgtgc  2580
ggccggcggc atttgggata cacccgtagg gtgggcgggg tgtgtcccag gcctaattcc  2640
atctttccac catgacagag atgcccttgt gaggctggcc tccttggcgc ctgtccccac  2700
ggccccccgca gcgtgagccca cgatgctccc cataccccac ccattcccga tacaccttac  2760
ttactgtgtg ttggcccagc cagagtgagg aaggagtttg gccacattgg agatggcggt  2820
agctgagcag acatgccccc acgagtagcc tgactccctg gtgtgctcct ggaaggaaga  2880
tcttggggac cccccaccg gagcacacct agggatcatc tttgcccgtc tcctggggac  2940
cccccaagaa atgtggagtc ctcgggggcc gtgcactgat gcgggggagtg tgggaagtct  3000
ggcggttgga ggggtgggtg ggggggcagtg ggggctgggc ggggggagtt ctggggtagg  3060
aagtggtccc gggagatttt ggatggaaaa gtcaggagga ttgacagcag acttgcagaa  3120
ttacatagag aaattaggaa ccccccaaatt tcatgtcaat tgatctattc ccctctcttg  3180
tttcttgggg cattttttcct ttttttttttt tttttgtttt ttttttaccc ctccttagct  3240
ttatgcgctc agaaaccaaa ttaaaccccc ccccccatgta acagggggc agtgacaaaa  3300
gcaagaacgc acgaagccag cctggagacc accacgtcct gcccccgcc atttatcgcc  3360
ctgattggat tttgttttttc atctgtccct gttgcttggg ttgagttgag ggtggagcct  3420
cctgggggc actggccact gagcccccctt ggagaagtca gaggggagtg gagaaggcca  3480
ctgtccggcc tggcttctgg ggacagtggc tggtccccag aagtcctgag ggcggagggg  3540
ggggttgggc agggtctcct caggtgtcag gagggtgctc ggaggccaca ggaggggggct  3600
cctggctggc ctgaggctgg ccggaggggga aggggctagc aggtgtgtaa acagagggtt  3660
ccatcaggct gggggcagggt ggccgccttc cgcacacttg aggaaccctc ccctctccct  3720
cggtgacatc ttgcccgccc ctcagcaccc tgccttgtct ccaggaggtc cgaagctctg  3780
tgggacctct tgggggcaag gtggggtgag gccggggagt agggaggtca ggcgggtctg  3840
agcccacaga gcaggagagc tgccaggtct gcccatcgac caggttgctt gggccccgga  3900
gcccacggct ctggtgatgc catagcagcc accaccgcgg cgcctagggc tgcggcaggg  3960
actcggcctc tgggaggttt acctcgcccc cacttgtgcc cccagctcag cccccctgca  4020
cgcagcccga ctagcagtct agaggcctga ggcttctggg tcctggtgac ggggctggca  4080
tgaccccggg ggtcgtccat gccagtccgc ctcagtcgca gagggtccct cggcaagcgc  4140
cctgtgagtg ggccattcgg aacattggac agaagccaa agagccaaat tgtcacaatt  4200
gtggaaccca cattggcctg agatccaaaa cgcttcgagg caccccaaat tacctgccca  4260
ttcgtcagga cacccaccca cccagtgtta tattctgcct cgccggagtg ggtgttcccg  4320
ggggcacttg ccgaccagcc ccttgcgtcc ccaggtttgc agctctcccc tgggccacta  4380
accatcctgg cccgggctgc ctgtctgacc tccgtgccta gtcgtggctc tccatcttgt  4440
ctcctcccg tgtccccaat gtcttcagtg gggggccccc tcttgggtcc cctcctctgc  4500
catcacctga agacccccac gccaaacact gaatgtcacc tgtgcctgcc gcctcggtcc  4560
accttgcggc ccgtgtttga ctcaactcaa ctcctttaac gctaatattt ccggcaaaat  4620
cccatgcttg ggttttgtct ttaaccttgt aacgcttgca atcccaataa agcattaaaa  4680
gtcatgatct tcaaaaaaaa aaaaaaaaaa                                     4710
```

SEQ ID NO: 178          moltype = AA   length = 1207
FEATURE                 Location/Qualifiers
source                  1..1207
                        mol_type = protein
                        organism = Homo sapiens

SEQUENCE: 178

```
MLLTLIILLP VVSKFSFVSL SAPQHWSCPE GTLAGNGNST CVGPAPFLIF SHGNSIFRID  60
TEGTNYEQLV VDAGVSVIMD FHYNEKRIYW VDLERQLLQR VFLNGSRQER VCNIEKNVSG  120
MAINWINEEV IWSNQQEGII TVTDMKGNNS HILLSALKYP ANVAVDPVER FIFWSSEVAG  180
SLYRADLDGV GVKALLETSE KITAVSLDVL DKRLFWIQYN REGSNSLICS CDYDGGSVHI  240
SKHPTQHNLF AMSLFGDRIF YSTWKMKTIW IANKHTGKDM VRINLHSSFV PLGELKVVHP  300
LAQPKAEDDT WEPEQKLCKL RKGNCSSTVC GQDLQSHLCM CAEGYALSRD RKYCEDVNEC  360
AFWNHGCTLG CKNTPGSYYC TCPVGFVLLP DGKRCHQLVS CPRNVSECSH DCVLTSEGPL  420
CFCPEGSVLE RDGKTCSGCS SPDNGGCSQL CVPLSPVSWE CDCFPGYDLQ LDEKSCAASG  480
PQPFLLFANS QDIRHMHFDG TDYGTLLSQQ MGMVYALDHD PVENKIYFAH TALKWIERAN  540
MDGSQRERLI EEGVDVPEGL AVDWIGRRFY WTDRGKSLIG RSDLNGKRSK IITKENISQP  600
RGIAVHPMAK RLFWTDTGIN PRIESSSLQG LGRLVIASSD LIWPSGITID FLTDKLYWCD  660
AKQSVIEMAN LDGSKRRRLT QNDVGHPFAV AVFEDYVWFS DWAMPSVMRV NKRTGKDRVR  720
LQGSMLKPSS LVVVHPLAKP GADPCLYQNG GCEHICKKRL GTAWCSCREG FMKASDGKTC  780
LALDGHQLLA GGEVDLKNQV TPLDILSKTR VSEDNITESQ HMLVAEIMVS DQDDCAPVGC  840
SMYARCISEG EDATCQCLKG FAGDGKLCSD IDECEMGVPV CPPASSKCIN TEGGYVCRCS  900
EGYQGDGIHC LDIDECQLGE HSCGENASCT NTEGGYTCMC AGRLSEPGLI CPDSTPPPHL  960
REDDHHYSVR NSDSECPLSH DGYCLHDGVC MYIEALDKYA CNCVVGYIGE RCQYRDLKWW  1020
ELRHAGHGQQ QKVIVVAVCV VVLVMLLLLS LWGAHYYRTQ KLLSKNPKNP YEESSRDVRS  1080
RRPADTEDGM SSCPQPWFVV IKEHQDLKNG GQPVAGEDGQ AADGSMQPTS WRQEPQLCGM  1140
GTEQGCWIPV SSDKGSCPQV MERSFHMPSY GTQTLEGGVE KPHSLLSANP LWQQRALDPP  1200
HQMELTQ                                                              1207
```

SEQ ID NO: 179          moltype = DNA   length = 5600
FEATURE                 Location/Qualifiers
source                  1..5600
                        mol_type = genomic DNA
                        organism = Homo sapiens

SEQUENCE: 179

```
aaaaagagaa actgttggga gaggaatcgt atctccatat ttcttctttc agccccaatc  60
```

-continued

```
caagggttgt agctggaact ttccatcagt tcttcctttc ttttttcctct ctaagccttt   120
gccttgctct gtcacagtga agtcagccag agcagggctg ttaaactctg tgaaatttgt   180
cataagggtg tcaggtattt cttactggct tccaaagaaa catagataaa gaaatctttc   240
ctgtggcttc ccttggcagg ctgcattcag aaggtctctc agttgaagaa agagcttgga   300
ggacaacagc acaacaggag agtaaaagat gccccaggtg tgaggcctcc gctcaggcag   360
ccgcatctgg ggtcaatcat actcaccttg cccgggccat gctccagcaa aatcaagctg   420
ttttcttttg aaagttcaaa ctcatcaaga ttatgctgct cactcttatc attctgttgc   480
cagtagtttc aaaatttagt tttgttagtc tctcagcacc gcagcactgg agctgtcctg   540
aaggtactct cgcaggaaat gggaattcta cttgtgtggg tcctgcaccc ttcttaattt   600
tctcccatgg aaatagtatc tttaggattg acacagaagg aaccaattat gagcaattgg   660
tggtggatgc tggtgtctca gtgatcatgg attttcatta taatgagaaa agaatctatt   720
gggtggattt agaaagacaa cttttgcaaa gagttttttct gaatgggtca aggcaagaga   780
gagtatgtaa tatagagaaa aatgtttctg gaatggcaat aaattggata aatgaagaag   840
ttatttggtc aaatcaacag gaaggaatca ttacagtaac agatatgaaa ggaaataatt   900
cccacattct tttaagtgct ttaaaatatc ctgcaaatgt agcagttgat ccagtagaaa   960
ggtttatatt ttggtcttca gaggtggctg gaagccttta tagagcagat ctcgatggtg  1020
tgggagtgaa ggctctgttg gagacatcag agaaaataac agctgtgtca ttggatgtgc  1080
ttgataagcg gctgttttgg attcagtaca acagagaagg aagcaattct cttatttgct  1140
cctgtgatta tgatggaggt tctgtccaca ttagtaaaca tccaacacag cataatttgt  1200
ttgcaatgtc cctttttggt gaccgtatct tctattcaac atggaaaatg aagacaattt  1260
ggatagccaa caaacacact ggaaaggaca tggttagaat taacctccat tcatccattg  1320
taccacttgg tgaactgaaa gtagtgcatc cacttgcaca acccaaggca gaagatgaca  1380
cttgggagcc tgagcagaaa ctttgcaaat tgaggaaagg aaactgcagc agcactgtgt  1440
gtgggcaaga cctccagtca cacttgtgca tgtgtgcaga gggatacgcc ctaagtcgag  1500
accgaagta ctgtgaagat gttaatgaat gtgctttttg gaatcatggc tgtactcttg  1560
ggtgtaaaaa caccccctgga tcctattact gcacgtgccc tgtaggattt gttctgcttc  1620
ctgatgggaa acgatgtcat caacttgttt cctgtccacg caatgtgtct gaatgcagcc  1680
atgactgtgt tctgacatca gaaggtccct tatgtttctg tcctgaaggc tcagtgcttg  1740
agagagatgg gaaaacatgt agcggttgtt cctcacccga taatggtgga tgtagccagc  1800
tctgcgttcc tcttagccca gtatcctggg aatgtgattg ctttcctggg tatgacctac  1860
aactggatga aaaaagctgt gcagcttcag gaccacaacc attttttgctg tttgccaatt  1920
ctcaagatat tcgacacatg cattttgatg gaacagacta tggaactctg ctcagccagc  1980
agatgggaat ggtttatgcc ctagatcatg accctgtgga aaataagata tactttgccc  2040
atacagccct gaagtggata gagagagcta atatggatgg ttcccagcga gaaaggctta  2100
ttgaggaagg agtagatgtg ccagaaggtc ttgctgtgga ctggattggc cgtagattct  2160
attggacaga cagagggaaa tctctgattg gaaggagtga tttaaatggg aaacgttcca  2220
aaataatcac taaggagaac atctctcaac cacgaggaat tgctgttcat ccaatggcca  2280
agagattatt ctggactgat acagggatta atccacgaat tgaaagttct tccctccaag  2340
gccttggccg tctggttata gccagctctg atctaatctg gcccagtgga ataacgatca  2400
acttcttaac tgacaagttg tactggtgcg atgccaagca gtctgtgatt gaaatggcca  2460
atctggatgg ttcaaaacgc cgaagactta cccagaatga tgtaggtcac ccatttgctg  2520
tagcagtgtt tgaggattat gtgtggttct cagattgggc tatgccatca gtaatgagag  2580
taaacaagag gactggcaaa gatagagtac gtctccaagg cagcatgctg aagccctcat  2640
cactggttgt ggttcatcca ttggcaaaac caggagcaga tccctgctta tatcaaaacg  2700
gaggctgtga acatatttgc aaaaagaggc ttggaactgc ttggtgttcg tgtcgtgaag  2760
gttttatgaa agcctcagat gggaaaacgt gtctggctct ggatggtcat cagctgttgg  2820
caggtggtga agttgatcta aagaaccaag taacaccatt ggacatcttg tccaagacta  2880
gagtgtcaga agataacatt acagaatctc aacacatgct agtggctgaa atcatggtgt  2940
cagatcaaga tgactgtgct cctgtgggat gcagcatgta tgctcggtgt atttcagagg  3000
gagaggatgc cacatgtcag tgtttgaaag gatttgctgg ggatggaaaa ctatgttctg  3060
atatagatga atgtgagatg ggtgtcccag tgtgccccccc tgcctcctcc aagtgcatca  3120
acaccgaagg tggttatgtc tgccggtgct cagaaggcta ccaaggagat gggattcact  3180
gtcttgatat tgatgagtgc caactggggg agcacagctg tggagagaat gccagctgca  3240
caaatacaga gggaggctat acctgcatgt gtgctggacg cctgtctgaa ccaggactga  3300
tttgccctga ctctactcca cccccctcacc tcagggaaga tgaccaccac tattccgtaa  3360
gaaatagtga ctctgaatgt cccctgtccc acgatgggta ctgcctccat gatggtgtgt  3420
gcatgtatat tgaagcattg gacaagtatg catgcaactg tgttgttggc tacatcggggg  3480
agcgatgtca gtaccgagac ctgaagtggt gggaactgcg ccacgctggc cacgggcagc  3540
agcagaaggt catcgtggtg gctgtctgcg tggtggtgct tgtcatgctg ctcctcctga  3600
gcctgtgtgg ggcccactac tacaggactc agaagctgct atcgaaaaac ccaaagaatc  3660
cttatgagga gtcgagcaga gatgtgagga gtcgcaggcc tgctgacact gaggatggga  3720
tgtcctcttg ccctcaacct tggtttgtgg ttataaaaga acaccaagac ctcaagaatg  3780
ggggtcaacc agtggctggt gaggatggcc aggcagcaga tgggtcaatg caaccaactt  3840
catggaggca ggagccccag ttatgtggaa tgggcacaga gcaaggctgc tggattccag  3900
tatccagtga taagggctcc tgtccccagg taatggagcg aagctttcat atgccctcct  3960
atgggacaca gaccccttgaa gggggtgtcg agagccccca ttctctccta tcagctaacc  4020
cattatggca acaaagggcc ctggacccac cacaccaaat ggagctgact cagtgaaaac  4080
tggaattaaa aggaaagtca agaagaatga actatgtcga tgcacagtat cttttctttc  4140
aaaagtagag caaaactata ggttttggtt ccacaatctc tacgactaat cacctactca  4200
atgcctggag acagatacgt agttgtgctt ttgtttgctc tttttaagcag tctcactgca  4260
gtcttatttc caagtaagag tactgggaga atcactaggt aacttattag aaacccaaat  4320
tgggacaaca gtgctttgta aattgtgttg tcttcagcag tcaatacaaa tagatttttg  4380
ttttttgttgt tcctgcagcc ccagaagaaa ttaggggtta aagcagacag tcacactggt  4440
ttggtcagtt acaaagtaat ttctttgatc tggacatgaa atttatatca gtttcatgaa  4500
atgattggaa tattacaata ccgttaagat acagtgtagg catttaactc ctcattggcg  4560
tggtccatgc tgatgatttt gcaaaatgag ttgtgatgaa tcaatgaaaa atgtaattta  4620
gaaactgatt tcttcagaat tagatggctt atttttttaaa atatttgaat gaaaacatt t  4680
tattttttaaa atattacaca ggaggcttcg gagtttctta gtcattactg tccttttccc  4740
ctacagaatt ttccctcttg gtgtgattgc acagaatttg tatgtatttt cagttacaag  4800
```

```
attgtaagta aattgcctga tttgttttca ttatagacaa cgatgaattt cttctaatta   4860
tttaaataaa atcaccaaaa acataaacat tttattgtat gcctgattaa gtagttaatt   4920
atagtctaag gcagtactag agttgaacca aaatgatttg tcaagcttgc tgatgtttct   4980
gttttttcgtt tttttttttt ttccggagag aggataggat ctcactctgt tatccaggct   5040
ggagtggtgca atggcacaat catagctcag tgcagcctca aactcctggg ctcaagcaat   5100
cctcctgcct cagcctcccg agtaactagg accacaggca caggccacca tgcctggcta   5160
aggtttttat ttttattttt tgtagacatg gggatcacac aatgttgccc aggctggtct   5220
tgaactcctg gcctcaagca aggtcgtgct ggtaattttg caaaatgaat tgtgattgac   5280
tttcagcctc ccaacgtatt agattatagg cattagccat ggtgcccagc cttgtaactt   5340
ttaaaaaaat tttttaatct acaactctgt agattaaaat ttcacatggt gttctaatta   5400
aatatttttc ttgcagccaa gatattgtta ctacagataa cacaacctga tatggtaact   5460
ttaaattttg ggggctttga atcattcagt ttatgcatta actagtccct ttgtttatct   5520
ttcatttctc aaccccttgt actttggtga taccagacat cagaataaaa agaaattgaa   5580
gtaaaaaaaa aaaaaaaaaa                                               5600
```

```
SEQ ID NO: 180        moltype = AA   length = 1166
FEATURE               Location/Qualifiers
source                1..1166
                      mol_type = protein
                      organism = Homo sapiens
SEQUENCE: 180
MLLTLIILLP VVSKFSFVSL SAPQHWSCPE GTLAGNGNST CVGPAPFLIF SHGNSIFRID   60
TEGTNYEQLV VDAGVSVIMD FHYNEKRIYW VDLERQLLQR VFLNGSRQER VCNIEKNVSG   120
MAINWINEEV IWSNQQEGII TVTDMKGNNS HILLSALKYP ANVAVDPVER FIFWSSEVAG   180
SLYRADLDGV GVKALLETSE KITAVSLDVL DKRLFWIQYN REGSNSLICS CDYDGGSVHI   240
SKHPTQHNLF AMSLFGDRIF YSTWKMKTIW IANKHTGKDM VRINLHSSFV PLGELKVVHP   300
LAQPKAEDDT WEPEQKLCKL RKGNCSSTVC GQDLQSHLCM CAEGYALSRD RKYCEDVNEC   360
AFWNHGCTLG CKNTPGSYYC TCPVGFVLLP DGKRCHQLVS CPRNVSECSH DCVLTSEGPL   420
CFCPEGSVLE RDGKTCSGCS SPDNGGCSQL CVPLSPVSWE CDCFPGYDLQ LDEKSCAASG   480
PQPFLLFANS QDIRHMHFDG TDYGTLLSQQ MGMVYALDHD PVENKIYFAH TALKWIERAN   540
MDGSQRERLI EEGVDVPEGL AVDWIGRRFY WTDRGKSLIG RSDLNGKRSK IITKENISQP   600
RGIAVHPMAK RLFWTDTGIN PRIESSSLQG LGRLVIASSD LIWPSGITID PLTDKLYWCD   660
AKQSVIEMAN LDGSKRRRLT QNDVGHPFAV AVFEDYVWFS DWAMPSVMRV NKRTGKDRVR   720
LQGSMLKPSS LVVVHPLAKP GADPCLYQNG GCEHICKKRL GTAWCSCREG FMKASDGKTC   780
LALDGHQLLA GGEVDLKNQV TPLDILSKTR VSEDNITESQ HMLVAEIMVS DQDDCAPVGC   840
SMYARCISEG EDATCQCLKG FAGDGKLCSD IDECEMGVPV CPPASSKCIN TEGGYVCRCS   900
EGYQGDGIHC LDSTPPPHLR EDDHHYSVRN SDSECPLSHD GYCLHDGVCM YIEALDKYAC   960
NCVVGYIGER CQYRDLKWWE LRHAGHGQQQ KVIVVAVCVV VLVMLLLLSL WGAHYRTQK   1020
LLSKNPKNPY EESSRDVRSR RPADTEDGMS SCPQPWFVVI KEHQDLKNGG QPVAGEDGQA   1080
ADGSMQPTSW RQEPQLCGMG TEQGCWIPVS SDKGSCPQVM ERSFHMPSYG TQTLEGGVEK   1140
PHSLLSANPL WQQRALDPPH QMELTQ                                        1166
```

```
SEQ ID NO: 181        moltype = DNA   length = 5477
FEATURE               Location/Qualifiers
source                1..5477
                      mol_type = genomic DNA
                      organism = Homo sapiens
SEQUENCE: 181
aaaaagagaa actgttggga gaggaatcgt atctccatat ttcttctttc agccccaatc   60
caagggttgt agctggaact ttccatcagt tcttcctttc ttttttcctct ctaagccttt   120
gccttgctct gtcacagtga agtcagccag agcagggctg ttaaactctg tgaaatttgt   180
cataagggtg tcaggtattt cttactggct tccaaagaaa catagataaa gaaatctttc   240
ctgtggcttc ccttggcagg ctgcattcag aaggtctctc agttgaagaa agagcttgga   300
ggacaacagc acaacaggag agtaaaagat gccccagggc tgaggcctcc gctcaggcag   360
ccgcatctgg ggtcaatcat actcaccttg cccgggccat gctccagcaa aatcaagctg   420
ttttcttttg aaagttcaaa ctcatcaaga ttatgctgct cactcttatc attctgttgc   480
cagtagtttc aaaatttagt tttgttagtc tctcagcacc gcagcactgg agctgtcctg   540
aaggtactct cgcaggaaat gggaattcta cttgtgtggg tcctgcaccc ttcttaattt   600
tctcccatgg aaatagtatc tttaggattg acacagaagg aaccaattat gagcaattgg   660
tggtggatgc tggtgtctca gtgatcatgg attttcatta taatgagaaa agaatctatt   720
gggtggattt agaaagacaa cttttgcaaa gagtttttct gaatgggtca aggcaagaga   780
gagtatgtaa tatagagaaa aatgtttctg gaatggcaat aaattggata aatgaagaag   840
ttatttggtc aaatcaacag gaaggaatca ttacagtaac agatatgaaa ggaaataatt   900
cccacattct tttaagtgct ttaaaatatc ctgcaaatgt agcagttgat ccagtgagaa   960
ggtttatatt ttggtcttca gaggtggctg gaagccttta tagagcagat ctcgatggtg   1020
tgggagtgaa ggctctgttg gagacatcag agaaaataac agctgtgtca ttggatgtgc   1080
ttgataagcg gctgtttttgg attcagtaca acagagaagg aagcaattct cttatttgct   1140
cctgtgatta tgatggaggt tctgtccaca ttagtaaaca tccaacacag cataatttgt   1200
ttgcaatgtc ccttttttggt gaccgtatct tctattcaac atggaaaatg aagacaattt   1260
ggatagccaa caaacacact ggaaaggaca tggttagaat taacctccat tcatcatttg   1320
taccacttgg tgaactgaaa gtagtgcatc cacttgcaca acccaaggca gaagatgaca   1380
cttgggagcc tgagcagaaa cttttgcaaat tgaggaaagg aaactgcagc agcactgtgt   1440
gtgggcaaga cctccagtca cacttgtgca tgtgtgcaga gggatacgcc ctaagtgag   1500
accggaagta ctgtgaagat gttaatgaat gtgcttttgg gaatcatggc tgtactcttg   1560
ggtgtaaaaa cacccctgga tcctattact gcacgtgccc tgtaggattt gttctgcttc   1620
ctgatgggaa acgatgtcat caacttgttt cctgtccacg caatgtgtct gaatgcagcc   1680
atgactgtgt tctgacatca gaaggtccct tatgtttctg tcctgaaggc tcagtgcttg   1740
agagagatgg gaaaacatgt agcggttgtt cctcacccga taatggtgga tgtagccagc   1800
tctgcgttcc tcttagccca gtatcctggg aatgtgattg ctttcctggg tatgacctac   1860
```

```
aactggatga aaaaagctgt gcagcttcag gaccacaacc attttttgctg tttgccaatt    1920
ctcaagatat tcgacacatg cattttgatg gaacagacta tggaactctg ctcagccagc    1980
agatgggaat ggtttatgcc ctagatcatg accctgtgga aaataagata tactttgccc    2040
atacagccct gaagtggata gagagagcta atatggatgg ttcccagcga gaaaggctta    2100
ttgaggaagg agtagatgtg ccagaaggtc ttgctgtgga ctggattggc cgtagattct    2160
attggacaga cagagggaaa tctctgattg gaaggagtga tttaaatggg aaacgttcca    2220
aaataatcac taaggagaac atctctcaac cacgaggaat tgctgttcat ccaatggcca    2280
agagattatt ctggactgat acagggatta tccacgaat tgaaagttct tccctccaag    2340
gccttggccg tctggttata gccagctctg atctaatctg gcccagtgga ataacgattg    2400
acttcttaac tgacaagttg tactggtgcg atgccaagca gtctgtgatt gaaatggcca    2460
atctggatgg ttcaaaacgc cgaagactta cccagaatga tgtaggtcac ccatttgctg    2520
tagcagtgtt tgaggattat gtgtggttct cagattgggc tatgccatca gtaatgagag    2580
taaacaagag gactggcaaa gatagagtac gtctccaagg cagcatgctg aagccctcat    2640
cactggttgt ggttcatcca ttggcaaaac caggagcaga tccctgctta tatcaaaacg    2700
gaggctgtga acatatttgc aaaaagaggc ttggaactgc ttggtgttcg tgtcgtgaag    2760
gttttatgaa agcctcagat gggaaaacgt gtctggctct ggatggtcat cagctgttgg    2820
caggtggtga agttgatcta aagaaccaag taacaccatt ggacatcttg tccaagacta    2880
gagtgtcaga agataacatt acagaatctc aacacatgct agtggctgaa atcatggtgt    2940
cagatcaaga tgactgtgct cctgtgggat gcagcatgta tgctcggtgt atttcagagg    3000
gagaggatgc cacatgtcag tgtttgaaag gatttgctgg ggatggaaaa ctatgttctg    3060
atatagatga atgtgagatg ggtgtcccag tgtgcccccc tgcctcctcc aagtgcatca    3120
acaccgaagg tggttatgtc tgccggtgct cagaaggcta ccaaggagat gggattcact    3180
gtcttgactc tactccaccc cctcacctca gggaagatga ccaccactat tccgtaagaa    3240
atagtgactc tgaatgtccc ctgtcccacg atgggtactg cctccatgat ggtgtgtgca    3300
tgtatattga agcattggac aagtatgcat gcaactgtgt tgttggctac atcggggagc    3360
gatgtcagta ccgagacctg aagtggtggg aactgcgcca gggcagcagc    3420
agaaggtcat cgtggtggct gtctgcgtgg tggtgcttgt catgctgctc ctcctgagcc    3480
tgtgggggggc ccactactac aggactcaga agctgctatc gaaaaaccca aagaatcctt    3540
atgaggagtc gagcagagat gtgaggagtc gcaggcctgc tgacactgag gatgggatgt    3600
cctcttgccc tcaaccttgg tttgtggtta taaaagaaca ccaagaccct aagaatgggg    3660
gtcaaccagt ggctggtgag gatggccagg cagcagatgg gtcaatgcaa ccaacttcat    3720
ggaggcagga gccccagtta tgtggaatgg gcacagagca aggctgctgg attccagtat    3780
ccagtgataa gggctcctgt ccccaggtaa tggagcgaag cttttcatatg ccctcctatg    3840
ggacacagac ccttgaaggg ggtgtcgaga agcccccattc tctcctatca gctaacccat    3900
tatggcaaca aagggccctg gacccaccac accaaatgga gctgactcag tgaaaactgg    3960
aattaaaagg aaagtcaaga agaatgaact atgtcgatgc acagtatctt ttctttcaaa    4020
agtagagcaa aactataggt tttggttcca caatctctac gactaatcac ctactcaatg    4080
cctggagaca gatacgtagt tgtgctttttg tttgctcttt taagcagtct cactgcagtc    4140
ttatttccaa gtaagagtac tgggagaatc actaggtaac ttattagaaa cccaaattgg    4200
gacaacagtg cttttgtaaat tgtgttgtct tcagcagtca atacaaatag attttttgttt    4260
ttgttgttcc tgcagcccca gaagaaatta ggggttaaag cagacagtca cactggtttg    4320
gtcagttaca aagtaatttc tttgatctgg acagaacatt tatatcagtt tcatgaaatg    4380
attggaatat tacaataccg ttaagataca gtgtaggcat ttaactcctc attggcgtgg    4440
tccatgctga tgattttgca aaatgagttg tgatgaatca atgaaaaatg taatttagaa    4500
actgatttct tcagaattag atggcttatt tttttaaaata tttgaatgaa acatttttat    4560
ttttaaaata ttacacagga ggcttcggag tttcttagtc attactgtcc ttttcccta    4620
cagaattttc cctcttggtg tgattgcaca gaatttgtat gtattttcag ttacaagatt    4680
gtaagtaaat tgcctgattt gttttcatta tagacaacga tgaatttctt ctaattattt    4740
aaataaaatc accaaaaaca taaacatttt attgtatgcc tgattaagta gttaattata    4800
gtctaaggca gtactagagt tgaaccaaaa tgatttgtca agcttgctga tgtttctgtt    4860
tttcgttttt ttttttttttc cggagagagg ataggatctc actctgttat ccaggctgga    4920
gtgtgcaatg gcacaatcat agctcagtgc agcctcaaac tcctgggctc aagcaatcct    4980
cctgcctcag cctcccgagt aactaggacc acaggcacag gccaccatgc ctggctaagg    5040
ttttttatttt tattttttgt agacatgggg atcacacaat gttgcccagg ctggtcttga    5100
actcctggcc tcaagcaagg tcgtgctggt aattttgtca aatgaattgt gattgacttt    5160
cagcctccca acgtattaga ttataggcat tagccatggt gcccagcctt gtaactttta    5220
aaaaaatttt ttaatctaca actctgtaga ttaaaatttc acatggtgtt ctaattaaat    5280
attttttcttg cagccaagat attgttacta cagataacac aacctgatat ggtaacttta    5340
aattttgggg gctttgaatc attcagttta tgcattaact agtcccctttg tttatctttc    5400
atttctcaac cccttgtact ttggtgatac cagacatcag aataaaaaga aattgaagta    5460
aaaaaaaaaa aaaaaaa                                                   5477
```

```
SEQ ID NO: 182           moltype = AA  length = 1165
FEATURE                  Location/Qualifiers
source                   1..1165
                         mol_type = protein
                         organism = Homo sapiens
SEQUENCE: 182
MLLTLIILLP VVSKFSFVSL SAPQHWSCPE GTLAGNGNST CVGPAPFLIF SHGNSIFRID    60
TEGTNYEQLV VDAGVSVIMD FHYNEKRIYW VDLERQLLQR VFLNGSRQER VCNIEKNVSG   120
MAINWINEEV IWSNQQEGII TVTDMKGNNS HILLSALKYP ANVAVDPVER FIFWSSEVAG   180
SLYRADLDGV GVKALLETSE KITAVSLDVL DKRLFWIQYN REGSNSLICS CDYDGGSVHI   240
SKHPTQHNLF AMSLFGDRIF YSTWKMKTIW IANKHTGKDM VRINLHSSFV PLGELKVVHP   300
LAQPKAEDDT WEPDVNECAF WNHGCTLGCK NTPGSYYCTC PVGFVLLPDG KRCHQLVSCP   360
RNVSECSHDC VLTSEGPLCF CPEGSVLERD GKTCSGCSSP DNGGCSQLCV PLSPVSWECD   420
CFPGYDLQLD EKSCAASGPQ PFLLFANSQD IRHMHFDGTD YGTLLSQQMG MVYALDHDPV   480
ENKIYFAHTA LKWIERANMD GSQRERLIEE GVDVPEGLAV DWIGRRFYWT DRGKSLIGRS   540
DLNGKRSKII TKENISQPRG IAVHPMAKRL FWTDTGINPR IESSSLQGLG RLVIASSDLI   600
WPSGITIDFL TDKLYWCDAK QSVIEMANLD GSKRRRLTQN DVGHPFAVAV FEDYVWFSDW   660
```

-continued

```
AMPSVMRVNK RTGKDRVRLQ GSMLKPSSLV VVHPLAKPGA DPCLYQNGGC EHICKKRLGT    720
AWCSCREGFM KASDGKTCLA LDGHQLLAGG EVDLKNQVTP LDILSKTRVS EDNITESQHM    780
LVAEIMVSDQ DDCAPVGCSM YARCISEGED ATCQCLKGFA GDGKLCSDID ECEMGVPVCP    840
PASSKCINTE GGYVCRCSEG YQGDGIHCLD IDECQLGEHS CGENASCTNT EGGYTCMCAG    900
RLSEPGLICP DSTPPPHLRE DDHHYSVRNS DSECPLSHDG YCLHDGVCMY IEALDKYACN    960
CVVGYIGERC QYRDLKWWEL RHAGHGQQQK VIVVAVCVVV LVMLLLLSLW GAHYYRTQKL   1020
LSKNPKNPYE ESSRDVRSRR PADTEDGMSS CPQPWFVVIK EHQDLKNGGQ PVAGEDGQAA   1080
DGSMQPTSWR QEPQLCGMGT EQGCWIPVSS DKGSCPQVME RSFHMPSYGT QTLEGGVEKP   1140
HSLLSANPLW QQRALDPPHQ MELTQ                                        1165

SEQ ID NO: 183          moltype = DNA   length = 5474
FEATURE                 Location/Qualifiers
source                  1..5474
                        mol_type = genomic DNA
                        organism = Homo sapiens
SEQUENCE: 183
aaaaagagaa actgttggga gaggaatcgt atctccatat ttcttctttc agccccaatc    60
caagggttgt agctggaact ttccatcagt tcttcctttc tttttcctct ctaagccttt   120
gccttgctct gtcacagtga agtcagccag agcagggctg ttaaactctg tgaaatttgt   180
cataagggtg tcaggtattt cttactggct tccaaagaaa catagataaa gaaatctttc   240
ctgtggcttc ccttggcagg ctgcattcag aaggtctctc agttgaagaa agagcttgga   300
ggacaacagc acaacaggag agtaaaagat gccccaggtc gctcaggcag   360
ccgcatctgg ggtcaatcat actcaccttg cccgggccat gctccagcaa aatcaagctg   420
tttttctttg aaagttcaaa ctcatcaaga ttatgctgct cactcttatc attctgttgc   480
cagtagtttc aaaatttagt tttgttagtc tctcagcacc gcagcactgg agctgtcctg   540
aaggtactct cgcaggaaat gggaattcta cttgtgtagg tcctgcaccc ttcttaattt   600
tctcccatgg aaatagtatc tttaggattg acacagaagg aaccaattat gagcaattgg   660
tggtggatgc tggtgtctca gtgatcatgg attttcatta taatgagaaa agaatctatt   720
gggtggattt agaaagacaa cttttgcaaa gagttttttct gaatgggtca aggcaagaga   780
gagtatgtaa tatagagaaa aatgtttctg gaatggcaat aaattggata aatgaagaag   840
ttatttggtc aaatcaacag gaaggaatca ttacagtaac agatatgaaa ggaaataatt   900
cccacattct tttaagtgct ttaaaatatc ctgcaaatgt agcagttgat ccagtagaaa   960
ggtttatatt ttggtcttca gaggtggctg gaagcctttma tagagcagat ctcgatggtg  1020
tgggagtgaa ggctctgttg gagacatcag agaaaataac agctgtgtca ttggatgtgc  1080
ttgataagcg gctgtttttgg attcagtaca acagagaagg aagcaattct cttatttgct  1140
cctgtgatta tgatggaggt tctgtccaca ttagtaaaca tccaacacag cataatttgt  1200
ttgcaatgtc cctttttggt gaccgtatct tctattcaac atggaaaatg aagacaattt  1260
ggatagccaa caaacacact ggaaaggaca tggttagaat taacctccat tcatcatttg  1320
taccacttgg tgaactgaaa gtagtgcatc cacttgcaca acccaaggca gaagatgaca  1380
cttgggagcc tgatgttaat gaatgtgctt tttggaatca tggctgtact cttgggtgta  1440
aaaacacccc tggatcctat tactgcacgt gccctgtagg atttgttctg cttcctgatg  1500
ggaaacgatg tcatcaactt gtttcctgtc cacgcaatgt gtctgaatgc agccatgact  1560
gtgttctgac atcagaaggt cccttatgtt tctgtcctga aggctcagtg cttggagagg  1620
atgggaaaac atgtagcggt tgttcctcac ccgataatgt tggatgtagc cagctctgcg  1680
ttcctcttag cccagtatcc tgggaatgtg attgctttcc tgggtatgac ctacaactgg  1740
atgaaaaaag ctgtgcagct tcaggaccac aaccattttt gctgtttgcc aattctcaag  1800
atattcgaca catgcatttt gatggaacag actatggaac tgctctcagc cagcagatg  1860
gaatggtttta tgccctagat catgaccctg tggaaaataa gatatacttt gcccatacag  1920
ccctgaagtg gatagagaga gctaatatgg atggttccca gcgagaaagg cttattgagg  1980
aaggagtaga tgtgccagaa ggtcttgctg tggactggat tggccgtaga ttctattgga  2040
cagacagagg gaaatctctg attggaagga gtgatttaaa tgggaaacgt tccaaaataa  2100
tcactaagga gaacatctct caaccacgag gaattgctgt tcatccaatg gccaagagat  2160
tattctggac tgatacaggg attaatccac gaattgaaag ttcttccctc caaggccttg  2220
gccgtctggt tatagccagc tctgatctaa tctggcccag tggaataacg attgacttct  2280
taactgacaa gttgtactgg tgcgatgcca agcagtctgt gattgaaatg gccaatctgg  2340
atggttcaaa acgccgaaga cttacccaga atgatgtagg tcacccattt gctgtagcag  2400
tgtttgagga ttatgtgtgg ttctcagatt gggctatgcc atcagtaatg agagtaaaca  2460
agaggactgg caaagataga gtacgtctcc aaggcagcat gctgaagccc tcatcactgg  2520
ttgtggttca tccattggca aaaccaggag cagatccctg cttatatcaa aacggaggct  2580
gtgaacatat ttgcaaaaag aggcttggaa ctgcttggtg ttcgtgtcgt gaaggtttta  2640
tgaaagcctc agatgggaaa acgtgtctgg ctctggatgg tcatcagctg ttggcaggtg  2700
gtgaagttga tctaaagaac caagtaacac cattggacat cttgtccaag actagagtgt  2760
cagaagataa cattacagaa tctcaacaca tgctagtggc tgaaatcatg gtgtcagatc  2820
aagatgactg tgctcctgtg ggatgcagca tgtatgctcg gtgtatttca gagggagagg  2880
atgccacatg tcagtgtttg aaaggatttg ctggggatgg aaaactatgt tctgatatag  2940
atgaatgtga gatgggtgtc ccagtgtgcc cccctgcctc ctccaagtgc atcaacaccg  3000
aaggtggtta tgtctgccgg tgctcagaag gctaccaagg agatgggatt cactgtcttg  3060
atattgatga gtgccaactg ggggagcaca gctgtggaga gaatgccagc tgcacaaata  3120
cagaggactg ctatacctgc atgtgtgctg gacgcctgtc tgaaccagga ctgatttgcc  3180
ctgactctac tccaccccct cacctcaggg aagatgacca ccactattcc gtaagaaata  3240
gtgactctga atgtcccctg tcccacgatg ggtactgcct ccatgatggt gtgtgcatgt  3300
atattgaagc attggacaag tatgcatgca actgtgttgt tggctacatc ggggagcgat  3360
gtcagtaccg agacctgaag tggtgggaac tgcgccacgc tggccacggg cagcagcaga  3420
aggtcatcgt ggtggctgtc tgcgtggtgg tgcttgtcat gctgctcctc ctgagcctgt  3480
ggggggccca ctactacagg actcagaagc tgctatcgaa aaacccaaag aatccttatg  3540
aggagtcgag cagagatgtg aggagtcgca ggcctgctga cactgaggat gggatgtcct  3600
cttgcccctca accttggttt gtggttataa aagaacacca agacctcaag aatggggtc  3660
aaccagtggc tggtgaggat ggccaggcag cagatgggt aatgcaacca acttcatgga  3720
ggcaggagcc ccagttatgt ggaatgggca cagagcaagg ctgctggatt ccagtatcca  3780
```

-continued

```
gtgataaggg ctcctgtccc caggtaatgg agcgaagctt tcatatgccc tcctatggga   3840
cacagaccct tgaaggggt gtcgagaagc cccattctct cctatcagct aacccattat     3900
ggcaacaaag ggccctggac ccaccacacc aaatggagct gactcagtga aaactggaat    3960
taaaaggaaa gtcaagaaga atgaactatg tcgatgcaca gtatctttc tttcaaaagt      4020
agagcaaaac tataggtttt ggttccacaa tctctacgac taatcaccta ctcaatgcct     4080
ggagacagat acgtagttgt gctttttgtt gctcttttaa gcagtctcac tgcagtctta     4140
tttccaagta agagtactgg gagaatcact aggtaactta ttagaaaccc aaattgggac     4200
aacagtgctt tgtaaattgt gttgtcttca gcagtcaata caaatagatt tttgtttttg     4260
ttgttcctgc agccccagaa gaaattaggg gttaaagcag acagtcacac tggtttggtc     4320
agttacaaag taatttcttt gatctggaca gaacatttat atcagtttca tgaaatgatt     4380
ggaatattac aataccgtta agatacagtg taggcattta actcctcatt ggcgtggtcc     4440
atgctgatga ttttgcaaaa tgagttgtga tgaatcaatg aaaaatgtaa tttagaaact     4500
gatttcttca gaattagatg gcttattttt taaaatattt gaatgaaaac attttatttt     4560
taaaatatta cacaggaggc ttcggagttt cttagtcatt actgtccttt tcccctacag     4620
aattttccct cttggtgtga ttgcacagaa tttgtatgta ttttcagtta caagattgta     4680
agtaaattgc ctgatttgtt ttcattatag acaacgatga atttcttcta attatttaaa     4740
taaaatcacc aaaaacataa acattttatt gtatgcctga ttaagtagtt aattatagtc     4800
taaggcagta ctagagttga accaaaatga tttgtcaagc ttgctgatgt ttctgttttt     4860
cgtttttttt ttttttccgg agagaggata ggatctcact ctgttatcca ggctggagtg     4920
tgcaatggca caatcatagc tcagtgcagc ctcaaactcc tgggctcaag caatcctcct     4980
gcctcagcct cccgagtaac taggaccaca ggcacaggcc accatgcctg gctaaggttt     5040
ttatttttat tttttgtaga catggggatc acacaatgt gcccaggctg gtcttgaact     5100
cctggcctca agcaaggtcg tgctggtaat tttgcaaaat gaattgtgat tgactttcag     5160
cctcccaacg tattagatta taggcattag ccatggtgcc cagccttgta acttttaaaa     5220
aaatttttta atctacaact ctgtagatta aaatttcaca tggtgttcta attaaatatt     5280
tttcttgcag ccaagatatt gttactacag ataacacaac ctgatatggt aactttaaat     5340
tttgggggct ttgaatcatt cagtttatgc attaactagt cccttgtt atctttcatt      5400
tctcaacccc ttgtactttg gtgataccag acatcagaat aaaaagaaat tgaagtaaaa     5460
aaaaaaaaa aaaa                                                        5474
```

```
SEQ ID NO: 184          moltype = AA  length = 2322
FEATURE                 Location/Qualifiers
source                  1..2322
                        mol_type = protein
                        organism = Homo sapiens
SEQUENCE: 184
MAGSVKRPMA RRPACFTGQN CEENIDDCPG NNCKNGGACV DGVNTYNCRC PPEWTGQYCT    60
EDVDECQLMP NACQNGGTCH NTHGGYNCVC VNGWTGEDCS ENIDDCASAA CFHGATCHDR    120
VASFYCECPH GRTGLLCHLN DACISNPCNE GSNCDTNPVN GKAICTCPSG YTGPACSQDV    180
DECSLGANPC EHAGKCINTL GSFECQCLQG YTGPRCEIDV NECVSNPCQN DATCLDQIGE    240
FQCICMPGYE GVHCEVNTDE CASSPCLHNG RCLDKINEFQ CECPTGFTGH LCQYDVDECA    300
STPCKNGAKC LDGPNTYTCV CTEGYTGTHC EVDIDECDPD PCHYGSCKDG VATFTCLCRP    360
GYTGHHCETN INECSSQPCR HGGTCQDRDN AYLCFCLKGT TGPNCEINLD DCASSPCDSG    420
TCLDKIDGYE CACEPGYTGS MCNINIDECA GNPCHNGGTC EDGINGFTCR CPEGYHDPTC    480
LSEVNECNSN PCVHGACRDS LNGYKCDCDP GWSGTNCDIN NNECESNPCV NGGTCKDMTS    540
GYVCTCREGF SGPNCQTNIN ECASNPCLNQ GTCIDDVAGY KCNCLLPYTG ATCEVVLAPC    600
APSPCRNGGE CRQSEDYESF SCVCPTGWQG QTCEVDINEC VLSPCRHGAS CQNTHGGYRC    660
HCQAGYSGRN CETDIDDCRP NPCHNGGSCT DGINTAFCDC LPGFRGTFCE EDINECASDP    720
CRNGANCTDC VDSYTCTCPA GFSGIHCENN TPDCTESSCF NGGTCVDGIN SFTCLCPPGF    780
TGSYCQHDVN ECDSQPCLHG GTCQDGCGSY RCTCPQGYTG PNCQNLVHWC DSSPCKNGGK    840
CWQTHTQYRC ECPSGWTGLY CDVPSVSCEV AAQRQGVDVA RLCQHGGLCV DAGNTHHCRC    900
QAGYTGSYCE DLVDECSPSP CQNGATCTDY LGGYSCKCVA GYHGVNCSEE IDECLSHPCQ    960
NGGTCLDLPN TYKCSCPRGT QGVHCEINVD DCNPPVDPVS RSPKCFNNGT CVDQVGGYSC   1020
TCPPGFVGER CEGDVNECLS NPCDARGTQN CVQRVNDFHC ECRAGHTGRR CESVINGCKG   1080
KPCKNGGTCA VASNTARGFI CKCPAGFEGA TCENDARTCG SLRCLNGGTC ISGPRSPTCL   1140
CLGPFTGPEC QFPASSPCLG GNPCYNQGTC EPTSESPFYR CLCPAKFNGL LCHILDYSFG   1200
GGAGRDIPPP LIEEACELPE CQEDAGNKVC SLQCNNHACG WDGGDCSLNF NDPWKNCTQS   1260
LQCWKYFSDG HCDSQCNSAG CLFDGFDCQR AEGQCNPLYD QYCKDHFSDG HCDQGCNSAE   1320
CEWDGLDCAE HVPERLAAGT LVVVVLMPPE QLRNSSFHFL RELSRVLHTN VVFKRDAHGQ   1380
QMIFPYYGRE EELRKHPIKR AAEGWAAPDA LLGQVKASLL PGGSEGGRRR RELDPMDVRG   1440
SIVYLEIDNR QCVQASSQCF QSATDVAAFL GALASLGSLN IPYKIEAVQS ETVEPPPPAQ   1500
LHFMYVAAAA FVLLFFVGCG VLLSRKRRRQ HGQLWFPEGF KVSEASKKKR REPLGEDSVG   1560
LKPLKNASDG ALMDDNQNEW GDEDLETKKF RFEEPVVLPD LDDQTDHRQW TQQHLDAADL   1620
RMSAMAPTPP QGEVDADCMD VNVRGPDGFT PLMIASCSGG GLETGNSEEE EDAPAVISDF   1680
IYQGASLHNQ TDRTGETALH LAARYSRSDA AKRLLEASAD ANIQDNMGRT PLHAAVSADA   1740
QGVFQILIRN RATDLDARMH DGTTPLILAA RLAVEGMLED LINSHADVNA VDDLGKSALH   1800
WAAAVNNVDA AVVLLKNGAN KDMQNNREET PLFLAAREGS YETAKVLLDH FANRDITDHM   1860
DRLPRDIAQE RMHHDIVRLL DEYNLVRSPQ LHGAPLGGTP TLSPPLCSPN GYLGSLKPGV   1920
QGKKVRKPSS KGLACGSKEA KDLKARRKKS QDGKGCLLDS SGMLSPVDSL ESPHGYLSDV   1980
ASPPLLPSPF QQSPSVPLNH LPGMPDTHLG IGHLNVAAKP EMAALGGGGR LAFETGPPRL   2040
SHLPVASGTS TVLGSSSGGA LNFTVGGSTS LNGQCEWLSR LQSGMVPNQY NPLRGSVAPG   2100
PLSTQAPSLQ HGMVGPLHSS LAASALSQMM SYQGLPSTRL ATQPHLVQTQ QVQPQNLQMQ   2160
QQNLQPANIQ QQQSLQPPPP PPQPHLGVSS AASGHLGRSF LSGEPSQADV QPLGPSSLAV   2220
HTILPQESPA LPTSLPSSLV PPVTAAQFLT PPSQHSYSSP VDNTPSHQLQ VPEHPFLTPS   2280
PESPDQWSSS SPHSNVSDWS EGVSSPPTSM QSQIARIPEA FK                       2322
```

```
SEQ ID NO: 185          moltype = AA  length = 2471
FEATURE                 Location/Qualifiers
source                  1..2471
```

```
                              mol_type = protein
                              organism = Homo sapiens
SEQUENCE: 185
MPALRPALLW ALLALWLCCA APAHALQCRD GYEPCVNEGM CVTYHNGTGY CKCPEGFLGE    60
YCQHRDPCEK NRCQNGGTCV AQAMLGKATC RCASGFTGED CQYSTSHPCF VSRPCLNGGT   120
CHMLSRDTYE CTCQVGFTGK ECQWTDACLS HPCANGSTCT TVANQFSCKC LTGFTGQKCE   180
TDVNECDIPG HCQHGGTCLN LPGSYQCQCP QGFTGQYCDS LYVPCAPSPC VNGGTCRQTG   240
DFTFECNCLP GFEGSTCERN IDDCPNHRCQ NGGVCVDGVN TYNCRCPPQW TGQFCTEDVD   300
ECLLQPNACQ NGGTCANRNG GYGCVCVNGW SGDDCSENID DCAFASCTPG STCIDRVASF   360
SCMCPEGKAG LLCHLDDACI SNPCHKGALC DTNPLNGQYI CTCPQGYKGA DCTEDVDECA   420
MANSNPCEHA GKCVNTDGAF HCECLKGYAG PRCEMDINEC HSDPCQNDAT CLDKIGGFTC   480
LCMPGFKGVH CELEINECQS NPCVNNGQCV DKVNRFQCLC PPGFTGPVCQ IDIDDCSSTP   540
CLNGAKCIDH PNGYECQCAT GFTGVLCEEN IDNCDPDPCH HGQCQDGIDS YTCICNPGYM   600
GAICSDQIDE CYSSPCLNDG RCIDLVNGYQ CNCQPGTSGV NCEINFDDCA SNPCIHGICM   660
DGINRYSCVC SPGFTGQRCN IDIDECASNP CRKGATCING VNGFRCICPE GPHHPSCYSQ   720
VNECLSNPCI HGNCTGGLSG YKCLCDAGWV GINCEVDKNE CLSNPCQNGG TCDNLVNGYR   780
CTCKKGFKGY NCQVNIDECA SNPCLNQGTC FDDISGYTCH CVLPYTGKNC QTVLAPCSPN   840
PCENAAVCKE SPNFESYTCL CAPGWQGQRC TIDIDECISK PCMNHGLCHN TQGSYMCECP   900
PGFSGMDCEE DIDDCLANPC QNGGSCMDGV NTFSCLCLPG FTGDKCQTDM NECLSEPCKN   960
GGTCSDYVNS YTCKCQAGFD GVHCENNINE CTESSCFNGG TCVDGINSFS CLCPVGFTGS  1020
FCLHEINECS SHPCLNEGTC VDGLGTYRCS CPLGYTGKNC QTLVNLCSRS PCKNKGTCVQ  1080
KKAESQCLCP SGWAGAYCDV PNVSCDIAAS RRGVLVEHLC QHSGVCINAG NTHYCQCPLG  1140
YTGSYCEEQL DECASNPCQH GATCSDFIGG YRCECVPGYQ GVNCEYEVDE CQNQPCQNGG  1200
TCIDLVNHFK CSCPPGTRGL LCEENIDDCA RGPHCLNGGQ CMDRIGGYSC RCLPGFAGER  1260
CEGDINECLS NPCSSEGSLD CIQLTNDYLC VCRSAFTGRH CETFVDVCPQ MPCLNGGTCA  1320
VASNMPDGFI CRCPPGFSGA RCQSSCGQVK CRKGEQCVHT ASGPRCFCPS PRDCESGCAS  1380
SPCQHGGSCH PQRQPPYYSC QCAPPFSGSR CELYTAPPST PPATCLSQYC ADKARDGVCD  1440
EACNSHACQW DGGDCSLTME NPWANCSSPL PCWDYINNQC DELCNTVECL FDNFECQGNS  1500
KTCKYDKYCA DHFKDNHCDQ GCNSEECGWD GLDCAADQPE NLAEGTLVIV VLMPPEQLLQ  1560
DARSFLRALG TLLHTNLRIK RDSQGELMVY PYYGEKSAAM KKQRMTRRSL PGEQEQEVAG  1620
SKVFLEIDNR QCVQDSDHCF KNTDAAAALL ASHAIQGTLS YPLVSVVSES LTPERTQLLY  1680
LLAVAVVIIL FIILLGVIMA KRKRKHGSLW LPEGFTLRRD ASNHKRREPV GQDAVGLKNL  1740
SVQVSEANLI GTGTSEHWVD DEGPQPKKVK AEDEALLSEE DDPIDRRPWT QQHLEAADIR  1800
RTPSLALTPP QAEQEVDVLD VNVRGPDGCT PLMLASLRGG SSDLSDEDED AEDSSANIIT  1860
DLVYQGASLQ AQTDRTGEMA LHLAARYSRA DAAKRLLDAG ADANAQDNMG RCPLHAAVAA  1920
DAQGVFQILI RNRVTDLDAR MNDGTTPLIL AARLAVEGMV AELINCQADV NAVDDHGKSA  1980
LHWAAAVNNV EATLLLLKNG ANRDMQDNKE ETPLFLAARE GSYEAAKILL DHFANRDITD  2040
HMDRLPRDVA RDRMHHDIVR LLDEYNVTPS PPGTVLTSAL SPVICGPNRS FLSLKHTPMG  2100
KKSRRPSAKS TMPTSLPNLA KEAKDAKGSR RKKSLSEKVQ LSESSVTLSP VDSLESPHTY  2160
VSDTTSSPMI TSPGILQASP NPMLATAAPP APVHAQHALS FSNLHEMQPL AHGASTVLPS  2220
VSQLLSHHHI VSPGSGSAGS LSRLHPVPVP ADWMNRMEVN ETQYNEMFGM VLAPAEGTHP  2280
GIAPQSRPPE GKHITTPREP LPPIVTFQLI PKGSIAQPAG APQPQSTCPP AVAGPLPTMY  2340
QIPEMARLPS VAFPTAMMPQ QDGQVAQTIL PAYHPFPASV GKYPTPPSQH SYASSNAAER  2400
TPSHSGHLQG EHPYLTPSPE SPDQWSSSSP HSASDWSDVT TSPTPGGAGG GQRGPGTHMS  2460
EPPHNNMQVY A                                                      2471

SEQ ID NO: 186       moltype = AA  length = 1235
FEATURE              Location/Qualifiers
source               1..1235
                     mol_type = protein
                     organism = Homo sapiens
SEQUENCE: 186
MPALRPALLW ALLALWLCCA APAHALQCRD GYEPCVNEGM CVTYHNGTGY CKCPEGFLGE    60
YCQHRDPCEK NRCQNGGTCV AQAMLGKATC RCASGFTGED CQYSTSHPCF VSRPCLNGGT   120
CHMLSRDTYE CTCQVGFTGK ECQWTDACLS HPCANGSTCT TVANQFSCKC LTGFTGQKCE   180
TDVNECDIPG HCQHGGTCLN LPGSYQCQCP QGFTGQYCDS LYVPCAPSPC VNGGTCRQTG   240
DFTFECNCLP GFEGSTCERN IDDCPNHRCQ NGGVCVDGVN TYNCRCPPQW TGQFCTEDVD   300
ECLLQPNACQ NGGTCANRNG GYGCVCVNGW SGDDCSENID DCAFASCTPG STCIDRVASF   360
SCMCPEGKAG LLCHLDDACI SNPCHKGALC DTNPLNGQYI CTCPQGYKGA DCTEDVDECA   420
MANSNPCEHA GKCVNTDGAF HCECLKGYAG PRCEMDINEC HSDPCQNDAT CLDKIGGFTC   480
LCMPGFKGVH CELEINECQS NPCVNNGQCV DKVNRFQCLC PPGFTGPVCQ IDIDDCSSTP   540
CLNGAKCIDH PNGYECQCAT GFTGVLCEEN IDNCDPDPCH HGQCQDGIDS YTCICNPGYM   600
GAICSDQIDE CYSSPCLNDG RCIDLVNGYQ CNCQPGTSGV NCEINFDDCA SNPCIHGICM   660
DGINRYSCVC SPGFTGQRCN IDIDECASNP CRKGATCING VNGFRCICPE GPHHPSCYSQ   720
VNECLSNPCI HGNCTGGLSG YKCLCDAGWV GINCEVDKNE CLSNPCQNGG TCDNLVNGYR   780
CTCKKGFKGY NCQVNIDECA SNPCLNQGTC FDDISGYTCH CVLPYTGKNC QTVLAPCSPN   840
PCENAAVCKE SPNFESYTCL CAPGWQGQRC TIDIDECISK PCMNHGLCHN TQGSYMCECP   900
PGFSGMDCEE DIDDCLANPC QNGGSCMDGV NTFSCLCLPG FTGDKCQTDM NECLSEPCKN   960
GGTCSDYVNS YTCKCQAGFD GVHCENNINE CTESSCFNGG TCVDGINSFS CLCPVGFTGS  1020
FCLHEINECS SHPCLNEGTC VDGLGTYRCS CPLGYTGKNC QTLVNLCSRS PCKNKGTCVQ  1080
KKAESQCLCP SGWAGAYCDV PNVSCDIAAS RRGVLVEHLC QHSGVCINAG NTHYCQCPLG  1140
YTGSYCEEQL DECASNPCQH GATCSDFIGG YRCECVPGYQ GVNCEYEVDE CQNQPCQNGG  1200
TCIDLVNHFK CSCPPGTRGM KSSLSIFHPG HCLKL                             1235

SEQ ID NO: 187       moltype = AA  length = 2321
FEATURE              Location/Qualifiers
source               1..2321
                     mol_type = protein
                     organism = Homo sapiens
```

```
SEQUENCE: 187
MGPGARGRRR RRRPMSPPPP PPPVRALPLL LLLLAGPGAAA PPCLDGSPCA NGGRCTQLPS   60
REAACLCPPG WVGERCQLED PCHSGPCAGR GVCQSSVVAG TARFSCRCPR GFRGPDCSLP  120
DPCLSSPCAH GARCSVGPDG RFLCSCPPGY QGRSCRSDVD ECRVGEPCRH GGTCLNTPGS  180
FRCQCPAGYT GPLCENPAVP CAPSPCRNGG TCRQSGDLTY DCACLPGFEG QNCEVNVDDC  240
PGHRCLNGGT CVDGVNTYNC QCPPEWTGQF CTEDVDECQL QPNACHNGGT CFNTLGGHSC  300
VCVNGWTGES CSQNIDDCAT AVCFHGATCH DRVASFYCAC PMGKTGLLCH LDDACVSNPC  360
HEDAICDTNP VNGRAICTCP PGFTGGACDQ DVDECSIGAN PCEHLGRCVN TQGSFLCQCG  420
RGYTGPRCET DVNECLSGPC RNQATCLDRI GQFTCICMAG FTGTYCEVDI DECQSSPCVN  480
GGVCKDRVNG FSCTCPSGFS GSTCQLDVDE CASTPCRNGA KCVDQPDGYE CRCAEGFEGT  540
LCDRNVDDCS PDPCHHGRCV DGIASFSCAC APGYTGTRCE SQVDECRSQP CRHGGKCLDL  600
VDKYLCRCPS GTTGVNCEVN IDDCASNPCT FGVCRDGINR YDCVCQPGFT GPLCNVEINE  660
CASSPCGEGG SCVDGENGFR CLCPPGSLPP LCLPPSHPCA HEPCSHGICY DAPGGFRCVC  720
EPGWSGPRCS QSLARDACES QPCRAGGTCS SDGMGFHCTC PPGVQGRQCE LLSPCTPNPC  780
EHGGRCESAP GQLPVCSCPQ GWQGPRCQQD VDECAGPAPC GPHGICTNLA GSFSCTCHGG  840
YTGPSCDQDI NDCDPNPCLN GGSCQDGVGS FSCSCLPGFA GPRCARDVDE CLSNPCGPGT  900
CTDHVASFTC TCPPGYGGFH CEQDLPDCSP SSCFNGGTCV DGVNSFSCLC RPGYTGAHCQ  960
HEADPCLSRP CLHGGVCSAA HPGFRCTCLE SFTGPQCQTL VDWCSRQPCQ NGGRCVQTGA 1020
YCLCPPGWSG RLCDIRSLPC REAAAQIGVR LEQLCQAGGQ CVDEDSSHYC VCPEGRTGSH 1080
CEQEVDPCLA QPCQHGGTCR GYMGGYMCEC LPGYNGDNCE DDVDECASQP CQHGGSCIDL 1140
VARYLCSCPP GTLGVLCEIN EDDCGPGPPL DSGPRCLHNG TCVDLVGGFR CTCPPGYTGL 1200
RCEADINECR SGACHAAHTR DCLQDPGGGF RCLCHAGFSG PRCQTVLSPC ESQPCQHGGQ 1260
CRPSPGPGGG LTFTCHCAQP FWGPRCERVA RSCRELQCPV GVPCQQTPRG PRCACPPGLS 1320
GPSCRSFPGS PPGASNASCA AAPCLHGGSC RPAPLAPFFR CACAQGWTGP RCEAPAAAPE 1380
VSEEPRCPRA ACQAKRGDQR CDRECNSPGC GWDGGDCSLS VGDPWRQCEA LQCWRLFNNS 1440
RCDPACSSPA CLYDNFDCHA GGRERTCNPV YEKYCADHFA DGRCDQGCNT EECGWDGLDC 1500
ASEVPALLAR GVLVLTVLLP PEELLRSSAD FLQRLSAILR TSLRFRLDAH GQAMVFPYHR 1560
PSPGSEPRAR RELAPEVIGS VVMLEIDNRL CLQSPENDHC FPDAQSAADY LGALSAVERL 1620
DFPYPLRDVR GEPLEPPEPS VPLLPLLVAG AVLLLVILVL GVMVARRKRE HSTLWFPEGF 1680
SLHKDVASGH KGRREPVGQD ALGMKNMAKG ESLMGEVATD WMDTECPEAK RLKVEEPGMG 1740
AEEAVDCRQW TQHHLVAADI RVAPAMALTP PQGDADADGM DVNVRGPDGF TPLMLASFCG 1800
GALEPMPTEE DEADDTSASI ISDLICQGAQ LGARTDRTGE TALHLAARYA RADAAKRLLD 1860
AGADTNAQDH SGRTPLHTAV TADAQGVFQI LIRNRSTDLD ARMADGSTAL ILAARLAVEG 1920
MVEELIASHA DVNAVDELGK SALHWAAAVN NVEATLALLK NGANKDMQDS KEETPLFLAA 1980
REGSYEAAKL LLDHFANREI TDHLDRLPRD VAQERLHQDI VRLLDQPSGP RSPPGPHGLG 2040
PLLCPPGAFL PGLKAAQSGS KKSRRPPGKA GLGPQGPRGR GKKLTLACPG PLADSSVTLS 2100
PVDSLDSPRP FGGPPASPGG FPLEGPYAAA TATAVSLAQL GGPGRAGLGR QPPGGCVLSL 2160
GLLNPVAVPL DWARLPPPAP PGPSFLLPLA PGPQLLNPGT PVSPQERPPP YLAVPGHGEE 2220
YPAAGAHSSP PKARFLRVPS EHPYLTPSPE SPEHWASPSP PSLSDWSEST PSPATATGAM 2280
ATTTGALPAQ PLPLSVPSSL AQAQTQLGPQ PEVTPKRQVL A              2321

SEQ ID NO: 188        moltype = AA  length = 2003
FEATURE               Location/Qualifiers
source                1..2003
                      mol_type = protein
                      organism = Homo sapiens
SEQUENCE: 188
MQPPSLLLLL LLLLLLCVSV VRPRGLLCGS FPEPCANGGT CLSLSLGQGT CQCAPGFLGE   60
TCQFPDPCQN AQLCQNGGSC QALLPAPLGL PSSPSPLTPS FLCTCLPGFT GERCQAKLED  120
PCPPSFCSKR GRCHIQASGR PQCSCMPGWT GEQCQLRDFC SANPCVNGGV CLATYPQIQC  180
HCPPGFEGHA CERDVNECFQ DPGPCPKGTS CHNTLGSFQC LCPVGQEGPR CELRAGPCPP  240
RGCSNGGTCQ LMPEKDSTFH LCLCPPGFIG PDCEVNPDNC VSHQCQNGGT CQDGLDTYTC  300
LCPETWTGWD CSEDVDECET QGPPHCRNGG TCQNSAGSFH CVCVSGWGGT SCEENLDDCI  360
AATCAPGSTC IDRVGSFSCL CPPGRTGLLC HLEDMCLSQP CHGDAQCSTN PLTGSTLCLC  420
QPGYSGPTCH QDLDECLMAQ QGPSPCEHGG SCLNTPGSFN CLCPPGYTGS RCEADHNECL  480
SQPCHPGSTC LDLLATFHCL CPPGLEGQLC EVETNECASA PCLNHADCHD LLNGFQCICL  540
PGFSGTRCEE DIDECRSSPC ANGGQCQDQP GAFHCKCLPG FEGPRCQTEV DECLSDPCPV  600
GASCLDLPGA FFCLCPSGFT GQLCEVPLCA PNLCQPKQIC KDQKDKANCL CPDGSPGCAP  660
PEDNCTCHHG HCQRSSCVCD VGWTGPECEA ELGGCISAPC AHGGTCYPQP SGYNCTCPTG  720
YTGPTCSEEM TACHSGPCLN GGSCNPSPGG YYCTCPPSHT GPQCQTSTDY CVSAPCFNGG  780
TCVNRPGTFS CLCAMGFQGP RCEGKLRPSC ADSPCRNRAT CQDSPQGPRC LCPTGYTGGS  840
CQTLMDLCAQ KPCPRNSHCL QTGPSFHCLC LQGWTGPLCN LPLSSCQKAA LSQGIDVSSL  900
CHNGGLCVDS GPSYFCHPP GFQGSLCQDH VNPCESRPCQ NGATCMAQPS GYLCQCAPGY  960
DGQNCSKELD ACQSQPCHNH GTCTPKPGGF HCACPPGFVG LRCEGDVDEC LDQPCHPTGT 1020
AACHSLANAF YCQCLPGHTG QWCEVEIDPC HSQPCFHGGT CEATAGSPLG FICHCPKGFE 1080
GPTCSHRAPS CGFHHCHHGG LCLPSPKPGF PPRCACLSGY GGPDCLTPPA PKGCGPPSPC 1140
LYNGSCSETT GLGGPGFRCS CPHSSPGPRC QKPGAKGCEG RSGDGACDAG CSGPGGNWDG 1200
GDCSLGVPDP WKGCPSHSRC WLLFRDGQCH PQCDSEECFT QPAYDQYCH 1260
DHFHNGHCEK GCNTAECGWD GGDCRPEDGD PEWGPSLALL VVLSPPALDQ QLFALARVLS 1320
LTLRVGLWVR KDRDGRDMVY PYPGARAEEK LGGTRDPTYQ ERAAPQTQPL GKETDSLSAG 1380
FVVVMGVDLS RCGPDHPASR CPWDPGLLLR FLAAMAAVGA LEPLLPGPLL AVHPHAGTAP 1440
PANQLPWPVL CSPVAGVILL ALGALLVLQL IRRRRREHGA LWLPPGFTRR PRTQSAPHRR 1500
RPPLGEDSIG LKALKPKAEV DEDGVVMCSG PEEGEEVGQA EETGPPSTCQ LWSLSGGCGA 1560
LPQAAMLTPP QESEMEAPDL DTRGPDGVTP LMSAVCCGEV QSGTFQGAWL GCPEPWEPLL 1620
DGGACPQAHT VGTGETPLHL AARFSRPTAA RRLLEAGANP NQPDRAGRTP LHAAVAADAR 1680
EVCQLLLRSR QTAVDARTED GTTPLMLAAR LAVEDLVEEL IAAQADVGAR DKWGKTALHW 1740
AAAVNNARAA RSLLQAGADK DAQDNREQTP LFLAAREGAV EVAQLLLGLG AARELRDQAG 1800
LAPADVAHQR NHWDLLTLLE GAGPPEARHK ATPGREAGPF PRARTVSVSV PPHGGGALPR 1860
CRTLSAGAGP RGGGACLQAR TWSVDLAARG GGAYSHCRSL SGVGAGGGPT PRGRRFSAGM 1920
```

```
RGPRPNPAIM RGRYGVAAGR GGRVSTDDWP CDWVALGACG SASNIPIPPP CLTPSPERGS    1980
PQLDCGPPAL QEMPINQGGE GKK                                            2003

SEQ ID NO: 189          moltype = AA  length = 462
FEATURE                 Location/Qualifiers
source                  1..462
                        mol_type = protein
                        organism = Homo sapiens
SEQUENCE: 189
MLLLLARCLLL VLVSSLLVCS GLACGPGRGF GKRRHPKKLT PLAYKQFIPN VAEKTLGASG    60
RYEGKISRNS ERFKELTPNY NPDIIFKDEE NTGADRLMTQ RCKDKLNALA ISVMNQWPGV    120
KLRVTEGWDE DGHHSEESLH YEGRAVDITT SDRDRSKYGM LARLAVEAGF DWVYYESKAH    180
IHCSVKAENS VAAKSGGCFP GSATVHLEQG GTKLVKDLSP GDRVLAADDQ GRLLYSDFLT    240
FLDRDDGAKK VFYVIETREP RERLLLTAAH LLFVAPHNDS ATGEPEASSG SGPPSGGALG    300
PRALFASRVR PGQRVYVVAE RDGDRRLLPA AVHSVTLSEE AAGAYAPLTA QGTILINRVL    360
ASCYAVIEEH SWAHRAFAPF RLAHALLAAL APARTDRGGD SGGGDRGGGG GRVALTAPGA    420
ADAPGAGATA GIHWYSQLLY QIGTWLLDSE ALHPLGMAVK SS                       462

SEQ ID NO: 190          moltype = AA  length = 606
FEATURE                 Location/Qualifiers
source                  1..606
                        mol_type = protein
                        organism = Homo sapiens
SEQUENCE: 190
MEPPRGPPAN GAEPSRAVGT VKVYLPNKQR TVVTVRDGMS VYDSLDKALK VRGLNQDCCV    60
VYRLIKGRKT VTAWDTAIAP LDGEELIVEV LEDVPLTMHN FVRKTFFSLA FCDFCLKFLF    120
HGFRCQTCGY KFHQHCSSKV PTVCVDMSTN RQQFYHSVQD LSGGSRQHEA PSNRPLNELL    180
TPQGPSPRTQ HCDPEHFPFP APANAPLQRI RSTSTPNVHM VSTTAPMDSN LIQLTGQSFS    240
TDAAGSRGGS DGTPRGSPSP ASVSSGRKSP HSKSPAEQRE RKSLADDKKK VKNLGYRDSG    300
YYWEVPPSEV QLLKRIGTGS FGTVFRGRWH GDVAVKVLKV SQPTAEQAQA FKNEMQVLRK    360
TRHVNILLFM GFMTRPGFAI ITQWCEGSSL YHHLHVADTR FDMVQLIDVA RQTAQGMDYL    420
HAKNIIHRDL KSNNIFLHEG LTVKIGDFGL ATVKTRWSGA QPLEQPSGSV LWMAAEVIRM    480
QDPNPYSFQS DVYAYGVVLY ELMTGSLPYS HIGCRDQIIF MVGRGYLSPD LSKISSNCPK    540
AMRRLLSDCL KFQREERPLF PQILATIELL QRSLPKIERS ASEPSLHRTQ ADELPACLLS    600
AARLVP                                                               606

SEQ ID NO: 191          moltype = AA  length = 609
FEATURE                 Location/Qualifiers
source                  1..609
                        mol_type = protein
                        organism = Homo sapiens
SEQUENCE: 191
MEPPRGPPAN GAEPSRAVGT VKVYLPNKQR TVVTVRDGMS VYDSLDKALK VRGLNQDCCV    60
VYRLIKGRKT VTAWDTAIAP LDGEELIVEV LEDVPLTMHN FVRKTFFSLA FCDFCLKFLF    120
HGFRCQTCGY KFHQHCSSKV PTVCVDMSTN RQQPSRFYHS VQDLSGGSRQ HEAPSNRPLN    180
ELLTPQGPSP RTQHCDPEHF PFPAPANAPL QRIRSTSTPN VHMVSTTAPM DSNLIQLTGQ    240
SFSTDAAGSR GGSDGTPRGS PSPASVSSRG KSPHSKSPAE QRERKSLADD KKKVKNLGYR    300
DSGYYWEVPP SEVQLLKRIG TGSFGTVFRG RWHGDVAVKV LKVSQPTAEQ AQAFKNEMQV    360
LRKTRHVNIL LFMGFMTRPG FAIITQWCEG SSLYHHLHVA DTRFDMVQLI DVARQTAQGM    420
DYLHAKNIIH RDLKSNNIFL HEGLTVKIGD FGLATVKTRW SGAQPLEQPS GSVLWMAAEV    480
IRMQDPNPYS FQSDVYAYGV VLYELMTGSL PYSHIGCRDQ IIFMVGRGYL SPDLSKISSN    540
CPKAMRRLLS DCLKFQREER PLFPQILATI ELLQRSLPKI ERSASEPSLH RTQADELPAC    600
LLSAARLVP                                                            609

SEQ ID NO: 192          moltype = AA  length = 186
FEATURE                 Location/Qualifiers
source                  1..186
                        mol_type = protein
                        organism = Homo sapiens
SEQUENCE: 192
MEPPRGPPAN GAEPSRAVGT VKVYLPNKQR TVVTVRDGMS VYDSLDKALK VRGLNQDCCV    60
VYRLIKGRKT VTAWDTAIAP LDGEELIVEV LEDVPLTMHN FVRKTFFSLA FCDFCLKFLF    120
HGFRCQTCGY KFHQHCSSKV PTVCVDMSTN RQQFYHSVQD LSGGSRQHEA PSNRPLNELL    180
TPQGPR                                                               186

SEQ ID NO: 193          moltype = AA  length = 766
FEATURE                 Location/Qualifiers
source                  1..766
                        mol_type = protein
                        organism = Homo sapiens
SEQUENCE: 193
MAALSGGGGG GAEPGQALFN GDMEPEAGAG AGAAASSAAD PAIPEEVWNI KQMIKLTQEH    60
IEALLDKFGG EHNPPSIYLE AYEEYTSKLD ALQQREQQLL ESLGNGTDFS VSSSASMDTV    120
TSSSSSSLSV LPSSLSVFQN PTDVARSNPK SPQKPIVRVF LPNKQRTVVP ARCGVTVRDS    180
LKKALMMRGL IPECCAVYRI QDGEKKPIGW DTDISWLTGE ELHVEVLENV PLTTHNFVRK    240
TFFTLAFCDF CRKLLFQGFR CQTCGYKFHQ RCSTEVPLMC VNYDQLDLLF VSKFFEHHPI    300
PQEEASLAET ALTSGSSPSA PASDSIGPQI LTSPSPSKSI PIPQPFRPAD EDHRNQFGQR    360
DRSSSAPNVH INTIEPVNID DLIRDQGFRG DGGSTTGLSA TPPASLPGSL TNVKALQKSP    420
GPQRERKSSS SSEDRNRMKT LGRRDSSDDW EIPDGQITVG QRIGSGSFGT VYKGKWHGDV    480
```

-continued

```
AVKMLNVTAP TPQQLQAFKN EVGVLRKTRH VNILLFMGYS TKPQLAIVTQ WCEGSSLYHH    540
LHIIETKFEM IKLIDIARQT AQGMDYLHAK SIIHRDLKSN NIFLHEDLTV KIGDFGLATV    600
KSRWSGSHQF EQLSGSILWM APEVIRMQDK NPYSFQSDVY AFGIVLYELM TGQLPYSNIN    660
NRDQIIFMVG RGYLSPDLSK VRSNCPKAMK RLMAECLKKK RDERPLFPQI LASIELLARS    720
LPKIHRSASE PSLNRAGFQT EDFSLYACAS PKTPIQAGGY GAFPVH                   766

SEQ ID NO: 194            moltype = AA  length = 648
FEATURE                   Location/Qualifiers
source                    1..648
                          mol_type = protein
                          organism = Homo sapiens
SEQUENCE: 194
MEHIQGAWKT ISNGFGFKDA VFDGSSCISP TIVQQFGYQR RASDDGKLTD PSKTSNTIRV     60
FLPNKQRTVV NVRNGMSLHD CLMKALKVRG LQPECCAVFR LLHEHKGKKA RLDWNTDAAS    120
LIGEELQVDF LDHVPLTTHN FARKTFLKLA FCDICQKFLL NGFRCQTCGY KFHEHCSTKV    180
PTMCVDWSNI RQLLLFPNST IGDSGVPALP SLTMRRMRES VSRMPVSSQH RYSTPHAFTF    240
NTSSPSSEGS LSQRQRSTST PNVHMVSTTL PVDSRMIEDA IRSHSESASP SALSSSPNNL    300
SPTGWSQPKT PVPAQRERAP VSGTQEKNKI RPRGQRDSSY YWEIEASEVM LSTRIGSGSF    360
GTVYKGKWHG DVAVKILKVV DPTPEQFQAF RNEVAVLRKT RHVNILLFMG YMTKDNLAIV    420
TQWCEGSSLY KHLHVQETKF QMFQLIDIAR QTAQGMDYLH AKNIIHRDMK SNNIFLHEGL    480
TVKIGDFGLA TVKSRWSGSQ QVEQPTGSVL WMAPEVIRMQ DNNPFSFQSD VYSYGIVLYE    540
LMTGELPYSH INNRDQIIFM VGRGYASPDL SKLYKNCPKA MKRLVADCVK KVKEERPLFP    600
QILSSIELLQ HSLPKINRSA SEPSLHRAAH TEDINACTLT TSPRLPVF                 648

SEQ ID NO: 195            moltype = DNA  length = 40
FEATURE                   Location/Qualifiers
misc_feature              1..40
                          note = Single strand DNA oligonucleotide
source                    1..40
                          mol_type = other DNA
                          organism = synthetic construct
SEQUENCE: 195
atgctgtccc cggacgatat tgaacaatgg ttcactgaag                          40

SEQ ID NO: 196            moltype = DNA  length = 34
FEATURE                   Location/Qualifiers
misc_feature              1..34
                          note = Single strand DNA oligonucleotide
source                    1..34
                          mol_type = other DNA
                          organism = synthetic construct
SEQUENCE: 196
atgctgtccc cgtgagccac cgtgcccact gaag                               34

SEQ ID NO: 197            moltype = AA  length = 1233
FEATURE                   Location/Qualifiers
source                    1..1233
                          mol_type = protein
                          organism = Homo sapiens
SEQUENCE: 197
MRGLPRGRGL MRARGRGRAA PPGSRGRGRG GPHRGRGRPR SLLSLPRAQA SWTPQLSTGL     60
TSPPVPCLPS QGEAPAEMGA LLLLEKETRGA TERVHGSLGD TPRSEETLPK ATPDSLEPAG    120
PSSSPASVTVT VGDEGADTPV GATPLIGDES ENLEGDGDLR GGRILLGHAT KSFPSSPSKG    180
GSCPSRAKMS MTGAGKSPPS VQSLAMRLLS MPGAQGAAAA GSEPPPATTS PEGQPKVHRA    240
RKTMSKPGNG QPPVPEKRPP EIQHFRMSDD VHSLGKVTSD LAKRRKLNSG GGLSEELGSA    300
RRSGEVTLTK GDPGSLEEWE TVVGDDFSLY YDSYSVDERV DSDSKSEVEA LTEQLSEEEE    360
EEEEEEEEEE EEEEEEEEEE DEESGNQSDR SGSSGRRKAK KKWRKDSPWV KPSRKRRKRE    420
PPRAKEPRGV SNDTSSLETE RGFEELPLCS CRMEAPKIDR ISERAGHKCM ATESVDGELS    480
GCNAAILKRE TMRPSSRVAL MVLCETHRAR MVKHHCCPGC GYFCTAGTFL ECHPDFRVAH    540
RFHKACVSQL NGMVFCPHCG EDASEAQEVT IPRGDGVTPP AGTAAPAPPP LSQDVPGRAD    600
TSQPSARMRG HGEPRRPPCD PLADTIDSSG PSLTLPNGGC LSAVGLPLGP GREALEKALV    660
IQESERRKKL RFHPRQLYLS VKQGELQKVI LMLLDNLDPN FQSDQQSKRT PLHAAAQKGS    720
VEICHVLLQA GANINAVDKQ QRTPLMEAVV NNHLEVARYM VQRGGCVYSK EEDGSTCLHH    780
AAKIGNLEMV SLLLSTGQVD VNAQDSGGWT PIIWAAEHKH IEVIRMLLTR GADVTLTDNE    840
ENICLHWASF TGSAAIAEVL LNARCDLHAV NYHGDTPLHI AARESYHDCV LLFLSRGANP    900
ELRNKEGDTA WDLTPERSDV WFALQLNRKL RLGVGNRAIR TEKIICRDVA RGYENVPIPC    960
VNGVDGEPCP EDYKYISENC ETSTMNIDRN ITHLQHCTCV DDCSSSNCLC GQLSIRCWYD   1020
KDGRLLQEFN KIEPPLIFEC NQACSCWRNC KNRVVQSGIK VRLQLYRTAK MGWGVRALQT   1080
IPQGTFICEY VGELISDAEA DVREDDSYLF DLDNKDGEVY CIDARYYGNI SRFINHLCDP   1140
NIIPVRVFML HQDLRFPRIA FFSSRDIRTG EELGFDYGDR FWDIKSKYFT CQCGSEKCKH   1200
SAEAIALEQS RLARLDPHPE LLPELGSLPP VNT                                1233

SEQ ID NO: 198            moltype = AA  length = 1176
FEATURE                   Location/Qualifiers
source                    1..1176
                          mol_type = protein
                          organism = Homo sapiens
SEQUENCE: 198
MAAAAGAAAA AAAEGEAPAE MGALLLEKET RGATERVHGS LGDTPRSEET LPKATPDSLE     60
```

```
PAGPSSPASV TVTVGDEGAD TPVGATPLIG DESENLEGDG DLRGGRILLG HATKSFPSSP      120
SKGGSCPSRA KMSMTGAGKS PPSVQSLAMR LLSMPGAQGA AAAGSEPPPA TTSPEGQPKV      180
HRARKTMSKP GNGQPPVPEK RPPEIQHFRM SDDVHSLGKV TSDLAKRRKL NSGGGLSEEL      240
GSARRSGEVT LTKGDPGSLE EWETVVGDDF SLYYDSYSVD ERVDSDSKSE VEALTEQLSE      300
EEEEEEEEE EEEEEEEEE EEEDEESGNQ SDRSGSSGRR KAKKKWRKDS PWVKPSRKRR      360
KREPPRAKEP RGVSNDTSSL ETERGFEELP LCSCRMEAPK IDRISERAGH KCMATESVDG      420
ELSGCNAAIL KRETMRPSSR VALMVLCETH RARMVKHHCC PGCGYFCTAG TFLECHPDFR      480
VAHRFHKACV SQLNGMVFCP HCGEDASEAQ EVTIPRGDGV TPPAGTAAPA PPPLSQDVPG      540
RADTSQPSAR MRGHGEPRRP PCDPLADTID SSGPSLTLPN GGCLSAVGLP LGPGREALEK      600
ALVIQESERR KKLRFHPRQL YLSVKQGELQ KVILMLLDNL DPNFQSDQQS KRTPLHAAAQ      660
KGSVEICHVL LQAGANINAV DKQQRTPLME AVVNNHLEVA RYMVQRGGCV YSKEEDGSTC      720
LHHAAKIGNL EMVSLLLSTG QVDVNAQDSG GWTPIIWAAE HKHIEVIRML LTRGADVTLT      780
DNEENICLHW ASFTGSAAIA EVLLNARCDL HAVNYHGDTP LHIAARESYH DCVLLFLSRG      840
ANPELRNKEG DTAWDLTPER SDVWFALQLN RKLRLGVGNR AIRTEKIICR DVARGYENVP      900
IPCVNGVDGE PCPEDYKYIS ENCETSTMNI DRNITHLQHC TCVDDCSSSN CLCGQLSIRC      960
WYDKDGRLLQ EFNKIEPPLI FECNQACSCW RNCKNRVVQS GIKVRLQLYR TAKMGWGVRA     1020
LQTIPQGTFI CEYVGELISD AEADVREDDS YLFDLDNKDG EVYCIDARYY GNISRFINHL     1080
CDPNIIPVRV FMLHQDLRFP RIAFFSSRDI RTGEELGFDY GDRFWDIKSK YFTCQCGSEK     1140
CKHSAEAIAL EQSRLARLDP HPELLPELGS LPPVNT                               1176

SEQ ID NO: 199          moltype = AA  length = 1233
FEATURE                 Location/Qualifiers
source                  1..1233
                        mol_type = protein
                        organism = Homo sapiens
SEQUENCE: 199
MRGLPRGRGL MRARGRGRAA PPGSRGRGRG GPHRGRGRPR SLLSLPRAQA SWTPQLSTGL      60
TSPPVPCLPS QGEAPAEMGA LLLEKETRGA TERVHGSLGD TPRSEETLPK ATPDSLEPAG      120
PSSPASVTVT VGDEGADTPV GATPLIGDES ENLEGDGDLR GGRILLGHAT KSFPSSPSKG      180
GSCPSRAKMS MTGAGKSPPS VQSLAMRLLS MPGAQGAAAA GSEPPPATTS PEGQPKVHRA      240
RKTMSKPGNG QPPVPEKRPP EIQHFRMSDD VHSLGKVTSD LAKRRKLNSG GGLSEELGSA      300
RRSGEVTLTK GDPGSLEEWE TVVGDDFSLY YDSYSVDERV DSDSKSEVEA LTEQLSEEEE      360
EEEEEEEEE EEEEEEEEE DEESGNQSDR SGSSGRRKAK KKWRKDSPWV KPSRKRRKRE      420
PPRAKEPRGV SNDTSSLETE RGFEELPLCS CRMEAPKIDR ISERAGHKCM ATESVDGELS      480
GCNAAILKRE TMRPSSRVAL MVLCETHRAR MVKHHCCPGC GYFCTAGTFL ECHPDFRVAH      540
RFHKACVSQL NGMVFCPHCG EDASEAQEVT IPRGDGVTPP AGTAAPAPPP LSQDVPGRAD      600
TSQPSARMRG HGEPRRPPCD PLADTIDSSG PSLTLPNGGC LSAVGLPLGP GREALEKALV      660
IQESERRKKL RFHPRQLYLS VKQGELQKVI LMLLDNLDPN FQSDQQSKRT PLHAAAQKGS      720
VEICHVLLQA GANINAVDKQ QRTPLMEAVV NNHLEVARYM VQRGGCVYSK EEDGSTCLHH      780
AAKIGNLEMV SLLLSTGQVD VNAQDSGGWT PIIWAAEHKH IEVIRMLLTR GADVTLTDNE      840
ENICLHWASF TGSAAIAEVL LNARCDLHAV NYHGDTPLHI AARESYHDCV LLFLSRGANP      900
ELRNKEGDTA WDLTPERSDV WFALQLNRKL RLGVGNRAIR TEKIICRDVA RGYENVPIPC      960
VNGVDGEPCP EDYKYISENC ETSTMNIDRN ITHLQHCTCV DDCSSSNCLC GQLSIRCWYD     1020
KDGRLLQEFN KIEPPLIFEC NQACSCWRNC KNRVVQSGIK VRLQLYRTAK MGWGVRALQT     1080
IPQGTFICEY VGELISDAEA DVREDDSYLF DLDNKDGEVY CIDARYYGNI SRFINHLCDP     1140
NIIPVRVFML HQDLRFPRIA FFSSRDIRTG EELGFDYGDR FWDIKSKYFT CQCGSEKCKH     1200
SAEAIALEQS RLARLDPHPE LLPELGSLPP VNT                                 1233

SEQ ID NO: 200          moltype = AA  length = 1298
FEATURE                 Location/Qualifiers
source                  1..1298
                        mol_type = protein
                        organism = Homo sapiens
SEQUENCE: 200
MAAADAEAVP ARGEPQQDCC VKTELLGEET PMAADEGSAE KQAGEAHMAA DGETNGSCEN      60
SDASSHANAA KHTQDSARVN PQDGTNTLTR IAENGVSERD SEAAKQNHVT ADDFVQTSVI      120
GSNGYILNKP ALQAQPLRTT STLASSLPGH AAKTLPGGAG KGRTPSAFPQ TPAAPPATLG      180
EGSADTEDRK LPAPGADVKV HRARKTMPKS VVGLHAASKD PREVREARDH KEPKEEINKN      240
ISDFGRQQLL PPFPSLHQSL PQNQCYMATT KSQTACLPFV LAAAVSRKKK RRMGTYSLVP      300
KKKTKVLKQR TVIEMFKSIT HSTVGSKGEK DLGASSLHVN GESLEMDSDE DDSEELEEDD      360
GHGAEQAAAF PTEDSRTSKE SMSEADRAQK MDGESEEEQE SVDTGEEEEG GDESDLSSES      420
SIKKKFLKRK GKTDSPWIKP ARKRRRRSRK KPSGALGSES YKSSAGSAEQ TAPGDSTGYM      480
EVSLDSLDLR VKGILSSQAE GLANGPDVLE TDGLQEVPLC SCRMETPKSR EITTLANNQC      540
MATESVDHEL GRCTNSVVKY ELMRPSNKAP LLVLCEDHRG RMVKHQCCPG CGYFCTAGNF      600
MECQPESSIS HRFHKDCASR VNNASYCPHC GEESSKAKEV TIAKADTTST VTPVPGQEKG      660
SALEGRADTT TGSAAGPPLS EDDKLQGAAS HVPEGFDPTG PAGLGRPTPG LSQGPGKETL      720
ESALIALDSE KPKKLRFHPK QLYFSARQGE LQKVLLMLVD GIDPNFKMEH QNKRSPLHAA      780
AEAGHVDICH MLVQAGANID TCSEDQRTPL MEAAENNHLE AVKYLIKAGA LVDPKDAEGS      840
TCLHLAAKKG HYEVVQYLLS NGQMDVNCQD DGGWTPMIWA TEYKHVDLVK LLLSKGSDIN      900
IRDNEENICL HWAAFSGCVD IAEILLAAKC DLHAVNIHGD SPLHIAAREN RYDCVVLFLS      960
RDSDVTLKNK EGETPLQCAS LNSQVWSALQ MSKALQDSAP DRPSPVERIV SRDIARGYER     1020
IPIPCVNAVD SEPCPSNYKY VSQNCVTSPM NIDRNITHLQ YCVCIDDCSS SNCMCGQLSM     1080
RCWYDKDGRL LPEFNMAEPP LIFECNHACS CWRNCRNRVV QNGLRARLQL YRTRDMGWGV     1140
RSLQDIPPGT FVCEYVGELI SDSEADVREE DSYLFDLDNK DGEVYCIDAR FYGNVSRFIN     1200
HHCEPNLVPV RVFMAHQDLR FPRIAFFSTR LIEAGEQLGF DYGERFWDIK GKLFSCRCGS     1260
PKCRHSSAAL AQRQASAAQE AQEDGLPDTS SAAAADPL                             1298

SEQ ID NO: 201          moltype = AA  length = 808
FEATURE                 Location/Qualifiers
```

-continued

```
source                  1..808
                        mol_type = protein
                        organism = Homo sapiens
SEQUENCE: 201
MAAADAEAVP ARGEPQQDCC VKTELLGEET PMAADEGSAE KQAGEAHMAA DGETNGSCEN    60
SDASSHANAA KHTQDSARVN PQDGTNTLTR IAENGVSERD SEAAKQNHVT ADDFVQTSVI   120
GSNGYILNKP ALQAQPLRTT STLASSLPGH AAKTLPGGAG KGRTPSAFPQ TPAAPPATLG   180
EGSADTEDRK LPAPGADVKV HRARKTMPKS VVGLHAASKD PREVREARDH KEPKEEINKN   240
ISDFGRQQLL PPFPSLHQSL PQNQCYMATT KSQTACLPFV LAAAVSRKKK RRMGTYSLVP   300
KKKTKVLKQR TVIEMFKSIT HSTVGSKGEK DLGASSLHVN GESLEMDSDE DDSEELEEDD   360
GHGAEQAAAF PTEDSRTSKE SMSEADRAQK MDGESEEEQE SVDTGEEEEG GDESDLSSES   420
SIKKKFLKRK GKTDSPWIKP ARKRRRRSRK KPSGALGSES YKSSAGSAEQ TAPGDSTGYM   480
EVSLDSLDLR VKGILSSQAE GLANGPDVLE TDGLQEVPLC SCRMETPKSR EITTLANNQC   540
MATESVDHEL GRCTNSVVKY ELMRPSNKAP LLVLCEDHRG RMVKHQCCPG CGYFCTAGNF   600
MECQPESSIS HRFHKDCASR VNNASYCPHC GEESSKAKEV TIAKADTTST VTPVPGQEKG   660
SALEGRADTT TGSAAGPPLS EDDKLQGAAS HVPEGFDPTG PAGLGRPTPG LSQGPGKETL   720
ESALIALDSE KPKKLRFHPK QLYFSARQGE LQKVLLMLVD GIDPNFKMEH QNKRSPLHAA   780
AEAGHVDICH MLVQFCRLGS PRSRGCLW                                     808

SEQ ID NO: 202         moltype = AA  length = 976
FEATURE                Location/Qualifiers
source                 1..976
                       mol_type = protein
                       organism = Homo sapiens
SEQUENCE: 202
MRGARGAWDF LCVLLLLLRV QTGSSQPSVS PGEPSPPSIH PGKSDLIVRV GDEIRLLCTD    60
PGFVKWTFEI LDETNENKQN EWITEKAEAT NTGKYTCTNK HGLSNSIYVF VRDPAKLFLV   120
DRSLYGKEDN DTLVRCPLTD PEVTNYSLKG CQGKPLPKDL RFIPDPKAGI MIKSVKRAYH   180
RLCLHCSVDQ EGKSVLSEKF ILKVRPAFKA VPVVSVSKAS YLLREGEEFT VTCTIKDVSS   240
SVYSTWKREN SQTKLQEKYN SWHHGDFNYE RQATLTISSA RVNDSGVFMC YANNTFGSAN   300
VTTTLEVVDK GFINIFPMIN TTVFVNDGEN VDLIVEYEAF PKPEHQQWIY MNRTFTDKWE   360
DYPKSENESN IRYVSELHLT RLKGTEGGTY TFLVSNSDVN AAIAFNVYVN TKPEILTYDR   420
LVNGMLQCVA AGFPEPTIDW YFCPGTEQRC SASVLPVDVQ TLNSSGPPFG KLVVQSSIDS   480
SAFKHNGTVE CKAYNDVGKT SAYFNFAFKG NNKEQIHPHT LFTPLLIGFV IVAGMMCIIV   540
MILTYKYLQK PMYEVQWKVV EEINGNNYVY IDPTQLPYDH KWEFPRNRLS FGKTLGAGAF   600
GKVVEATAYG LIKSDAAMTV AVKMLKPSAH LTEREALMSE LKVLSYLGNH MNIVNLLGAC   660
TIGGPTLVIT EYCCYGDLLN FLRRKRDSFI CSKQEDHAEA ALYKNLLHSK ESSCSDSTNE   720
YMDMKPGVSY VVPTKADKRR SVRIGSYIER DVTPAIMEDD ELALDLEDLL SFSYQVAKGM   780
AFLASKNCIH RDLAARNILL THGRITKICD FGLARDIKND SNYVVKGNAR LPVKWMAPES   840
IFNCVYTFES DVWSYGIFLW ELFSLGSSPY PGMPVDSKFY KMIKEGFRML SPEHAPAEMY   900
DIMKTCWDAD PLKRPTFKQI VQLIEKQISE STNHIYSNLA NCSPNRQKPV VDHSVRINSV   960
GSTASSSQPL LVHDDV                                                  976

SEQ ID NO: 203         moltype = AA  length = 972
FEATURE                Location/Qualifiers
source                 1..972
                       mol_type = protein
                       organism = Homo sapiens
SEQUENCE: 203
MRGARGAWDF LCVLLLLLRV QTGSSQPSVS PGEPSPPSIH PGKSDLIVRV GDEIRLLCTD    60
PGFVKWTFEI LDETNENKQN EWITEKAEAT NTGKYTCTNK HGLSNSIYVF VRDPAKLFLV   120
DRSLYGKEDN DTLVRCPLTD PEVTNYSLKG CQGKPLPKDL RFIPDPKAGI MIKSVKRAYH   180
RLCLHCSVDQ EGKSVLSEKF ILKVRPAFKA VPVVSVSKAS YLLREGEEFT VTCTIKDVSS   240
SVYSTWKREN SQTKLQEKYN SWHHGDFNYE RQATLTISSA RVNDSGVFMC YANNTFGSAN   300
VTTTLEVVDK GFINIFPMIN TTVFVNDGEN VDLIVEYEAF PKPEHQQWIY MNRTFTDKWE   360
DYPKSENESN IRYVSELHLT RLKGTEGGTY TFLVSNSDVN AAIAFNVYVN TKPEILTYDR   420
LVNGMLQCVA AGFPEPTIDW YFCPGTEQRC SASVLPVDVQ TLNSSGPPFG KLVVQSSIDS   480
SAFKHNGTVE CKAYNDVGKT SAYFNFAFKE QIHPHTLFTP LLIGFVIVAG MMCIIVMILT   540
YKYLQKPMYE VQWKVVEEIN GNNYVYIDPT QLPYDHKWEF PRNRLSFGKT LGAGAFGKVV   600
EATAYGLIKS DAAMTVAVKM LKPSAHLTER EALMSELKVL SYLGNHMNIV NLLGACTIGG   660
PTLVITEYCC YGDLLNFLRR KRDSFICSKQ EDHAEAALYK NLLHSKESSC SDSTNEYMDM   720
KPGVSYVVPT KADKRRSVRI GSYIERDVTP AIMEDDELAL DLEDLLSFSY QVAKGMAFLA   780
SKNCIHRDLA ARNILLTHGR ITKICDFGLA RDIKNDSNYV VKGNARLPVK WMAPESIFNC   840
VYTFESDVWS YGIFLWELFS LGSSPYPGMP VDSKFYKMIK EGFRMLSPEH APAEMYDIMK   900
TCWDADPLKR PTFKQIVQLI EKQISESTNH IYSNLANCSP NRQKPVVDHS VRINSVGSTA   960
SSSQPLLVHD DV                                                      972

SEQ ID NO: 204         moltype = AA  length = 454
FEATURE                Location/Qualifiers
source                 1..454
                       mol_type = protein
                       organism = Homo sapiens
SEQUENCE: 204
MDFFRVVENQ QPPATMPLNV SFTNRNYDLD YDSVQPYFYC DEEENFYQQQ QQSELQPPAP    60
SEDIWKKFEL LPTPPLSPSR RSGLCSPSYV AVTPFSLRGD NDGGGGSFST ADQLEMVTEL   120
LGGDMVNQSF ICDPDDETFI KNIIIQDCMW SGFSAAAKLV SEKLASYQAA RKDSGSPNPA   180
RGHSVCSTSS LYLQDLSAAA SECIDPSVVF PYPLNDSSSP KSCASQDSSA FSPSSDSLLS   240
STESSPQGSP EPLVLHEETP PTTSSDSEEE QEDEEEIDVV SVEKRQAPGK RSESGSPSAG   300
GHSKPPHSPL VLKRCHVSTH QHNYAAPPST RKDYPAAKRV KLDSVRVLRQ ISNNRKCTSP   360
```

```
RSSDTEENVK RRTHNVLERQ RRNELKRSFF ALRDQIPELE NNEKAPKVVI LKKATAYILS    420
VQAEEQKLIS EEDLLRKRRE QLKHKLEQLR NSCA                                 454

SEQ ID NO: 205           moltype = AA  length = 464
FEATURE                  Location/Qualifiers
source                   1..464
                         mol_type = protein
                         organism = Homo sapiens
SEQUENCE: 205
MPSCSTSTMP GMICKNPDLE FDSLQPCFYP DEDDFYFGGP DSTPPGEDIW KKFELLPTPP    60
LSPSRGFAEH SSEPPSWVTE MLLENELWGS PAEEDAFGLG GLGGLTPNPV ILQDCMWSGF    120
SAREKLERAV SEKLQHGRGP PTAGSTAQSP GAGAASPAGR GHGGAAGAGR AGAALPAELA    180
HPAAECVDPA VVFPFPVNKR EPAPVPAAPA SAPAAGPAVA SGAGIAAPAG APGVAPPRPG    240
GRQTSGGDHK ALSTSGEDTL SDSDDEDDEE EDEEEEIDVV TVEKRRSSSN TKAVTTFTIT    300
VRPKNAALGP GRAQSSELIL KRCLPIHQQH NYAAPSPYVE SEDAPPQKKI KSEASPRPLK    360
SVIPPKAKSL SPRNSDSEDS ERRRNHNILE RQRRNDLRSS FLTLRDHVPE LVKNEKAAKV    420
VILKKATEYV HSLQAEEHQL LLEKEKLQAR QQQLLKKIEH ARTC                     464

SEQ ID NO: 206           moltype = AA  length = 364
FEATURE                  Location/Qualifiers
source                   1..364
                         mol_type = protein
                         organism = Homo sapiens
SEQUENCE: 206
MDYDSYQHYF YDYDCGEDFY RSTAPSEDIW KKFELVPSPP TSPPWGLGPG AGDPAPGIGP    60
PEPWPGGCTG DEAESRGHSK GWGRNYASII RRDCMWSGFS ARERLERAVS DRLAPGAPRG    120
NPPKASAAPD CTPSLEAGNP APAAPCPLGE PKTQACSGSE SPSDSENEEI DVVTVEKRQS    180
LGIRKPVTIT VRADPLDPCM KHFHISIHQQ QHNYAARFPP ESCSQEEASE RGPQEEVLER    240
DAAGEKEDEE DEEIVSPPPV ESEAAQSCHP KPVSSDTEDV TKRKNHNFLE RKRRNDLRSR    300
FLALRDQVPT LASCSKAPKV VILSKALEYL QALVGAEKRM ATEKRQLRCR QQQLQKRIAY    360
LTGY                                                                 364

SEQ ID NO: 207           moltype = AA  length = 448
FEATURE                  Location/Qualifiers
source                   1..448
                         mol_type = protein
                         organism = Homo sapiens
SEQUENCE: 207
MAHVGDCTQT PWLPVLVVSL MCSARAEYSN CGENEYYNQT TGLCQECPPC GPGEEPYLSC    60
GYGTKDEDYG CVPCPAEKFS KGGYQICRRH KDCEGFFRAT VLTPGDMEND AECGPCLPGY    120
YMLENRPRNI YGMVCYSCLL APPNTKECVG ATSGASANFP GTSGSSTLSP FQHAHKELSG    180
QGHLATALII AMSTIFIMAI AIVLIIMFYI LKTKPSAPAC CTSHPGKSVE AQVSKDEEKK    240
EAPDNVVMFS EKDEFEKLTA TPAKPTKSEN DASSENEQLL SRSVDSDEEP APDKQGSPEL    300
CLLSLVHLAR EKSATSNKSA GIQSRRKKIL DVYANVCGVV EGLSPTELPF DCLEKTSRML    360
SSTYNSEKAV VKTWRHLAES FGLKRDEIGG MTDGMQLFDR ISTAGYSIPE LLTKLVQIER    420
LDAVESLCAD ILEWAGVVPP ASQPHAAS                                       448

SEQ ID NO: 208           moltype = AA  length = 466
FEATURE                  Location/Qualifiers
source                   1..466
                         mol_type = protein
                         organism = Homo sapiens
SEQUENCE: 208
MCNTNMSVPT DGAVTTSQIP ASEQETLVLF YLGQYIMTKR LYDEKQQHIV YCSNDLLGDL    60
FGVPSFSVKE HRKIYTMIYR NLVVVNQQES SDSGTSVSEN RCHLEGGSDQ KDLVQELQEE    120
KPSSSHLVSR PSTSSRRRAI SETEENSDEL SGERQRKRHK SDSISLSFDE SLALCVIREI    180
CCERSSSSES TGTPSNPDLD AGVSEHSGDW LDQDSVSDQF SVEFEVESLD SEDYSLSEEG    240
QELSDEDDEV YQVTVYQAGE SDTDSFEEDP EISLADYWKC TSCNEMNPPL PSHCNRCWAL    300
RENWLPEDKG KDKGEISEKA KLENSTQAEE GFDVPDCKKT IVNDSRESCV EENDDKITQA    360
SQSQESEDYF QPSTSSSIIY SCQEDVKEFE REETQDKEES VESSLPLNAI EPCVICQGRP    420
KNGCIVHGKT GHLMACFTCA KKLKKRNKPC PVCRQPIQMI VLTYFP                   466

SEQ ID NO: 209           moltype = AA  length = 233
FEATURE                  Location/Qualifiers
source                   1..233
                         mol_type = protein
                         organism = Homo sapiens
SEQUENCE: 209
MELPTKPGTF DLGLATWSPS FQGETHRAQA RRRDVGRQLP EYKAVVVGAS GVGKSALTIQ    60
LNHQCFVEDH DPTIQDSYWK ELTLDSGDCI LNVLDTAGQA IHRALRDQCL AVCDGVLGVF    120
ALDDPSSLIQ LQQIWATWGP HPAQPLVLVG NKCDLVTTAG DAHAAAAALA HSWGAHFVET    180
SAKTRQGVEE AFSLLVHEIQ RVQEAMAKEP MARSCREKTR HQKATCHCGC SVA           233

SEQ ID NO: 210           moltype = AA  length = 393
FEATURE                  Location/Qualifiers
source                   1..393
                         mol_type = protein
                         organism = Homo sapiens
SEQUENCE: 210
```

```
MEEPQSDPSV EPPLSQETFS DLWKLLPENN VLSPLPSQAM DDLMLSPDDI EQWFTEDPGP   60
DEAPRMPEAA PRVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRRCPHHE  180
RCSDSDGLAP PQHLIRVEGN LRVEYLDDRN TFRHSVVVPY EPPEVGSDCT TIHYNYMCNS  240
SCMGGMNRRP ILTIITLEDS SGNLLGRNSF EVHVCACPGR DRRTEEENLR KKGEPHHELP  300
PGSTKRALSN NTSSSPQPKK KPLDGEYFTL QIRGRERFEM FRELNEALEL KDAQAGKEPG  360
GSRAHSSHLK SKKGQSTSRH KKLMFKTEGP DSD                               393

SEQ ID NO: 211           moltype = AA   length = 317
FEATURE                  Location/Qualifiers
source                   1..317
                         mol_type = protein
                         organism = Homo sapiens
SEQUENCE: 211
MFQAAERPQE WAMEGPRDGL KKERLLDDRH DSGLDSMKDE EYEQMVKELQ EIRLEPQEVP   60
RGSEPWKQQL TEDGDSFLHL AIIHEEKALT MEVIRQVKGD LAFLNFQNNL QQTPLHLAVI  120
TNQPEIAEAL LGAGCDPELR DFRGNTPLHL ACEQGCLASV GVLTQSCTTP HLHSILKATN  180
YNGHTCLHLA SIHGYLGIVE LLVSLGADVN AQEPCNGRTA LHLAVDLQNP DLVSLLLKCG  240
ADVNRVTYQG YSPYQLTWGR PSTRIQQQLG QLTLENLQML PESEDEESYD TESEFTEFTE  300
DELPYDDCVF GGQRLTL                                                 317

SEQ ID NO: 212           moltype = AA   length = 381
FEATURE                  Location/Qualifiers
source                   1..381
                         mol_type = protein
                         organism = Homo sapiens
SEQUENCE: 212
MTAMEESQSD ISLELPLSQE TFSGLWKLLP PEDILPSPHC MDDLLLPQDV EEFFEGPSEA   60
LRVSGAPAAQ DPVTETPGPV APAPATPWPL SSFVPSQKTY QGNYGFHLGF LQSGTAKSVM  120
CTYSPLNKL FFQLAKTCPV QLWVSATPPA GSRVRAMAIY KKSQHMTEVV RRCPHHERCS  180
DGDGLAPPQH LIRVEGNLYP EYLEDRQTFR HSVVVPYEPP EAGSEYTTIH YKYMCNSSCM  240
GGMNRRPILT IITLEDSSGN LLGRDSFEVR VCACPGRDRR TEEENFRKKE VLCPELPPGS  300
AKRALPTCTS ASPPQKKKPL DGEYFTLKIR GRKRFEMFRE LNEALELKDA HATEESGDSR  360
AHSSLQPRAF QALIKEESPN C                                            381

SEQ ID NO: 213           moltype = DNA   length = 12359
FEATURE                  Location/Qualifiers
source                   1..12359
                         mol_type = genomic DNA
                         organism = Homo sapiens
SEQUENCE: 213
tgaaacggag tctctcgctg tcacccaggc tggagtgcag tagcacgatc ttggctcact    60
gcaacatctg cctcccgggt tcaagcaatt ctcctgcctc agcctcctga gtagctggga   120
ctacaggtgc gctccaccac ccccagctaa tttttgtatt tttagtggag acggggtttc   180
accatgttgg tcaggctggt cttgaactcc tgacctcatg atcctctcac ctcggcctca   240
caaagtgcta ggattacagg cgcatggcca agaatgaatg attatttgtg ccttcctatg   300
tgaaaaaaaa atgtttcctc tagctacaca ctattctgtt ctgtgaggcc gccccatcag   360
actgttgacc tagagtccca accccggccc tccaggagac ctgcctgttc ttagaagccc   420
aacccactca gcagcagctc caaataacag ggggagccaa caaaaaagag tgctgctaga   480
gcaacaagca aggggcaatt agtcagaagg caacttccat ggtcttccaa aaaaaattga   540
ggtgaaagac caaagatgtc cctaaaatgt cttcctaaaa gataaacttc atcaactacc   600
tctgactggt cagtattaag aaccactttc aggccaggtg tcatggttca cgcctgtaac   660
tccatctact ccagaggctg aggcaggaca attgcttcag gccggaggat tgcttgaggc   720
caggagctgg agaccaagcc tgagcaacac agtgagacct catctctacc aaaaatgtac   780
ctctattaaa aaacaaaaaa gaagaagaag aagaagaaga aggagaggag gctgggtatg   840
gtggctaatg cctttgtaat cccagaactt tggaaggctg aggaggagga atcacttagg   900
ctgaggcagg agaatcacca gagtctagga gtttgagacc agcctgggca acatagtgag   960
accccatct ctacaaaaaa aaaaattcaa aaattagcca agcgtggggt ttgtgcctgt  1020
agacccaact actcaggagg ctcaggtagg aggatcagcc gagtccaggg aggtcgaggc  1080
tgcagtgagt catgattatt ccactgcctt ccagcctaga ctacagggtg agaccctgtc  1140
ttaaaaaaaa aattaaagaa gaaaaaactc tcttttcttt tctttcttc ttcttcttct  1200
tttcttttt tttttttctt tttttttttt tagagatggc acgtcaccac attgcccagg  1260
ctgttgtcga actcctggcc tcaaacgatg ctcccacttg agcctccaa agtgctggga  1320
ctacaagcat aagccaccac acacggcctt tccttttctt tttctatttc tcaatggatt  1380
tttccaatgg acacgtatca ctttggtagt tatacatgat actagttgta atctcagcca  1440
tttttcaacc cagcaaatgt ctattctagg tcaaatatgt ctcaaaaatt actaaaagaa  1500
aatcagttat gtcctttaac ctggctgagg tctggctttg ttttctctca tgtaaaaatg  1560
gagatggcac aaaacaactc caagctgtta cttgaaagta acacctcagg tgatgtcaca  1620
agcctgaggg agagtgaggt taagttctga acccacagc attatatctg cctggggttc  1680
acatgcccta cactggactg gcataaattg agagtcagat ccgaagatgt ggtatatccg  1740
ccatctttag caactttcaa aaactaccct atgaggtcaa gctggaccta cttttggttt  1800
tgccattgtt gtttgtttgt tgttgagggt tttctttgag gggcggggag tgcatgcccc  1860
tgtggagagc actcatttag cttcaattag agtaatgcca aaagtgccag attcctggga  1920
aatccagtca caaggctcct gcgggaagga acctccactg ccagaagtcc ttagggcatt  1980
taagtgatca gacaccgtca gggattcttt gccccgtaaa aacctacttg accagggaca  2040
cgtgccaggt aaatttcctt cacatttact tcaaccttat tgcatactca ttttagtatt  2100
aaaacctta ataaaatgct cctattcctt cacacttttt ttctatgaga tctcaaatac  2160
cccttcttgc tattaaaaaa aatcacttat tattcaccag cccaatattt taaaagtaaa  2220
aataataagc caaggccagg agcgatgact cgcacttgta ttcccagcag tttcagaggc  2280
```

-continued

```
aaaggccgaa ggatcgcttt aaccgaggag tttgagacca gcctgggcaa catgaccaga   2340
ctgcctctct acaaaaagtt taaaaaatta accgggtgtg gtggtgcact gcactcccag   2400
ctactgggct ggggtatcag gctgaggtag gaggtttgct ttgagcccgg ggggatcgag   2460
gctgcagtga gctttgattg tgccactgca ctccagcctg ggtgacagaa ggagaccctg   2520
tctcaaaaat aataagaata ataattaata ataataggcc aaaccaaata cccatcacct   2580
tctgctgtgc ctcccctttc cccaataaat ccagtgtctt gctttcaaat tttgtggtta   2640
aaaaagatga tgagtttcta agacgtgggg gctaaagctt gtttggccgt tttagggttt   2700
gttggaattt ttttttcgtc tatgtacttg tgaattattt cacgtttgcc attaccggtt   2760
ctccataggg tgatgttcat tagcagtggt gataggttaa ttttcaccat ctcttatgcg   2820
gttgaatagt cacctctgaa ccactttttc ctccagtaac tcctctttct tcggaccttc   2880
tgcagccaac ctgaaagaat aacaaggagg tggctggaaa cttgtttaa ggaaccgcct    2940
gtccttcccc cgctggaaac cttgcacctc ggacgctcct gctcctgccc ccacctgacc   3000
cccgccctcg ttgacatcca ggcgcgatga tctctgctgc cagtgagggg cacacttact   3060
ttactttcgc aaacctgaac gcgggtgctg cccagagagg gggagggaag aaagacgctt   3120
tgcagcaaaa tccagcatag cgattggttg ctccccgcgt ttgcggcaaa ggcctggagg   3180
caggagtaat ttgcaatcct taaagctgaa ttgtgcagtg catcggattt ggaagctact   3240
atattcactt aacacttgaa cgctgagctg caaactcaac gggtaataac ccatcttgaa   3300
cagcgtacat gctatacacg cacccctttc ccccgaattg ttttctcttt tggaggtggt   3360
ggagggagag aaaagtttac ttaaaatgcc tttgggtgag ggaccaagga tgagaagaat   3420
gtttttttgtt tttcatgccg tggaataaca caaaatagaa aatcccgagg gaatatacat   3480
tatatattaa atatagatca tttcaggag caaacaaatc atgtgtgggg ctgggcaact    3540
agctaagtcg aagcgtaaat aaaatgtgaa tacacgtttg cgggttacat acagtgcact   3600
ttcactagta ttcagaaaaa attgtgagtc agtgaactag gaaattaatg cctggaaggc   3660
agccaaattt taattagctc aagactcccc cccccccaaa aaaaggcacg gaagtaaatac  3720
tcctctcctc ttctttgatc agaatcgatg cattttttgt gcatgaccgc atttccaata   3780
ataaaagggg aaagaggacc tggaaaggaa ttaaacgtcc ggtttgtccg gggaggaaag   3840
agttaacggt ttttttcaca agggtctctg ctgactcccc cggctcggtc cacaagctct   3900
ccacttgccc cttttaggaa gtccggtccc gcggttcggg tacccctgc ccctcccata    3960
ttctcccgtc tagcacctt gatttctccc aaacccggca gcccgagact gttgcaaacc    4020
ggcgccacag ggcgcaaagg ggatttgtct cttctgaaac ctggctgaga aattgggaac   4080
tccgtgtggg aggcgtgggg gtgggacggg ggggtacaga ctggcagaga gcaggcaacc   4140
tccctctcgc cctagcccag ctctggaaca ggcagacaca tctcagggct aaacagacgc   4200
ctcccgcacg gggccccacg gaagcctgag caggcggggc aggaggggcg gtatctgctg   4260
ctttggcagc aaattggggg actcagtctg ggtggaaggt atccaatcca gatagctgtg   4320
catacataat gcataataca tgactccccc caacaaatgc aatgggagtt tattcataac   4380
gcgctctcca agtatacgtg gcaatgcgtt gctgggttat tttaatcatt ctaggcatcg   4440
ttttcctcct tatgcctcta tcattcctcc ctatctacac taacatccca cgctctgaac   4500
gcgcgcccat taataccctt ctttcctcca ctctccctgg gactcttgat caaagcgcgg   4560
cccttcccc agccttagcg aggcgccctg cagcctggca cgcgcgtggc gtggcggtgg    4620
gcgcgcagtg cgttctcggt gtggagggca gctgttccgc ctgcgatgat ttatactcac   4680
aggacaagga tgcggtttgt caaacagtac tgctacggag gagcagcaga gaaagggaga   4740
gggtttgaga gggagcaaaa gaaaatggta ggcgcgcgta gttaattcat gcggctctct   4800
tactctgttt acatcctaga gctagagtgc tcggctgccc ggctgagtct cctccccacc   4860
ttccccaccc tccccaccct ccccataagc gcccctcccg ggttcccaaa gcagagggcg   4920
tgggggaaaa gaaaaaagat cctctctcgc taatctccgc ccaccggccc tttataatgc   4980
gagggtctgg acggctgagg accccgagc tgtgctgctc gcggccgcca ccgccgggcc    5040
ccggccgtcc ctggctcccc tcctgcctcg agaagggcag ggcttctcag aggcttggcg   5100
ggaaaaagaa cggagggagg gatcgcgctg agtataaaag ccggttttcg gggctttatc   5160
taactcgctg tagtaattcc agcgagaggc agagggagcg agcgggcggc cggctagggt   5220
ggaagagccg ggcgagcaga gctgcgctgc gggcgtcctg ggaagggaga tccggagcga   5280
atagggggct tcgcctctgg cccagccctc ccgctgatcc cccagccagc ggtccgcaac   5340
ccttgccgca tccacgaaac tttgcccata gcagcgggcg ggcactttgc actggaactt   5400
acaacacccg agcaaggacg cgactctccc gacgcgggga ggctattctg cccatttggg   5460
gacacttccc cgccgctgcc aggacccgct tctctgaaag gctctccttg cagctgctta   5520
gacgctggat ttttttcggg tagtggaaaa ccaggtaagc accgaagtcc acttgccttt   5580
taatttattt ttttatcact ttaatgctga gatgagtcga atgcctaaat agggtgtctt   5640
ttctcccatt cctgcgctat tgacacttt ctcagagtag ttatggtaac tggggctggg    5700
gtggggggta atccagaact ggatcggggt aaagtgactt gtcaagatgg gagaggagaa   5760
ggcagaggga aaacgggaat ggttttttaag actacccttt cgagatttct gccttatgaa   5820
tatattcacg ctgactcccg gccggtcgga cattcctgct ttattgtgtt aattgctctc   5880
tgggttttgg ggggctgggg gttgctttgc ggtgggcaga aagcccttg catcctgagc    5940
tccttggagt agggaccgca tatcgcctgt gtgagccaga tcgctccgca gccgctgact   6000
tgtccccgtc tccgggaggg catttaaatt tcggctcacc gcatttctga cagccggaga   6060
cggacactgc ggcgcgtccc gcccgcctgt ccccgcggcg attccaaccc gccgctgtgt   6120
ttttaagaag ttggcatttg gctttttaaa aagcaataat acaatttaaa acctgggtct   6180
ctagaggtgt taggacgtgg tgttgggtag gcgcaggcag gggaaaaggg aggcgaggat   6240
gtgtccgatt ctcctggaat cgttgacttg gaaaaaccag ggcgaatctc cgcacccagc   6300
cctgactccc ctgccgcggc cgccctcggg tgtcctcgcg cccgagatgc ggaggaactg   6360
cgaggagcgg ggctctggc ggttccagaa cagctgctac ccttggtggg gtggctccgg    6420
gggaggtatc gcagcggggt ctctggcgca gttgcatctc cgtattgagt gcgaagggag   6480
gtgcccctat tattatttga cacccccctt gtatttatgg aggggtgtta aagcccgcgg   6540
ctgagctcgc cactccagcc ggcgagagaa agaagaaaag ctggcaaaag gagtgttgga   6600
cggggcggt actgggggtg gggacggggg cggtggagag ggaaggttgg gaggggctgc    6660
ggtgccggcg gggtaggag agcggctagg gcgcagtgga gacgcgaggg agcggagggag   6720
cccccggcgcg gagcgggtt cacgcagccg ctagcgccca ggcgcctctc gccttctcct   6780
tcaggtggcg caaacctttg tgccttggat tttggcaaat tgtttttcctc accgccacct   6840
cccgcggctt cttaagggcg ccaggccga tttcgattcc tctgccgctg cggggccgac    6900
tcccgggctt tgcgctccgg gctcccgggg gagcggggc tcggcgggca ccaagccgct    6960
ggttcactaa gtgcgtctcc gagatagcag gggactgtcc aaaggggtg aaagggtgct    7020
```

```
cccctttattc ccccaccaag accacccagc cgctttaggg gatagctctg caaggggaga   7080
ggttcgggac tgtggcgcgc actgcgcgct gcgccaggtt tccgcaccaa gacccctta    7140
actcaagact gcctcccgct ttgtgtgccc cgctccagca gcctcccgcg acgatgcccc   7200
tcaacgttag cttcaccaac aggaactatg acctcgacta cgactcggtg cagccgtatt   7260
tctactgcga cgaggaggag aacttctacc agcagcagca gcagagcgag ctgcagcccc   7320
cggcgcccag cgaggatatc tggaagaaat tcgagctgct gcccaccccg cccctgtccc   7380
ctagccgccg ctccgggctc tgctcgcccct cctacgttgc ggtcacaccc ttctcccttc   7440
ggggagacaa cgacgcggt ggcgggagct tctccacggc cgaccagctg gagatggtga    7500
ccgagctgct gggaggagac atggtgaacc agagtttcat ctgcgacccg gacgacgaga   7560
ccttcatcaa aaacatcatc atccaggact gtatgtggag cggcttctcg gccgccgcca   7620
agctcgtctc agagaagctg gcctcctacc aggctgcgcg caaagacagc ggcagcccga   7680
accccgcccg cggccacagc gtctgctcca cctccagctt gtacctgcag gatctgagcg   7740
ccgccgcctc agagtgcatc gacccctcgg tggtcttccc ctaccctctc aacgacagca   7800
gctcgcccaa gtcctgcgcc tcgcaagact ccagcgcctt ctctccgtcc tcggattctc   7860
tgctctcctc gacggagtcc tccccgcagg gcagccccga gccctggtg ctccatgagg    7920
agacaccgcc caccaccagc agcgactctg gtaagcgaag cccgcccagg cctgtcaaaa   7980
gtgggcggct ggatacctttt cccatttttca ttggcagctt atttaacggg ccactcttat   8040
taggaaggag agatagcaga tctggagaga tttgggagct catcacctct gaaacctttgg   8100
gctttagcgt ttcctcccat cccttcccct tagactgccc atgtttgcag ccccccctccc   8160
cgtttgtctc ccacccctca ggaatttcat ttaggttttt aaaccttctg gcttatctta   8220
caactcaatc cacttcttct tacctcccgt taacatttta attgccctgg ggcggggtgg   8280
cagggagtgt atgaatgagg ataagagagg attgatctct gagagtgaat gaattgcttc   8340
cctcttaact tccgagaagt ggtgggattt aatgaactat ctacaaaaat gaggggctgt   8400
gtttagaggc taggcagggc ctgcctgagt gcgggagcca gtgaactgcc tcaagagtgg   8460
gtgggctgag gagctgggat cttctcagcc tattttgaac actgaaaagc aaatccttgc   8520
caaagttgga cttttttttt tcttttattc cttcccccgc cctcttggac ttttggcaaa   8580
actgcaattt tttttttttt atttttcatt tccagtaaaa tagggagttg ctaaagtcat   8640
accaagcaat ttgcagctat catttgcaac acctgaagtg ttcttggtaa agtccctcaa   8700
aaataggagg tgcttgggaa tgtgctttgc tttgggtgtg tccaaagcct cattaagtct   8760
taggtaagaa ttggcatcaa tgtcctatcc tgggaagttg cacttttctt gtccatgcca   8820
taacccagct gtctttccct ttatgagact cttaccttca tggtgagagg agtaaggggtg   8880
gctggctaga ttggttcttt tttttttttt ttccttttt aagacggagt ctcactctgt   8940
cactaggctg gagtgcagtg gcgcaatcaa cctccaaccc cctggttcaa gagattctcc   9000
tgcctcagcc tcccaagtag ctgggactac aggtgcacac caccatgcca ggctaatttt   9060
tgtaatttta gtagagatgg ggtttcatcg tgttggccag gatggtctct cctgacctca   9120
cgatccgccc acctcggcct cccaaagtgc tgggattaca ggtgtgagcc agggcaccag   9180
gcttagatgt ggctctttgg ggagataatt ttgtccagag acctttctaa cgtattcatg   9240
ccttgtattt gtacagcatt aatctggtaa ttgattattt taatgtaacc ttgctaaagg   9300
agtgatttct atttcctttc ttaaagagga ggaacaagaa gatgaggaag aaatcgatgt   9360
tgtttctgtg gaaaagaggc aggctcctgg caaaaggtca gagtctggat caccttctgc   9420
tggaggccac agcaaacctc ctcacagccc actggtcctc aagaggtgcc acgtctccac   9480
acatcagcac aactacgcag cgcctccctc cactcggaag gactatcctg ctgccaagag   9540
ggtcaagttg gacagtgtca gagtcctgag acagatcagc aacaaccgaa aatgcaccag   9600
ccccaggtcc tcggacaccg aggagaatgt caagaggcga acacacaacg tcttggagcg   9660
ccagaggagg aacgagctaa aacggagctt ttttgccctg cgtgaccaga tcccggagtt   9720
ggaaaacaat gaaaaggccc ccaaggtagt tatccttaaa aaagccacag catacatcct   9780
gtccgtccaa gcagaggagc aaaagctcat ttctgaagga gacttgttgc ggaaacgacg   9840
agaacagttg aaacacaaac ttgaacagct acggaactct tgtgcgtaag gaaaagtaag   9900
gaaaacgatt ccttctaaca gaaatgtcct gagcaatcac ctatgaactt gtttcaaatg   9960
catgatcaaa tgcaacctca caaccttggc tgagtcttga gactgaaaga tttagccata   10020
atgtaaactg cctcaaattg gactttgggc ataaagaacc tttttatgc ttaccatctt    10080
tttttttttct ttaacagatt tgtatttaag aattgttttt aaaaaatttt aagatttaca  10140
caatgtttct ctgtaaatat tgccattaaa tgtaaataac tttaataaaa cgtttatagc   10200
agttacacag aatttcaatc ctagtatata gtacctagta ttataggtac tataaaccct   10260
aatttttttt atttaagtac attttgcttt ttaaagttga tttttttttag ttgtttttag  10320
aaaaaataaa ataactggca aatatatcat tgagccaaat cttaagttgt gaatgttttg   10380
tttcgtttct tcccctccc aaccaccacc atccctgtt gttttcatca attgcccctt     10440
cagagggtgg tcttaagaaa ggcaagagtt ttcctctgtt gaaatgggtc tgggggcctt   10500
aaggtcttta agttcttgga ggttctaaga tgcttcctgg agactatgat aacagccaga   10560
gttgacagtt agaaggaatg gcagaaggca ggtgagaagg tgagaggtag gcaaaggaga   10620
tacaagaggt caaaggtagc agttaagtac acaaagaggc ataaggactg gggagttggg   10680
aggaaggtga ggaagaaact cctgttactt tagttaacca gtgccagtcc cctgctcact   10740
ccaaacccag gaattctgcc cagttgatgg ggacacggtg ggaaccagct tctgctgcct   10800
tcacaaccag gcgccagtcc tgtccatggg ttatctcgca ggaaccagag gatctctggg   10860
aggaatgcta ctattaaccc tatttcacaa acaaggaaat agaagagctc aaagaggtta   10920
tgtaacttat ctgtagccac gcagataata caaagcagca atctggaccc attctgttca   10980
aaacacttaa cccttcgcta tcatgccttg gttcatctgg gtctaatgtg ctgagatcaa   11040
gaaggtttag gacctaatgg acagactcaa gtcataacaa tgctaagctc tatttgtgtc   11100
ccaagcactc ctaagcattt tatccctaac tctacatcaa ccccatgaag gagatactgt   11160
tgatttcccc atattagaag tagagagggga agctgaggca cacaaagact catccacatg   11220
cccaagattc actgataggg aaaagtggaa gcgagatttg aacccaggct gtttactcct   11280
aacctgtcca agccacctct cagacgacgg taggaatcag ctggctgctt gtgagtacag   11340
gagttacagt ccagtgggtt atgtttttta agtctcaaca tctaagcctg gtcaggcatc   11400
agttccccttt ttttttgtgat ttattttgtt tttattttgt tgttcattgt ttaatttttc  11460
cttttacaat gagaaggtca ccatcttgac tcctaccttta gccatttgtt gaatcagact   11520
catgacggct cctgggaaga agccagttca gatcataaaa taaaacatat ttattctttg   11580
tcatgggagt cattatttta gaaactacaa actctccttg cttccatcct tttttacata   11640
ctcatgcacac atgctcatcc tgagtccttg aaaaggtatt tttgaacatg tgtattaatt   11700
ataagcctct gaaaacctat ggcccaaacc agaaatgatg ttgattatat aggtaaatga   11760
```

```
aggatgctat tgctgttcta attacctcat tgtctcagtc tcaaagtagg tcttcagctc    11820
cctgtacttt gggattttaa tctaccacca cccataaatc aataaataat tactttcttt    11880
gactctgact cctagaataa tctattcaaa accttaatgt cttttcttg atccttcttt     11940
tgagtcctaa gtaccgccat tacagcttca aattggcacg tcatataggc gaatttcaaa    12000
gggagatgca atccacagaa gtatagtagt tcaaaggcat acaaaagcaa ggcgctctta    12060
aacagctcag tctttgcccc tttgtgtgcct agggctggag tgcagctctg gggtgactca    12120
cttgggaatc gggaaggtgt tagtctgaat cactaagtcc aggcaagccc tcagaatagg    12180
agagagtgtt cctagcaagg aaaacaactc tccattccaa ataatcagga aagaacttta    12240
gggatgtgga gcttggctat gggaatagaa aggaaccatt ccaagtgcct attaggccgc    12300
tcttacctt actgagccag agaatggctc tgaaaacagg acagatgcca acttccttc      12359
```

```
SEQ ID NO: 214            moltype = DNA   length = 13447
FEATURE                   Location/Qualifiers
source                    1..13447
                          mol_type = genomic DNA
                          organism = Homo sapiens
SEQUENCE: 214
acatttcccg tctgtaacta tagacctaac acattatttt tagtgggtgt atgtaattcc    60
actgcatgga tgtattacat accattctcc tgtttaattt gttttagtta tggatattta    120
gattgcttat agtattttg ttattgagaa tgatgcagcc acacacattc ttgtttatat      180
gctttttatgt gtttgtctta ttatttctcg taggatggat catgaagagt ggaattgctt    240
ttcctcttgg ggcaggcaca ccaacagtgt atgtgaggcc ctgctcccca ctccccaggc     300
tggccagtac tttgggccaa tctgctagac ccaaaaatgt taatctcact gagatttaat    360
ttgcattccc ctgactaccg gtgaagttga gcatctttttc atatgtttat tgacaatttg    420
catttcttat tcagtaaatt acctgctcgt atcctagagt catatttctg tctgcccgtt     480
tttttctatt caatttgtgg gagctctttg tatacctggg atctaatctt tgactcatat     540
atatggcaag tattttctat tactgttgtc aacttttat catagtaaaa ttcttacatc       600
cagcacccc accctcccc tgcccttttt ttttttttt ttgcatttgg gttaggcaga         660
gagctagctt tactgttttc caaatgaagt caatcgatcc caaggatttt taaattattt     720
aatcagtaaa aatgtacaca ttttgaggga ggtgtgaaaa tcctaggaga aactgtgctc     780
ttgtccctga agacagactc agtagatctt ttttttttc ttttgagaca aggtctcact      840
ctgtcatcca ggctggagtg cagtggtgtg atgatggcac actgcagcct tgatctccct     900
gggctcaggt gatcttcctg cctcagcctc ccaagtagct gggaccacag gcacgcaccc     960
accacgccca gctaattttt atattttttg tagagacagg gtttcaccat gttgcccagg     1020
ccggtctcaa aatcctgggc tcaagccatc tgccctcctc agactcttga agtgccagga    1080
ttacaggcgt gagccaccat gcctggccaa cccagcagat ctttaattca caatctggaa    1140
aaaccatcta gaggctgttg ctctcctagc cagtcatgat ttgggcccctt ctcaacatgt    1200
gtatgtgtgt gttgtttctt tgtgtgtgtg tgtcttagta aagaggagt ttgtaaacta       1260
aaatattctc ctctctcaaa aatcaccta attataaacc aaatgctgtg tataactcta      1320
tcctagcagt tggtgattag attgaggcat ccatttcaga tgtgggtctc cttccctggt     1380
ccacagtgag ctccttgcgg ctgtacctta acttacctct gttccaaacc cacccagggg    1440
ctcagacaca gtaatagatg ggtacttgtc tcagttcatt ttgtgttgct ataacctaat     1500
agcacagact gggtaattta taaagaaaag aaatgtattt ctcatgtttc tggaggctga    1560
gaagtccaat atcaaggtgc cagcaattgc tgagggcctt catggcgtac catcccctgg    1620
caggaaaaag gaagagaggg caagagatca aactcctagc ctcaagccct tttataatta    1680
gcattaatcc attcacaaga gtggagccct catgacctaa acacctcaca ttaggtcctg    1740
agacaggaat aatataaggt ggctgcagaa taatagaaga ttttgggcag caatttcaca    1800
tgactagcaa aaggaaactg ttgaaatggc tgcagaggcc atgggctaag accgtgaaaa    1860
acagagtgta gaccaagctg gctaagaccc actgaaccca gcatggcact ggatttgacc    1920
taggtttctc ctaggacctc attatacgct cattaacata ctaaatcaca caccccacta    1980
gcatcatgac acttccgaga acacccatat ttggtttaaa aataggtggt gtcacagttc    2040
tgagaaatct ccttctttt ctaggaatga tcatgaatat tctgcctctt ggttaaagaa      2100
acccgtaaag gtagcaaccc caaaccccct ttcgtgtgag tctctcgagt acacccatat     2160
tcccttttct tgagtgtgta cttttcctt tgcaataaat cgtactttca ctattttcca       2220
actggtcttt gaattcattc tcttgatggt gtcaagagcc tggacactgg ctggggtcta    2280
ggtcccactg gcatttgggg acctccctc caacactgtt gcactggggg ttaaacttcc       2340
aacgtgtttt tttttggagg acacattcaa accatggcag tactgaacaa aaccttggct    2400
ttgaaaccat atgaagattt gtttgtgtg tgttcacata gttgaagtat ttcaacattt       2460
ttaagaggga ttttcaggct tctctataag cagactaaga atcagcatta gcatgttttc    2520
tccatgtaca aagtctttta tctttctact tacaaatgaa ggtaaccaat aaatatttgt    2580
tgaattttat cattctgtta accttcagat tcagacttgt cagtaattac tggcttgcat    2640
taaaagcagg agattagaga ttgaggtcca ggaagtataa atgatttgct caaaggcatg    2700
tagagtaacc aggtctcctg tccctctgtc ccccttttct gctacacctt gtccctcgac    2760
aaagggtgaa tgacctagtg atggtcattc atctgaggag aaaggacaaa ggtaggactt    2820
tgaatcggag caactgaacc catcctggcc tattttcaca gtcttgccac agaagatctg    2880
gccaccttag aaggactcat tcagtgatct tggtcttgaa taataccatg agtacttact    2940
atatacaggt acactgctgt gccgtaagga ttccctctgg agcaaaactg acccaggtca    3000
caggttagtg agggagactg agcctgtctt ccacagtgtc acggaagtga gcactaaaca    3060
aatactccca ggcatggatc attacaaatg gaggtgagtg ctggacagga aaggacagga    3120
tgctaggcga gaattcagca ggagggcttg gtgtgcgatta gggggctagg gaaaagcaga   3180
agtggggctg taaaaggctt ttgcaaagat gaaggctttt acatttgtga gggaaataac    3240
aataataaag gtgcttggaa gggctgctca tccgcattca tgggcctctt cctagaactc    3300
tgggaatctt tctccctaga gctctgtagg cgtccaggt cagggctgga aaggccttca     3360
caaatgctaa tctgtgagca ttttatgggt tgccccgtca ccctcagcat cctcctcctt    3420
aactagatcc aatggtgagg tgaagaggtg ggggcgatgg agaatggcat ttccagtttg    3480
gagaaaaaag tagggagagg cgggggaagcc ttcccacccc aatcccaggg ccaggttccc   3540
ctctctccaa acaagcctaa ggaatgtttt tcaaggcaaa atcccacctc actgtgtatt    3600
tggttgtgaa gggggctgtc caggagatca gggttgtttt tggagagttt ggagggcagg    3660
ggcaataatg tctgaccccc tgcaaacaaa tacacctgta agaaaagcta gaccagagtg    3720
```

-continued

```
aagtaaagcc aggatttgat ggtggcggga agggaagggg ccaatgctgc tgctggacag   3780
aggggtgtta ttttccccag aagaatagca tgtcgtggtc atcatcataa taatagctga   3840
cacaactatt atgggctggg gacttataag agctttcata actctcaggt aggaggcact   3900
acgaactcca tttcacaatt gaggaaactg aggcacaaag aaacgaagta gtgacagcag   3960
ctttcctttt tcccttcaac agtttggaat caagctgttt gagccgaggc tgggtctcag   4020
gaggtgtgga cagcacttcc atctcggtaa atcagattcg cctgcccata actgggggaga   4080
atggtggctt tgaaaaggtt aacttgggag ccctggggac ggctgcaggg aacgtacgcc   4140
cattcccct aggaagcaga gccaggccgc ctcctcctcc gcagtggtga ggacgcgtgg   4200
acagtcccgc gggggcggcg ggagacctgc ggagtggccg cactccaggt ccgcgccaag   4260
gccgggcagc tccgctttct gctcagtctc cgcgaggtgt cgccttcggc cgaagaaacc   4320
accgcggcgc caccctcgta gctcgcactt atttatttat ttattttcaa acaaggggggg   4380
cgcccctctt ctttcaattt gaaactggaa acatccagag gtcttgttcc taaggggggcg   4440
cgtcctctcc ctgctatttt gcaccttcgg actacccttc tttcgtaatt acacaggagc   4500
aacctccctg caaggccttg ctcaacgttg gcctcgcgct cagctgcaca acacgcagtc   4560
aaagcggggg ctgggttaga agcatcggtc tcccctcccc aacacacacc cccggagccc   4620
tccgtaattt ttttttcttt taatgacaag caattgccag gctcgcaggg tgggtgctgc   4680
attgcaccgc tccgcgcgca gctggttctc agagtgcagc cggtgcaagc ccggggggtcc   4740
aaaagggcgg gaggagcaca ccctgggctt cccagctttg cagccttctc tctgcaaaga   4800
aaagcaagtg gcttttggcg cgaaagcctt ggcgcctccc ctgattttta tggaaatcag   4860
gagggcgggg taaagccgct ttcctctcct ttctccctcc cccttgtctg cgccacagcc   4920
cccttctctc cccgcccccc gggtgtgtca gatttttcag ttaataatat cccccgagct   4980
tcaaagcgca ggctgtgaca gtcatctgtc tggacgcgct gggtggatgc gggggggctcc   5040
tgggaactgt gttggagccg agcaagcgct agccaggcgc aagcgcgcac agactgtagc   5100
catccgagga caccccgcc cccccggccc acccggagac acccgcgcag aatcgcctcc   5160
ggatcccctg cagtcggcgg gaggtaagga gcagggcttg caaaccgccc ggcgcccagg   5220
gaagcgacga gcgccggggc aaggcaagcc ctggacgggga ttgcgacgtg cgcaccgggc   5280
gccctaatat gcccggggga ctgtttctgc ttccgaaaca aaaccatctc tgggttttcc   5340
cagaaaagcc agttccagcc ccgaaggcat cctggctaga ggagaccgc cctaatcctt   5400
ttgcagccct taccgggggg agtaatggct tctgcgaaaa gaaattccct cggctctaga   5460
agatctgtct gtgtttgagc tgtcggagag ccggtgcgct cccaccccag gctgggggttc   5520
ttctccaaag ggtgccctg gaggaagaag aggggggggat taggcagggc gaggccgccg   5580
cggtcgcaat ctgggtcacg gctgctccag cttggaggag aggcggctct cccggcgacc   5640
ctcctcgcgc gggcgcccct gccattcccg ggaacagggg ctcagcctct ccctccctgg   5700
aagaggacgt tgtcgtgggt ttggaagagc aggggtgggc ttagagagct tccaattaag   5760
ctattggcag gagtatccct gcagcgggtg aatgccgagg ggcgtttgct caaatttggg   5820
gaggggaagg atttgtggat atgggtgtct gttgttggtc tctgtctaga gaaaggcttt   5880
tttttatttg caaagttttc taaatcccct gctatcattt gcactcctga ggttgcattt   5940
ttacaaaggg ggtagaaggt actccaaata ccattcccgg tagctgggtc ggagagcctg   6000
gggcttcccc tgagcagccg gccccacacc gctgcgagtg cggttgtctg cgtgctcgtg   6060
agagctagaa ttctgcagcc aggaacagcc ccctccccca ggcagtgcct tgtgtgaatg   6120
aaatggcagt ttccaaagtt gcggagcctc gccaccaccc cctgcatctg catgcccct   6180
cccacccct gtcgtagaca gcttgtacac aaaaggaggg cgggaggggag ggagcgagag   6240
gcacaacttc ctccaccttc gggagcagtg ggcagagtgg gggcttgga gggaagattg   6300
gggaacctgg ttagagggggg cgcccattgc ctatccctc ggtctgcccc gtttgcccac   6360
cctctccggt gtgtctgtcg gttgcagtgt tggaggtcgg cgccggcccc cgccttccgc   6420
gcccccacg ggaaggaagc accccggta ttaaaacgaa cggggcggaa agaagcccc   6480
agtcgccggc cgggaggcga gccgatgccg agctgctcca cgtccaccat gccgggcatg   6540
atctgcaaga acccagacct cgagtttgac tcgctacagc cctgcttcta cccgacgaa   6600
gatgacttct acttcggcgg ccccgactcg accccccgg gggaggacat ctggaagaag   6660
tttgagctgc tgcccacgcc cccgctgtcg cccagccgtg gcttcgcgga gcacagctcc   6720
gagcccccga gctgggtcac ggagatgctg cttgagaacg agctgtgggg cagcccggcc   6780
gaggaggacg cgttcggcct ggggggggactg ggtggcctca cccccaaccc ggtcatcctc   6840
caggactgca tgtggagcgg cttctccgcc cgcagagaag ctggagcgcgc cgtgagcgag   6900
aagctgcagc acggccgcgg gccgccaacc gccggttcca ccgcccagtc cccgggagcc   6960
ggcgccggca gccctgcggg tcgcgggcac ggcggggctg cgggagccgg ccgcgccggg   7020
gccgccctgc ccgccgagct cgcccacccg gccgccgagt gcgtggatcc cgccgtggtc   7080
ttcccctttc ccgtgaacaa gcgcgagcca gcgcgccgtgc ccgcagcccc ggccagtgcc   7140
ccggcggcgg gccctgcggt cgcctcgggg gcgggtattg ccgcccagc cggggccccg   7200
ggggtcgccc ctccgcgccc aggcggccgc cagaccagcg gcggcgacca caaggccctc   7260
agtacctccg gagaggacac cctgagcgat tcaggtaaag accgaactcg ggtccggctg   7320
cctcctgggg gcactggacc ccgggtcgcg tcccctttgt tagtgctcgt atgtcttggc   7380
ctgggggagca ttttgggaggc agtgctaggg gcagagaggt cctgtttccc ccaagtctct   7440
cctcgggggta aagagaaggg gctgagagaa tgccgttgca aaagggggtgc tctccaattc   7500
tcgccttcac taaagttcct tccaccctct cctggggggagc cctcctctag gccatcacgg   7560
gccctcaccc ggtcccccac ctctcttttg cagcgcagtc tgaggaataa aattggagaa   7620
agttggtggc taaaccgggt ggggggtttag ggggttgctg ggtgcactgc ctggacagaa   7680
acctgttagc gcaggggtga aagggactct ctggcccagg tcaggggagg gaaagacatc   7740
ccgagaagat tcaagggctg tgcaaagccc tgtttaaggc gcagaactt ataggagggt   7800
tgcacagatg gctagagccg attttctatt cttttttctt ttcttttttt tttttttca   7860
aatgtcggta cctttcctt cccccatcct cggtggggtgg tgggctattt gctcctggtg   7920
cgtggccagc aggcggcgat atgcgaggcc agcaggcggg cccgggatct gaaaggctgg   7980
gggtggtggg ggcaccctcc ctccctccat tcagcagctg gctgcaagtg caacagcagt   8040
tgtgtacatt ctcaggggggc ctcctcttc cagtgtgcag tggaaactgg ctgtagtttt   8100
gtcttccagc ctgaattcca ggcctaattt gagatgtgag ttgtatctgt aacccagtgc   8160
ccttgaaggt gagggcaggc actcagcagc ctctccagga aggctcacat cctggggga   8220
ctcactgatt agttctattg tgttcatttg tctgtgtctt aagctgaagg gaagagttaa   8280
aaccaagcct ttccctgggg gtctggatga acagaactca acccaaagag tggcattgcc   8340
ttgtccttgg agcagggagc tgggaccccc cttggacttt gaaaaccagt gttttcagaa   8400
tgcaggtgga taacaagcct aaatttactt ctgggctgag gagagatctt tgaggctcct   8460
```

-continued

```
ggaaggaaac ttggtgataa gcctccagtt tgaaacggct ctgtcccttt aatgtctgtg   8520
ccttgacagc ttttggtgag gaagcacttc cttccaacag ctgtcttctt ggcagaaaac   8580
caaaacattg gcttaaaggg acccacagac tggaacagcc tcacatttcg gctttagaac   8640
aaatcccaca attgttcagc tttccggtcc ccttcagatc aagcagaaga tatgtttttga  8700
ttttcatgct tgtattttaa acaataattt tctaccccag cgtggtagtc aatgaggaga   8760
gaggggaaga atgcgcacat gatgctacac gtttctgttg ttgctgttat tattggtggc   8820
tttgaggaga gctgctccca tttgggggtt tataccaact gtggattatg gctttgtcat   8880
taagatttga tctttgttaa atgaaaaact gtttattgta taaaactcag gtttgtggac   8940
gaaaagttgt ttttttttctt cagttaatta aattgttcct caagtttgtt taaggactta   9000
aaatcaaaca caaccatgtg taaactgcta aatgaggctc ctaaaatgag aggcctcaac   9060
tctttaagtg tggagctaga aatgtaaata agtccacagg gcagactggt gattatgata   9120
aaagctacca tttactgagc atctgtctac taggctcagc tctatgctaa gtctacatgt   9180
tatctgtcaa agtggtatca tccccattta atagctgagg aaacagaggc ttagaaaggc   9240
tgggtaactt gaccagggtc atgcaactag tctgcggtgg agccaggatt ctgtctgacc   9300
ctaaaggcca agttctttat atttatttct accacctgct aaagtcttga atggaggctg   9360
aaagcacagt tgggggtatgg ggaagaaaaa tatatataca tacatatatg tatatgtatg   9420
tatgtatgta tgggggggtg ttttgttttt gttttttgata aggagttttg ctcttgttgc   9480
ccaggctgga gtgcagtggt atgatctggg ctcactgcaa cctccgcctc ccgggttcaa   9540
gtcattctcc tgcctcagcc tcccgagtag ctgggattac cggagcatgc caccacaccc   9600
agcaaagttt tgtattttta gtagagacag ggtttcacca tgttggccag gctgatcttg   9660
aactcctcat ctcaggtgat ctgcccgcct ccgcttccca aagtgctggg attacaggtg   9720
tgagtcaccg cgtccggcct acagatatat ttaatttaaa ggatctaaa acaaatacaa    9780
aactgtccac atctatgttg atggacccat aaaaatagca gtctgccagg gtctgccgga   9840
agagacagat aagcatacat attaacatgg atatatatgt gaatttcatt caaatggttc   9900
tcacatgaga gtaactagca tctttctctc agatgatgaa gatgatgaag aggaagatga   9960
agaggaagaa atcgacgtgg tcactgtgga gaagcggcgt tcctcctcca acaccaaggc   10020
tgtcaccaca ttcaccatca ctgtgcgtcc caagaacgca gccctgggtc ccgggagggc   10080
tcagtccagc gagctgatcc tcaaacgatg ccttcccatc caccagcagc acaactatgc   10140
cgcccctct ccctacgtgg agagtgagga tgcaccccca cagaagaaga taaagagcga   10200
ggcgtcccca cgtccgctca agagtgtcat cccccaaag gctaagagct tgagcccccg   10260
aaactctgac tcggaggaca gtgagcgtcg cagaaaccaa aacatcctgg agcgccagcg   10320
ccgcaacgac cttcggtcca gctttctcac gctcagggac cacgtgccgg agttggtaaa   10380
gaatgagaag gccgccaagg tggtcatttt gaaaaaggcc actgagtatg tccactccct   10440
ccaggccgag gagcaccagc ttttgctgga aaaggaaaaa ttgcaggcaa gacagcagca   10500
gttgctaaag aaaattgaac acgctcggac ttgctagacg cttctcaaaa ctggacagtc   10560
actgccactt tgcacatttt gatttttttt ttaaacaaac attgtgttga cattaagaat   10620
gttggttac tttcaaatcg gtccctgtc gagttcggct ctgggtgggc agtaggacca   10680
ccagtgtggg gttctgctgg gaccttggag agcctgcatc ccaggatgct gggtggccct   10740
gcagcctcct ccacctcacc tccatgacag cgctaaacgt tggtgacggt tgggagcctc   10800
tggggctgtt gaagtcacct tgtgtgttcc aagtttccaa acaacagaaa gtcattcctt   10860
cttttaaaa tggtgcttaa gttccagcag atgccacata aggggtttgc catttgatac    10920
ccctgggaa catttctgta aataccattg acacatccgc cttttgtata catcctgggt    10980
aatgagaggt ggcttttgcg gccagtagta gactggaagt tcatacctaa gtactgtaat   11040
aataacctcaa tgtttgagga gcatgttttg tatacaaata tattgttaat ctctgttatg   11100
tactgtacta attcttacac tgcctgtata ctttagtatg acgctgatac ataactaaat   11160
ttgatactta tattttcgta tgaaaatgag ttgtgaaagt tttgagtaga tattactttta   11220
tcactttttg aactaagaaa ctttttgtaaa gaaatttact atatatatat gcctttttcc   11280
tagcctgttt cttcctgtta atgtatttgt tcatgtttgg tgcatagaac tgggtaaatg   11340
caaagttctg tgtttaattt cttcaaaatg tatatattta gtgctgcatc ttatagcact   11400
ttgaaatacc tcatgtttat gaaaataaat agcttaaaat taaatgatgc aactcaacct   11460
tttccttaat ggcattacac tctgtccctt aaggagcaac cataaataat ccataaccta   11520
tagagggaat ttggtttccg taaatagccc tttttgcacc tgtacaatcc tggttggggg   11580
gcatgagtca ttgtccccac ttaaggtgga gggaactgag tttggggaaa ttaaggcagt   11640
tctccaagat tatgcagaat agagatgtta ttagcgacta ttgtgtgcat tgtagcaatg   11700
gcatttgata atttacagag cacttctgta tactgtggct ccttagtgga attaagctga   11760
gacctcagat cagtcccttt aaaagaaaag taaaaaatagc cacagggttg tttaactcgc   11820
ttgtattggg ctttggtagt attcgtccca ttggcagaca gtcttctatt ttaaggtaga   11880
gcatagtttg tctccaagaa ttcattgtta aaaacattca ctaggatctg tggaggttct   11940
aggctaagca gagtaagcag aataaacaga tggaaatggg ttcctccctt caatgaactc   12000
aacctgattc accaaagtgt aattcacgag tgacagttac gtagtccaga gcaagtacca   12060
ggtgcaggag agacctgggg gtcacaatgg agacccccata tgggtggcat ggctctctac   12120
ttgccattcc tattacacag cagtgtcttg gctacttggg ctgcccttttg gaaatgggat   12180
caatcttgca ggctccagaa gacagagcca agacttgtgt gttaaggaga tagtttacct   12240
gttgggacat aagagccttg cttgtaagca gcttctcaga actaaaagtg tacaaataac   12300
ctatttctct tttgagtgtc aggttgtact cggttatttc tctagggttt tgttcatctc   12360
agatttttaa ctgtgagccg aaaaaaaaga aaaaggcctt ttgcttcact gagaagaaag   12420
caggtccaga gatgagacag ctttgcttgc ctggacacac agtttgtcag gggcagagat   12480
gggagacacc aagccatgtg tccttgtctg ctttggtcat tttttatttgt ttctttttgag   12540
atggagtctc actctggtgc ccaggctaga gtgcagtggt gcaatctggc tcactcactgcaa 12600
cttccgcctc ccgggttcaa gcgattctcc tgcctcagcc tcctgagtag ctgggactac   12660
aggtgtgtgc caccatgccc ggctaatttt ttgcagtttt agtagagacc aagtttcacc   12720
atgttagcca ggatggtctc gatctcctga ccttgtgatc cacctacctc gacctcccaa   12780
agttctggaa ttgcaggcgt gaaccaccat gcccagccgc tttggtcatt ttataaaggc   12840
aagtaggagt ttagaactca gtcctcctta tcctgcttat cgcacaccct tgagatacga   12900
ggttggtgat actaccatgg acatcttttct gatggtctcg ccatgtagaa aataagataa   12960
aatgcccttt aattctccta gtcccatccc ccagactaaa aaataatgca cccttttcttt   13020
ttgaattgtc attcaaaaaa cttccgttcg tttgcatttt acaggcccca aatcactcac   13080
ggcctctgcc cctgtgtgtg tgcaagagcc aaaagaaagt taagcaacct cacattaatt   13140
gtgtacctaa gattcttgaa gcccagctca gtcatcccag tttctctatt tgtgattacc   13200
```

```
ataaggaacc tacctgagtg tgtccaatga aatggaatgc ttaaccgtga agaaagaaaa   13260
ctgttcatat gaatgaggcc actaaaactac aattcctact atgctctctt tttgctcggg   13320
ctgctgggaa gctcagagcc aaattccacc ccctctaaca tctccagtgg tcattctctt   13380
ctaaatgttt acggtttctt gttttccatt gttaggttag tcatctttttt aatgtatata   13440
atgtagt                                                             13447

SEQ ID NO: 215            moltype = DNA  length = 3624
FEATURE                  Location/Qualifiers
source                   1..3624
                         mol_type = genomic DNA
                         organism = Homo sapiens SEQUENCE: 215
aatgcgcctg cagctcgcgc tcccgcgccg atcccgagag cgtccgggcc gccgtgcgcg   60
agcgagggag ggcgcgcgcg cggggggggc gcgcttgtga gtgcgggtcg cgctctcggc   120
ggcgcgcatg tgcgtgtgtg ctggctgccg ggctgccccg agccggcggg gagccggtcc   180
gctccaggtg gcgggcggct ggagcgaggt gaggctgcgg gtggccaggg cacgggcgcg   240
ggtcccgcgg tgcgggctgg ctgcaggctg ccttctgggc acggcgcgcc cccgcccggc   300
cccgccgggc cctgggagct gcgctccggg cggcgctggc aaagtttgct ttgaactcgc   360
tgcccacagt cgggtccgcg cgctgcgatt ggcttccct accactctga cccgggggccc  420
ggcttcccgg gacgcgagga ctgggcgcag gctgcaagct ggtgggggttg gggaggaacg   480
agagcccggc agccgactgt gccgagggac ccggggacac ctccttcgcc cggccggcac   540
ccggtcagca cgtccccccct tccctcccgc agggagcgga catggactac gactcgtacc   600
agcactattt ctacgactat gactgcgggg aggatttcta ccgctccacg gcgccagcg   660
aggacatctg gaagaaattc gagctggtgc catcgccccc cacgtcgccg ccctgggct   720
tgggtcccgg cgcaggggac ccggcccccg ggattggtcc cccggagccg tggcccggag   780
ggtgcaccgg agacgaagcg gaatcccggg gccactcgaa aggctggggc aggaactacg   840
cctccatcat acgccgtgac tgcatgtgga gcggcttctc ggcccgggaa cggctggaga   900
gagctgtgag cgaccggctc gctcctggcg cgccccgggg gaacccgccc aaggcgtccg   960
ccgccccgga ctgcactccc agcctcgaag ccggcaaccc ggcgcccgcc gcccctgtc   1020
cgctgggcga acccaagacc caggcctgct ccgggtccga gagcccaagc gactcggaga   1080
atgaagaaat tgatgttgtg acagtagaga agaggcagtc tctgggtatt cggaagccgg   1140
tcaccatcac ggtgcgagca gaccccctgg atcctgcat gaagcatttc cacatctcca   1200
tccatcagca acagcacaac tatgctgccc gttttcctcc agaaagctgc tcccaagaag   1260
aggcttcaga gaggggtccc caagaagagg ttctggagag agatgctgca ggggaaaagg   1320
aagatgagga ggatgaagag attgtgagtc ccccaccccgt agaaagtgag gctgcccagt   1380
cctgccaccc caaacctgtc agttctgata ctgaggatgt gaccaagagg aagaatcaca   1440
acttcctgga gcgcaagagg cggaatgacc tgcgttcgcg attcttggcg ctgagggacc   1500
aggtgcccac cctggccagc tgctccaagg cccccaaagt agtgatccta agcaaggcct   1560
tggaatactt gcaagccctg gtgggggctg agaagaggat ggctacagag aaaagacagc   1620
tccgatgccg gcagcagcag ttgcagaaaa gaattgcata cctcactggc tactaactga   1680
ccaaaaagcc tgacagttct gtcttacgaa gacacaagtt tatttttttaa cctccctctc   1740
cccttttagta atttgcacat tttggttatg gtgggacagt ctggacagta gatcccagaa   1800
tgcattgcag ccggtgcaca cacaataaag gcttgcattc ttggaaacct tgaaacccag   1860
ctctccctct tccctgactc atgggagtgc tgtatgttct ctggcgcctt tggcttccca   1920
gcaggcagct gactgaggag cctggggtc tgcctagctc actagctctg aagaaaaggc   1980
tgacagatgc tatgcaacag gtggtggatg ttgtcagggg ctccagcctg catgaaatct   2040
cacactctgc atgagcttta ggctaggaaa ggatgctccc aactggtgtc tctggggtga   2100
tgcaaggaca gctgggcctg gatgctctcc ctgaggctcc tttttccaga agacacacga   2160
gctgtcttgg gtgaagacaa gcttgcagac ttgatcaaca ttgaccatta cctcactgtc   2220
agacacttta cagtagccaa ggagttgaa accctttat attatgatgt tagctgaccc   2280
ccttcctccc actcccaatg ctgcgaccct gggaacactt aaaaagcttg gcctctagat   2340
tctttgtctc agagccctct gggctctctc ctctgaggga gggacctttc tttcctcaca   2400
agggactttt ttgttccatt atgccttgtt atgcaatggg ctctacagca ccctttccca   2460
caggtcagaa atatttcccc aagacacagg gaaatcggtc ctagcctggg gcctggggat   2520
agcttggagt cctggcccat gaacttgatc cctgcccagg tgtttccga ggggcacttg   2580
aggcccagtc ttttctcaag gcaggtgtaa gacacctcag agggagaact gtactgctgc   2640
ctctttccca cctgcctcat ctcaatcctt gagcggcaag tttgaagttc ttctggaacc   2700
atgcaaatct gtcctcctca tgcaattcca aggagcttgc tggctctgca gccacccttg   2760
ggcccctttcc agcctgccat gaatcagata tctttcccag aatctgggcg tttctgaagt   2820
tttggggaga gctgttggga ctcatccagt gctccagaag gtggacttgc ttctggtggg   2880
ttttaaagga gcctccagga gatatgctta gccaaccatg atggattta ccccagctgg   2940
actcggcagc tccaagtgga atccacgtgc agcttctagt ctgggaaagt cacccaacct   3000
agcagttgtc atgtgggtaa cctcaggcac ctctaagcct gtcctggaag aaggaccagc   3060
agcccctcca gaactctgcc caggacagca ggtgcctgct ggctctgggt ttggaagttg   3120
gggtgggtag ggggtggtaa gtactatata tggctctgga aaaccagctg ctacttccaa   3180
atctattgtc cataatggtt tctttctgag gttgcttctt ggcctcagag acccccaggg   3240
gatgtttgga aatagcctct ctacccttct ggagcatggt ttacaaaagc cagctgactt   3300
ctggaattgt ctatggagga cagtttgggt gtaggttact gatgtctcaa ctgaatagct   3360
tgtgttttat aagctgctgt tggctattat gctgggggag tcttttttttt ttatattgta   3420
tttttgtatg cctttgcaa agtggtgtta actgttttttg tacaaggaaa aaaactcttg   3480
gggcaatttc ctgttgcaag ggtctgattt attttgaaag gcaagttcac ctgaaatttt   3540
gtatttagtt gtgattactg attgcctgat tttaaaatgt tgccttctgg gacatcttct   3600
aataaaagat ttctcaaaca tgtc                                          3624

SEQ ID NO: 216            moltype = DNA  length = 101902
FEATURE                  Location/Qualifiers
source                   1..101902
                         mol_type = genomic DNA
                         organism = Homo sapiens
```

-continued

```
SEQUENCE: 216
tgcttacata atggaggtgg tgggggccgt ctcaaaccct ggctggggag cagagagagc   60
ttaggccacg ggagagggca tgcctttgcc ctgcacgaag ctcctggcct gaagctttcc  120
ttcatccatg gaggtggttc attatggtcc ttcctttatg tgaccagagt cattattgac  180
agctgtgttc caaatccagc ttgcattttt aataaggtgt ccatggggga aatcctgggc  240
aaatgggaag tgctgtggtc tgggtgtctg tgtctcccct gaaattcata tattgaaatc  300
ctaagctcct aggtgatggt atttggaggt ggggtctttg ggaggtgatt aggtcatgga  360
ggctagagat ggagcctcat gaatgggatt agtgcccttg taaatgacac cccagacagc  420
ggcctcaccc catctgccat gggagatgac cagacactgg gtctgctggg caccttgatc  480
tcggacttcc cagcctccag aactgggaga aacaaatgtc tgttgttgag gcctcccagc  540
ctacaatatt tttgttatag cagcccaagc taaggcaggt agccaaagga aagccaggct  600
tttgtttaat cagtagcagg gggtcagtgt tcaaagttta gttaaataac taaatgcaga  660
atctcattct ccaatagggt acaatcaacg caaagcccag ctctttcctc tgcctttgac  720
ctggagctgt cccatctgaa tttatgctgg gggaggacag atcacccaag cttgacaatg  780
gttcacatag catttcatct cccggtatct aggtgacacc ctaaaggccc tccctctgtg  840
caaatactcc cccagactta gtctctccct ttcctcattt tgctaaggat agtggcccat  900
tttacttcta aaacaagttt ccatcatttt caaatcatga tatacttgga atagaatcca  960
tacccttttg tccagccccc acgtggaatg tggtctctac caccctttcct gggctgggct 1020
cagctgcctc ccaggccagc tccctgcttt gtggccacag tttcctgtca gtttcctcag 1080
cacacctggc tctgggcccc acaggacctt tgtacaagac ctttggtcca tctgaaacac 1140
cttctgccca actctgcagg actgccttct tccttcgcaa gtcttggtca actttccttc 1200
tcaacaacca aagcaccgcc cctcacaccc ccttacccct acatcagctt gctggtgtcc 1260
gccgtatcac ccaattccat tctcatattt taggcacatt tgcaagccta ggaaggtgtg 1320
gttcctaaga gagactttaa atcacaaata tttatattcc tgtttttttct gcctatggaa 1380
ctgtgaccac atgagtagcg ggtgctctga gatgatactt taaaaactag ctggccagtg 1440
ctgaggaggg cagagccctg tgaggttacc actgacagag ctgggggacaa acgcatttta 1500
ggaaagcaaa gaagccaggc caggtcagtc ctgggagcca ctgtgccacg aggcaggggc 1560
aacgttcttc cagaaaacag tcccagttgt gggacaaatt tgaagctgca aactctacac 1620
tatagacaga actgtgatca ttttattctg aataacttag tgggtgtcac catgagcata 1680
aaaacatttc atcaaatata cacacactgt gttaggattt gagcaatgtc atttcctgga 1740
aggtttttctg agatagactt cacctgcagg taaccagaag tttacttgct gtggtgagtt 1800
gttaggtgaa accaattata tgtcagggcc cagctgccag acaggagcat cttgcttttg 1860
gagtgtttga ttcccctgcc acttttttgag acagtaatta gtagcaggaa actgtcacca 1920
gccaactgat aatcccctca catacaaaca caaataatcc aggcatcctg tgcaccettg 1980
cttatcacgg ccaagaagta cttttcatct ccatttcata acttgattac tctatgcctc 2040
cccaaacaga gcataagctt cttgaggcca gcgattttga ctgttgttct cattgtgatc 2100
tacccagcaa ctggaacagt accggcacgt agaagacgtg acgtgcattt gctgcatgaa 2160
taaacacatg aacatgatgg cataggagaa tgctactttg atggggtaca tgggtatcaa 2220
ggattttctt tctgctcaca caacatgaga tttgtaatta agacacagat ttaaggtgaa 2280
tccggtggct cacacctgta gtcccagcac tttgggaggc tgaggcagga ggatcacttg 2340
aagtcaggag ttcgagacca gcctggccaa catggtgaaa ctctgtctct actaaaaata 2400
caaaaattag atgggagcag tggcacatgt ctgtaatccc agctcctcgg gaggctgaga 2460
atcgcttaaa cctgggaggc agaggttcca gtgggccaag atcacgctac tgcactccag 2520
tctgggcgag agagcaagac tctgtctcac caaaaaaata aaagacacaa atttaaaatc 2580
acgatgacca gaatatggct ctgtttcact cactggaaat tatctgatct gcaagataat 2640
tcttaccaac ccctgagtgt tttttacagg gatgggagtc cattgactct ctaaaatcac 2700
ttgcgaagtt ttgttgctgc ggagctgaga gctggggcca gctgcctgt tgtgcccctc 2760
cataagactc ctggccatgc atttgagcac acctcatgaa gggggcaggt ggctggccgg 2820
gctgttatgt gtagcaagca tgtgttctaa attacaattc atttgttcta aattacattc 2880
atcatttcta aatttgttct aaatttagaa cacagcccca ggagacccc ttcacccaac 2940
catgttctgc agtcttgatt cattttctta cttaaaaaat gctattgata acctgttgct 3000
atttctgcct cagtctctta ggaaatgtat aaaacagaaa atcacatatc ttccaaagctc 3060
tggagcttta catgatgaag ataagcaatg atttctcatt tcattctttc tcttaatcaa 3120
ctgaattaat tatatactca ttttcatttg gatatgatga ctaggcagac ttcaagtata 3180
accatccata accttgctta atgccatgat gtttggattt ttttcaaaga gaggaaaaaa 3240
ctcccttggc ttctattaca gcatccatat tttgtgccat tttaattttt tcttgtgtct 3300
ttttttctctc tctttgggaa atatcagtat cattcctttt ggtaaatttt aaatcaccac 3360
ttaatttcca atagaaaaaa tgtttttagtt acacctaaaa taatcccaaa cctcaaacac 3420
actgtgagca caccagaaag taaaaattat atggagtaga acagattagc ccagaatacc 3480
tcccattcat tttcccaggt tcctaattta ataatttcag tgactttaat ttatcacaga 3540
ccctcagtct gaactcggca tgagcagggt agacaaccaa acctgaaaat tcaagttaaa 3600
attcttgttt gggagcttat attatctaga ttaatcatcc acaaggatca agtcagctaa 3660
gtaactctgg ttcagcttaa tctctgtgga ggcagaatta gtcctttaca gtctaggtcc 3720
ttgccccagc cccatacatt tctgtctgct tttttctttt cttttctttt ctgttttgag 3780
acagattctc gctctgttgc ccaggctgga gtgcagtggc acaatctcgg ctcactgcaa 3840
cttccatctc ctgggttcga acaattctcc tgctttagcc tccacacatg ccaccaccgg 3900
ctaattttttg tatatttttt ttttttttt ttttgagac ggagtctcgc tctgtcaccc 3960
aggccggact gcggactgca gtggcgcaat ctcggctcac tgcaagctcc gcttcccggg 4020
ttcacgccat tctcctgcct cagcctcccg agtagctgga actacaggcg cccgccacca 4080
cgccggcta attttttgta ttttttagtag agacgggggtt tcaccttgtt agccaggatg 4140
gtctcgatct cctgacctca tgatccaccc gcctcggcct cccaaagtgc tgggattaca 4200
ggcgtgagcc accgcgcccg gcctaatttt tgtattttta gtagggacgg agtttcacca 4260
tgttggccag gctgatccca aactcctgac ctcaagtgat ctgcccgcct cagcctccaa 4320
agtgctgggg ttacaggtgt gagccacgca gcccagactg tttctttctt aagctcttac 4380
tttctcatgt gtgagttacc ttgtaggttt ccaaggcaga ggggacaaga tggaaaagga 4440
gaacacagaa atctagcctg gaggagctgc tctgttcctg tatttatctg tgtaggtgtg 4500
aatgagggag aaaatgacaa gagaatgaca ttattttaag gctgtttttcc ccccccaat 4560
catttacttt ttgagaaata attgcccaat actgaaaggt atgtcctttc aaaatgttga 4620
tgtttcaaat ggcttcctaa ttacctagtt atacgggggg tgtgtatggt tatctgaagt 4680
```

-continued

```
tacatgggta tacactggtg gtgtgaggtg tccagagaga ggaaaggaag agcagtcctg  4740
gtggctcaaa ccctgaggga tgtgcggggg atgggtgaga atgtgaacag acatgttgga  4800
agctgaatcc gtgcagtggc acccatgcct gtagccatct cagtgggggg tccttctacg  4860
aacaagcttt gattaatgat attttaatgc tagtttagct ttttagcact cccacgccta  4920
aaggctctga tagaagcaag gcccccaccc ctgcaaaaaa aaaaatccat gattttacg  4980
cattccaaca gatctcttaa ggggcagacg gccggagagc caggtgtgcc agggacctat  5040
ggcagcaggg ctgaacgtgc ccgctccagc ctctccagtg ctgggagaga cctctagatg  5100
gtgcaggtga gtttgcaatg agggaaagcc cctcggcaag gactgagttt ccaaacttgc  5160
agacagggca gggagcggtc aaggaagagt tcccgggaag ccctttaaac ggaaaggaag  5220
cggggctagt gtcagagagg tgtgccaggt cccaggcagc cctgctggcc cctaaggaca  5280
tagagtacct gcttctgaga gggctgccac ggtggccacc tgtgaagcct gtcacccaga  5340
actggatggt acctgacttt cttcatagac ccatcttctg ctgggactga agctgacctc  5400
caacagaagc caggtaagcc ctggtccttt cctctggttt tctaaactct tcagctgtgg  5460
ccgagacgga ggtgtcatgg gctgggagag aggctgggtg catttttgaa atgcatgtca  5520
tttttgggtt gcgtttgaac aagctttacc gattgcagta tgtctgcgct accagttcta  5580
agacctgaga ttgttccttt gttttagaaa aacatcagaa accctgtttt gctgttggtt  5640
gcacatttgg ttagggagac aaattctgtg tgtgcttcac aggctttaag atttgggcta  5700
ctgaagcaac gggttcctcc agggagcgtg aaaagtatgt ttctcaggtt tgccctgtg  5760
cccggctcac tggggaaggc aggcgcggca gggactctag ctgggctctg tacctgcctc  5820
caactctgcg tacccgctgt gacctaagag accttccaag tggggtttcc agtcgtgtct  5880
gagacccccc atatcctggc ctctgtgttg gtggcggggg agcggggaga gggagagaag  5940
gaggggagtg ggtacctatt tgtgatgatt gaggtttttca tttccagcca agaggttcct  6000
ctcaacactc tgacagaccg tggggtgggt tgggctccta gacaggagtc ggctctgatt  6060
cagtcggctc tgattcccag cctcctgcag cagccaagct ttgagatgtc agctcaggga  6120
gaagcggggtg gctgggcagg gaggtcagca ggcgaggttc ccactgggtt tccctgccca  6180
tgttgtgctg ggtcagcaac aagagggaca gttaaaatca acaagcaggg cagatgccga  6240
tcagtgggca atcccacaca gccaggggta cacgcatgtg aggagacgta cggagagaca  6300
ggagcaccac cgtcctcttc cccagtcccc aggccactgc tctgtggctc tcaagtggca  6360
tttttgagac actttctaag caagagtgaa agtgtaacaa agaagtgaag agccataata  6420
gactgaagga aaaaagggat ccaggcatct aaaatagaga atgtttcttg cctggcttaa  6480
tactctgaga tttgtaagtc atagccactt aaaacctta aagatacatt ttgacagagg  6540
ccaccaaaaa gagagtgact ctggtcaagg cttggaaata agcgttcgtt ccgatgacag  6600
tccacgtgta cccttcacgg ctgggaaagt ttggcgatcc tggtggcgat tggccggggg  6660
tctccactgt acccctcccc atccctaagt gggccaggct gtgctgtggg aggattaatt  6720
tgtgacagca cagttggagg ataatcttgg aaggaccagt ctttgggagg aaaaagtaaa  6780
tacactttcc ctgaaatgct tgattttcac tccctggcca ctacctggtt tcttgctttt  6840
gtgagctgga cttcattttt gttgggcata cacatttgtg aagcacagac atgtcagggg  6900
ctcatctttg tttctcaggc atcatggtac cctcttgcct agcccagtgc ctgccattgg  6960
gcggcagccc aacattgctc cggagtgcag acagacctgg tcttacccca tctcacggag  7020
cgcaaaacct acttgcctct gttaaatggg gagcctcttc tagtcaaagt tcctcaggtc  7080
tcataggccc acagatggaa gctgggttac ctgacgctcc tttctgggtc caagtgagtg  7140
cgtttttgtgt tttccaaaga atagaattta ttctcaagga aatgcccagg aacccagctt  7200
caaagactca agcaaatctg aaattcaaat acaggagctg taaacaggat ggtgtttggc  7260
agacagcctt gctgcttaag tggctcagcc cctcagctgg gctcagtttc ccctcaccct  7320
cctcctagcc tgcctagtga ctgcctgcat gcctcaatta tcctggatga cacctgcctg  7380
ctcgttcctt tgatgctgtt tgaggctctg cctaggtatt ccacccacca atagtatcat  7440
taattaactt acattaagcc cacttagcac attagatcaa ttaggggaca aaagccccag  7500
ccagcctttc ctgtgagtat gccgcctcca tctcaatgcc tacgattctg tccttactga  7560
attcgtatat tgcaggaagg aatttttttt aagtcccaaa gattactatt ttcctaaaaa  7620
ataaagcaag gaaacataag ctgatgtcta atcatttaac ctctgctgta catttctatg  7680
gcactttaca aagcgttgtc atgaatgtct tctctatttt cccaataagg aaattgaggc  7740
tcagagaggt tcactgtctt gcccgaagtc ccacagctca taatgattat gggaacacca  7800
agaactggtc taggttagca ctcagtatgc ccaggcctcg tgtggagcct gtcactcata  7860
attggagggg ctgagactag aacctgtgtc ctctgcctcc aacactgaca catttgcccc  7920
cacaaggaga tggtgcaatg acagccacca gggattataa aaataagagt ggagtaagca  7980
aacactcccc ctcctgtatc ttagtttccc agggtcgtgt cagccccaga cacactcatc  8040
tcctgtcctc agaggcgagg gatcaagagg aaacagtctc agttttgttc tttgtgaacc  8100
ctcctgataa aagttagagt gtttgtagtt tttatatagt gaaaaaaact gtcaaatata  8160
ggccattgta ggtggttcag tctaagatag tctagtaact aaaaaaaaac tcaaaatggc  8220
atttggggct caggcatccc aacagcccac tggcccctga gacaaatgag cttgaccata  8280
tttaatttt catcattgcc cttagagtgt cacaaagcat tacccaagga tagctgaccc  8340
tgtacagtca aagctatgaa aaaagctttg ccctgggtct tggcagggat cagccattca  8400
ttaggtcatg tattaaggga tcctacaacc tgaagtgtct tcagtcatag cacaccccaa  8460
ggacatcatg cactccatga aaatatgtcc aatgaatgaa tgaatgatg ggctccttca  8520
tccttcttgt cagagaaagg tcaccaattg ttccaatgac acagttaggg acaaggggc  8580
tgctcaaaca tcagcatccc ctaagtcaat aagcaaacaa atcctagtta gcaaagctac  8640
cctctctggg ggcagagaca cctgttattt ctcaaatgct ggatgcccaa gggtggcaaa  8700
cacactgttt ggaccccagg aaggagcaga cacatgtggg tgaagctgga ggtcctgctt  8760
ccttgcccag atcctcttgc ccagacacac tctggaaatg ccatcattt tatacaccta  8820
cgtacacatg taaccagcca ggatgccttt gtttttccatt tccgagaaaa cagaggacta  8880
tggaaaacag gtgggccgta aggagcccta cagaggaaga tgcacctgtg gcggtagccc  8940
tgcctgcacc accctgcgag ctcatgccag cttaactcac ttcacggtca atcagaccta  9000
ctgctccaaa cacagtagga aggcgcgcct tcacttgtga gtcggacgaa atcagcaatg  9060
agggcaataa caaccacagt cacgttactc ttagtaacag ccctgagcc cgcagtgtag  9120
cacagaagcc aagcttagtg gtgggcttaa ggctgatgtt gttaactgat accattcaat  9180
agctagatat aggcaactaa aaggtgagcc caaatactga aataagatac agtattagtc  9240
tcctgaaaat aaaaaagagt tgattctgcc aacaacacct taatcctgag agaaagcact  9300
ttcttaggat agaagaaaga catgcaaaac cagactgcaa gcaaaaaatg agagggcatg  9360
cactgttttg acgactctca gatggttacc aaatctcttc tcttaaaact tccatttgcc  9420
```

-continued

```
atatttccaa tcccatgttt gcacagaatc ctgcatgcac aggaggaagc aggcaggatt   9480
tcaagttggt tttagtgcac attcattcat tcagcaaatg ttttctgggc atctgctaca   9540
tgccaggcac catgctggga tgtagtgagt aacacagtgg tcccatgggt gaggagagag   9600
aacatccctg cactcacaga gcttagattc tgctgcaggg agagaagcta taatgcataa   9660
atccacgcgcc atgaaaaaaa aacaaacaaa ctagcagggc aggtagaaag aaggtgccca   9720
gggtagtagt gggggcctct tgggaaatga aatagttgag taaagacctg gatgaagtga   9780
gggagtgaac caggacaccc gcaagaaagg aggccctggg gtggggtgag ctggagatgt   9840
cccagcacca gcaggaaggc catgctgccg gagcagaggg aaaggagggt tgaacagaag   9900
gagaggagag gagaaccagg agcctgagcg ggccgtggca aggggggctgg gctctcattg   9960
agggtgatgg aaaggcaaac agaagtcaag tcagggcgga agttcagcca tggtggctca  10020
cgccctgtgt tgttctggga cagtcagtgc ccacaccacc ccatcccatg ccacgccggt  10080
tgctgtaatt tgcttctaag gagctgggtc tccaagtagc ctcttcctgg gagagttggc  10140
ttggctgagg tgcagggcag gaagggcagg cagcaggaag ggtggcagga gaggaatgat  10200
ccattttcac caacacctgc tcccttggcc gttaacacat gccaaaggga tccattctga  10260
gaaaaattat gaagacccta acctgaaaca catgattaca cttccaaaaa tctgaaagta  10320
gattatcaag actcaataag ttgtgcagag aaagaacact tagcaacaga catcgccgtc  10380
gcccccccttg cagccctgct gggacactcc cacagtcgca gagccactgg ccagctgcac  10440
tcgcttcctc ctcacttgga gagagggaca ccttccagca tcgggtgtga gatggagtgg  10500
ggacgcagtg gctctctgat ggctcagttg gcaaaattgt tggagaacgg gttcagagat  10560
cactgatgcc cttggccagc atgccagacc tgttcctgtt gactccatat ggcctttgga  10620
gttggagaga aggtggcttc cctgccccgt cccgcacgga gccaccagca cctggaaagt  10680
ttgatttcct tcctcgtatc tggaagatgc aggtcgatta ggagggaagt cagtctggag  10740
gaggatacct gtctctggga actccagggc agtcaaggca gacagatgga tcacgaggga  10800
ggagctggaa gggcgggatt gttgacttga tgtctggttg gggtctgatg aatacaggaa  10860
agtggaaggc cacggggaat gctccagtgg gatgcagatg tctattaagt tggctgattt  10920
tatttaccca gttagatgtg gttttatggt ttactgtttg gattgaggct ctgtgtcctt  10980
gggtaataaa cattcacctct ggccccaaaa aatcctaatc cttaaaaata tggaaatgca  11040
ctgagcatcc ctaaaaggta ctttagagga gtctcaaggt tcattttctt taagatttag  11100
tccttaataa agactcaaaa tggctgttcc taaagcctcc tgtccataat gaagaagata  11160
aatcagagtg tacactttgg ggatgtgtgtt gttgacatgc ggcatcctct gcagaaagcc  11220
tgtatctcca agaagcgtgg ccaagggagg gcactgacag ctgagtttag agtgggattt  11280
gtaagcagca caaactaatt gtgcatcggt agatttgcag agtgtggttt tctgttgatg  11340
gatttctttta tgggcaataa aatctccaat aagtaccatt tacattcagc agaactcttt  11400
ttgaatttta gctcattctt agagagattt ggagagaagg agaccatccc tgcacatgca  11460
gcaggcacct ggcctgtctg ggtggccagt ccttgttctg tggccactgt gaaccccgcc  11520
aatgtcctag tttcccgcca gcactcacta agcaattttg cttctcattt tacgggcaga  11580
cgtaaccaaa gcaaggagac ttaggtgact cgggacactc ggttttgagt caattctaaa  11640
aaccaggaga ccaaactttc tctagaatta ctgccagttg gtttccaaat tgaggtttcc  11700
agatgaaaat tattatccaa acagaccaca cacagcactc tgacttgcct tctgtgcctg  11760
gcatgtgcga gggaaatggc gctggagaat attatcctga tgattatcac agttgttgct  11820
tttgaaggca aatatttatt ttgtgaagat tgcaaaatga agtacaacag aatgttgagc  11880
tcctccttat gtttacagaa taaacagaac tgagacactg gcaaacgcca atgtccctag  11940
ttcttaaagg actggctgca tgcctcccac ggcatcagtt aaagcaggag cctctggaga  12000
tggaggcctt tggtggcagg acagcctccc accaggagg gtctgaggct tccacccacc  12060
tccctgggtt catctctgta aacagctctc ccagtgtggg ctggatgggg tttgaggtgg  12120
ctgctttcct gtttacccty gaacatttct ttgttagaga ggccactgca tttgctgtaa  12180
gacaacgggc tctagatctt tctcaaggct ttgggagatc taatagaaat aaaagacctg  12240
gcccctattc tcatggccta aagcattgaa aggaggaaat aggagagata gccaaattgc  12300
atggtgctgt tactgagccg ttaaacatct gtccctgccg ttgcactgac tgtgccctct  12360
ttgaggacgg gaagcatccg tctgttcatt ctctggcacc tagcacagtg gctgcacaca  12420
gtaggtattc aataaatgtt gaagaaaccc acatttattg ggcatttgtt gcttccttag  12480
cgtttccgtc ttaatctgca cagcagtcct gtgaaataga gacaatcatc actgcttcac  12540
acatgtgcag agtaaggctt ggagaggtga ggtggcttgc ctgagacctc cctcctggta  12600
agttcatgga cttcgccttg ctgtcgtttc catgggctcg ttcagaaatg agagctggga  12660
tgatgtgggc tgtttcaaat tagcttgaag tctaaccttg tatcataact atctcgggtg  12720
tggggatagt atatatcgag cagaggtcta ggtatagaca gatgtgtgaa atgctaaaca  12780
tggctgaact ccccagagac acctcagcag acagccctgc tggctagccc cggatcctgg  12840
acaggtgttg tttgggctgc aggatgctgg gagctagagc ggaaaatgga agcttctctt  12900
tgtatcccca aggccaagag cagacctggc cagccattct tctcacaata gcagtcatac  12960
cagacctaag acgcgccaga caacttcaac ctcaggagcc tttcttcttc cctgaagttg  13020
gggtggactg gtcctggtgg ggttggactg gcatgggcta gccacctggg gcgggtgcgg  13080
ctctggaaag aatgctggcg gcagggtggg gaggagccca gcctcaggtg gacacaggcc  13140
cagagccagc cccttcccgt gctggtggtg gaacgtcaga tcatcattgc tgggtaactt  13200
ctgtcacttc agttccccga ggaaggtca catacttgcc tcatgggaat attatgtgga  13260
tttccgagag ccaaggcagg cagagtgctt agagcgggcc gtgagcacat ggaagtcct  13320
gctcatgctc tgtatgcact cacgggctga gtttaacggg tcagctcaac ctctgcctgg  13380
cagtcattcc cacggtctag tccgtcagag gtccctgtct ttccttggag cagtctatca  13440
atttggccag gtttcaaaac accatgagga ccctgcagtt aaggggcagc tacacgggg  13500
ttggtgtggg gacacagcag gctctgccag ccccatgga gtatggtgcc aggttggcca  13560
cctccccacc agtgacaccg tgaccccact ctggccacac tgattcaagc tcagggctgc  13620
cgcatttgtt ccctctgccc aaaacgcgct ggcccaagat gtctgtgtgt cttgctcatt  13680
cccttcaggt ctatgctaac acgtcgtctt atcagagaaa ccctccctgg ccccacactg  13740
tataaaacag cagctcccac ccctggactc ctgttttacc tttatccata acagtgtcca  13800
ctcaacgact tatacatatg catgtaatat cacataaata tatatatgta aatatataca  13860
tacacacata atatcacata agtattatat atatgtgaat atatatatat ttgaacctag  13920
aacttggtga gtaataagta ttagtttaaa atcacgactt gctgctgagg tgagcggcag  13980
ggcgtgccca ccagagcatt agtggcagtt tcctccttgc tctccagagc ctcccaaggg  14040
ggcttttgct ctcctcacct tcacagaggt ttcgggatgt gactcacctg ggcctccctg  14100
ggattctctc actgcagaac tgtccggaat cagtgaagca aataggggaag agaatgaaat  14160
```

-continued

```
gagctggggt taaagaacaa ccaggagacc ttgaaatagt aaagtatcag gttgagaaca   14220
gagaaagtgg tgagtgactt gcccagcccc ccaccgacc ccaccccacc ccaccccaca   14280
ccattcattt gaacttgacg atgggcgatc tgttaagtgt gagtgtgtcc atggtcactg   14340
atacagcaag cttgagaggt gaatgcatca cactgatttt caagtgaaga agcagaggcc   14400
aggagactca cttgcacacc tcatctcagc caggataata gagccacagc accctgcttc   14460
ccaccgccca gcagtgatgc caggtgtccc ccctacccgt gtgctgcccg tcagagccag   14520
gctggctgtc agggcctagc aggaagcatg tcatgtcaga tggccaaagt gaagaaactc   14580
tattcaaggg acccatttgg ctggtgacat gcgcctcagt ggctcctcct ctgttggcta   14640
ctgctgcctg gacctgctca agccctcctc tcctctgcag ttcctgccat ctgcatcctt   14700
catgattaat ctgaccctgg gtagggaggc aggaggggct tctcttctcc acagccctgc   14760
acctcagcag catggctcag ggtctccaag tccccagccg ccacctgaca tgcccctagc   14820
ttactagctt gctttctcca gcccccactt cagctcctgg ggtgtgccat gcgtgtgtgt   14880
gtgtgtgtgt gtgtgtgtgt gtgtgagaga gagagagaca gagacagaga gagagaaaga   14940
gagagagaga cagcaaccaa agcttgggat ggggcttgga ccaggctggg ggaagtggtg   15000
gggcaggggg cagcccaggg tcagccccag caaacaagag tgttggagga gtgaggttcg   15060
ccaaatggaa gaggcaaatc tgactaaact tctccaacca gatgacacct ttaattctgc   15120
atgtctgggc tctaagacgc agattctcct tttacccaac agcaagaaag agctgttcct   15180
taagtaaggg tcaagtactc gggcagtgga tggagaaaca cagtgagagg aggggcagcc   15240
ttggcatcct cagatgtttc cacgtttccg aattttcagt gaatctggtt ttccacaaca   15300
ctgaatgttt ttgaagctgg cacctctctg cttactgagt agatgcctaa ttggaaatgg   15360
aatgtctgta cttcacacac tacaccccct cctgcccctg ctgagaactt tcccgggtta   15420
atggtttcct tttggaaagc tttcaaatgg tcttcgttgg agtttacatt atctgcttcc   15480
ctctgctctg tatgtggatt atttgcctgt tgggtttaat ttaaccagat ttgcagctgt   15540
gctaacaact tcattggtgc cctcctgctt tcagaatgga ttttcccgtc ttttctccag   15600
cttaccgata gactgtctcc ataccaaaac ctgcacgggg ttgggcattg tctgctggtg   15660
ttctgcctca ctacagaacc tgtttcctct gaccaaactt cactgcacct caggttctaa   15720
ctaggtctct ctaatatttt aatatgaata gttaaaatga attatttatt aaaaatcact   15780
gttaaacaag aaaaaaaaac ttttcctcgg tgctctgaac ctcagcctcc ttgggaggat   15840
ctgcatgttc cctaagcccg tggctccctc ggagctctac cctctagaaa tacgttgcaa   15900
aactcttgag gcgtctaaca aatatgacaa gcccacagat tagcaaagac acgcagagtc   15960
gaccaagttt gatatttttg ttttttact gagctttttg tacttaatag gagacctggc   16020
cacctaataa gatggtgatt attggaaacc acagagatgt aatcagatgt tctagacatg   16080
gatggtgtat ttaacccctt gaaacacttc cacgccctgc ctggatcctt ttctgcttca   16140
tagaccaatg atgagttcct aaaagatatg cacgtctatc ccagtgaagg gccgtagctc   16200
agcaggccct gtacttggca ttacaggggc gggacctgtg tagccttgcc ctctggggcc   16260
ctttgctggt cttcctaccc tgggctcttc cctatgtcag tgccatttgt cgggagaagg   16320
aagaacgact ttgaaccgca gccctgttct gtggatgaag ttggctggag ttcctctacg   16380
agaatagaag ctccctgagg agtttcatct gcatccacag agtccataga tcctgcctat   16440
agataagaga ataagcaaat ggctgttgtt tctttactgt gtcatttaat atgatgtctt   16500
gtggttgatg aaggcttaaa aagtgtgtga accagaagta gaacaagaaa agagggtgcg   16560
gctctcagca ggaactgtcc tgaggtggct gtgggtcctt cagacactga ggcctgtttc   16620
cacctcagc tctgaggcct tctgttcact gaggaatctc cagggctttg tcagcatttg   16680
aaacaacagt gactcctagt gagagccggg tcccaggagg gacgacgtcc agatgtcccc   16740
agtccctcct cactccaagg aacagtcttc cacttcagga acactcaaaa aaggcgagct   16800
cctggccagg ctcggtggct cacgcctgta atcccagcac tttgggaggc cgaggctggc   16860
ggatcacgag gtcaggagat cgagaccatc ctggcgaaca cagtgaaacc gcgtctctac   16920
taaaaataca aaaaaaatta gccaggcatg gtggcgggtg cctgtagtcc cagctacttg   16980
ggaggctgag gcaggagaat ggcgtgaacc cgggaggcgc agcttgcagt gagccgagat   17040
cgcgccactg cattccagcc tgggcgacag agcgagactc catctcaaaa aaaagaaaag   17100
gcgagcttct caggagccaa gctgagaggc caccagatct cccggcggca aaggcagtgc   17160
tgatggtcca tggggtggtc aggggtgcag ggcctgttgg caccctttag ccttagccat   17220
ctaggaaaac ccaggcccgg gccagtgggg gccactggaa tcatcagtgc ctccttattg   17280
gcgtcctgat cacagcacag gtgtctttct aaatgagagc ttgttctttc caaactggga   17340
agtcagaggt atttggggca ccctcagaca cctttttcatc ttagcatttg tcagtcctca   17400
ctgtgcaccc agatctggga ttctaatgcc aatctccagt gaaaggaacc aggactcctt   17460
ggagaagtgg ctgactccag agctggggca gggaaaatac aagaggagcc tggagcacct   17520
tgtagtgcca gaaagtaaag aggtcctaag aaaagaaaaa gaagaaaaag aaaaaaaaat   17580
ggtagtatgt ctaagggaca cacaaaccaa ctaaagagc tcccagtcac catagctgag   17640
acaatttgag caacaaaata aataagtaa tattgggtta aacccagag tttaaaataa   17700
atacccatgt gttcacactg acaaataaat aatggacgga tggacaaata cataacagag   17760
aagaggcagg tctcccgtgc agaggaactc caggtaattc atgtagatgc tgtgcccttg   17820
aggaggttaa acggataact ccctcccta agtgtgcgct ccgcctggag acttccttcc   17880
aaggagcacc ggaaggagtc acttcagagt ggggaatcct gccagtcact gcttcatccc   17940
agtgatcaag gccagcatca gcaatcctga gccatgctgg tagcatggac cttcatgcct   18000
atgagaatgg cacattgcct ctgtggtctt cctctcaaac ccatagcccc agtctgtcac   18060
gagaaaaaca tctgacaact ctcagttgag gaggattcta caaaacacct gtccagtgct   18120
cctcaaaact tctgagtcat caaaaacaag gcaagtcaga aattgtcttg ttagccaaga   18180
agagcctaag gatgtgtgat gattaaatgt aaagtgggat cctggatggg atcctggaac   18240
agaaaaagaa cgttaggaga aaactaagga catctgaagt tgtatgaact tcagttcacc   18300
agtattgcac cagtatttgt tcatcaggga tgaccactgt attgcatcat gtaagatcct   18360
aaaaggaaaa ctggtgtggg gtccccggga acactctgta ttgaatttac aacttgtcta   18420
taaatctaaa actgtcctaa agcagaagaa atcccttgtc tagatgattc agtcaccctc   18480
ctctttgccc tgccctttcc accatccaca gaacgccgtc cagcagttga ggggtggcct   18540
tgacttctcg agctcgttca ggagtgacca caagacatct gatgccgca ggagcctgg   18600
ccgacagtgc caccccttctc ttgctggacc aatgaatttg tgtcctcatg tcatttcctc   18660
cgaccaccac agggctctgg ccaggggctt cgcaagctcc ttagctccca gaccgcaccc   18720
ctgttcccc ggctctattt taggcttatt ggtgctggct gcctccccaa agctgctgcc   18780
ctgcttccag tgctggggta ggaatgagct gagcctacag tccacccacc cacctcttct   18840
cactccggca tccatctggt caccaagcta ccgcgggttg acccaggcta gggtcccagg   18900
```

-continued

```
ttaaagtaga cgcaggtctt gctctcatgt gctggcgcta tccatgtctc gccggcccat   18960
gctccagccc tctccctgat gctgtgccca gggctgagct gcacccacaa gctcccttgc   19020
ccccagcctc cagctggatt tgacccatag aagacacggg tgggaaccca ggcaggagca   19080
tggtggccgg caggggattt actctgcacc tttctgcctg aggccgcagc tgctatccct   19140
gtgttcagat cctctctctc ctttgcccct tcccacacag gctggactgc agctcctgga   19200
gtgctgcacc atcatttgct cccctttgga ccctgcccag caccctcaga cagggtccct   19260
gctgcactcg ccccaggtgg cacttggggc taggctccgt ggaaaagcag attccacaat   19320
ggggccgtgg tttcccaggc caggtagaaa ggcagtgctt gctgagggga cttgcagaat   19380
ggctgcctga gaggctcagg ggttgatggg ctcttccttc tgactcctga atctccacca   19440
gagccctgca cacctcagaa aggctagagc tccagcatgc agactgcaag tgttgtgggc   19500
aggcctggtg aggcagctcg gggtggtggg aagagctaga ccccagctct gccatttgct   19560
ggctatttca agttccctct accctctcag tttcagtttc agtttcttta tctgaaaaat   19620
gggaatagta tctttttttt tttgagatgg agtcttgctc tgtcacccag ggtggagtgc   19680
agtggcgcta tctcggctca ctgaaacctt cgcctgccgg gttcaagcga ttctcctgcc   19740
tcagcctccc aagtagctgg gattacaggc acacaccacc atgcccagct aattttttgtg  19800
tttttagtag agatggggtt tcatcatgtt ggtcaggctg gtctccaact cctgacctgg   19860
tgatccaccc cccttggcct cccaaagtgc tgggattaca gacgtgagcc accatgccca   19920
gtcatgtcta cttttcatgg tgtaatcatt aagataatgt tcataaacag ggtaccatcg   19980
tgtctaagac aaaatacaca gtcaatatgt ggcatttctt tttttttttt tttttttttt   20040
tttgagacgg atcctcgctc tgtctcccag gctatagtgc agtggtgtga tctcagctca   20100
ctgcaagctc cgcctcccgg gttcatgcca ttctcctgcc tcaacctccc aactagctgg   20160
gactacaggc gcctgccacc acgcccagct aattttttgt atttttttagt agagacgggg   20220
tttcaccatg ttagccagga tggtctcgat ctcctgacct cgtgatccac ccacctcggc   20280
ctcccaaagt gctgggatta caggcgtgag ccaccgcgcc tgaccaatat gtggcatttc   20340
tatttttctt attatttcta tttggagaat gaatggacag gatggtctta ctctcctgga   20400
agtggattgt tgagcctttt gtgaacaaag gtgatgctta cagctccgta attggtttaa   20460
aatgggtaag agccttgtgc tgaaaacct gtgatcctca tcttgaatcc caagaaatgt   20520
tgttatttac ataaaaccaa aagtctgtgg ggcattcaaa agttgaaggg cctttgagaa   20580
ctctgatgat gtttttcgtta ttgtgagatg gaagccaagc ttgtggctcc agccaaaaaa   20640
tttccaggtt ttgtagtcgg tgtggaggtc agaacaggca ggcggtcacca tgtgtggcat   20700
gggttctagg acacacgacc cctggaaagt gcatttctcc ttctgttctt ccggaggcag   20760
ccagcaccct gcagatgagg gaagaagtca ttgaggattc caggagccac actcacaggc   20820
tggaaatgtc catggcagtc aagaaagaaa gattctgcca gggttcaggc ccttggcatc   20880
ctcaggtact ggaaagcact ggaaagcagg agaaatgaag gcaggaggca gccagcactg   20940
cactgagccc agacctccca ggtctcaggg gctgatggcg gacactctct ctgcaccgcc   21000
ctcctgccct agccagcccc ctgagtcagc ttctaatggt ctgtctcaca acttgcaggg   21060
aggcggcact atacacacat gctgaggcca ggtgcggtgg ctcatgcctg taatcccaga   21120
actttgggag gccgaagcag gcagaacacc tgatgtcagg agttcaacac cagcctggcc   21180
aacatggtga aacccccatct ctactaaaaa tacaaaaaat tagtgggaca tggtggcggg   21240
tgccattaat cccagctaat ggggaggctg acgcatgaga ggtgcttgaa cctgggaggc   21300
agaggttacg gtgagctgaa attgcgccac tgcagtctag cctggatgac aagagtgaaa   21360
ctccatctca aaaaaaaaaa ttcaattaaa ataaataaaa aaataaacac ctgctgagac   21420
ctcttcctaa gaaattcttt ggacttggag cacaggttgc cttgttctgg gcgtgcccag   21480
ctcagagagc tctagaagaa agttcaagaa ggcaaagagg agaatccagc tagccaaggt   21540
tggggaggtt ggaggaagag tgaacgcccc tgccggaggc cccccggtcc tcaccccctt   21600
ctgagtctca gcatctgcat gggctgtgag ccattgtttt gtgactgaca aatcagatga   21660
gggctgctta tttttcaaat gatcacgtca agttctctga tcacagccat agctacaagg   21720
caagcagagt ggggaagaca cccgtcaccc ttgtgcagac acttgtttta ccaacacttg   21780
gcgtgcaggg caaggcacca gcttctgaac ccaggtcacc tacaatctct tttttcctag   21840
gctgcctcgg cccgttgcag cctgaccttg ccctgccccg gcactccac agcgggcagg   21900
attggaaagg gcagtgtctg gcacgttggc atgaaagcca gccaggaggg ttgggcaagg   21960
gctccagggc ccgtgaggaa ggagtggaga ccacaccatg cagtgccctg cccctgtttt   22020
gatttggtca tcattgtctg tgttcaatcc taagcttgtc gagaactggg ccggcatggc   22080
tattgaagtt ctgtggaaca gaagttggtc tcttacaggg gtgtgctga aacagcaaag   22140
gactggaagg cgtattagtc atctgtgctg tgtaataaat gactcccaaa tgtaactgct   22200
taaaacaaca aatgtgacca tcccacagat tttgagggtc aggaatcagg gagcggctcc   22260
gctgggtggt tctggctcag tgtccttcct gaggctgcag tcggctgggc tgcaacatct   22320
gcgggccagg ccaggctgga ggaccacat ccagaggcct cgcaagtggc tgcggcagga   22380
ggcctcagct ccgggccacg ggagctcccc acggctgtcc ctctgttgcc cctatgtgac   22440
tgagcagcag ccacggcaca gcaggaagct cagtgccttt ggtgacctgg tctctgtaat   22500
tgcaccgtct cttctgccct tttttctgtt ggctagaaac gagtcactaa aatccagccc   22560
gttcacacag ggagaggaat taggctccac cttttgaagg tggtatcaaa gagtttgtgt   22620
atgtgttata aaccacaaca cctgacttct aatgccaact cctctttaac ttctgtgtaa   22680
ccttgggcaa attgctctaa atctctcagc ctcagtttct tcttccataa aatgagagag   22740
ctgatcctat ctctaatacc cttcctctca gccctcacac cctcacacct tcattcattc   22800
tgggtattta tttactaaac atttactcag ctctctgcta gaatgcctgg ggagtttcaa   22860
aaagactgat gcctggtttt aagtctcccc tagtgatgct actgtgcggg cagggttgag   22920
agtcctcctt ctggagtcat aatctgaaaa tgtgatttgc acgcaaatca cctgggggtc   22980
ttgttacaat gaagattttg atactgaggg tctcgggtgc ggctgcgaaat ttggcatttc   23040
taacgagctc ctgggtaatg cagtgcatcc cagggaccac tctttgaact cctcagagcc   23100
agtttctaga tgctggaaga aaggcgcaga aatataaaga tataaaaata taaagatgat   23160
tcccacccto atgaacaag gaatccagtt ggagacggaa aacatgtagc cagcaccatc   23220
agggtctgac cgcctgccca ggatgtggtc caggcaccag gactgagtcg gagggggtga   23280
agaatccccc agtgagcacg gtctcgccgg acctgtgat ttccccacca ccagcatcat   23340
cccctgtccc ctcaggtcca cagcaggaca cagcatcaat ccagatcctt ctgtgatctt   23400
tggaagtctt ccacaaatta ggttgttttg ctgaacggta gttatttcca cagggaaaga   23460
aaagaattag caaatctatc acttgtattt gttcagtcct gtagactatt ccccaggtta   23520
aacatttgtt tagtgagcct gcttttattg gcaccacaaa caaattaaag tgtatttttcc   23580
gaacttatct tcagggtgta aaattccagg cttatggaaa ttctagtaaa atagctttta   23640
```

-continued

```
aaaaaccatc atcttagctt ttattctttc taccttatgg tttttctgtc ttctccaaag  23700
ggccctcttc ccatcccctg agcaggaagg aagtgaagta ttcccacaac cttagacctt  23760
ggtccctgc cccaccctgg ttattctctg tgtggcctgc ctgcaatcct gtccacctcc   23820
ctgcccagtc aggctccctg ggcaccgtcc agaggcccca gctcccagac catctccact  23880
cagtgtcctg ccctccttgt gtctcagtat aaccaaggca atgtcaggat cctcctcact  23940
tcatatctca gcctctgaaa cagactccta ggtgaactct gggctcccag gttctcttct  24000
tgctaacctt tacacaccat ttgcagatta atagtcctga aatatttcct gcatcctgtc  24060
actgactcca aacatctcat gtctcctggt gtcgtaaaga agcttcttta actcaaatgc  24120
gtaccacctg gggttctgct aaaaatgtag attctgaccc actgggcctc gggtaggggc  24180
ctgagatttt ccagctctga ggagctccca ggcgatgctc ccctctcagt gcaaagctca  24240
agcagcaaga ttctgcagga tgaggccaca ctacccatcc gtcattttcc acaggggaaa  24300
gtgtcttctt agccagactc atcacgtcat ccagatagcc aaggctcaga cgtcaccaaa  24360
gcctgtgctg ggctggctag accctccatt agcaatttcc ccacttttaa ctgtgtttaa  24420
agaaatctga gttgtatgtt cttatgaccc agattgaact ctggattctc ctgaagcctt  24480
ctctaactca gtgattcttt cacccctttt tggatccctg cacaagttag ctcttcattg  24540
cacactgcct tgcgttgtta ttaatatttt gggtttttctt cttttacatg tttctgtctt  24600
tccagctagc tgctgaagcc cctgggactg cagctcacac tcctttcact tcttttatat  24660
ttctttcagc actgagatgg tgctgtgcct ttagtaagca cttaataaat atctttttctt  24720
taaatgaccc aaagcaaaat tcctgtactt aatgaaaaat tagtttgaga aataaaggga  24780
ataaaaatga aattgaaaca gaatgacccc cattttacag ccctccctga atagcatata  24840
aaggtctgct tcatgccaac atcctcactg agtcctcggg gccaggacct gtatgcctt  24900
ggaggcctgg catggtgtct ggccccataa acatttgaaa aatgcttgat tcgtgagttc  24960
attaatcgtt ctcctctcac cggagataca accatccgaa cttagccagc acatacagat  25020
caatagcagc aagaacaaga ccaagaaagt gggtaatttc aaataaggtc ttggaaagac  25080
agaatcaaag tgcatatcta aaaataggtg gggtggaggt tggagctgag ggcagagaga  25140
agagcaggaa aaaaaaaaag aaggttgtca aagccagggt tcagctgcta gagatcaaga  25200
ccagccatag agcagaggtg ccttctttct tcatcaccct tgttgaatcc aattctcaag  25260
gagctaaaac catgactgtc acacaacgta aactgactgt gcatcaggga ctcattcagc  25320
tccttaatga gggatccctt gaggtggcct tgctgattcc gggagcttct gaggaatgga  25380
ataagttagg ataacaaaac tgcttaaggt cccacagagc agtgaagtct tacaatcttt  25440
gtggttgtct tttttatcag gctaaaatct gcaagctaac atgtaaccct accgtgactg  25500
ggctttggcc aaatagtgca tagcagagtg aagctcaggt acacgcccct ggagatgaca  25560
tcatctcagg caggcctgag tccctggaaa gctagtttcc ttccacatga ccttatttcc  25620
tagtgttcga tggctttttg tatcagcatc aagctttaac ccagggctac ccagagtaaa  25680
gggggcaaat tctgtgcaca gcagtgcaga agaaggtgcc agctcacttc ttccctggta  25740
gctaggaaga aaagagaaca ccatgcctgt gatcaggagg cgccacagac agactggtca  25800
cccatgcagc cttggcttgc cctctgagta tgcctaccac ccttctgctc caattctcaa  25860
caagccagaa tatttctgtg ggatctgtgt tacctcatcc tggttagaac tgctggggac  25920
aaacctcccc ataatgaaca gaaaatgcta catccctggt ttgcaaaact tcaacagtca  25980
aaaggatgca tgtacaatta ttttttctata gggatgcata atccaaaaaa caaaaaaagg  26040
cttgaagacc tatgagctaa accattccat cttaaatgtt gaagtatgtc tgggtcagct  26100
ctgatttagt agatctaggg ggctccaggt tcttcatttc caacaggctc tctggcgatg  26160
ctgatgcagc tggtatgtgg accccacttt gagaagagac agtttccact aaagtgagaa  26220
caatgacggc gccttcccca ggtggtggct gtgaaaatca ggtgatatta tccctgtgca  26280
gcactcagct ccatcccagg gcctgggact gaggcattct tgggacagtg ggcgcatgtc  26340
ctatgctcaa taacacatct ctctatgatc tctccacgcg tcctgttctg tgtgcatgag  26400
ctgttttcta cccctgtggc tggggccctc cagctccgca aagccggatt tgacaggtct  26460
tagactcact aatcttgagg gttttccatc ttttgtttct gtgaagtcac tgctctcaat  26520
aacattgtta cctgaagaga aatttatctt ggtgggttct tactttcctt ttaaaaaata  26580
tccacatatg aagctctcaa acaagcagaa atccaccgtc tagtttttcc caatagactg  26640
tgttattgga agctttgagg gataagggga aaagaaattg gtttatgaag taaaattgaa  26700
gcaattaaag gatcaaaatc accttacatt ttcctacaaa gacacactct gtcaggcatg  26760
gacagccccc tgctctttca agttttatag ccaccccgtc ttggcagaaa aattaggaag  26820
tcacttgttg tgcacaagac tgttgtaaac ctctttgata ataaaaaaag gataaaaaga  26880
caagtaggag acccgtaaac acgaacttta aaggcctgga gaacagcagg cttccccttc  26940
ttctgctcct gctcttagcc cacaagccct caaaccattt tctacagcac atttgctgca  27000
gcctcaggga gaacatgaac tattgaagta aaaaaaattc tagcctttga tattcttcat  27060
gttttttttcc tgttttttccc tgtgaaatat gaacctgcaa ctgattatcc cagggacttg  27120
atctcaaaaa cataatttgg ccgggtgcag tggctcatgc ctgtaatcta agcactttgg  27180
gaggccaagg caggtggatc agttgagggc aggagttcaa aaccagccta accaacatga  27240
caaaactccg tctctactaa aaatacaaaa attagcctgg catggtagcg ggtgcctgta  27300
atcccagcta cttgggaggc tgaggcagaa gaattgcttg aacctgggaa gcagaggttt  27360
cagtgggcca agactgtgcc acagcactcc agcctgggca acagagtgag actccatctc  27420
aaacaaacaa acaaacccat gcacaattgg ctggtcttca ctggtcaacc cagtaaagag  27480
ggtccctctc tgtctccctt tcacttcatc atgttagtgg agttgtttgt cctactcagc  27540
agtttagcca agaatagtgg tccccaggca atcaatcctc cctccactgt gctcccttcc  27600
agggctggca cttggcctct gccagcaggc catgtgggct cagtagcttg ggaagccctt  27660
ctctacaggc agagccaaca cagctgaagc tcattttctc agaaccccta tagccaaaca  27720
cagtagtgtt cctgaagaca gtagggtttc cttactattt gaatgcactt gggcaccgta  27780
gaactctctg atgactattg tccagacaga agatgacctc ttcctcatag tcttcaggtt  27840
gaaagagcac agggtatggc tgagaccaca ggctctgacc ccacataact gcaccggggc  27900
ccgcgagatg aggcataggc cttcctgtgc cctgtgagga gtcactccag aggagctctg  27960
cctgcggctg gcctccaatg ccactgcatt tcttaaggct ttgaagggac ttaatgccag  28020
tctcagcata gtaaatctaa accctcacc caaagttcat gtgttaattg caaagatcat  28080
ctgactttaa aatattgata atagaaatga caaagacgga acttgagtag gcaacaacat  28140
gcaaggcaga caggtctttg cattcttgaa atttgatact taagatgaca ggggcaataa  28200
aagaccagga ggagaggctt gcttcaaagt tggtcttatc aaaacacctt gaggtgttaa  28260
tgactttctt aacagaactc caaggctata aactgcttta gatccaagga tatggtgata  28320
ttgaatgttt taattgtggt attaacagcc ccagttgtaa aagggaaggt gtcactcaaa  28380
```

-continued

```
gatgagggac aaggcctgaa ttttataacc gaatttaatt ggcactgatt tgacgttgat  28440
agtacctggt ttttccagtt ttcaggaaat atttcttttgc ctggggggag aggggggagc  28500
acagaaggga aaggtggagg gagagtacat gatgcaggag gggaggagag ggtgctgcac  28560
atcaaaaggc ccatcttgaa tttcctgtga tgtgctaaaa ccccagcccc ccaccaccac  28620
atcaatgcac agagcagtca cacctctcct acatcaaacc ccaattacta cacacccagg  28680
gaaggtgccc agctctccca ctgcagcagt cacccaaatg agaaggaagg aggcatacag  28740
acacccaaag gtaagaggaa aagacccaaa gccagtagag cccaggagga gaaaatcctg  28800
atggggtaaa aaccttctaa ggatcttcct gtctgtaatg tttttctctc cccaaaagac  28860
ctgtatctgg gaacaactgg gtcatttatt atcttttttt ttttttttga gacgaaatct  28920
cgctctgtct cccaggttgg agtgcagtgg cgtgacctcg gcctcccggg ttcatgccat  28980
tctcctgcct cagcctcccg agtagctggg actacaggca cccaccacca cgcccagcta  29040
attttgtttt tgtattttta gtagagatgg ggtttcacca tgttagccag gatggtctcg  29100
atctcctgac ctcatgatcc gcctgcctcg gcctcccaaa gtgctgggat tacagtcgtg  29160
agccaccgcg cctggcccat ttgttgtcat taaaagatat aatcatgaca ctttggacac  29220
tcaaaaaata aataccagta cccttcacac acacacacag acacacacat gcttgcgtgc  29280
acacacactt ttctaagtgg gtggcatagt taaaaaatgt ttggaggaat attaaagtaa  29340
gttttttagaa tgttcatgta aaagaggcag gttgtgctat tgaagagagt cttagatcat  29400
taaaaaaaat ttaaatgtta agctgaactt tataggattt aattagaatg aatgaactgt  29460
tccttattcc agacgtgctg ttattaagta tgttttttgtc atgctacaca gtttgtggaa  29520
ttatttccaa acatttgggg tctgtggctc tctggaaggt cttctgatta ggaacctcag  29580
ctctctgggt agaagcaagc caagggctgc tgcctgctgt cacttagtga gcactgagtg  29640
tggcgtaacg gagagtgtgg attccagcac tgggatgctc tcctgtggac acgccttcag  29700
cacttcttct ttctggaatt ggagtgctat ttgctgctcc atttgctcag agaaacctag  29760
ttctttaaac agctgccctt tgttgttaaa agattatcct catttcagtc actggtgact  29820
gtggtttggt tgggctttttg gagtttgttg gggtttttttt cccccaaagt acctgatttc  29880
ctcttagagt agggacttttt atttctcata ttttgggttt cctcttcagt ttagggaaag  29940
atgaacagct ccatgacctg atcccttttc gtcacagttc cctgttagtg ggactgcttt  30000
ggagccgtgg catcatgtgg cagagactga gacttgaact ggagtccaga tgacctggca  30060
ggggcttctg gctgtagcac aggtcaccgg tggacctcag aaaagtcctg gatctctcag  30120
agtctcagtt tccccaggag taaataaaaa acgtgccccca tctatacaag cctggatgtt  30180
tttaattaga gcatttcagg aggtgggagg gatctgaaag actatcttct gtgctgccca  30240
gtgggggtagc cacagccata cgtgtctgtt taaatttaaa ttaagtagaa ttcattaaca  30300
tgagaaactc agtgcttcag gggcagtggc cacagttcag gctcagcagc cacagaggcc  30360
atagtcctgg acagtgccag gctcagctgc ctcagctgat ggttgaggaa aatggtccaa  30420
gaagtgagtc caggattggc ccatgctcca gccagagccg accctactgg ctcctcagtc  30480
tatggtcatc tgcttctgag tgtgtggggtg tctctccagc cagctcacac tttcctcttt  30540
ctgccttatc ttcccacaag aaggcagagt ctacagatgg aagggtccct ctttgcaggt  30600
tgcaggcccc aggccaggca gtcctgtgat acccatagcc tgggaattgc ccagaattgg  30660
ccgcaacatt ctgcagtgct ctcaggttca ttcttctgat gaaagggctc ctggctcttg  30720
cagatcatgg agtttattaa aacggagtct ctaaaacccc tcttgtaatt gtcttctgtc  30780
ttgactatat tgctgtccac acctgactac tgtgcaggtg ccatcatcct gtaattttac  30840
cagacgaaac cattgggggta cattgggtaa cggggacatg ggatctctct gtattatctc  30900
ttacaagtgc acgtgaatcc actttcaaat agaaagctca attttttaa atgtccttgt  30960
gcagttttta caattcgaat cttcttgaat tttagaacgt cggctctagg catcctagaa  31020
acagattttg aagggctctt gaaagcaaat tgaattcttt tctcatagtt gctatgaaca  31080
gtttaacagt gtgtagtgcg tgatcatttt tgcttacgta gccctttac gttggccaca  31140
gagtttcaga taagaataca tcatgtaaaa cttcagatgt attttcccaa aactggaatg  31200
tgtctctgtt gttggactcg tgcacacagt caagtggttg aagctagggg tgtacagcag  31260
tttgcggcct ctgcagggct ggactgggga cttacaagtg acagtgagtg accttcagtg  31320
acgcagagcc accagatttt gttcagttca attgatcgct ggtgcagatg tccctggcaa  31380
gggtaagaca agtgcacagt gagccctcct gtccttggca tctctgtagc tctctcctta  31440
tcctagaaca acactgggat tgtctgcaga tctcttgttt gtagatcttt gacaaaacca  31500
ttgaagagtg aggatctttg gatttgtgct tttaattcag catcactctg ctcagtctct  31560
tggacagaat ggtactgcgg ttggttttga aaagggtgtg tgtgcgatgg tgtcatgcca  31620
ggaagagttg gccttggcat gggaggccct tgaattgcat tcctttctct cttttttttt  31680
tttttttttt ttttttttga gacgagtct cgctctgtcg cccaggctgg agggcagtgg  31740
agcgatctcg gctctctgca agctccgcct cctgggttca cgccattctc ctgcctcagc  31800
ctcccgagta gctgggacta caggcgcccg ccaccacgcc cggctaattt tttttgtatt  31860
tttagtagag acagggtttc actgtgttcg ccaggatggt ctcgatctcc tgacctcatg  31920
atccaccagc ctcggcctcc caaagtgctg ggattacagg cgtgagccac cgcgtctggc  31980
cgattgtgtt cctttttcat cacttattgg ctatttgagc tttgacaatt atcccaaact  32040
ctttaatcct ccatttcatt acctgtaaga cagggacaac acaacctacc tatttcataa  32100
gattttcctg cgaatgaacg ttggttcaca tgtgtgaaag gctgtgagag cgtccgagca  32160
tctcagcgca atctgcaatg cgccatctgc catcagggaa ccctaaggaa aggctgagag  32220
gctgcctaga cagggcgcca catgctaccc taccagagtt cacagtctca cttggacatc  32280
tttgtggatt tccttctgtg atttacacag ggaaaaaagt ctctccagga ttttatccaa  32340
actgttagat tctgggagag gtgttgggag aaacagctca tgacttatct tacagctgcg  32400
cttcccctct ttgatttccc tgaacacagc tagagttttt cttacaaata ttaacttgga  32460
aaaatgagag ttggcccagc tatgcttgct atggactcac tgcttccatt catttccagc  32520
acagggccca ttagtgtgaa gcaagggtct ccctcccccag gctcaggtca cgagagagca  32580
gcagcaggtt aaaagaccca acacatgggc tgatcacttc tcacctcttc caggaagcct  32640
ccccaggctt ttccgcaccc acccaaggct gagctgagcc caaggcccct tgcatcagaa  32700
tgaatgtgtt ctgaccatag agtttcagaa aagaaaacgt aacaataaca ccatctgcca  32760
gtgagtgctt ttttaatgta aatgtctgtt tttgcagaac gtccataacc aaaagacgag  32820
ttcaaccttc agcatgtaaa tctgatgtag gcagcgggaa ccaggagctc tacctccctc  32880
tgaagagggc ctggctgtga gcagggcagg gcagccaagg agggtggctg gtcccagaga  32940
agctgtgctc caatgctggc tcctccctgc ctgcctccac tggtggtggg tgtgccagat  33000
gcccttgagt gagtgagggg aggtcagcct agactggtgg gtcctggggg cagaggcctc  33060
caggctgcag tgtgtctccc cctcttaatt atttaggagg gaaaggactg gcaactgttc  33120
```

-continued

```
cctttcctga atctggttct ttaccctttc attaaaaatt atggtcagtc ttcttttttct  33180
gtctgggcct ccaaaaccca gtcagggcca ggcccagagg ctctgcagcg ggggccactc  33240
tgcagggtct gctccagtgc tggtcgggag gtggccgagc atttctgcat ccatgcgtgc  33300
tcacccacca ctcatttata cgcctggcct ctgacccaac agttctacca ctgggactct  33360
attgtaagga aataattaga agtctatcca ctgtgtcttt tatgtacgtt gtggcgttca  33420
ttataatagt gaaaaacttt gaaataaagt cgaatgtcca gccttagggg atactcttcg  33480
tacatccaca tggtggaata ctatatagcc atgttcctga agaatatttc aaatgaagag  33540
gctcattaaa tcattaagca aacaggatac aaaactcaat atacgatatg actccttatg  33600
atatatctat atatctatac atagtaaaag gaaatatatc aaaatctcaa taatgtttcc  33660
atatggtagg accagcagtg attttttagtt ttcttcttta tacttttaca tgtttgaaaa  33720
cttctttaca attagtagtg ttttttacaat caggaaaata tgaaaaaaaa tgtaaaaacc  33780
tatcagtgac agagccagcg tggtggaagt tgttgtccac ttttctgctg gctgacgggg  33840
cagcagagac aggtgtgcac cctgccctgg ctcctcatgc ccccaccttc caaacattcc  33900
agattatact tattctttgc ctgatctgag aaattctggt atcctgtttt tggggggagc  33960
accacaggtg aacccataga ggcattcatc agcaagagcg tcttgagaac atagaccacc  34020
ctccactaaa cattctgagg cagtgagcac ttttttttgtt cagacaatct cctaggaaag  34080
tgtcaaacca gctcctaaaa acagagttaa aaccttgggg gatcctcagt ttgaggctct  34140
tgtggacaaa tagagaaact gcagccccgg ggagaactgg tggttgccag gacacccagg  34200
ccagactgag ccagggctgg gatcccaccc ccgctcctct tagcaccctg tactatcagt  34260
ggacccagcc acagggtgtg cagggtggac aggccagcac ccagcttccc tctttggagg  34320
gcactgcttt ctcagagcca ccgtggccac gttagtgcat catgacattg actgagtggc  34380
tgcagactag catgtttttaa atggaaaggg accatgtggt atagcactgt gtaacatggt  34440
ctaggatgga gaatgttgtg tagggcaagt gttggtttca cttggatatg tgtgtgcttg  34500
tatgtatgtg cgagtatttt tagagaaggc ttgagtttct tgagagacct gtggaaaagc  34560
tggtgtctca gaagacatat ctttctcatt ttcagccagc actcctcatc aagctcctga  34620
atccccctgta gacatttggc tctcatacgc tggggaaagg cgaaatctcc actgcccacg  34680
gccccagcag ccattcaccg ggcatccaga gctgagtccc agggcgcatg ccacagccgg  34740
cactggcctg gctggagccc caagggtgtg tgaggcccca gctcccctca gccccatgac  34800
tgctgtgaga accaggtccc ttggaaacct gacaacctga gtcatcttgg cacaggtttt  34860
aagcatcaca gagaaacaaa gcattgaaag atgcaatatt ctgctcatga aagacccagg  34920
aggacctgaa ctgggttgga tcagggagaa ccccaagtca cagcccagcg tccccgtcat  34980
tacagacact ggggagctct gatttctctg ctgcatgtct tgctctttgg gaaaacaaat  35040
ctccaacacc aggtcatctc tccatccacc aggctgtaag agttcccaga tcgcagacca  35100
cagggcttca taggccatca tcagcccctc tgcacaaact tggccttgca atggccccat  35160
cagctttact gaagccttgg ctttcctcgg gccacctgcc accagcatgc cccatataca  35220
ctccattagt cacgattcta gctgttccag agtcaggaat tcacgggaag ccacagagaa  35280
ctggtgttga tacacgtttt tctggctcta acccactttc taagcatgat tttgggagca  35340
cagtgtcccg ttcttcatgg gtgccaattc caatggcctc agccactagc catggaggcc  35400
acttcttgag gacttgcagg gaagtggcat tccatgatgt ggatgtggct cccaggttct  35460
ctcatgaact gtgttgtcac ctgcccaaa cttggtgcct tttcccagcc agccatgagc  35520
ctggagagcc cactatctct ggctgacact tccaagtggc tgtaacattc aacagaattc  35580
attcacatcc agtcacaaca ttcaacaaaa tcagaagcct tgcgcttgag ctttaggtct  35640
cctgggccag atatctaggg gtgttccaac agaagtcacc tgcaaaggcc tgagagctgg  35700
acttgggctt cttaactaca gagactgact cctggctctg ccattgctaa gggagctagc  35760
tgtcccgagc aataggggcgg ccatggggtg ccctcccacc gtccttctgc cctctctact  35820
gtgcgtcctg ggtccagggt cttgccatgc cccctgttc tgcccctgc ctgaacaaac  35880
gcacccttgt gagcctctg cctcagctcc tggaaggcac tgccctgggg tttttttgt  35940
tttttgtttt ttgttttttt tttcctgctg aaggaataac tatttcatgg ttattaatga  36000
aagtgatagc aattccctgt gtatttatct tagattatgt ggtcgttacg agctgaagta  36060
cctcaagcag ccagtctgcg gttgatttga aaacaggcga gtctcaacag tgagcttaag  36120
gaaagtgtc aggtataaat cttgtcttca aacagccagg gtgcattcca gacttcagag  36180
acacttcttt gtataaaggc cctttttttc tctcccgcct ttctttctcc tgggcctgga  36240
ggaggatgaa agtgcagggg tgtgtgcgtt cgtttagtct gataatgagg gtgaggctca  36300
cgggcatggt aatttggcag ctttggcact tcctgtaaca gttttgattt tttttttaatc  36360
caaagggctg cttaaagaca aacatttttt gttaaactgc tggtagttca ttttctgcag  36420
gaactgtgca attaatcttg tttatattaa agagacaggt tgcttttgtc agctttcctg  36480
cgctataatt aataaagatc aaaaacgtta caaaaacata atatttagct taatgcagat  36540
gaggctaggc aacagctgca tcaattagag gagcaaaagg ggaaagaaat accctttgct  36600
ttggaataac tcggatgcat taaaaaacat ggattgtgag gcttctcacc tccactagcc  36660
tcgcctggta ggcccggtga aggatggggt ttggacatca aatagtttgt aaggccgcat  36720
caattatgtt gtaaatgcag ttggaggcac ctactcttaa cccacgttta tccaggtgtg  36780
tggctgtgga tcagaagcat ggagcctgag gatctctgca gtggaggagg gtgaagaaat  36840
cagatggcag gcagaacctg atagaaccat ccagcccct gggggggcctc catgagcccg  36900
gggccacttg atttatagcc ctctatttga aggactgtta ttagaaacca aaacagtgat  36960
tagatatgcc caaacagatg tcattacctg ccccgactt cctaaaccag tgactaagac  37020
ctttggcttc cacatgagag ttcaaacagg gtcatctctg cccataaaca agaggcgttg  37080
ctgtttccag gctttcatct gtctcacgaa gcgaaggtga acagccacct gggagcccac  37140
cagaaatttg gtgagatgc agtgtgaggg ctggaactgg ttgtcagtgg cacccaggcc  37200
agttacctca cttagatttc aaggaattga ggcctgggga aagtgtagaa ctgcaagtcc  37260
cacagttaca cagcctttgc cttggctggg cgtggcggct cacgcctgta attccagcac  37320
tttgggaggc cgaggcaggc agatcacctg aggtcgggag tttgacacca gtctgaccaa  37380
cgtggagaaa ccccgtctct actaaaaata caaaaaatta gcggggcgtg gtggtaggtg  37440
cctgtaatcc cagctactcg ggaggctgag gcaggagaac cgcttgaacc tgggaggtgg  37500
aggttgcggt gtgctgagat cgtgccattg cactgtagcc tgggcaacaa gaacaaaaac  37560
tctgtctcaa aaaaacaaa aaaaaaaga gagcttcgc ctttcctgct gagcttcaaa  37620
acttgggatc ctaatcgtaa aagtccagga caaggaggga tatgcaaaat gaatcataac  37680
ccaaatattt tcagcaaatt ctggtggcat aagaaggtgg ctgagcagat ggaaggaact  37740
gcccataatc aagcatctat gagggaaatt tcactgtcag tcaaccatct aaccagaaaa  37800
gcacccaagg gagccttgtg ccttgccaga tttcaatgcc atgtgtagtt tcttggctac  37860
```

-continued

```
ccagaatgga ctgataaaca tcagaacctg ctgacgtgag agactcttgg tgcagtgcta   37920
gtggaggaca tggagggatt tgagtggcat caggaatgcc agtattctaa accaaatgga   37980
gttcctacct gaaaccaaac caaagtcatc tccaagtttt agaggacacc tctacaggca   38040
tcataacact ctcatgccct ttaacttcta ctcttcagaa tgtataaaaa gggtatctcc   38100
agccaggcac aaagatgttc attgcaactg tatttatgac agtgaaaatt gggaaccagc   38160
ctgaaggaca aatattaggg gattggttga tttaattatg gcttgttcat ttgatgggat   38220
actttcaatc cattaaaaag gctgttgtta agaataatta agacaatagg gaatgaaaca   38280
gtcaaaccac aagtagcccg aacagtgttt taatctaatt ttattttatt tattttattt   38340
ttttgagaca gagtcttgcc ctgttgccca ggctggagta cagtggcacc atctcggctc   38400
actgcaagct ccacctcctg ggttcccgcc attcttctgc ctcagcctcc cgagtagctg   38460
ggactacagg cgcctgccac catgcccggc taattttttg tatttttttt agtacagaca   38520
gtatttcgcc gtgttagcca ggatggtctc aatctcctga ccttgtggtc tgcccgcctc   38580
ggcctcccaa agtgctggga ttacaggcat gagccaccgc gccctacctc taattttatt   38640
ttatgttatt gtatttattt attttttgag acagagtctc actctgtcgc ccaggctata   38700
gtgcagtggt gtgatctcgg ctcactgcaa cctccgcctc ctgggctcaa gattgtcctg   38760
cttcagtctc ccaggtagct gggattacag gcaagtgcca ccacaccatg ttggccaggc   38820
aggtctcaaa cccctgacct caggtgatct gcccaccacg gcctcccaga gtgctaggat   38880
tacaggtgtg agccactgca cctggcctaa tttcatttta gaagatatat atgtctctac   38940
aaataaggga ctgaaagaaa atgccaaaac ccaaaattaa tgggttatga tttttatttct   39000
ttatatttt ctttttatttt acaattcttc cataattgga aaataattat attaccttgc   39060
attcattagc acttactgtt gtaaatactt tatacacatc atctcattta atttatctca   39120
ttaatcctca cattctgacc taggttctat taatatcata attttactga tgagacaacc   39180
aaggcacaga catttagatt acttgcccaa agttgcatag ctagtaaatt aagcccaaat   39240
ttgaacccag gaaatcagac attagagtcc tgttcttata atcactaccc tttaatgcta   39300
ttattaaaat tagttgtgag cgcttccctc agggagatgt gccagtcact catagcctgg   39360
tgggagttcc tgtgtaagat tatcttcccg gccaggtctg gtggctcacg catgtaatcc   39420
cagcactttg ggaggctgag gcagacggat cacctgaggt caggagttca aggccagcct   39480
ggccaacgtg gtgaaatccc gtctcaatta aaaatacatg tatacaaaaa ttagccggcc   39540
atggtggcgg gcgcctgtaa tactagctac tcaggaggct gagacaggag aatcgcttga   39600
acctgggagg tggaggttgc agtgagccga gatcacgcca ttgcactcca gcctggtcaa   39660
tagagcgaga ctctgtctca gaaaaaaaaa aaaagattat cttcccagtg acagctgctt   39720
gaataaaggt cactgaggga atgtgacaga ggaaagcaga cagagacaca gaattcaggg   39780
accatacata ccaggcacag ggctgggtgg gatgagcgtt gactaagatg aaaagagcaa   39840
agcatgtggc tcacaatttt gccaaggaga gtgggtgggg agccttttcc aaggatagtt   39900
tcaggactgg tggccacata atgggataga gaccaccaca cctatccaaa gtttgcaggg   39960
cgagagaggg caggtaggct gcagaatgtc tgtgaaattc ctttaagtaa tgagctattc   40020
aaataataag catatacatt aagatgggaa aatggcagcc catatatctt ggggtatagg   40080
tcttgatgta tagctatctg cccacacacc acaatcgct gctggtctcc ggaacaggat   40140
ctccagttct aaagagaaaa tgatctagga cataacatgg aaatgccatc tatgctatct   40200
aggttgccat aactgcagga ttttataaga aggtggtgag ggaattggtg gataaggtgc   40260
gttacttttc ctcactgggt tatctgagag accatagcaa gaaatcatag aggggatagg   40320
cttatacaga gagaggggct cctttaattc tctttgtctg accctagaag acttatcatg   40380
cctttcagga gcaaccaaag aagttttagg atcttggtaa tctttagtgt ctcacttata   40440
atatgtagaa aaacattatt tcaaaggata tccatattct tgatccctct gacctgtctg   40500
gttcaacttc acttgaccct tgggcacaca aatggtgtta aagagcagag gaaaggctca   40560
aagcctcaga accattttct tctgcctaac tggcctctcc acctgccagt tttctggtgc   40620
ttcttattg tttccatcgc caccagccta ccttaggtcc ttgttcacat agctacctcc   40680
agtgtctcat cagtcacatc catccgacaa tgcagcacc aaattagtct tcctagaaaa   40740
tcatctggtt gtgtcctggt ctaccaaaaa caactataga actggacaag tatgggaggt   40800
aactgcaact gtcatcaggt attggacaac aaacagcaca ggaccgtgag ccttaagaaa   40860
agtaaaatat acccattcac cctggcttcc tagccagagg gaatttgtag actgtagtga   40920
ggccaagcag agaggatgtc ttaatgagat gaagaggcag agtttagaga taaagtatct   40980
acaatttgtg gaacaggata ccagagaaga gagtactgca cagaagaaag tcccagaaat   41040
cagcatgaag tttaccggtg ggtcttggcc aagactcggc acaagctagc agacaacaga   41100
gaacacctgt tgtggacagc agagctcaga tgcctcacag ggataagcaa ttctgaagca   41160
tcggcttagc cagaatgcag aaaagctcagc caccactttg agctttcaat agagactcca   41220
agagcacaga tggattattt gtaacacaaa ggataaatgc ttgaggggat ggataccca   41280
cttttcatga tgtggttatt acgcattgca tgcctatatc aaaatatctc atgtaccaca   41340
taaatatgta cacctactac atacacacaa aaattaaacg tttttttaaaa agacctcaga   41400
aagtctatac ttcaggaatc aggataatgc cttggaacta aaagcagaaa cataaataga   41460
ccaaccctaa taaagaaaaa agtcaagact gacaggtttg ggaggatctt ccagtaattt   41520
gacacttgcc cagagtaaaa ctcagtgcta tttaaagtag atttcacata tcattacgat   41580
gtctggcata tgataaaaca ttaccacaca tacgaagaaa taggaaaatg tgacccataa   41640
tccaaaaata atgaattcaa tagaaacaga ccccaggata atccggatgt tggaattaac   41700
taagacttta gaataactca tattaatatg ttcaaggatt taaagaaaaa gttggattta   41760
atgagtgaac agatggagaa tctcagcaga gcaagtgaaa gtattttta aaaaggaaat   41820
cctagaagtg aaaagtatat ctgaaatgaa aaattcacca gaagggcttt acaatgtatt   41880
ggaggctgta gaagagagaa gcagtgaatt aaagtcagat caattgaacc ttcctaatct   41940
gcataataga gtattttaaa aatttcatca tgtcctcatt attcagaaac cctcctctcc   42000
tatcttgtgt acttaaagga aacaaaatcc tgatatttaa agtattttgc aattagtcac   42060
caaactacct tctacccaat ctcccagtcc ccttcacatg aacccattat ttaaaccaaa   42120
tcaatcaaca agctgcccca gcacctgtac ctccccacct tggcccttcc acacatggtg   42180
ctcatacctg aaattctctc ccctctttca ggtccttgag atgatatcaa atgccaccat   42240
tttaaccttc ttcaatgtgc ctaactagca atgtgatttc tccctttga ccttccgtca   42300
aacaaacaaa tgaaaaaaca aagcagtaac aagagaaaaa taaaacatgc ttttgcttct   42360
ttgtgaaaat attcttggtc ctgcctgcat ggtcttttgt cttggatcta agccctctta   42420
ttagactgta agagtgtcaa gggaaagtct atgtcttact catcattgta caccattcaa   42480
tacctcaaga gaccttggga agatcataat gtctgccgaa ttaattggaa tataactgtg   42540
atttgagaag atagtccata acacaggcat tggttctgat atagtgttgc caagagcttt   42600
```

-continued

```
cactgcatat catagatcta agagaacctc gtggactcgc agaaatggaa gaacctttag    42660
aatgatctag tataagaccc tcattttaca gttaaagaaa ttgcaggctt tagtgaagtg    42720
tcttacccaa ggccccatcc tgatccagtg cccttccctg taaaccatat caccttttatc   42780
cctgtgccaa tatctataca ggattgtgta taggatttgg aacaataaat ttaaacacac    42840
atctaaattt tgacaagaat aagcccctcc catcaagctg tgctttatat taaattcatt    42900
tcagtttttc tggagttcac tacgtgctag tacaataatc acataagaca tcctggcctt    42960
tctggtcgaa ttcctgtatg accttggaca caatgctgcc cagctaacag aaataactga    43020
tggttcagtt ctttgtgacc atttgctaag ttcagagttt cttcaatacc tgtacagtag    43080
tgtggtcatt ggaattacat ggcattggcc tggtcaaatg cagaagaccg atattggagc    43140
ccttcaagac acagctgcta taggggaaac tgagctcata taaccaggag aaggggaaag    43200
atgggtttct gaaaaaaggc ttcaagctac atagaatcct ctcaggatgc tgagaaactc    43260
ccagggcagg tagttatcag cctggtgagc aagtgcaaga aataactgga ttatgagagg    43320
catgcctcac aagtggcccc ttcaatatag aagcatcagt gctcccagat gctggacaat    43380
ggatggcaga caaaggctgc agctgagtcc cccaactggc agctgccctt gggtgaagaa    43440
gcctgcctca tgcaaggtca caccccttcc tgggggcctg gttaatgtgg atgtgtgaag    43500
gcctgggtcc cttgctccag ttcaggacag ctctgtaggg ccatccctgt gctgagaatg    43560
tattgcccct tctgccaaca gtgttgattc caaagccttc tgataaatat cttgcactta    43620
catctccagc ccaaggtctg attcccggag aactggactc atgaagggag caagggcagg    43680
gatgtggaga aggctgaggg cagctccaac agagcagagg ggacagcata tggctgtgtg    43740
tcacgtccag aatgcagact tggagctttg tggtgttcag gatgaagtca cacactgtcc    43800
agctttcagc tacatcatgt cagaatatga acgaataaac aatctcttgt gcttccctgg    43860
ttgatctggc cttgtctggc tcatgtgctg ttaaacacca tcggcccta taaacagaaa    43920
tacaacatgc tctacataaa gacatcacat ctaaattagc cagaggcagt ggcatgcacc    43980
tgtactccca gctactcttg aggctgaggc gggaggatca ttcgagccca aaaatttgat    44040
gctgcagtga gctatgcttg actgagaccc gcctgtcaaa aaaagaaaaa aagaaagaa    44100
agaaaaagaa aaggaatgga gggagggaag gaggagggag gaggagggaa agggagggag    44160
ggaggggagt agggagggaa ggaaagagaa aaaagacatg acatcttaga tggctgtcat    44220
ctgttctgcc ttgtagggct gaacatgtcc ctatgtgtgc tgcattcact cttcagccag    44280
caggcccctc ctggggtcat aagtgcccct ccccatggca ccatgcccag gccgcactca    44340
gtgaataaac catctgacaa ttgatttgtc cagtttgctg cacccaatct ccacagttcc    44400
ccctactccc atatacattt gttatttcaa aaacctcagg aaatgagggc attggcctcc    44460
atgagctcat agaatctttg atttggaagg gacatattac tcggaggtta ttttccagtc    44520
acatctgctt ctaaggcacc atgaagacct aacccatgat aaatcattgg ctacatacct    44580
catcatctta actgagtcac tcttttctctt tggagtttga gaagaaataa ggacatgcat    44640
gttccatatg gcacacagga ctggggttca gtggcctctc tggttggatg attagttcct    44700
gcagccccaa accaatcctc caacctcaga tgattatgtt ttatgagcaa gagggagaaa    44760
tctcatcaca ttttttaggaa aaaaaaagat tttatgatgc aattaattgc aagtcatgca    44820
ctggtttgga ggctgttagc taagacctga tggcagcagg aagtggatgt ccccatagag    44880
ttgtgggacg cagtaggcaa tattattcag agccaactgg aggctcaggt caaacacagc    44940
tgtttgtcag cataagatgc ccaagccgta tcttcccact gactgaaaag caaaattatc    45000
agatattgtg catgtgaata ttaatgcatt gcttttctct ttggaataat taatacttgt    45060
attattgctt ttattaaaaa tagcctatgt tagccaggct tggtggctca cacctgtaat    45120
cctagcactt tgggagggca aggcaggtgg aacacttgag ctcaggagta caccaccagt    45180
gtcggcaaca tggggaaatc ccatctctac aaaaaaacta aaaaaaaatt acccaggcat    45240
ggtgtttcaa gcctgtagat ccagctactc aggaggctga ggtgagagaa tcacttgagc    45300
tctggaggtc gagactgcag tgaagccatg attgtaccac tgcactccag cctgggtgac    45360
agagtgagac tctgcctaaa aacatgtatg tgtttttaac taattttttt aagttttta    45420
gtgatggggg tctcactgtc ttgtccagac cagtcttgaa ctcctggcct caagtgatca    45480
tcctgcctcg gcatcccaaa gtgctgggat tatacgcatg agccaccatg cctggccaac    45540
tctacttttt agtatatgat gatttgtctc tgtgtcccca gccaaatctc atctcaaact    45600
gtaatcccca catgtccagg gagagacctg gtgggaggtg gttggatcat gggagcagtt    45660
ttccccatgt tgttctcatg atattgagtt agttctcagg atatttggtt gtttgataag    45720
tgtctggcac tccccacttc actctctctc tctctcctgc caccatgtga gacgtgcctt    45780
gcttcccctt tgccttctgc gatgactgtg agtttcctga ggcctccag ccattcagaa     45840
ctgtgaatca attaaatctc ctttctttat aaattaccca gtctcaggta gtatctttat    45900
agcagtgtga gaacggacta atacagagaa ttggtactgg tagattgggg tactgctata    45960
aagacaacct gaaaatttgg aagcaacttt ggaactgagt aacagacaga ggttgaaata    46020
gtttggaaag ctcagaagaa gacaggaaga catgggaacg tttggaactt cctacagact    46080
tgttgaatga ttttgaccaa aatgccaata gtgatatgga caatgaagtc caggcttagg    46140
tggtctcaga tggagatgag ggacttattg ggaactgaag caaaggtcac tcttgctatg    46200
ctttagcaaa gagactggtg gcattttgcc cctgctctag agatccgtgg aactttgaaa    46260
ttgagagaga tgatttaggg catctggcag aagaaatttc tatagcaaag cattcaagat    46320
gtgacctggc ttttttctgaa agcattcagt catgtgcatt cacagaaaga tggtttgaaa    46380
ttggaactta tgtttaaaaa ggaagcagag cataaaggtt tggaaaattt gcaacctaac    46440
tatatggtag aaaagaaaaa cccattttct ggggaggaat tcaaactggc tgcagaaatt    46500
tgcataagta acaaggagtt gaatgttaat agtcaagaca gtggaggaaa tgtctccagg    46560
gcatgtcagt gatcttcaca ccagcctctc ccaccacaga cccggaggcc tgggagggaa    46620
aaatggtttc atgggccctg tgcagcccca ggacttggca tcctgcatcc cagccactcc    46680
agctccagct gcagctaaaa ggggccaagg tacagctcag gccattgctt cagagggtgc    46740
aagtcccaag ccttggcaac ttccacttgg tgttgggact gcgggggtgc agaagacaag    46800
aattgagctt tgggagtctc cacctagatt tcagagtatg tatgaaaatg cctggatgtc    46860
caggcagaag tctactgcag gggtgaagcc ctcatggaga acctctacca aggcaatgca    46920
gttggagccc ccacacagag tccccactgg ggcactgcct agtggagctg tgagacgagc    46980
accaccattt tccagacccg agaatggtag atccaccgac agctgccac atgcacttgg     47040
aaaatccaca ggcactcaac accagcccat gaaagcagtt acaggagctg taccctgcag    47100
agccacagag gcagagctgt ccaaagccat gggagcccac cccttgcatc agcatgccct    47160
ggatgtgaga catggagtca aggaagattt tggagcttta agtttaatg actgcccggc     47220
caggtttcag acttttgcat ggggcctatg gcccctttgt tttggccaat ttttcccatt    47280
tggaatggaa actcaatggc tgtatctcca ttgtatcttg gaagtaacta acttgctttt    47340
```

-continued

```
gattttacag gcttataggc agaagggatt tgccttgtct cagatgagac tttggacttt   47400
tgggttaatg ctggagtcag taagactttg ggagactgtt gggaaggcat gattggtttt   47460
gaaatgtgaa aaaaagatg agatttggga gggaccaggg gcggaataag gtttggctct    47520
gtgtccccac ccaaatctca tctcaaattg taattccat gtgtcaaggg agaaacatgg     47580
tgggaggtga ttggatcatg gggcgctttc ccccatgatg ttctcatgat agtgagtgag   47640
ttctcatgag atctggttgt ttgatatgta tctggcactt ccctcttcac tgtctttctc   47700
ttgccactgt gtaagatgtg ttttgcctcc cctttgcctt ctgctatgac tgtaagtttc    47760
ctgaggcctg ccagccatgt ggaactgtga gtcaattaaa ccttctttct ttataagtta   47820
cccagtcttt atagcagtgt gagaatggga gaatggacta atataattcc acttttttagt  47880
atgtaaaata tgtgtttggc cagagagcca acttttttaag aattgtttgg tgctgccaat   47940
attcctgaca ccagtcccca aggggttgtc tttgtgcata attcagctct gcaagtcttt   48000
accaagcccc atggtgtgca ggcacagggc aatgctgaac acactcagat atgtgttgtc   48060
ccaggtgcta ctcccgtcac tgtcacccgt aggtactgac atgagtttgg ggtgtatctg   48120
aagagcctgt gataaagtcg gggaggctg agtataccca gtcatgccct ggtgcatttt     48180
gtacctgaca gctcctcaca gctgctggga cacactccga gcacatctca caggtgtgg     48240
acgactgcca ggaggagggg ctggtgtgtc cttggagtca ccagaaactt ggcagccctc   48300
cctaatgtca gattccttca tgtctgagga ctagtgctgc cagtactagt gcagagaatg   48360
gagtcagaaa atgcaatcaa gtcattagtt tgcttgaact gtcttttatt ttgaggaagg   48420
gtcaaatgga agcataggat agaataggca tcttcatgac aaagtaacat gtgcccctgg   48480
caacccacat tctactttcc gtctctgtga atctgactac tctggggacc tcatacaagt   48540
gggatcacat gatatttgtc cttttcatgac tggcttatct tacttagcaa aatgtcctca   48600
aggttcatgc atactgtagc atgtgtcaga aagtcttttcc tttttaaggc tgagtaatat   48660
tccattgtgt gcatatgcca tactttgttt atccatttgg gatccatggc atttagaaat   48720
aaatagatct caaatttta gaaagttagc tgcattttta ttttcctttc atttccagtc      48780
cttttttcctg gtgttctttg tggctggcat ttaaaatgca gacagtgcca acaagcccag   48840
cttatccatc ctgttcagcc ctctgctggc tcctcttaag acccagagac attgcccctt     48900
ttagtaattt aataaaattag taagtctcaa ggctttaaaa caggtttaa ttttatttta     48960
gtaccagcat actctagttc caaatgcctt ggcgttgctt gggggctctt ggcatgggga    49020
taaataaata aatggccttg gaactgctgg agtagtgaaa tgtgtaatga aacacctaat   49080
aaaagatgtc tttaaagatt acatgcttgg actcagtggc atagcatccc attggcccct    49140
ggaatataca gtgccccagg acggggagct cgcccccacc caagctgggc ttggctgagt   49200
gccctatagc tgttgctccc cacacaggat cgagcttcct gagctgcctc acggacaggc   49260
agcgcccaca tacatagtca caactccttt gcgcattcaa gggcagaaag caccagactg   49320
tacaatgcaa gccagacagc aggggcaac tttttcaaat caccaggctg gtataatacg    49380
gtgatcactg aaaccttgcc cttgcacca cgggaaacat ccaagcaggg acaccctagg    49440
ccttctgctc atgtcaaagg gctcaaagca cctccccggc gtcagttcct ctgggacctg   49500
caggtggcgg cgaccatagc tcctggcctg ggattagaag cttggcctct gcggtcagct   49560
ctctggctca gccttctccc ttgactctgt gacctcagga aggtctggga ccggctctgt   49620
gccacagctc cctcctctgc acggtggggg tgctgcagcc cctccctccc aggcccagac   49680
accaggaccc agggcctctc cttgtttttgc tgcctttgcc caccctatcc cccaccctgg   49740
cacttagccc agcagggctt cgtaaggtct gctgagggca ggaatgtggg ccaggtctgc   49800
ttgtgaagga gcccattatc aatccaggag agcctgcttc acccacagcc agattaacag    49860
ccccatgagg ttagaggcaa cagcattggc tccatggcca ttgttgccgc agccatagtc   49920
aaactatttt aaattatctg aaagaatata ccattcctgg gccgggcacg gtggttcacg   49980
cctgtaatcc cagcactttg ggaggccaag gcgggtggat tacctgaggt caggagttca   50040
ggaccagccc cgccaacatg gtgaaacccc gtctctacta aaaatacaaa aatttgccag   50100
gcatgttggt acagccctgt aatcccagct acttgggagg ctgaggcagg agaattgctt   50160
gagcccagga ggcagaggtt gcagtgagcc gagatcgtgc cactgcactc cagcctggct   50220
gacagagcga gactctgtct caaaaaaaag aatataccat tcctgccgaa cagagacaga   50280
aacaggaaca gagtgtttgc tcctacgtgg ctggatagca attgcctgtg tacattcctg   50340
agaaaccaca atctacatca agcctttac attcaaaaca cttccacatg cattcacctc    50400
agtttaccct ctgagaaatg agtgagcagg aaaacctgtc tccctgtttt ggaagcaacg   50460
taactgaggt gcagtgggtg gaaatggtat gcaaggttat aggctcagag gaattctagt   50520
ctctgctcag ccccgggctg gcatccagcc ctctgcccca gcctgaggtg tgctgcggag    50580
caacacagag catcctggag aaaggagggg tgctcagccc catggattca tctcccccaa    50640
actggagagc agacaccagc caccaagaaa gagccaagaa aggatggctg ctgttactca    50700
acacaccagg ccacggaaaa tacgcggagt cttcgctctg gacattctgt tgtgctcgga   50760
agtgagtcct cccaagcccg tggtgactgc cccatgtcac actggttctg gataattcgg   50820
actagtcacc acctgcccca gcaatctctt tttcaaaaag tttgtccagg gcttcggtag   50880
taacatcagc tctttcacct tggaaaaaag gcacagggta gagagatgaa tacggtgtga   50940
ttgcagttta atctgtatcc cattcataca taatttaact atataaagaa tgaggtgagc   51000
cagaaatgaa aggtttttact ctgatcccca agctctgagg gatagaaagc ctccctctg   51060
tttctcccag ggtgcagcag agccctttgg agtcggagca gacccgtctc aggtgctcta   51120
gctaggtacc tctgctgagc ttgcccttct caaggccttc ccgttactgt acttgaaaag   51180
agaatgacga agaaacgaat tctctttcaa accggtagaa caagaccctg agtttgacag   51240
gaaggatcca aatttatgag ttctttgctt catgctggga ctcgaatgta agggagggaa   51300
aaaaagccca ctctgaaagg gacatgtaat ggttatttat agccctgcac catgcgggtc   51360
acctgcccgg tgaaacgcca tctgtgccgg gttacctgca cgtcagcgaa ggggccggga   51420
aggcatggtc taatcccagg attaggagca gggagaaaat ccatctattg aatcgttcaa   51480
aacaaacaaa caaacaaaaa tcctacccgc tcaaacttaa aagactggga gcctgaaaat   51540
gtttttgttg ctgctgttga gttttcttag cgcgcctcct cctgaagttc tcagggcacg   51600
aaccttcgtg agagtccaga tggccagggt ggtgcctggg agcgaagctg gcttcgtggt   51660
aaaaggagag gcgggaacag gaacgcgctg gaaccgcagg gctcccgccg tcttgaaagg   51720
cctctggcgt ggaaagcagg tggcggaacc gcccgcctca cggcctcact cagcgcagac   51780
tcacaaaatg aaggcaccat ttatgtcttc tagaacggga gggagacggg gacgctggcc    51840
cctgccgtcg ccgtggttca tcgtggttca cctggcctcc ccgggaactt gccaactgcc    51900
acaggtccac aggggtggga tgaaaccaag tccatgcatc cacgcccagg ccccttgact    51960
cgcttggagc ccttcctccc ctcagcccca gccatcgcca gcctttctct tggctcccag   52020
acctctgttc ccaaagctgt gtagaagtgt cgaaagttga gtagatccgg cattgtgcct   52080
```

-continued

```
cggctctccc acctctgtct gtgtgacctt agcaagtcgc tcaccctctc tgagccgcca   52140
ttgactccat gtgttatgtg gggagtagtg agtgcctccc ttgcaatgct ggggaggttt   52200
agtgacacgt ctggcgctgg ataggccctt cacgaatatg ctcagcaggc tgagagatgg   52260
ggcctctgcc cccagcacac acacctgcag gtccacttcc aaacacaggt tccggaagaa   52320
gcccagcgaa ctttctctga ggcacctgtg gagtttccat cacacaaggg gcacctgaaa   52380
ggcagccacc ttcccagcc agcagggaac cgtggcatgg acaggcctct ctgtgcagca   52440
gagctttgtc agctgtgacc tgataagctc ccacctgctg tcgggcactg gcctccttgg   52500
gcatacacgt tcactgaggc tgggaagagg ctgctgggac cagggcagaa gtgcccttgc   52560
gtagtgaggg cctcacacat gggctgtttg cttctcctct gagccaattc tgtgtgcgag   52620
cataatacac atcctaggag agaaggcttg ggttgagggt gattatttat aatggcagtc   52680
aggttgttgt aagacaccat cttttggaag tgacttgttg agaactagtc cctgggtgcc   52740
tctgggccaa ggagatcgtt tttcttctcc ttctactctt ccctgttggc catgccccca   52800
gctggtgcag aggaccctca gagctgagtg taagttaccc atggcagctg ccagctggtc   52860
aggaagggtc gccaggaagc ccctcaaagg gaacagctca ggggaagctg tttggaagct   52920
cagtgcctcc gccttgccct ggtgactggg aggaaggctg tgagctacca ggactctcct   52980
ctggccagag cagattcaga caaaagccag gggcagcccc tttgggaacc tgcctcacgt   53040
ttgagtcacc gacatcaaaa gcaaggtcag gactgcccag gcccagaaaa caaccaaaaa   53100
ccattttgca aatgtagtct tagcaaaaac aaatggaatg ggcaaatgga gaaacattgt   53160
ggtttacgaa tgcagtggaa tacgattcgg caataaaaag gactaaagtc ctaattccca   53220
caacgcagac gcatcacagg tattatattc agtgaaagaa accagctgcc cgattccatg   53280
tatatgaaga tctagaacag gcaaaatcgg tttaaattta tagtgatgac cggtgacagc   53340
ccagcgtggg gcagattgat gatcaagggc gcaagagatg ctctggaaga gatgggctct   53400
gtatcaagcc acaggggtg tatatacgtt atcaaagtct cccacctgta actggaaaat   53460
gtgaagctta ttgcaagtta attacaactc aataaacgtg attagtttta aaactatcat   53520
ctgagcaata agaatacaaa aatctgtgcc actaatcagg acatcaactt gtaggttctt   53580
ggggaacatg cagagtctga gaacaccact ctcatcattt tgcactgttg cccctggaag   53640
cctgccccgt tcagacccac gtcatcgcgt ggtgtgacgt gttgtaattg cgcttggtct   53700
ttgctcagaa gctgcttctt tgttattcta cacgtgactc cacattcaca ttgtgtgacg   53760
acggcactgg atgcttgata cagaggagga gcagagagcc tggctgctct cacctccgcc   53820
cgatctgggg ctcaggcatg gcccagggga gcccagagta catgggccac gcactgagat   53880
tcccactact ccctgggctc atagtggctt caaagggca gctgaggtgg ggagtgggag   53940
gcaagggctg cagagtagga ggcacgtggg ccggctcggc catggaggag ccacacgtgc   54000
tttgccagcc cccatacgtc ctccctccct gcaccttccc cttcagacca tccgagccat   54060
cctgggaggc tcagcctcca ccacccatgt gggcaccttc tgcattacct acaatagcca   54120
gcctgagagg agcagcaagc cctctgcagg ccctcgggac acgtaataat ggcagtcatc   54180
tttaccgcct cttcacgtca ttgcctgcgg cagctctgtg ctattttaga ctctattgat   54240
cctggtgcca ataaatggtt catattcttc aacttcctta acttagaggc tatcgtctca   54300
gtcaaattga tgtcttctgt ctggctgaca tagcttggga ttctagtagc gtgtctttca   54360
atgattaagg attacgttct tgtttttgctt ttgttgtgaa gcagaatcag cgtcactgag   54420
acacgttcat gcaggaggcc tcgtctccat cacaccacaa atactttaag gtgccaactt   54480
tctgttctct agtggagtcc agatccaaca ggaatggctg ggtctggggg aggcagggca   54540
ggctgaaagt attgctttcc aaatatctct gagctgatga gagcaaagaa atgaggacaa   54600
gagctgaggg aggacccagc acagtagccc atggcagaa aacaagaaag agttcttggt   54660
tttatcagaa tgcagttaag caaataactc attcatctat tgctgagaga agagggtata   54720
gcaatggcct tacaggggat acactgtgac tgcacttcct aacgggacat gttctcctcc   54780
tcccagccct cacccacact gttccctctc tctctacttt tccattgtga ttcctggcta   54840
actcttagcc atcatctctt cttgggactt gggacagtcc tcctgacctc cccacctggt   54900
aatctgtcat tagcacccat tttcacatac gcatactctg cactagacac ttgaagtcag   54960
gagttcaaga ccagccttgc caacatggtg aaaccccatc tctactacaa atacaaaaat   55020
tagccaagtg tggtggcgca cgcctgtagt cccagctact acggaggctg aggcaggaga   55080
atcactgaa cctgggaggc ggaggttgcg gaggttgcag gtgagctgaga tcgtgccact   55140
acactgtagc ctgggtgaca gagcaagact ccatctcaaa aacaacaaca acaaatggaa   55200
ggatgagtgg catgtgtatt aaagtgctga agagtggctc ctatcatgtt tcaacaaaac   55260
ttcatgttac tatgcttata taagagtcct agagtggcca ggcacggtgg ctcatgcctg   55320
taatcccagc actttgggag gctgaggtgg gcagatcatg aggtcaggag ttcgagacca   55380
gcctgaccaa catggtgaaa ccccgtctct aataaaaata caaaaattag ttggatgtgg   55440
tggcgggtgc ctgtagtcgc agctactcga gaggctgagg caggagaatt gcttgaaccc   55500
aggaggtgga ggttgcagtg agccaagatc atgccactgc cagcctgggc tacagagcaa   55560
gactctgggg ggtggggcgg ggggggaaga agtcctagaa aaacttgcat tttgtaattt   55620
aaagcaatgt gttagttatg ataacttttc tgatttcacc ctgaaaatgc tttccctcaa   55680
ttttgataag gcaaaaaagt agggatttt tttttcaaaa cttctccaag cttgtcagtt   55740
cgacaagatc ctttcagctc tgaggcattc aatgaaacag aaatgaaatt gtgaacacat   55800
atctttacag caggacattg ggatgaggat aagtgctctc cctctgaact tctgcatgga   55860
tatttgcaag ccacgttatt ttcgtgagca atcctccaag agtgcagagc acccgagcac   55920
cacaaactgc gggaaatgca gagagagctt ccttcctctt tgggacgcca gcccccagttc   55980
tgtgtacaag tgcacacaca cctgcttcat aacataatta gcattctgag aagcccaaac   56040
ctagtctgac aagcagcaat aaccatgttg gtgttcagaa atgttttttag gccacgactg   56100
tttactgcac ttcagaaatt atcatcgtca ctggtttata tgtaggaaaa taaagactag   56160
cggaaaaagt tgagtcaaat agaaagatga gatgtgtcca gatgtgtcca aaatactgat   56220
tttccatgct cttcctgcct ctgtgggttc tgctgaagat tcagtgatgc acagagagtt   56280
ctgaagaatt ggacatgctt atttgtatta gtagtgatcc ttcaaaagaa aatctagaag   56340
taaataagtg tttcatgcat tatatttatt attctacgtg tgcaagaata tctgttttct   56400
gagtattatc tcaattcaaa ttaacaaagg aaacttggga acttggattt taaactttca   56460
actcaaacct acctctgtcc acgtcttttg ggaaggcccc acccgagggc tcagggccat   56520
ttggtttgcc ctcatctgtg cctctccccg caggtccact gtgcatgggg cctgtctggg   56580
tttgccacat acacacacat acattcacac acatacattc atatgcatac actcatacac   56640
agatacacac acacatacac acacatacac tcacacacat acacatcaca tacacttata   56700
ctcacacata taaacataca catatacaca cacaaacata aacatacaga cactcacaca   56760
catatacaca cactcatata caaatacact tacacataag catacacaca cacataacat   56820
```

-continued

```
tcacacactc acacacatac actcacctac acttacacat gcatacattc atacacatac   56880
acatactctt atgcacacac tcacatatac acatgcatac acacatcctc acatatacaa   56940
tacatacact cacacatagg tgctcacaga tacacataca ctcacgtgta tgcacacact   57000
cacacccata tgtttgggGt gggcaacacc cttgagacac ttagggcctg agagaatgca   57060
gggacacagc ccaccccttt gaggggctgc caaaggtcag tttgcccctc atagccctga   57120
aatcttcacc agggagtttg caaatgaaag attttcagtg cagtgataaa gaagagtggc   57180
tgcttataaa cccccatgtg atgctgtttg aaactctggg gcccgccagt gtgctctgtt   57240
gccagtcact tctgtttcag cgtcaccctc cactccagcc ttgggaagga cggtgcctgt   57300
ggtcttgcca agacgtttgg cctgtgctct gcgtgtctgt tccccggcac agcactgtgg   57360
ggggcctccc ctgcctggcc agagaggctg ggaacaggac cggctattta atttgtggga   57420
cccagtgcaa aatggaaatg ggtcagaaat cactgaggac ttcaggctgg caaggccagc   57480
aggacactaa gtgctgcatg gggcaggagg gactcccagg ctaccttctc tgctttcctc   57540
ctgctccggt gaaacagatc cgactaaagc agaagtggaa agagaatgca tccctctcct   57600
cccaatctaa tattaattag cactactcag ctgagacagg gaagattcag agctgtaaat   57660
cacatcaaat ggaagtgttt tcagctgctc tgatggtgac cttgcgggct ccctacaggg   57720
aagggaggtc tgtctgggtt gatgggaagt gggggcttca gggaggcggg ggagtactga   57780
atcctgctgg gtgtggggag gaggccacca gcagcctccc cttgggtctt cctggaggaa   57840
ggagagcgtg ggaggccggg gaaggagagt agcgctgggt gggcagggag cccgcagcca   57900
gctctgtggc tgcctcccag acacaggcag ttgccagcac cttgcctccc gccatggaag   57960
agcttgtgcc catggagctg agtgggccag ccacagcctc tcccctcect gtccgtgatg   58020
cggtcaaccc aggcgtggca agccctgctg ggccaggcca ggtaagcacg ctggaggggc   58080
cacagacaaa agggacatcc gtcctacaga ctttaaaagg taactccgaa ccatcaggcc   58140
tgccaaggct tcccacagcc acctggcctc agctgcttcc cacagatatg aggtgtggcc   58200
ctttcaggga gaagcttttg gaagaggtag caccgtcaca gtcaaggggg gcccaactgg   58260
gtggaagaat gggaagtccc ggaggctgga ccatctgcca gccgaggcag tgactctgct   58320
tctcctaaag gtggtgacca gtagggagga cggccacctt cttcctgcag tgggcactgt   58380
ctgtgctctg gaggcagccg tgatgacaag tatagacagt caaagccaca ccaccaaggg   58440
tgaaggccat tccaagaggc gagcagctca gagaggagac tgagtctagg ggaggacggc   58500
taggaaaggg ggccaaactt gtatataatg atgtgtcttcca tgtctggctc cctggacaga   58560
taaaggccca atagagcagg gacccctatct gtctggcacc gtccttaggg cctataagat   58620
tgccacatag tagcagctcc acagctcttt gttgaataaa tgaatgaact ctaacaagat   58680
taagggaatc ggtgtctagt gcagagtctg cgtgtgtgtg tgtgtgaaaa ggggtgctaa   58740
tgacggcatt tgttctttgg aagaaggcca gaacttaaag agggagagac ccagccaagg   58800
ctttcttcct gggctcccag aaggaattaa acattaatta aacattaaac attctctcct   58860
cacctcagca agatgttgct aggagatcgt ctagaccagt gcttctcaaa ctttaatgtg   58920
cacacagacc acctgcagat ctggttgaaa agcagatccc agacagcagg tctgggcggg   58980
gctgagattc tgcatttcta atgagctccc agctgatgct aatgctgctg gtccaggggc   59040
cccactttga gcaacaaagt ggcaatggtg aggattaagc catggtagtg cctggctggg   59100
gtctgagctc agtagtcata agctgatgtg attacagctg tgtcatcatt ctagatggga   59160
attgaggaag gaagggccaa aggcagagga agagagagca ggtcggggaa gagaagctgt   59220
taattcaggc aggagtggca gacctttcc gtaaagcgcc agatttgaga tattctagac   59280
ttacctggtc atgcggtctc ttatatcatg aaatgcctac aggcactagg taaccaacag   59340
gtgacgcttg actccaaaag agtgtgttca cagaacctgc tgggtggcga ctggcttcac   59400
aacccctgaa ctggatcact agccaattaa ctggttagtt ccacaagtta agcagcagcc   59460
ttgtctgcct caggtgggaa gagacatttc cacgctgctt tggtttgaat gttttcccca   59520
cagtttatgt gttaaaaact taatccctta atccccagtg aacaggtttg aaaggtgggg   59580
aggtgatgag gtcgtgaggc tctgccctca tgaatgactt aatgtcatca tcgcgggagt   59640
gggttcgtta tctcgagagt gggctggtta taacagtgaa ttggccctgc ttgcactctc   59700
ttatcaccat gtgatgccct ctgccatatt atgacatgga aagaaggctc tcaccggatg   59760
cagccagtcg ctcttggact tcccagaacc agaaccccaa ataaacttca gttcattagc   59820
cagtccgtgg tattctgttc tagcagcaca aagcagacta agacaggtgc tccctctccc   59880
catcactgtc acaaatatgg gagctcagtg tgcacgaggc tggagcccca cgtcagtcag   59940
gtccttggtc tcatacccca gcagcatcgc caggcactga tggagattgg ggatccccaa   60000
agtaaaacaa acaggagatc acgactggga gccgtcagcc ccccagcgcc cagtggccca   60060
cctcctgcct gtatctgcag tctgagaagt gggatccaaa ccacaggctg ccctgtgctc   60120
ccctccccca gacccccactc accctctcag agaattggta acaataatga aacacatcta   60180
aggccacaga ctttttagttc tgctttgtgt atctattttt cttttctctc tgcttgggtt   60240
tacctgggaa cgtttta att gcgcctttcg ataagtgctc ctggttgaca ctaaggtgcg   60300
gcaggcccag cccttctcag ttattcaggg aagccctccg aggctcagct ataattagaa   60360
gtcaattaaa ttagaaacca ttcatatggt tcttggaagg cctccagccc tgctgagagc   60420
ctctggccct atccacagac tcagtggaaa cctatctctg ctaaccccac catcctgaag   60480
ccaagtccag ggctgctggg aggggggaaca ggctcctatc agttcccctt caggcctttg   60540
cttgcaccca accctccccc acctgacggg ctgcaggtcg cccttgcctc cccgccaccc   60600
cgatctcccg tcgctgcctg ccccagcttg ctctgttgct agaaggaaaa cacccagcga   60660
gttcaccact ggggtggctg gctcctcaat cttgcctcag tccatttagt gtttttccaaa   60720
cggtaaatgc aacactaaag tgcaggcagt gtgtgggaaa aggcagtttt tgaacctcat   60780
caagagggtc tggaaacaga actcttcctt ccccaaagcc acctggaggt ctccaccaag   60840
tgagacacct ccaaggtgac tgggccaaca gccgagaccc aaggaaagac ccaggaccac   60900
tgctgtgctt tgccagtgac cccagtcagg tctgtcctct ggatctccc ctgggacccc   60960
cttctcccac ctattcttag agcagccagg gacacacgct ttttccttta tcacagaatt   61020
catactctct cttctagacc actcagacaa tacagacctg cataaaataa aaagtgaatg   61080
ttccccagaa tgctccctca gtccttggtc accccaccc gatttcagtt actgccaaaa   61140
aaatctttgc tggaagttca gcaggcatcg ctccagacct gctttcatgc atttagaaac   61200
tttacaaata cacccgaggg cattcttctc tatcatttct ttctcaccca acaacaggtg   61260
ttacagccct gcttggtgtt ccaggaaact gaagttcctt tggatttttt gtgggtgttt   61320
atttgttgca atgataaaca agcgtaccat cttaaggccc tgccaggatt ctgcccaccc   61380
tcttcctacg ggacgagggg catgtgctgt tgtactcggg aggcaggaca ggcgtgctcc   61440
ccagggatct ctggaaggcc tgcagactgg aagctcccta gcagccagtt aactgattag   61500
ttccacaagt taagcagcag ccttgtctgc ctcggatggg aagagacatt tccatgctgc   61560
```

-continued

```
tatggtttga atgtttttccc cacggtttat gtgttaaaaa cacatatgta cttggcattg 61620
ggtgcatctc ctaaaggacc attctctttc cagaaatctc agtgaagaag cccttaagtc 61680
ctgggggatt tggaaaagaa gattgtccat gtcagtcccc actgacaggg cccttggtct 61740
tttgctcttc tccaccgttc cctggctgct gacttacaca gctctcacct ccttctccaa 61800
cttaattctt aatttctttc ttttttttttt tttttttttt ttttgagaca gagtctcact 61860
ctgtcgccca ggctggagtg cagtggcaca atctcggctc actgcaagct ccgcctcccg 61920
ggttcatgcc attctcctgc ctcagcctcc cgagtagctg ggactacagg tgcccaccac 61980
catgcccggg taattttttt gtattttttag tagagacgag gtttcacctt gttagccagg 62040
atggtctgga tctcctgacc tcgtgatccg cccgtctcag cctcccaaag tgctgggatt 62100
acaggtgtga gccaccgcgc tcagcctctc caacttaatt tatttccaat aatctttcgc 62160
taatttctac ctaatgcctt taggctgttg caggactttt ccaaaagaaa gaaagaaaag 62220
gaggaaggga gggaaggttc ctgtgcatca tggcatatgt tcgtcacggt gtttttgtgt 62280
gtggtattgg gaattagttg gtttttcatga ccaatggtag cttgctaagg acgagagaat 62340
tctgagggtg aaaggtctta gggagtttgg gttccatggc ccagctggtc ttctgggctg 62400
tgtcagtggt tgattctgga aggttcctca cacaacccag catctagaag agtacttgct 62460
gtttttgttgt ggcaagagga cagtgaacca gagtgcagcc actggggaat ttaggcgatc 62520
actagagcac attatctctc tttgtagagc caggctaatt aatacccaga ctaccaagta 62580
aaattgcttt gagtcagaaa cacaggtctc cattcagaaa gtgaaaaaac aagcaaaaaa 62640
aaagaaaaaa aaacccacct cctccttcaa gggaatgcat tcgtgtaata ttaatagttg 62700
gtgaaaagta tctgaacacc tgaacagctg cagccatgct caatcccttc aatcccttaa 62760
gtagctgtgt gacctggggc aaatcactta acctctctgg gctcccacta tctcaactgt 62820
aaagttaggt tattggactt gtccactttg atggacaacc tgttcttaac agagagaggg 62880
aagaacacta agctggggct gggagagcat ccagaggggc aaagaccaga atctaattcc 62940
tggcagtctc tccaggggtc ctcctaagtc ctggagccca gaggccagga ctggcctgga 63000
ggactccaga cttaaagctc atgtaaggct aggtttctcc aaaccctctg agcacgagaa 63060
acacaatcac taacctcggg tttaaccttg ggccctccgt gtgctcctag cctcctctca 63120
ggctccctcc caggcatggc tgcgaggctg ggaaggcccc agagtcagcc caagtggcat 63180
gggtacagct tcagcttcat gtctgctttt cttttaggat gtatagtttc ccctctgttt 63240
gctggaaggc accttatatc cagtgggtt aaataaaggt agccagaccc ccggctgggg 63300
tgctaccgcc agtgcccagc taatgacgca tgtctttcag gtgagccctt gggagaggat 63360
ggcccatgtg ggggactgca cgcagacgcc ctggctcccc gtcctggtgg taagtggtct 63420
gagccccctta cccccacagc accctcatcc tcatgatggt tggactgttt cttggcctct 63480
tcagctgtaa aatgggaatg ctgatcatag tccctcctcc acagggttct tctgagggtg 63540
aaatgaaacc aggcctgcaa agcacagaac tctgccccag gctgaagtta cattgatttc 63600
gttggtagct cccttcatag ggtctcatgg atataaacgt tcttgattgc ttgtttgtgg 63660
tgtgatacac acagccctgt gtctatgtga tgagctcatg cttgggggcc gcgcagctaa 63720
gaaagacttg gaagactcag acccctaccc ccatcctcct ggacacgccg gtgttctgag 63780
aagccactgt attagaggct cagtggggga caggggcgcc tcctccatga ccttggcaag 63840
tgcgttgatg aggagaactc agagcaggcc ttgatggtgg gatggggctt ggccagcagg 63900
ggtgaggcag ggtggttcta gtgggggctg gccgtgccca ggtgatcaac caggagccac 63960
tggagactta gcagcagtga gcactcacaa gcgggcacct tcccagaccg agcccccagc 64020
agagccccca ccgcagggca ccccccttcct atgtcaacct tggggtcttg caggagtcac 64080
atgtgtttct aaggaggtac ggaggccaca acacccccct ttgttggcag gtgtctctga 64140
tgtgctcagc ccgagcggaa tactcaaact gcggtgagaa cgagtactac aaccagacta 64200
cggggctgtg ccaggagtgc cccccgtgtg ggccgggaga ggagccctac ctggtaagga 64260
cccagccctc ctggagcctg gtgcgctctc aggggaggcc tcctgcttgt ggcattgttg 64320
ccctggacct gccttgctgt gtgaggggat gccagggtat atcaaaccag ccggtcacgc 64380
tccctggacg ttgagattga tggcaagagc tgccgtgagc ccaggaatgg cactcaccag 64440
ctaagcattc ataaacagat ttttcaggag ttctgaaatg tttttaaagg atcactttcc 64500
cactctaccc tgattaaatg agcgtcagat catctgattg gaagcaggat tgaaatattc 64560
tccagtacta gtacatttttt tcctgagtgc tgcatctccc tccgcctctg ggcaagctaa 64620
gcctgagtgt tctgttcagc actaaggaa acctccgggg tttcagtgtc cggttcttgt 64680
agcaagctga ggaaagtcag atgccaagtg ctacctgcac tgcctgggca ttccagcagc 64740
tcgctgaatt catctcgggg aggctcagaa aaggggcagc atctggagcc tgagagtggc 64800
gaggagaggg gcaagcccag agcatgagct ggttcctggg gggtttttgca gttaggacaa 64860
ctcaggaaac caaggcccgg caagagtagc ttctggagac agctggcacg tcactgccca 64920
aggactgtgg gccgagtccg tatggtttgg ctgctgcact cacctgtgtc ccctgtcctc 64980
tttccctgga cagtcctgtg gctacggcac caaagacgag gactacggct gcgtcccctg 65040
cccggcggag aagtttttcca aaggaggcta ccagatatgc aggcgtcaca aagactgtga 65100
gggcttcttc cgggccaccg tgctgacacc aggggacatg gagaatgacg ctgagtgtgg 65160
cccttgcctc cctgggtaag cacaggccct cctggcaaac cctggcatgc tttctgcaga 65220
aaaccccgag gggctacggg caaggacctt gggaacaggg gtcatggata ctgcaggcct 65280
cggtgcagcc gcacacctgg ccttggtccc atcccacaag gagcagcatc caggacggag 65340
agtcctggcc cctccggtgg acaggcagcc catcaggctc tgcctctgtg tctcctaagt 65400
ggccattaac catcataata tcttctgacc accaaaagga aacaaattgc ttgaatactt 65460
acagtcagt agcgcatgtg aaacactttg ggaaaaagaa aactaaaatt tcatgcaaaa 65520
gcagcatttt tagtatcctg ggaacactct ggggaagcta ctaataaaaa tatttgagtc 65580
atatgatacc tataatccct ccaaaatgat tatgcatcag aagtcttcaa aaagctgaaa 65640
atgcaattag cctgaaagag agaaagataa aatcttcctt tttccaggca tgacacctca 65700
gcaaattctg ccaggacca ggaaaatcaca gactctcaat ccccagaaaa tcctgagcca 65760
tgatcattgc tgcttcctcc ccctagtggc cacaacacat catgctttgc aagggctaca 65820
aatagagact aaagataaaa gcagtggtgg tgtccctggt acagctggta caggtgggag 65880
aggtgatggc agtgatgagg ctggtgggga caagggaggg gatggcagtg atgaggccag 65940
tggggacggg gaggtgacc acagcttagt gcataaggca cactcagagt gtcctaggag 66000
ttgcagaagg acctctcacc tcatggctgg ggaggtagtg tcagcagagg cttgggaga 66060
tttgtgtgagg tgatgcctgg atgagttagg ctaagaagta ggactaggac agaggcctgc 66120
aagtggagat gccgacgcca gagttcagag ggctgagcag ctgggcagtg cctgggggctc 66180
tgattgggtc cctgtggcca gagcaagagt tgtacacctg ggggtgtgga caagctgggc 66240
aggagggcag ggagcagatg gaaccaggct ctggaaacca ccgctgaaga cttgagcctt 66300
```

-continued

```
ccgctcgaag ctgatgcagg tcaacacgca gactgctgag ccagggatgc tgtgggcagg  66360
gagagggctg gagcagaggc accggggggtg gaggagagga agaatctgag agccccctga  66420
aagacagcac tgaccagggg tgcagatggc actcagaagg ggaaagagat tcagaagagg  66480
atactcaggt gtctccatga ctggccatgt ggaaatagtg ccatttgtca gctgcagaag  66540
acaggacgaa gagggtgctt ggtggggagg tggagggagg atagaggttg tgtgtgtgga  66600
atttgagggg actatgggac atccagacct agatagctaa cccagagatg gcctgaacct  66660
ccaggcagag atccagagct gggaagtcac tatgcactca gggtgctggg ggccggctgta  66720
gtagaagggt tccccatggg gcaaattcct actgcaggga gagggtgggt gcaccacgga  66780
acctcgccga cctatgctgc tggctctggc ctggctacgg ttcagacctg agaaggtgtc  66840
catcagtacc cgaaggccag ggctgactct atggcctgaa gaccacgtgc ttggttctga  66900
tacatttacc agaaagtgtg taattactaa agaagttgga cactggaagg gtggtgagct  66960
ccctgcctct agaagaattc aggcgaatgt ggacagccat ctgcagaatt agtgggcagg  67020
ctgctctctg ggcttttaaa cattctttcc agtgctggaa tcttgatgcc tcccgccta  67080
ctccatggga cagtgacctg ctcagtccac accactctca gcacccagga catagcaagg  67140
cccagcacac ctgctgggca ggcaagggac cctgtgcaga gacaccctca gcacgtgcct  67200
cagagtgcct tcgcactgct ccgcagggggt gcagacgatg gggacagttt ccaggttggc  67260
tccatgatgt gctgtgtctg ctcaaagcct cactgccagt cccaacgccc accaaaattg  67320
aaggcccccg cctcacctcc gaatcccagc ccctctcagg ggctcatgct gccccctcta  67380
ctgcagacaa ggcttcccca gggtaggacc ctggaggccc cacttcctct tacgaggctg  67440
tcacgctgtg tcacagagga ggatcacagg agtcttggca ggccggtgtg actagctcca  67500
tgaaaggctg cgttcattcc tgaatccaag tggctgtcag gctgtggatg cggattgcct  67560
tgtcccagtc tctcctgggc ccaggcccct gcctgcggt tggcaggtgc ttctcctgat  67620
gctccgccct ccccacagtg tggccaggac acttgctgaa caatgagcag cacccgaggc  67680
tttcctgttg ggagaggttg tgtgggagga cctgggaacc aaaacaggag gaaaggggga  67740
gagagaggtt acgcttcctc acctctccag gcctcacccc ggaggagctc caccacccg  67800
cgattctgga tggcgggggc aggggggcagg acacagcgac tctgcactgg ttctgcacac  67860
caacacggtt ggaggaaaat gaacatctgg gaatctgcgg cgtcccttac aggcatgaga  67920
gtcctgaaga aaggaactct ctgggaaaat gtacacctat tgactgagag aaagtcagtc  67980
cttaaacaac agatcccagg ggacccattt aaactgactc ttgtcctggg ctatacacct  68040
gaatcaacct atgtagaaca ggggttgggg ggctagggaa aaagtcaaat atggatcaaa  68100
aagtagcaaa ttagaccttt ccagaaagac gaagggaccg gacactctgt agctgggcca  68160
gagatcccta aatgaacacc tgatttcggg ttggtgacaa gcccaggcag aaaaagacag  68220
ccacatgttc tttgttgctg tgcagcccag gatgagagac ccaggtgtaa gccaggcggt  68280
gaggagttta gcctagtcct acagagagaa cctaacattt agaaatgttg catgcagcaa  68340
tacgtgctag aaaacggtgg cttctccttg tcaggaggca ctgaacactc actgggtgag  68400
gaaggacagt ttcataacag cctcttggag ccaatgtttt tttaaaagtt tatcaccggt  68460
caggctcggt ggttcacgcc tgtaatccca atactttggg atgccaaggc aggtggatca  68520
cttgaggtca gaagtttgag accagcctgg ccaacaggtg aaaccccatc tctattaaaa  68580
tataaaaatt agccaggcgt cgtggtgcat gcctgtaatc ccagctactt gggaggctga  68640
ggcaggagaa ttgtttgcac ctgggaggcg gaagttgcgg tgagccaaga ttgcttctct  68700
gtactccagc atgggcaaca gaaggagact gtttcagggg gaaaaaaaa agtgtatcac  68760
ctttcaatat tccttaactg agtgacttga taggttgcat agcttgaccc atacacatga  68820
ccccacaga tgagggtggc cagcctgtga cagaaggtgc ctcgtgccca ggacaagtca  68880
aagacacagt cgtgggacag agccaccacc ctccccatgc tcaaaatgta gtggccccat  68940
tgggcaccca tcataaagcc gggtgttgtg catccgccgt gtagccttgg agctttaccc  69000
atgacagaga ccaagcccgg cacctggggt gtgaactagg atgggcagag aggccttttg  69060
gggcctctgt ccacctcagc atcaaagttc cacggagaag aacttggtgt cattcattca  69120
ttcagccaat gtttacagac aatcatcctt ccttagtacc tagcacaagg tccaaggaat  69180
agagacgtga acaaggcttg ccctggaggg cctcccagcc caggagcggg accaatagac  69240
gtgaacaagg cttgccctgg agggcctccc agcccaggag cgggaccaat cccctaggt  69300
gggagagaa atgcgtggag gtagagtgag aaaaggtgga ggaggcaagg gcgaggaagt  69360
gaggcacaga ggaggtgaga tggggagcag gtgggcacct aggagcctga gatgtttctc  69420
agaagtgtca gcgtgggcca gggacgttag aaagctgcag gttgacctgg tctgccccac  69480
atgcccgtga actcacaagg ccacgtggca gacacctgcc ttggcctgcc tcatagaaag  69540
aagtggcttc tggagggcag aaggtagatt tgcgagaggc ttagctgtaa aactggctgt  69600
cgtggcttct ctgggaggtg ttttgagatt ggttaattaa tgtttacaag atacacaggg  69660
atctgaggat aaagggcttt gagggagggc aggcaattat ggtcctaaca ttactggtaa  69720
cagtccaggc tcaggaaggc aggagcccac agaccccgt gccaggctgc tgcttagcac  69780
taccgtcagc gagggcctcc atggggcctg gctaataaaa aagagattag aaagcagcca  69840
tggaaatatt ccttctcatc ccagttcttg aatcgcaata gggaaagtgt tggcaccgct  69900
cacgttattt aatcgactac tcacagtgtg acaaatggct ccatgctctc cgctgagcat  69960
ttgtttatgt aaaatgggcc caggctagga taggagctag agcctgcaga gggaaggcgc  70020
ccgagctggg agcccaagg agagggtggt gccagcaggg gctgtgcctg ggagcgggac  70080
ggctgcaggg agcacagcca cagggcagac ccctgagagc aggacctgag cagtcatata  70140
gccacggggc tggcactgtg acatcgggga gctgaaagac ataatggaac atcactggga  70200
gctgaaggac ttcaaacaga gctactgtga atgatttgtc ccttgcactg tgtgtgcagc  70260
cccagcgtaa aggcttgcac ttccaagggt gtcttctgtc aagtgctttc tgagaaggag  70320
gcacttacaa cctggttgtg ttgccagcta tcatgagggc cacctgcatt gacctctctg  70380
gacagcacaa ccgtctgtct cctgcagctg cactctggta gcattcagca gcagtaaaga  70440
tggcttggga gttccaaggg tcccagaggc acactgatgc ctataatccc actaggctgc  70500
aggctctggg gagggtgctc acagagggca tgttcctcct ccaggaaggt ctggccttgg  70560
ttggtgtgac ccctggggggg ctaagcaggc cctacatgtg ggggcacagg gatatttctg  70620
gtggatgatg tgatggcaca cacactaaac acagccacca gagagaggaa ccagaaaggg  70680
gctgagatca aaagaaaggc ccacgttggc agctcaatat tgttaaaaga atgctccatt  70740
tcaagacagg ctgaaacccc aaggaaactg agtggacaga gcaggtgact gagtgggcgt  70800
ggcctcatgc ccgacttgat tgtgggcctg cagactggcc accgtgctct ctgcaccagt  70860
ccctgcctgt gtgctgtcca gctcacctgt ctctgttttg tcttgtctct ccccgtagc  70920
tactacatgc tggagaacag accgaggaac atctatggca tggtctgcta ctcctgcctc  70980
ctggcacccc ccaacaccaa ggaatgtgag tgtctttgtc cttccaccag cacggtattt  71040
```

-continued

```
gttcagcacg gatcccttc actacagagg gtgtaggaaa gagccggtcc tggcacctgg     71100
acaaggtgaa tcacagtaac agcactagtg aaagtgctcc tgtggcctgt ccaggcaggt     71160
ctatgaaggg agggatgttt gccacatctg agccttgagt cagaggctga ggttctagtg     71220
caggttggcc accagctacc tgacaagtca cttaacctcc atgagcctcg gttttctcat     71280
cggtaatatg ggggtactaa catctgacct tcccatctct cacggtcatt gtgaaaacaa     71340
aggagatcac agaggcaaag tactactatt ttgcaaagta ctacaaagtg ctaggtgaca     71400
gtgaggccaa ggaaaatata aatgtgatca caattaatga aacagattcc acaaagcaca     71460
tgtaaacagt ctcaggagtt tataatcctg ccttgggggtg tttctttcct gttatccttt     71520
ctggctttca tgggcatctg tttatgacga agggccaggt acctctgcct cagaggaatg     71580
tgctgtgtag actcttagat gtgtggtctg gggagagacg gaggcaggta ggacaagcag     71640
ctgggaggaa gctgggtgtc tggtgccggg ctgcaggagc acttgccacc ctctggctcc     71700
ttcaagggtg gaggaggagc tgaccctggg accctgcctc tctttgctct ccataaggcg     71760
ccactacccc catgtctcat aataatgttg tccaggagaa gaaggagagc ctgcgtctta     71820
tcacgctgga aagaagggga ggagcaggaa tggggcgcag catctcctct ctcctttgg     71880
tcaagccagg aggagggttc tgtgctgtgg gctgtgctgc aggaggagca atgcatgagc     71940
cctgcaccaa tgtgtttgct cgtcttcaaa gccattttcc tggccagcca tatgctaatt     72000
aattcacaaa ttagaggagg ccgcagctcg gctgccagcc tgactcatgg tgaagccagc     72060
tgccatggcc cgcatgtcct ctgtgggggat ctaggctgat tcaaggccag atcattctgg     72120
gttgaagaac cagtctggaa agatgtcaga cactccccac ctattcacaa aagcatcttt     72180
gcctgtggaa cctgggagag gagcagtcct cctcaggggc ttttctgttc aagagttctc     72240
acatggcaca gccttcaatg ttcaatgtct ggcagccaga gcagacttga gtcacggcag     72300
gggcgcctct ctaagtccag caatgaggtc tatcacatgt ggaaagcaag caaagtcccc     72360
tgagtcctca agattttaaa gatgagcgca ccccactccc accccagcc cttgcctgct     72420
ttactgaaag ccggctccga ggaaagcctc ggggtagggc cttagaatcc ggccctgaag     72480
gaggtcagca gagaaataga cagtcctgct gtgttcccat tagaggcccc ttgggcaagg     72540
ccccagacct cggcttgccc atctgggaaa tggggagatg cggccagata ggccttgggg     72600
tggatggagc cctctgggtt agggcctcgg tgtgaatgcc aaacagagtg atgccctcca     72660
cccctgggcc tgccctggtc tcaatccaga gatctcttta ctcagagcac ctgcccagca     72720
gtcagcaaaa acgtcggagc tagaaagccc catggagtca ctaagaccca cacacacagg     72780
actgccatca gcagccccac tctgggcagc aaacatttca tcaggagccc gaagttgcca     72840
actggctgcc caggtccagc aggccctgtc tttgtcaaac ccacagttgt ggtcaagagc     72900
acctcttcct cccctctgtt ttcttgattt acctgggccc tcgccaaaca aagtgcacat     72960
ccttggtact ctgcagcaac aaatggtgga ttacgcaaac caccgtcaga cttgccaagg     73020
gcccctggct gaggatgaca cccacctagg agagctacag cagacaatgg gtcgcagctg     73080
caggggagac accagccagg agtgagccca ggtcagtgtc agggtctccc cagcctagga     73140
gtgcccacag ctctgcccca cacctcccag gctctaaccc tatgcctagg cacctgtgca     73200
atgcaattac ctcctatcct taaagagacg gcagcttctc tgcacctctg tgaagcagag     73260
ggtttcaggg gggtgattcg caggggagca ccctgggggt ttcttatgac tcgaattgct     73320
tggcccaccc ccgattcatc aggtctgggt gagccagaga atgtacattt ttaacaagtt     73380
tgggaaccac tacggtaggt tatgagcctg ctctggaact tcactgcctg agttagacga     73440
gttatctcac ctcccagagc ctcatgtcct ctcctgcccc gggcagctcc cagtggtgcc     73500
cactgcccag gctcctgtgt ggctcaggcg caattttgcc caccaaatcc tcccagaagc     73560
acatcatgag tgccccaggg cgttaattaa tgtggtgcag ccctcaaat aaccctgagg     73620
agaaatgaaa aagcaacata tattttcctt taaaatggaa taaaatcatt ccagtttctg     73680
gggttgccaa gtaatgagag ggaaaccaaa gaggacaggc gtcagattgc agatcagtcc     73740
tggctgtggg ttggttgtca ccttggattg gaacatactc gcccccagct ctgagcctgt     73800
actcagtgac tgcaatactg tggagccctg tagcccggtg aaaagagatg aaaaggcctt     73860
cggttatttt tcagttaact taaagagcaa gatgtgacttg gggtgaccag agctttctgg     73920
ttttctgttt tccctgcacc atcctgcata aagggatctg tgatttaatg acagtggggg     73980
cagggaggtc aacccgttgc cctgccgtaa cagagaggaa gatagggtcc agcatcaggc     74040
ttggatttca ttacaagtta tcacccctgg gaaagtgtcc tcatctgcaa aatggggaca     74100
tgattgttgg gaggaaagat gtgatgacgt gggcgatgca tgtggagtgc ttactccagt     74160
gccaggcgcc aggcactgac cagagatgaa gcatcccagc ccagcaggcg gcatggctcc     74220
acggcacgtg agctggcctg cacttccctc actgactggc ggtgtggaca gcacacagaa     74280
ggggaaagag attcagatga ggactcaggt gtctctgtga ctggccatgt ggacatggtg     74340
ccacttgctc agctgcagaa ggcagaggca agagggtgct tggtggggag gtagagggag     74400
gatgaaggct gtgtgtgtgg aatttgaggg gactgtggga catccagacc aagatagcta     74460
acccagagat ggcctgaagc tccaggcgga gagatccagg gctgggaagt cagctacgca     74520
ctcagggtgc cgggagccac tgggcagaag ggctccccat gaggcagctt cgtagtgcga     74580
ggagagggca ggtgcccac ggagcctcgc tgacctacac tgccggctct ggcccgggcta     74640
cagttcaaac ccgagaaggc accccagagc ctgggcact gggcagcaga aatccttccc     74700
tagaaaagca gtcagggcca ggcgcagtgg ctcacacctg aaatctcagc actctgggag     74760
gcctaagcag gcagatcatc taaggttggg agttcaagat cagcctggcc aacatggaga     74820
aaacccgtct ctactaaaaa tacaaaatta gctgggcgtg gtggtgcctg cctgtaatcc     74880
cagctactcg ggaggctgag gcaggagaat cactgggaacc tgggagatgg aggttgcggt     74940
gaactgagat tgcgccattg cactccagcc tgggcaacaa gagcgaaact ccgcctctaa     75000
ataaataaat aaataaaaag cggtcagagg gttaatgaaa gaacgcaata gcctggcagc     75060
tgttttctta tcatcagtga cgaagtcccc tcaggcaaat ccagacagg ctggccttt     75120
ggagaaatct ctgctactct gcgtactccc gtggtttccg tctcttgtgc cggatgctc     75180
ttccgtgaca ctaaacagca agcactgccc ctcaggtgtg aagcgggcct cccagcctcc     75240
cagacaccgg cgctcagttg ctcctggctc agagcctctc agacctgact gcacacacat     75300
ctccaggac ccgctgagca atggattctg acacagcggg tcccagtggg cccgagactc     75360
agcatttcta gcaggttccc aggggacccc actttgagca gctagagagt ctctgcgagt     75420
ctgcccacag ttcagaatct gccactgggg gtacacagcc agtgccacag tctgggaccc     75480
cttgttgaca gctctaagaa tcaacaaaca gatcattcct aaaaatgcaa tcttttaccc     75540
tctgcagaga atcccagcca gcctctaatg catactggtg agattctaaa ttgtgtggat     75600
taacagacct caaagacccc catatgagct attgtggctg taaatggagg cgtagctccc     75660
tccagccatg tgcttctggc tcactgagca ttcctgggga aggggaacac agtgcccggc     75720
aggaccctcc ccggagtcac cactgcctcg aactccacgc gaggtaggca gaaccagtcc     75780
```

-continued

```
ccgctcattt tcactttaaa ataggccttg tgaggacatt tttgcctgtt ttgtggaact   75840
gcagttcata ccagctttta tcaaacaccc cagccttgct tattcgaaac tcaggtgcac   75900
acggaagtgt acaaggggag atggacccgc agttggccac ccaacagaaa cccacctgga   75960
gcaccttgca cttaacaagc atcccaagag gcagatgaac cgaaacacac agcacacagt   76020
ggaccggggt gaaacctcca gacactgtat atttggttag tgcagagtta atcctcagta   76080
gacaggcata gaccctggcc caggagaact tgggtgcagg tgcagggggt gccggtgcct   76140
atcctggggg ctgcacaggg ctgcatctcc accaggggtc gcgccccacc ctggtttgtc   76200
tgtggacccc cagctggtga cagtggaagg agtggacatg gtgggaagag gatcagccca   76260
gaccgctctc ttttcctttt aatattctgg gttttgccca aacctctttt agacatcacg   76320
tgcattcaac atgatgctgg tgcgctaata atataaaaat gcatacttgt atgattctgt   76380
gatggatttt tttcaagcat ttaggggtaa tgcagagtag gtgcttgttt tccatggcaa   76440
tttttctgac tcgcctggaa aacagcagac ccacccaggg ctgattatcc aacctctgct   76500
tcaggctctg caggtgcctt cattagctgc cctcaaacca cacccattgc tgcccaaggt   76560
tggcactttg ggaccggatc tgctcacctg ttcttgtgtg ttatatgtgt agtgacagtg   76620
gcagcaagca gaggtgagac acttgtgtgg ggggctgacc tcaccctcat gaggtcagcc   76680
ctgcagccag ggatggcaag gcccaccgcc tcccgtttga ccccccctcta gtcttagcat   76740
accttctgtc ttgcccgggg gcagaggcac tgaattgtgt acaaaaaaga ccaagtaagc   76800
tagatgcttg ttcttctttc aattgataca taataattgc acatgtttat ggggtacaga   76860
gtgaaatttc catacatgta tacaaagtgt catgatctga tcagggtaat tatgatatcc   76920
atgacctcaa acgtttatca cttctttgtg ttgggaacac tgcaaatcct ctcttgtagc   76980
tgtgagaaat atacaatgca ttattgtccg ctgtagtcac cctgcagcgt gccagagctc   77040
agaacaactc ctcctgcccg gctggacttt tgtatttgtt aaccagcccc tccttcccca   77100
cctctgttct gctccacttc tatgagatcc actcctttgg cttccacacg agccgcgcgt   77160
tgcttttatg aaacagctgt gcttggggca gatccatttc ctttttttgcc acaagcacct   77220
tccctcgcct gtcggccacg gagctgtgac tctgaaaatt ctggcacacc cttgcctta    77280
tctgtggttt gagggtcttt gctcctctcc ctttctgctga aaaggcagct ccattcctta   77340
ttgccgagct ccgagcgcag ggaagaggcc cattgtcagg aagtgagctg ctgccctttg   77400
gtggcctggg tggcctgtgg gcaagtctga atccccatgt cctcctgctc cttgggcaat   77460
gatctagtga ctgtgattct cctgaccagt cttgtgagaa gtgtctccct gcagatgctc   77520
tagtggccct gggaactttg gaacgtgagg gggcttgtgg ggtctggctg attgggtgct   77580
ggctttcagc ttcagtcctg acacgagagg ctgagctctg gagaaatgtc agggtccacc   77640
atcccaccca tcttgcccccc acctcctcgg ctgcgcacac gtgctcagag caagcatttc   77700
tctcaccaac tcagggatcc ctgcacacca gggagcaccc agcctacacc tgcagcctgg   77760
cacagtttggg gaccgtttag ttggtgccag ctggaggtgt ttggagggaa ccatccggtg   77820
atcaggatag aggcacagct ggccgagggc aggtgggcgc ctgtgggtgc aggaagatgt   77880
cacatctgca ggcattgttt ggggacgtca ttgtgtaacc agccctgcag ggctgcagag   77940
gcatcccaca agtctgtgtg ctctctaggc tgcgtttatt gccccactct agaccacagg   78000
cctgggcata tttgtgtccc catccccaac cctgtcacct gaagcagcct gcgagccccg   78060
acaggaaggg acaagaagag gcgaagatga caaacattca cagacagccc acggctgttc   78120
ttttgctctg acagtgtatc ttaagctccc ttgagcgcct tactgaacag atagatcagc   78180
ttcttttcaa tctcttgttt gctcttataa aggaaattag gtcatgctgg aaactatgcc   78240
atgatgcccc tatgctcact cacctgatga agtgtgggag gctacccccc agcaaacaga   78300
aatgggcaca caatctgaag cctccttatc acactggaga cttccagagc aacttcagta   78360
aggtctgtga gggggaacgc tctgttgttt gacatgggct tgtggctttc agctaggggc   78420
acgcacttct ccaccagctc ttttttttatt tttatttatt tttatttttt ttttttgagat   78480
ggagtttcgc tcttgttgcc cagcatggag tgcaatggcg tggtctcgac tcactgcaac   78540
ctccgcctcc cgggttccag cgattctctt gcctcagcct cccagtagc tgggattaca   78600
ggcacctgcc accaggccca gctaattttt gtactttag tagagttggg gtttcaccat   78660
gttggccagg gtggtctcaa actcctctta ggtgatcctc ccgcctcggc ctcccaaagt   78720
gctgggatta taggcatgag ccaccgtgcc tgggcagctc tttccctaat aagaacactg   78780
gttctgaggc caagtaagag gctaaattaa gaaagcaaag atttatcata agtttgaagc   78840
ccacgaggaa aaaagcctcc attcatcatc cagaaacaca aggaaacatc atttgcccct   78900
cagtggacag gtgatgtttc ttacataccc tatgacatag ctgccctggt ccctcccaag   78960
cccaatgttt cattggccaa gcttccaatt tgctttacaa ggtgtgagga cagagaagca   79020
tccagcccat tctcctgtgg ccctgctcca tttagagcag acacgagtgg atagctcagc   79080
tggtcactag ctcctgggct gcccccactc acagaacaag agtgtgcgtt tctcctgaga   79140
acttcctact aaagaaaaca gccagcccag gcatggatta caggctcaca cctgtaatcc   79200
cagcactttg ggaggccaag gcaggtggat cacttgaggt caggagttca agaccagcct   79260
ggccaacgtg cattttttctc tataaaaaat acaaaaagta ggtggtggtgg cacacacctg   79320
tactcccagc atctcaggag gctgaggtgg gaggatcact tgagcccagg aggcagaggt   79380
tgcagtgagc caagatcgtg ccactgcact ccagcctggg tgacagagtg agaccttgtc   79440
tcaaacaaaa cagaaaaaca gtccaactag gaagcttgct tctcccggaa gccttgctgc   79500
atgggctgac caggcacagt gctgggccat tccactgggc tgggccaggc tggggaggta   79560
ccttgatttg gggatggcag ctggccttgt ccttgactca gggctgctt ttctgtagac   79620
caagtgcact tcacggattt ctccagaact ggtagagaca aaagtgagag agtgggagat   79680
gcatttgaag catgttggct ttattatttg caaaactgaa gtctggccca aaagaaggtt   79740
gatcttcttt taggaggtct ggaacaggac gtggtctctt ctgtggtgga atgttttttgt   79800
tttggctgaa tggttgcgtc ttagtgattt gactgagagc aaaatcagct tccattttat   79860
ccccgctaag tcacacttt tccatagaag gggagttgtg ggaagcatag ctttaaggga   79920
aggcaaagca caccttgctc tgaaactctt tggtcacaac catgtaaaaa catgtctgag   79980
gaaaaatcct aggcagaaat acagcaaaag tccacttagc caaggaggcc atgggtagtt   80040
cttttcctcc tttcttgtgt tcttattttt ccagattttt attttttattt tatttttatt   80100
ttatttttttt ttgagacaaa gtttcacgtt tgttgcccag gctagagtgc agtggtgtga   80160
tctcggctca ctgcaacctc cacctcccgg gttcaagcga ttctcctacc tcagcctcct   80220
aagtagctgg gattacaggc atgcgccatc atgcctggct aatttttttgt attcagtaga   80280
gatgcggttt caccaggttg gccaggctag tcttgaactc ctgacctcaa gtgatccacc   80340
caccttggcc tcccaaagtg ctgggattat aggcatgagc taccgcgccc ggcccctttt   80400
ctagattttt ttttttttttt tttgagacgg aatcgcactg tgtcacccag gctggagtgc   80460
agtggcgcaa tctcagctca ctgcaagctc cgcctcctgg gttcacgcca ttctcctgcc   80520
```

-continued

```
tcagcctccc gagtagctgg gactacaggc gcctgccacc acgcccggct aattttttgt  80580
attttttagta gagacggggt ttccctgtgt tagccaggat gatcttgatc tcctgacctc  80640
gtgatccgcc acctcttgtc cttctaacaa gaagaactca tacccatact acgtaaagat  80700
agctatcgca tacactttta tcaccagcct ccttcccaca acaatattta tatgtataaa  80760
tcaagaagct attatttcaa actgatgctg aacaacaatc ccaaagtgct gggattacag  80820
gcgtgagcca ccatgcctgg cccccttttc cagattttta atagtgagca tatattactt  80880
ttatgactgg aaaaagtatt aacacattcc tactctatgt aattgaagga attagtcaag  80940
tattgtatca ccctaatagt actttcatgt acacactcta tgttgcttat ttttatggat  81000
ttcatatact ttgtctccac gcataggaaa attgagttgg tgaggcttgc aaaactcccc  81060
aacccacact gtttagtttt agcagactta tcacatgagt gttttcattt aaagaacaat  81120
aaccagccgg gcgcggtggc tcatgcctgt aatcccagca ctttgggagg ccgaggcggg  81180
cagatcacaa ggtcaggaga tcgagcccat cctggctaac atggtgaaac cccgtctcta  81240
ctaaaaatac aaaaaaatta gccaggtgtg gtggtgggtg cctgtagtcc cagttacttg  81300
ggaggctgag acaggagaat ggcgtcaacc agggaggcag agcttgcagt gagccgagat  81360
cacgccactg cactgtagcc tgggcaacag agcaagactc cgtctcacca aaaaaaaaaa  81420
aaaagaacaa taacgatgac tctttagggt tcattaaaca gtctaagaaa tacaaatatt  81480
tagctcccct cagccatcac tgcctcaggc ccattcatga tcatgaatcc agatccatga  81540
gctctgtggc agcgtctttg aaggtggagc ttctctggat catttgaggg actctatttt  81600
ccttgcaggt gtgggagcca cttcaggagc ttctgccaac ttccctggca cctcgggcag  81660
cagcaccctg tctcccttcc agcacgccca caaaggtgag gagggtgctc aggtatcgat  81720
cacctggagt taggtggtac tcggatgaaa gctcagaaga ggagaggaaa tgatcatgag  81780
tgatgattat ggtgcgcttc cccacctggc ctcacctccc taatgtaatt gaatgacatg  81840
ttgcccccg tgcaggaagt cattatatct gcaatcagag ttgatccctc tatgggtgtc  81900
ctgggaccgc tgggaggtgc tggtggtgaa ggcgggggca tagcggcagg tggacagcac  81960
aggcagctgc aagcccggcc aggaggagag accaggcgtc ctgggctttg gtttggccgg  82020
gagttaacag caattctatc actggttttc atataaacat gctgaccata gcactttaat  82080
attaacttgc agaatgtaca tttcattctc cctaaccagg gaagaaggga ttgaggagga  82140
ccccaaagtt taatatgtct ctcagagtca gccctccagc tggcttggcc tttctctctc  82200
actggtttag tgccagccca ttattgaagc atgtttcggg cccaggtctc agcgagccgt  82260
gaggtaccct ccagagccct cagagcaccc agctcgtcag cttcatctct gggcctccca  82320
cgcgctaacg cagagcaaaa ggcaggactg ctgggcgagg atatatgaat ctcatttgca  82380
caggccccgg ggggagtagc tcaaaacacg gagaatatta aaacacttat gtcatcccaga  82440
cctggcatgc taacgctatt acaggtattc cccagatgat gctgggaggc tggttttcct  82500
gcagatgcac ccacagggga ggctcagcgc ccacatgcgg ggttctcagc tctggcacta  82560
cctcccccga gatgatttgg gagcttcaga tgctggtctc ctgtctattt gggtggtggc  82620
aaatctggat cttagttcaa gacaatcaga gtccgtgtttg gttatttttag agaatgagaa  82680
tgagcttcag ggcattttat gcatccaggg tcgacattaa cctgggaact gagcaaaatc  82740
ccccggggtg actgagggac tgcctggtgg aggcggcagt gcaggtggaa taggtggccc  82800
agccgaggca cccctgtgc cctggggctc ttacaatgac acttaggttg aaattgcatg  82860
aggtcaaga tggagccaaa cctggaatcc agagctgact ttcgcatcct gacttttgtt  82920
tggaaatgcc caaacttgaa ttgtgctgcc ttccagccac tcttgttcac tggcctttct  82980
tcctctccac accaaaccct gccctcaggt tgccaaagca gtagaagcaa gagcaaactc  83040
cctaggaaca atcaggtgac cccagagaag tctggagagg ccagtctgag ggcagcgagc  83100
agggctgtgg gcagtcctgg tctggcagcc aaaaccagcg cggaggattt ggttctcagt  83160
ctaagcaagc acctcagatt tcagggttcc ctgaaagcat cccaggggca gggccattgc  83220
ttccaggggc cggagtcctg gagggaagac cagcagggat cctgagctct gggtcattca  83280
tgccttctct ccaccacag aactctcagg ccaaggacac ctggccactg ccctgatcat  83340
tgcaatgtcc accatcttca tcatggccat cgccatcgtc ctcatcatca tgttctacat  83400
cctgaagaca aagcccctg ccccaggtga cggcccccat gcgccggtgc cctgcttcct  83460
ggactctccg tcaactcccc ctgtcggaga gcctggctgc tcactccctc ctctctcccc  83520
agcctgttgc accagccacc cggggaagag cgtggaggcc caagtgagca aggacgagga  83580
gaagaaagag gccccaggtc tgtgaaccag ggcttccaca caccatgtgc acggtgccca  83640
tctctgggtg gagggcgttc ccagaagcag cctcctcgct gcttctgctc tcacatgctg  83700
aaccatactg tgcttaccgt ggggtggtgc cacacagaca ccgggcagct ctgcccaaca  83760
ggaagagcag ggttgggctg agcgcagcag catgagccaa ttctaactcc tatctcccca  83820
acctccccat ttccctgcag acaacgtggt gatgttctcc gagaaggatg aatttgagaa  83880
gctgacagca actccagcaa agcccaccaa gaggtatgtg gaagccccca gcaccaagct  83940
gaagctgggg tcctgtggat cctgagcagg gaggggaacc agggtgcagc cgagtgaact  84000
gacaggctag cctgggacac tatgggggacg ttcggcgaca gacagtcccc accacctctt  84060
tgctgactgg caggggtcag gtggtgtgag gagcctgtgg aaacagctgc ctgctgctct  84120
cgggtcaggc ccctgtccct gcatcctgcc aaattccctg ggccttcctc cttaacatcc  84180
gaattcctca tgcccttct ccagactggg agggcagaac ataaagccaa ggatgcatgc  84240
ctgttgcggc caacacacca gtaccacccg tgccggtgcc agtactgctg ccaccgtaat  84300
gctggtaaca accgtggtga tgacggctaa cagcatttgg tgcctactgc ccaccaagtg  84360
ctgggctagg gctgtgaaca catcctccct ccacagccca ggagcaaggt gcttgtatca  84420
tccctgttta taggatacca cactgaggta tggaagttgt cactcgccca aggtcacaca  84480
ctagtgaaca gcagggctgg ggtccgagtc caggctccca aggagccaca tggtgtaaag  84540
aggcctctgg aggaggagat ttggcaggtg aagcctttcc cgcgtttacc acacatgaag  84600
gtgtgaacc agcccctgct ctaaaatcga gggtagaggg aagtcaatat tttattcatc  84660
cagtgggatg gtcatttgga cttggtcctg cgtagcttcc aaaaatcaac cccacagcat  84720
cagctcccag ccaggcaatg tgctcggacc ccctgccag gcctctgccc gacagccact  84780
gcaggctgcg cctggaagga cacccccgca acagtgcctc ccttggcaga tggggcacag  84840
aggccaccag aaggtcacca aactggttac aggaagagca gaggttaagc cctcctctcc  84900
tgcccccacc ccatgatctt cctatgattc accttgcaaa gccattccaa tcgatccagc  84960
atctgtgtgg agatcctgtg tgccagatcc aagctgctgc tcccaggacc aagggcagga  85020
cctggtcacc ctgcatggaa ctcttaaata gggcctccct agagactgaa tttgctcctc  85080
agcctccagc ccagccttat ctcattctgt ctcagcctct cccttctgat attcaggctt  85140
ttcttattcc cagaaatcaa aaaggcagag acgtgcccca tgacttgagt tgcagttgaa  85200
gacagggaaa atttggaggc cctattagga aaaaatatat actgctttca tacacgaata  85260
```

```
ttaaatacaa attgaaccct gacacttgta cgttaaaaga cagcaaggca ctgagctttt    85320
gtccctgctg tttgtcctta ggtctcagag acaggacctg gggtgccacc tcacctgctc    85380
cacctcacct tctctcgagt ggggacaggg atgggtccta ccacctcctt gtgaggccct    85440
gaagcctgat gaggaagtgg gtcccactgg ggcttcatga tggttctcat tgtctttgta    85500
ttaccctgtc tctagggttg tgtttgcata tgggcttcac tgctgtaacc tagttactaa    85560
caaatataat ccttttttta agaaaaaaag gtcttcagcc aaaccacagg aagcaagcag    85620
gatgcctcta aaaaagaata ttgttttttca tatacttgga atggttttaa gagagtttaa    85680
gctccaaccc acatgtgcct agggcagacc ctgggttctt tgtgggctgt gagccacagg    85740
gcggcatgaa cctgggcttg gtgggtccga ccgcccaccc agctcacccg ctggggcttg    85800
ctgtgccacc ccctgcaatg cacacaggtc agccaggtca cccccctagt caagagggggg   85860
cttttccaggc acaaggctcc attcagctcc ctttttcaatg actccagaga gccagcatgg    85920
attcagcgcc agctgcatca atctgtttgc ttaacatgaa gacaccagtt gaacttggtg    85980
cttactggga ttaaatacag agatctagga catattcaat gaaccttcac ggagcatcca    86040
ttgtgtgtca ggtagcaggg aaggagaggc ccgtggatgc ctcccacacg cagtggcagc    86100
cccagccccT tagacgcctg caggtcaccc accacggact tgtttgtttg gaaagaagca    86160
ggaagccacc ggtgtatgtc tcgtctcatg tccccctggtc ccgtgcccac aaggtgccca    86220
gtaaacacct gaaaaacaag tcattgcccc ccactgtcca cagctgggca atggacaagt    86280
tcaccacagg agaacttgtc agggctgcag ccccccccagg cactgctaat gaccatcgct    86340
cttgtttttg cagcgagaac gatgcctcat ccgagaatga gcagctgctg agccggagcg    86400
tcgacagtga tgaggagccc gcccctgaca agcagggctc cccggagctg tgcctgctgt    86460
cgctggttca cctggccagg gagaagtctg ccaccagcaa caagtcagcc ggggtgaggc    86520
tcctgcaggt gccatgatga gctgtgagat gtggctcact cacagccgca agactaaaac    86580
tttcttattg aatcagctct cctgcaagac ggggtgtttc tcccagaagt ccaagatagg    86640
agacctggac agtgacaagt tcacagcaag atagtcaaaa gggaaaaaaa ccctttcgtt    86700
tttgagtttt gttttttttt tttggagatg agagtcttgc tctgtcaccc agcctggagt    86760
gcagtggtgc gatctcggct cactacaacc tccgcctcct gggttcaagc aattctcctg    86820
tctcagcctc ccaagtagct aggactacag gtgcacgctg ccacacccag ctaattttt   86880
ttatatttta gtagagacga ggtttcactg tgttgcccag gctgctctca aactcctgag    86940
ttcaggcaat ccacccgcct cggccttcca aagcactagg attacaggtg tgagctacca    87000
cgcccagcca cttTgttTtt attatatagc ttcatacaca aaaacgaaaa ataataagca    87060
aggagaaaaa aggtaaaatc acttggaatg ccagagggca gaaaaagacc cttgtaaata    87120
tacggggTtt tatctaacca gacaattTtc tagacacaca cacacacaac gtttTtcTtc    87180
tatgcatttt taaaaatata aaaacaggtt cacatgtaga aactgtcccc agggtttTat    87240
cacctaccgc cctgtaatgt gctgtggcca ggagcagggc aggggtgagg gcaaaggtgg    87300
ccagagccct cttgggctcc ctgtagacct ggcctgtggt cgtccctcta gcctgtgccc    87360
ctggctgcag gccccagccg caggacagct gtgttgctag gcaacatcac tgatggcaaa    87420
aatgcccagt tgggatcctg gctccagcct ggtcctgata ggatgccaag ctctgcctgc    87480
cccgagttca gtgacctctg taatggggct gccacttgca gagaccctgg aagcctgtgg    87540
ggttgttaca agggagatag gtggccatgg ccccgggact cttcagccag ggccactgag    87600
cagctgtgca ccgtgggcct ggtctcctgg caccagccac gtgatccggg atgggagccc    87660
cgcacggctc tgctgcagca cagatgtcct gagggcaagt gggggtcccc atggtcatct    87720
tttcaaacag actgatgcca ggggtgtccc caagtatctt acgagtctga ccacccagct    87780
gagcctaaga cgcacccgtg gtagacccca aaaatgtttg aataggaaaa cctgaagaag    87840
gccctcctcc ctgtgtgtca gggctgggct gctgacacgg gggctgtgtg cagcgtctct    87900
ggtgttgggc gtagctgctg cctgcccctg ctgacatgga ggatttgcct cctttctact    87960
gttgcccctt tctggagatg aaaattctcg actctttttc acagattcaa agccggagga    88020
aaaagatcct cgatgtgtat gccaacgtgt gtggagtcgt ggaaggtaag ctgaaaaaaa    88080
agcctgggag aggtggtgcc caccccaccg acatgaaggg ctgggcccgg agccctgagg    88140
ctcctgtgag gggaactgag ggaagccgcc catccagttg ccgcactttg gtcagaatgg    88200
ccgctggaaa ctatttcagg tgtgggaaa cagaatcttg ttcccagata tcggaaggca    88260
tctcccagtg cttccatggg ccttcccctc atggggcggg agacagcctg gtgcaggcac    88320
ccactgtagg gaaacgcagg gtcggtgagc agcagccacg gagcctcaga cctcccgtgt    88380
ccccagagac cgtgtccaca ctggcatcat catctgggaa acgtgatcag tcatttatcc    88440
tagacttagc tgccctctcc ctgccctcga gcatccccga tgtctgatag ccctgggagc    88500
ctccagcctc ccctcccagc ggccttctga gctaagtcag gctgtctccc cataacctgg    88560
gcttgagtgt gggcaggtta agaggcaaca ggataggacc gtcagtgctg caatctgaaa    88620
tcataatcct cagcttccag ttcctgcaaa atccactttc taaattacct tcttattaac    88680
cccaaagata aatccctcat ggctgaggtc aggggtTTTc ctgctgctgg actcgctggc    88740
ctccctccgt ggactccttg atctggccgg gcagcgggag tggagcctgg tgcatgctgg    88800
gcagctcacc aatgccccca ttaccctcc tcccaccccc acaccccacc gtaggccaaa    88860
tgcagcccccc tgtgccctgg caggctttct gatccagtgc tttgttggcc agaaataact    88920
atactgtggg tgagttccag ggccaagaat tcttggctgc cgctgaaatg tggcatctct    88980
ccataaacgc atgccccagg tcagcctgcc tgatctcacc tggcatggcc tggggctgtc    89040
agctgcccag gggaggatgg tctaggactc accttcctcc caccaggaag ctcttcctctg   89100
ttccaaaaaa tgttgagttc acacccctgg gacagaggtt ttcaaacctc agccagggct    89160
gagaacctgt gctccatgcc cagctctgat gaacattaga gtcacctgca ggtcttaaca    89220
ccctctctgc ccatccagcc cacccaatct gcccaaacac cctgatgtaa ttagtcaggg    89280
gtgaatccca ggcatctgtg tctctttgtt ttttgttttg ttttgtcttt aattaaactt    89340
tttattttga gatacttctt accatgcagt ggtaagagat aatacagaga gatcctacat    89400
gccctttacc cagtttctcc taacgataac atcttgcaaa actatacaca gaagtcacaa    89460
ccaggacact gatattgaca cagtgtatatc gactcagctc ccatacaaaa actcctcctg   89520
ttgcctttta tagccacagc caatttccac ccaccccacc ctcacctagg cccctgggaaa   89580
ccagtaatct gttctccatt cctataattt tgtcatttca agagtgttat aaaagtggaa    89640
tcacaaggta tgtaaccgtg gtgaatggct tTTTTcactc agcataattc actggaggtc    89700
catccaggtt gttgcatgta tcaatagtcc attcctctct cttgctgagt agtagtctgt    89760
ggcataaatg gaccagagtt ggtttaacca ttcacttgtt gaaggacatc agggttattt    89820
ccacttaacg gctattatga ataaaggtgc tataaatatt tgtgtatagg ttTTTgtgtg    89880
gacatcagtc gtgatttatc tgggataaag acccaggagt acatttgttg ggttgtatga    89940
tagttgcatg gttgattatt ttaaaaaact gccaaaccgt tttctaaagt tattgtacca    90000
```

```
ttttacattc ctactagcag tgtgggaacg gtctagtttc tccatatgct tgccagcatt   90060
tggtggtgtt actatgtttt gttttagcta ttctgagaag tgtgttatga tatcttattg   90120
tggtctcaat ttgcatgttc ctattgttta aatatgtttt cttgtgtttt tttcatctgt   90180
gtgtcctctt cagtaaaatg aatgtttctt catgtctttt gcccattttt caatggtatc   90240
gtatgatttt tttgctgttg agttttgagg gtttttaaaa atatattcta gacactagtc   90300
ctatgatgga tatgtggttt tataaatgtt ttctccattc tatagtttag cttatctttt   90360
cagtctctta acagggtctt tcatagaatg atgtttaaa tttttatgag tcaaatttat    90420
gaaactaatt ataaagtttt ctttttatgg atgatgcttt tgtgtcaaat ctaagatctc   90480
tcttgcctag tcctagatcc cagagatttg ctcccacaat tttttctaga agtttatag    90540
cttaatgttt tacattctaa gtccacatag tttttatgtt ttacatttaa gttcacatag   90600
ttttatattt tgcatttaag tttgagttga tttttataga agatatgaaa cttgggtcaa   90660
agttcatttt tttgtctatg gatgtccaat tgctccagca ccattttttt gaaaaattat   90720
ctttcctcca ttgaattgct tttcaaactt tgtcaaaaat cagtttggca tatttgtata   90780
ggtctatttt ctgggttgc tgttctgttg catttatcta catgtctgtc cctctgataa    90840
taccacaagg tcttgattct tgtatataaatt atgtaataac atataagtcc tgaaatcaaa  90900
tggactgctc ccattttcct ttatttttttt ttcaaaaatc ttttagctat tctagttcct   90960
ttgcctttcc atataagttt tataataatc ttccctatat gtacaaaatg ccttgctggg   91020
attttaatga gttgcaacaa aactgtatat caatctggga agatttgaca tctttattat   91080
gtcgagtctt ctgagccatg ggcatggtat atctcttcat ttatttagca caacttttaat  91140
ttttttttcat ctgcattgtg tagcttccga aatacaagtt ctgtgcatat tttgttagat   91200
ttacaccata tcatttattt tttgagccac tgtaaacgac aatttaaatt cagtagccat   91260
acattcattg ttagttatat agaaaatacaa ttgatttttg tatgtttatc ctgtatcctg   91320
tgaccttgct gaattcactt ataagatctg ggagtttttct tgtagatgcc ttgggatttt   91380
ctacatagat aatcacatct gcaaatggga ccgtttttatt tcttcctttc caatctgtgt   91440
accgtttctt tcctttttctc attttattgc actggctata ccttccagca ctacagtgaa   91500
tataaatgat gaagcagaag cagaaatcct tgccttattt ctgatcttaa aagcattcca   91560
tttttcacca ttaagtataa tattagctct aggcttttta taaattgttg acattaatttt  91620
tttgagtgga ttacaataat ttttaaatat tgaaccagcc ttgcctccct ggaataagcc   91680
atacctgatg tggtacaatt ctttttttatg gttgcattct atttgctaat attttgttaa   91740
ggattttgca tttatattca tgagagatct tggtctttgg tttgtggttt gttttttgtc   91800
tttgtctggt tttgggtatcc agtttatact accctcatag aataagttag gaagtgtttc   91860
ttcctttttct atgtctagaa aagatcgtgt agaattgcta ttctttctta aacattttgt   91920
agaattcttc agtgaaatcg tgaggaccta gagatttctt ttggggaggt tttttttgttt  91980
tgttttgttt tgttttttgag atggagtctc gctatgtcac ccaggctgga gtgcagtggc   92040
acaatcctcg ctcactgcaa cctctgcctc tccagttcaa gtgattctct tgcctcagcc   92100
tcccaagtag ctgggattat aggcacatgc caccatggcc cagctaattt tttttttttt   92160
tttttgagac ggagtctcac tctgtcccag gctggcaacc tccacctccc aggtttaagc   92220
gattctcctt tctcagcctc ctgggtagct gggattacat gtgcatgcca ccatgcccag   92280
ctaattttttg tatttttagt agatatgggg tttcaccatg ttggccaggc tggtcttgaa   92340
ctcctgacct tgtggtccac ctgcctttggc ctcccaaagt gctgggatta caggcttgag   92400
ccaccatgcc cagccctaat ttttgtattt tagtagaaat gaggtttcac catcttggcc   92460
agactggtct tgaactcctg acctcaagca atatacccac ctcggcctcc caaagtgctg   92520
ggattacagg cgtgagccac cgcgtttggc tagatatttt tacagttaca aattcagctt   92580
ccttaatagt tataagtctg ttcaaatgat ctattttata ttgggtaagt tgtgatagtt   92640
tatgtttttt gaggaattgt ttattttcat ctaagttatc aaatttatat gtgtagagtt   92700
aaagttgcaa gttttatctt attatctgtt tgatatctat ggtgtgtata gtgatatctc   92760
ctgcttcatt cttgatattg gtaatttgtg tcttctctat tttttccttg tcagttatat   92820
tgatctttttc aaataactgt ctcttttcat attgatctct tttactttat agttttcaat   92880
ttcattgatt actgctctta tttctcaaatt acttatttcc ttctatgtac atttggttta   92940
ttttgttaat cttttttctaa gtgcttgaaa tgggagctta gattgttaac ttgagttttc   93000
ctcctttgta tgtatctgtc ctataaattt cactctcagt actactttag ctgtgtctca   93060
caaatattga catcttgtat ttttattttc attcattttt aaattgtctt tgagacttcc   93120
tctttgacct gtggattatt tagaagactg ttgtctggtt ttcaagtgtg tgaagatttt   93180
tctgttatat atttatattc tgattctatt gtggtagggg aatatccttt gtataatttc   93240
aattcttttta atttgttgag gtttaaggcc aataattatg aacaatgtgt attctgctgt   93300
tgttgaatgg agtgttctat aaatgttgat tagatcgtgt tggttgatga tgttggtaag   93360
ttctatattc ttgatttttt ttctaattgt tctatcattt actgagggag gaatgttaaa   93420
gtcttcaact ataattgtgg acttatctct tctttcaggt ctatcagttt ttgtttcaca   93480
tattttggag tctgttgtt tggtgcatat tcatttagga ttgctatgtc ttcttggatt   93540
gacccttaa tcattattaa atgtcacttt ctggtaattt tttcctctga agtctactttt  93600
aactgatgtt atagccactc tgccttcttg ttattgaagt ttgcatgata tgtatttttc   93660
catccttttac ttccaacgcc tctctcatta tattgaagtg agtttcttct aggcagcata   93720
taactgggaa aattttttaag tctactctac caagctctac ctttttagttt ttttgttttg   93780
gtttggtttg ggttttttgt tttttttttt ttctttttt ttggagtttc cactcctgtt   93840
gcccaggctg gagtgcaatg gcatgatctt ggctcactgc aacctctgcc tcccaggttc   93900
aagtggttct cctgcctcag cctcccaagt agttgggatc acaggcatgt gccaccacac   93960
cagctaatttt tgtatatttta gtagaaacag ggtttcaccg tgttaccag gctggtctag   94020
aactcctgac ctcagctaat ccatctgcct tggcctccca aagtgctggg attacaggca   94080
tgagccacca ggcccagcct ttagttggta tttaaaccat ttacattaaa tgtagtcatt   94140
gttagggctt aagtctgcta ttttatattt tgtttactgt ttgttgtctc tgttttttcat  94200
ttctgtgttt ttttattcct gctttactgt gggtcacttg aacatatttc agaattcgat   94260
tttggtgttt tttgagtgat acattttgat tttatctctt tccatagtta ttttagtagt   94320
ttctctagac attgcattga cacatataac ttatcagtcc actggtgtta ttattattat   94380
tattttgac atggagtttt actctgccac ccaggttgga gacagtgac acgatctcgg   94440
ctcactgcaa cctccgcctc ccaggttcaa gcgattctcc tgcctcagcc tcccgagtag   94500
ctgggattac aggtgtgcac taccacgcca atgtgttttt tgtgttttta gtagagacgg   94560
ggtttcacca tgttggccag gctagtcttg aactcctgac ctcaggtgat ctgcccacct   94620
tggcctcccg aagtgcttgg attataggtg tgagccaccg tgcccagcct tactggtgtt   94680
attattttgc cagtttgaat gaagtataaa aaccttacct ttctctatgt ccctttacct   94740
```

-continued

```
tctctgttta cagtagttgt aaatatttcc tctacatata tttagaacca cataaattgc   94800
ttcaactgcc taatgtaatt cagaaaactt aaaaagagaa ggaaagtcta ttgtatgtgc   94860
ccatattttt gctcactatg ttcttttctg atgtctcaag tttcattctt ttactatttc   94920
ctttctgttt atagaatttc cttttgcttc ttttaggata ggtctgctgg tgaaaaattc   94980
ttaacttttc tttggcttgg aatgtcttga tattctcatg ctttcctgaa ggatattttc   95040
actcagctca ctgcaacctg gtatgcaact ctgggttgaa agttcttttc tttcagtact   95100
tggaaatact gtgctacttc tctctggtct ccaggtttct gattataagt ctactgtcat   95160
tctaattctt ttccctctct aggtcaggcg ttgtttttct ttggctgttt ctaagacttt   95220
gtctttagtt ttcagaagtt catttatgat gtatcttgac atgaatatat ttgggtttat   95280
cctgtttggg atttgcttat cttcttgaat ctgtagactt acgtctcttt acaaatttgg   95340
agagttctaa accatcattt atttgagtat ttatttagtc ccactctctt ctcctctcct   95400
tctgaaactt cttgacacaa atgttagctc ttctgttata actccacagt tccctaaggc   95460
tctgtgtttt tcagtttatt ttctctgatt gagtaatttc cacttctagt ttccattatc   95520
catctcactg attctttcct ctgtcttact ctgtcattga gcacatctac tgagcttttt   95580
attgtggtta ttgtactttt gtagttctaa tattttcatt tctttttttac attttctatt   95640
atttttcctg aggatttcta tttttgcatt taagcatgtt cataattgct tgttgaagca   95700
cttttattat gaattcttta aaacctttt cagattatct aacatctgtc atctcagtgt   95760
tagcatctat tgatttttctt ttttactca tttgacatct tcttggttct tggtatgatg   95820
agtgaattca ctttgagacc tgtgtagttt tatgtcctga tatgaaactc tgggtcttat   95880
ttaagccttc tattttagct ggctcctttt gatagctctg tggcaggaga atgagggtgc   95940
tgtcttgcta ctgttgggtg aaggtagaca tccaaattcc ccactcaacc ttcactaaca   96000
ctcaaggggg attccttttt actgctactt ggggtttggg agtatggcta ctgacatggt   96060
caccacgggg gcagaggagt ttttaccagc tggttgatga gaaagcccca gctccctaca   96120
tggcctttcc tgacaccacc tggcacagtg ttacagcctg gtgagggtgg aattctaggc   96180
tccccactca gcctttgcta ccctggatag agtggggaca cagttttct gtgatgtttg   96240
gctggaatag agcaattatt gtctaaatgt tttatgcttg ctaggctgct cttttcctag   96300
tgctctgact agagacagaa gactttttgtt ggggctgttt ttgtctgtgg ttgctattat   96360
ttccagattt ttggactttt ctgccccatg tctggaattt atgaggcaaa agaaaaccca   96420
gggaacttac caccatcacc atcctaaggt atcgaggtcc ctagttggtc tgtcttcttt   96480
tctccacttt tcagacttct tgtatttgtt ttacacagaa tgtccaggge ttttagctgt   96540
acttagtggg aggattaggg aaaattatat ctactcttat cttccagaaa cagcaatatc   96600
aagtttttaa atgctcctag gtgagtctaa tgtacagtga agcccaagaa ccatcagacc   96660
actgagttgg cagtgacttg gttcagataa ccccaatctg gggctatcat tgagagcagc   96720
catcacaaag ttgactactg ttccctaaag agacatgaca ctgtcccttt gaacccctcc   96780
tcagcccagc cccatgggag acagggttac ccaactaagg ataacttgtc ttgaagtctt   96840
tgagaactgc taaaaatggt catgagggaa ttattatcat tgtcaatata gcagtcattt   96900
tcctagtggg gaaggggcta ttaccggggt cagggtacat gcacagccct ctcttgtggc   96960
tggcagcgtt ctaggtgtcg tttgccttaa gttatgcatt tgtttttaggt ggctttctgc   97020
atgtttata attttaaaaa aattttttttc aaataatttt tatttcattt aaataatttt   97080
tcagtgttga ccttctattg actgttgactt gcaacatcta actgtggcca ttggtgtctg   97140
taggtcttag ccccacggag ctgccatttg attgcctcga gaagactagc cgaatgctca   97200
gctccacgta caactctgag aaggctgttg tgaaaacgtg gcgccacctc gccgagagct   97260
tcggcctgaa gagggatgag attggggggca tgacagacgg catgcaactc tttgaccgca   97320
tcagcacggc aggctacagc atccctgagc tactcacaaa actggtgcag attgagcggc   97380
tggatgctgt ggagtccttg tgtgcagaca tactggagtg ggcggggggtt gtgccacctg   97440
cctcccagcc acatgctgca tcctgaaaag catgcctgtg ggctgtcctc ccaggacaag   97500
ccaaggagcc aacgagggct ctggagctgt gagtggtgcc aaaagactgc caagaatcaa   97560
ggcttttgtg atatgtcacc gtatgcctta ggatgttcaa ggagccagac gaaataaggc   97620
ctgtcttcca atttaaccaa agataaagga ctagagccgg gatactttca gatgctcgcc   97680
tgtacctcac caggcagagt aaatatctac tcactcatac agccagccca ccagcccacc   97740
attaactcac tgaacaatga gacaatgttg aggactcaaa tgaatcaaac cccgtgggaa   97800
tgacagaagt gaagaatctg gtccctgtct ttaaggagtt tgcactccag tagaagacag   97860
aaggaacgta tgtttacaaa ccacttcact ggaaagacgtc aaacaagctg aatgaagggg   97920
cgcttagaaa acgttaatag aagttctaag cgggagatga ctccctactg ggatgatgaa   97980
ggatggcatc ctagtgaaga agcagctcaa acattttgat aaaatggcaa caaaatgcag   98040
acaccctgct ccaggtatta tttcaggttt agtacaagtc tgttaatacc ctatgtggtt   98100
tcattaggat aactttttac ctatccttga ggtcatccat attcttacag gccttccagt   98160
caataatgga agagctcact ctatacaaaa ccaatatgca aggcatgtgt ttgtccaagc   98220
aattggatgt gtgcagtagc caatttcatt tactgcatta ctctttggcc tgggaacct   98280
gtggtctgca ctacatgtga atggccttcc acttcagtct taggcagatt tgacctttta   98340
ggggcagcaa tgctgaagga cacagcaatt taaattataa tgtgtcaggc tgtgtttca   98400
cttcaaacat gtatgagtag tcagctgtaa ttagagaaat gatgacttcc taagagttca   98460
gccacgcata attctagatt tcaagagcat ctaagacttg tggattagcc tcatggcatg   98520
agagtttcag actcagcctt ctgagccagt cagggaaagt ggttgctgc agcgcaaatg   98580
agagcctggg cttgatgtcg agggagctgg cttctagttg tgccaccttg ggccttgtct   98640
tttcctctct ctgcctcagt ttctcgtctg ccaatgagat gttagttagt gattctataa   98700
ttggggcagg tagggttcag gtgagcaaaa agaaagtgga gctataggaa atgccaggcc   98760
tttgaggtgc tctatggaag tcaacacagt gtggtttgtc catttaaatg ggaataaaaa   98820
cagaaaaact cagacttggc attttcacaa taactgcaat ggtttgacat aacatttata   98880
ggcagaaagt taataaactg gcattgttct tggcatatta ttgtactatc cctgtaactg   98940
ccaagagctc aggagccagg ctagtgatca caccagggt tagagttcac tgctgaactc   99000
cctgatggca ggtctgtgtt tattactaca ttaaaacaaa gtctctgact tataaagcga   99060
ggttgtaaaa attacaagtt gcatgactga aaaaatgctt taggggggaaa atcagtcata   99120
tctttaacac caacaagcaa tttcccacca acgaatgtag tacatactgt gagaggatca   99180
taatgaggtc ctgaatattt aatatcatca tttactgtgt ctgtttgctg ctgtttttcg   99240
aacctatttg gtttacccctg caagctaaat actccacggc agagcttaat tatccttta   99300
attcctcttt gaaatcctgt ggtgcccct tcccctgcc ttgtgatgat gatgagtgag   99360
tctcccctta attagactgc aaatgtcact tgtgatgagt gtgccattcc aggataacag   99420
cttgcaccct cctcagaatg tttttcagcga aagagtgggg tggctgttct ctgctcctgg   99480
```

-continued

```
tgctttggcc tcatttcaca ctattagaat tctggggctg taaggccagc cagtgtcagc    99540
tcatgttcca ttggctctcc acctgccatt tttaggagc tattccttat atagttacaa    99600
attcccttgt catttactta tttggaaaca tgggatttac tctgacaagc tttagcctat    99660
gttatgggat tcagaacaat gagatcataa taattctcac tgaccaaagc tgggactcca    99720
tcctgccatt tttgtgtgga gatattcata attctgcaat actttaaaac atttagaaaa    99780
caccccaggg taggtctgtg gcccttagac agtgaagtct taattgtcaa tattattttt    99840
gtctaattct gtatatatat aacttattat attttataat ctcaataaac acattaataa    99900
gatttataga ctaccgtaat gtgagctctc tttgtatttg gggtggtggg tcggggggtg    99960
agtggggaag gttctgattg ctctgttcct ggttattgcc ctatgtatga tgagactgta   100020
ggattgcaac cagctataaa caaagtgcct aaaatgttat ggcctgggac attcactagg   100080
cagaagcaaa cattacaaag agatcatgta aaaaccacct ggagcattgc tttccaagtt   100140
gccatcatta gctcataagg cattgtatca cttatctatt tctgtgtaac aaactgtctt   100200
gtcttaaaat tcaatggctt aaagcaacag tcatttatta tcatagctcg ggggttagta   100260
gggggtcagt cagctgactt aggttgggct cagttgaatg tgggtcaact ggggcctctg   100320
tctgttggaa taccttaact ggggcagctc tactccatca tctctgtcaa cctagataga   100380
taacagagag aggctctcta aaagaaagaa aatgatatgt attggggaat agggcattgc   100440
aatgggaata catgtgccat agtaaactat gcgtgttttt gaagaggtaa aggaagacaa   100500
tggttcttag aggaaaataa ggaggattac ataattattt tgagacaatt atccttggct   100560
acaaggataa taagggtggt gccagtccag ggttggacag ggagttgctg ggcagaggtc   100620
cttgcaggag tctttgtgtg tgtttaagat tgtcatggcc tttgtgcaag gttttcgttt   100680
tttcagtctt gtgatggctc ttgttatcag tgatttatgc agggagaacc cttctttcct   100740
ggccttccat gactctattt gtcagttttg ttttgttttt taagcacaag tgactccttt   100800
ataattctga caacttccac atttccccca tttgatcaag atctttatca gaaagcatcc   100860
ccagtgagtc atcccatatt attccttcgt gccaggatag acctgtccta ggtggctggt   100920
ctggtctcac attggaggga tttgatggt actaggagtc agtgtcaaaa ccctttagcc   100980
atgtttgaac aaatgggaag tttggagaga gtggctctca gctaggtct acttgaagtc   101040
tactgttaaa tttgattttg tctgttctgt aaacatttgc tatcatcatc tcaaaatgca   101100
gggccagtat tattctgtta gaaggtgtac ttctactgag atttgacaag taacaggaag   101160
tttaaaaaag gaaaatataa aggaaaatta aaatcaatag taatatgaga atcccagttt   101220
gcatgatgat tttgagccat gaatgtaggt ttaaaggcaa ccaaatgaat aaatgaaata   101280
accatgagga attaggtgac ccttcttta tccttgtggc ctctttcttt attttgtgaa   101340
catgggtctc aactttccca gaggaattta cctaggtaca gcaatgtagt attagaaata   101400
gcacagacaa agatggctac tagaagcatt tcatgccagc ctcttccact tagaacaaaa   101460
acagtgtgta gacagtcaca ctttgaatac attatccaag agagaacact ggaattcaac   101520
agagaagtgg caggaaacac caaaagcagg gaaggagag ggagacaagc agcctgccta   101580
gccaggatca actaggagct gggagtgact tcccaattca gggaaagggt gaataagaga   101640
cttccagtgg cccagatccc cagcatgaac tcatgtaatc ctggccatga gagaccctc   101700
aaccctccca accactgaag ctaacatagg gagctgctgg gagaccatgg gatggaactg   101760
ctccagagat ggagtttgca ctggatccca cacctttctg agacctaagc aactacagca   101820
agacaccatt ttcaaaccta gccttgggta gattgcatgc tgtcctgggg cccagaggca   101880
ctgggactga ggtgttacag aa                                           101902
```

SEQ ID NO: 217          moltype = DNA  length = 1401
FEATURE                 Location/Qualifiers
source                  1..1401
                        mol_type = genomic DNA
                        organism = Homo sapiens
SEQUENCE: 217

```
atgtgcaata ccaacatgtc tgtacctact gatggtgctg taaccacctc acagattcca     60
gcttcggaac aagagaccct ggttcttttt tatcttggcc agtatattat gactaaacga    120
ttatatgatg agaagcaaca acatattgta tattgttcaa atgatcttct aggagattta    180
tttggcgtgc caagcttctc tgtgaaagag cacaggaaaa tatataccat gatctacagg    240
aacttggtag tagtcaatca gcaggaatca tcggactcag gtacatctgt gagtgagaac    300
aggtgtcacc ttgaaggtgg gagtgatcaa aaggaccttg tacaagagct tcaggaagag    360
aaaccttcat cttcacattt ggtttctaga ccatctacct catctagaag gagagcaatt    420
agtgagacag aagaaaattc agatgaatta tctggtgacc gacaaagaaa acgccacaaa    480
tctgatagta tttccctttc ctttgatgaa agcctggctc tgtgtgtaat aagggagata    540
tgttgtgaaa gaagcagtag cagtgaatct acagggacgc catcgaatcc ggatcttgat    600
gctggtgtaa gtgaacattc aggtgattgg ttggatcagg attcagtttc agatcagttt    660
agtgtagaat ttgaagttga atctctcgac tcagaagatt atagccttag tgaagaagga    720
caagaactct cagatgaaga tgatgaggta tatcaagtta ctgtgtatca ggcagggggag    780
agtgatacag attcatttga agaagatcct gaaatttcct tagctgacta ttggaaatgc    840
acttcatgca atgaaatgaa tccccccctt ccatcacatt gcaacagatg ttgggccctt    900
cgtgagaatt ggcttcctga agataaaggg aaagataaag ggaaatctc tgagaaagcc    960
aaactggaat actcaacaca agctgaagag ggctttgatg ttcctgattg taaaaaaact   1020
atagtgaatg attccagaga gtcatgtgtt gaggaaaatg atgataaat tacacaagct   1080
tcacaatcac aagaaagtga agactatttt cagccatcaa cttctagtag cattatttat   1140
agctgccaag aagatgtgaa agagtttgaa agggaagaaa cccaagacaa agaagagagt   1200
gtggaatcta gtttgcccct taatgccatt gaaccttgtg tgatttgtca aggtcgacct   1260
aaaaatggtt gcattgtcca tggcaaaaca ggacatctta tggcctgctt tacatgtgca   1320
aagaagctaa agaaaaggaa taagccctgc ccagtatgta gacaaccaat tcaaatgatt   1380
gtgctaactt atttcccccta g                                           1401
```

SEQ ID NO: 218          moltype = DNA  length = 826
FEATURE                 Location/Qualifiers
source                  1..826
                        mol_type = genomic DNA
                        organism = Homo sapiens
SEQUENCE: 218

-continued

```
agagcgtccc agcgcgcccg cctccccacg gacacagagc ctgctgccca cgtctcttcc   60
ctgagctgcc tgctggggtc atggagctgc caacaaagcc tggcaccttc gacctgggcc  120
tggccacatg gagcccttcc ttccagggg aaacccaccg ggctcaggca cgccgcaggg   180
atgttggcag gcagctgcct gagtacaag ctgtggtggt gggcgccagt ggcgtgggca   240
agagtgcgct gaccatccag ctgaaccacc agtgcttcgt ggaggaccac gacccacca   300
tccaggattc ctactggaag gagttgaccc tggacagtgg ggactgcatt ctgaatgtgc   360
tggacacagc agggcaggcc atccataggg ccctgcgtga ccagtgcctg gctgtctgtg   420
atggtgtgct gggcgtcttc gctctcgatg acccctcgtc tctgatccag ctgcagcaga   480
tatgggccac ctgggcccct cacccgccc agcccttgt cctcgtgggc aacaagtgtg   540
accttgtgac cactgctgga gatgctcatg ccgctgctgc agccctcgca cacagctggg   600
gggcccactt cgtggagacc tcggccaaaa cacggcaagg cgtggaggag gccttttccc   660
tgctggtcca tgagatccag agggtccagg aggccatggc gaaggagccc atggcaaggt   720
cctgtaggga gaagacccgg caccagaagg ccacctgcca ctgtggctgc tctgtggcct   780
gaaggtcttg gccaagaaat gtagacctt ccccaggcca gggtga             826
```

SEQ ID NO: 219          moltype = AA  length = 239
FEATURE                 Location/Qualifiers
REGION                  1..239
                        note = Single strand DNA oligonucleotide
source                  1..239
                        mol_type = protein
                        organism = synthetic construct
SEQUENCE: 219
```
MVSKGEELFT GVVPILVELD GDVNGHKFSV SGEGEGDATY GKLTLKFICT TGKLPVPWPT   60
LVTTLTYGVQ CFSRYPDHMK QHDFFKSAMP EGYVQERTIF FKDDGNYKTR AEVKFEGDTL  120
VNRIELKGID FKEDGNILGH KLEYNYNSHN VYIMADKQKN GIKVNFKIRH NIEDGSVQLA  180
DHYQQNTPIG DGPVLLPDNH YLSTQSALSK DPNEKRDHMV LLEFVTAAGI TLGMDELYK   239
```

SEQ ID NO: 220          moltype = DNA  length = 720
FEATURE                 Location/Qualifiers
misc_feature            1..720
                        note = Single strand DNA oligonucleotide
source                  1..720
                        mol_type = other DNA
                        organism = synthetic construct
SEQUENCE: 220
```
atggtgagca aggcgagga gctgttcacc ggggtggtgc ccatcctggt cgagctggac   60
ggcgacgtaa acggccacaa gttcagcgtg tccggcgagg cgagggcga tgccacctac  120
ggcaagctga ccctgaagtt catctgcacc accggcaagc tgcccgtgcc ctggcccacc  180
ctcgtgacca ccctgaccta cggcgtgcag tgcttcagcc gctacccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaagtaa  720
```

SEQ ID NO: 221          moltype = AA  length = 225
FEATURE                 Location/Qualifiers
REGION                  1..225
                        note = Single strand DNA oligonucleotide
source                  1..225
                        mol_type = protein
                        organism = synthetic construct
SEQUENCE: 221
```
MRSSKNVIKE FMRFKVRMEG TVNGHEFEIE GEGEGRPYEG HNTVKLKVTK GGPLPFAWDI   60
LSPQFQYGSK VYVKHPADIP DYKKLSFPEG FKWERVMNFE DGGVTVTQD SSLQDGCFIY   120
KVKFIGVNFP SDGPVMQKKT MGWEASTERL YPRDGVLKGE IHKALKLKDG GHYLVEFKSI  180
YMAKKPVQLP GYYYVDSKLD ITSHNEDYTI VEQYERTEGR HHLFL               225
```

SEQ ID NO: 222          moltype = DNA  length = 678
FEATURE                 Location/Qualifiers
misc_feature            1..678
                        note = Single strand DNA oligonucleotide
source                  1..678
                        mol_type = other DNA
                        organism = synthetic construct
SEQUENCE: 222
```
atgaggtctt ccaagaatgt tatcaaggag ttcatgaggt ttaaggttcg catggaagga   60
acggtcaatg ggcacgagtt tgaaatagaa ggcgaaggag aggggaggcc atacgaaggc  120
cacaataccg taaagcttaa ggtaaccaag gggggacctt tgccatttgc ttgggatatt  180
ttgtcaccac aatttcagta tggaagcaag gtatatgtca agcaccctgc cgacatacca  240
gactataaaa agctgtcatt tcctgaagga tttaaatggg aaagggtcat gaactttgaa  300
gacggtggcg tcgttactgt aacccaggat tccagtttgc aggatggctg tttcatctac  360
aaggtcaagt tcattggcgt gaactttcct tccgatggac tgttatgca aaagaagaca  420
atgggctggg aagccagcac tgagcgtttg tatcctcgtg atggcgtgtt gaaaggagag  480
attcataagg ctctgaagct gaaagacggt ggtcattacc tagttgaatt caaaagtatt  540
```

-continued

```
tacatggcaa agaagcctgt gcagctacca gggtactact atgttgactc caaactggat   600
ataacaagcc acaacgaaga ctatacaatc gttgagcagt atgaaagaac cgagggacgc   660
caccatctgt tcctttaa                                                 678
```

MEDIA FOR CULTURING NAIVE HUMAN PLURIPOTENT STEM CELLS

RELATED APPLICATIONS

This application is a Continuation of U.S. patent application Ser. No. 15/500,163 filed on Jan. 30, 2017, which is a National Phase of PCT Patent Application No. PCT/IL2015/050785, having International Filing Date of Jul. 30, 2015, which claims the benefit of priority under 35 USC § 119 (e) of U.S. Provisional Patent Application Nos. 62/167,469, filed on May 28, 2015 and 62/030,792, filed on Jul. 30, 2014. The contents of the above applications are all incorporated by reference as if fully set forth herein in their entirety.

SEQUENCE LISTING STATEMENT

The XML file, entitled 98606SequenceListing.XML, created on Feb. 3, 2024, comprising 604,864 bytes, submitted concurrently with the filing of this application is incorporated herein by reference.

FIELD AND BACKGROUND OF THE INVENTION

The present invention, in some embodiments thereof relates to novel culture media which can be used to generate and expand pluripotent stem cells in general and more particularly naive pluripotent stem cells.

ESC-like cells, termed induced pluripotent (iPS) cells can be generated from somatic cells by ectopic expression of different transcription factors, originally Oct4, Sox2, Klf4 and c-Myc, that share all defining features with naive mouse ESCs. The reprogramming process typically requires extensive cell proliferation of a period of at least one week, after which a certain fraction of the cell progeny successfully converts into ES-like state in an unpredictable pattern and with different time latencies. Great progress has been achieved in identifying additional and alternative transcriptional factors and small molecules that can substitute some of the exogenous factor or boost reprogramming efficiency when combined with Oct4, Sox2, Klf4 and c-Myc (OSKM). A variety of enzymes and chromatin remodelers have been identified to cooperate with the reprogramming factors in facilitating the required early and late chromatin changes leading to authentic iPSC reprogramming in a fraction of donor cell progeny (e.g., Wdr5, Utx, Tet2).

Despite of these advances, the reprogramming efficiency of somatic cells remains low. Further, for each individual somatic epigenome challenged with the overexpression of reprogramming factors, the outcome is highly stochastic, and the majority of cells assume different levels of reprogramming.

Embryonic stem cells (ESCs) were first isolated from mouse embryos by explanting the inner cell mass (ICM) of developing embryos in vitro in the presence of the leukemia inhibitory factor (LIF) cytokine and mouse embryonic feeder (MEF) cells. Mouse ESCs recapitulate molecular signatures of the nascent ICM and are, therefore, termed "naive pluripotent cells". This includes expression of Oct4, Nanog and Klf pluripotency genes, lack of epiblast and somatic early lineage specific markers, and maintenance of a pre X-inactivation state with both X chromosomes active in female cells. Further, the cells retain a non-restricted developmental potential as they can robustly differentiate into all cell types in vitro and, upon injection into the mouse blastocyst, they efficiently contribute to the three germ layers and to the germ-line of chimeric animals. Finally, the high growth rate and open chromatin confirmation of mouse ES cells, has rendered these cells as one of the most valuable tools for mouse genetics by allowing efficient gene specific targeting via homologous recombination.

Recently, a dramatically different type of pluripotent cells, termed EpiSCs, were derived by explanting the post-implantation epiblast in growth conditions supplemented with FGF2 [also known as "basic fibroblast growth factor (bFGF)"] and Activin. Although EpiSCs are pluripotent, they have a restricted developmental potential in comparison to ESCs and therefore are termed as "primed pluripotent cells". EpiSCs are highly inefficient in generating animal chimeras, have already undergone X chromosome inactivation, and demonstrate heterogeneous expression of early lineage-commitment markers Whereas naive murine pluripotent cells can differentiate into a primed EpiSC-like state in vitro by promoting Activin and FGF2 signaling, EpiSCs can epigenetically revert back to ESC-like naive pluripotency by defined signaling stimuli.

Remarkably, ESCs derived from humans share several defining features with EpiSC cells, rather than with mouse ESCs. In contrast to mouse ESCs, the maintenance of human ES cells requires FGF2 and Activin A (rather than LIF/Stat3 signaling), they are highly sensitive to passaging as single cells, display heterogeneous expression of epiblast and lineage commitment markers, and utilize the proximal enhancer element to drive the expression of Oct4 in the post-implantation Epiblast (rather than the distal Oct4 enhancer active in the ICM). Thus, the molecular and biological similarities of human ESCs with mouse epiblast EpiSCs suggest that human ESCs correspond to the primed pluripotent state rather than the naive state of mouse ESCs and that this could be the underlying reason for the biological properties of conventional human ESCs that impede their use for disease related research This includes laborious culture conditions, low gene targeting efficiencies by homologous recombination and the dramatic heterogeneity in differentiation propensity among different human ESC and iPSC lines.

The fact that conventional/primed human ESCs are derived from the ICM has led to the mistaken belief that the primed state is the only or "default" state of pluripotency that can be isolated in humans. Mouse naive ESC cells can be derived from Non-obese diabetogenic (NOD) mice blastocysts only if additional signaling molecules or transcription factors are exogenously provided together with LIF cytokine (e.g. Naive NOD ESC and iPSCs could be propagated in PD0325901/CHIR99021/LIF or Kenopaullone/CHIR99021/LIF or constitutive expression of Klf4/Lif and c-Myc/LIF conditions). In the absence of these additional factors (or in LIF only conditions), the naive state, even if isolated from the mouse ICM, is masked by in vitro acquisition of pluripotent state that is nearly indistinguishable from EpiSC cells in a process that probably imitates in vivo differentiation during normal early development. These findings allowed the generation of fully pluripotent naive ES and iPS cells from previously considered "non-permissive' strains. Experiments in NOD mice have raised the question whether appropriate conditions that allow derivation of naive or mouse ESC-like stem cell in humans have not been devised yet and that stabilization of a naive human pluripotent state requires additional undefined factors (similar or different from those applied to NOD mouse and rat ESCs/iPSCs). Further support for the possibility that explanted blastocysts differentiate in vitro into a primed state was generated by close monitoring of X chromosome dynamics in human female ESC lines derived in vitro and demonstrated that the cells undergo X chromosome inactivation as a part of an in vitro adaptation process following this derivation, and this can be accelerated by high oxygen concentrations, and attenuated partially by addition of LIF or specific types of feeder cells that provide undefined signals. These results indicated that XaXa (X-active, X-active, based on absence of XIST bodies) naive cells might be present in the human ICM, and that in vitro captured conventional human ESCs poorly reflect their ICM counterparts.

These observations have raised the possibility that appropriate conditions may have not been devised to allow isolation of naive stem cells from a range of species that have yielded thus far primed or EpiSC-like cells, possibly including humans. Indeed in a follow-up work evidence was provided for the possibility to derive alternative human pluripotent cell states that more extensively share defining features with murine ESCs. As previously shown (Hanna et al., 2010b), a screening approach was taken that involved introducing reprogramming factors and/or small molecules that support the naive pluripotent state led to in vitro stabilization of a novel pluripotent cell state that shares several defining features with murine ESCs (Hanna et al., 2010b). The propagation in LIF cytokine and ERK1/2 inhibitor PD0325901 and GSK3b inhibitor CHIR99021 (abbreviated as 2i supplemented conditions-two small molecule inhibitors of ERK1/2 signaling and GSK3β to promote WNT signaling, abbreviated as "PD/CH" or "2i" conditions) together with over-expression of OCT4/KLF4 or KLF2/KLF4 induced conversion of conventional human ES and iPS cells to what was then mistakenly referred as human naive pluripotent state reminiscent of that of mouse ESCs (Hanna et al., 2010b). These previously described naive human ESCs were pluripotent by several available criteria including embryonic body differentiation and in vivo teratoma formation. Importantly, they were epigenetically and molecularly distinct from conventional "primed" human ESCs/iPSCs. "Naive" hPSCs generated by Hanna et al., 2010b exhibited XIST methylation on both X alleles, high single cell cloning efficiency and showed a gene expression pattern that resembled that of naive mouse ES cells (lack of MHC class I expression, and clustered with murine naive ESCs in cross-species unbiased gene clustering for 9773 expressed orthologue genes) (Hanna et al., 2010b). Nevertheless, a major limitations and unsolved questions remain that cast doubt on the true pluripotency of previously published/established lines and their stability. Only transgene dependent naive ESC/iPSCs could be maintained for over 18 passages. Forskolin enabled replacement of exogenous factors together with 2i/LIF, but only for no more than 19 passages and the cultures retained high differentiation propensity (Hanna et al., 2010b). XIST was completely methylated in the previously referred naive human ESC/iPSCs and the cells lacked any XIST transcription (Hanna et al., 2010b), which is inconsistent with in vivo results on human blastocysts that clearly show XIST transcription (without forming XIST bodies, i.e., XIST coated X chromosomes) (Okamoto et al., 2011). Collectively, these findings suggest that the isolated cells thus far do not reflect authentic features of human ICM, and retain a compromised pluripotency and enhanced propensity for differentiation. Substantial published data generated by many different groups highlight the rationale behind the concept that genetically unmodified pluripotent naive human stem cells have not been adequately isolated so far, and that the conditions allowing expansion of such cells and their molecular properties (if they indeed are proven to exist) are not known (De Los Angeles et al., 2012; Hanna et al., 2010b).

Multicellular organisms have evolved tissue homeostasis mechanisms to ensure life-long fitness of their organs and systems. Among these mechanisms, those that regulate the elimination of unwanted less-fit cells are fundamental for tissue development and homeostasis. Whereas overtly damaged or hyper proliferative cells usually trigger well-characterized cell-autonomous apoptotic pathways or cause cancer, mechanisms that survey viable cell fitness to optimize a tissue's cell composition are less well understood. A candidate mechanism is the phenomenon of "Cell Competition" (also known as "Cell Cheating"), first described in Drosophila.

Studies in flies have shown that the cells of growing organs are able to compare their fitness with that of neighboring cells, and the less-fit but otherwise viable cells are eliminated (out-competed) when confronted with a fitter cell population (competitor). Cell competition for survival is an active process because, in addition to a contribution from differential proliferation, it is executed through the apoptotic or senescence mediated elimination of the less-fit population by cell non-autonomous mechanisms. Cell parameters that trigger competition in flies include differences in protein synthesis capacity, growth factor receptivity and the expression level of dMyc, a major activator of cell anabolism. Super competition or Cheating is a variant of cell competition in which cells moderately overexpressing Myc outcompete wild-type (WT) cells. The replacement of cell populations through cell competition is phenotypically silent, because the competitor cells mostly conform to size-control mechanisms. This process is potentially important for the long-term maintenance of tissue performance, as it might provide a mechanism for elimination of suboptimal cells from stem-cell niches and progenitor-cell pools. In addition, cell competition for survival might serve to enhance tissue replacement during regeneration.

Recently cell competition has been characterized in mice. One study showed that cell competition is promoted by an imbalance in Myc dose between neighboring cells in the mouse epiblast E6.5 stage, and that c-Myc overexpressing cells in the mouse embryo behave like "cheaters" and outcompete their neighbors within the same mouse embryo belonging to the same species (Dejosez M et al., 2013. "Safeguards for cell cooperation in mouse embryogenesis shown by genome-wide cheater screen". See comment in PubMed Commons belowScience. 2013 Sep. 27; 341 (6153): 1511-4; and Clavería C., et al., 2013. "Myc-driven endogenous cell competition in the early mammalian embryo". Nature. 2013 Aug. 1; 500 (7460): 39-44). Other studies showed that partial or complete depletion of P53 in mouse embryonic stem cells or in hematopoietic stem cells endows them the ability to outcompete WT mouse cells in the same.

Additional background art includes Xu Y., et al., 2013 (Journal of Biological Chemistry, 288:9767-9778); Luo M., et al., 2013 (Stem Cells. March 26. doi: 10.1002/stem.1374. [Epub ahead of print]); International Application No. PCT/US08/04516 ("Reprogramming of Somatic Cells", Jaenisch; Rudolf; et al.); Kim, H., Wu, J., Ye, S., Tai, C.-I., Zhou, X., Yan, H., Li, P., Pera, M., and Ying, Q.-L. (2013). Modulation of b-catenin function maintains mouse epiblast stem cell and human embryonic stem cell self-renewal. Nature Communications 4, 1-11; Li, X., Zhu, L., Yang, A., Lin, J., Tang, F., Jin, S., Wei, Z., Li, J., and Jin, Y. (2011). Calcineurin-NFAT Signaling Critically Regulates Early Lineage Specification in Mouse Embryonic Stem Cells and Embryos. Stem Cell 8, 46-58 and Shimizu, T., Ueda, J., Ho, J. C., Iwasaki, K., Poellinger, L., Harada, I., and Sawada, Y. (2012). Dual Inhibition of Src and GSK3 Maintains Mouse Embryonic Stem Cells, Whose Differentiation Is Mechanically Regulated by Src Signaling. Stem Cells 30, 1394-1404.

SUMMARY OF THE INVENTION

According to an aspect of some embodiments of the present invention there is provided a culture medium comprising a STAT3 activator, an ERK1/2 inhibitor and an Axin stabilizer.

According to some embodiments of the invention, the culture medium further comprising a PKC inhibitor.

According to an aspect of some embodiments of the present invention there is provided a culture medium comprising a STAT3 activator, an ERK1/2 inhibitor, an Axin stabilizer and a PKC inhibitor.

According to some embodiments of the invention, the culture medium further at least one agent selected from the group consisting of: a ROCK inhibitor, a SRC inhibitor, ascorbic acid, a PKA agonist, a YAP/TAZ inhibitor, a NOTCH inhibitor, an SHH inhibitor, a TGFβR inhibitor, a BMP inhibitor, an FGFR inhibitor, a JNK inhibitor, an ERK5 inhibitor, a BRAF inhibitor, an ARAFi, a CRAFi, a p38 inhibitor, a GSK3b inhibitor, an LSD1 inhibitor, a PI3K activator, a SMAD activator and a DOT1L inhibitor.

According to some embodiments of the invention, the SMAD activator is selected from the group consisting of: activin A, TGFβ1 and BMP4.

According to some embodiments of the invention, the PI3K activator is selected from the group consisting of: IGF1, IGF2, SCF and FGF2.

According to some embodiments of the invention, the medium further comprising a GSK3b inhibitor.

According to an aspect of some embodiments of the present invention there is provided a culture medium a STAT3 activator, an ERK1/2 inhibitor, an Axin stabilizer, a PKC inhibitor and a GSK3b inhibitor.

According to some embodiments of the invention, the culture medium further comprising at least one agent selected from the group consisting of: a ROCK inhibitor, an SRC inhibitor, ascorbic acid, a PKA agonist, a YAP/TAZ inhibitor, a NOTCH inhibitor, an SHH inhibitor, a TGFβR inhibitor, a BMP inhibitor, an FGFR inhibitor, a JNK inhibitor, an ERK5 inhibitor, a BRAF inhibitor, an ARAFi, a CRAFi, a p38 inhibitor, an LSD1 inhibitor, a PI3K activator, a SMAD activator and a DOT1L inhibitor.

According to some embodiments of the invention, the culture medium further comprising at least one agent selected from the group consisting of: basic fibroblast growth factor (bFGF), transforming growth factor beta 1 (TGFβ1), ACTIVIN A, a GSK3b inhibitor, a ROCK inhibitor, a P38 inhibitor, a JNK inhibitor, a NOTCH inhibitor, a SRC inhibitor, insulin-like growth factor 1 (IGF1), insulin-like growth factor II (IGFII), a bone morphogenetic protein (BMP) signaling inhibitor, a Sonic Hedgehog path way (SHH) inhibitor, an ERK5 inhibitor, Forskolin, Kenpaullone, BayK8644, an inhibitor of G9a and/or Glp (e.g., BIX01294 or UNC0638), stem cell factor (SCF), YAP/TAZ inhibitor, L-Ascorbic Acid, LSD1 inhibitor, and a DOT1L inhibitor.

According to some embodiments of the invention, the culture medium further comprising at least one agent selected from the group consisting of: a transforming growth factor receptor (TGFR) inhibitor, a fibroblast growth factor receptor (FGFR) inhibitor, ACTIVIN A, a GSK3b inhibitor, a ROCK inhibitor, a P38 inhibitor, a JNK inhibitor, a NOTCH inhibitor, a SRC inhibitor, insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, an inhibitor of G9a and/or Glp (e.g., BIX01294 or UNC0638), stem cell factor (SCF), YAP/TAZ inhibitor, L-Ascorbic Acid, LSD1 inhibitor, and DOT1L inhibitor.

According to some embodiments of the invention, the culture medium further comprising at least one agent selected from the group consisting of: Activin A, transforming growth factor beta 1 (TGFβ1), a fibroblast growth factor receptor (FGFR) inhibitor, a GSK3b inhibitor, a ROCK inhibitor, a P38 inhibitor, a JNK inhibitor, a NOTCH inhibitor, a SRC inhibitor, insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, an inhibitor of G9a and/or Glp (e.g., BIX01294 or UNC0638), stem cell factor (SCF), YAP/TAZ inhibitor, L-Ascorbic Acid, LSD1 inhibitor, and DOT1L inhibitor.

According to some embodiments of the invention, the culture medium further comprising at least one agent selected from the group consisting of: basic fibroblast growth factor (bFGF), a transforming growth factor receptor (TGFR) inhibitor, a GSK3b inhibitor, a ROCK inhibitor, a P38 inhibitor, a JNK inhibitor, a NOTCH inhibitor, a SRC inhibitor, insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, an inhibitor of G9a and/or Glp (e.g., BIX01294 or UNC0638), stem cell factor (SCF), YAP/TAZ inhibitor, L-Ascorbic Acid, LSD1 inhibitor, and DOT1L inhibitor.

According to an aspect of some embodiments of the present invention there is provided a culture medium comprising an ERK1/2 inhibitor, a STAT3 activator and a SRC inhibitor.

According to some embodiments of the invention, the culture medium further comprising an AXIN complex stabilizer (AXINs).

According to some embodiments of the invention, the culture medium further comprising a GSK3β inhibitor.

According to some embodiments of the invention, the culture medium further comprising a p38 inhibitor.

According to an aspect of some embodiments of the present invention there is provided a culture medium comprising an ERK1/2 inhibitor, a GSK3β inhibitor, a p38 inhibitor, a STAT3 activator and at least one agent selected from the group consisting of a SRC inhibitor and an AXIN complex stabilizer (AXINs).

According to an aspect of some embodiments of the present invention there is provided a culture medium comprising an ERK1/2 inhibitor, a GSK3β inhibitor, a p38 inhibitor, a JNK inhibitor, a STAT3 activator, a transforming growth factor beta receptor (TGFβR) inhibitor, a PKC inhibitor, a p38 inhibitor and basic fibroblast growth factor (bFGF).

According to an aspect of some embodiments of the present invention there is provided a cell culture comprising cells and the culture medium of some embodiments of the invention.

According to an aspect of some embodiments of the present invention there is provided a method of generating a naive pluripotent stem cell (PSC), comprising:

incubating a non-naive PSC cell in the culture medium of some embodiments of the invention, which allow generation of the naive PSC from the non-naive PSC, wherein:

(i) when the naive PSC is a female PSC, then the naive female PSC has two unmethylated alleles of the promoter of the X-inactive specific transcript (XIST) gene; and (ii) when the naive PSC is a male PSC, then the naive male PSC has an unmethylated allele of the promoter of the XIST gene; and/or an expression level of transcription factor E3 (TFE3) in the naive PSC is characterized by a nucleus to cytoplasm expression ratio which is equal to or higher than 1 as determined by an immunostaining assay; and/or the naïve PSC is characterized by a positive expression of C-KIT (CD117) on the cell surface of the naïve PSC, thereby generating the naive PSC.

According to an aspect of some embodiments of the present invention there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the promoter of the XIST gene; and (ii) when the naive PSC is a male PSC, then the naive male PSC has an unmethylated allele of the promoter of the XIST gene, and/or an expression level of transcription factor E3 (TFE3) characterized by a nucleus to cytoplasm expression ratio which is equal to or higher than 1 as determined by an immunostaining assay, wherein the conditions comprise a culture medium which comprises KO-DMEM, N2 supplement (Gibco), B27 supplement, LIF, ERK1/2 inhibitor, PKC inhibitor, Axin stabilizer thereby generating the naive PSC.

According to an aspect of some embodiments of the present invention there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the promoter of the XIST gene; and (ii) when the naive PSC is a male PSC, then the naive male PSC has an unmethylated allele of the promoter of the XIST gene, and/or an expression level of transcription factor E3 (TFE3) characterized by a nucleus to cytoplasm expression ratio which is equal to or higher than 1 as determined by an immunostaining assay, wherein the conditions comprise a culture medium which comprises DMEM-F12/NEURObasal (GIBCO) 1:1 mix, N2 supplement (Gibco), B27 supplement (GIBCO), LIF (STAT3 activator), ERK1/2 inhibitor, PKC inhibitor, Axin stabilizer thereby generating the naive PSC.

According to an aspect of some embodiments of the present invention there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the promoter of the XIST gene; and (ii) when the naive PSC is a male PSC, then the naive male PSC has an unmethylated allele of the promoter of the XIST gene, and/or an expression level of transcription factor E3 (TFE3) characterized by a nucleus to cytoplasm expression ratio which is equal to or higher than 1 as determined by an immunostaining assay, wherein the conditions comprise a culture medium which comprises DMEM-F12, N2 supplement (Gibco), B27 supplement, LIF (STAT3 activator), ERK1/2 inhibitor, PKC inhibitor, Axin stabilizer thereby generating the naive PSC.

According to an aspect of some embodiments of the present invention there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the promoter of the XIST gene; and (ii) when the naive PSC is a male PSC, then the naive male PSC has an unmethylated allele of the promoter of the XIST gene, and/or an expression level of transcription factor E3 (TFE3) characterized by a nucleus to cytoplasm expression ratio which is equal to or higher than 1 as determined by an immunostaining assay, wherein the conditions comprise a culture medium which comprises KO-DMEM, N2 supplement (Gibco), B27 supplement, LIF, ERK1/2 inhibitor, GSK3b inhibitor, PKC inhibitor, Axin stabilizer thereby generating the naive PSC.

According to an aspect of some embodiments of the present invention there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the promoter of the XIST gene; and (ii) when the naive PSC is a male PSC, then the naive male PSC has an unmethylated allele of the promoter of the XIST gene, and/or an expression level of transcription factor E3 (TFE3) characterized by a nucleus to cytoplasm expression ratio which is equal to or higher than 1 as determined by an immunostaining assay, wherein the conditions comprise a culture medium which comprises DMEM-F12/NEURObasal (GIBCO) 1:1 mix, N2 supplement (Gibco), B27 supplement (GIBCO), LIF (STAT3 activator), ERK1/2 inhibitor, GSK3b inhibitor, PKC inhibitor, Axin stabilizer thereby generating the naive PSC.

According to an aspect of some embodiments of the present invention there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the promoter of the XIST gene; and (ii) when the naive PSC is a male PSC, then the naive male PSC has an unmethylated allele of the promoter of the XIST gene, and/or an expression level of transcription factor E3 (TFE3) characterized by a nucleus to cytoplasm expression ratio which is equal to or higher than 1 as determined by an immunostaining assay, wherein the conditions comprise a culture medium which comprises DMEM-F12, N2 supplement (Gibco), B27 supplement, LIF (STAT3 activator), ERK1/2 inhibitor, GSK3b inhibitor, PKC inhibitor, Axin stabilizer thereby generating the naive PSC.

According to some embodiments of the invention, incubating is performed under culture conditions devoid of feeder cells.

According to some embodiments of the invention, incubating is performed under culture conditions which comprise culturing on feeder cells.

According to an aspect of some embodiments of the present invention there is provided a method of improving generation of induced pluripotent stem cells (iPSCs) from a somatic cell, comprising:

(a) expressing within the somatic cell a first factor selected from the group consisting of Nanog, ESRRB, KLF2, TBX3, ERAS and KLF17, and a second factor selected from the group consisting of Nanog, ESRRB, KLF2, TBX3, ERAS, Oct4, Sox2, Klf4, c-Myc, and KLF17, wherein the first and second factor are non-identical; and (b) inhibiting Mbd3 and/or Gatad2a expression and/or activity in the somatic cell, thereby improving generation of the iPSCs from a somatic cell.

According to some embodiments of the invention, the culture medium further comprises a ROCK inhibitor.

According to some embodiments of the invention, the culture medium further comprises a JNK inhibitor.

According to some embodiments of the invention, the culture medium further comprises at least one agent selected from the group consisting of basic fibroblast growth factor (bFGF), transforming growth factor (TGF) inducer, a transforming growth factor receptor (TGFR) inhibitor and a fibroblast growth factor receptor (FGFR) inhibitor.

According to some embodiments of the invention, the culture medium further comprises at least two agents selected from the group consisting of: basic fibroblast growth factor (bFGF), transforming growth factor (TGF) inducer, a transforming growth factor receptor (TGFR) inhibitor and a fibroblast growth factor receptor (FGFR) inhibitor.

According to some embodiments of the invention, the culture medium further comprises a TGF inducer, wherein the TGF inducer is selected from the group consisting of transforming growth factor beta 1 (TGFβ1), transforming growth factor beta 2 (TGFβ2) and Activin.

According to some embodiments of the invention, the TGF inducer is selected from the group consisting of transforming growth factor beta 1 (TGFβ1), transforming growth factor beta 2 (TGFβ2) and Activin.

According to some embodiments of the invention, the culture medium further comprises a protein kinase C (PKC) inhibitor and/or a BMP inhibitor.

According to some embodiments of the invention, the culture medium further comprises at least one additional agent selected from the group consisting of: insulin-like growth factor 1 (IGF1), insulin-like growth factor II (IGFII), bone morphogenetic protein 4 (BMP4), a Sonic Hedgehog pathway (SHH) inhibitor, an ERK5 inhibitor, Forskolin, Kenpaullone, BayK8644, an inhibitor of G9a and/or Glp (e.g., BIX01294 or UNC0638), and stem cell factor (SCF).

According to some embodiments of the invention, the culture medium further comprises a STAT3 activator, an ERK1/2 inhibitor, a GSK3β inhibitor, a P38 inhibitor, a JNK inhibitor, bFGF, TGFβ1, a ROCK inhibitor, AXIN stabilizer and SRC family kinase inhibitor.

According to some embodiments of the invention, the culture medium comprises a STAT3 activator, an ERK1/2 inhibitor, a GSK3β inhibitor, a P38 inhibitor, a JNK inhibitor, bFGF, TGFβ1, a ROCK inhibitor, AXIN stabilizer and SRC family kinase inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, bFGF, TGFβ1, a ROCK inhibitor, AXIN stabilizer and SRC family kinase inhibitor and a PKC inhibitor.

According to some embodiments of the invention, the culture medium comprising a STAT3 activator, an ERK1/2 inhibitor, a GSK3β inhibitor, a P38 inhibitor, a bFGF, TGFβ1, a ROCK inhibitor, AXIN stabilizer, SRC family kinase inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, bFGF, TGFβ1, a ROCK inhibitor, AXIN stabilizer and SRC family kinase inhibitor, a BMP inhibitor and a PKC inhibitor.

According to some embodiments of the invention, the culture medium comprises a STAT3 activator, an ERK1/2 inhibitor, a GSK3β inhibitor, a P38 inhibitor, a bFGF, TGFβ1, a ROCK inhibitor, AXIN stabilizer and SRC family kinase inhibitor.

According to some embodiments of the invention, the culture medium comprises a STAT3 activator, an ERK1/2 inhibitor, a GSK3β inhibitor, a P38 inhibitor, a bFGF, TGFβ1, a ROCK inhibitor, AXIN stabilizer, SRC family kinase inhibitor and a BMP inhibitor.

According to some embodiments of the invention, the culture medium comprises a STAT3 activator, an ERK1/2 inhibitor, a GSK3β inhibitor, a P38 inhibitor, a bFGF, TGFβ1, a ROCK inhibitor, AXIN stabilizer, SRC family kinase inhibitor and a PKC inhibitor.

According to some embodiments of the invention, the culture medium comprises a STAT3 activator, an ERK1/2 inhibitor, a GSK3β inhibitor, a P38 inhibitor, a bFGF, TGFβ1, a ROCK inhibitor, AXIN stabilizer, SRC family kinase inhibitor, a BMP inhibitor and a PKC inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, AXIN stabilizer and SRC family kinase inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, AXIN stabilizer, a SRC family kinase inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, AXIN stabilizer, a SRC family kinase inhibitor and a PKC inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, AXIN stabilizer, a SRC family kinase inhibitor, a PKC inhibitor and a BMP inhibitor.

According to some embodiments of the invention, the culture medium comprises a STAT3 activator, an ERK1/2 inhibitor, a GSK3 inhibitor, a P38 inhibitor, a JNK inhibitor, FGF2, TGFβ1, a ROCK inhibitor and a SRC family kinase inhibitor.

According to some embodiments of the invention, the culture medium comprises a STAT3 activator, an ERK1/2 inhibitor, a GSK3β inhibitor, a P38 inhibitor, a JNK inhibitor, FGF2, TGFβ1, a ROCK inhibitor, a SRC family kinase inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, FGF2, TGFβ1, a ROCK inhibitor, a SRC family kinase inhibitor and a PKC inhibitor.

According to some embodiments of the invention, the culture medium comprises a STAT3 activator, an ERK1/2 inhibitor, a GSK3β inhibitor, a P38 inhibitor, a JNK inhibitor, FGF2, TGFβ1, a ROCK inhibitor, a SRC family kinase inhibitor, a PKC inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor and a SRC family kinase inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, a SRC family kinase inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, a SRC family kinase inhibitor and a PKC inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, a SRC family kinase inhibitor, a PKC inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, a ROCK inhibitor, an AXIN stabilizer and a SRC family kinase inhibitor.

According to some embodiments of the invention, the culture medium comprises a STAT3 activator, an ERK1/2 inhibitor, a GSK3β inhibitor, a P38 inhibitor, a JNK inhibitor, a ROCK inhibitor, an AXIN stabilizer, a SRC family kinase inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, a ROCK inhibitor, an AXIN stabilizer, a SRC family kinase inhibitor and a PKC inhibitor.

According to some embodiments of the invention, the culture medium comprises a STAT3 activator, an ERK1/2 inhibitor, a GSK3β inhibitor, a P38 inhibitor, a JNK inhibitor, a ROCK inhibitor, an AXIN stabilizer, a SRC family kinase inhibitor, a PKC inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor and an AXIN stabilizer.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer and a BMP inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer and a PKC inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, a PKC inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, an SRC family kinase inhibitor and a FGF receptor inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, an SRC family kinase inhibitor, a FGF receptor inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, an SRC family kinase inhibitor, a FGF receptor inhibitor and a PKC inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, an SRC family kinase inhibitor, a FGF receptor inhibitor, a PKC inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer and a FGF receptor inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, a FGF receptor inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, a FGF receptor inhibitor and a PKC inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, a FGF receptor inhibitor, a PKC inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, Src family kinase inhibitor and a TGF receptor inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, Src family kinase inhibitor, a TGF receptor inhibitor and a BMP inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, Src family kinase inhibitor, a TGF receptor inhibitor and a PKC inhibitor.

According to some embodiments of the invention, the culture medium comprises a STAT3 activator, an ERK1/2 inhibitor, a GSK3β inhibitor, a P38 inhibitor, a JNK inhibitor, TGFβ1, a ROCK inhibitor, an AXIN stabilizer, Src family kinase inhibitor, a TGF receptor inhibitor, a PKC inhibitor and a BMP inhibitor.

According to some embodiments of the invention, the STAT3 activator is selected from the group consisting of leukemia inhibitory factor (LIF) and interleukin 6 (IL6).

According to some embodiments of the invention, the culture medium comprises at least one agent selected from the group consisting of a BMP inhibitor, a ROCK inhibitor, a SRC inhibitor and an AXIN complex stabilizer (AXINs).

According to some embodiments of the invention, the culture medium which comprises an ERK1/2 inhibitor, a GSK3β inhibitor, a p38 inhibitor, a JNK inhibitor, a STAT3 activator, a transforming growth factor beta receptor (TGFβR) inhibitor, a PKC inhibitor, a p38 inhibitor and basic fibroblast growth factor (bFGF), further comprises at least one agent selected from the group consisting of a BMP inhibitor, a ROCK inhibitor, a SRC inhibitor and an AXIN complex stabilizer (AXINs).

According to some embodiments of the invention, the culture medium further comprises a supplement selected from the group consisting of N2 supplement and B27 supplement.

According to some embodiments of the invention, the culture medium further comprises ascorbic acid.

According to some embodiments of the invention, the culture medium further comprises oleic Acid.

According to some embodiments of the invention, the culture medium further comprises Linoleic Acid and/or pipecolic acid.

According to some embodiments of the invention, the culture medium is devoid of animal serum.

According to some embodiments of the invention, the culture medium further comprises serum replacement.

According to some embodiments of the invention, the medium is capable of maintaining pluripotent stem cells in an undifferentiated state for at least 2 passages.

According to some embodiments of the invention, the pluripotent stem cells are naïve pluripotent stem cells.

According to some embodiments of the invention, the culture medium further comprises an MBD3 inhibitor.

According to some embodiments of the invention, the culture medium further comprises a chromodomain helicase DNA binding protein 4 (CHD4) inhibitor.

According to some embodiments of the invention, the culture medium further comprises P66 alpha coiled-coil domain or p66alpha inhibitor.

According to some embodiments of the invention, the non-naive PSC is selected from the group consisting of a primed PSC, a blastocyst, an induced pluripotent stem cell (iPSC) and a somatic cell.

According to some embodiments of the invention, the non-naive PSC comprises a somatic cell then the method further comprises subjecting the somatic cell to de-differentiation conditions, to thereby obtain an induced pluripotent stem cell.

According to some embodiments of the invention, the de-differentiation conditions comprise exogenously expressing within the somatic cell at least two factors selected from the group consisting of Oct4, Sox2, Klf4, Nanog, ESRRB, KLF2, TBX3, ERAS, c-Myc and KLF17.

According to some embodiments of the invention, the inhibiting the Mbd3 activity is performed by inhibiting binding of the Mbd3 to the nucleosome remodeling and deacetylase (NuRD) complex.

According to some embodiments of the invention, the inhibiting the binding of the Mbd3 to the NuRD complex is performed using a chromodomain helicase DNA binding protein 4 (CHD4) inhibitor.

According to some embodiments of the invention, the inhibiting the binding of the Mbd3 to the NuRD complex is performed using a P66 alpha coiled-coil domain.

According to some embodiments of the invention, inhibiting the Mbd3 activity is performed by inhibiting binding of the Mbd3 to the nucleosome remodeling and deacetylase (NuRD) complex, wherein inhibiting the binding of the Mbd3 to the NuRD complex is performed using a P66 alpha coiled-coil domain.

According to some embodiments of the invention, the inhibiting the Mbd3 expression is performed using a protein kinase C (PKC) inhibitor.

According to some embodiments of the invention, the method further comprises exogenously expressing ES cell expressed Ras (ERAS) coding sequence or activating endogenous expression of the ERAS in the somatic cell.

According to some embodiments of the invention, the expressing is effected for at least 48 hours such that the inhibiting the Mbd3 is effected to 10-30% of a level of the Mbd3 prior to the expressing.

According to some embodiments of the invention, the expressing is effected for about 48 hours and the inhibiting is effected after the about 48 hours.

According to some embodiments of the invention, the iPSC is a murine iPSC.

According to some embodiments of the invention, the method further comprises culturing the murine iPSC in a medium which comprises LIF, an ERK1/2 inhibitor and a GSK3b inhibitor.

According to some embodiments of the invention, the medium further comprises an agent selected from the group consisting of a SRC inhibitor and an AXIN complex stabilizer (AXINs).

According to some embodiments of the invention, when the iPSC is a human iPSC, the method further comprising:

(c) culturing the human iPSC in a culture medium which comprises LIF, an ERK1/2 inhibitor, a GSK3b inhibitor, a P38 inhibitor, a JNK inhibitor, basic fibroblast growth factor (bFGF) and transforming growth factor-beta 1 (TGFβ1).

According to some embodiments of the invention, the medium further comprises a ROCK inhibitor.

According to some embodiments of the invention, the medium further comprises SRC inhibitor and an AXIN complex stabilizer (AXINs).

According to some embodiments of the invention, the step (c) is performed following about 48 hours from the expressing of step (a).

According to some embodiments of the invention, the expressing is performed using DNA transfection of the factors.

According to some embodiments of the invention, the expressing is performed using RNA transfection of the factors.

According to some embodiments of the invention, the expressing is performed using protein transfection of the factors.

According to some embodiments of the invention, the unmethylated alleles of the promoter of the XIST gene in a female cell comprise less than 20% of CpG sites in the XIST promoter amplicon set forth by SEQ ID NO:70 being methylated.

According to some embodiments of the invention, the unmethylated allele of the promoter of the XIST gene in a male cell comprises less than 20% of CpG sites in the XIST promoter amplicon set forth by SEQ ID NO:70 being methylated.

According to some embodiments of the invention, the inhibitor of the G9a and/or the inhibitor of the Glp is selected from the group consisting of: BIX01294 and UNC0638.

According to some embodiments of the invention, the inhibitor of the G9a and/or the inhibitor of the Glp is BIX01294.

According to an aspect of some embodiments of the present invention there is provided an isolated naïve pluripotent stem cell genetically modified to over-express an oncogenic protein selected from the group consisting of: C-MYC, N-MYC, L-MYC, EDAR (ectodysplasin A receptor), MDM2, and ERAS, and/or to downregulate a tumor suppressor protein selected from the group consisting of P53 and NF kappa B inhibitor alpha.

According to some embodiments of the invention, the downregulation of said tumor suppressor gene is performed by introducing into the cell a dominant negative mutant of said tumor suppressor protein.

According to some embodiments of the invention, the dominant negative of said tumor suppressor protein comprises the P53 R172H dominant negative mutation in the P53 protein set forth in GenBank Accession No. AAA39883.1 (SEQ ID NO:212).

According to some embodiments of the invention, the dominant negative of said tumor suppressor protein comprises the R175H, G245S, R248W, R249S, R273H and/or R282W dominant negative mutation(s) in the P53 protein set forth in GenBank Accession No. BAC16799.1 (SEQ ID NO:210).

According to some embodiments of the invention, the dominant negative of said tumor suppressor protein comprises the S32D and S36D mutations, the S32E and S36E mutations, the S32D and S36E mutations and/or the S32E and S36D mutations in the NF kappa B inhibitor alpha protein set forth in GenBank Accession No. NP_065390.1 (SEQ ID NO: 211).

According to some embodiments of the invention, the genetically modified isolated naïve pluripotent stem cell of some embodiments of the invention is characterized by:

wherein (i) when said naive PSC is a female PSC, then said naive female PSC has two unmethylated alleles of the promoter of the X-inactive specific transcript (XIST) gene; and (ii) when said naive PSC is a male PSC, then said naive male PSC has an unmethylated allele of said promoter of said XIST gene, and/or an expression level of transcription factor E3 (TFE3) in said naive PSC is characterized by a nucleus to cytoplasm expression ratio which is equal to or higher than 1 as determined by an immunostaining assay, and/or the naïve PSC is characterized by a positive expression of C-KIT (CD117) on the cell surface of the naïve PSC.

According to some embodiments of the invention, the naïve pluripotent stem cell is a primate cell.

According to some embodiments of the invention, the naïve pluripotent stem cell is a human cell.

According to an aspect of some embodiments of the present invention there is provided a method of generating a chimeric animal comprising introducing the isolated naïve pluripotent stem cell of some embodiments of the invention or the primordial germ cells of some embodiments of the invention into an embryo of a host animal, thereby generating the chimeric animal.

According to some embodiments of the invention, the embryo is a pre-implantation embryo.

According to some embodiments of the invention, the method further comprising allowing said pre-implantation embryo to grow ex vivo or in vivo.

According to some embodiments of the invention, the introducing is performed in vivo.

According to some embodiments of the invention, the introducing is performed in vitro or ex vivo.

According to some embodiments of the invention, the pre-implantation embryo comprises at least 4 cells.

According to some embodiments of the invention, the pre-implantation embryo comprises no more than 128 cells.

According to some embodiments of the invention, the host animal is a mouse.

According to some embodiments of the invention, the isolated naïve pluripotent stem cell is allogeneic to the host animal.

According to some embodiments of the invention, the isolated naïve pluripotent stem cell is xenogeneic to the host animal.

According to an aspect of some embodiments of the present invention there is provided a cell culture comprising the isolated naïve pluripotent stem cell of some embodiments of the invention and a culture medium.

According to some embodiments of the invention, the culture medium is capable of maintaining said pluripotent stem cell in a naïve state for at least 5 passages.

According to some embodiments of the invention, the culture medium included in the cell culture of the invention is any of the culture media described hereinabove and herein under.

According to some embodiments of the invention, the culture medium included in the cell culture of the invention is the culture medium of some embodiments of the invention. According to some embodiments of the invention, the culture medium included in the cell culture of the invention is any of the culture media 1-147.

According to some embodiments of the invention, the culture medium included in the cell culture of the invention is any of the culture media described in WO2014/174470 which is fully incorporated herein by reference in its entirety.

According to some embodiments of the invention, the culture medium included in the cell culture of the invention comprises an ERK1/2 inhibitor, a GSK3β inhibitor, a p38 inhibitor, a JNK inhibitor, a STAT3 activator and at least one agent selected from the group consisting of: basic fibroblast growth factor (bFGF), transforming growth factor beta 1 (TGFβ1), a protein kinase C (PKC) inhibitor, a ROCK inhibitor and a NOTCH inhibitor.

According to some embodiments of the invention, the culture medium included in the cell culture of the invention comprises an ERK1/2 inhibitor, a GSK3β inhibitor, a p38 inhibitor, a JNK inhibitor, a STAT3 activator and at least one agent selected from the group consisting of: a transforming growth factor receptor (TGFR) inhibitor, a fibroblast growth factor receptor (FGFR) inhibitor, a protein kinase C (PKC) inhibitor, a ROCK inhibitor and a NOTCH inhibitor.

According to some embodiments of the invention the STAT3 activator is selected from the group consisting of leukemia inhibitory factor (LIF) and interleukin 6 (IL6).

According to some embodiments of the invention the culture medium further comprising at least one additional agent selected from the group consisting of: insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, Bix 1294, and stem cell factor (SCF).

According to some embodiments of the invention the culture medium further comprising at least one additional agent selected from the group consisting of: insulin-like growth factor 1 (IGF1), insulin-like growth factor II (IGFII), bone morphogenetic protein 4 (BMP4), a Sonic Hedgehog pathway (SHH) inhibitor, an ERK5 inhibitor, Forskolin, Kenpaullone, BayK8644, Bix1294, and stem cell factor (SCF).

According to some embodiments of the invention, the STAT3 activator comprises the LIF, and wherein the at least one agent comprises the PKC inhibitor.

According to some embodiments of the invention, the STAT3 activator comprises the LIF, and wherein the at least one agent comprises the TGFβ1 and the protein kinase C inhibitor.

According to some embodiments of the invention, the culture medium further comprises an FGFR inhibitor.

According to some embodiments of the invention, the culture medium further comprises TGFR inhibitor.

According to some embodiments of the invention, the STAT3 activator comprises the LIF and wherein the at least one agent comprises the TGFβ1 and the protein kinase C inhibitor.

According to some embodiments of the invention, the culture medium further comprises an FGFR inhibitor.

According to some embodiments of the invention, the STAT3 activator comprises the LIF, and wherein the at least one agent comprises the bFGF and the TGFβ1.

According to some embodiments of the invention, the culture medium further comprises a ROCK inhibitor.

According to some embodiments of the invention, the culture medium further comprises a protein kinase C inhibitor.

According to some embodiments of the invention, the STAT3 activator comprises the LIF and wherein the at least one agent comprises the bFGF, the ROCK inhibitor, a bone morphogenetic protein (BMP) inhibitor, the NOTCH inhibitor, and a transforming growth factor receptor (TGFR) inhibitor.

According to some embodiments of the invention, the culture medium further comprises a Sonic Hedgehog pathway (SHH) inhibitor.

According to some embodiments of the invention, the STAT3 activator comprises the LIF and wherein the at least one agent comprises the NOTCH inhibitor, and a fibroblast growth factor receptor (FGFR) inhibitor.

According to some embodiments of the invention, the culture medium further comprises an agent selected from the group consisting of insulin-like growth factor II (IGFII), stem cell factor (SCF) and transforming growth factor beta 1 (TGFβ1).

According to an aspect of some embodiments of the present invention there is provided a culture medium comprising leukemia inhibitor factor (LIF), an ERK1/2 inhibitor, a GSK3b inhibitor, a p38 inhibitor, a JNK inhibitor, and a protein kinase C inhibitor.

According to some embodiments of the invention, the culture medium of some embodiments of the invention further comprises an FGFR inhibitor.

According to some embodiments of the invention, the culture medium of some embodiments of the invention further comprises a TGFR inhibitor.

According to an aspect of some embodiments of the present invention there is provided a culture medium comprising leukemia inhibitor factor (LIF), an ERK1/2 inhibitor, a GSK3b inhibitor, a p38 inhibitor, a JNK inhibitor, TGFβ1 and a protein kinase C inhibitor.

According to some embodiments of the invention, the culture medium of some embodiments of the invention further comprises a FGFR inhibitor.

According to an aspect of some embodiments of the present invention there is provided a culture medium comprising leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1).

According to some embodiments of the invention, the culture medium of some embodiments of the invention further comprises a ROCK inhibitor.

According to some embodiments of the invention, the culture medium of some embodiments of the invention further comprises a protein kinase C inhibitor.

According to some embodiments of the invention, the culture medium of some embodiments of the invention further comprising a factor selected from the group consisting of: bone morphogenetic protein 4 (BMP4), IGF1, IGFII, Forskolin, FGFR inhibitor, TGFR inhibitor, Kenpaullone, BayK8644, Bix 1294, and stem cell factor (SCF).

According to some embodiments of the invention, the culture medium of some embodiments of the invention further comprising BMP type I receptors (ALK2,3,6) inhibitor.

According to some embodiments of the invention, the culture medium of some embodiments of the invention further comprises ascorbic Acid.

According to some embodiments of the invention, the culture medium of some embodiments of the invention further comprises oleic Acid.

According to some embodiments of the invention, the culture medium of some embodiments of the invention further comprises Linoleic Acid.

According to some embodiments of the invention, the culture medium of some embodiments of the invention further comprises Pipecolic Acid.

According to some embodiments of the invention, the culture medium of some embodiments of the invention being devoid of animal serum.

According to some embodiments of the invention, the culture medium of some embodiments of the invention further comprises serum replacement.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1, 2:
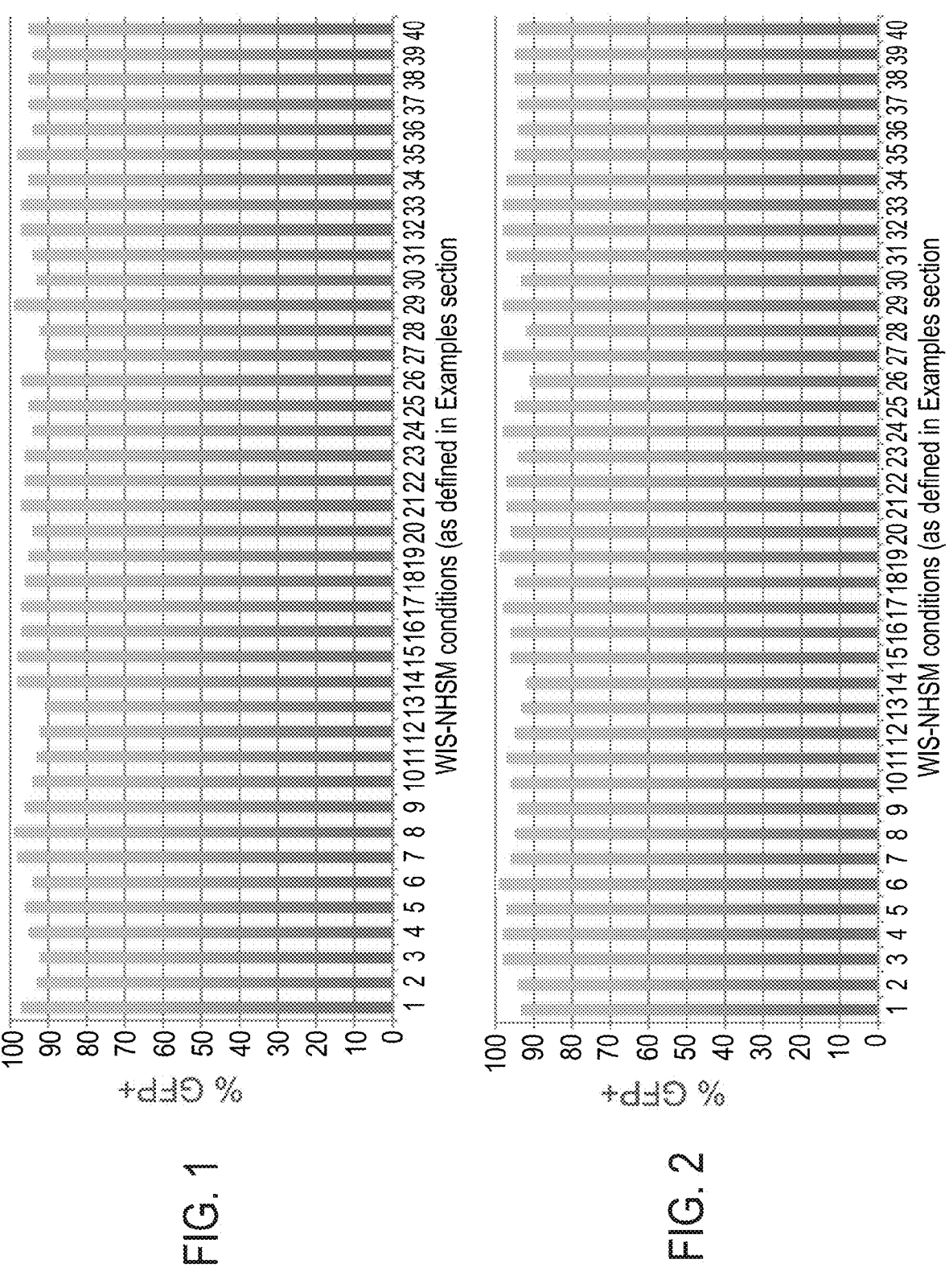

FIG. 1 is a graph illustrating FACS analysis of WIBR3 hESC line carrying Oct4-GFP reporter. The cells were expanded on Gelatin/DR4 feeder coated plates in 5% 02 with the indicated supplements of conditions 1-40 to the following base medium: 1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml (Biological Industries-02-022-1B), NEAA-5 ml (Biological Industries 01-340-1B), 50 μl of 50 mM stock Beta-mercaptoethanol (1 vile), 5 ml B27 supplement (Invitrogen 17504-044), Insulin (Sigma I-1882), Apo-transferrin (Sigma T-1147), 100 μg/ml final concentration, Progesterone (Sigma P8783), 0.02 μg/ml final concentration, Putrescine (SigmaP5780), 16 μg/ml final concentration, Sodium selenite (Sigma S5261), L-ascorbic acid 2-phosphate (Sigma A8960) (50 μg/ml final concentration), BSA (100× Fraction V 7.5% Solution Gibco 15260-037. The cells were expanded for up to 21 passages and evaluated by FACS analysis for OCT4-GFP+ reporter. The results show the cells maintain their pluripotency in the conditions described.

FIG. 2 is a graph illustrating FACS analysis of WIBR3 hESC line carrying deltaPEOct4-GFP reporter (described in Gafni et al. Nature 2013). The cells were expanded on Gelatin/DR4 feeder coated plates in 5% 02 with the indicated supplements of conditions 1-40 to the following base medium: 1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml (Biological Industries-02-022-1B), NEAA-5 ml (Biological Industries 01-340-1B), 50 μL of 50 mM stock Beta-mercaptoethanol (1 vile), 5 ml B27 supplement (Invitrogen 17504-044), Insulin (Sigma I-1882) 12.5 microg/ml insulin), Apo-transferrin (Sigma T-1147), 100 μg/ml final concentration, Progesterone (Sigma P8783), 0.02 μg/ml final concentration, Putrescine (SigmaP5780), 16 μg/ml final concentration, Sodium selenite (Sigma S5261), add 5 μl of 3 mM stock solution per 500 ml of medium., L-ascorbic acid 2-phosphate (Sigma A8960) (50 μg/ml final concentration), BSA (100× Fraction V 7.5% Solution Gibco 15260-037. The cells were expanded for up to 21 passages and evaluated by FACS analysis for OCT4-GFP+ reporter. The results show the cells maintain their pluripotency in the conditions described.

Figures 3A, 3B, 3C, 3D, 3E, 3F:
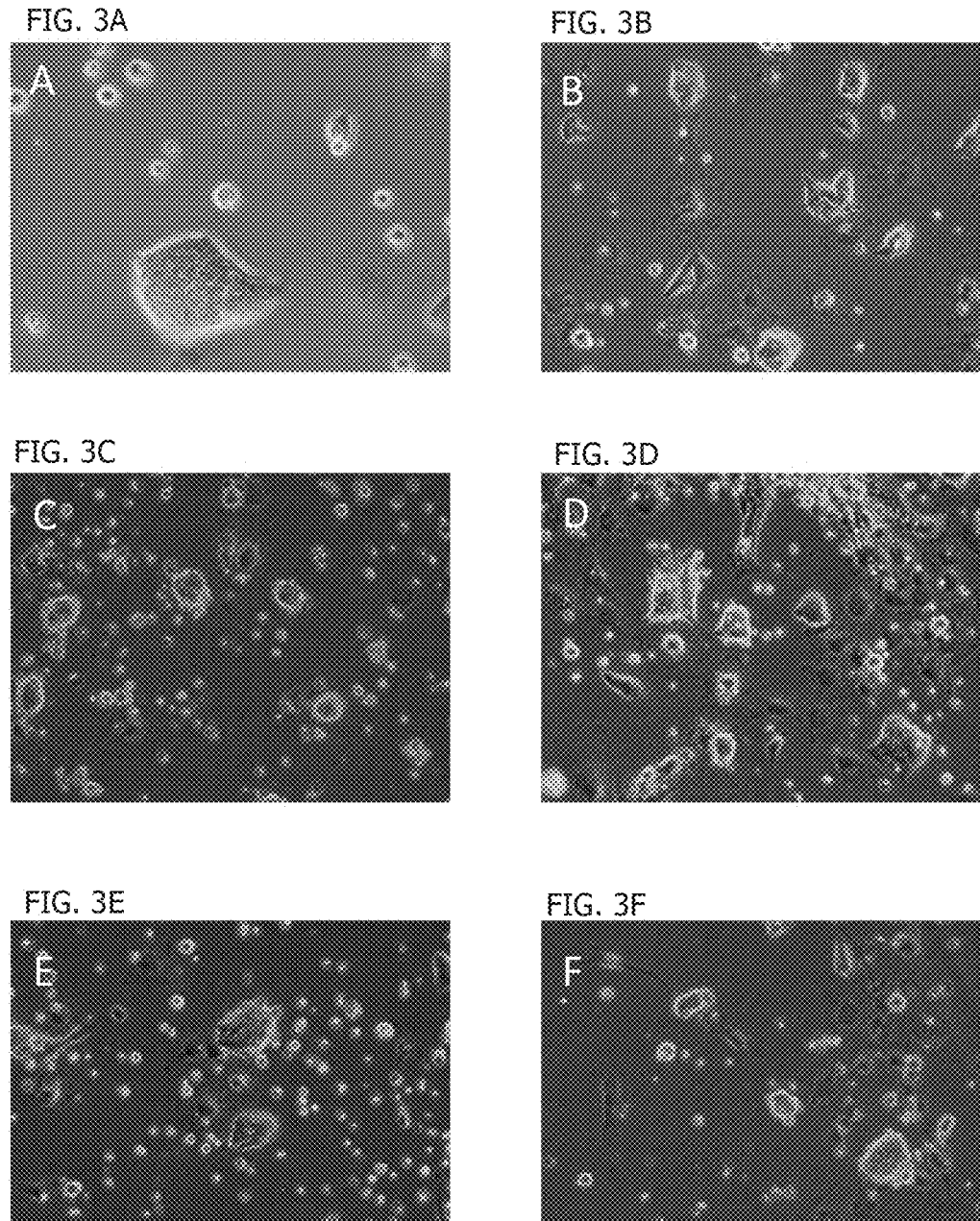

FIGS. 3A, 3B, 3C, 3D, 3E and 3F are representative images of pluripotent cell colonies at P12 in the selected conditions shown. FIG. 3A-conditions 1; FIG. 3B-conditions 2; FIG. 3C-conditions 3; FIG. 3D-conditions 4; FIG. 3E-conditions 9; FIG. 3F-conditions 11. The WIS2 hESC line was expanded on vitronectin coated plates in 5% 02 with the following base medium: 1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml (Biological Industries-02-022-1B), NEAA-5 ml (Biological Industries 01-340-1B), 50 μL of 50 mM stock Beta-mercaptocthanol (1 vile), 5 ml B27 supplement (Invitrogen 17504-044), Insulin (Sigma I-1882)-12.5 microg/ml insulin), Apo-transferrin (Sigma T-1147), 100 μg/ml final concentration, Progesterone (Sigma P8783), 0.02 μg/ml final concentration, Putrescine (SigmaP5780), 16 μg/ml final concentration, Sodium selenite (Sigma S5261), add 5 μl of 3 mM stock solution per 500 ml of medium, L-ascorbic acid 2-phosphate (Sigma A8960) (50 μg/ml final concentration), BSA (100× Fraction V 7.5% Solution Gibco 15260-037.

Figures 4A, 4B, 4C, 4D:
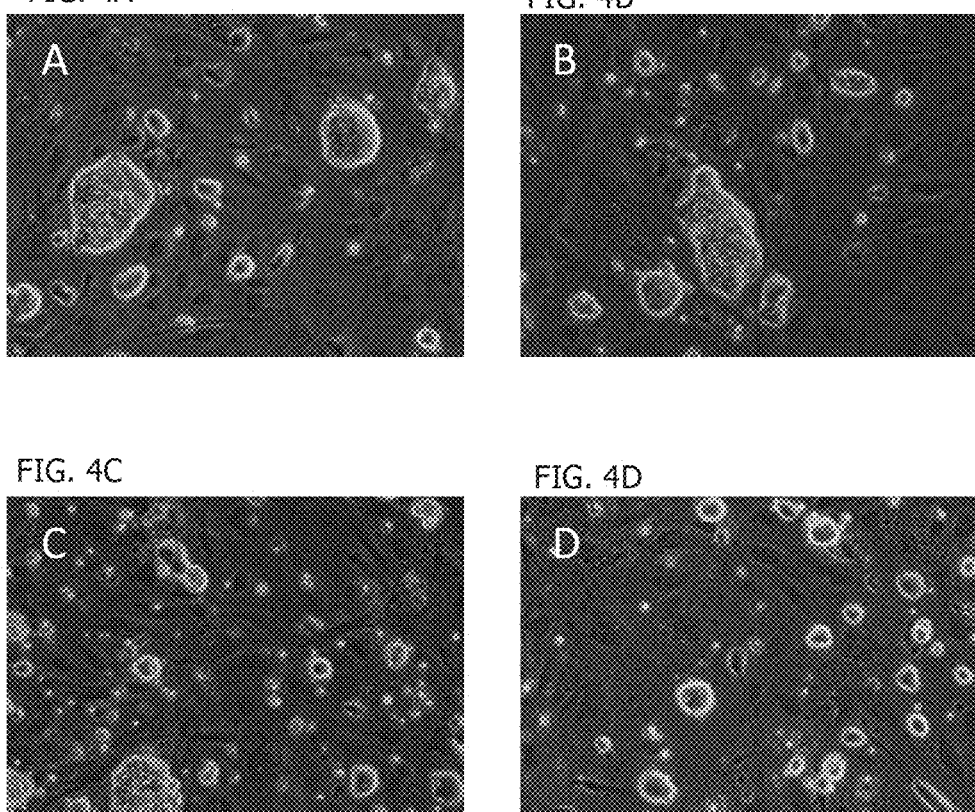

FIGS. 4A, 4B, 4C and 4D are representative images of pluripotent cell colonies at P20 in the selected conditions shown. FIG. 4A-conditions 9; FIG. 4B-conditions 10; FIG. 4C-conditions 11; FIG. 4D-conditions 4. The WIS2 hESC line was expanded on Gelatin/DR4 feeder cell coated plates in 5% $O_2$ with the following base medium: 1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml (Biological Industries-02-022-1B), NEAA-5 ml (Biological Industries 01-340-1B), 50 μL of 50 mM stock Beta-mercaptocthanol (1 vilc), 5 ml B27 supplement (Invitrogen 17504-044), Insulin (Sigma I-1882) 12.5 microg/ml insulin), Apo-transferrin (Sigma T-1147), 100 μg/ml final concentration, Progesterone (Sigma P8783), 0.02 μg/ml final concentration, Putrescine (SigmaP5780), 16 μg/ml final concentration, Sodium selenite (Sigma S5261), add 5 μl of 3 mM stock solution per 500 ml of medium., L-ascorbic acid 2-phosphate (Sigma A8960) (50 μg/ml final concentration), BSA (100× Fraction V 7.5% Solution Gibco 15260-037-0.16 ml per 500 ml media bottle.

Figure 5A:
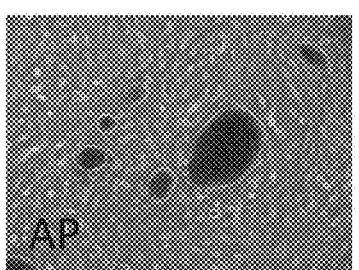
Figure 5B:
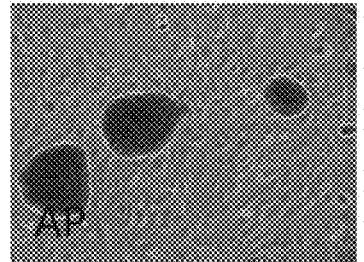
Figure 5C:
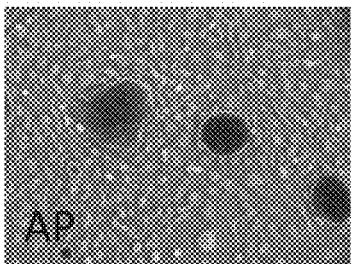

FIGS. 5A, 5B and 5C are representative images of pluripotent cell colonies at P18-20 in the selected conditions shown. FIG. 5A-conditions 9; FIG. 5B-conditions 10; FIG. 5C-conditions 4. WIS2 hESC line was expanded on Gelatin/DR4 feeder cell coated plates in 5% 02 with the following base medium: 1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml (Biological Industries-02-022-1B), NEAA-5 ml (Biological Industries 01-340-1B), 50 µL of 50 mM stock Beta-mercaptoethanol (1 vile), 5 ml B27 supplement (Invitrogen 17504-044), Insulin (Sigma I-1882)-12.5 microg/ml insulin), Apo-transferrin (Sigma T-1147), 100 µg/ml final concentration, Progesterone (Sigma P8783), 0.02 µg/ml final concentration, Putrescine (SigmaP5780), 16 µg/ml final concentration, Sodium selenite (Sigma S5261), add 5 µl of 3 mM stock solution per 500 ml of medium., L-ascorbic acid 2-phosphate (Sigma A8960) (50 µg/ml final concentration), BSA (100× Fraction V 7.5% Solution Gibco 15260-037-0.16 ml per 500 ml media bottle. Cell were stained for alkaline phosphatase stem cell marker (AP), and were found positive as shown for the representative images of pluripotent cell colonies at P18-20 in the selected conditions shown.

Figure 6A:
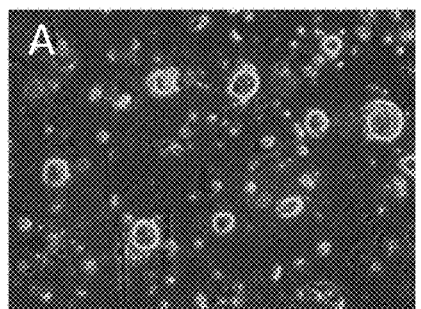
Figure 6B:
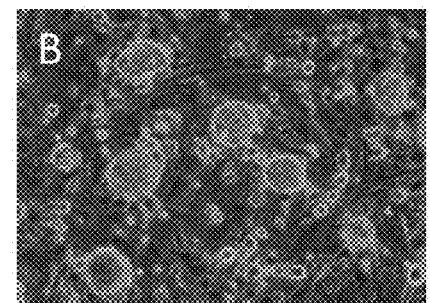
Figure 6C:
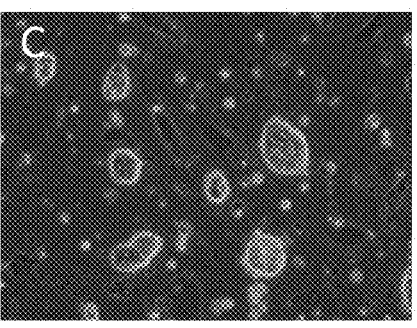
Figure 6D:
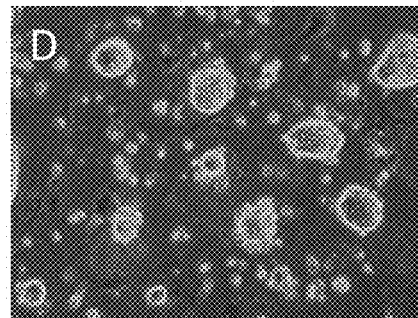
Figure 6E:
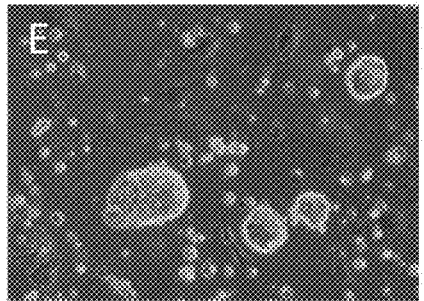
Figure 6F:
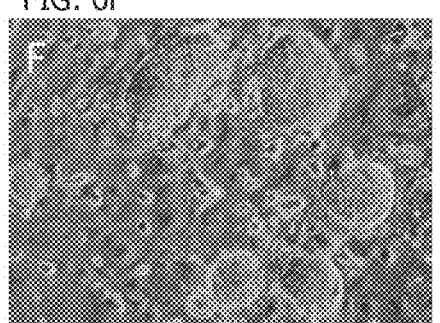

FIGS. 6A, 6B, 6C, 6D, 6E and 6F are images of human naïve ESCs/iPSCs which were expanded under particular conditions without L-glutamine. FIG. 6A-conditions 1; FIG. 6B-conditions 2; FIG. 6C-conditions 3; FIG. 6D-conditions 4; FIG. 6E-conditions 9; FIG. 6F-conditions 11. FX71 human iPSC line was expanded on Gelatin/DR4 feeder cell coated plates in 5% 02 with the following base medium: 1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), NEAA—5 ml (Biological Industries 01-340-1B), 50 µL of 50 mM stock Beta-mercaptoethanol (1 vile), 5 ml B27 supplement (Invitrogen 17504-044), Insulin (Sigma I-1882)-12.5 microg/ml insulin), Apo-transferrin (Sigma T-1147), 100 µg/ml final concentration, Progesterone (Sigma P8783), 0.02 µg/ml final concentration, Putrescine (SigmaP5780), 16 µg/ml final concentration, Sodium selenite (Sigma S5261), add 5 µl of 3 mM stock solution per 500 ml of medium, L-ascorbic acid 2-phosphate (Sigma A8960) (50 µg/ml final concentration), BSA (100× Fraction V 7.5% Solution Gibco 15260-037-0.16 ml per 500 ml media bottle. Representative images of cells in the different WIS-NHSM conditions are shown, indicating expansion of colonies without exogenous L-glutamine supplementation in these conditions.

Figure 7:
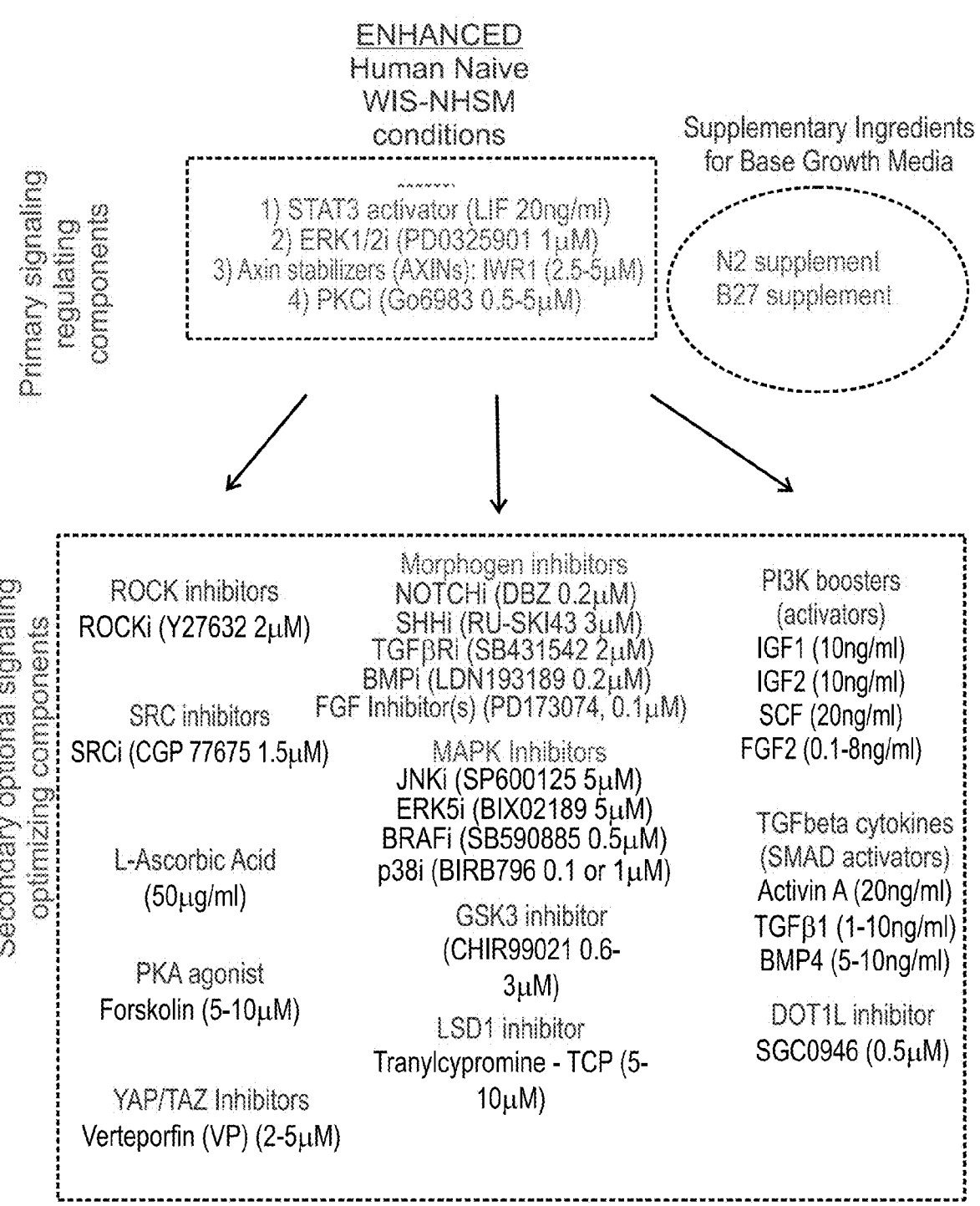

FIG. 7 is a schematic illustration depicting a strategy for designing the WIS-NHSM conditions, and includes non-limiting examples of small molecules and concentration ranges thereof.

FIG. 8 depicts the supplements of different WIS-NHSM examples (conditions 41-60) tested for human naïve iPSCs and ESC derivation and maintenance. The base media used is described in Example 5 below.

FIG. 9 depicts the supplements of different WIS-NHSM examples tested (conditions 61-80) for human naïve iPSCs and ESC derivation and maintenance. The base media used is described in Example 5 below.

FIG. 10 depicts the supplements of different WIS-NHSM examples tested (conditions 81-99) for human naïve iPSCs and ESC derivation and maintenance. The base media used is described in Example 5 below.

FIG. 11 depicts the supplements of different WIS-NHSM examples tested (conditions 100-119) for human naïve iPSCs and ESC derivation and maintenance. The base media used is described in Example 5 below.

FIG. 12 depicts the supplements of different WIS-NHSM examples tested (conditions 120-131) for human naïve iPSCs and ESC derivation and maintenance. The base media used is described in Example 5 below.

Figure 13:
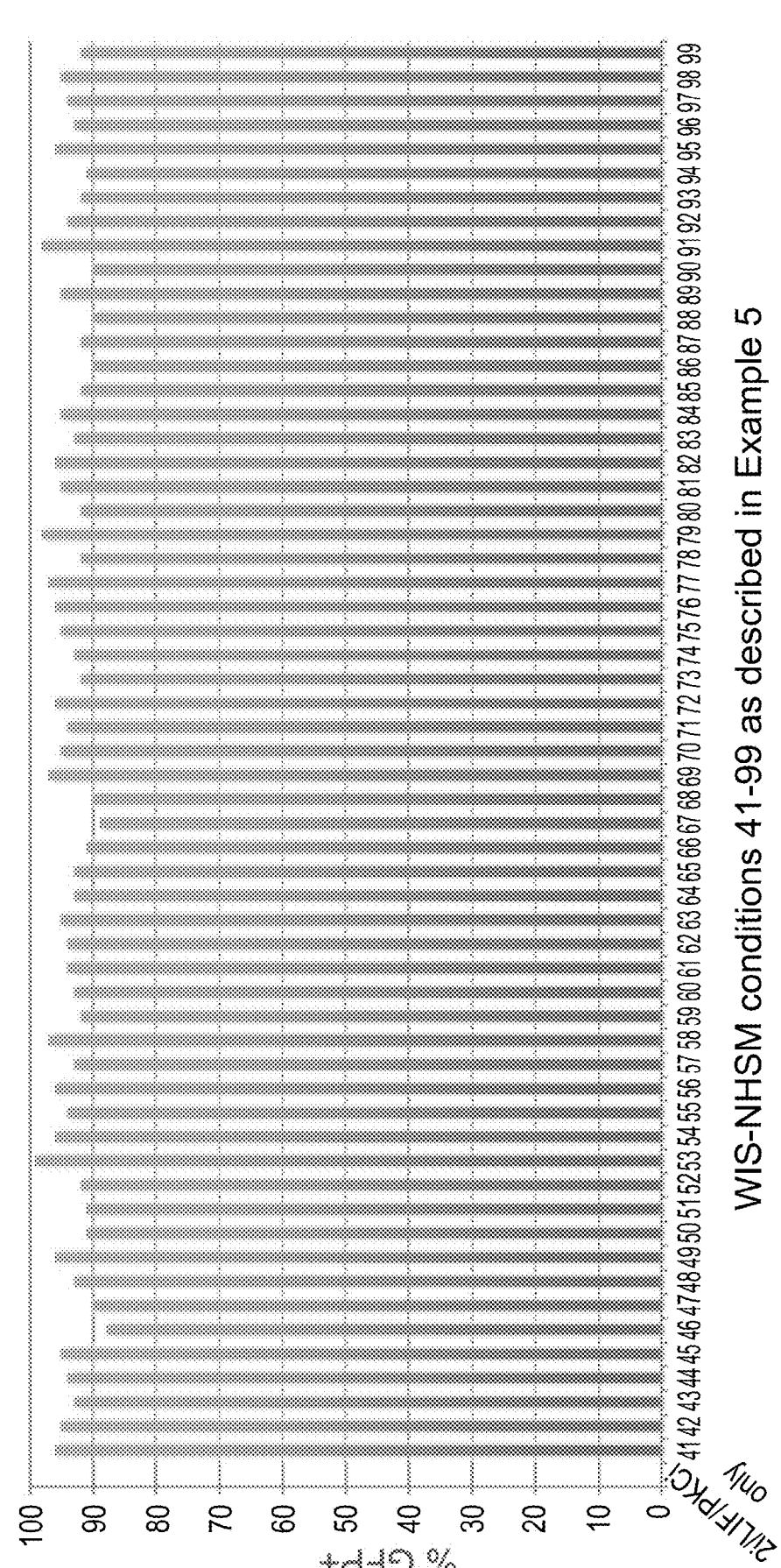

FIG. 13 is a graph illustrating FACS analysis of WIBR3 hESC line carrying deltaPEOct4-GFP reporter (described in Gafni et al. Nature 2013). The cells were expanded on Gelatin/DR4 feeders coated plates in 5% 02 with the indicated supplements of conditions 41-99 (described in Example 5, hereinbelow) to the following base medium: 1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml (Biological Industries-02-022-1B), NEAA-5 ml (Biological Industries 01-340-1B), 50 µL of 50 mM stock Beta-mercaptoethanol (1 vile), 10 ml B27 supplement (Invitrogen 17504-044), Insulin (Sigma I-1882)-add 6.25 mg insulin per 1 bottle to give approximately additional 12.5 microg/ml insulin), Apo-transferrin (Sigma T-1147), 100 µg/ml final concentration, Progesterone (Sigma P8783), 0.02 µg/ml final concentration, Putrescine (Sigma P5780), 16 µg/ml final concentration, Sodium selenite (Sigma S5261), add 5 µl of 3 mM stock solution per 500 ml of medium, BSA (100× Fraction V 7.5% Solution Gibco 15260-037-add 0.16 ml per 500 ml media bottle. The cells were expanded for 28 days (total of 6 passages) passages and evaluated by FACS analysis for OCT4-GFP+ reporter. The results show the cells maintain their pluripotency in the conditions described. 2i/LIF/PKCi (5 microM) conditions were used as negative controls, as the cells lose their pluripotency in these conditions.

Figure 14:
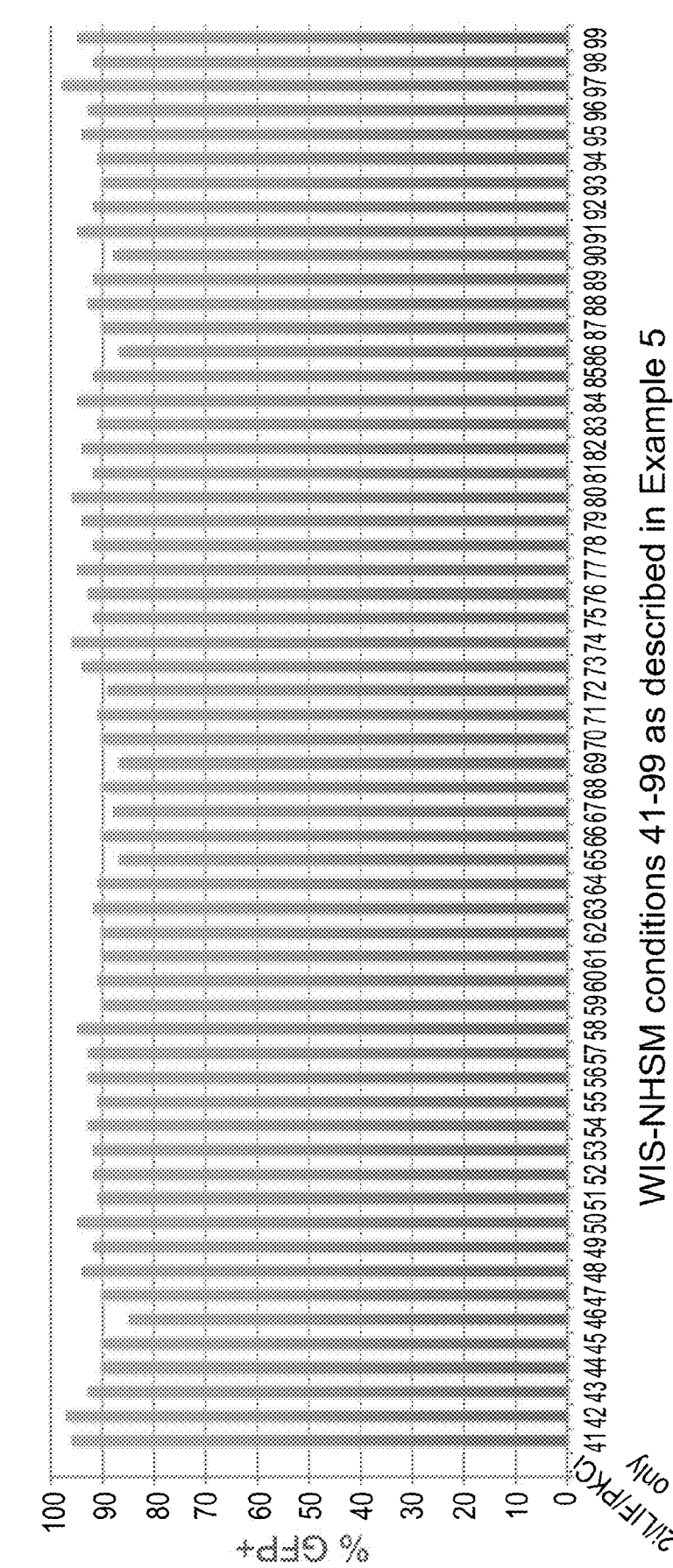

FIG. 14 is a graph illustrating FACS analysis of WIBR3 hESC line carrying deltaPEOct4-GFP reporter (described in Gafni et al. Nature 2013). The cells were expanded on LAMININ-521 coated plates (BIOLAMINA INC.-Catalogue number: www(dot)biolamina(dot)com/product-In-521) in 5% 02, with the indicated supplements of conditions 41-99 (described in Example 5, hereinbelow) to the following base medium: 1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml (Biological Industries-02-022-1B), NEAA-5 ml (Biological Industries 01-340-1B), 50 µL of 50 mM stock Beta-mercaptoethanol (1 vile), 10 ml B27 supplement (Invitrogen 17504-044), Insulin (Sigma I-1882)-add 6.25 mg insulin per 1 bottle to give approximately additional 12.5 microg/ml insulin), Apo-transferrin (Sigma T-1147), 100 µg/ml final concentration, Progesterone (Sigma P8783), 0.02 µg/ml final concentration, Putrescine (SigmaP5780), 16 µg/ml final concentration, Sodium selenite (Sigma S5261), add 5 µl of 3 mM stock solution per 500 ml of medium, BSA (100× Fraction V 7.5% Solution Gibco 15260-037-add 0.16 ml per 500 ml media bottle. The cells were expanded for 28 days (total of 6 passages) passages and evaluated by FACS analysis for OCT4-GFP+ reporter. The results show the cells maintain their pluripotency in the conditions described. 2i/LIF/PKCi (5 microM) conditions were used as negative controls, as the cells lose their pluripotency in these conditions.

Figure 15:
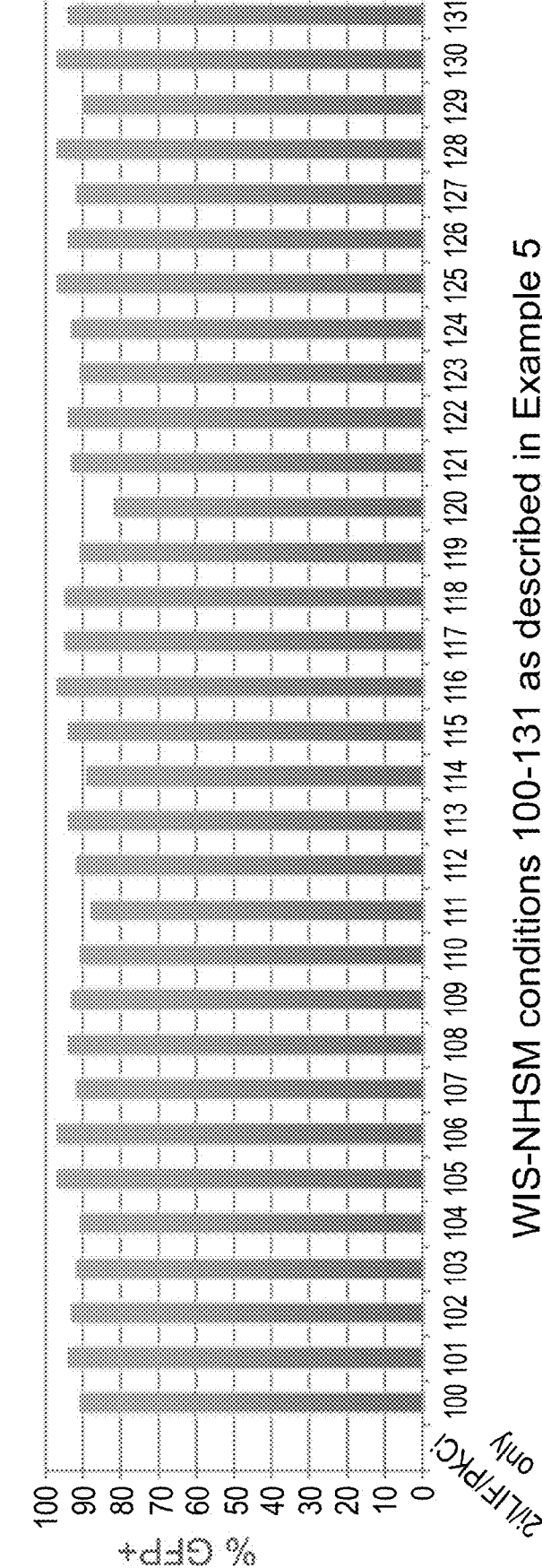

FIG. 15 is a graph illustrating FACS analysis of WIBR3 hESC line carrying deltaPEOct4-GFP reporter (described in Gafni et al. Nature 2013). The cells were expanded on Gelatin/DR4 feeders coated plates in 5% 02 with the indicated supplements of conditions 100-131 (described in Example 5, hereinbelow) to the following base medium: 1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml (Biological Industries-02-022-1B), NEAA-5 ml (Biological Industries 01-340-1B), 50 μL of 50 mM stock Beta-mercaptoethanol (1 vile), 10 ml B27 supplement (Invitrogen 17504-044), Insulin (Sigma I-1882)-add 6.25 mg insulin per 1 bottle to give approximately additional 12.5 microg/ml insulin), Apo-transferrin (Sigma T-1147), 100 μg/ml final concentration, Progesterone (Sigma P8783), 0.02 μg/ml final concentration, Putrescine (Sigma P5780), 16 μg/ml final concentration, Sodium selenite (Sigma S5261), add 5 μl of 3 mM stock solution per 500 ml of medium, BSA (100× Fraction V 7.5% Solution Gibco 15260-037-add 0.16 ml per 500 ml media bottle. The cells were expanded for 28 days (total of 6 passages) passages and evaluated by FACS analysis for OCT4-GFP+ reporter. The results show the cells maintain their pluripotency in the conditions described. 2i/LIF/PKCi (5 microM) conditions were used as negative controls, as the cells lose their pluripotency in these conditions.

Figure 16:
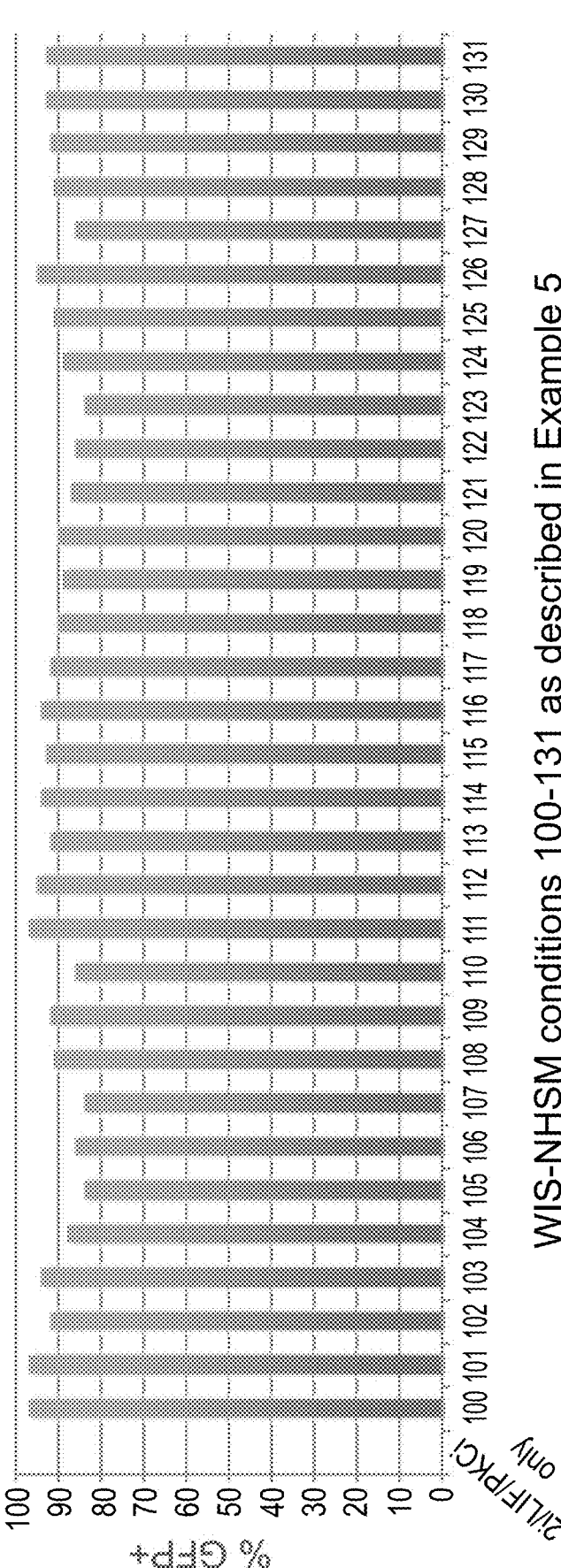

FIG. 16 is a graph illustrating FACS analysis of WIBR3 hESC line carrying deltaPEOct4-GFP reporter (described in Gafni et al. Nature 2013), was expanded on LAMININ-521 coated plates (BIOLAMINA INC.—Catalogue number: www(dot)biolamina(dot)com/product-In-521) in 5% O2, with the indicated supplements of conditions 100-131 (described in Example 5, hereinbelow) to the following base medium: 1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml (Biological Industries-02-022-1B), NEAA-5 ml (Biological Industries 01-340-1B), 50 μL of 50 mM stock Beta-mercaptocthanol (1 vile), 10 ml B27 supplement (Invitrogen 17504-044), Insulin (Sigma I-1882)-add 6.25 mg insulin per 1 bottle to give approximately additional 12.5 microg/ml insulin), Apo-transferrin (Sigma T-1147), 100 μg/ml final concentration, Progesterone (Sigma P8783), 0.02 μg/ml final concentration, Putrescine (SigmaP5780), 16 μg/ml final concentration, Sodium selenite (Sigma S5261), add 5 μl of 3 mM stock solution per 500 ml of medium, BSA (100× Fraction V 7.5% Solution Gibco 15260-037-add 0.16 ml per 500 ml media bottle. The cells were expanded for 28 days (total of 6 passages) passages and evaluated by FACS analysis for OCT4-GFP+ reporter. The results show the cells maintain their pluripotency in the conditions described. 2i/LIF/PKCi (5 microM) conditions were used as negative controls, as the cells lose their pluripotency in these conditions.

FIGS. 17A-F depict bisulfite sequencing analyses of the XIST promoter. Shown are bisulfite-sequencing analyses of six CpG sites in single clones of an XIST promoter amplicon. Filled circles=methylated CpG sites; Empty circles=Unmethylated CpG sites. For naïve PSCs, the cells were expanded in the indicated culture media (FIGS. 17A-E) for 14 days on DR4 irradiate MEF cells and 0.2% gelatin coated plates in 5% O2 conditions at 37 C. All culture media included L-ascorbic acid (at a final concentration of 50 μg/ml). For non-naïve conditions (primed PSCs), the cells were cultured in mTESR1 (Stem Cell Technologies-catalogue number 05850) on Matrigel coated plates. FIG. 17A-culture medium included: Srci 1 μM, ERK1/2i 1 μM, LIF 20 ng/ml; FIG. 17B-culture medium included: AXINs 5 μM, ERK1/2i 1 μM, LIF 20 ng/ml; FIG. 17C-culture medium included: AXINs 5 μM, ERK1/2i 1 μM, LIF 20 ng/ml, PKCi 4 μM, GSK3i 1.5 μM; FIG. 17D-culture medium included: AXINs 5 μM, ERK1/2i 1 μM, LIF 20 ng/ml, PKCi 4 μM, GSK3i 1.5 μM, P38i 2 μM, and JNKi 5 μM. FIG. 17E-culture medium included: AXINs 5 μM, ERK1/2i 1 μM, LIF 20 ng/ml, PKCi 4 μM, GSK3i 1.5 μM, P38i 2 μM, JNKi 5 μM, and SRCi 1 μM. Key for small molecule abbreviation: LIF (20 ng/ml), ERK1/2i (PD0325901 1 μM), AXINs (IWR1 5 μM), PKCi (Go6983 4 μM), GSK3βi (CHIR99021 1.5 μM), P38i (BIRB796 2 μM), JNKi (SP600125 5 μM), SRCi (CGP77675 1 μM). Note that in naive PSCs both alleles are demethylated (unmethylated) (FIGS. 17A-E, female cells). In contrast, note that in non-naïve (i.e., primed PSCs) the XIST promoter is completely methylated in the male cells, and methylated on one allele of the female cells (FIG. 17F). These results conclusively demonstrate that male and female Naive hESCs/iPSCs retain a unique pre-X inactivation state under various WIS-NHSM conditions.

FIG. 18 is a scheme presenting strategy for maintaining pluripotent stem cells in a naïve state, and includes examples of small molecules and concentration ranges for a culture medium according to some embodiments of the invention.

FIG. 19 provides non-limiting examples of the culture medium of some embodiments of the invention, which is capable of maintaining human naïve PSC in a naïve and undifferentiated state, and for ESC derivation. The base medium is described in Example 6 hereinbelow.

Figure 20:

FIG. 20 is a histogram depicting the percentage of GFP-positive cells ("GFP+") when cultured in the culture medium of some embodiments of the invention (media 132-147, described in Example 6 hereinbelow and in FIG. 19). WIBR3 hESC line carrying Oct4-GFP reporter (described in Gafni et al. Nature 2013), was expanded on Gelatin/DR4 irradiated MEF coated plates in 5% O2 with the base medium described in Example 6 of the Examples section below, wherein the base medium used for these experiments included also L-ascorbic acid 2-phosphate (Sigma A8960) (50 μg/ml final concentration). The cells were expanded for up to 23 passages and evaluated by FACS analysis for OCT4-GFP+ reporter. The results show the cells maintain their pluripotency in the conditions described. 2i/LIF/PKCi (5 microM) conditions were used as negative controls, as the cells lose their pluripotency in these conditions.

Figure 21:
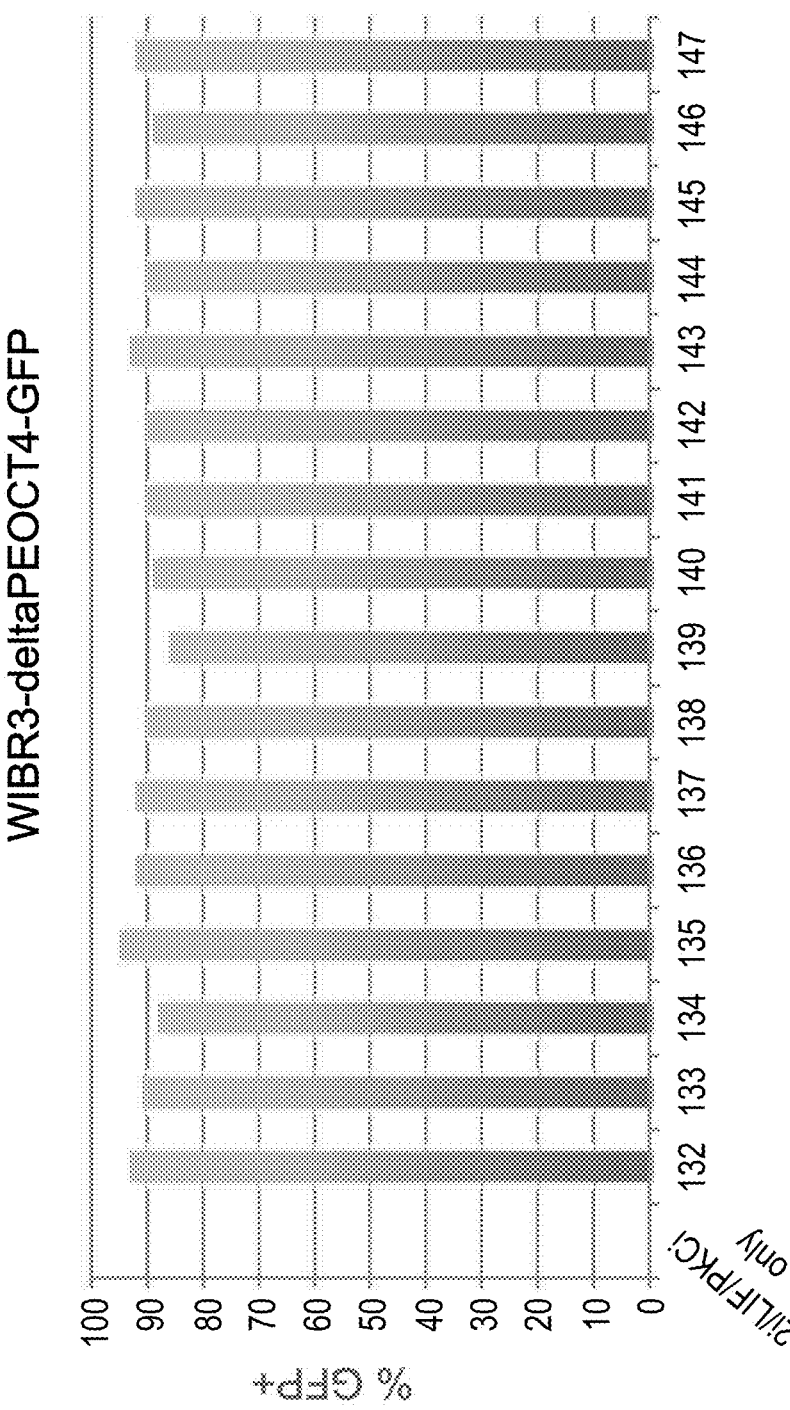

FIG. 21 is a histogram depicting the percentage of GFP-positive cells ("GFP+") when cultured in the culture medium of some embodiments of the invention (media 132-147, described in Example 6 hereinbelow and in FIG. 19). WIBR3 hESC line carrying deltaPEOct4-GFP reporter (described in Gafni et al. Nature 2013), was expanded on Matrigel coated plates in 5% $O_2$ with the base medium described in Example 6 of the Examples section below, wherein the base medium used for these experiments included also L-ascorbic acid 2-phosphate (Sigma A8960) (50 μg/ml final concentration). The cells were expanded for up to 23 passages and evaluated by FACS analysis for OCT4-GFP+ reporter. The results show the cells maintain their pluripotency in the conditions described. 2i/LIF/PKCi (5 microM) conditions were used as negative controls, as the cells lose their pluripotency in these conditions.

Figures 22A, 22B:
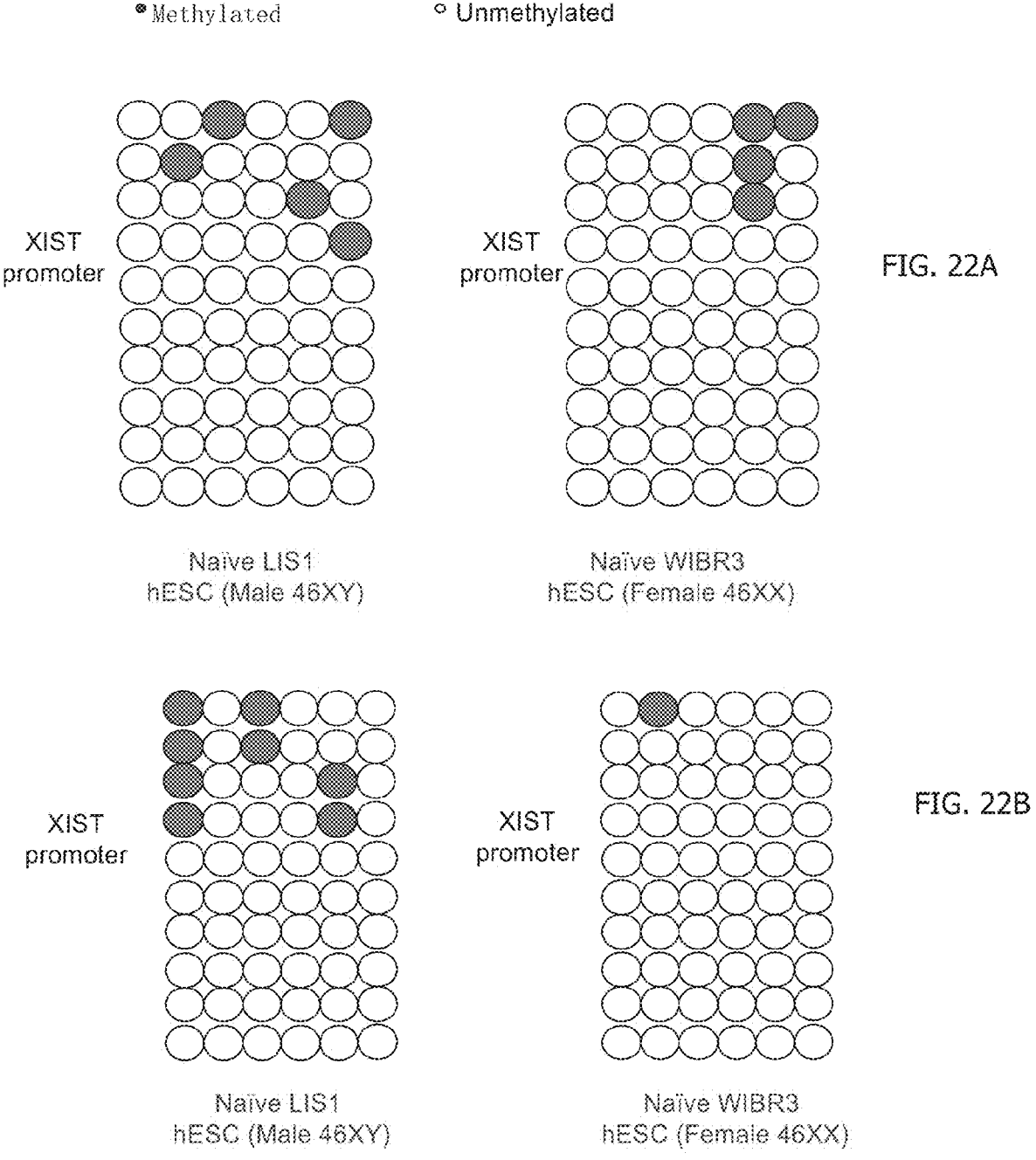
Figure 22C:
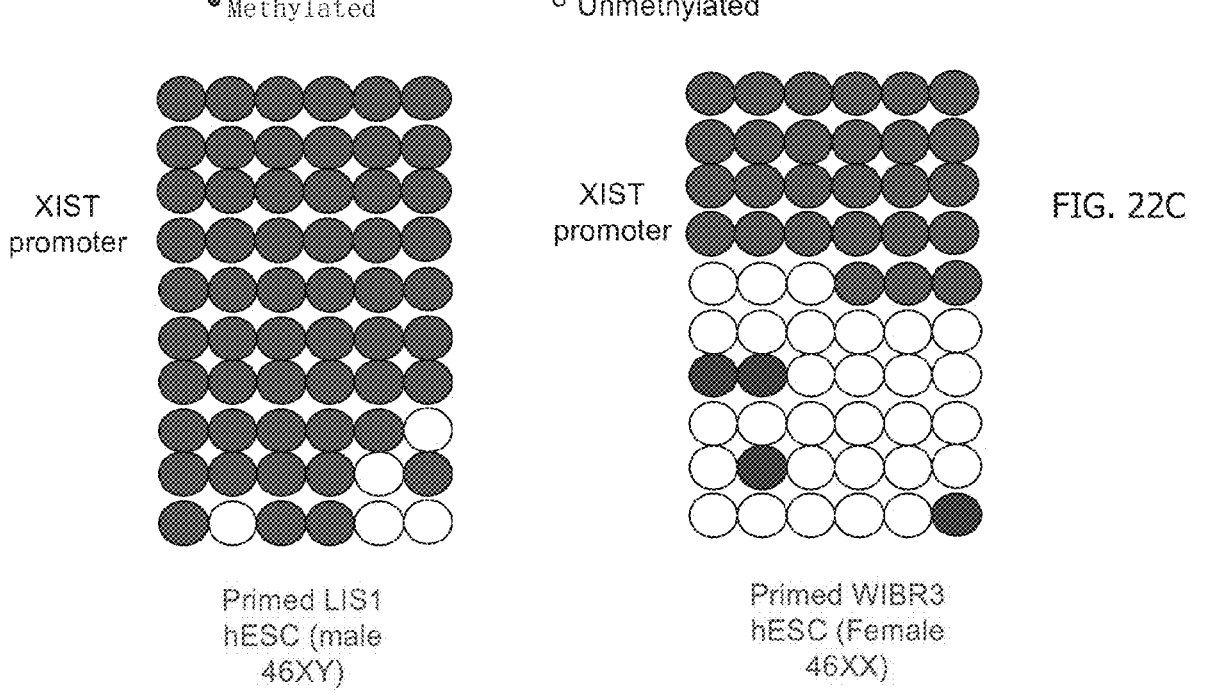

FIGS. 22A-C show the results of a bisulfite sequence analysis demonstrating that the male and female naïve hESCs or iPSCs retain a unique pre-X inactivation state in WIS-NHSM conditions (the medium of some embodiments of the invention). Filled circles=methylated CpG sites; Empty circles=Unmethylated CpG sites. Shown are bisulfite sequencing analyses of six CpG sites in single clones of an XIST promoter amplicon. Note that in naive cells both alleles are demethylated. The cells were expanded in the indicated culture conditions for 14 days on DR4 irradiate MEF cells and 0.2% gelatin coated plates in 5% O2 conditions at 37° C. All culture media included L-ascorbic acid (50 μg/ml). FIG. 22A-culture medium included: AXINs 5 μM, ERK1/2i 1 μM, LIF 20 ng/ml, PKCi 2 μM, GSK3i 1.5 μM, P38i 0.25 μM, JNKi 5 μM, SRCi 0.5 μM. FIG. 22B-culture medium included: AXINs 5 μM, ERK1/2i 1 μM, LIF 20 ng/ml, PKCi 2 μM, GSK3i 1.5 μM, P38i 0.25 μM, JNKi 5 μM, SRCi 0.5 μM, and G9ai 0.5 M. Key for small molecule abbreviation: LIF (20 ng/ml), ERK1/2i (PD0325901, 1 μM), AXINs (IWR1, 5 μM), PKCi (Go6983, 2 μM), GSK3βi (CHIR99021, 1.5 μM), P38i (BIRB796, 0.25 μM), JNKi (SP600125, 5 μM), SRCi (CGP77675, 0.5 μM), and G9ai (BIX01294, 0.5 μM). FIG. 22C-non-naïve conditions (primed PSCs) included culturing the cells in mTESR1 (Stem Cell Technologies-catalogue number 05850) on Matrigel coated plates. Note that in naive PSCs both alleles of female cells are demethylated (unmethylated) (FIGS. 22A-B, right panels showing female cells). In contrast, note that in non-naïve (i.e., primed PSCs) the XIST promoter is completely methylated in the male cells (FIG. 22C, left panel, male cell), and methylated on one allele of the female cells (FIG. 22C, right panel, female cell). These results conclusively demonstrate that male and female Naive hESCs/iPSCs retain a unique pre-X inactivation state under various culture medium of some embodiments of the invention.

FIGS. 23A-D depict the generation of the LIS 38 tg-pTrip lck EGFP hTP53 crispr. FIG. 23A-Shown are the sequences of the wild type LIS38 (SEQ ID NO: 195) and of the Crispr_C2 (SEQ ID NO: 196). The sequence alignment between the two sequences (SEQ ID NOs: 134 and 135) demonstrates the deletion of part of Exon 3 of TP53 via CRISPR/CAS9-sgRNA targeted region. FIG. 23B-Western Immunoblot showing loss of WT p53 protein in the LIS38 tg-pTrip lck EGFP p53 crispr targeted cells (right lane) as compared to the WT parental cell line (left lane). FIG. 23C-Karyotype analysis of the LIS38 tg-pTrip lck EGFP p53 crispr cells, indicating 46XY normal karyotype. FIG. 23D-Representative images of the LIS38 tg-pTrip lck EGFP p53 crispr cells. Left: Bright field image; Right: Dark field images showing GFP fluorescence positive signal. This indicates that the cell line is constitutively labeled with GFP fluorescent protein, which enables tracking of this cell line derived cells in host tissues after micro-injection. In summary, these results describe a method to generate human naïve PSC lines depleted for P53 protein, in this case via CRISPR/CAS9 sgRNA mediated targeting, and subsequently labeling the cells with constitutively expressed fluorescent protein. These cells can be injected into host embryos to generate chimeric embryos.

Figures 24A, 24B:
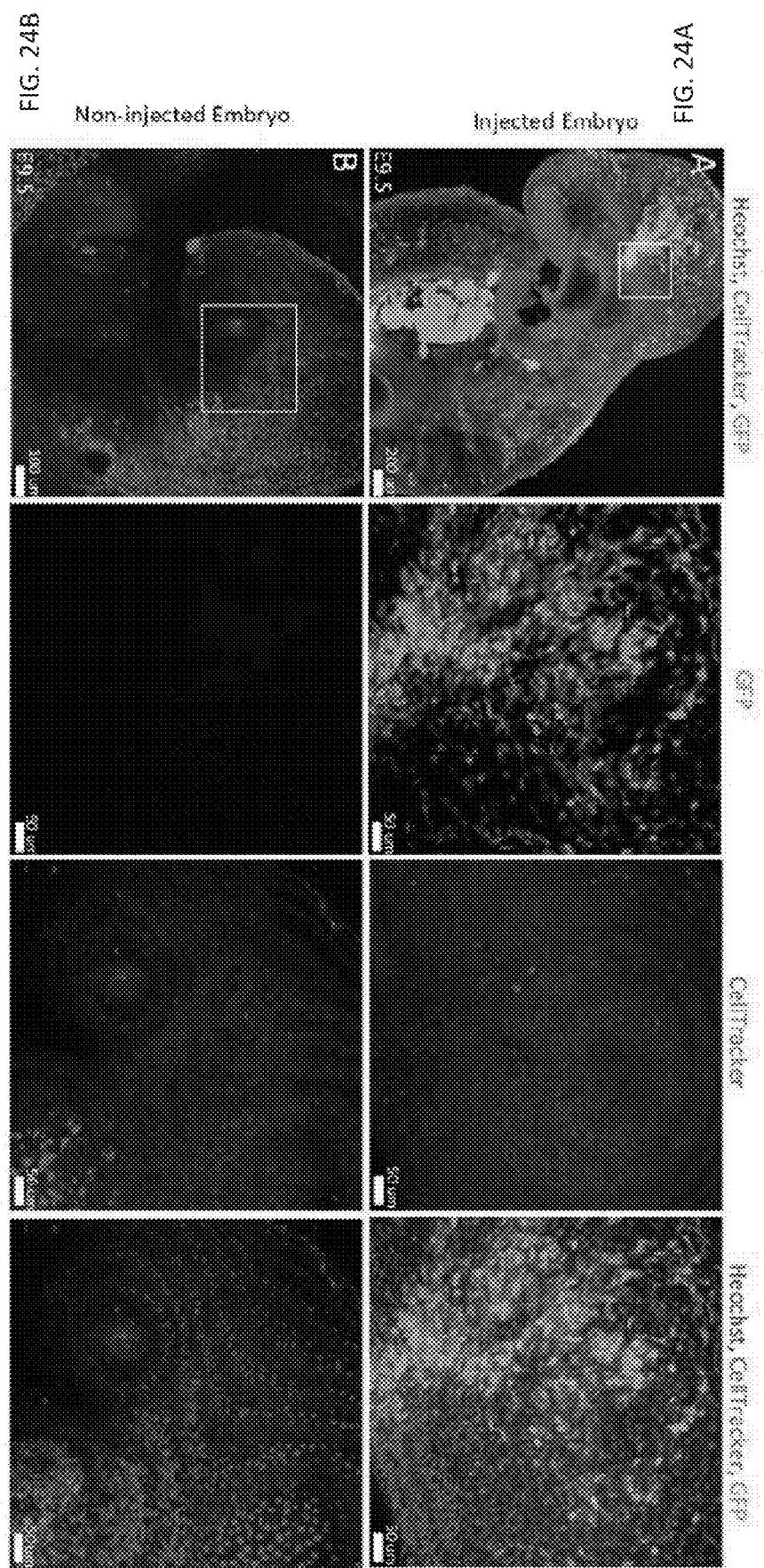

FIGS. 24A-B show that microinjection of LIS 38 EGFP hTP53 C2 naive human iPS cells into mouse morulas generates cross-species chimaeric humanized mice with high contribution and chimerism levels. FIG. 24A-mouse embryos injected with the LIS 38 EGFP hTP53 naive human iPS cells. FIG. 24B-non-injected mouse embryos using the same analysis. Shown are representative images demonstrating widespread integration of GFP-labeled human naive iPS-derived cells into different locations of an E9.5 mouse embryo. Hoechst and CellTracker were used for counterstaining. The first column shows the whole embryo. The 2nd-4th columns (from the left) show a zoom in images focusing on the head region (white squares in the images of the first column). FIG. 24A shows an injected embryo, where the human iPS-derived cells (GFP-positive cells) integrated into a large portion of superficial cranial tissues. FIG. 24B shows a control embryo that was not injected with human naive iPS-derived cells; there are no GFP positive cells detected in this control embryo.

Figure 25A:
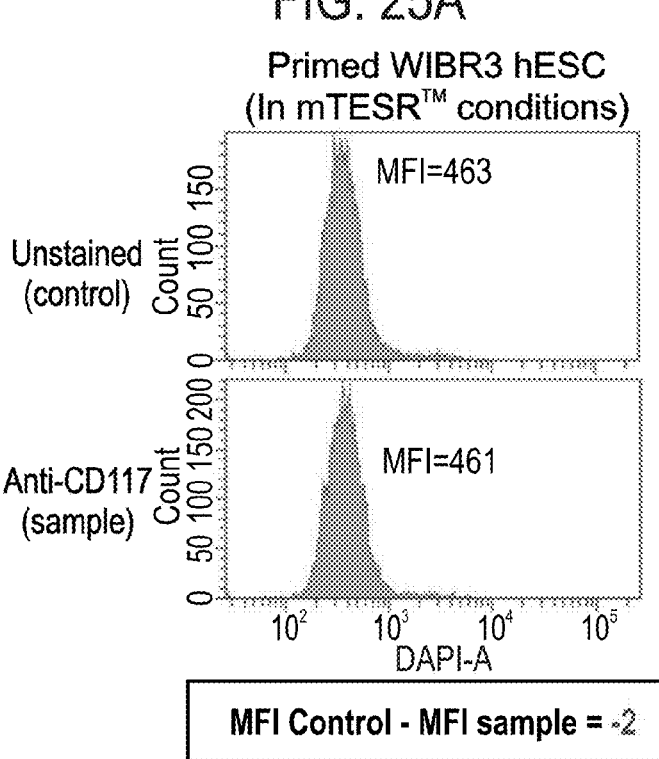
Figures 25B, 25C:
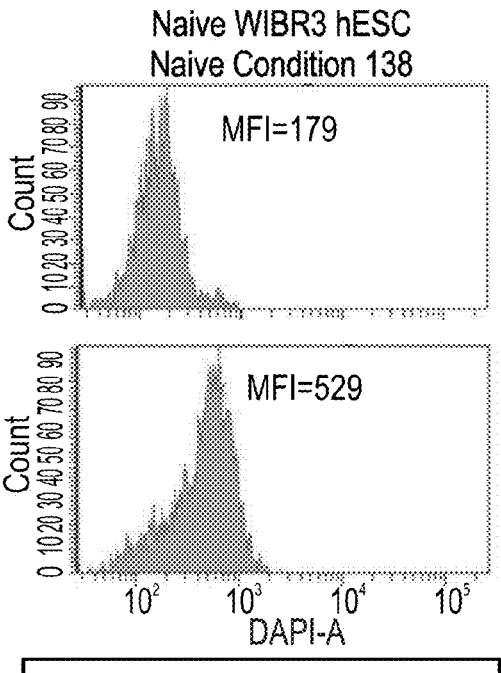

FIGS. 25A-C depict FACS analyses of WIBR3 hESCs primed or naïve PSC for expression of the C-KIT (CD117) cell surface protein. WIBR3 hESCs, grown under conditions for primed PSC (as described below) or under "naïve" conditions (in medium 136 or 138) and were then dissociated to a single-cell suspension using 0.05% trypsin-EDTA. For labeling of cell surface antigens, cells were incubated with primary antibody (Brilliant Violent 421-conjugated mouse anti-human CD117 (C-KIT) IgG, BD catalog #: 562434, dilution 1:200) or remained unstained (control) in ice-cold FACS buffer (2% (vol/vol) Fetal bovine serum (FBS) in PBS) for 30 minutes and followed by washing twice. Then cell labeling was analyzed using the flow cytometer FACSAria II with FACSDiva software version 6.1.3 (BD Biosciences). MFI=Mean fluorescence intensity. Note that while the primed PSC do not express C-KIT (i.e., they are CD117-negative) (FIG. 25A), the naive PSC express C-KIT (i.e., they are CD117-positive) (FIGS. 25B and 25C). These results support the conclusion that C-KIT is a novel marker for human naïve, but not primed, PSCs.

Figure 26D:
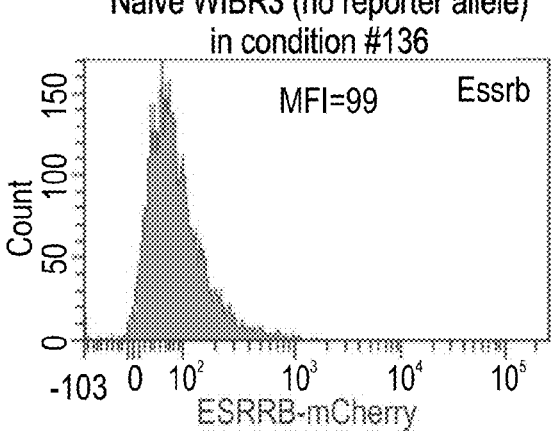
Figure 26G:
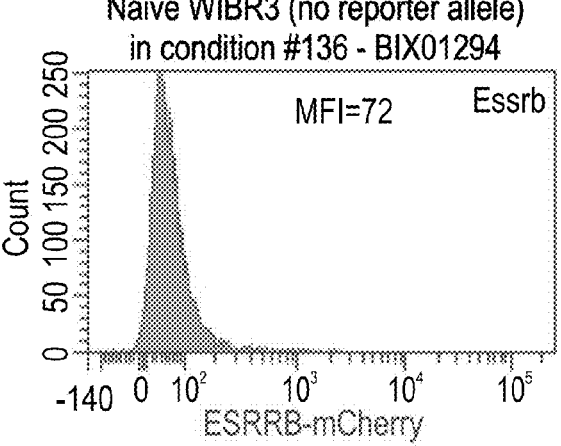
Figure 26E:
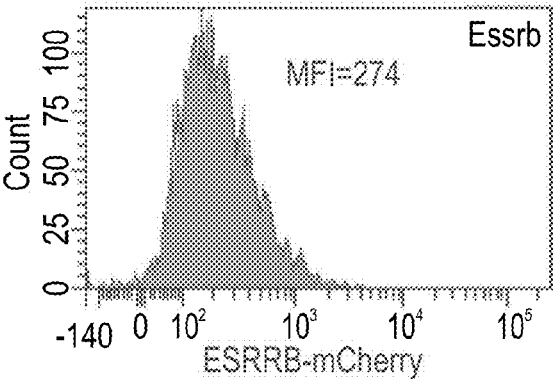
Figure 26H:
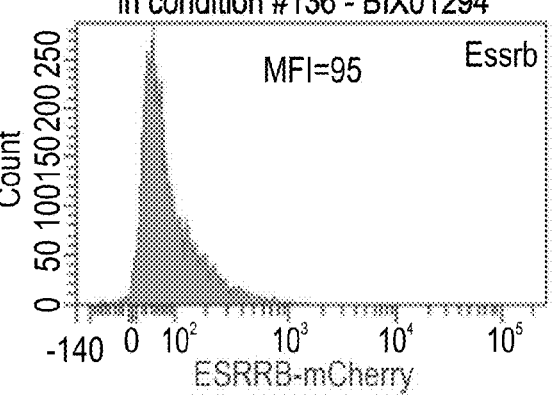

FIGS. 26A-C depict the targeting human ESRRB (a gene/transcription factor) locus with knockin mCherry fluorescent reporter. FIG. 26A-Targeting scheme is illustrated. Scissors indicate CRISPR-sgRNA cut site. In order to create mCherry reporter co-expressed with endogenous human ESRRB locus, the present inventors have chosen to knock in p2a-mCherry coding sequence in frame with the last exon of the human ESRRB gene. The present inventors have inserted oligos specific for the stop codon region of ESRRB gene into px335 plasmid which encodes CAS9 nickase and sgRNA. The donor construct was made as indicated in FIG. 26A. The present inventors have targeted WIBR3 human ESC OCT4 GFP knockin cell line. The efficiency of the targeting was about 30% (15 out of 48 clones) as verified by external PCR. Correct targeting was also verified by Southern Blot (SB) with external and anti-mCherry probes (FIG. 26B). After Neo cassette excision with Flippase, the whole targeted locus from one of the clones was amplified and sequenced. Clones 2-6 were correctly targeted (FIG. 26C).

Figure 26F:
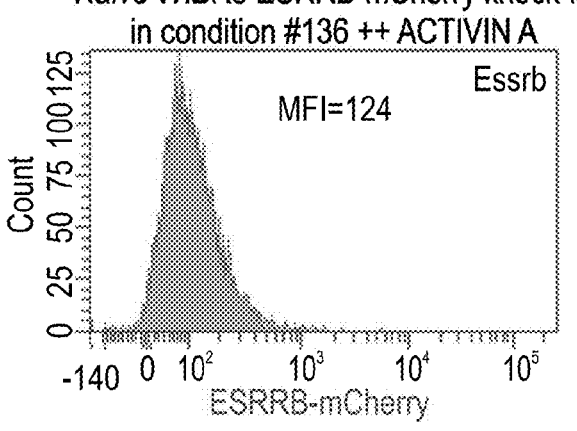

FIGS. 26D-H are FACS analyses depicting expression of ESRRB-mCherry reporter in PSCs. WIBR3 hESCs, with (FIGS. 26E, 26F, and 26H) or without (FIGS. 26D and 26G) ESRRB mCherry knock-in reporter, expanded in the indicated conditions were dissociated to a single-cell suspension using 0.05% trypsin-EDTA, and resuspended in ice-cold FACS buffer (2% (vol/vol) Fetal Bovine Serum (FBS) in PBS (phosphate buffered saline). Then cells were simultaneously analyzed using the flow cytometer FACSAria II with FACSDiva software version 6.1.3 (BD Biosciences) for the ESRRB-mCherry expression. MFI=Mean fluorescence intensity. The results indicate how Naïve conditions 136 specifically induce ESRRB mCherry expression (compare FIG. 26E to 26D) and that this effect is lost when BIX01294 is removed from the culture medium (FIG. 26H as compared to FIG. 26E), or when Activin A is added (FIG. 26F). These results show that some of the naïve compositions described herein specifically induce the naïve pluripotent transcription factor ESRRB.

DESCRIPTION OF SPECIFIC EMBODIMENTS OF THE INVENTION

The present invention, in some embodiments thereof, relates to novel culture media which can be used to generate and expand pluripotent stem cells in general and more particularly naive pluripotent stem cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered novel conditions, which are required for isolating and generating a primate (e.g., human) naive pluripotent stem cell, and maintaining same in the naive state.

Thus, as shown in Example 5 of the Examples section which follows, and in FIGS. 7-16, the present inventors have uncovered that the novel conditions including a culture medium capable of maintaining naive PSCs in the "naive state" as explained herein under, and as was evidenced by the expression of OCT4-GFP+ (positive) cells. Such a culture medium comprises a STAT3 activator, MEK/ERK1/2 inhibitor (e.g., PD0325901), and an Axin stabilizer.

As used herein the phrase "naive state" refers to being in an undifferentiated state wherein both alleles of the promoter of the X-inactive specific transcript (XIST) gene of the female cell are unmethylated, or wherein the promoter of the XIST allele of the male cell is unmethylated.

According to an aspect of some embodiments of the present invention there is provided a culture medium comprising a STAT3 activator, an ERK1/2 inhibitor and an Axin stabilizer.

As used herein the phrase "culture medium" refers to a solid or a liquid substance used to support the growth of stem cells and maintain them in an undifferentiated state. Preferably, the phrase "culture medium" as used herein refers to a liquid substance capable of maintaining the stem cells in an undifferentiated state.

The culture medium used by the present invention can be a water-based medium which includes a combination of substances such as salts, nutrients, minerals, vitamins, amino acids, nucleic acids, proteins such as cytokines, growth factors and hormones, all of which are needed for cell proliferation and are capable of maintaining the stem cells in an undifferentiated state. For example, a culture medium can be a synthetic tissue culture medium such as Ko-DMEM (Gibco-Invitrogen Corporation products, Grand Island, NY, USA), DMEM/F12 (Gibco-Invitrogen Corporation products, Grand Island, NY, USA), Neurobasal medium (Invitrogen Corporation products, Grand Island, NY, USA 21103-049) or DMEM/F12 (without HEPES; Biological Industries, Beit Haemek, Israel), supplemented with the necessary additives as is further described herein under.

According to a particular embodiment, the medium is a 1:1 mix of Neurobasal medium and DMEM F/12.

According to still another embodiment, the medium is MTESRI (Stem Cell Technologies). In some instances, this medium already comprises TGF beta and FGF2 and accordingly is only appropriate for preparation of those media which comprise these growth factors. In other instances, the medium is made without FGF and TGF (see for example Ludwing and Thomson: Curr. Protoc. Stem Cell Biol. 2:1C.2.1-1C.2.16).

Preferably, all ingredients included in the culture medium of the present invention are substantially pure, with a tissue culture grade.

According to some embodiments of the invention, the culture medium is devoid of serum, e.g., devoid of any animal serum.

According to some embodiments of the invention, the culture medium is devoid of any animal contaminants, i.e., animal cells, fluid or pathogens (e.g., viruses infecting animal cells), e.g., being xeno-free.

According to some embodiments of the invention, the culture medium is devoid of human derived serum.

According to some embodiments of the invention, the culture medium further comprises a serum replacement (i.e., a substitute of serum) such as KNOCKOUT™ Serum Replacement (Gibco-Invitrogen Corporation, Grand Island, NY USA), ALBUMAX®II (Gibco®; Life Technologies-Invitrogen, Catalogue No. 11021-029; Lipid-rich bovine serum albumin for cell culture) or a chemically defined lipid concentrate (Gibco®; Invitrogen, Life Technologies-Invitrogen, Catalogue No. 11905-031).

According to some embodiments of the invention, the culture medium further comprises N2 supplement (Gibco®; Life Technologies-Invitrogen, Catalogue No. 17502-048) a chemically defined, serum-free supplement. For a 500 ml of culture medium 5 ml of the N2 mix (Invitrogen) can be added.

Alternatively, the following materials (substitute the N2 supplement) can be added to a 500 ml culture medium: Recombinant Insulin (Sigma I-1882) at a 12.5 microg/ml (μg/ml) final concentration; Apo-Transferrin (Sigma T-1147) at a 500 μg/ml final concentration; Progesterone (Sigma-P8783) at a 0.02 μg/ml final concentration; Putrescine (Sigma-P5780) at a 16 μg/ml final concentration; and 5 microL (μl) of 3 mM stock of Sodium Selenite (Sigma-S5261) are added per 500 ml culture medium [i.e., at a final concentration of 3 nM (e.g., the WIS-NHSM)].

According to some embodiments of the invention, the KNOCKOUT™ Serum Replacement is provided at a concentration of at least 0.5%, e.g., in the range of about 0.5%-25%, e.g., about 5%, about 10%, about 15%, about 20% or about 25%.

According to some embodiments of the invention, the ALBUMAX™ is provided at a concentration of at least 0.01%, e.g., in the range of about 0.01%-10%, e.g., about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9% or about 10%, e.g., 1%.

According to some embodiments of the invention, the defined lipid concentrate is provided at a concentration of at least about 0.1%, e.g., in the range of 0.1-5%, e.g., about 0.2%, about 0.3%, about 0.4%, about 0.5%, about 0.6%, about 0.7%, about 0.8%, about 0.9%, about 1%, about 2%, about 3%, about 4%, about 5%, e.g., 1%.

According to some embodiments of the invention, the culture medium comprises the N2 supplement (e.g., 5 ml N2 per 500 ml of culture medium) and the defined lipid concentrate (5 ml defined lipid concentrate per 500 ml medium).

According to some embodiments of the invention, the culture medium comprises the N2 supplement (e.g., 5 ml N2 per 500 ml of culture medium) and ALBUMAX®II (e.g., 1% Albumax®II; Gibco®; Life Technologies-Invitrogen).

According to some embodiments of the invention, the culture medium can further include antibiotics (e.g., PEN-STREP), L-glutamine, NEAA (non-essential amino acids).

As used herein the term "STAT3" refers to the signal transducer and activator of transcription 3 gene product (acute-phase response factor) (Gene ID 6774). In response to cytokines and growth factors, STAT family members are phosphorylated by the receptor associated kinases, and then form homo- or heterodimers that translocate to the cell nucleus where they act as transcription activators. Known STAT3 activators include, but are not limited to, interferon (IFN), epidermal growth factor (EGF), interleukin 5 (IL5), interleukin 6 (IL6), hepatocyte growth factor (HGF), leuke-
mia inhibitory factor (LIF) and bone morphogenetic protein
2 (BMP2).

According to some embodiments of the invention, the
STAT3 activator, which is used in the medium of some
embodiments of the invention, is selected from the group
consisting of LIF, IL6 and EGF.

According to some embodiments of the invention, the
STAT3 activator, which is used in the medium of some
embodiments of the invention, is selected from the group
consisting of LIF and IL6.

According to some embodiments of the invention, the
STAT3 activator, which is used in the medium of some
embodiments of the invention is LIF.

As used herein the term "leukemia inhibitor factor (LIF)"
refers to a polypeptide which comprises the amino acid
sequence as set forth by GenBank Accession No.
NP_001244064.1 (SEQ ID NO:119), encoded by the
nucleotide sequence set forth in GenBank Accession No.
NM_001257135 (SEQ ID NO:30). Preferably, the LIF used
by the method according to some embodiments of the
invention is capable of supporting, along with other factors
which are described herein, the undifferentiated growth of
naive primate (e.g., human) PSCs, while maintaining their
pluripotent capacity. LIF can be obtained from various
manufacturers such as Millipore, Peprotech, and R&D sys-
tems.

According to some embodiments of the invention, LIF is
provided at a concentration range from about 0.5 nanogram
per milliliter (ng/ml) to about 1000 ng/ml, e.g., about 1-1000
ng/ml, e.g., about 1-900 ng/ml, e.g., about 1-800 ng/ml, e.g.,
about 1-700 ng/ml, e.g., about 1-600 ng/ml, e.g., about
1-500 ng/ml, e.g., about 1-400 ng/ml, e.g., about 1-300
ng/ml, e.g., about 1-200 ng/ml, e.g., about 1-100 ng/ml, e.g.,
about 1-50 ng/ml, e.g., about 2-50 ng/ml, e.g., about 4-50
ng/ml, e.g., about 5-50 ng/ml, e.g., about 10-50 ng/ml, e.g.,
about 10-40 ng/ml, e.g., about 10-30 ng/ml, e.g., about 20
ng/ml.

As used herein the term "interleukin 6 (IL6)" refers to a
polypeptide which comprises the amino acid sequence set
forth by GenBank Accession No. NP_000591.1 (SEQ ID
NO: 120), which is encoded by the nucleic acid set forth by
GenBank Accession No. NM_000600.3 (SEQ ID NO: 111).
Preferably, the IL6 used by the method according to some
embodiments of the invention is capable of supporting,
along with other factors which are described herein, the
undifferentiated growth of naive primate (e.g., human)
PSCs, while maintaining their pluripotent capacity. IL6 can
be obtained from various manufacturers such as Speed
BioSystems, Millipore, Peprotech, and R&D systems.

According to some embodiments of the invention, IL6 is
provided at a concentration range from about 0.1 ng/ml to
about 100 ng/ml, e.g., about 0.1-90 ng/ml, e.g., about 0.1-80
ng/ml, e.g., about 0.1-70 ng/ml, e.g., about 0.1-50 ng/ml,
e.g., about 0.1-40 ng/ml, e.g., about 0.1-30 ng/ml, e.g., about
0.1-20 ng/ml, e.g., about 0.1-10 ng/ml, e.g., about 0.1-8
ng/ml, e.g., about 0.1-7 ng/ml, e.g., about 0.1-6 ng/ml, e.g.,
about 0.1-5 ng/ml, e.g., about 0.1-4 ng/ml, e.g., about 0.1-3
ng/ml, e.g., about 0.1-4 ng/ml, e.g., about 0.5-4 ng/ml, e.g.,
about 0.5-4 ng/ml, e.g., about 3 ng/ml.

As used herein the term "EGF" refers to the epidermal
growth factor gene product. The encoded protein (EGF) is
synthesized as a large precursor molecule that is proteolyti-
cally cleaved to generate the 53-amino acid epidermal
growth factor peptide. The EGF protein acts a potent mito-
genic factor that plays an important role in the growth,
proliferation and differentiation of numerous cell types; it acts by binding the high affinity cell surface receptor,
epidermal growth factor receptor. The EGF protein, which
can be used according to some embodiments of the inven-
tion comprises any of the EGF isoforms 1-3, which result
from alternate splicing. Thus, transcript variant 1 [GenBank
Accession No. NM_001963.4 (SEQ ID NO: 179)], repre-
sents the longest transcript and encodes the longest isoform,
i.e., isoform 1 [GenBank Accession No. NP_001954.2 (SEQ
ID NO: 178)]. Transcript variant 2 [GenBank Accession No.
NM_001178130.1 (SEQ ID NO: 181)], which lacks an
in-frame exon in the coding region compared to variant 1,
encodes isoform 2 [GenBank Accession No.
NP_001171601.1 (SEQ ID NO:180)]. Transcript variant 3
[GenBank Accession No. NM_001178131.1 (SEQ ID NO:
183)], which lacks an in-frame exon in the coding region,
compared to variant 1, encodes isoform 3 [GenBank Acces-
sion No. NP_001171602.1 (SEQ ID NO:182)].

According to some embodiments of the invention, EGF is
provided at a concentration range from about 1 ng/ml to
about 20 ng/ml, e.g., between about 2-20 ng/ml, e.g.,
between about 3-19 ng/ml, e.g., between about 4-18 ng/ml,
e.g., between about 5-15 ng/ml, e.g., about 1 ng/ml, e.g.,
about 2 ng/ml, e.g., about 3 ng/ml, e.g., about 4 ng/ml, e.g.,
about 5 ng/ml, e.g., about 6 ng/ml, e.g., about 7 ng/ml, e.g.,
about 8 ng/ml, e.g., about 9 ng/ml, e.g., about 10 ng/ml, e.g.,
about 11 ng/ml, e.g., about 12 ng/ml, e.g., about 13 ng/ml,
e.g., about 14 ng/ml, e.g., about 15 ng/ml, e.g., about 16
ng/ml, e.g., about 17 ng/ml, e.g., about 18 ng/ml, e.g., about
19 ng/ml, e.g., about 20 ng/ml.

As used herein the term "ERK1" refers to the mitogen-
activated protein kinase 3 (MAPK3) isoform 1 set forth by
GenBank Accession No. NP_002737.2 (SEQ ID NO:33),
the MAPK3 isoform 2 set forth by GenBank Accession No.
NP_001035145.1 (SEQ ID NO: 34), the MAPK3 isoform 3
set forth by GenBank Accession No. NP_001103361.1 (SEQ
ID NO:35) and/or ERK1 set forth in GenBank Accession
No. M84490 (SEQ ID NO: 36) having the MAPK signaling
activity.

As used herein the term "ERK2" refers to the mitogen-
activated protein kinase 1 (MAPK1) set forth by GenBank
Accession No. NP_002736.3 (SEQ ID NO:37) and/or Gen-
Bank Accession No. NP_620407.1 (SEQ ID NO:38) having
the MAPK signaling activity.

As used herein the term "ERK1/2 inhibitor" refers to any
molecule capable of inhibiting the activity of ERK1/2 as
determined by Western blot protein detection of phospho-
rylated ERK1/2 proteins.

Non-limiting examples of ERK1/2 inhibitors (also known
as MEK1/2 inhibitors) include PD0325901 (AXONMED-
CHEM-AXON 1408), PD98059 (AXONMEDCHEM—
Axon 1223), and PD184352 (AXONMEDCHEM-AXON
1368).

It will be appreciated that inhibition of ERK1/2 activity
can be also achieved by inhibition of a protein(s) which
activity thereof directly affects the activity of ERK1/2. Such
a protein(s) is considered to be "upstream" of the MEK/ERK
pathway, i.e., a protein (e.g., A-RAF, B-RAF and C-RAF),
which inhibition thereof results in a subsequent inhibition of
the ERK1/2 protein activity. Non-limiting examples of
inhibitors of the BRAF and CRAF proteins which also result
in inhibition of ERK1/2 activity include Sorafenib tosylate
(also known as BAY 43-9006 AXONMEDCHEM-AXON
1397) or SB 590885 (TOCRIS #2650) as is further described
hereinbelow.

According to some embodiments of the invention,
PD0325901 is provided at a concentration range from about
0.01 microM (μM) to about 50 μM, e.g., between about 0.05-45 μM, e.g., between about 0.1-50 μM, e.g., between about 0.1-45 μM, e.g., between about 0.1-40 μM, e.g., between about 0.1-35 μM, e.g., between about 0.1-30 μM, e.g., between about 0.1-25 μM, e.g., between about 0.1-20 μM, e.g., between about 0.1-15 μM, e.g., between about 0.1-10 μM, e.g., between about 0.2-10 μM, e.g., between about 0.3-10 μM, e.g., between about 0.4-10 μM, e.g., between about 0.5-10 μM, e.g., between about 0.6-10 μM, e.g., between about 0.7-10 μM, e.g., between 0.8-10 μM, e.g., between 0.9-10 μM, e.g., between 0.9-9 μM, e.g., between 0.9-8 μM, e.g., between 0.9-7 μM, e.g., between 0.9-6 μM, e.g., between 0.8-5 μM, e.g., between 0.8-4 μM, e.g., between 0.8-3 μM, e.g., between 0.8-2 μM, e.g., between 0.8-1.5 μM, e.g., between 0.9-1.2 μM, e.g., about 1 μM.

According to some embodiments of the invention, PD98059 is provided at a concentration range from about 0.1 microM (μM) to about 70 μM, e.g., between about 0.1-65 μM, e.g., between about 0.1-55 μM, e.g., between about 0.1-50 μM, e.g., between about 0.1-45 μM, e.g., between about 0.1-40 μM, e.g., between about 0.1-35 μM, e.g., between about 0.1-30 μM, e.g., between about 0.1-25 μM, e.g., between about 0.1-20 μM, e.g., between about 0.1-15 μM, e.g., between about 2-20 μM, e.g., between about 5-15 μM, e.g., about 10 μM, e.g., between about 0.1-10 μM, e.g., between about 0.2-10 μM, e.g., between about 0.3-10 μM, e.g., between about 0.4-10 μM, e.g., between about 0.5-10 μM, e.g., between about 0.6-10 μM, e.g., between about 0.7-10 UM, e.g., between 0.8-10 μM, e.g., between 0.9-10 μM, e.g., between 0.9-9 UM, e.g., between 0.9-8 μM, e.g., between 0.9-7 μM, e.g., between 0.9-6 μM, e.g., between 0.8-5 μM, e.g., between 0.8-4 μM, e.g., between 0.8-3 μM, e.g., between 0.8-2 μM, e.g., between 0.8-1.5 μM, e.g., between 0.9-1.2 μM.

According to some embodiments of the invention, PD184352 is provided at a concentration range from about 0.1 microM (μM) to about 70 μM, e.g., between about 0.1-60 μM, e.g., between about 0.1-50 M, e.g., between about 0.5-50 μM, e.g., between about 0.5-45 μM, e.g., between about 0.5-40 μM, e.g., between about 0.1-35 μM, e.g., between about 0.5-30 μM, e.g., between about 0.5-25 M, e.g., between about 0.5-20 μM, e.g., between about 0.5-15 μM, e.g., between about 0.5-10 μM, e.g., between 0.5-9 μM, e.g., between 0.5-8 μM, e.g., between 0.5-7 μM, e.g., between 0.9-6 μM, e.g., between 0.8-5 μM, e.g., between 0.8-4 μM, e.g., between 0.8-3 μM, e.g., about 3 μM. e.g., between 0.8-2 μM, e.g., between 0.8-1.5 M, e.g., between 0.9-1.2 μM.

The AXIN destruction complex is a multiprotein "destruction complex" that includes the tumor suppressors Axin and adenomatous polyposis coli (APC), the Ser/Thr kinases GSK-3 and CK1.

The use of GSK3b inhibitors allows stabilization of beta-catenin effector that has cytoplasmic and nuclear downstream functions. The use of small molecules that stabilize AXIN destruction complex together with GSK3b inhibitors allow increasing the stabilized beta-catenin function in the cytoplasm at the expense of that found in the nucleus. Such an approach has been used to reduce dependence on FGF2 signaling in mouse and human primed cells (Kim, H., et al., 2013. Modulation of b-catenin function maintains mouse epiblast stem cell and human embryonic stem cell self-renewal. Nature Communications 4, 1-11).

Recently, two groups of chemical substances (IWR-1-Sigma Aldrich 10161; and XAV939-TOCRIS cat. No.3748, or Sigma cat. No. X3004) have been identified which stabilize the destruction complex structure and/or activity (Chen et al., Nat. Chem. Biol. 5:100-107, 2009; and Huang et al., Nature: 461: 614-620, 2009). By blocking the PARP domain of Tankyrase, XAV939 and IWR-1 are thought to alter the PARsylation and ubiquitination of AXIN2 that results in its increased stability and in inhibition of canonical Wnt signaling. IWR compounds induce stabilization of Axin proteins via a direct interaction, which is a part of the beta-catenin destruction complex (consists of Apc, Axin1/2, Ck1 and Gsk3b).

Additional AXIN stabilizers which can be used according to some embodiments of the invention include, but are not limited to, IWP2 (available from TOCRIS Cat. No. 3533, e.g., at a concentration of about 2 microM); Lysophosphatidilic acid (LPA; available from Santa Cruz, Cat. No. sc201053, e.g., at a concentration of about 1-10 microM); WNT5a (available from RnD system, Cat. No. 645-WN-010, e.g., at a concentration of about 1-20 ng/ml).

According to a particular embodiment, the AXIN complex stabilizer is a small molecule compound.

According to another embodiment, the AXIN complex stabilizer is IWR-1.

According to some embodiments of the invention, the AXIN stabilizer (e.g. IWR-1) is provided at a concentration range of between about 0.1-70 μM, e.g., from about 0.2 μM to about 70 μM, e.g., between about 0.2-60 μM, e.g., between about 0.2-55 μM, e.g., between about 0.2-50 μM, e.g., between about 0.2-45 μM, e.g., between about 0.2-40 μM, e.g., between about 0.2-35 M, e.g., between about 0.2-30 μM, e.g., between about 0.2-25 M, e.g., between about 0.2-20 M, e.g., between about 0.2-15 μM, e.g., between about 0.2-10 μM, e.g., between about 0.3-10 μM, e.g., between about 0.4-10 μM, e.g., between about 0.5-10 μM, e.g., between about 0.6-10 μM, e.g., between about 0.7-10 μM, e.g., between about 0.8-10 μM, e.g., between 0.9-10 μM, e.g., between 0.9-9 μM, e.g., between 1-8 μM, e.g., between 1-7 μM, e.g., between 1-6 μM, e.g., between 1-5 μM, e.g., about 1-3 μM, e.g., about 2 μM, e.g., about 5 μM.

According to another embodiment, the AXIN complex stabilizer is XAV939.

According to some embodiments of the invention, the AXIN stabilizer (e.g. XAV939, IWP2 and/or LPA) is provided at a concentration range of between about 0.1-70 μM, e.g., about 0.1-20 μM, e.g., from about 0.2 μM to about 70 μM, e.g., between about 0.2-60 μM, e.g., between about 0.2-55 μM, e.g., between about 0.2-50 μM, e.g., between about 0.2-45 μM, e.g., between about 0.2-40 μM, e.g., between about 0.2-35 μM, e.g., between about 0.2-30 μM, e.g., between about 0.2-25 μM, e.g., between about 0.2-20 μM, e.g., between about 0.2-15 μM, e.g., between about 0.2-10 μM, e.g., between about 0.3-10 μM, e.g., between about 0.4-10 μM, e.g., between about 0.5-10 μM, e.g., between about 0.6-10 μM, e.g., between about 0.7-10 μM, e.g., between 0.8-10 μM, e.g., between 0.9-10 μM, e.g., between 1-10 μM, e.g., between 0.9-9 μM, e.g., between 1-8 μM, e.g., between 1-7 μM, e.g., between 1-6 μM, e.g., between 1-5 μM, e.g., about 1-3 μM, e.g., about 2 μM.

According to some embodiments of the invention, the AXIN stabilizer WNT5a is provided at a concentration range of between about 1 ng/ml and about 20 ng/ml, e.g., about 2-20 ng/ml, e.g., about 3-20 ng/ml, e.g., about 4-20 ng/ml, e.g., about 5-20 ng/ml, e.g., about 6-20 ng/ml, e.g., about 7-20 ng/ml, e.g., about 8-20 ng/ml, e.g., about 9-20 ng/ml, e.g., about 10-20 ng/ml, e.g., about 10-19 ng/ml, e.g., about 10-18 ng/ml, e.g., about 10-15 ng/ml, e.g., about 20 ng/ml.

According to some embodiments of the invention, the culture medium further comprises a PKC inhibitor.

According to an aspect of some embodiments of the present invention there is provided a culture medium comprising a STAT3 activator, an ERK1/2 inhibitor, an Axin stabilizer and a PKC inhibitor.

As used herein the term "protein kinase C (PKC)" refers to PKCα (alpha), PKCβ (beta), PKCγ (gamma), PKCδ (delta), PKCζ (zeta) and PKCμ (mu) protein isoforms.

As used herein the term "protein kinase C inhibitor" refers to any molecule capable of inhibiting the activity of protein kinase C as determined by reducing the levels of phosphorylated versus non phosphorylated PKC isoforms.

A non-limiting example of a protein kinase C inhibitor is Go6983 (CAS 133053-19-7), a potent, cell-permeable, reversible, and ATP-competitive inhibitor of protein kinase C (PKC) with a broad spectrum protein kinase C (PKC) inhibitor (IC50 values are 7, 7, 6, 10, 60 and 20000 nM for PKCα, PKCβ, PKCγ, PKCδ, PKCζ and PKCμ respectively). Go6983 is available from various suppliers such as Calbiochem (Catalogue number 365251-500UG), and TOCRIS (Catalogue number 2285).

According to some embodiments of the invention, Go6983 is provided at a concentration range of between about 0.5-100 μM, e.g., from about 1 μM to about 100 μM, e.g., between about 1-90 μM, e.g., between about 1-80 μM, e.g., between about 1-70 μM, e.g., between about 1-60 μM, e.g., between about 1-55 μM, e.g., between about 1-50 μM, e.g., between about 1-45 μM, e.g., between about 1-40 μM, e.g., between about 1-35 μM, e.g., between about 1-30 μM, e.g., between about 1-25 μM, e.g., between about 1-20 μM, e.g., between about 1-15 μM, e.g., between about 1-10 μM, e.g., between about 2-10 μM, e.g., between about 3-10 μM, e.g., between about 4-10 μM, e.g., between about 4-6 μM, e.g., about 5 μM.

According to some embodiments of the invention, the medium further comprises a GSK3b inhibitor.

Thus, according to an aspect of some embodiments of the present invention there is provided a culture medium comprising a STAT3 activator, an ERK1/2 inhibitor, an Axin stabilizer, a PKC inhibitor and a GSK3b inhibitor.

As used herein the term "GSK3b" refers to the glycogen synthase kinase 3 beta protein set forth by GenBank Accession Nos. NP_002084.2 (SEQ ID NO: 121) and/or NP_001139628.1 (SEQ ID NO: 122) having the WNT signaling regulatory activity via its kinase activity.

As used herein the term "GSK3b inhibitor" refers to any molecule capable of inhibiting the activity of GSK3b as determined by specifically inhibiting levels of phosphorylated GSK3b (out of total GSK3b present in a cell).

Non-limiting examples of GSK3b inhibitors include CHIR99021 (AXONMEDCHEM-AXON 1386), BIO (AXONMEDCHEM-Axon 1693), and Kenpaullone (TOCRIS—cat no. 1398).

According to some embodiments of the invention, CHIR99021 is provided at a concentration range of between about 0.1-50 μM, e.g., from about 0.2 μM to about 50 μM, e.g., between about 0.2-45 M, e.g., between about 0.2-50 μM, e.g., between about 0.2-45 μM, e.g., between about 0.2-40 μM, e.g., between about 0.2-35 M, e.g., between about 0.2-30 μM, e.g., between about 0.2-25 μM, e.g., between about 0.2-20 μM, e.g., between about 0.2-15 μM, e.g., between about 0.2-10 μM, e.g., between about 0.2-10 M, e.g., between about 0.3-10 μM, e.g., between about 0.4-10 μM, e.g., between about 0.5-10 μM, e.g., between about 0.6-10 μM, e.g., between about 0.7-10 μM, e.g., between about 0.8-10 μM, e.g., between about 0.9-10 μM, e.g., between 0.9-9 μM, e.g., between 1-8 μM, e.g., between 1-7 μM, e.g., between 1-6 μM, e.g., between 1-5 μM, e.g., between 2-4 μM, e.g., about 3 μM.

According to some embodiments of the invention, BIO is provided at a concentration range of between about 0.1-70 μM, e.g., from about 0.2 μM to about 70 μM, e.g., between about 0.2-60 μM, e.g., between about 0.2-55 μM, e.g., between about 0.2-50 M, e.g., between about 0.2-45 μM, e.g., between about 0.2-40 M, e.g., between about 0.2-35 μM, e.g., between about 0.2-30 μM, e.g., between about 0.2-25 μM, e.g., between about 0.2-20 μM, e.g., between about 0.2-15 μM, e.g., between about 0.2-10 μM, e.g., between about 0.3-10 μM, e.g., between about 0.4-10 μM, e.g., between about 0.5-10 μM, e.g., between about 0.6-10 μM, e.g., between about 0.7-10 μM, e.g., between 0.8-10 μM, e.g., between 0.9-10 μM, e.g., between 0.9-9 μM, e.g., between 1-8 μM, e.g., between 1-7 μM, e.g., between 1-6 μM, e.g., between 1-5 μM, e.g., about 5 μM, e.g., between 2-4 μM.

According to some embodiments of the invention, Kenpaullone is provided at a concentration range of between about 0.1-70 μM, e.g., from about 0.2 M to about 70 μM, e.g., between about 0.2-60 μM, e.g., between about 0.2-55 M, e.g., between about 0.2-50 μM, e.g., between about 0.2-45 μM, e.g., between about 0.2-40 μM, e.g., between about 0.2-35 μM, e.g., between about 0.2-30 μM, e.g., between about 0.2-25 μM, e.g., between about 0.2-20 μM, e.g., between about 0.2-15 μM, e.g., between about 0.2-10 μM, e.g., between about 0.3-10 μM, e.g., between about 0.4-10 μM, e.g., between about 0.5-10 μM, e.g., between about 0.6-10 μM, e.g., between about 0.7-10 μM, e.g., between 0.8-10 μM, e.g., between 0.9-10 μM, e.g., between 0.9-9 μM, e.g., between 1-8 μM, e.g., between 1-7 M, e.g., between 1-6 μM, e.g., between 1-5 μM, e.g., between 2-4 μM, e.g., about 5 μM.

According to some embodiments of the invention, the medium further comprises at least one agent selected from the group consisting of: a ROCK inhibitor, an SRC inhibitor, ascorbic acid, a PKA agonist, a YAP/TAZ inhibitor, a NOTCH inhibitor, an SHH inhibitor, a TGFβR inhibitor, a BMP inhibitor, an FGFR inhibitor, a JNK inhibitor, an ERK5 inhibitor, a BRAF inhibitor, a CRAF inhibitor, an ARAF inhibitor, a p38 inhibitor, a GSK3b inhibitor, an LSD1 inhibitor, a PI3K activator (or booster), a SMAD activator and a DOT1L inhibitor.

As used herein the term "ROCK" refers to the protein set forth by GenBank Accession No. NP_005397.1 (P160ROCK; SEQ ID NO: 50); and NP_004841.2 (ROCK2; SEQ ID NO:51) having the serine/threonine kinase activity, and regulates cytokinesis, smooth muscle contraction, the formation of actin stress fibers and focal adhesions, and the activation of the c-fos serum response element.

As used herein the term "ROCK inhibitor" refers to any molecule capable of inhibiting the activity of ROCK as determined by inhibition of ROCK phosphorylation levels (detected by western blot analysis).

Non-limiting examples of ROCK inhibitors include Y27632 (TOCRIS, Catalogue number 1254), Blebbistatin (TOCRIS Catalogue number 1760) and Thiazovivin (Axon Medchem-Axon 1535). Blebbistatin is a selective inhibitor of myosin II ATpase, a downstream effector of ROCK pathway, and thus effectively leads to ROCK pathway inhibition (Chen G1, Hou Z et al. Actin-myosin contractility is responsible for the reduced viability of dissociated human embryonic stem cells. Cell Stem Cell. 2010; 7 (2): 240-8, which is fully incorporated herein by reference in its entirety).

According to some embodiments of the invention, Y27632 is provided at a concentration range of between about 0.1-100 M, e.g., from about 0.1 μM to about 90 μM, e.g., between about 0.1-85 μM, e.g., between about 0.1-80 M, e.g., between about 0.1-70 μM, e.g., between about 0.1-60 μM, e.g., between about 0.1-55 μM, e.g., between about 0.1-50 μM, e.g., between about 0.1-45 μM, e.g., between about 0.1-40 μM, e.g., between about 0.1-35 M, e.g., between about 0.1-30 μM, e.g., between about 0.1-25 μM, e.g., between about 1-20 μM, e.g., between about 1-15 μM, e.g., between about 1-10 μM, e.g., between about 2-10 μM, e.g., between about 3-10 μM, e.g., between about 4-10 μM, e.g., between about 4-6 μM, e.g., about 5 μM.

According to some embodiments of the invention, Blebbistatin is provided at a concentration range of between about 0.5 μM to about 10 μM, e.g., from about 0.5 μM to about 9 μM, e.g., between about 0.5-8.5 μM, e.g., between about 0.5-8 μM, e.g., between about 0.5-7 μM, e.g., between about 0.5-6 μM, e.g., between about 0.5-5.5 μM, e.g., between about 0.5-5 μM, e.g., between about 0.5-4.5 μM, e.g., between about 0.5-4 μM, e.g., between about 0.5-3.5 μM, e.g., between about 0.5-3 μM, e.g., between about 0.5-2.5 μM, e.g., between about 1-2 μM, e.g., e.g., about 5 μM.

According to some embodiments of the invention, Thiazovivin is provided at a concentration range of between about 0.1 μM to about 5 μM, e.g., from about 0.1 μM to about 4 μM, e.g., from about 0.1 to about 3 μM, e.g., from about 0.2 μM to about 2.5 μM, e.g., from about 0.3 μM to about 2 μM, e.g., from about 0.3 μM to about 1 μM, e.g., from about 0.3 to about 0.8 μM, e.g., between 0.4-0.6 μM, e.g., about 0.4 μM, e.g., about 0.5 μM As used herein the term "SRC" refers to the SRC proto-oncogene, non-receptor tyrosine kinase, which may play a role in the regulation of embryonic development and cell growth. The protein encoded by this gene is a tyrosine-protein kinase whose activity can be inhibited by phosphorylation by c-SRC kinase. Two transcript variants encoding the same protein (GenBank Accession NO. NP_005408.1 (SEQ ID NO:134) have been found for this gene [GenBank Accession Nos. NM_005417.4 (SEQ ID NO:135) and NM_198291.2 (SEQ ID NO:136)].

Sre signaling promotes epithelial to mesenchymal transition and is an upstream stimulator of JNK pathway. Small molecule inhibitions of SRC pathways has been shown to support expansion of mouse pluripotent cells (Li, X., et al., 2011. Calcineurin-NFAT Signaling Critically Regulates Early Lineage Specification in Mouse Embryonic Stem Cells and Embryos. Stem Cell 8, 46-58; and Shimizu, T., et al., 2012. Dual Inhibition of Src and GSK3 Maintains Mouse Embryonic Stem Cells, Whose Differentiation Is Mechanically Regulated by Src Signaling. Stem Cells 30, 1394-1404). The phrase "src family kinase inhibitor" refers to any agent which is effect to impede or inhibit the function of the src kinase family. Such agents include, without limitation, small molecules, chemical compounds and nucleic acid molecules which function to down regulate expression of target genes and inhibit the function of direct and indirect c-Src substrates, such as the focal adhesion kinase, signal transducer and activator of transcription 3 (STAT3), vascular endothelial growth factor (VEGF), paxillin, Cas, p190RhoGAP, Ras, E-cadherin, c-Jun amino-terminal kinase, NEDD9, and others. Exemplary agents include dasatinib, SU6656, and AZD05530. Src inhibitors are also available from Wyeth and include for example, 4-[(2,4-Dichloro-5-methoxyphenyl) amino]-7-[3-(4-ethyl-1-piperazinyl) propo-xy]-6-methoxy-3-quinolinecarbonitrile; 4-[(2,4-Dichloro-5-methoxyphenyl)amino]-6-methoxy-7-[2-(4-methyl-1-pipera-zinyl)ethoxy]-3-quinolinecarbonitrile; 4-[(2,4-Dichloro-5-methoxyphenyl)amino]-7-[2-(4-ethyl-1-piperazinyl)ethox-y]-6-methoxy-3-quinolinecarbonitrile; 4-[(2,4-Dichloro-5-methoxyphenyl)amino]-6-methoxy-7-[(1-methylpiperidin-4-yl)methoxy]-3-quinolinecarbonitrile; 4-[(2,4-Dichloro-5-methoxyphenyl)amino]-6-methoxy-7-[2-(1-methylpiperidin-4-yl)ethoxy]-3-quinolinecarbonitrile; 4-[(2,4-Dichloro-5-methoxyphenyl)amino]-6-methoxy-7-[3-(1-methylpiperidin-4-yl)propoxy]quinoline-3-carbonitrile; 4-[(2,4-Dichloro-5-methoxyphenyl)amino]-7-[(1-ethylpiperidin-4-yl)methoxy-]-6-methoxyquinoline-3-carbonitrile; 4-[(2,4-Dichloro-5-methoxyphenyl)amino]-6-ethoxy-7-[3-(4-methylpiperazin-1-yl)propoxy]quinoline-3-carbonitrile; 4-[(2,4-Dichloro-5-methoxyphenyl)amino]-6-ethoxy-7-[(1-methylpiperidin-4-yl)methoxy]quinoline-3-carbonitrile; 4-[(2,4-Dichloro-5-methoxyphenyl)amino]-6-ethoxy-7-[3-(4-ethylpiperazin-1-yl)propoxy]quinoline-3-carbonitrile; 4-[(2,4-Dichloro-5-methoxyphenyl)amino]-6-ethoxy-7-[3-(1-methylpiperidin-4-yl)propoxy]quinoline-3-carbonitrile; 4-[(2,4-Dichloro-5-methoxyphenyl)amino]-6-ethoxy-7-[2-(4-methyl-1-piperaz-inyl)ethoxy]quinoline-3-carbonitrile; 4-[(2,4-Dichloro-5-methoxyphenyl)amino]-6-ethoxy-7-[2-(1-methylpiperidin-4-yl)ethoxy]quinoline-3-carbonitrile; or 4-[(2,4-Dichloro-5-methoxyphenyl)amino]-6-methoxy-7-[3-(4-propyl-1-pipera-zinyl)propoxy]-3-quinolinecarbonitrile; and pharmaceutically acceptable salts thereof.

According to a particular embodiment, the agent which possesses inhibitory activity against the Src family kinase is a small molecule agent.

According to a particular embodiment, the agent which possesses inhibitory activity against the Src family kinase is a chemical agent.

Suitable compounds possessing inhibitory activity against the Src family of non-receptor tyrosine kinases include the quinazoline derivatives disclosed in International Patent Applications WO 01/94341, WO 02/16352, WO 02/30924, WO 02/30926, WO 02/34744, WO 02/085895, WO 02/092577 (arising from PCT/GB 02/02117), WO 02/092578 (arising from PCT/GB 02/02124) and WO 02/092579 (arising from PCT/GB 02/02128), the quinoline derivatives described in WO 03/008409 (arising from PCT/GB 02/03177), WO 03/047584 and WO 03/048159 and the quinazoline derivatives described in European Patent Applications 02292736.2 (filed 4 Nov. 2002) and 03290900.4 (filed 10 Apr. 2003).

It is disclosed in Journal Medicinal Chemistry, 2001, 44, 822-833 and 3965-3977 that certain 4-anilino-3-cyanoquinoline derivatives are useful for the inhibition of Src-dependent cell proliferation. The 4-anilino-3-cyanoquinoline Src inhibitor known as SKI 606 is described in Cancer Research, 2003, 63, 375.

Other compounds which possess Src kinase inhibitory properties are described in, for example, International Patent Applications WO 96/10028, WO 97/07131, WO 97/08193, WO 97/16452, WO 97/28161, WO 97/32879 and WO 97/49706.

Other compounds which possess Src kinase inhibitory properties are described in, for example, J Bone Mineral Research, 1999, 14 (Suppl. 1), S487, Molecular Cell, 1999, 3, 639-647, Journal Medicinal Chemistry, 1997, 40, 2296-2303, Journal Medicinal Chemistry, 1998, 41, 3276-3292 and Bioorganic & Medicinal Chemistry Letters, 2002, 12, 1361 and 3153.

Particular Src kinase inhibitors include the following:

(i)  4-amino-5-(3-methoxyphenyl)-7-{(4-[2-(2-methoxy-ethylamino)  ethox-yl]phenyl)-}-pyrrolo[2,3-d]pyrimi-dine and 4-amino-5-(3-methoxyphenyl)-7-(4-{(2-[di-(2-methoxyethyl)amino]ethoxy}phe-nyl) pyrrolo[2,3-d]pyrimidine  which  are  obtainable  by  methods described in International Patent Application WO 96/10028:

(ii)  4-amino-7-tert-butyl-5-(4-tolyl)  pyrazolo[3,4-d]py-rimidine which is also known as PP1 and is described in Molecular Cell, 1999, 3, 639-648;

(iii)  2-(2,6-dichloroanilino)-6,7-dimethyl-1,8-dihydro-imidazo[4,5-h]isoquinolin-9-one and 2-(2,6-dichloroa-nilino)-7-[(E)-3-diethylaminoprop-1-enyl]-6-met-hyl-1,8-dihydroimidazo[4,5-h]isoquinolin-9-one which are obtainable by methods described in Journal Medicinal Chemistry, 2002, 45, 3394;

(iv)  1-[6-(2,6-dichlorophenyl)-2-(4-diethylaminobutyl) pyrido[2,3-d]pyrimidin-7-yl]-3-ethylurea  which  is obtainable by methods described in Journal Medicinal Chemistry, 1997, 40, 2296-2303 and Journal Medicinal Chemistry, 2001, 44, 1915;

(v)  6-(2,6-dichlorophenyl)-2-[4-(2-diethylaminoethoxy) anilino]-8-me-thyl-8H-pyrido[2,3-d]pyrimidin-7-one which is also known as PD166285 and is described in J. Pharmacol. Exp. Ther., 1997, 283, 1433-1444;

(vi)  the compound known as PD 162531 which is described in Mol. Biol. Cell, 2000, 11, 51-64;

(vii)  the compound known as PD166326 which is described in Biochem Pharmacol., 2000, 60, 885-898; and (viii)  the compound known as PD173955 which is described in Cancer Research, 1999, 59, 6145-6152.

Other compounds which may possess Src kinase inhibi-tory properties are described in, for example, International Patent Applications WO 02/079192, WO 03/000188, WO 03/000266,  WO  03/000705,  WO  02/083668,  WO 02/092573, WO 03/004492, WO 00/49018, WO 03/013541, WO 01/00207, WO 01/00213 and WO 01/00214.

Particular Src inhibitors include those provided in Inter-national Patent Application WO 01/94341.

Further particular Src inhibitors include the following compounds from International Patent Application WO 02/16352, WO 02/30924, WO 02/30926 and WO 02/34744. Exemplary agents include, without limitation, dasatinib, and AZD0530.

Other exemplary agents include CGP77675 (AXON MEDCHEM 2097), SU 6656, AZD0530, Dasatinib, Bosu-tinib and WH-4-023.

According to some embodiments of the invention, the Src family kinase inhibitor (e.g. CGP77675) is provided at a concentration range of between about 0.1-100 μM, e.g., 0.1-70 μM, e.g., from about 0.2 μM to about 70 μM, e.g., between about 0.2-60 μM, e.g., between about 0.2-55 μM, e.g., between about 0.2-50 μM, e.g., between about 0.2-45 μM, e.g., between about 0.2-40 μM, e.g., between about 0.2-35 μM, e.g., between about 0.2-30 μM, e.g., between about 0.2-25 μM, e.g., between about 0.2-20 μM, e.g., between about 0.2-15 μM, e.g., between about 0.2-10 μM, e.g., between about 0.3-10 μM, e.g., between about 0.4-10 μM, e.g., between about 0.5-10 μM, e.g., between about 0.6-10 μM, e.g., between about 0.7-10 μM, e.g., between 0.8-10 μM, e.g., between 0.9-10 μM, e.g., between 0.9-9 μM, e.g., between 1-8 μM, e.g., between 1-7 μM, e.g., between 1-6 μM, e.g., between 1-5 μM, e.g., about 1-3 μM, e.g., about 1.5 μM.

Ascorbic acid (also known as vitamin C) is a sugar acid (C6H806; molecular weight 176.12 grams/mole) with anti-oxidant properties. The ascorbic acid used by the culture medium of some embodiments of the invention can be a natural ascorbic acid, a synthetic ascorbic acid, an ascorbic acid salt (e.g., sodium ascorbate, calcium ascorbate, potas-sium ascorbate), an ester form of ascorbic acid (e.g., ascorbyl palmitate, ascorbyl stearate), a functional deriva-tive thereof (a molecule derived from ascorbic acid which exhibits the same activity/function when used in the culture medium of the invention), or an analogue thereof (e.g., a functional equivalent of ascorbic acid which exhibits an activity analogous to that observed for ascorbic acid when used in the culture medium of the invention). Non-limiting examples of ascorbic acid formulations which can be used in the culture medium of some embodiments of the invention include L-ascorbic acid and ascorbic acid 3-phosphate.

Ascorbic acid can be obtained from various manufactur-ers such as Sigma, St Louis, MO, USA (e.g., Catalogue numbers: A2218, A5960, A7506, A0278, A4403, A4544, A2174, A2343, 95209, 33034, 05878, 95210, 95212, 47863, 01-6730, 01-6739, 255564, A92902, W210901).

The concentration of ascorbic acid comprised in the culture medium of some embodiments of the invention is between about 1 μg/ml up to 200 μg/ml, e.g., between 10-150 μg/ml, e.g., between 10-100 μg/ml, e.g., between 10-60 μg/ml, e.g., 20-60 μg/ml, e.g., 30-60 μg/ml, e.g., 50 μg/ml.

As used herein the term "PKA" refers to Protein Kinase A (PKA), which is also known as cAMP-dependent protein kinase, e.g., as set forth by GenBank Accession Nos. NP_001229786.1 (SEQ ID NO:137), NP_001229787.1 (SEQ ID NO:138), NP_001229788.1 (SEQ ID NO:139), NP_001229789.1 (SEQ ID NO:140), NP_001229790.1 (SEQ ID NO:141), NP_001229791.1 (SEQ ID NO:142), NP_002722.1 (SEQ ID NO:143), NP_891993.1 (SEQ ID NO:144), NP_997461.1 (SEQ ID NO:145), NP_002721.1 (SEQ ID NO:146) and NP_997401.1 (SEQ ID NO:147).

The phrase "PKA agonist" as used herein refers to any molecule (e.g., a small molecule, a peptide, an RNA, a cDNA) which increases the level and/or activity of PKA. For example, an RNA or cDNA encoding the PKA protein (or at least the catalytic domain thereof) can be used to increase the level and/or activity of PKA. Additionally or alternatively, an agonist of PKA can be also cyclic AMP (CAMP), which binds to PKA and activates it. Additionally or alternatively, an agonist of PKA can be any activator of the enzyme Adenylate Cyclase which catalyzes the conver-sion of adenosine triphosphate (ATP) to 3',5'-cyclic AMP (CAMP) and pyrophosphate, and accordingly, increases the level of cAMP. Non-limiting examples of PKA agonists which can be used in the culture medium of some embodi-ments of the invention include Forskolin and AICAR.

According to some embodiments of the invention, the concentration of Forskolin comprised in the culture medium of some embodiments of the invention is between about 0.1 μM to 20 μM, e.g., about 0.5 μM to about 15 μM, e.g., about 1 μM to about 10 μM, e.g., about, 2-8 UM, e.g., about 4-6 μM.

As used herein the term "YAP" or "YAP1", which are interchangeably used herein, refers to the "Yes-associated protein 1". As used herein the term "TAZ" refers to Tafazzin.

As used herein the term "YAP/TAZ inhibitor" refers to any molecule capable of inhibiting the function of "YAP" and/or "TAZ". Examples include, but are not limited to, Verteporfin (VP), which can be included at a concentration of about 0.1 μM to about 10 μM; and 9E1, which can be included at a concentration of about 0.1 μM to about 5 μM.

Further information regarding the Verteporfin can be obtained from Johnson R. and Halder G. 2014 ("The two faces of Hippo: targeting the Hippo pathway for regenerative medicine and cancer treatment". Nat. Rev. Drug Discov. 13 (1): 63-79. doi: 10.1038/nrd4161. Epub 2013 Dec. 13. Review; which is fully incorporated herein by reference in its entirety). Members of the Notch family of Type 1 transmembrane proteins share structural characteristics including an extracellular domain consisting of multiple epidermal growth factor-like (EGF) repeats, and an intracellular domain consisting of multiple, different domain types. Notch family members play a role in a variety of developmental processes by controlling cell fate decisions. The Notch signaling network is an evolutionarily conserved intercellular signaling pathway which regulates interactions between physically adjacent cells. In humans, the Notch family includes notch 1 [GenBank Accession No. XP_011517019.1 (SEQ ID NO:184)], which is cleaved in the trans-Golgi network, and presented on the cell surface as a heterodimer; notch 2 [GenBank Accession Nos. NP_077719.2 isoform 1 (SEQ ID NO:185) and NP_001186930.1 isoform 2 (SEQ ID NO:186)], which is cleaved in the trans-Golgi network, and presented on the cell surface as a heterodimer; notch 3 [GenBank Accession No. NP_000426.2 (SEQ ID NO:187)]; and notch 4 [GenBank Accession No. NP_004548.3 (SEQ ID NO:188)], which is cleaved in the trans-Golgi network, and presented on the cell surface as a heterodimer.

NOTCH signaling inhibitors include, but are not limited to the following gamma secretase inhibitors: DAPT (Axon Medchem 1484-0.05-50 microM final concentration), LY2886721 hydrochloride (Axon Medchem 1964-0.05-50 microM final concentration)], DBZ (Axon Medchem-Axon 1488-0.05-50 microM final concentration).

Sonic Hedgehog pathway (SHH) protein [GenBank Accession NO. NP_000184.1, SEQ ID NO: 189] is instrumental in patterning the early embryo. It has been implicated as the key inductive signal in patterning of the ventral neural tube, the anterior-posterior limb axis, and the ventral somites. The protein is made as a precursor that is autocatalytically cleaved; the N-terminal portion is soluble and contains the signalling activity while the C-terminal portion is involved in precursor processing. More importantly, the C-terminal product covalently attaches a cholesterol moiety to the N-terminal product, restricting the N-terminal product to the cell surface and preventing it from freely diffusing throughout the developing embryo.

Sonic Hedgehog pathway (SHH) inhibitors include, but are not limited to the following: GANT61 (SigmaAldrich-0.05-50 microM final concentration), RU-SKI 43 (Axon Medchem-Axon 2035-0.05-50 microM final concentration)].

As used herein the term "transforming growth factor receptor (TGFR)" (also known as "TGFβR") refers to TGF-ß type I receptor ALK5, type I activin/nodal receptor ALK4 and type I nodal receptor ALK7.

As used herein the term "TGFR inhibitor (or TGFRi)" refers to a molecule capable of inhibiting TGFR expression and/or activity level as determined by phosphorylated ALK4, 5 and 7.

Non-limiting examples of TGFR inhibitors include SB431542 and A 83-01 small molecule compound.

According to some embodiments of the invention, the TGFR inhibitor is provided at a concentration range of about 0.1-30 μM, e.g., about 1-30 μM, e.g., 5-25 μM, e.g., 5-10 μM, e.g., 0.1-5 μM, e.g., 0.2-4 μM, e.g., 0.5-3 μM.

BMP (bone morphogenic protein) signaling inhibitors include, but are not limited to: LDN193189 (AXON 1509-0.01-20 microM final concentration, e.g. 0.2 microM), K02288 (Axon 2189; 0.1-20 microM final concentration), Dorsomorphin hydrochloride (AXON 2150 0.1-20 microM final concentration).

As used herein the term "fibroblast growth factor receptor (FGFR)" refers to FGFR1, FGFR2 and FGFR3.

As used herein the term "FGFR inhibitor (or FGFRi)" refers to a molecule capable of inhibiting FGFR expression and/or activity level as determined by levels of phosphorylated FGFR1, 2, and 3.

Non-limiting examples of FGFR inhibitors include PD173074 and SU5401.

According to some embodiments of the invention, the FGFR inhibitor (FGFRi) is PD173074 and is provided in a concentration range between about 0.01-40 μM, e.g., between about 0.02-40 μM, e.g., between about 0.05-40 μM, e.g., between, about 0.1-40 μM, about 0.5-40 μM, about 1-40 μM, e.g., about 2-40 μM, about 5-40 μM, about 10-40 μM, e.g., between about 0.05-5 μM, e.g., about 0.1-5 μM.

According to some embodiments of the invention, the FGFR inhibitor (FGFRi) is SU5401 and is provided at a concentration range of about 0.1-40 μM, e.g., about 0.5-40 μM, about 1-40 μM, e.g., about 2-40 μM, about 5-40 μM, about 10-40 μM.

As described above, the culture medium includes an ERK1/2 inhibitor (ERK1/2i). It should be noted that ERK1/2 inhibitors belong to a family of MAPK inhibitor(s), which also includes JNK inhibitor(s) (JNKi), ERK5 inhibitor(s) (ERK5i; e.g., BIX02189), BRAF inhibitor(s) (BRAFi; e.g., SB590885), ARAF inhibitor(s) (ARAFi), CRAF inhibitor(s) (CRAFi), and p38 inhibitor(s) (p38i; e.g., BIRB796, AXONMEDCHEM-Axon 1358).

According to some embodiments of the invention, the medium of some embodiments of the invention further comprises an inhibitor selected from the group consisting of a JNK inhibitor, an ERK5 inhibitor (e.g., BIX02189), a BRAF inhibitor (e.g., SB590885), ARAFi, CRAFi, and a p38 inhibitor (e.g., BIRB796, AXONMEDCHEM-Axon 1358).

As used herein the term "JNK" refers to the mitogen-activated protein kinase 8 (MAPK8) protein set forth by GenBank Accession Nos. NP_620637.1 (isoform alpha2) (SEQ ID NO:46), NP_620635.1 (isoform beta2) (SEQ ID NO:47), NP_620634.1 (isoform beta1) (SEQ ID NO:48), NP_002741.1 (isoform alpha1) (SEQ ID NO:49) which are involved in a wide variety of cellular processes such as proliferation, differentiation, transcription regulation and development.

As used herein the term "JNK inhibitor" refers to any molecule capable of inhibiting the activity of JNK as determined by phosphorylation of JNK family member protein by western blot analysis. Examples include, but are not limited to SP600125 (TOCRIS-Cat no. 1496), and AEG3482 (AXONMEDCHEM-AXON 1291, e.g., at a concentration of 0.1 μM-10 μM).

According to some embodiments of the invention, SP600125 is provided at a concentration range of between about 0.5-100 μM, e.g., from about 1 μM to about 100 μM, e.g., between about 1-90 μM, e.g., between about 1-80 μM, e.g., between about 1-70 μM, e.g., between about 1-60 μM, e.g., between about 1-55 μM, e.g., between about 1-50 μM, e.g., between about 1-45 μM, e.g., between about 1-40 μM, e.g., between about 1-35 μM, e.g., between about 1-30 μM, e.g., between about 1-25 µM, e.g., between about 1-20 µM, e.g., between about 1-15 µM, e.g., between about 1-10 µM, e.g., between about 2-10 µM, e.g., between about 3-10 µM, e.g., between about 4-10 µM, e.g., between about 4-6 µM, e.g., about 5 µM.

According to some embodiments of the invention, the ERK5 inhibitor, e.g., BIX02189, is provided at a concentration range of between about 0.5-100 µM, e.g., from about 1 µM to about 100 µM, e.g., between about 1-90 µM, e.g., between about 1-80 µM, e.g., between about 1-70 µM, e.g., between about 1-60 µM, e.g., between about 1-55 µM, e.g., between about 1-50 µM, e.g., between about 1-45 µM, e.g., between about 1-40 µM, e.g., between about 1-35 µM, e.g., between about 1-30 µM, e.g., between about 1-25 µM, e.g., between about 1-20 µM, e.g., between about 1-15 µM, e.g., between about 1-10 µM, e.g., between about 2-10 µM, e.g., between about 3-10 µM, e.g., between about 4-10 µM, e.g., between about 4-6 µM, e.g., about 5 µM.

As described, the culture medium of some embodiments of the invention may also comprise a RAF kinase inhibitor.

RAF kinase is a serine/threonine kinase that functions in the MAP kinase signaling pathway. The RAF kinase proteins which are inhibited by the RAF inhibitor used in the medium of some embodiments of the invention include ARAF [A-Raf proto-oncogene, serine/threonine kinase; isoform 1 (GenBank Accession No. NP_001645.1, SEQ ID NO: 190); isoform 2 (GenBank Accession No. NP_001243125.1, SEQ ID NO:191); and isoform 3 (GenBank Accession No. NP_001243126.1, SEQ ID NO:192)], BRAF [B-Raf proto-oncogene serine/threonine kinase, GenBank Accession No. NP_004324.2 (SEQ ID NO: 193)] and RAFI [also known as CRAF, or c-Raf; Raf-1 proto-oncogene serine/threonine kinase, GenBank Accession No. NP_002871.1 (SEQ ID NO:194)].

RAF inhibitors are, e.g., compounds which inhibit wild-type C-Raf at an IC50 of from 0.05 mmol/L to more than 4.0 mmol/L.

Exemplary RAF kinase inhibitors are disclosed in WO 00/09495 and WO 05/028444, the contents of which are incorporated herein by reference.

Examples of RAF kinase inhibitors include (4-tert-butyl-phenyl)-4-pyridin-4-ylmethyl-isoquinolin-1-yl)-amine; [4,7]biisoquinolinyl-1-yl-4-(tert-butyl-phenyl)-amine; (4-tert-butyl-phenyl)-(4-quinazolin-6-yl-isoquinolin-1-yl)-amine; [4,7]biisoquinolinyl-1-yl-(2-tert butyl-pyrimidin-5-yl)-amine.

A non-limiting example of a RAF inhibitor, which is more specific for C-Raf, but also has also an inhibitory activity against B-RAF is Sorafenib.

According to some embodiments of the invention, Sorafenib is provided at a concentration range from about 0.1 microM (µM) to about 70 µM, e.g., between about 0.1-60 µM, e.g., between about 0.1-50 µM, e.g., between about 0.5-50 µM, e.g., between about 0.5-45 µM, e.g., between about 0.5-40 µM, e.g., between about 0.1-35 µM, e.g., between about 0.5-30 µM, e.g., between about 0.5-25 µM, e.g., between about 0.5-20 µM, e.g., between about 0.5-15 µM, e.g., between about 0.5-10 µM, e.g., between 0.5-9 µM, e.g., between 0.5-8 µM, e.g., between 0.5-7 µM, e.g., between 0.9-6 µM, e.g., between 0.8-5 µM, e.g., about 5 µM, e.g., between 0.8-4 µM, e.g., between 0.8-3 µM, e.g., between 0.8-2 µM, e.g., between 0.8-1.5 µM, e.g., between 0.9-1.2 µM.

According to some embodiments of the invention, BRAFi (e.g., SB590885) is provided at a concentration range of between about 0.1-100 M, e.g., between about 0.1-90 µM, e.g., between about 0.1-80 µM, e.g., between about 0.1-70

µM, e.g., between about 0.1-60 µM, e.g., between about 0.1-50 M, e.g., between about 0.1-40 µM, e.g., between about 0.1-30 µM, e.g., between about 0.1-20 µM, e.g., between about 0.1-10 µM, e.g., between about 0.1-5 µM, e.g., between about 0.1-2 µM, e.g., between about 0.1-1 µM, e.g., about 0.5 µM.

As used herein the term "p38" refers to the "p38a (alpha)" mitogen-activated protein kinase 14 (MAPK14), which includes MAPK14 isoform 1 set forth by GenBank Accession No. NP_001306.1 (SEQ ID NO:39), MAPK14 isoform 2 set forth by GenBank Accession No. NP_620581.1 (SEQ ID NO:40), MAPK14 isoform 3 set forth by GenBank Accession No. NP_620582.1 (SEQ ID NO:41) and MAPK14 isoform 4 set forth by GenBank Accession No. NP_620583.1 (SEQ ID NO:42); "p38ß (beta)" (MAPK11), which is set forth by GenBank Accession No. NP_002742.3 (SEQ ID NO:43); "p38Y (gamma)" (MAPK12) which is set forth by GenBank Accession No. NP_002960.2 (SEQ ID NO: 44); and/or "p388 (delta)" (MAPK13) which is set forth in GenBank Accession No. NP_002745.1 (SEQ ID NO:45), all of them having kinase activity and involved in signal transduction.

As used herein the term "p38 inhibitor" refers to any molecule (e.g., small molecules or proteins) capable of inhibiting the activity of p38 family members as determined by Western blot quantification of phosphorylated p38 levels.

Non-limiting examples of p38 inhibitors include SB203580 (AXONMEDCHEM—Axon 1363), and SB 202190 (AXONMEDCHEM-Axon 1364), LY 2228820 (AXONMEDCHEM-Axon 1895), BIRB796 (Axon Medchem 1358) and PD169316 (AXONMEDCHEM-Axon 1365, e.g., at a concentration of about 0.1 µM to about 10 µM).

As BMP signaling is an activator for p38 signaling, examples of p38 inhibitors also include BMP inhibitors like Dorsomorphin (AXONMEDCHEM-Axon 2150) and LDN193189 (AXON MEDCHEM AXON 1509) or other inhibitors of the BMP pathway such as recombinant NOG-GIN protein [GenBank Accession No. NP_005441.1 (SEQ ID NO: 118)] can be used to replace small molecule inhibitors of BMP signaling.

According to some embodiments of the invention, SB203580 is provided at a concentration range of between about 0.5-70 µM, e.g., from about 1 µM to about 70 µM, e.g., between about 1-60 µM, e.g., between about 1-55 µM, e.g., between about 1-50 µM, e.g., between about 1-45 µM, e.g., between about 1-40 µM, e.g., between about 1-35 µM, e.g., between about 1-30 µM, e.g., between about 1-25 µM, e.g., between about 1-20 µM, e.g., between about 1-15 µM, e.g., between about 1-10 µM, e.g., between about 2-10 µM, e.g., between about 3-10 µM, e.g., between about 4-10 µM, e.g., between about 4-6 µM, e.g., about 5 µM, e.g., about 10 µM.

According to some embodiments of the invention, SB 202190 is provided at a concentration range of between about 0.1 µM to about 50 µM, e.g., from about 0.5 µM to about 50 µM, e.g., from about 1 µM to about 50 M, e.g., between about 1-45 µM, e.g., between about 1-40 µM, e.g., between about 1-35 µM, e.g., between about 1-30 µM, e.g., between about 1-25 µM, e.g., between about 1-20 µM, e.g., between about 1-15 µM, e.g., between about 1-10 µM, e.g., between about 1-9 µM, e.g., between about 1-8 µM, e.g., between about 1-7 µM, e.g., between about 2-7 µM, e.g., between about 3-7 µM, e.g., between about 4-7 µM, e.g., between about 4-6 µM, e.g., about 5 µM.

According to some embodiments of the invention, BIRB796 is provided at a concentration range of between about 0.05 to about 30 µM, e.g., from about 0.1 to about 30

μM, e.g., between about 0.2-30 M, e.g., between about 0.2-25 μM, e.g., between about 0.2-20 μM, e.g., between about 0.2-15 M, e.g., between about 0.2-10 μM, e.g., between about 0.2-8 μM, e.g., between about 0.2-6 μM, e.g., between about 0.5-6 μM, e.g., between about 0.5-5 μM, e.g., between about 0.5-4 μM, e.g., between about 0.5-3 μM, e.g., between about 0.5-2 μM, e.g., between about 1-3 μM, e.g., between about 1-2.5 μM, e.g., about 2 μM, e.g., about 0.1 μM, e.g., about 1 μM.

As used herein, the term "LSD1" refers to the lysine (K)-specific demethylase 1A (Gene ID KDM1A) nuclear protein that is a component of several histone deacetylase complexes. The protein contains a SWIRM domain, a FAD-binding motif, and an amine oxidase domain, and it silences genes by functioning as a histone demethylase.

Non-limiting examples of LSD1 inhibitors include, but are not limited to Tranylcypromine (TCP), at a concentration between about 0.1 μM to about 10 μM, e.g., at about 5 μM.

Examples of PI3K boosters include for example insulin-like growth factor 1 (IGF1; e.g., at a range 0.1-100 ng/ml final concentration), insulin-like growth factor II (IGFII; e.g., at a range 0.1-100 ng/ml final concentration), stem cell factor (SCF; e.g., at a range 0.1-100 ng/ml final concentration) and FGF2.

The term "insulin-like growth factor 1 (IGF1)" refers to any of the insulin-like growth factor isoforms 1-4 as set forth in GenBank Accession Nos. NP_001104753.1 (SEQ ID NO:162), NP_001104754.1 (SEQ ID NO:164), NP_001104755.1 (SEQ ID NO: 166) and NP_000609.1 (SEQ ID NO:160), which are encoded by GenBank Accession Nos. NM_001111283.1 (SEQ ID NO:163), NM_001111284.1 (SEQ ID NO:165), NM_001111285.1 (SEQ ID NO:167) and NM_000618.3 (SEQ ID NO:161), respectively.

The term "insulin-like growth factor 2 (IGF2)" refers to isoform 1 (encoded by variants 1, 2, 4 and 5) and isoform 2 (encoded by variant 3) of the insulin like growth factor II. Variant 1 represents the most predominant transcript [GenBank Accession Nos. NM_000612.5 (SEQ ID NO:169) and NP_000603.1 (SEQ ID NO:168)]. Variant 2 contains two alternate 5' non-coding exons, therefore, has a different 5' UTR compared to variant 1 [GenBank Accession Nos. NM_001007139.5 (SEQ ID NO:171) and NP_001007140.2 (SEQ ID NO:170)]. Variant 3 contains two alternate exons at the 5' end, one non-coding and another coding, compared to variant 1. This results in the use of an upstream AUG (not found in variants 1 and 2) and a longer isoform (2) with a distinct N-terminus compared to isoform 1 [GenBank Accession Nos. NM_001127598.2 (SEQ ID NO: 173) and NP_001121070.1 (SEQ ID NO:172)]. Variant (4) differs in the 5' UTR exon, compared to variant 1 [GenBank Accession Nos. NM_001291861.2 (SEQ ID NO: 175) and NP_001278790.1 (SEQ ID NO:174)]. This variant (5) differs in the 5' UTR exon, compared to variant 1 [GenBank Accession Nos. NM_001291862.2 (SEQ ID NO: 177) and NP_001278791.1 (SEQ ID NO:176)].

The term "stem cell factor" or "SCF", which is interchangeably used herein, refers to the ligand of the tyrosine-kinase receptor encoded by the KIT locus. (also known as "KIT ligand" or "KITLG"), e.g., the kit ligand isoform b precursor set forth in GenBank Accession No. NP_000890.1 (SEQ ID NO: 156) which is encoded by GenBank Accession No. NM_000899.4 (SEQ ID NO:157), and kit ligand isoform a precursor set forth in GenBank Accession No. NP_003985.2 (SEQ ID NO:158), which is encoded by GenBank Accession No. NM_003994.5 (SEQ ID NO:159).

According to a particular embodiment, the PI3K booster is FGF2.

The phrases "basic fibroblast growth factor (bFGF)" or "FGF2" which are interchangeably used herein refer to a polypeptide of the fibroblast growth factor (FGF) family, which bind heparin and possess broad mitogenic and angiogenic activities. The mRNA for the BFGF gene contains multiple polyadenylation sites, and is alternatively translated from non-AUG (CUG) and AUG initiation codons, resulting in five different isoforms with distinct properties. The CUG-initiated isoforms are localized in the nucleus and are responsible for the intracrine effect, whereas, the AUG-initiated form is mostly cytosolic and is responsible for the paracrine and autocrine effects of this FGF.

According to some embodiments of the invention, the bFGF used by the medium of some embodiments of the invention is provided in GenBank Accession No. NP_001997 (SEQ ID NO:29). BFGF can be obtained from various manufacturers such as Peprotech, RnD systems, Millipore. According to some embodiments of the invention, the bFGF used by the medium of some embodiments of the invention is provided from R&D Systems (Catalog Number: 233-FB).

According to some embodiments of the invention, bFGF is provided at a concentration range from about 0.5 nanogram per milliliter (ng/ml) to about 500 ng/ml, e.g., about 1-500 ng/ml, e.g., about 1-400 ng/ml, e.g., about 1-300 ng/ml, e.g., about 1-200 ng/ml, e.g., about 1-100 ng/ml, e.g., about 1-80 ng/ml, e.g., about 1-70 ng/ml, e.g., about 1-70 ng/ml, e.g., about 1-60 ng/ml, e.g., about 1-50 ng/ml, e.g., about 1-40 ng/ml, e.g., about 1-30 ng/ml, e.g., about 1-20 ng/ml, e.g., about 2-20 ng/ml, e.g., about 2-10 ng/ml, e.g., about 3-10 ng/ml, e.g., about 4-10 ng/ml, e.g., about 8 ng/ml.

As used herein the term "SMAD" refers to a family of proteins which are phosphorylated and activated by transmembrane serine-threonine receptor kinases in response to TGF-beta signaling. It should be noted that potential SMAD activators are the TGFβ cytokines.

According to some embodiments of the invention, the SMAD activator is selected from the group consisting of Activin A, TGFβ1, and bone morphogenetic protein 4 (BMP4).

Transforming growth factor (TGF) inducers include for example, TGFβ1, TGFβ2 and Activin.

According to a particular embodiment, the Transforming growth factor (TGF) inducer is TGFβ1.

As used herein the phrase "TGFβ1" refers to an isoform beta-1 (1) of the transforming growth factor beta (e.g., *Homo sapiens* TGFβ1, GenBank Accession No. NP_000651; SEQ ID NO:28, which is encoded by the sequence depicted in GenBank Accession No. NM_000660.5; SEQ ID NO:31). TGFβ acts in inducing transformation and also acts as a negative autocrine growth factor. TGFβ 1 isoform can be obtained from various commercial sources such as R&D Systems Minneapolis MN, USA.

According to some embodiments of the invention, TGFβ1 is provided at a concentration range from about 0.1 nanogram per milliliter (ng/ml) to about 500 ng/ml, e.g., about 0.1-400 ng/ml, e.g., about 0.1-300 ng/ml, e.g., about 0.1-200 ng/ml, e.g., about 0.1-100 ng/ml, e.g., about 0.1-50 ng/ml, e.g., about 0.1-30 ng/ml, e.g., about 0.1-20 ng/ml, e.g., about 0.1-10 ng/ml, e.g., about 1-10 ng/ml, e.g., about 0.1-8 ng/ml, e.g., about 0.1-7 ng/ml, e.g., about 0.1-6 ng/ml, e.g., about 0.1-5 ng/ml, e.g., about 0.1-4 ng/ml, e.g., about 0.1-3 ng/ml, e.g., about 0.1-2 ng/ml, e.g., about 0.5-2 ng/ml, e.g., about 0.5-1.5 ng/ml, e.g., about 1 ng/ml.

According to some embodiments of the invention, activators of TGF/ACTIVIN pathway including ACTIVIN A (also known as Inhibin beta A, INHBA, Gene ID: 3624; GenBank Accession No. NM_002192.2 (SEQ ID NO:123), which encodes GenBank Accession No. NP_002183.1; SEQ ID NO:117) can be used to replace TGFβ1.

According to some embodiments of the invention, the TGFβ1 cytokine can be replaced with recombinant Nodal and/or Activin, and/or transforming growth factor beta 2 (TGFβ2) and/or GDF3 and/or GDF-9.

According to some embodiments of the invention, the concentration of Activin A in the culture medium of some embodiments of the invention is about 1-40 ng/ml, e.g., about 20 ng/ml.

As used herein the term "BMP4" refers to a member of the bone morphogenetic protein family [GenBank Accession No. NP_001193.2 (SEQ ID NO:148)] which is part of the transforming growth factor-beta superfamily. The superfamily includes large families of growth and differentiation factors. BMP4 plays an important role in the onset of endochondral bone formation in humans, and a reduction in expression has been associated with a variety of bone diseases.

According to some embodiments of the invention, the concentration of the BMP4 protein in the culture medium is between about 0.1 ng/ml to about 20 ng/ml, e.g., between about 5-10 ng/ml.

As used herein the term "DOT1L" [DOT1-like histone H3K79 methyltransferase protein; GenBank Accession No. NP_115871.1 (SEQ ID NO:149)] refers to a histone methyltransferase that methylates lysine-79 of histone H3. DOT1L is inactive against free core histones, but shows significant histone methyltransferase activity against nucleosomes.

Non-limiting examples of DOT1L inhibitors include, but are not limited to SGC0946.

According to some embodiments of the invention, the concentration of SGC0946 in the culture medium is between about 0.05 μM to about 10 μM, e.g., at a concentration of about 0.1 to about 10 μM, e.g., about 1 μM, e.g., about 2 μM, e.g., about 5 μM.

According to some embodiments of the invention, the medium further comprises an inhibitor of G9a [also known as "EHMT2 euchromatic histone-lysine N-methyltransferase 2" GenBank Accession Nos. NP_001276342.1 (isoform a; SEQ ID NO: 197), NP_079532.5 (isoform b; SEQ ID NO: 198), NP_001276342.1 (isoform c; SEQ ID NO: 199)] and/or Glp (also known as "EHMT1 euchromatic histone-lysine N-methyltransferase 1" GenBank Accession Nos. NP_079033.4 (isoform 1; SEQ ID NO: 200) and NP_001138999.1 (isoform 2; SEQ ID NO:201)], which form part of the H3K9me2 [dimethylation (me2) of Lys (K) 9 on histone H3] (Kubicek S1, O'Sullivan R J, et al., Reversal of H3K9me2 by a small-molecule inhibitor for the G9a histone methyltransferase. Mol Cell. 2007, 25 (3): 473-81; and Vedadi M1, Barsyte-Lovejoy D, et al. A chemical probe selectively inhibits G9a and GLP methyltransferase activity in cells. Nat. Chem. Biol. 2011, 7 (8): 566-74; each of which is fully incorporated herein by reference in its entirety). Protein lysine methyltransferases G9a and GLP modulate the transcriptional repression of a variety of genes via dimethylation of Lys9 on histone H3 (H3K9me2) as well as dimethylation of non-histone targets.

According to some embodiments of the invention, the inhibitor can selectively impair the G9a histone lysine methyltransferase (HMTase) activity and/or the generation of H3K9me2 in vitro.

A non-limiting example of an inhibitor of G9a and/or Glp which can be used in the culture medium of some embodiments of the invention include for example an siRNA or antisense RNA which knockdowns the level of G9a and/or GLP RNA or protein product.

A non-limiting example of an inhibitor of G9a and/or Glp which can be used in the culture medium of some embodiments of the invention include for example a small molecule which specifically inhibits the activity of G9a and/or Glp, and/or prevents or impairs generation of the H3K9me2.

According to some embodiments of the invention the small molecule that inhibits G9a and/or Glp, and/or prevents or impairs generation of the H3K9me2 is BIX-01294 (diazepin-quinazolin-amine derivative) and/or UNC0638.

According to some embodiments of the invention the small molecule that inhibits G9a and/or Glp, and/or prevents or impairs generation of the H3K9me2 is BIX-01294 (also referred to hereinbelow as "BIX01294").

According to some embodiments of the invention the concentration of BIX01294 in the culture medium is between about 0.05 microM to about 5 microM, e.g., between 0.05 microM (μM) to about 4 μM, e.g., between about 0.08-3 μM, e.g., between about 0.1-3 μM, e.g., between about 0.1-2 μM, e.g., between about 0.1-1 μM, e.g., between about 0.2-1 μM, e.g., between about 0.3-1 μM, e.g., between about 0.4-1 μM, e.g., between about 0.4-0.8 μM, e.g., between about 0.4-0.6 μM, e.g., between about 0.5-0.6 μM, e.g., about 0.5 microM.

According to some embodiments of the invention, the concentration of BIX01294 in the culture medium is between about 0.05 UM to about 5 μM.

According to some embodiments of the invention the concentration of UNC0638 in the culture medium is between about 0.01 μM to about 5 μM, e.g., between 0.02-5 μM, e.g., between 0.04-5 M, e.g., between 0.06-5 μM, e.g., between 0.05 microM (μM) to about 4 μM, e.g., between about 0.08-3 μM, e.g., between about 0.08-2 μM, e.g., between about 0.08-1 μM, e.g., between about 0.08-0.5 μM, e.g., between about 0.1-1 μM, e.g., between about 0.1-0.8 μM, e.g., between about 0.1-0.6 μM, e.g., between about 0.1-0.4 μM, e.g., between about 0.1-0.3 μM, e.g., between about 0.1-0.2 μM, e.g., about 0.1 microM.

According to some embodiments of the invention, the medium further comprises an at least one agent selected from the group consisting of: basic fibroblast growth factor (bFGF), transforming growth factor beta 1 (TGFβ1), ACTIVIN A, a GSK3b inhibitor, a ROCK inhibitor, a P38 inhibitor, a JNK inhibitor, a NOTCH inhibitor, a SRC inhibitor, insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, G9a and/or Glp inhibitor (e.g., BIX01294 or UNC0638), stem cell factor (SCF), YAP/TAZ inhibitor, L-Ascorbic Acid, LSD1 inhibitor and DOT1L inhibitor.

According to some embodiments of the invention, the concentration of BayK8644 in the culture medium is between about 0.5 μM to about 10 μM.

According to some embodiments of the invention, the medium further comprises an at least one agent selected from the group consisting of: a transforming growth factor receptor (TGFR) inhibitor, a fibroblast growth factor receptor (FGFR) inhibitor, ACTIVIN A, a GSK3b inhibitor, a ROCK inhibitor, a P38 inhibitor, a JNK inhibitor and a NOTCH inhibitor, a SRC inhibitor, insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, G9a and/or Glp inhibitor (e.g., BIX01294 or UNC0638), stem cell factor (SCF), YAP/TAZ inhibitor, L-Ascorbic Acid, LSD1 inhibitor, and DOT1L inhibitor.

According to some embodiments of the invention, the medium further comprises an at least one agent selected from the group consisting of: Activin A, transforming growth factor beta 1 (TGFβ1), a fibroblast growth factor receptor (FGFR) inhibitor, a GSK3b inhibitor, a ROCK inhibitor, a P38 inhibitor, a JNK inhibitor and a NOTCH inhibitor, a SRC inhibitor, insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, G9a and/or Glp inhibitor (e.g., BIX01294 or UNC0638), stem cell factor (SCF), YAP/TAZ inhibitor, L-Ascorbic Acid, LSD1 inhibitor, and DOT1L inhibitor.

According to some embodiments of the invention, the medium further comprises an at least one agent selected from the group consisting of: basic fibroblast growth factor (bFGF), a transforming growth factor receptor (TGFR) inhibitor, a GSK3b inhibitor, a ROCK inhibitor, a P38 inhibitor, a JNK inhibitor, a NOTCH inhibitor, a SRC inhibitor, insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, G9a and/or Glp inhibitor (e.g., BIX01294 or UNC0638), stem cell factor (SCF), YAP/TAZ inhibitor, L-Ascorbic Acid, LSD1 inhibitor, and DOT1L inhibitor.

According to some embodiments of the invention, the culture medium of some embodiments of the invention is any of the culture media described in Example 5 of the Examples section which follows (e.g., culture media 41-131).

Additionally or alternatively, FIGS. 1-2 and Examples 1-4 of the Examples section which follows, demonstrate additional conditions which can be used to maintain naive PSCs in the "naive state", as is evidenced by the expression of OCT4-GFP+ (positive) cells.

According to an aspect of some embodiments of the present invention there is provided a culture medium comprising an ERK1/2 inhibitor, a STAT3 activator and a SRC inhibitor.

According to some embodiments of the invention, the culture medium of some embodiments of the invention further comprises an AXIN complex stabilizer (AXINs).

According to some embodiments of the invention, the culture medium of some embodiments of the invention further comprises a GSK3β inhibitor.

According to some embodiments of the invention, the culture medium of some embodiments of the invention further comprises a p38 inhibitor.

According to an aspect of some embodiments of the present invention there is provided a culture medium comprising an ERK1/2 inhibitor, a GSK3β inhibitor, a p38 inhibitor, a STAT3 activator and at least one agent selected from the group consisting of a SRC inhibitor and an AXIN complex stabilizer (AXINs).

The media of this aspect of the present invention may comprise an Src family kinase inhibitor and not an AXIN complex stabilizer. Alternatively, the media of this aspect of the present invention may comprise an AXIN complex stabilizer and not an Src family kinase inhibitor. Still alternatively, the media of this aspect of the present invention may comprise an Src family kinase inhibitor and an AXIN complex stabilizer.

According to some embodiments of the invention, the culture medium of some embodiments of the invention is chemically defined and xeno free (devoid of animal contaminant, or devoid of non-human contaminants).

It should be noted that supplementation of the culture medium with SRCi and/or AXINs small molecule compounds allows expansion of human naive pluripotent cells in media that does not include animal components (ALBU-MAX1, ALBUMAX2, Knockout-serum replacement-Invitrogen), and can rely only on the use of defined supplements like B27 (defined or Xenofree B27 supplement from INVITROGEN).

According to some embodiments of the invention, the culture medium further comprising a ROCK inhibitor.

According to some embodiments of the invention, the culture medium further comprising a JNK inhibitor.

According to some embodiments of the invention, the culture medium comprises KO-DMEM with $N_2$ supplement (e.g., about 5 ml N2 per 500 ml of culture medium) with about 5 ml defined lipid concentrate per 500 ml medium, LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 μM), and JNKi (SP600125, about 5-10 UM).

According to some embodiments of the invention, the culture medium comprises KO-DMEM with $N_2$ supplement (e.g., about 5 ml N2 per 500 ml of culture medium) with about 1-2% Albumax®II, LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 M), and JNKi (SP600125, 5-about 10 μM).

According to some embodiments of the invention, the culture medium comprises KO-DMEM with $N_2$ supplement (e.g., about 5 ml N2 per 500 ml of culture medium) with about 15% Knockout SR (Gibco), LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 μM), JNKi (SP600125, about 5-10 μM).

In one embodiment, the media which comprise an ERK1/2 inhibitor, a GSK3ß inhibitor, a p38 inhibitor, a STAT3 activator and at least one agent selected from the group consisting of a SRC inhibitor and an AXIN complex stabilizer (AXINs) also comprises a ROCK inhibitor.

In another embodiment, the media which comprise an ERK1/2 inhibitor, a GSK3β inhibitor, a p38 inhibitor, a STAT3 activator, at least one agent selected from the group consisting of a SRC inhibitor and an AXIN complex stabilizer (AXINs) also comprises a ROCK inhibitor and optionally a ROCK inhibitor also comprise a JNK inhibitor.

The culture media described herein may comprise additional signaling optimizing components. Such optimizing components may include PI3K boosters, TGF cytokines (or inducers), morphogene inhibitors and FGF receptor inhibitors.

Examples of morphogene inhibitors include NOTCH inhibitors, SHH inhibitors and TGFβ receptor inhibitors.

Particular combinations of optimizing agents considered by the present invention include at least one of the following agents: bFGF, TGFβ1, TGFR inhibitor and a FGF receptor inhibitor.

According to a particular embodiment, the morphogene inhibitor is a TGFβ receptor inhibitor.

Other combinations of optimizing agents considered by the present invention include at least two of the following agents: bFGF, TGFβ1, TGFR inhibitor and a FGF receptor inhibitor.

In certain embodiments the media of the present invention may include a protein kinase C inhibitor and/or a BMP inhibitor.

In other embodiments the media of the present invention are devoid of a protein kinase C inhibitor and/or a BMP inhibitor.

According to some embodiments of the invention, the culture medium further comprising at least one additional agent selected from the group consisting of: insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, G9a and/or Glp inhibitor (e.g., BIX01294 or UNC0638), and stem cell factor (SCF).

According to some embodiments of the invention, the culture medium further comprising at least one additional agent selected from the group consisting of: insulin-like growth factor 1 (IGF1), insulin-like growth factor II (IGFII), bone morphogenetic protein 4 (BMP4), a Sonic Hedgehog pathway (SHH) inhibitor, an ERK5 inhibitor, Forskolin, Kenpaullone, BayK8644, G9a and/or Glp inhibitor (e.g., BIX01294 or UNC0638), and stem cell factor (SCF).

Exemplary media contemplated by the present invention include:

A medium comprising a STAT3 activator, an ERK1/2 inhibitor, a GSK3β inhibitor, a P38 inhibitor, a JNK inhibitor, bFGF, TGFβ1, a ROCK inhibitor, AXIN stabilizer and SRC family kinase inhibitor.

A medium comprising a STAT3 activator, an ERK1/2 inhibitor, a GSK3β inhibitor, a P38 inhibitor, a JNK inhibitor, bFGF, TGFβ1, a ROCK inhibitor, AXIN stabilizer and SRC family kinase inhibitor and a BMP inhibitor.

A medium comprising a STAT3 activator, an ERK1/2 inhibitor, a GSK3β inhibitor, a P38 inhibitor, a JNK inhibitor, bFGF, TGFβ1, a ROCK inhibitor, AXIN stabilizer and SRC family kinase inhibitor and a PKC inhibitor.

A medium comprising a STAT3 activator, an ERK1/2 inhibitor, a GSK3β inhibitor, a P38 inhibitor, a JNK inhibitor, bFGF, TGFβ1, a ROCK inhibitor, AXIN stabilizer and SRC family kinase inhibitor, a BMP inhibitor and a PKC inhibitor.

A medium comprising a STAT3 activator, an ERK1/2 inhibitor, a GSK3β inhibitor, a P38 inhibitor, a bFGF, TGFβ1, a ROCK inhibitor, AXIN stabilizer and SRC family kinase inhibitor.

A medium comprising a STAT3 activator, an ERK1/2 inhibitor, a GSK3β inhibitor, a P38 inhibitor, a bFGF, TGFβ1, a ROCK inhibitor, AXIN stabilizer, SRC family kinase inhibitor and a BMP inhibitor.

A medium comprising a STAT3 activator, an ERK1/2 inhibitor, a GSK3β inhibitor, a P38 inhibitor, a bFGF, TGFβ1, a ROCK inhibitor, AXIN stabilizer, SRC family kinase inhibitor and a PKC inhibitor.

A medium comprising a STAT3 activator, an ERK1/2 inhibitor, a GSK3β inhibitor, a P38 inhibitor, a bFGF, TGFβ1, a ROCK inhibitor, AXIN stabilizer, SRC family kinase inhibitor, a BMP inhibitor and a PKC inhibitor.

A medium comprising a STAT3 activator, an ERK1/2 inhibitor, a GSK3β inhibitor, a P38 inhibitor, a JNK inhibitor, TGFβ1, a ROCK inhibitor, AXIN stabilizer and SRC family kinase inhibitor.

A medium comprising a STAT3 activator, an ERK1/2 inhibitor, a GSK3β inhibitor, a P38 inhibitor, a JNK inhibitor, TGFβ1, a ROCK inhibitor, AXIN stabilizer, a SRC family kinase inhibitor and a BMP inhibitor.

A medium comprising a STAT3 activator, an ERK1/2 inhibitor, a GSK3β inhibitor, a P38 inhibitor, a JNK inhibitor, TGFβ1, a ROCK inhibitor, AXIN stabilizer, a SRC family kinase inhibitor and a PKC inhibitor.

A medium comprising a STAT3 activator, an ERK1/2 inhibitor, a RAF inhibitor, a GSK3β inhibitor, a P38 inhibitor, a JNK inhibitor, TGFβ1, a ROCK inhibitor, AXIN stabilizer, a SRC family kinase inhibitor and a PKC inhibitor.

A medium comprising a STAT3 activator, an ERK1/2 inhibitor, a RAF inhibitor, a GSK3β inhibitor, a P38 inhibitor, a JNK inhibitor, TGFβ1, a ROCK inhibitor, AXIN stabilizer, and a SRC family kinase inhibitor.

A medium comprising a STAT3 activator, an ERK1/2 inhibitor, a RAF inhibitor, a GSK3 inhibitor, a P38 inhibitor, a JNK inhibitor, TGFβ1, a ROCK inhibitor, AXIN stabilizer, a SRC family kinase inhibitor and a PKC inhibitor.

A medium comprising a STAT3 activator, an ERK1/2 inhibitor, a RAF inhibitor, a bFGF, a GSK3β inhibitor, a P38 inhibitor, a JNK inhibitor, TGFβ1, a ROCK inhibitor, AXIN stabilizer, and a SRC family kinase inhibitor.

A medium comprising a STAT3 activator, an ERK1/2 inhibitor, a GSK3β inhibitor, a P38 inhibitor, a JNK inhibitor, TGFβ1, a ROCK inhibitor, AXIN stabilizer, a SRC family kinase inhibitor, a PKC inhibitor and a BMP inhibitor.

A medium comprising a STAT3 activator, an ERK1/2 inhibitor, a GSK3β inhibitor, a P38 inhibitor, a JNK inhibitor, FGF2, TGFβ1, a ROCK inhibitor and a SRC family kinase inhibitor.

A medium comprising a STAT3 activator, an ERK1/2 inhibitor, a GSK3β inhibitor, a P38 inhibitor, a JNK inhibitor, FGF2, TGFβ1, a ROCK inhibitor, a SRC family kinase inhibitor and a BMP inhibitor.

A medium comprising a STAT3 activator, an ERK1/2 inhibitor, a GSK3β inhibitor, a P38 inhibitor, a JNK inhibitor, FGF2, TGFβ1, a ROCK inhibitor, a SRC family kinase inhibitor and a PKC inhibitor.

A medium comprising a STAT3 activator, an ERK1/2 inhibitor, a GSK3β inhibitor, a P38 inhibitor, a JNK inhibitor, FGF2, TGFβ1, a ROCK inhibitor, a SRC family kinase inhibitor, a PKC inhibitor and a BMP inhibitor.

A medium comprising a STAT3 activator, an ERK1/2 inhibitor, a GSK3β inhibitor, a P38 inhibitor, a JNK inhibitor, TGFβ1, a ROCK inhibitor and a SRC family kinase inhibitor.

A medium comprising a STAT3 activator, an ERK1/2 inhibitor, a GSK3β inhibitor, a P38 inhibitor, a JNK inhibitor, TGFβ1, a ROCK inhibitor, a SRC family kinase inhibitor and a BMP inhibitor.

A medium comprising a STAT3 activator, an ERK1/2 inhibitor, a GSK3β inhibitor, a P38 inhibitor, a JNK inhibitor, TGFβ1, a ROCK inhibitor, a SRC family kinase inhibitor and a PKC inhibitor.

A medium comprising a STAT3 activator, an ERK1/2 inhibitor, a GSK3β inhibitor, a P38 inhibitor, a JNK inhibitor, TGFβ1, a ROCK inhibitor, a SRC family kinase inhibitor, a PKC inhibitor and a BMP inhibitor.

A medium comprising a STAT3 activator, an ERK1/2 inhibitor, a GSK3β inhibitor, a P38 inhibitor, a JNK inhibitor, a ROCK inhibitor, an AXIN stabilizer and a SRC family kinase inhibitor.

A medium comprising a STAT3 activator, an ERK1/2 inhibitor, a GSK3β inhibitor, a P38 inhibitor, a JNK inhibitor, a ROCK inhibitor, an AXIN stabilizer, a SRC family kinase inhibitor and a BMP inhibitor.

A medium comprising a STAT3 activator, an ERK1/2 inhibitor, a GSK3β inhibitor, a P38 inhibitor, a JNK inhibitor, a ROCK inhibitor, an AXIN stabilizer, a SRC family kinase inhibitor and a PKC inhibitor.

A medium comprising a STAT3 activator, an ERK1/2 inhibitor, a GSK3β inhibitor, a P38 inhibitor, a JNK inhibitor, a ROCK inhibitor, an AXIN stabilizer, a SRC family kinase inhibitor, a PKC inhibitor and a BMP inhibitor.

A medium comprising a STAT3 activator, an ERK1/2 inhibitor, a GSK3β inhibitor, a P38 inhibitor, a JNK inhibitor, TGFβ1, a ROCK inhibitor and an AXIN stabilizer.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer and a BMP inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer and a PKC inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer, a PKC inhibitor and a BMP inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer, an SRC family kinase inhibitor and a FGF receptor inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer, an SRC family kinase inhibitor, a FGF receptor inhibitor and a BMP inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer, an SRC family kinase inhibitor, a FGF receptor inhibitor and a PKC inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer, an SRC family kinase inhibitor, a FGF receptor inhibitor, a PKC inhibitor and a BMP inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer and a FGF receptor inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer, a FGF receptor inhibitor and a BMP inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer, a FGF receptor inhibitor and a PKC inhibitor.

A medium comprising a STAT3 activator, an ERK1/2 inhibitor, a GSK3ß inhibitor, a P38 inhibitor, a JNK inhibitor, TGFβ1, a ROCK inhibitor, an AXIN stabilizer, a FGF receptor inhibitor, a PKC inhibitor and a BMP inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer, Src family kinase inhibitor and a TGF receptor inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer, Src family kinase inhibitor, a TGF receptor inhibitor and a BMP inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer, Src family kinase inhibitor, a TGF receptor inhibitor and a PKC inhibitor.

A medium comprising a STAT3 activator, an ERK1/2 inhibitor, a GSK3β inhibitor, a P38 inhibitor, a JNK inhibitor, TGFβ1, a ROCK inhibitor, an AXIN stabilizer, Src family kinase inhibitor, a TGF receptor inhibitor, a PKC inhibitor and a BMP inhibitor.

Another contemplated culture medium is one which comprises an ERK1/2 inhibitor, a GSK3β inhibitor, a p38 inhibitor, a JNK inhibitor, a STAT3 activator, a transforming growth factor beta receptor (TGFβR) inhibitor, a PKC inhibitor, a p38 inhibitor and basic fibroblast growth factor (bFGF).

This medium may also comprise at least one, at least two, at least three or four of the agents selected from the group consisting of a BMP inhibitor, a ROCK inhibitor, a SRC inhibitor and an AXIN complex stabilizer (AXINs).

Non-limiting examples of culture medium which can be used according to some embodiments of the invention are described in Example 1 of the Examples section which follows (e.g., culture media 1-40).

It will be appreciated that any of the proteinaceous factors used in the culture medium of some embodiments of the invention (e.g., the LIF, IL6, TGFβ1, or bFGF) can be recombinantly expressed or biochemically synthesized. In addition, naturally occurring proteinaceous factors such as bFGF and TGFβ can be purified from biological samples (e.g., from human serum, cell cultures) using methods well known in the art.

Biochemical synthesis of the proteinaceous factors of the present invention (e.g., the LIF, IL6, TGFβ1, or bFGF) can be performed using standard solid phase techniques. These methods include exclusive solid phase synthesis, partial solid phase synthesis methods, fragment condensation and classical solution synthesis.

Recombinant expression of the proteinaceous factors of the present invention (e.g., the LIF, IL6, TGFβ1, or bFGF) can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

For example, to generate the LIF, IL6, TGFβ1, or bFGF, a polynucleotide sequence encoding the LIF, IL6, TGFβ1, or bFGF [e.g., the polynucleotide set forth by SEQ ID NO: 30 (LIF, GenBank Accession No. NM_001257135), SEQ ID NO: 31 (TGFβ1, GenBank Accession NO. NM_000660), SEQ ID NO: 32 (BFGF, GenBank Accession NO. NM_002006), SEQ ID NO:111 (IL6, GenBank Accession No. NM_000600.3)] is preferably ligated into a nucleic acid construct suitable for expression in a host cell [i.e., a cell in which the polynucleotide encoding the polypeptide-of-choice (e.g., the LIF, IL6, TGFβ1, or bFGF) is expressed]. Preferably, to generate an LIF, IL6, TGFβ1, or bFGF with the amount and pattern of glycosylation as of the naturally occurring LIF, IL6, TGFβ1, or bFGF, the host cell employed is a eukaryotic host cell, more preferably a mammalian host cell such as human cell or CHO cell). Additional description of nucleic acid constructs (or expression vectors) which can be used to produce a polypeptide-of-interest (e.g., the proteinaceous factors described above) is provided herein under.

According to some embodiments of the invention, the culture medium further comprises an MBD3 inhibitor.

As used herein the term "MBD3" refers to the Methyl-CpG-binding domain 3 protein set forth by GenBank Accession No. NP_003917.1 (SEQ ID NO:7) having the co-repressor and chromatin remodeling functional activity.

As used herein the term "MBD3 inhibitor" refers to any agent (e.g., a molecule) capable of downregulating the expression level and/or activity of MBD3, and/or capable of interfering between the interaction of MBD3 with OCT4, and/or MBD3 with SOX2, and/or MBD3 and KLF4 and/or MBD3 and C-Myc, and/or inhibiting the binding of MBD3 to the nucleosome remodeling and deacetylase (NuRD). Downregulation of MBD3 can be effected on the genomic and/or the transcript level using a variety of molecules which interfere with transcription and/or translation [e.g., RNA silencing agents (e.g., antisense, siRNA, shRNA, micro-RNA), Ribozyme and DNAzyme], or on the protein level using e.g., an antibody (e.g., a neutralizing antibody), an antagonist, e.g., small molecules which inhibit MBD3 activity or ability to directly interact with any of the reprogramming factors (Oct4, Sox2, Klf4or c-Myc), enzymes that cleave the polypeptide and the like.

Non-limiting examples of MBD3 inhibitors include siRNA directed against MBD3 mRNA, such as those provided from Invitrogen, mBD3HSS147581 (3_RNAI) (Invitrogen): AGGUCAAGGGCAAGCCCGACCUGAA (SEQ ID NO:52); and MBD3HSS147581 (3_RNAI) (Invitrogen): UUCAGGUCGGGCUUGCCCUUGACCU (SEQ ID NO:53). Another suitable siRNA directed against MBD3 mRNA which can be used is the commercially available MBD3 Stealth siRNAs that include HSS147580 and HSS147581 components (Life Technologies™, catalogue number 1299001) that were found efficient for MBD3 knockdown in human cells.

According to some embodiments of the invention, inhibiting the binding of Mbd3 to the NuRD complex is performed using a chromodomain helicase DNA binding protein 4 (CHD4) inhibitor.

Non-limiting examples of CHD4 inhibitors include the human CHD4 siRNA, such as the CHD4 stealth siRNA HSS101850 available from Life Technologies™, which was found to efficiently knockdown CHD4 in human cells.

According to some embodiments of the invention, inhibiting the binding of Mbd3 to the NuRD complex is performed using a P66 alpha coiled-coil (P66α-CC) domain.

The peptide of the P66α-CC (SEQ ID NO: 114) can be added to the medium as is, or can be recombinantly expressed from a vector encoding the P66α-CC sequence (e.g., a vector which comprises the nucleotide sequence set forth in SEQ ID NO: 113).

According to some embodiments of the invention, inhibiting the binding of Mbd3 to the NuRD complex is performed using an inhibitor of the GATA zinc finger domain containing 2A (GATAD2A) protein [also known as "transcriptional repressor p66-alpha; e.g., isoform 1, GenBank Accession Nos. NP_001287875.1 (SEQ ID NO:150 for protein) and NM_001300946.1 (SEQ ID NO: 151 for polynucleotide), and isoform 2, GenBank Accession Nos.

NP_060130.3 (SEQ ID NO:152 for protein) and NM_017660.3 (SEQ ID NO: 153 for polynucleotide). Such inhibitor can be, for example, a small molecule, an siRNA directed against the polynucleotide encoding GATAD2A, or dominant negative peptide.

According to some embodiments of the invention, inhibiting Mbd3 expression is performed using a protein kinase C (PKC) inhibitor (e.g., using the agents and molecules as described above).

According to some embodiments of the invention, the medium further comprises an agent which increases expression of endogenous ERAS and/or a recombinant ERAS.

According to some embodiments of the invention, the MBD3 inhibitor is provided in an amount sufficient to downregulate the expression level of the MBD3 RNA and/or protein in the cell by at least about 30%, e.g., at least about 35%, e.g., at least about 40%, e.g., at least about 45%, e.g., at least about 50%, e.g., at least about 55%, e.g., at least about 60%, e.g., at least about 65%, e.g., at least about 70%, e.g., at least about 75%, e.g., at least about 80% as compared to the expression level of the MBD3 RNA and/or protein, respectively, in the same cell when incubated and/or cultured under the same (e.g., identical) conditions yet without the MBD3 inhibitor.

According to some embodiments of the invention, the MBD3 inhibitor is provided in an amount sufficient to downregulate the expression level of the MBD3 RNA and/or protein in the cell by about 30-90%, e.g., about 30-85%, e.g., about 40-85%, e.g., about 50-85%, e.g., about 60-85%, e.g., about 70-85%, e.g., about 80-85%, e.g., about 85% as compared to the expression level of the MBD3 RNA and/or protein, respectively, in the same cell when incubated and/or cultured under the same (e.g., identical) conditions yet without the MBD3 inhibitor.

The expression level of the MBD3 in the cell can be determined by various methods such as real time reverse transcription PCR, Western blot and the like. For example, when such an assay was employed, there was about 85% inhibition of MBD3 protein level in cells transformed with the MBD3$^{flox/-}$ construct (Data not shown).

Additional culture media contemplated by the present invention include those disclosed in PCT IB 2014/060954, the entire contents of which is incorporated herein by reference.

According to an aspect of some embodiments of the invention, there is provided a cell culture comprising cells and the culture medium of some embodiments of the invention.

The cells may be any cells, e.g., prokaryotic or eukaryotic cells, e.g., primate cells, e.g., mammalian cells, e.g., human cells.

According to some embodiments of the invention, the cells are somatic cells, stem cells, primed pluripotent stem cells, non-naïve pluripotent stem cell and/or naive pluripotent stem cells.

According to some embodiments of the invention, the culture medium is capable of maintaining naive pluripotent stem cell in an undifferentiated state for at least 2 passages, e.g., for at least 5, 10, 20, 30, 40, 50, 60, 70, 80, 90 or 100 passages.

According to some embodiments of the invention, the primate naive pluripotent stem cell is of *Homo sapiens* (human), monkey, chimpanzee, Gorillas, Rhesus and/or Baboon.

The phrase "naive pluripotent stem cell (PSC)" refers to a cell capable of forming a PSC, and that exhibits a pre-X-inactivation state, and therefore is considered to be the origin of the PSC.

It should be noted that the naive PSCs of some embodiments of the invention (which are in a pre-X inactivation and a naive state) can upon differentiation inactivate one of the X chromosome alleles and methylate one of the alleles of the promoter of the XIST gene.

The pre-X-inactivation state according to some embodiments of the invention is characterized by presence of two unmethylated alleles of the promoter of the X-inactive specific transcript (XIST) gene in the female cell, and presence an unmethylated allele of the promoter of the XIST gene in a male cell.

The XIST gene is located on human Xq13.2 chromosome and has the sequence depicted in clone NC_000023.10 (73040486.73072588, complement, based on GenBank version GRCh37.p10. The XIST gene has a non-coding RNA which is provided in GenBank Accession NO. NR_001564.2 (SEQ ID NO:20).

According to some embodiments of the invention, presence of two unmethylated alleles of the promoter of the XIST gene in a female cell refers to having below about 20% of CpG methylated reads sequenced in the XIST promoter (i.e., less than 20% of CpG sites in the XIST promoter amplicon set forth by SEQ ID NO:70 being methylated), e.g., below about 19%, below about 18%, below about 17%, below about 16%, below about 15%, below about 14%, below about 13%, below about 12%, below about 11%, below about 10%, below about 9%, below about 8%, below about 7%, below about 6%, below about 5%, below about 4%, below about 3%, below about 2%, below about 1%, e.g., 0% (e.g., complete absence) of CpG methylated reads sequenced in the XIST promoter.

According to some embodiments of the invention, presence of one unmethylated allele of the promoter of the XIST gene in a male cell refers to having below about 20% of CpG methylated reads sequenced in the XIST promoter (i.e., less than 20% of CpG sites in the XIST promoter amplicon set forth by SEQ ID NO:70 being methylated), e.g., below about 19%, below about 18%, below about 17%, below about 16%, below about 15%, below about 14%, below about 13%, below about 12%, below about 11%, below about 10%, below about 9%, below about 8%, below about 7%, below about 6%, below about 5%, below about 4%, below about 3%, below about 2%, below about 1%, e.g., 0% of CpG methylated reads sequenced in the XIST promoter.

A non-limited example of the XIST promoter which includes CpG islands which can be either methylated or unmethylated is provided in the XIST promoter amplicon set forth by SEQ ID NO:70.

According to some embodiments of the invention, the unmethylated alleles of the promoter of the XIST gene in a female cell comprise less than 20% of CpG sites in the XIST promoter amplicon set forth by SEQ ID NO:70 being methylated. Non-limiting examples of such unmethylated alleles of the XIST gene in a female naïve pluripotent stem cell are shown in FIGS. 17A-E.

According to some embodiments of the invention, the unmethylated allele of the promoter of the XIST gene in a male cell comprises less than 20% of CpG sites in the XIST promoter amplicon set forth by SEQ ID NO:70 being methylated. Non-limiting examples of an unmethylated allele of the XIST gene in a male naïve pluripotent stem cell are shown in FIGS. 17A-E.

According to some embodiments of the invention, the human naive PSC is characterized by a reduced methylation of CpG islands in the promoter of the XIST gene as compared to a level of methylation of the CpG islands in a human primed PSC.

Human naive ESCs are characterized by significantly low levels of total methylated cytosine out of the total guanine nucleotides in each cell (e.g., 1-2%) as determined by Liquid Chromatography-Mass Spectrometry (LC-MS) quantitative analysis.

According to some embodiments of the invention, the human naive PSC is characterized by 0-3% of total methylated cytosine out of the total Guanine nucleotides in the naive PSC cell. For comparison, the primed PSC or a somatic cell has between 3.5%-5% of total methylated cytosine out of the total Guanine nucleotides in the primed PSC cell.

Thus, the naive pluripotent stem cell of some embodiments of the invention is in the "naive state" as explained above.

Thus, the culture medium of some embodiments of the invention is capable of maintaining naïve PSC in a naïve state. As used herein the term "isolated" refers to at least partially separated from the natural environment e.g., from the primate (e.g., mammalian) embryo or the primate (e.g., mammalian) body.

According to some embodiments of the invention, the non-naive PSC is selected from the group consisting of a primed PSC, an embryonic stem cell, a blastocyst, an induced pluripotent stem cell (a primed iPSC) and a somatic cell.

According to some embodiments of the invention, the non-naive PSC is not an embryonic stem cell.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-program the cell to acquire embryonic stem cells characteristics. According to some embodiments of the invention, the induced pluripotent stem cells are formed by inducing the expression of Oct-4, Sox2, Kf14 and c-Myc in a somatic stem cell.

The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting.

The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282:1145, 1998; Curr. Top. Dev. Biol. 38:133, 1998; Proc. Natl. Acad. Sci. USA 92:7844, 1995]; Bongso et al., [Hum Reprod 4:706, 1989]; and Gardner et al., [Fertil. Steril. 69:84, 1998].

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

It will be appreciated that commercially available stem cells can also be used according to some embodiments of the invention. Human ES cells can be purchased from the NIH human embryonic stem cells registry [Hypertext Transfer Protocol://grants(dot)nih(dot)gov/stem_cells/registry/current(dot)htm]. Non-limiting examples of commercially available embryonic stem cell lines are BG01, BG02, BG03, BG04, CY12, CY30, CY92, CY10, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Encavour-2, WIBR1, WIBR2, WIBR3, WIBR4, WIBR5, WIBR6, HUES 45, Shef 3, Shef 6, BJNhem19, BJNhem20, SA001, SA001.

In addition, ES cells can be obtained from other species as well, including mouse (Mills and Bradley, 2001), golden hamster [Doetschman et al., 1988, Dev Biol. 127:224-7], rat [Iannaccone et al., 1994, Dev Biol. 163:288-92] rabbit [Giles et al. 1993, Mol Reprod Dev. 36:130-8; Graves & Moreadith, 1993, Mol Reprod Dev. 1993, 36:424-33], several domestic animal species [Notarianni et al., 1991, J Reprod Fertil Suppl. 43:255-60; Wheeler 1994, Reprod Fertil Dev. 6:563-8; Mitalipova et al., 2001, Cloning. 3:59-67] and non-human primate species (Rhesus monkey and marmoset) [Thomson et al., 1995, Proc Natl Acad Sci USA. 92:7844-8; Thomson et al., 1996, Biol Reprod. 55:254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, MO, USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95:13726, 1998] and U.S. Pat. No. 6,090,622.

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1 (1): 39-49; Aoi T, et al., Generation of Pluripotent Stem Cells from Adult Mouse Liver and Stomach Cells. Science. 2008 Feb. 14. (Epub ahead of print); IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

Culturing the cells in the media described herein may be effected in any vesicle, e.g. plate, chamber, bioreactor etc.

The number of cells that may be selected and/or cultured according to the method of the present invention may be any number including small batches—e.g. $100 \times 10^4$ cells to larger batches—e.g. $100 \times 10^6$ or $100 \times 10^7$ cells.

The cells may be cultured in a bioreactor (or in multi-level industrial flasks), the size of which is selected according to the number of cells being cultured.

As used herein, the term "bioreactor" refers to any device in which biological and/or biochemical processes develop under monitored and controlled environmental and operating conditions, for example, pH, temperature, pressure, nutrient supply and waste removal. According to one embodiment of the invention, the basic classes of bioreactors suitable for use with the present invention include static bioreactors, stirred flask bioreactors, rotating wall bioreactors, hollow fiber bioreactors and direct perfusion bioreactors.

According to a particular embodiment, the cells are cultured (i.e. expanded) on an adherent surface.

Examples of such surfaces are provided herein under.

1. Laminin/Fibronectin coated plates. Sources for Fibronectin: Sigma Aldrich Bovine Fibronectin F1141, or human Fibronectin Millipore FC010. Sources for Laminin: Sigma Aldrich Ewing Sarcoma derived Laminin L2020, Human Biolaminin 511 or Human Biolaminin 521 (Biolamina INC). For example, such a surface can be prepared by mixing laminin and fibronectin at a final concentration of 2 μg/ml, and coating wells of plates for at least 2 hours at 37° C., to obtain Laminin/Fibronectin-coated plates.

2. Cells can be expanded on gelatin and vitronectin coated plates (e.g. 0.2% gelatin and 1 μg/ml Vitronectin coated plates). For example, such a surface can be prepared by mixing gelatin solution with vitronectin, and using the mix to coat wells, for at least 1 hour at 37° C. It should be noted that coated plates can be left for up to 4 days in 37° C. and can still be used for cells.

3. Cells can be expanded on plates coated with 0.2% gelatin/irradiated mouse or human fibroblast feeder cells.

4. Human naïve cells can be expanded on plates coated with only 0.2% gelatin coated plates.

5. Human naïve cells can be expanded on plates coated with only Matrigel or geltrex (BD Biosciences). For example, such a surface can be prepared by incubating the plates with the MatrigelR™ (Corning Life Sciences) solution for 1 hour at 37° C.

The culture media described in the present application may be used for a myriad of purposes.

According to a particular embodiment, the culture media are used for expanding (i.e., increasing the number of) cells, e.g., expanding naive PSCs.

It should be noted that culturing the naive PSC involves replacing the culture medium with a "fresh" medium (of identical composition) every 24-48 hours, and passaging each culture dish (e.g., a plate) to 2 or 3 culture dishes (e.g., plates) every 3-5 days. Thus, when cells in the culture reach about 60-90% confluence the supernatant is discarded, the culture dishes are washed [e.g., with phosphate buffered saline (PBS)] and the cells are subjected to enzymatic dissociation from the culture dish, e.g., using trypsinization (0.25% or 0.05% Trypsin+EDTA), e.g., until single cells or cell clumps are separated from each other.

It should be noted that the culture conditions uncovered by the present inventors enables maintenance of human PSCs such as human iPSCs in the naive PSC state without the need of further exogenous expression of the Oct4, Sox2, Klf4 and/or c-Myc factors. This is in sharp contrast to all prior attempts to generate naive human PSCs which required exogenous expression of the Oct4, Sox2, Klf4 and/or c-Myc factors, and which upon withdrawal of these factors the naive PSCs spontaneously differentiated, and could not be maintained in the undifferentiated and pluripotent stem cells (See e.g., Hanna J, 2010b).

Thus, according to another aspect, the culture media described herein are used to generate naïve pluripotent stem cells.

More specifically, according to another aspect of the present invention there is provided a method of generating a naive pluripotent stem cell (PSC), comprising:

incubating a non-naive PSC cell in any of the culture medium described herein, the culture medium allowing generation of the naive PSC from the non-naive PSC, wherein:

(i) when the naive PSC is a female PSC, then the naive female PSC has two unmethylated alleles of the promoter of the X-inactive specific transcript (XIST) gene; and (ii) when the naive PSC is a male PSC, then the naive male PSC has an unmethylated allele of the promoter of the XIST gene; and/or an expression level of transcription factor E3 (TFE3) in the naive PSC is characterized by a nucleus to cytoplasm expression ratio which is equal to or higher than 1 as determined by an immunostaining assay; and/or the naïve PSC is characterized by a positive expression of C-KIT (CD117) on the cell surface of the naïve PSC, thereby generating the naive PSC.

Thus, the naive PSC of the invention is characterized by a naive state. This is demonstrated, for example, in FIGS. 17A-E and FIGS. 22A-B, which show that all of the tested culture media were capable of retaining a unique pre-X inactivation state which characterizes the naïve PSC. Thus, FIGS. 17A-E show examples of such unmethylated alleles as determining in the XIST promoter (in the amplicon set forth in SEQ ID NO:70). These results conclusively demonstrate that male and female Naive hESCs/iPSCs which are cultured on all of the tested culture media retain a unique pre-X inactivation state under various WIS-NHSM conditions.

In contrast, FIGS. 17F and 22C show examples of non-naïve PSC in which the promoter of the XIST gene in the male cells is completely methylated (i.e., most of the CpG sites in the XIST promoter are methylated), and one allele of the promoter of the XIST gene is methylated in the female cells.

As described above, the naïve PSC of some embodiments of the invention is characterized by a unique expression level of transcription factor E3 (TFE3). Thus, the expression level of TFE3 in the naive PSC is characterized by a nucleus to cytoplasm expression ratio which is equal to or higher than 1 as determined by an immunostaining assay.

Table 1 in Example 5 of the Examples section which follows shows that all of the tested culture media were capable of maintaining the naïve PSCs in a naïve state which is characterized by a ratio higher than 1 between the nuclear and cytoplasmic TFE3 enrichment.

As described above, and shown in FIGS. 25A-C, the naïve PSC of some embodiments of the invention is characterized by a positive expression on the cell surface of the PSC of the C-KIT protein (also known as CD117). It should be noted that primed PSC do not express C-KIT at all, let alone on the cell surface of the cells. The results shown in FIGS. 25A-C support the conclusion that C-KIT is a novel marker for human naïve, but not primed, PSCs.

C-KIT, the human homolog of the proto-oncogene c-kit, was first identified as the cellular homolog of the feline sarcoma viral oncogene v-kit. This protein is a type 3 transmembrane receptor for MGF (mast cell growth factor, also known as "stem cell factor"). The sequence of the C-KIT protein is provided in GenBank Accession No. NP_000213.1 (SEQ ID NO:202 for isoform 1 precursor) and NP_001087241.1 (SEQ ID NO: 203 for isoform 2 precursor).

The expression of C-KIT on the naïve PSC cells can be determined by any immunostaining assay, such as using flow-cytometry (e.g., FACS analysis) and/or by immuno fluorescence techniques, e.g., using a fluorescent microscope, and/or by a radioactively labeled antibody.

Exemplary culture medium for generating naïve pluripotent stem cells from non-naïve pluripotent stem cells include:

1. A culture medium which comprises KO-DMEM, N2 supplement, B27 supplement, LIF, ERK1/2 inhibitor, GSK3b inhibitor, p38 inhibitor, and an SRC inhibitor;

2. A culture medium which comprises DMEM-F12/NEURObasal (GIBCO) 1:1 mix, N2 supplement, B27 supplement, LIF, ERK1/2 inhibitor, GSK3b inhibitor, p38 inhibitor and an SRC inhibitor; or 3. A culture medium which comprises DMEM-F12, N2 supplement, B27 supplement, LIF, ERK1/2 inhibitor, GSK3b inhibitor, p38 inhibitor, and an SRC inhibitor.

4. A culture medium which comprises KO-DMEM, N2 supplement (Gibco), B27 supplement, LIF, ERK1/2 inhibitor, PKC inhibitor, and Axin stabilizer.

5. A culture medium which comprises DMEM-F12/NEURObasal (GIBCO) 1:1 mix, N2 supplement (Gibco), B27 supplement (GIBCO), LIF (STAT3 activator), ERK1/2 inhibitor, PKC inhibitor, and Axin stabilizer.

6. A culture medium which comprises DMEM-F12, N2 supplement (Gibco), B27 supplement, LIF (STAT3 activator), ERK1/2 inhibitor, PKC inhibitor, and Axin stabilizer.

7. A culture medium which comprises KO-DMEM, N2 supplement (Gibco), B27 supplement, LIF, ERK1/2 inhibitor, GSK3b inhibitor, PKC inhibitor, and Axin stabilizer.

8. A culture medium which comprises DMEM-F12/NEURObasal (GIBCO) 1:1 mix, N2 supplement (Gibco), B27 supplement (GIBCO), LIF (STAT3 activator), ERK1/2 inhibitor, GSK3b inhibitor, PKC inhibitor, and Axin stabilizer.

9. A culture medium which comprises DMEM-F12, N2 supplement (Gibco), B27 supplement, LIF (STAT3 activator), ERK1/2 inhibitor, GSK3b inhibitor, PKC inhibitor, and Axin stabilizer.

10. A culture medium comprising a STAT3 activator, an ERK1/2 inhibitor and an Axin stabilizer.

11. A culture medium comprising a STAT3 activator, an ERK1/2 inhibitor, an Axin stabilizer and a PKC inhibitor.

12. A culture medium comprising a STAT3 activator, an ERK1/2 inhibitor, an Axin stabilizer, a PKC inhibitor and a GSK3b inhibitor.

13. A culture medium comprising an ERK1/2 inhibitor, a STAT3 activator and a SRC inhibitor.

14. A culture medium comprising an ERK1/2 inhibitor, a STAT3 activator, a SRC inhibitor and an AXIN complex stabilizer (AXINs).

15. A culture medium comprising an ERK1/2 inhibitor, a STAT3 activator, a SRC inhibitor, an AXIN complex stabilizer (AXINs) and a GSK3$\beta$ inhibitor.

16. A culture medium comprising an ERK1/2 inhibitor, a STAT3 activator, a SRC inhibitor, an AXIN complex stabilizer (AXINs), a GSK3$\beta$ inhibitor and a p38 inhibitor.

17. A culture medium comprising an ERK1/2 inhibitor, a GSK3$\beta$ inhibitor, a p38 inhibitor, a STAT3 activator and at least one agent selected from the group consisting of a SRC inhibitor and an AXIN complex stabilizer (AXINs).

18. A culture medium comprising an ERK1/2 inhibitor, a GSK3$\beta$ inhibitor, a p38 inhibitor, a JNK inhibitor, a STAT3 activator, a transforming growth factor beta receptor (TGF$\beta$R) inhibitor, a PKC inhibitor, a p38 inhibitor and basic fibroblast growth factor (bFGF).

19. Any of the culture media described in Example 1 (culture media 1-40), Example 5 (culture media 41-131) and in Example 6 (culture media 132-147) in the Examples section which follows.

According to some embodiments of the invention, incubating the non-naive PSC cell in the culture medium is performed under culture conditions devoid of feeder cells, i.e., under feeder layer free conditions (e.g., on a Matrigel, Laminin, and/or fibronectin-coated surface).

According to some embodiments of the invention, incubating the non-naive PSC cell in the culture medium is performed under culture conditions which comprise culturing on feeder cells, such as fibroblasts [e.g., mouse embryonic fibroblasts (MEFs)], which support the growth of the pluripotent stem cells.

According to some embodiments of the invention, wherein when the non-naive PSC is derived from a somatic cell then the method further comprising subjecting the somatic cell to de-differentiation conditions, to thereby obtain an induced pluripotent stem cell.

According to some embodiments of the invention, de-differentiation conditions comprise exogenously expressing within the somatic cell at least two, e.g., at least three, at least four or more growth factors selected from the group consisting of OCT4 [GenBank Accession Nos.

NP_002692.2 (SEQ ID NO:54) and NM_002701.4 (SEQ ID NO:55)], SOX2 [GenBank Accession Nos. NP_003097.1 (SEQ ID NO:56) and NM_003106.3 (SEQ ID NO:57)], KLF4 [GenBank Accession Nos. NP_004226.3 (SEQ ID NO:58) and NM_004235.4 (SEQ ID NO:59)], c-Myc [GenBank Accession Nos. NP_002458.2 (SEQ ID NO: 60), and NM_002467.4 (SEQ ID NO:61)], ESRRB Estrogen-Related Receptor Beta GenBank Accession Nos. NM_004452.3 (SEQ ID NO: 124) and NP_004443.3 (SEQ ID NO: 125), Kruppel like factor 2, KLF2, [GenBank Accession Nos.: NP_057354.1 (SEQ ID NO: 126) and NM_016270.2 (SEQ ID NO:127)] TBX3 [GenBank Accession Nos.: NP_005987.3 NP_057653.3 (SEQ ID NO:128 and 129) _NM_005996.3 NM_016569.3 (SEQ ID NO:130 and SEQ ID NO: 131)], ERAS [GenBank Accession Nos.: NP_853510.1 (SEQ ID NO:132) and NM_181532.3 (SEQ ID NO:133) and Kruppel-like factor 17, KLF17 [GenBank Accession Nos.: NP_775755.3 (SEQ ID NO:154) and NM_173484.3 (SEQ ID NO:155, transcript encoding KLF17 protein)].

As used herein the phrase "exogenously expressing" refers to expressing a heterologous nucleic acid sequence which may not be naturally expressed within the cell or which overexpression in the cell is desired. The exogenous polynucleotide may be introduced into the cell in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the cell.

According to still another aspect of the present invention there is provided a method of improving generation of induced pluripotent stem cells (iPSCs) from a somatic cell, comprising:

(a) expressing within the somatic cell a first factor selected from the group consisting of Nanog, ESRRB, KLF2, TBX3, ERAS and KLF17, and a second factor selected from the group consisting of Nanog, ESRRB, KLF2, TBX3, ERAS, Oct4, Sox2, Klf4, c-Myc, and KLF17, wherein the first and second growth factor are non-identical; and (b) inhibiting Mbd3 and/or Gatad2a expression and/or activity in the somatic cell, thereby improving generation of the iPSCs from a somatic cell.

According to some embodiments of the invention, expressing the factors is performed using DNA transfection of the factors.

Methods of DNA transfections into mammalian cells are known in the art and include those described in Reference (Mansour et al. 2012), which is fully incorporated herein by reference in its entirety. Further description of preparation of expression vectors and modes of administering them into cells are provided herein under.

According to some embodiments of the invention, expressing the factors is performed using RNA transfection of the growth factors.

Methods of RNA transfections into mammalian cells are known in the art and include those described for example in (Warren et al. 2010) which is fully incorporated herein by reference in its entirety.

Once obtained, the cells are cultured in a medium (e.g. those disclosed herein above) and are serially passaged.

According to some embodiments of the invention, exogenous expression of the factors is effected for a limited time, such as for no more than 10 days in culture, e.g., for no more than 1 passage.

According to some embodiments of the invention, once the naive iPSCs are generated from the somatic cells, they are further being cultured in the culture medium of some embodiments of the invention (e.g., the WIS-NHSM medium) without exogenous expression of the Nanog, ESRRB, KLF2, TBX3, ERAS Oct4, Sox2, Klf4c-Myc factors by the naive iPSCs, and without addition of the isolated Nanog, ESRRB, KLF2, TBX3, ERAS Oct4, Sox2, Klf4c-Myc factors to the culture medium.

As used herein the phrase "isolated . . . factors" refers to factors that are recombinantly expressed from an expression vector in a host cell (e.g., a bacteria), being biochemically synthesized, or being isolated from a biological sample (e.g., serum or cells).

The method of some embodiments of the invention can be used to improve generation of iPSCs from somatic cells as compared to generation of iPSC from somatic cells using expression of the Nanog, ESRRB, KLF2, TBX3, ERAS Oct4, Sox2, Klf4c-Myc factors in somatic cells without further inhibition of the Mbd3 expression (e.g. using the media disclosed herein above).

For example, when human somatic cells are used, the method may be effected using a medium which comprises leukemia inhibitor factor (LIF), an ERK1/2 inhibitor, a GSK3b inhibitor, a p38 inhibitor, a JNK inhibitor, basic fibroblast growth factor (bFGF), transforming growth factor-beta 1 (TGFβ1), and an MBD3 inhibitor, and optionally also a ROCK inhibitor. When the somatic cells are subject to de-differentiation using DNA transfection of the growth factors (e.g., at least two of the Oct4, Sox2, Klf4 and c-Myc), then the method results in at least about 30%, e.g., at least about 40%, at least about 50%, e.g., at least about 60%, at least about 70%, e.g., at least about 80%, at least about 90%, e.g., at least about 95%, at least about 99%, e.g., 100% more iPSCs as compared to the yield of the iPSCs obtained when the Oct4, Sox2, Klf4 and c-Myc are expressed using DNA transfection in the somatic cell without further inhibition of the Mbd3 expression.

For example, when human somatic cells are used, the method may be effected using a medium which comprises leukemia inhibitor factor (LIF), an ERK1/2 inhibitor, a GSK3b inhibitor, a p38 inhibitor, a JNK inhibitor, basic fibroblast growth factor (bFGF), transforming growth factor-beta 1 (TGFβ1), and an MBD3 inhibitor, and optionally also a ROCK inhibitor. When the somatic cells are subject to de-differentiation using RNA transfection of the growth factors (e.g., at least two of the Oct4, Sox2, Klf4 and c-Myc), then the method results in at least about 5%, e.g., at least about 10%, at least about 20%, e.g., at least about 30%, at least about 40%, e.g., at least about 50%, at least about 60%, e.g., at least about 75%, at least about 99%, e.g., 100% more iPSCs as compared to the yield of the iPSCs obtained when the Oct4, Sox2, Klf4 and c-Myc are expressed using RNA transfection in the somatic cell without further inhibition of the Mbd3 expression. Moreover, while the prior art methods (without MBD3 inhibition and without the medium of some embodiments of the present invention) employ 10-20 rounds of RNA transfection in order to achieve de-differentiation of human somatic cells, the method of some embodiments of the invention employs 1-4 rounds of RNA transfection in order to achieve de-differentiation of human somatic cells, and thus is far more efficient and time consuming.

The present inventors have uncovered that overexpression of ERAS or activation of endogenous human ERAS in pluripotent stem cells can be used to induce a naive state in pluripotent stem cells.

According to some embodiments of the invention, the method further comprising exogenously expressing ES cell expressed Ras (ERAS) coding sequence (e.g., SEQ ID NO: 109) or activating endogenous expression of the ERAS in the somatic cell.

According to some embodiments of the invention, activating endogenous expression of ERAS is performed by removing the premature poly adenylation sites of the endogenous ERAS gene (SEQ ID NO: 108), e.g., in A-1, A2 or A-3 boxed sequences in FIG. 3 by Kameda et al. Stem Cells 2005; 23:1535-1540; which is fully incorporated herein by reference in its entirety.

According to some embodiments of the invention, expressing is effected for at least 48 hours such that the inhibiting the Mbd3 is effected to 10-30% of a level of the Mbd3 prior to the expressing.

According to some embodiments of the invention, expressing is effected for about 48 hours and the inhibiting is effected after the about 48 hours.

It should be noted that when inhibition of Mbd3 is performed after 48 hours, the inhibition can be of 100% of the expression level of activity of MBD3.

According to some embodiments of the invention, the iPSC is a murine iPSC.

According to an aspect of some embodiments of the invention there is provided a method of generating differentiated cells, comprising subjecting the naive pluripotent stem cells generated according to the method of some embodiments of the invention or the iPSCs generated according to the methods of some embodiments of the invention to differentiating conditions, thereby generating the differentiated cells.

According to some embodiments of the invention, the naive PSCs or the iPSCs of some embodiments of the invention can be used to generate lineage specific cells.

As used herein, the phrase "generating lineage specific cells" refers to the enrichment of a mixed population of cells in a culture with cells predominantly displaying at least one characteristic associated with a specific lineage phenotype. It will be appreciated that all cell lineages are derived from the three embryonic germ layers. Thus, for example, hepatocytes and pancreatic cells are derived from the embryonic endoderm, osseous, cartilaginous, elastic, fibrous connective tissues, yachts, myocardial cells, bone marrow cells, vascular cells (namely endothelial and smooth muscle cells), and hematopoietic cells are differentiated from embryonic mesoderm and neural, retina and epidermal cells are derived from the embryonic ectoderm.

Lineage specific cells can be obtained by directly inducing the expanded, undifferentiated naive PSCs to culturing conditions suitable for the differentiation of specific cell lineage.

Following is a non-limiting description of a number of procedures and approaches for inducing differentiation of EBs to lineage specific cells. It will be appreciated that the present invention contemplates additional protocols for the ex vivo differentiation of the cells described herein, which do not work through the generation of EBs.

Neural Precursor Cells

To differentiate the EBs of some embodiments of the invention into neural precursors, four-day-old EBs are cultured for 5-12 days in tissue culture dishes including DMEM/F-12 medium with 5 mg/ml insulin, 50 mg/ml transferrin, 30 nM selenium chloride, and 5 mg/ml fibronectin (Its medium, Okabe, S. et al., 1996, Mech. Dev. 59: 89-102). The resultant neural precursors can be further transplanted to generate neural cells in vivo (Bristle, O. et al., 1997. In vitro-generated neural precursors participate in mammalian brain development. Proc. Natl. Acad. Sci. USA. 94:14809-14814). It will be appreciated that prior to their transplantation, the neural precursors are trypsinized and triturated to single-cell suspensions in the presence of 0.1% DNase.

Oligodendrocytes and Myelinate Cells

EBs of some embodiments of the invention can differentiate to oligodendrocytes and myelinate cells by culturing the cells in modified SATO medium, i.e., DMEM with bovine serum albumin (BSA), pyruvate, progesterone, putrescine, thyroxine, triiodothyronine, insulin, transferrin, sodium selenite, amino acids, neurotrophin 3, ciliary neurotrophic factor and Hepes (Bottenstein, J. E. & Sato, G. H., 1979, Proc. Natl. Acad. Sci. USA 76, 514-517; Raff, M. C., Miller, R. H., & Noble, M., 1983, Nature 303:390-369]. Briefly, EBs are dissociated using 0.25% Trypsin/EDTA (5 min at 37° C.) and triturated to single cell suspensions. Suspended cells are plated in flasks containing SATO medium supplemented with 5% equine serum and 5% fetal calf serum (FCS). Following 4 days in culture, the flasks are gently shaken to suspend loosely adhering cells (primarily oligodendrocytes), while astrocytes are remained adhering to the flasks and further producing conditioned medium. Primary oligodendrocytes are transferred to new flasks containing SATO medium for additional two days. Following a total of 6 days in culture, oligospheres are either partially dissociated and resuspended in SATO medium for cell transplantation, or completely dissociated and a plated in an oligosphere-conditioned medium which is derived from the previous shaking step [Liu, S. et al., (2000). Embryonic stem cells differentiate into oligodendrocytes and myelinate in culture and after spinal cord transplantation. Proc. Natl. Acad. Sci. USA. 97:6126-6131].

Mast Cells

For mast cell differentiation, two-week-old EBs of some embodiments of the invention are transferred to tissue culture dishes including DMEM medium supplemented with 10% FCS, 2 mM L-glutamine, 100 units/ml penicillin, 100 mg/ml streptomycin, 20% (v/v) WEHI-3 cell-conditioned medium and 50 ng/ml recombinant rat stem cell factor (rrSCF, Tsai, M. et al., 2000. In vivo immunological function of mast cells derived from embryonic stem cells: An approach for the rapid analysis of even embryonic lethal mutations in adult mice in vivo. Proc Natl Acad Sci USA. 97:9186-9190). Cultures are expanded weekly by transferring the cells to new flasks and replacing half of the culture medium.

Hemato-Lymphoid Cells

To generate hemato-lymphoid cells from the EBs of some embodiments of the invention, 2-3 days-old EBs are transferred to gas-permeable culture dishes in the presence of 7.5% $CO_2$ and 5% $O_2$ using an incubator with adjustable oxygen content. Following 15 days of differentiation, cells are harvested and dissociated by gentle digestion with Collagenase (0.1 unit/mg) and Dispase (0.8 unit/mg), both are available from F. Hoffman-La Roche Ltd, Basel, Switzerland. CD45-positive cells are isolated using anti-CD45 monoclonal antibody (mAb) M1/9.3.4.HL.2 and paramagnetic microbeads (Miltenyi) conjugated to goat anti-rat immunoglobulin as described in Potocnik, A. J. et al., (Immunology Hemato-lymphoid in vivo reconstitution potential of subpopulations derived from in vitro differentiated embryonic stem cells. Proc. Natl. Acad. Sci. USA. 1997, 94:10295-10300). The isolated CD45-positive cells can be further enriched using a single passage over a MACS column (Miltenyi).

It will be appreciated that since EBs are complex structures, differentiation of EBs into specific differentiated cells, tissue or organ may require isolation of lineage specific cells from the EBs.

Such isolation may be effected by sorting of cells of the EBs via fluorescence activated cell sorter (FACS) or mechanical separation of cells, tissues and/or tissue-like structures contained within the EBs.

Methods of isolating EB-derived-differentiated cells via FACS analysis are known in the art. According to one method, EBs are disaggregated using a solution of Trypsin and EDTA (0.025% and 0.01%, respectively), washed with 5% fetal bovine serum (FBS) in phosphate buffered saline (PBS) and incubated for 30 min on ice with fluorescently-labeled antibodies directed against cell surface antigens characteristics to a specific cell lineage. For example, endothelial cells are isolated by attaching an antibody directed against the platelet endothelial cell adhesion molecule-1 (PECAM1) such as the fluorescently-labeled PECAM1 antibodies (30884X) available from PharMingen (PharMingen, Becton Dickinson Bio Sciences, San Jose, CA, USA) as described in Levenberg, S. et al., (Endothelial cells derived from human embryonic stem cells. Proc. Natl. Acad. Sci. USA. 2002. 99:4391-4396). Hematopoietic cells are isolated using fluorescently-labeled antibodies such as CD34-FITC, CD45-PE, CD31-PE, CD38-PE, CD90-FITC, CD117-PE, CD15-FITC, class I-FITC, all of which IgGI are available from PharMingen, CD133/1-PE (IgG1) (available from Miltenyi Biotec, Auburn, CA), and glycophorin A-PE (IgG1), available from Immunotech (Miami, FL). Live cells (i.e., without fixation) are analyzed on a FACScan (Becton Dickinson Bio Sciences) by using propidium iodide to exclude dead cells with either the PC-LYSIS or the CELL-QUEST software. It will be appreciated that isolated cells can be further enriched using magnetically-labeled second antibodies and magnetic separation columns (MACS, Miltenyi) as described by Kaufman, D. S. et al., (Hematopoictic colony-forming cells derived from human embryonic stem cells. Proc. Natl. Acad. Sci. USA. 2001, 98:10716-10721).

An example for mechanical isolation of beating cardiomyocytes from EBs is disclosed in U.S. Patent Appl. No. 20030022367 to Xu et al. Briefly, four-day-old EBs of some embodiments of the invention are transferred to gelatin-coated plates or chamber slides and are allowed to attach and differentiate. Spontaneously contracting cells, which are observed from day 8 of differentiation, are mechanically separated and collected into a 15-mL tube containing low-calcium medium or PBS. Cells are dissociated using Collagenase B digestion for 60-120 minutes at 37° C., depending on the Collagenase activity. Dissociated cells are then resuspended in a differentiation KB medium (85 mM KCl, 30 mM $K_2HPO_4$, 5 mM $MgSO_4$, 1 mM EGTA, 5 mM creatine, 20 mM glucose, 2 mM $Na_2ATP$, 5 mM pyruvate, and 20 mM taurine, buffered to pH 7.2, Maltsev et al., Circ. Res. 75:233, 1994) and incubated at 37° C. for 15-30 min. Following dissociation cells are seeded into chamber slides and cultured in the differentiation medium to generate single cardiomyocytes capable of beating.

It will be appreciated that the culturing conditions suitable for the differentiation and expansion of the isolated lineage specific cells include various tissue culture medium, growth factors, antibiotic, amino acids and the like and it is within the capability of one skilled in the art to determine which conditions should be applied in order to expand and differentiate particular cell types and/or cell lineages [reviewed in Fijnvandraat A C, et al., Cardiovasc Res. 2003; 58:303-12;

Sachinidis A, et al., Cardiovasc Res. 2003; 58:278-91; Stavridis M P and Smith A G, 2003; Biochem Soc Trans. 31 (Pt 1): 45-9].

In addition to the lineage-specific primary cultures, EBs of the invention can be used to generate lineage-specific cell lines which are capable of unlimited expansion in culture.

Cell lines of some embodiments of the invention can be produced by immortalizing the EB-derived cells by methods known in the art, including, for example, expressing a telomerase gene in the cells (Wei, W. et al., 2003. Mol Cell Biol. 23:2859-2870) or co-culturing the cells with NIH 3T3 hph-HOX11 retroviral producer cells (Hawley, R. G. et al., 1994. Oncogene 9:1-12).

Following are non-limiting examples of culturing conditions which are suitable for differentiating and/or expanding lineage specific cells from the naive PSCs or iPSCs of some embodiments of the invention. It should be noted that for inducing differentiation of the naive PSCs or iPSCs into differentiated cells, the medium which was used to maintain the cells in the naive undifferentiated and pluripotent state should be replaced with the appropriate differentiation medium.

Mesenchymal stromal cells which are CD73-positive and SSEA-4-negative can be generated from naive PSCs by mechanically increasing the fraction of fibroblast-like differentiated cells formed in cultures of naive hPSCs, essentially as described in Trivedi P and Hematti P. Exp Hematol. 2008, 36 (3): 350-9. Briefly, to induce differentiation of hESC the intervals between medium changes are increased to 3-5 days, and the cells at the periphery of the naive PSCs colonies become spindle-shaped fibroblast-looking cells. After 9-10 days under these conditions when about 40-50% of the cells in the culture acquire the fibroblast-looking appearance, the undifferentiated portions of naive PSCs colonies are physically removed and the remaining differentiated cells are passaged to new culture plates under the same conditions.

To induce differentiation of naive hPSCs into dopaminergic (DA) neurons, the cells can be co-cultured with the mouse stromal cell lines PA6 or MS5, or can be cultured with a combination of stromal cell-derived factor 1 (SDF-1/CXCL12), pleiotrophin (PTN), insulin-like growth factor 2 (IGF2) and ephrin B1 (EFNB1) essentially as described in Vazin T, et al., PLOS One. 2009 Aug. 12; 4 (8): e6606; and in Elkabetz Y., et al., Genes Dev. 2008 Jan. 15; 22:152-165.

To generate mesencephalic dopamine (mesDA) neurons, naive hPSCs can be genetically modified to express the transcription factor Lmx1a (e.g., using a lentiviral vector with the PGK promoter and Lmx1a) essentially as described in Friling S., et al., Proc Natl Acad Sci USA. 2009, 106: 7613-7618.

To generate lung epithelium (type II pneumocytes) from naive hPSCs, the naive PSCs can be cultured in the presence of a commercially available cell culture medium (Small Airway Growth Medium; Cambrex, College Park, MD), or alternatively, in the presence of a conditioned medium collected from a pneumocyte cell line (e.g., the A549 human lung adenocarcinoma cell line) as described in Rippon H J., et al., Proc Am Thorac Soc. 2008; 5:717-722.

To induce differentiation of naive hPSCs cells into neural cells, the pluripotent stem cells can be cultured for about 5 days in the presence of a serum replacement medium supplemented with TGF-b inhibitor (SB431542, Tocris; e.g., 10 nM) and Noggin (R&D; e.g., 500 ng/ml), following which the cells are cultured with increasing amounts (e.g., 25%, 50%, 75%, changed every two days) of N2 medium (Li X J., et al., Nat Biotechnol. 2005, 23:215-21) in the presence of 500 ng/ml Noggin, essentially as described in Chambers S M., et al., Nat Biotechnol. 2009, 27:275-280.

The invention, according to some embodiments thereof, contemplates the use of cells, tissues and organs generated from the naive pluripotent stem cells of the invention using any differentiation protocol known in the art.

It will be appreciated that since the lineage-specific cells or cell lines obtained according to the teachings of some embodiments of the invention are developed by differentiation processes similar to those naturally occurring in the human embryo they can be further used for human cell-based therapy and tissue regeneration.

Thus, the invention according to some embodiments thereof envisages the use of the expanded and/or differentiated lineage-specific cells or cell lines of some embodiments of the invention for treating a disorder requiring cell replacement therapy.

For example, diseases presently expected to be treatable by therapeutic transplantation of PSC or PSC-derived cells include Parkinson's disease, cardiac infarcts, juvenile-onset diabetes mellitus, and leukemia (Gearhart J. Science 1998, 282:1061; Rossant and Nagy, Nature Biotech. 1999, 17:23).

For example, oligodendrocyte precursors can be used to treat myelin disorders (Repair of myelin disease: Strategies and progress in animal models. Molecular Medicine Today. 1997. pp. 554-561), chondrocytes or mesenchymal cells can be used in treatment of bone and cartilage defects (U.S. Pat. No. 4,642,120) and cells of the epithelial lineage can be used in skin regeneration of a wound or burn (U.S. Pat. No. 5,716,411).

For certain disorders, such as genetic disorders in which a specific gene product is missing [e.g., lack of the CFTR gene-product in cystic fibrosis patients (Davies J C, 2002. New therapeutic approaches for cystic fibrosis lung disease. J. R. Soc. Med. 95 Suppl 41:58-67)], PSC-derived cells are preferably manipulated to over-express the mutated gene prior to their administration to the individual. It will be appreciated that for other disorders, the PSC-derived cells should be manipulated to exclude certain genes.

Over-expression or exclusion of genes can be effected using knock-in and/or knock-out constructs [see for example, Fukushige, S. and Ikeda, J. E.: Trapping of mammalian promoters by Cre-lox site-specific recombination. DNA Res 3 (1996) 73-50; Bedell, M. A., Jerkins, N. A. and Copeland, N. G.: Mouse models of human disease. Part I: Techniques and resources for genetic analysis in mice. Genes and Development 11 (1997) 1-11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751-62].

In addition to cell replacement therapy, the lineage specific cells of some embodiments of the invention can also be utilized to prepare a cDNA library. mRNA is prepared by standard techniques from the lineage specific cells and is further reverse transcribed to form cDNA. The cDNA preparation can be subtracted with nucleotides from embryonic fibroblasts and other cells of undesired specificity, to produce a subtracted cDNA library by techniques known in the art.

The lineage specific cells of some embodiments of the invention can be used to screen for factors (such as small molecule drugs, peptides, polynucleotides and the like) or conditions (such as culture conditions or manipulation) that affect the differentiation of lineage precursor to terminally differentiated cells. For example, growth affecting substances, toxins or potential differentiation factors can be tested by their addition to the culture medium.

The naïve pluripotent stem cells, generated as described herein, can be used as a starting material for the generation of primordial cells.

Thus, according to another aspect of some embodiments of the invention, there is provided a method of generating a primordial germ cell, comprising culturing primate naive pluripotent stem cells in a culture medium selected capable of inducing the primate naive pluripotent stem cells into primordial germ cell.

According to a particular embodiment, the culture medium comprises a Rho kinase (ROCK) inhibitor and bone morphogenetic protein 4 (BMP4).

According to some embodiments of the invention, the primate naive pluripotent stem cell comprises:

an unmethylated X-inactive specific transcript (XIST) gene, wherein:

(i) when the naive PSC is a female PSC, then the naive female PSC has two unmethylated alleles of the promoter of the XIST gene; and (ii) when the naive PSC is a male PSC, then the naive male PSC has an unmethylated allele of the promoter of the XIST gene; and/or an expression level of transcription factor E3 (TFE3) characterized by a nucleus to cytoplasm expression ratio which is equal to or higher than 1 as determined by an immunostaining assay.

According to some embodiments of the invention, the primordial germ cell is characterized by a CD61 (integrin beta 3) positive expression pattern.

According to some embodiments of the invention, the primordial germ cell is characterized by a CD61$^+$/SSEA4$^+$ expression pattern (expression signature).

According to some embodiments of the invention, the culture medium selected capable of inducing the primate naive pluripotent stem cells into primordial germ cell further comprises at least one agent selected from the group consisting of: leukemia inhibitory factor (LIF), Stem Cell Factor (SCF) and Epidermal Growth Factor (EGF).

According to an aspect of some embodiments of the invention, there is provided an isolated population of primate primordial germ cells comprising primate primordial germ cells generated according to the method of some embodiments of the invention.

According to some embodiments of the invention, the isolated population of primate primordial germ cells comprising at least about 50%, e.g., at least about 60%, e.g., at least about 70%, e.g., at least about 80%, e.g., at least about 90%, e.g., at least about 95%, e.g., at least about 99%, e.g., 100% of primordial germ cells characterized by CD61$^+$/SSEA4$^+$ expression pattern.

It should be noted that the isolated primordial germ cells (PGCs) of some embodiments of the invention can be injected into adult human testis or ovary to complete their maturation and generate sperm or eggs.

According to an aspect of some embodiments of the invention, there is provided a method of treating a subject in need thereof, comprising administering the primordial germ cells of some embodiments of the invention to a gonad tissue of the subject, thereby treating the subject in need thereof.

The term "subject" refers to a mammal, e.g., a primate, preferably a human being at any age which suffer from the pathology.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

According to some embodiments of the invention, the subject suffers from infertility.

According to an aspect of some embodiments of the invention, there is provided a kit comprising the primate primordial germ cells of some embodiments of the invention and a medicament for treating infertility.

The kit may also include appropriate buffers and preservatives for improving the shelf-life of the kit.

The kit may include appropriate instructions for use and labels indicating FDA approval for use in treating a subject, such as treating infertility in the subject.

The isolated naïve PSC of some embodiments of the invention may be used for generation of a chimeric human-mouse organism, and to contribute to development of mouse embryo in vivo, essentially as described elsewhere (Gafni et al. Nature 2013; December 12; 504 (7479): 282-6. doi: 10.1038/nature12745. Epub 2013 Oct. 30, which is fully incorporated herein by reference).

The present inventors have uncovered that specific genetic modification(s) of the donor cells (e.g., of the isolated naïve pluripotent stem cell of some embodiments of the invention, primed PSC, or the primordial germ cell of some embodiments of the invention) can improve the efficiency of generation of a chimeric animal. For example, over expression of an oncogenic protein selected from the group consisting of: C-MYC, N-MYC, L-MYC, EDAR (ectodysplasin A receptor), MDM2, and ERAS, and/or downregulation of a tumor suppressor protein selected from the group consisting of P53 and NF kappa B inhibitor alpha in the donor cells can improve the generation of a chimeric animal.

Thus, according to an aspect of some embodiments of the invention there is provided an isolated naïve pluripotent stem cell genetically modified to over-express an oncogenic protein selected from the group consisting of: C-MYC, N-MYC, L-MYC, EDAR (ectodysplasin A receptor), MDM2, and ERAS, and/or to downregulate a tumor suppressor protein selected from the group consisting of P53 and NF kappa B inhibitor alpha.

For example, as described in Example 8 and shown in FIG. 24A, the present inventors were capable of generating cross-species chimeric humanized mice by microinjection of LIS 38 EGFP hTP53 C2 naive human iPS cells (which were used as the human donor cells) into mouse morulas (which were used as host cells).

Over-expression of an oncogenic protein can be performed by upregulating an endogenous expression of the oncogenic protein in the cell (e.g., adding and/or replacing promoter and/or enhancer elements, and/or introducing molecules which increase endogenous expression of the oncogene, e.g., a small molecule), and/or by expression of a heterologous polynucleotide encoding at least the functional portion of the oncogenic protein(s) described hereinbelow using a nucleic acid construct (or expression vector) as is further described herein under.

As used herein the term "C-MYC" (also known as MRTL; MYCC; c-Myc; bHLHe39) refers to the oncogenic protein which is the v-myc avian myelocytomatosis viral oncogene homolog from *Homo sapiens* (Gene ID 4609), e.g., to the protein set forth by GenBank Accession No. NP_002458.2 (SEQ ID NO: 204). Overexpression of the c-MYC can be performed by expression of a heterologous polynucleotide comprising the nucleic acid sequence set forth by GenBank Accession No. NG_007161.1 (SEQ ID NO: 213) or a functional portion thereof, e.g., a nucleic acid sequence encoding amino acids 1-454 of GenBank Accession No. NP_002458.2 (SEQ ID NO: 204).

As used herein the term "N-MYC" (also known as MYCN, NMYC; ODED; MODED; N-myc; bHLHe37) refers to the oncogenic protein v-myc avian myelocytomatosis viral oncogene neuroblastoma derived homolog from *Homo sapiens* (Gene ID 4613), e.g., to the protein set forth by GenBank Accession No. NP_001280157.1 (SEQ ID NO:205). Overexpression of the N-MYC can be performed by expression of a heterologous polynucleotide comprising the nucleic acid sequence set forth by GenBank Accession No. NG_007457.1 (SEQ ID NO:214) or a functional portion thereof, e.g., a nucleic acid sequence encoding amino acids 1-464 of GenBank Accession No. NP_001280157.1 (SEQ ID NO:205).

As used herein the term "L-MYC" (also known as LMYC; L-Myc; MYCL1; bHLHe38) refers to the oncogenic protein v-myc avian myelocytomatosis viral oncogene lung carcinoma derived homolog from *Homo sapiens* (Gene ID 4610) e.g., to the protein set forth by GenBank Accession No. NP_001028253.1 isoform 1 (SEQ ID NO:206). Overexpression of the L-MYC can be performed by expression of a heterologous polynucleotide comprising the nucleic acid sequence set forth by GenBank Accession No. NM_001033081.2 (SEQ ID NO:215) or a functional portion thereof, e.g., a nucleic acid sequence encoding amino acids 1-365 of GenBank Accession No. NP_001028253.1 isoform 1 (SEQ ID NO:206).

As used herein the term "EDAR" (also known as DL; ED3; ED5; ED1R; EDA3; HRM1; EDA1R; ECTD10A; ECTD10B; EDA-AIR) refers to the oncogenic protein ecto-dysplasin A receptor from *Homo sapiens* (Gene ID 10913), e.g., to the protein set forth by GenBank Accession No. NP_071731.1 (SEQ ID NO:207). Overexpression of the EDAR can be performed by expression of a heterologous polynucleotide comprising the nucleic acid sequence set forth by GenBank Accession No. NG_008257.1 (SEQ ID NO: 216) or a functional portion thereof, e.g., a nucleic acid sequence encoding amino acids 1-484 of GenBank Accession No. NP_071731.1 (SEQ ID NO:207).

As used herein the term "MDM2" (also known as HDMX; hdm2; ACTFS) refers to the proto-oncogene, E3 ubiquitin protein ligase from *Homo sapiens* (Gene ID 4193; GenBank: GQ848196.1), e.g., to the protein set forth by GenBank Accession No. ACX31156.1 (SEQ ID NO:208). Overexpression of the MDM2 can be performed by expression of a heterologous polynucleotide comprising the nucleic acid sequence set forth by GenBank Accession No. GQ848196.1 (SEQ ID NO:217) or a functional portion thereof, e.g., a nucleic acid sequence encoding amino acids 1-466 of GenBank Accession No. ACX31156.1 (SEQ ID NO:208).

As used herein the term "ERAS" (also known as HRAS2; HRASP) refers to the ES cell expressed Ras from *Homo sapiens* Gene ID 3266), e.g., to the protein set forth by GenBank Accession No. NP_853510.1 (SEQ ID NO: 209). Overexpression of the ERAS can be performed by expression of a heterologous polynucleotide comprising the nucleic acid sequence set forth by GenBank Accession No. NM_181532.3 (SEQ ID NO:218) or a functional portion thereof, e.g., a nucleic acid sequence encoding amino acids 1-233 of GenBank Accession No. NP_853510.1 (SEQ ID NO: 209).

Downregulation of a tumor suppressor protein can be achieved by various modes.

As used herein the term "P53" (also known as TP53; BCC7; LFS1; TRP53) refers to the tumor protein P53 (Gene ID: 7157), such as the protein set forth by GenBank Accession No. BAC16799.1 (SEQ ID NO:210).

As used herein the term "NF kappa B inhibitor alpha" (NFKBIA, also known as IKBA; MAD-3; NFKBI) refers to the nuclear factor of kappa light polypeptide gene enhancer in B-cells inhibitor, alpha from *Homo sapiens* (Gene ID: 4792), e.g., the protein set forth by GenBank Accession No. NP_065390.1 (SEQ ID NO:211).

Downregulation of the tumor suppressor protein of some embodiments of the invention (e.g., P53 and/or NF kappa B inhibitor alpha) can be effected on the genomic and/or the transcript level using a variety of molecules which interfere with transcription and/or translation [e.g., RNA silencing agents (e.g., antisense, siRNA, shRNA, micro-RNA), Ribozyme and DNAzyme or using a dominant negative mutant]. It should be noted that the downregulation can be a complete absence of protein production and/or a complete inhibition of protein activity, or it can be a partial inhibition of protein production and/or activity. In addition, it should be noted that the downregulation can be permanent or transient, depending on the cell in which downregulation occurs and in the purpose of the downregulation, and/or on the effect of the downregulation of the tumor suppressor protein on the cell or on the generated chimeric animal. Description of the downregulation agents is provided herein under.

P53 dominant negative mutant is described as a mutated mouse or human p53 protein that suppresses endogenous p53 activity in a dominant-negative fashion by forming mixed tetramers with wild-type mouse or human p53, and thus reducing p53 binding to the p53-responsive element in its target genes (described in de Vries et al., 2002. Proc. Natl. Acad. Sci. U.S.A. 99 (5): 2948-53; Willis et al., 2004 (Oncogene 23, 2330-2338, each of which is fully incorporated herein by reference in its entirety).

Non-limiting examples of P53 dominant negative mutants which can be used to downregulate P53 in the cells of some embodiments of the invention include:

A). R172H dominant negative mutant in the mouse P53 protein set forth by GenBank: AAA39883.1 (SEQ ID NO: 212), essentially as described in de Vries et al., 2002 (Proc. Natl. Acad. Sci. U.S.A. 99 (5): 2948-53); Willis et al., 2004 (Oncogene, 23, 2330-2338). It should be noted that according to the accepted nomenclature for genetic mutations, the "R172H" refers to substitution of "R" amino acid (i.e., Argninc) at position 172 of the sequence depicted in GenBank: AAA39883.1 (SEQ ID NO: 212) with an "H" amino acid (i.e., histidine).

B). R175H, G245S, R248W, R249S, R273H or R282W dominant negative mutants in the human P53 protein set forth by GenBank Accession No. BAC16799.1 (SEQ ID NO:210), essentially as described in Petitjean A et al., Hum Mutat. 2007 June; 28 (6): 622-9." Impact of mutant p53 functional properties on TP53 mutation patterns and tumor phenotype: lessons from recent developments in the IARC TP53 database "; and in Freed-Pastor W A ct al., See comment in PubMed Commons belowGenes Dev. 2012 Jun. 15; 26 (12): 1268-86. "Mutant p53: one name, many proteins"), each of which is fully incorporated herein by its entirety.

A dominant negative mutant of NF-kappa-B inhibitor alpha, which acts like an oncogene and inhibits P53 function, was made by changing both S32 and S36 amino acid residues into either D (aspartic acid-Asp) or E (glutamic acid-Glu) (Zhou M. et al., 2003. "Transfection of a dominant-negative mutant NF-kB inhibitor (IkBm) represses p53-dependent apoptosis in acute lymphoblastic leukemia cells: interaction of IkBm and p53." Oncogene. 22 (50): 8137-44).

According to some embodiments of the invention, the NF kappa B inhibitor alpha dominant negative mutant which can be used to downregulate NF kappa B inhibitor alpha in the cell of some embodiments of the invention comprises the S32D and S36D mutations in the human NF-kappa-B inhibitor alpha protein set forth in SEQ ID NO:211 [meaning substitution of the "S" (Serine) amino acid at position 32 with the "D" (Aspartic Acid) amino acid, and substitution of the "S" amino acid at position 36 with "D" amino acid].

According to some embodiments of the invention, the NF kappa B inhibitor alpha dominant negative mutant which can be used to downregulate NF kappa B inhibitor alpha in the cell of some embodiments of the invention comprises the S32E and S36E mutations in the human NF-kappa-B inhibitor alpha protein set forth in SEQ ID NO:211 [meaning substitution of the "S" (Serine) amino acid at position 32 with the "E" (Glutamic Acid) amino acid, and substitution of the "S" amino acid at position 36 with "E" amino acid].

According to some embodiments of the invention, the NF kappa B inhibitor alpha dominant negative mutant which can be used to downregulate NF kappa B inhibitor alpha in the cell of some embodiments of the invention comprises the S32D and S36E mutations in the human NF-kappa-B inhibitor alpha protein set forth in SEQ ID NO:211 [meaning substitution of the "S" (Serine) amino acid at position 32 with the "D" (Aspartic Acid) amino acid, and substitution of the "S" amino acid at position 36 with "E" (Glutamic Acid)].

According to some embodiments of the invention, the NF kappa B inhibitor alpha dominant negative mutant which can be used to downregulate NF kappa B inhibitor alpha in the cell of some embodiments of the invention comprises the S32E and S36D mutations in the human NF-kappa-B inhibitor alpha protein set forth in SEQ ID NO:211 [meaning substitution of the "S" (Serine) amino acid at position 32 with the "E" (Glutamic Acid) amino acid, and substitution of the "S" amino acid at position 36 with "D" amino acid].

According to some embodiments of the invention, the genetically modified isolated naïve pluripotent stem cell of some embodiments of the invention is characterized as follows:

wherein (i) when said naive PSC is a female PSC, then said naive female PSC has two unmethylated alleles of the promoter of the X-inactive specific transcript (XIST) gene; and (ii) when said naive PSC is a male PSC, then said naive male PSC has an unmethylated allele of said promoter of said XIST gene, and/or an expression level of transcription factor E3 (TFE3) in said naive PSC is characterized by a nucleus to cytoplasm expression ratio which is equal to or higher than 1 as determined by an immunostaining assay, and/or the naïve PSC is characterized by a positive expression of C-KIT (CD117) on the cell surface of the naïve PSC.

According to some embodiments of the invention, the genetically modified naïve pluripotent stem cell is a primate cell.

According to some embodiments of the invention, the genetically modified naïve pluripotent stem cell is a human cell.

According to an aspect of some embodiments of the present invention there is provided a method of generating a chimeric animal comprising introducing the isolated naïve pluripotent stem cell of some embodiments of the invention, or the primordial germ cells of some embodiments of the invention, into an embryo of a host animal, thereby generating the chimeric animal.

According to some embodiments of the invention, the isolated naïve pluripotent stem cell which is used for generating the chimeric animal is genetically modified to over-express an oncogenic protein selected from the group consisting of: C-MYC, N-MYC, L-MYC, EDAR (ectodysplasin A receptor), MDM2, and ERAS, and/or to downregulate a tumor suppressor protein selected from the group consisting of P53 and NF kappa B inhibitor alpha.

As used herein, the phrase "chimeric animal" refers to an animal comprising cells of at least two genetically distinct individuals.

It is noted that the chimeric animal can be composed of cells of two different individuals belonging to two different species, or to the same species.

According to some embodiments of the invention, the isolated naïve pluripotent stem cell or the primordial germ cell is allogeneic to the host animal.

As used herein, the term "allogeneic" refers to at least two genetically different individuals of the same species.

According to some embodiments of the invention, the isolated naïve pluripotent stem cell or the primordial germ cell is xenogeneic to the host animal.

As used herein, the term "xenogeneic" refers to at least two individuals of different species.

According to some embodiments of the invention, the host animal is a primate, e.g., a mammal.

According to some embodiments of the invention, the host animal is mouse.

According to some embodiments of the invention, the host animal is pig.

According to some embodiments of the invention, the host animal is monkey.

According to some embodiments of the invention, the host animal is chimpanzee.

According to some embodiments of the invention, the host animal is not human.

According to some embodiments of the invention, the embryo is a pre-implantation embryo.

As used herein, the term "pre-implantation embryo" refers to an embryo at an 8-cell stage, 16-cell stage embryo, early morula, late morula, early blastocyst, and/or a late blastocyst.

It should be noted that since the isolated naïve pluripotent stem cells or the primordial germ cells are introduced into the pre-implantation embryo they are likely to form a normal embryo.

According to some embodiments of the invention, the pre-implantation embryo comprises at least 4 cells.

According to some embodiments of the invention, the pre-implantation embryo comprises no more than 128 cells.

According to some embodiments of the invention, introducing the donor cell to the host animal is performed in vivo.

Methods of in vivo administration of cells into a morula of an animal are well known in the art, such as in Gafni O, Weinberger L, Mansour A A, Manor Y S, Chomsky E, Ben-Yosef D, Kalma Y, Viukov S, Maza I, Zviran A, Rais Y, Shipony Z, Mukamel Z, Krupalnik V, Zerbib M, Geula S, Caspi I, Schneir D, Shwartz T, Gilad S, Amann-Zalcenstein D, Benjamin S, Amit I, Tanay A, Massarwa R, Novershtern N, Hanna J H. Nature. 2013 Dec. 12; 504 (7479): 282-6. doi:

10.1038/nature12745. Epub 2013 Oct. 30; and Manipulating the Mouse Embryo: A Laboratory Manual, Fourth Edition. By Richard Behringer; Marina Gertsenstein; Kristina Vintersten Nagy; Andras Nagy, each of which is fully incorporated herein by reference.

According to some embodiments of the invention, introducing the donor cells (e.g., the isolated naïve pluripotent stem cell of some embodiments of the invention, or the primordial germ cells of some embodiments of the invention) into an embryo of a host animal is performed by microinjection of the donor cells into host early pre-implantation embryos.

According to some embodiments of the invention, the morula comprises at least 4 cells.

According to some embodiments of the invention, the morula comprises no more than 128 cells.

According to some embodiments of the invention, the introducing is performed in vitro or ex vivo.

According to some embodiments of the invention, introducing the cells is performed in vitro or ex vivo via direct injection or aggregation with the developing host embryo.

According to some embodiments of the invention, introducing the donor cells (e.g., the isolated naïve pluripotent stem cell of some embodiments of the invention, or the primordial germ cells of some embodiments of the invention) into an embryo of a host animal is performed by aggregation (e.g., for a few hours, or overnight) of the donor cells with a host pre-implantation embryos.

According to some embodiments of the invention, the method further comprising allowing the pre-implantation embryo to grow ex vivo or in vivo.

According to some embodiments of the invention, the method further comprising testing a level of chimerism in the chimeric animal.

Once formed, the level of chimerism in the chimeric animal can be evaluated by various means which follow the donor cells within the host cells. This can be achieved by, for example, genetically modifying the donor cells (prior to their introducing into the host animal) to express a trackable label (a reporter protein), such as to express a fluorescent protein [e.g., red fluorescent protein (RFP) (SEQ ID NO: 222 (for DNA) and SEQ ID NO: 221 (for protein)), green fluorescent protein (GFP) (SEQ ID NO: 220 (for DNA) and SEQ ID NO: 219 (for protein)) and the like, the sequences of which are well known and available via the NCBI web site (ncbi (dot) nlm (dot) nih (dot) gov], which can be viewed using a fluorescent microscope. See e.g., FIGS. 24A-B herein.

As used herein Methods of genetically modifying cells to express a protein-of-interest (e.g., a fluorescent protein) are known in the art, and are further described herein under.

Thus, one can easily evaluate the efficiency of generation of chimeric animals. Briefly, after the donor cells are introduced into the host animal, the developing embryos can be viewed using a fluorescent microscope and fluorescently-labeled embryos are counted out of the total number of injected embryos.

In addition, in each embryo, the number of donor cells (e.g., which are labeled with GFP) is counted per each chimeric animal.

It should be noted that using the genetically modified naive PSCs of some embodiments of the invention, with downregulated P53 (due to the dominant negative P53) the present inventors were capable of obtaining chimeric animals at a success rate of at least 20%, wherein the average percentage of donor cells within each chimeric animal was between about 10% to about 49% (FIGS. 24A-B and data not shown).

According to an aspect of some embodiments of the present invention there is provided a cell culture comprising the isolated genetically modified naïve pluripotent stem cell of some embodiments of the invention and a culture medium.

According to some embodiments of the invention, the culture medium is capable of maintaining said pluripotent stem cell in a naïve state for at least 5 passages, e.g., at least about 10, 15, 20, 25, 30, 40, 50, 100, 200, 500, 1000, e.g., 3000 passages.

According to some embodiments of the invention, the culture medium included in the cell culture of the invention is any of the culture media described herein.

According to some embodiments of the invention, the culture medium included in the cell culture of the invention is the culture medium of some embodiments of the invention.

According to some embodiments of the invention, the culture medium included in the cell culture of the invention is any of the culture media 1-147.

According to some embodiments of the invention, the culture medium included in the cell culture of the invention is any of the culture media described in WO2014/174470 which is fully incorporated herein by reference in its entirety.

According to some embodiments of the invention, the culture medium included in the cell culture of the invention comprises an ERK1/2 inhibitor, a GSK3β inhibitor, a p38 inhibitor, a JNK inhibitor, a STAT3 activator and at least one agent selected from the group consisting of: basic fibroblast growth factor (bFGF), transforming growth factor beta 1 (TGFβ1), a protein kinase C (PKC) inhibitor, a ROCK inhibitor and a NOTCH inhibitor.

According to some embodiments of the invention, the culture medium included in the cell culture of the invention comprises an ERK1/2 inhibitor, a GSK3β inhibitor, a p38 inhibitor, a JNK inhibitor, a STAT3 activator and at least one agent selected from the group consisting of: a transforming growth factor receptor (TGFR) inhibitor, a fibroblast growth factor receptor (FGFR) inhibitor, a protein kinase C (PKC) inhibitor, a ROCK inhibitor and a NOTCH inhibitor.

According to some embodiments of the invention the STAT3 activator is selected from the group consisting of leukemia inhibitory factor (LIF) and interleukin 6 (IL6).

According to some embodiments of the invention the culture medium further comprising at least one additional agent selected from the group consisting of: insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, Bix01294, and stem cell factor (SCF).

According to some embodiments of the invention the culture medium further comprising at least one additional agent selected from the group consisting of: insulin-like growth factor 1 (IGF1), insulin-like growth factor II (IGFII), bone morphogenetic protein 4 (BMP4), a Sonic Hedgehog pathway (SHH) inhibitor, an ERK5 inhibitor, Forskolin, Kenpaullone, BayK8644, Bix01294, and stem cell factor (SCF).

According to some embodiments of the invention, the STAT3 activator comprises the LIF, and wherein the at least one agent comprises the PKC inhibitor.

According to some embodiments of the invention, the STAT3 activator comprises the LIF, and wherein the at least one agent comprises the TGFβ 1 and the protein kinase C inhibitor.

According to some embodiments of the invention, the culture medium further comprises an FGFR inhibitor.

According to some embodiments of the invention, the culture medium further comprises TGFR inhibitor.

According to some embodiments of the invention, the STAT3 activator comprises the LIF and wherein the at least one agent comprises the TGFβ1 and the protein kinase C inhibitor.

According to some embodiments of the invention, the culture medium further comprises an FGFR inhibitor.

According to some embodiments of the invention, the STAT3 activator comprises the LIF, and wherein the at least one agent comprises the bFGF and the TGFβ1.

According to some embodiments of the invention, the culture medium further comprises a ROCK inhibitor.

According to some embodiments of the invention, the culture medium further comprises a protein kinase C inhibitor.

According to some embodiments of the invention, the STAT3 activator comprises the LIF and wherein the at least one agent comprises the bFGF, the ROCK inhibitor, a bone morphogenetic protein (BMP) inhibitor, the NOTCH inhibitor, and a transforming growth factor receptor (TGFR) inhibitor.

According to some embodiments of the invention, the culture medium further comprises a Sonic Hedgehog pathway (SHH) inhibitor.

According to some embodiments of the invention, the STAT3 activator comprises the LIF and wherein the at least one agent comprises the NOTCH inhibitor, and a fibroblast growth factor receptor (FGFR) inhibitor.

According to some embodiments of the invention, the culture medium further comprises an agent selected from the group consisting of insulin-like growth factor II (IGFII), stem cell factor (SCF) and transforming growth factor beta 1 (TGFβ1).

According to an aspect of some embodiments of the present invention there is provided a culture medium comprising leukemia inhibitor factor (LIF), an ERK1/2 inhibitor, a GSK3b inhibitor, a p38 inhibitor, a JNK inhibitor, and a protein kinase C inhibitor.

According to some embodiments of the invention, the culture medium of some embodiments of the invention further comprises an FGFR inhibitor.

According to some embodiments of the invention, the culture medium of some embodiments of the invention further comprises a TGFR inhibitor.

According to an aspect of some embodiments of the present invention there is provided a culture medium comprising leukemia inhibitor factor (LIF), an ERK1/2 inhibitor, a GSK3b inhibitor, a p38 inhibitor, a JNK inhibitor, TGFβ 1 and a protein kinase C inhibitor.

According to some embodiments of the invention, the culture medium of some embodiments of the invention further comprises a FGFR inhibitor.

According to an aspect of some embodiments of the present invention there is provided a culture medium comprising leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1).

According to some embodiments of the invention, the culture medium of some embodiments of the invention further comprises a ROCK inhibitor.

According to some embodiments of the invention, the culture medium of some embodiments of the invention further comprises a protein kinase C inhibitor.

According to some embodiments of the invention, the culture medium of some embodiments of the invention further comprising a factor selected from the group consisting of: bone morphogenetic protein 4 (BMP4), IGF1, IGFII, Forskolin, FGFR inhibitor, TGFR inhibitor, Kenpaullone, BayK8644, Bix01294, and stem cell factor (SCF).

According to some embodiments of the invention, the culture medium of some embodiments of the invention further comprising BMP type I receptors (ALK2,3,6) inhibitor.

According to some embodiments of the invention, the culture medium of some embodiments of the invention further comprises ascorbic Acid.

According to some embodiments of the invention, the culture medium of some embodiments of the invention further comprises oleic Acid.

According to some embodiments of the invention, the culture medium of some embodiments of the invention further comprises Linoleic Acid.

According to some embodiments of the invention, the culture medium of some embodiments of the invention further comprises Pipecolic Acid.

According to some embodiments of the invention, the culture medium of some embodiments of the invention being devoid of animal serum.

According to some embodiments of the invention, the culture medium of some embodiments of the invention further comprises serum replacement.

It should be noted that once the chimeric animal is formed, and allowed to grow, the cells of the chimeric animal can be used for cell therapy. For example, the mature differentiated cells (e.g., hematopoietic stem cells, liver hepatocytes, insulin producing Beta cells) generated in the chimeric animal based on some embodiments of the invention can be used for transplantation in adult humans or for biomedical applications.

Thus, according to an aspect of some embodiments of the invention, there is provided a method of isolating differentiated cells, cell lineages, tissues or organs from the chimeric animal of some embodiments of the invention.

Methods of isolating such differentiated cells, tissues or organs are well known in the art and are also described hereinabove.

Thus, in case the naive PSCs that were used to form the chimeric animal are human cells, these cells can be further isolated from the formed chimeric animal and used for treating a human subject.

According to some embodiments of the invention, the method further comprises isolating human-derived (human-originated) cells or tissues from the chimeric animal.

Non-limiting examples of using such human-originated cells, tissues or organs include cell based therapy, tissue replacement, organ or tissue implantation.

Following is a non-limiting description of expression vectors and modes of administering thereof into cells which can be used to express a polypeptide-of-interest (e.g., any of the proteins described hereinabove, e.g., OCT4, c-MYC, SOX2, KLF4, LIF, bFGF, TGFβ1, an oncogenic protein such as C-MYC, N-MYC, L-MYC, EDAR (ectodysplasin A receptor), MDM2, and ERAS, a reporter protein such as GFP or RFP) in a cell.

To express an exogenous protein in mammalian cells, a polynucleotide sequence encoding the polypeptide-of-interest is preferably ligated into a nucleic acid construct suitable for mammalian cell expression. Such a nucleic acid construct includes a promoter sequence for directing transcription of the polynucleotide sequence in the cell in a constitutive or inducible manner.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding a protein-of-interest can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1 (+/−), pGL3, pZeoSV2 (+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-IMTHA, and vectors derived from Epstein Bar virus include pHEBO, and p205. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149:51-60).

Recombinant viral vectors are useful for in vivo expression of the protein-of-interest since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14 (1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the polypeptide-of-interest of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the protein-of-interest and the heterologous protein, the protein-of-interest can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of *E. coli* expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art and are further described hereinbelow can also be used by some embodiments of the invention.

Transformed cells are cultured under effective conditions, which allow for the expression of high amounts of the recombinant polypeptide-of-interest (e.g., the LIF, TGFβ1, bFGF, OCT4, c-myc, SOX2, KLF-4). Following a predetermined time in culture, recovery of the recombinant polypeptide is effected. The phrase "recovery of the recombinant polypeptide" used herein refers to collecting the whole fermentation medium containing the polypeptide and need not imply additional steps of separation or purification.

Thus, polypeptide-of-interest can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

The polypeptide-of-interest is preferably retrieved in "substantially pure" form.

As used herein, the phrase "substantially pure" refers to a purity that allows for the effective use of the polypeptide-of-interest (e.g., the LIF, TGFβ1, bFGF) in maintaining the human embryonic stem cells in an undifferentiated state while in culture.

Following is a non-limiting description of downregulation agents which can be used according to some embodiments of the invention.

As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects-see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13 (5): 381-392. doi: 10.1089/154545703322617069.

The invention according to some embodiments thereof also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDE-CAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296:550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the tumor suppressor mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl Chem-Biochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (ambion (dot) com/techlib/tn/91/912 (dot) html).

Second, potential target sites are compared to an appropriate genomic database (e.g., human, mouse, rat etc.) using any sequence alignment software, such as the BLAST software available from the NCBI server (nebi (dot) nlm (dot) nih (dot) gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348, 185, the contents of which are expressly incorporated herein by reference. The cell-penetrating peptides of some embodiments of the invention preferably include, but are not limited to, penetratin, transportan, pIsl, TAT (48-60), pVEC, MTS, and MAP.

According to another embodiment the RNA silencing agent may be a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

Below is a brief description of the mechanism of miRNA activity.

Genes coding for miRNAs are transcribed leading to production of an miRNA precursor known as the pri-miRNA. The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nucleotide precursor known as the pre-miRNA. Drosha cleaves the pri-miRNA with a staggered cut typical of RNase III endonucleases yielding a pre-miRNA stem loop with a 5' phosphate and ~2 nucleotide 3' overhang. It is estimated that approximately one helical turn of stem (~10 nucleotides) extending beyond the Drosha cleavage site is essential for efficient processing. The pre-miRNA is then actively transported from the nucleus to the cytoplasm by Ran-GTP and the export receptor Ex-portin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA eventually become incorporated as a single-stranded RNA into a ribonucleoprotein complex known as the RNA-induced silencing complex (RISC). Various proteins can form the RISC, which can lead to variability in specifity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLOS 3-c85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

MiRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-0,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

It will be appreciated from the description provided herein above, that contacting pluripotent stem cells with a miRNA may be affected in a number of ways:

1. Transiently transfecting the pluripotent stem cells with the mature double stranded miRNA;
2. Stably, or transiently transfecting the pluripotent stem cells with an expression vector which encodes the mature miRNA.
3. Stably, or transiently transfecting the pluripotent stem cells with an expression vector which encodes the pre-miRNA. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA.
4. Stably, or transiently transfecting the pluripotent stem cells with an expression vector which encodes the pri-miRNA The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof.

Preparation of miRNAs mimics can be effected by chemical synthesis methods or by recombinant methods.

Another agent capable of downregulating the tumor suppressor protein of some embodiments of the invention (e.g., P53 and/or NF-kappa-B inhibitor alpha) is a DNAzyme molecule capable of specifically cleaving an mRNA transcript or DNA sequence of the tumor suppressor protein. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro, S. W. & Joyce, G. F. Proc. Natl, Acad. Sci. USA 199; for rev of DNAzymes see Khachigian, LM [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 2002, Abstract 409, Ann Meeting Am Soc Gen Ther www(dot)asgt(dot)org)). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of the tumor suppressor gene of some embodiments of the invention (e.g., P53 and/or NF-kappa-B inhibitor alpha) can also be effected by using an antisense polynucleotide capable of specifically hybridizing with an mRNA transcript encoding the tumor suppressor protein.

Design of antisense molecules which can be used to efficiently downregulate a tumor suppressor protein must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76:75-6 (1998); Kronenwett et al. Blood 91:852-62 (1998); Rajur et al. Bioconjug Chem 8:935-40 (1997); Lavigne et al. Biochem Biophys Res Commun 237:566-71 (1997) and Aoki et al. (1997) Biochem Biophys Res Commun 231:540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65:1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16:1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating the tumor suppressor protein of some embodiments of the invention (e.g., P53 and/or NF-kappa-B inhibitor alpha) is a ribozyme molecule capable of specifically cleaving an mRNA transcript encoding the tumore suppressor protein. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase I trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated-WEB home page).

An additional method of regulating the expression of the tumor suppressor protein of some embodiments of the invention (e.g., P53 and/or NF-kappa-B inhibitor alpha) in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

```
oligo
3'--A G G T duplex
5'--A G C T duplex
3'--T C G A
```

However, it has been shown that the A-AT and G-GC triplets have the greatest triple helical stability (Reither and Jeltsch, BMC Biochem, 2002 September12, Epub). The same authors have demonstrated that TFOs designed according to the A-AT and G-GC rule do not form non-specific triplexes, indicating that the triplex formation is indeed sequence specific.

Thus for any given sequence in the tumor suppressor gene regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

As used herein the term "about" refers to +10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells-A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, C T (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, C A (1990); Marshak et al., "Strategies for Protein Purification and Characterization-A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Base Medium

1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml of 200 mM solution (at a 2 mM final concentration) (Biological Industries-02-022-1B), Non-Essential Amino Acid (NEAA)-5 ml (Biological Industries 01-340-1B), 50 μl of 50 mM stock Beta-mercaptocthanol (1 vile), 5 ml B27 supplement (Invitrogen 17504-044), Insulin (Sigma I-1882; 12.5-25 μg/ml final concentration), Apo-transferrin (Sigma T-1147; 100 μg/ml final concentration), Progesterone (Sigma P8783) 0.02 μg/ml final concentration, Putrescine (SigmaP5780; 16 μg/ml final concentration, Sodium selenite (Sigma S5261; at a final concentration of 3 nM), L-ascorbic acid 2-phosphate (Sigma A8960; 50 μg/ml final concentration), bovine serum albumin (BSA) (100× Fraction V 7.5% Solution Gibco 15260-037. It is noted that the Insulin, Apo-transferrin, Progesterone, Putrescine and Sodium selenite are components of the N2 mix.

Supplements

Culture Medium 1: LIF (20 ng/ml), ERK1/2i (PD0325901, 1 μM), GSK3βi (CHIR99021, 3 μM), P38i (BIRB796, 2 μM), JNKi (SP600125, 5 μM), FGF2 (8 ng/ml), TGFβ1 (2 ng/ml), ROCKi (Y27632 10 μM), AXINs (IWR1, 2 μM) and SRCi (CGP77675, 1.5 μM).

Culture Medium 2: LIF (20 ng/ml), ERK1/2i (PD0325901, 1 μM), GSK3βi (CHIR99021, 3 μM), P38i (BIRB796, 2 μM), JNKi (SP600125, 5 M), FGF2 (8 ng/ml), TGFβ1 (2 ng/ml), ROCKi (Y27632 10 μM), AXINs (IWR1, 2 μM), SRCi (CGP77675, 1.5 μM), BMPi (LDN-193189 0.2 μM).

Culture Medium 3: LIF (20 ng/ml), ERK1/2i (PD0325901, 1 μM), GSK3βi (CHIR99021, 3 μM), P38I (BIRB796, 2 μM), JNKi (SP600125, 5 μM), FGF2 (8 ng/ml), TGFβ1 (2 ng/ml), ROCKi (Y27632 10 μM), AXINs (IWR1, 2 μM), SRCi (CGP77675, 1.5 μM) and PKCi (Go6983 0.5 μM).

Culture Medium 4: LIF (20 ng/ml), ERK1/2i (PD0325901, 1 μM), GSK3βi (CHIR99021, 3 μM), P38i (BIRB796, 2 μM), JNKi (SP600125, 5 μM), FGF2 (8 ng/ml), TGFβ1 (2 ng/ml), ROCKi (Y27632 10 μM), AXINs (IWR1, 2 μM), SRCi (CGP77675, 1.5 μM), BMPi (LDN-193189 0.2 μM) and PKCi (Go6983 0.5 M).

Culture Medium 5: LIF (20 ng/ml), ERK1/2i (PD0325901, 1 μM), GSK3βi (CHIR99021, 3 μM), P38i (BIRB796, 2 μM), FGF2 (8 ng/ml), TGFβ1 (2 ng/ml), ROCKi (Y27632 10 μM), AXINs (IWR1, 2 M), SRCi (CGP77675, 1.5 μM).

Culture Medium 6: LIF (20 ng/ml), ERK1/2i (PD0325901, 1 μM), GSK3βi (CHIR99021, 3 μM), P38i (BIRB796, 2 μM), FGF2 (8 ng/ml), TGFβ1 (2 ng/ml), ROCKi (Y27632 10 μM), AXINs (IWR1, 2 μM), SRCi (CGP77675, 1.5 μM), BMPi (LDN-193189 0.2 μM).

Culture Medium 7: LIF (20 ng/ml), ERK1/2i (PD0325901, 1 μM), GSK3βi (CHIR99021, 3 μM), P38i (BIRB796, 2 μM), FGF2 (8 ng/ml), TGFβ1 (2 ng/ml), ROCKi (Y27632 10 μM), AXINs (IWR1, 2 μM), SRCi (CGP77675, 1.5 μM) and PKCi (Go6983 0.5 μM).

Culture Medium 8: LIF (20 ng/ml), ERK1/2i (PD0325901, 1 μM), GSK3βi (CHIR99021, 3 μM), P38i (BIRB796, 2 μM), FGF2 (8 ng/ml), TGFβ1 (2 ng/ml), ROCKi (Y27632 10 μM), AXINs (IWR1, 2 μM), SRCi (CGP77675, 1.5 μM), BMPi (LDN-193189 0.2 μM) and PKCi (Go6983 0.5 μM).

Culture Medium 9: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), SRCi (CGP77675, 1.5 μM).

Culture Medium 10: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), SRCi (CGP77675, 1.5 μM), BMPi (LDN-193189 0.2 μM).

Culture Medium 11: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), SRCi (CGP77675, 1.5 μM) and PKCi (Go6983 0.5 μM).

Culture Medium 12: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), SRCi (CGP77675, 1.5 μM), BMPi (LDN-193189 0.2 μM) and PKCi (Go6983 0.5 μM).

Culture Medium 13: LIF (20 ng/ml), ERK1/2i (PD0325901, 1 μM), GSK3βi (CHIR99021, 3 μM), P38i (BIRB796, 2 μM), JNKi (SP600125, 5 μM), FGF2 (8 ng/ml), TGFβ1 (2 ng/ml), ROCKi (Y27632 10 μM), SRCi (CGP77675, 1.5 μM).

Culture Medium 14: LIF (20 ng/ml), ERK1/2i (PD0325901, 1 μM), GSK3βi (CHIR99021, 3 μM), P38i (BIRB796, 2 μM), JNKi (SP600125, 5 μM), FGF2 (8 ng/ml), TGFβ1 (2 ng/ml), ROCKi (Y27632 10 μM), SRCi (CGP77675, 1.5 μM), BMPi (LDN-193189 0.2 μM).

Culture Medium 15: LIF (20 ng/ml), ERK1/2i (PD0325901, 1 μM), GSK3βi (CHIR99021, 3 μM), P38i (BIRB796, 2 μM), JNKi (SP600125, 5 μM), FGF2 (8 ng/ml), TGFβ1 (2 ng/ml), ROCKi (Y27632 10 μM), SRCi (CGP77675, 1.5 μM) and PKCi (Go6983 0.5 μM).

Culture Medium 16: LIF (20 ng/ml), ERK1/2i (PD0325901, 1 μM), GSK3βi (CHIR99021, 3 μM), P38i (BIRB796, 2 μM), JNKi (SP600125, 5 μM), FGF2 (8 ng/ml), TGFβ1 (2 ng/ml), ROCKi (Y27632 10 μM), SRCi (CGP77675, 1.5 μM), BMPi (LDN-193189 0.2 μM) and PKCi (Go6983 0.5 μM).

Culture Medium 17: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), SRCi (CGP77675, 1.5 μM).

Culture Medium 18: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), SRCi (CGP77675, 1.5 μM), BMPi (LDN-193189 0.2 μM).

Culture Medium 19: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), SRCi (CGP77675, 1.5 μM) and PKCi (Go6983 0.5 μM).

Culture Medium 20: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), SRCi (CGP77675, 1.5 μM), BMPi (LDN-193189 0.2 μM) and PKCi (Go6983 0.5 μM).

Culture Medium 21: LIF (20 ng/ml), ERK1/2i (PD0325901, 1 μM), GSK3βi (CHIR99021, 3 μM), P38i (BIRB796, 2 μM), JNKi (SP600125, 5 μM), ROCKi (Y27632 10 μM), AXINs (IWR1, 2 μM), SRCi (CGP77675, 1.5 μM).

Culture Medium 22: LIF (20 ng/ml), ERK1/2i (PD0325901, 1 μM), GSK3βi (CHIR99021, 3 μM), P38i (BIRB796, 2 μM), JNKi (SP600125, 5 μM), ROCKi (Y27632 10 μM), AXINs (IWR1, 2 μM), SRCi (CGP77675, 1.5 μM), BMPi (LDN-193189 0.2 μM).

Culture Medium 23: LIF (20 ng/ml), ERK1/2i (PD0325901, 1 μM), GSK3βi (CHIR99021, 3 μM), P38i (BIRB796, 2 μM), JNKi (SP600125, 5 μM), ROCKi (Y27632 10 μM), AXINs (IWR1, 2 μM), SRCi (CGP77675, 1.5 μM) and PKCi (Go6983 0.5 μM).

Culture Medium 24: LIF (20 ng/ml), ERK1/2i (PD0325901, 1 μM), GSK3βi (CHIR99021, 3 μM), P38i (BIRB796, 2 μM), JNKi (SP600125, 5 μM), ROCKi (Y27632 10 μM), AXINs (IWR1, 2 μM), SRCi (CGP77675, 1.5 μM), BMPi (LDN-193189 0.2 μM) and PKCi (Go6983 0.5 μM).

Culture Medium 25: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM).

Culture Medium 26: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), BMPi (LDN-193189 0.2 μM).

Culture Medium 27: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM) and PKCi (Go6983 0.5 μM).

Culture Medium 28: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), BMPi (LDN-193189 0.2 μM) and PKCi (Go6983 0.5 μM).

Culture Medium 29: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), SRCi (CGP77675, 1.5 μM), FGFRi (PD173074 0.1 μM).

Culture Medium 30: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), SRCi (CGP77675, 1.5 μM), FGFRi (PD173074 0.1 μM), BMPi (LDN-193189 0.2 μM).

Culture Medium 31: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), SRCi (CGP77675, 1.5 μM), FGFRi (PD173074 0.1 μM) and PKCi (Go6983 0.5 μM)

Culture Medium 32: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), SRCi (CGP77675, 1.5 μM), FGFRi (PD173074 0.1 μM), BMPi (LDN-193189 0.2 μM) and PKCi (Go6983 0.5 μM).

Culture Medium 33: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), FGFRi (PD173074 0.1 μM).

Culture Medium 34: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), FGFRi (PD173074 0.1 μM), BMPi (LDN-193189 0.2 μM).

Culture Medium 35: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), FGFRi (PD173074 0.1 μM) and PKCi (Go6983 0.5 μM).

Culture Medium 36: LIF (20 ng/ml), ERK1/2i (PD0325901, 1 μM), GSK3βi (CHIR99021, 3 μM), P38i (BIRB796, 2 μM), JNKi (SP600125, 5 μM), ROCKi (Y27632 10 μM), AXINs (IWR1, 2 μM), FGFRi (PD173074 0.1 μM), BMPi (LDN-193189 0.2 μM) and PKCi (Go6983 0.5 μM).

Culture Medium 37: LIF (20 ng/ml), ERK1/2i (PD0325901, 1 μM), GSK3βi (CHIR99021, 3 μM), P38i (BIRB796, 2 μM), JNKi (SP600125, 5 μM), TGFβ1 (2 ng/ml), ROCKi (Y27632 10 μM), AXINs (IWR1, 2 μM), SRCi (CGP77675, 1.5 μM), TGFRi (SB431542 2 μM).

Culture Medium 38: LIF (20 ng/ml), ERK1/2i (PD0325901, 1 μM), GSK3βi (CHIR99021, 3 μM), P38i (BIRB796, 2 μM), JNKi (SP600125, 5 μM), ROCKi (Y27632 10 μM), AXINs (IWR1, 2 μM), SRCi (CGP77675, 1.5 μM), TGFRi (SB431542 2 μM), BMPi (LDN-193189 0.2 μM).

Culture Medium 39: LIF (20 ng/ml), ERK1/2i (PD0325901, 1 μM), GSK3βi (CHIR99021, 3 μM), P38i (BIRB796, 2 μM), JNKi (SP600125, 5 μM), ROCKi (Y27632 10 μM), AXINs (IWR1, 2 μM), SRCi (CGP77675, 1.5 μM), TGFRi (SB431542 2 μM) and PKCi (Go6983 0.5 μM).

Culture Medium 40: LIF (20 ng/ml), ERK1/2i (PD0325901, 1 μM), GSK3βi (CHIR99021, 3 μM), P38i (BIRB796, 2 μM), JNKi (SP600125, 5 μM), ROCKi (Y27632 10 μM), AXINs (IWR1, 2 μM), SRCi (CGP77675, 1.5 μM), TGFRi (SB431542 2 μM), BMPi (LDN-193189 0.2 μM) and PKCi (Go6983 0.5 μM).

Cells: WIBR3 hESC line carrying Oct4-GFP reporter (described in Gafni et al. Nature 2013; December 12; 504 (7479): 282-6. doi: 10.1038/nature12745. Epub 2013 Oct. 30).

WIBR3 hESC line carrying deltaPEOct4-GFP reporter (described in Gafni et al. Nature 2013; December 12; 504 (7479): 282-6. doi: 10.1038/nature12745. Epub 2013 Oct. 30).

The cells were expanded for up to 21 passages on Gelatin/DR4 coated plates in 5% $O_2$.

Analysis: The cells were evaluated by FACS analysis for OCT4-GFP+ reporter or deltaPEOct4-GFP reporter.

Results

FIG. 1 is a graph illustrating FACS analysis of WIBR3 hESC line carrying Oct4-GFP reporter. The results show the cells maintain their pluripotency in the conditions described.

FIG. 2 is a graph illustrating FACS analysis of WIBR3 hESC line carrying deltaPEOct4-GFP reporter. The results show the cells maintain their pluripotency in the conditions described.

Example 2

Materials and Methods

Base Medium

1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml (Biological Industries-02-022-1B), NEAA-5 ml (Biological Industries 01-340-1B), 50 μL of 50 mM stock Beta-mercaptoethanol (1 vile), 5 ml B27 supplement (Invitrogen 17504-044), Insulin (Sigma I-1882)-12.5 microg/ml insulin), Apo-transferrin (Sigma T-1147), 100 μg/ml final concentration, Progesterone (Sigma P8783), 0.02 μg/ml final concentration, Putrescine (SigmaP5780), 16 μg/ml final concentration, Sodium selenite (Sigma S5261), add 5 μl of 3 mM stock solution per 500 ml of medium, L-ascorbic acid 2-phosphate (Sigma A8960) (50 μg/ml final concentration), BSA (100× Fraction V 7.5% Solution Gibco 15260-037.

Supplements

As in Example 1.

Cells: WIS2 hESC line

The cells were expanded for 12 passages and 20 passages on vitronectin coated plates in 5% O2.

Analysis: The cells were evaluated by microscopically.

Results

FIGS. 3A-F are representative images of pluripotent cell colonies at P12 in the selected conditions shown. FIG. 3A—conditions 1; FIG. 3B—conditions 2; FIG. 3C—conditions 3; FIG. 3D—conditions 4; FIG. 3E—conditions 9; FIG. 3F—conditions 11.

FIGS. 4A-D are representative images of pluripotent cell colonies at P20 in the selected conditions shown. FIG. 4A—conditions 9; FIG. 4B—conditions 10;

FIG. 4C—conditions 11; FIG. 4D—conditions 4.

Example 3

Materials and Methods

Base Medium

1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), L-glutamine 5 ml (Biological Industries-02-022-1B), NEAA-5 ml (Biological Industries 01-340-1B), 50 μL of 50 mM stock Beta-mercaptoethanol (1 vile), 5 ml B27 supplement (Invitrogen 17504-044), Insulin (Sigma I-1882)-12.5 microg/ml insulin), Apo-transferrin (Sigma T-1147), 100 μg/ml final concentration, Progesterone (Sigma P8783), 0.02 μg/ml final concentration, Putrescine (SigmaP5780), 16 μg/ml final concentration, Sodium selenite (Sigma S5261), add 5 μl of 3 mM stock solution per 500 ml of medium, L-ascorbic acid 2-phosphate (Sigma A8960) (50 μg/ml final concentration), BSA (100× Fraction V 7.5% Solution Gibco 15260-037-0.16 ml per 500 ml media bottle.

Supplements

As in Example 1.

Cells: WIS2 hESC line

The cells were expanded for 18-20 passages on Gelatin/DR4 coated plates in 5% $O_2$.

Analysis: The cells were stained for alkaline phosphatase stem cell marker (AP) and evaluated microscopically.

Results

FIGS. 5A-C are representative images of pluripotent cell colonies at P18-20 in the selected conditions shown. FIG. 5A—conditions 9; FIG. 5B—conditions 10; FIG. 5C—conditions 4.

Example 4

Materials and Methods

Base Medium

1:1 mix of Neurobasal Medium (Invitrogen 21103-049) and DMEM/F12 (Biological Industries 06-1170-50-1A)-total 475 ml, Pen-strep 5 ml (Biological Industries 03-033-1B), NEAA-5 ml (Biological Industries 01-340-1B), 50 μL of 50 mM stock Beta-mercaptoethanol (1 vile), 5 ml B27 supplement (Invitrogen 17504-044), Insulin (Sigma I-1882)-12.5 microg/ml insulin), Apo-transferrin (Sigma T-1147), 100 μg/ml final concentration, Progesterone (Sigma P8783), 0.02 μg/ml final concentration, Putrescine (SigmaP5780), 16 μg/ml final concentration, Sodium selenite (Sigma S5261), add 5 μl of 3 mM stock solution per 500 ml of medium., L-ascorbic acid 2-phosphate (Sigma A8960) (50 μg/ml final concentration), BSA (100× Fraction V 7.5% Solution Gibco 15260-037-0.16 ml per 500 ml media bottle.

Supplements

As in Example 1.

Cells: FX71 human iPSC line was expanded on Gelatin/ DR4 feeder cell coated plates in 5% O$_2$.

Analysis: The cells were stained for alkaline phosphatase stem cell marker (AP) and evaluated microscopically.

Results

FIGS. 6A-F are images of human naïve ESCs/iPSCs which were expanded under particular conditions without L-glutamine. FIG. 6A—conditions 1; FIG. 6B—conditions 2; FIG. 6C—conditions 3; FIG. 6D—conditions 4; FIG. 6E—conditions 9; FIG. 6F—conditions 11. Representative images of cells in the different WIS-NHSM conditions are shown, indicating expansion of colonies without exogenous L-glutamine supplementation in these conditions.

Example 5

Materials and Methods

Base Medium

1:1 mix of Neurobasal Medium (Invitrogen 21103-049) and DMEM/F12 (Biological Industries 06-1170-50-1A)-total 475 ml. Alternatively, 475 ml of the DMEM/F12 (Biological Industries 06-1170-50-1A without HEPES). The medium was supplemented with: Pen-strep 5 ml (Biological Industries 03-033-1B), L-glutamine 5 ml of 200 mM solution (at a 2 mM final concentration) (Biological Industries-02-022-1B), Non-Essential Amino Acid (NEAA; Biological Industries 01-340-1B)-5 ml of the X100 solution into a total of 500 ml medium [Composition of the X100 solution: L-Alanine 0.89 gram/liter; L-Asparagine·H2O 1.50 gram/liter; L-Aspartic Acid 1.33 gram/liter; L-Glutamic Acid 1.47 gram/liter; Glycine 0.75 gram/liter; L-Proline 1.15 gram/liter; and L-Serine 1.05 gram/liter], 50 μl of 50 mM stock Beta-mercaptoethanol (1 vile), 10 ml B27 supplement (Invitrogen 17504-044) or Xeno-free B27 (Invitrogen A14867-01), Insulin (Sigma I-1882; 12.5 μg/ml final concentration), Apo-transferrin (Sigma T-1147; 100 μg/ml final concentration), Progesterone (Sigma P8783, 0.02 μg/ml final concentration), Putrescine (Sigma P5780; 16 μg/ml final concentration), Sodium selenite (Sigma S5261; 5 μl of 3 mM stock solution per 500 ml medium, resulting in a final concentration of 3 nM), human serum albumin (10% solution from Biological Industries 05-720-1B, add 2 ml per 500 ml media bottle, resulting in a final concentration of 0.4% Human Serum Albumin) or bovine serum albumin (BSA) (100× Fraction V 7.5% Solution Gibco 15260-037, add 0.16 ml per 500 ml media bottle, resulting in a final concentration of 0.0024% BSA).

It is noted that the base medium according to some embodiments of the invention does not include ascorbic acid, and that ascorbic acid can be supplemented in some media as shown below.

FIG. 7 schematically illustrates the composition of the medium of some embodiments of the invention.

FIGS. 8-12 provide non-limiting examples of culture media supplements (conditions 41-131) which are added to the base medium described hereinabove (in Example 5), as follows:

Supplements

Medium 41: LIF (20 ng/ml), ERK1/2i (PD0325901, 1 μM), AXINs (IWR1, 5 μM), and PKCi (Go6983 2 μM).

Medium 42: LIF (20 ng/ml), ERK1/2i (PD0325901, 1 μM), AXINs (IWR1, 5 μM), PKCi (Go6983 2 μM), and L-ascorbic acid (50 μg/ml).

Medium 43: LIF (20 ng/ml), ERK1/2i (PD0325901, 1 μM), AXINs (IWR1, 5 μM), PKCi (Go6983 2 μM), and GSK3βi (CHIR99021, 1.5 μM).

Medium 44: LIF (20 ng/ml), ERK1/2i (PD0325901, 1 μM), AXINs (IWR1, 5 μM), PKCi (Go6983 2 μM), GSK3βi (CHIR99021, 1.5 μM), and L-ascorbic acid (50 μg/ml).

Medium 45: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), and ROCKi (Y27632 2 μM).

Medium 46: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), ROCKi (Y27632 2 μM), and SRCi (CGP77675, 1.5 μM).

Medium 47: LIF (20 ng/ml), ERK1/2i (PD0325901, 1 μM), AXINs (IWR1, 5 μM), PKCi (Go6983 2 μM), GSK3βi (CHIR99021, 1.5 M), L-ascorbic acid (50 μg/ml), and P38i (BIRB796, 1 μM).

Medium 48: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), ROCKi (Y27632 2 μM), and P38i (BIRB796, 1 μM).

Medium 49: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), and SRCi (CGP77675, 1.5 μM).

Medium 50: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), ROCKi (Y27632 2 μM), and RAFi (SB590885, 0.5 μM).

Medium 51: LIF (20 ng/ml), ERK1/2i (PD0325901, 1 μM), AXINs (IWR1, 2.5 μM), PKCi (Go6983 2 μM), GSK3βi (CHIR99021, 1.5 μM), L-ascorbic acid (50 μg/ml), and RAFi (SB590885, 0.5 μM).

Medium 52: LIF (20 ng/ml), ERK1/2i (PD0325901, 1 μM), AXINs (IWR1, 2.5 μM), PKCi (Go6983 2 μM), GSK3βi (CHIR99021, 1.5 μM), L-ascorbic acid (50 μg/ml), ROCKi (Y27632 2 μM), and P38i (BIRB796, 0.1 μM).

Medium 53: LIF (20 ng/ml), ERK1/2i (PD0325901, 1 μM), AXINs (IWR1, 2.5 μM), PKCi (Go6983 2 μM), GSK3βi (CHIR99021, 1.5 M), L-ascorbic acid (50 μg/ml), SRCi (CGP77675, 1.5 μM), and RAFi (SB590885, 0.5 μM).

Medium 54: LIF (20 ng/ml), ERK1/2i (PD0325901, 1 μM), AXINs (IWR1, 2.5 μM), PKCi (Go6983 2 μM), GSK3βi (CHIR99021, 1.5 μM), L-ascorbic acid (50 μg/ml), ROCKi (Y27632 2 μM), RAFi (SB590885, 0.5 μM), and SRCi (CGP77675, 1.5 μM).

Medium 55: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), RAFi-SB590885, 0.5 μM, and P38i (BIRB796, 0.1 μM).

Medium 56: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), ROCKi (Y27632 2 μM), P38i (BIRB796, 0.1 μM), and SRCi (CGP77675, 1.5 μM).

Medium 57: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), SRCi (CGP77675, 1.5 M), RAFi (SB590885, 0.5 μM), and BMPi (LDN-193189, 0.2 μM).

Medium 58: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), ROCKi (Y27632 2 μM), RAFi (SB590885, 0.5 μM), SRCi (CGP77675, 1.5 μM), and BMPi (LDN-193189 0.2 μM).

Medium 59: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), RAFi (SB590885, 0.5 μM), P38i (BIRB796, 0.1 μM), and BMPi (LDN-193189 0.2 μM).

Medium 60: LIF (20 ng/ml), ERK1/2i (PD0325901, 1 μM), AXINs (IWR1, 5 M), PKCi (Go6983 2 μM), GSK3βi (CHIR99021, 1.5 μM), L-ascorbic acid (50 μg/ml), ROCKi (Y27632 2 μM), P38i (BIRB796, 0.1 μM), SRCi (CGP77675, 1.5 M), and BMPi (LDN-193189 0.2 μM).

Medium 61: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), SRCi (CGP77675, 1.5 μM), and BMP4 (5 ng/ml).

Medium 62: LIF (20 ng/ml), ERK1/2i (PD0325901, 1 μM), AXINs (IWR1, 5 M), PKCi (Go6983 2 μM), GSK3βi (CHIR99021, 1.5 μM), L-ascorbic acid (50 μg/ml), ROCKi (Y27632, 2 μM), RAFi (SB590885, 0.5 μM), SRCi (CGP77675, 1.5 μM), and BMP4 (5 ng/ml).

Medium 63: LIF (20 ng/ml), ERK1/2i (PD0325901, 1 μM), AXINs (IWR1, 5 M), PKCi (Go6983, 2 μM), GSK3βi (CHIR99021, 1.5 μM), L-ascorbic acid (50 μg/ml), RAFi (SB590885, 0.5 μM), P38i (BIRB796, 0.1 μM), and BMP4 (5 ng/ml).

Medium 64: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), P38i (BIRB796, 0.1 μM), SRCi (CGP77675, 1.5 μM), and BMP4 (5 ng/ml).

Medium 65: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), and BMP4 (5 ng/ml).

Medium 66: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), and BMP4 (5 ng/ml).

Medium 67: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), and BMP4 (5 ng/ml).

Medium 68: LIF (20 ng/ml), ERK1/2i (PD0325901, 1 M), AXINs (IWR1, 5 μM), PKCi (Go6983, 2 μM), GSK3βi (CHIR99021, 1.5 μM), L-ascorbic acid (50 μg/ml), P38i (BIRB796, 0.1 μM), ROCKi (Y27632, 2 μM), and BMP4 (5 ng/ml).

Medium 69: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), and BMPi (LDN-193189, 0.2 μM).

Medium 70: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), and BMPi (LDN-193189, 0.2 μM).

Medium 71: LIF (20 ng/ml), ERK1/2i (PD0325901, 1 μM), AXINs (IWR1, 5 M), PKCi (Go6983, 2 μM), GSK3βi (CHIR99021, 1.5 μM), L-ascorbic acid (50 μg/ml), ROCKi (Y27632, 2 M), SRCi (CGP77675, 1.5 μM), and BMPi (LDN-193189, 0.2 μM).

Medium 72: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), P38i (BIRB796, 0.1 μM), and BMPi (LDN-193189, 0.2 μM).

Medium 73: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), and FGFRi (PD173074, 0.1 μM).

Medium 74: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), and FGFRi (PD173074, 0.1 μM).

Medium 75: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), SRCi (CGP77675, 1.5 μM), and FGFRi (PD173074, 0.1 μM).

Medium 76: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), P38i (BIRB796, 0.1 μM), and FGFRi (PD173074, 0.1 μM).

Medium 77: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), SRCi (CGP77675, 1.5 μM), and FGFRi (PD173074, 0.1 μM).

Medium 78: LIF (20 ng/ml), ERK1/2i (PD0325901, 1 μM), AXINs (IWR1, 5 M), PKCi (Go6983, 2 μM), GSK3βi (CHIR99021, 1.5 M), L-ascorbic acid (50 μg/ml), ROCKi (Y27632, 2 μM), P38i (BIRB796, 0.1 μM), and FGFRi (PD173074, 0.1 μM).

Medium 79: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), P38i (BIRB796, 0.1 μM), and FGFRi (PD173074, 0.1 μM).

Medium 80: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), SRCi (CGP77675, 1.5 μM), FGFRi (PD173074, 0.1 μM), and P38i (BIRB796, 1 μM).

Medium 81: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), SRCi (CGP77675, 1.5 μM), RAFi (SB590885, 0.5 μM), and Activin A (20 ng/ml).

Medium 82: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), RAFi (SB590885, 0.5 μM), SRCi (CGP77675, 1.5 M), and Activin A (20 ng/ml).

Medium 83: LIF (20 ng/ml), ERK1/2i (PD0325901, 1 μM), AXINs (IWR1, 5 M), PKCi (Go6983, 2 μM), GSK3βi (CHIR99021, 1.5 μM), L-ascorbic acid (50 μg/ml), RAFi-SB590885, 0.5 μM, P38i (BIRB796, 0.1 μM), and Activin A (20 ng/ml).

Medium 84: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 M), P38i (BIRB796, 0.1 μM), SRCi (CGP77675, 1.5 μM), and Activin A (20 ng/ml).

Medium 85: LIF (20 ng/ml), ERK1/2i (PD0325901 1 μM), AXINs (IWR1 2.5 μM), PKCi (Go6983 2 μM), GSK3βi (CHIR99021 1.5 μM), L-ascorbic acid (50 μg/ml), ROCKi (Y27632 2 μM), and Activin A (20 ng/ml).

Medium 86: LIF (20 ng/ml), ERK1/2i (PD0325901, 1 M), AXINs (IWR1, 5 μM), PKCi (Go6983, 2 μM), GSK3βi (CHIR99021, 1.5 μM), L-ascorbic acid (50 μg/ml), and Activin A (20 ng/ml).

Medium 87: LIF (20 ng/ml), ERK1/2i (PD0325901, 1 μM), AXINs (IWR1, 5 M), PKCi (Go6983, 2 μM), GSK3βi (CHIR99021, 1.5 M), L-ascorbic acid (50 μg/ml), ROCKi (Y27632, 2 μM), and Activin A (20 ng/ml).

Medium 88: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), P38i (BIRB796, 0.1 μM), ROCKi (Y27632, 2 μM), and Activin A (20 ng/ml).

Medium 89: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), and TGFRi (SB431542, 2 μM).

Medium 90: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), and TGFRi (SB431542, 2 μM).

Medium 91: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), SRCi (CGP77675, 1.5 μM), TGFRi (SB431542, 2 μM).

Medium 92: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), P38i (BIRB796, 0.1 μM), and TGFRi (SB431542, 2 μM).

Medium 93: LIF (20 ng/ml), ERK1/2i (PD0325901, 1 μM), AXINs (IWR1, 5 M), PKCi (Go6983, 2 μM), GSK3βi (CHIR99021, 1.5 μM), L-ascorbic acid (50 μg/ml), ROCKi (Y27632, 2 μM), FGFRi (PD173074, 0.1 μM), and TGFRi (SB431542, 2 μM).

Medium 94: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), FGFRi (PD173074, 0.1 μM) and TGFRi (SB431542, 2 μM).

Medium 95: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), FGFRi (PD173074, 0.1 μM), TGFRi (SB431542, 2 μM), and SRCi (CGP77675, 1.5 μM).

Medium 96: LIF (20 ng/ml), ERK1/2i (PD0325901, 1 μM), AXINs (IWR1, 5 μM), PKCi (Go6983 2 μM), GSK3βi (CHIR99021, 1.5 μM), L-ascorbic acid (50 μg/ml), ROCKi (Y27632, 2 μM), P38i (BIRB796, 0.1 μM), FGFRi (PD173074, 0.1 μM), and TGFRi (SB431542, 2 μM).

Medium 97: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), SRCi (CGP77675, 1.5 μM), FGFRi (PD173074, 0.1 μM), and TGFRi (SB431542, 2 μM).

Medium 98: LIF (20 ng/ml), ERK1/2i (PD0325901 1 μM), AXINs (IWR1, 5 μM), PKCi (Go6983, 2 μM), GSK3βi (CHIR99021, 1.5 μM), L-ascorbic acid (50 μg/ml), ROCKi (Y27632, 2 μM), RAFi (SB590885, 0.5 μM), FGFRi (PD173074, 0.1 μM), and TGFRi (SB431542, 2 μM).

Medium 99: LIF (20 ng/ml), ERK1/2i (PD0325901, 1 μM), AXINs (IWR1, 5 μM), PKCi (Go6983, 2 μM), GSK3βi (CHIR99021, 1.5 μM), L-ascorbic acid (50 μg/ml), SRCi (CGP77675, 1.5 μM), FGFRi (PD173074, 0.1 μM), TGFRi (SB431542, 2 μM) and P38i (BIRB796, 0.1 μM).

Medium 100: LIF (20 ng/ml), ERK1/2i (PD0325901, 1 μM), AXINs (IWR1, 5 μM), PKCi (Go6983, 4 μM), GSK3βi (CHIR99021, 3 μM), and L-ascorbic acid (50 μg/ml).

Medium 101: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml) and ROCKi (Y27632, 2 μM).

Medium 102: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml) and P38i (BIRB796, 2 μM).

Medium 103: LIF (20 ng/ml), ERK1/2i (PD0325901, 1 μM), AXINs (IWR1, 5 μM), PKCi (Go6983, 4 μM), GSK3βi (CHIR99021 3 μM), L-ascorbic acid (50 μg/ml), ROCKi (Y27632, 2 μM) and P38i (BIRB796, 2 μM).

Medium 104: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), P38i (BIRB796, 2 μM) and JNKi (SP600125, 5 μM).

Medium 105: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM), P38i (BIRB796, 2 μM) and JNKi (SP600125, 5 M).

Medium 106: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), P38i (BIRB796, 2 μM), and ERK5i (BIX02189, 5 μM).

Medium 107: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM), P38i (BIRB796, 2 μM), and ERK5i (BIX02189, 5 μM).

Medium 108: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml) and TGFRi (SB431542, 2 μM).

Medium 109: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM), and TGFRi (SB431542, 2 M).

Medium 110: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), and FGFRi (PD173074, 0.1 μM).

Medium 111: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM), and FGFRi (PD173074, 0.1 μM).

Medium 112: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), P38i (BIRB796, 2 μM), and TGFRi (SB431542, 2 μM).

Medium 113: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM), P38i (BIRB796, 2 μM) and TGFRi (SB431542, 2 μM).

Medium 114: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), P38i (BIRB796, 2 μM) and FGFRi (PD173074, 0.1 μM).

Medium 115: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM), P38i (BIRB796, 2 μM), and FGFRi (PD173074, 0.1 μM).

Medium 116: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), and LSDi (TCP, 5 μM).

Medium 117: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM) and LSDi (TCP, 5 μM).

Medium 118: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), P38i (BIRB796, 2 μM) and LSDi (TCP, 5 μM).

Medium 119: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), P38i (BIRB796, 2 μM) and LSDi (TCP, 5 μM).

Medium 120: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml) and Forskolin (5 μM).

Medium 121: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM) and Forskolin (5 μM).

Medium 122: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), P38i (BIRB796, 2 μM), and Forskolin (5 μM).

Medium 123: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632 2, μM), P38i (BIRB796, 2 μM), and Forskolin (5 μM).

Medium 124: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), and DOT1Li (SGC0946, 5 μM).

Medium 125: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM), and DOT1Li (SGC0946, 5 μM).

Medium 126: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 g/ml), P38i (BIRB796, 2 μM) and DOT1Li (SGC0946, 5 μM).

Medium 127: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM), P38i (BIRB796, 2 μM), and DOT1Li (SGC0946, 5 M).

Medium 128: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), P38i (BIRB796, 2 μM), JNKi (SP600125 5 μM), and ERK5i (BIX02189, 5 μM).

Medium 129: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM), P38i (BIRB796, 2 μM), JNKi (SP600125, 5 μM), and ERK5i (BIX02189, 5 M).

Medium 130: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), and ERK5i (BIX02189, 5 μM).

Medium 131: LIF (20 ng/ml), ERK1/2i (PD0325901, 1 μM), AXINs (IWR1, 5 μM), PKCi (Go6983, 4 μM), GSK3βi (CHIR99021, 3 μM), L-ascorbic acid (50 μg/ml), ROCKi (Y27632, 2 μM) and ERK5i (BIX02189, 5 μM).

As mentioned, the culture medium of some embodiments of the invention is capable of maintaining naïve PSC in a naïve state, wherein:

(i) when the naive PSC is a female PSC, then the naive female PSC has two unmethylated alleles of the promoter of the X-inactive specific transcript (XIST) gene; and (ii) when the naive PSC is a male PSC, then the naive male PSC has an unmethylated allele of the promoter of the XIST gene, and/or an expression level of transcription factor E3 (TFE3) in said naive PSC is characterized by a nucleus to cytoplasm expression ratio which is equal to or higher than 1 as determined by an immunostaining assay.

FIGS. 17A-E show examples of such unmethylated alleles as determining in the XIST promoter (in the amplicon set forth in SEQ ID NO:70). These results conclusively demonstrate that male and female Naive hESCs/iPSCs which are cultured on all of the tested culture media retain a unique pre-X inactivation state under various WIS-NHSM conditions.

In contrast, FIG. 17F shows an example of a non-naïve cell in which the XIST allele in the male cell is completely methylated (i.e., most of the CpG sites in the XIST promoter are methylated), and one allele of the promoter of the XIST gene is methylated in the female cell.

In addition, Table 1 herein below, summarizes the Relative Nuclear/Cytoplasmic TFE3 Enrichment (average value) in naïve PSCs cultured in the culture medium of some embodiments of the invention.

TABLE 1

Naïve PSCs were expanded in the indicated culture media for 14 days on DR4 irradiate MEF cells and 0.2% gelatin coated plates in 5% O2 conditions at 37° C. All culture media included L-ascorbic acid (at a final concentration of 50 μg/ml). Key for small molecule abbreviation: LIF (20 ng/ml), ERK1/2i (PD0325901 1 μM), AXINs (IWR1 5 μM), PKCi (Go6983 4 μM), GSK3βi (CHIR99021 1.5 μM), P38i (BIRB796 2 μM), JNKi (SP600125 5 μM), SRCi (CGP77675 1 μM).

| Relative Nuclear/Cytoplasmic TFE3 Enrichment (average value) | Culture medium comprises: |
|---|---|
| 1.4 | Srci 1 μM, ERK1/2i 1 μM, LIF 20 ng/ml |
| 1.4 | AXINs 5 μM, ERK1/2i 1 μM, LIF 20 ng/ml |
| 1.7 | AXINs 5 μM, ERK1/2i 1 μM, LIF 20 ng/ml, PKCi 4 μM, GSK3i 1.5 μM |
| 1.7 | AXINs 5 μM, ERK1/2i 1 μM, LIF 20 ng/ml, PKCi 4 μM, GSK3i 1.5 μM, P38i 2 μM, JNKi 5 μM |
| 1.7 | AXINs 5 μM, ERK1/2i 1 μM, LIF 20 ng/ml, PKCi 4 μM, GSK3i 1.5 μM, P38i 2 μM, JNKi 5 μM, SRCi 1 μM |

As shown in the above Table 1, all of the tested culture media were capable of maintaining the naïve PSCs in a naïve state which is characterized by a ratio higher than 1 between the nuclear and cytoplasmic TFE3 enrichment.

Example 6

Materials and Methods

Base Medium

1:1 mix of Neurobasal Medium (Invitrogen 21103-049) and DMEM/F12 (Biological Industries 06-1170-50-1A)-total 475 ml. Alternatively, 475 ml of the DMEM/F12 (Biological Industries 06-1170-50-1A without HEPES). The medium was supplemented with: Pen-strep 5 ml (Biological Industries 03-033-1B), L-glutamine 5 ml of 200 mM solution (at a 2 mM final concentration) (Biological Industries-02-022-1B), Non-Essential Amino Acid (NEAA; Biological Industries 01-340-1B)-5 ml of the X100 solution into a total of 500 ml medium [Composition of the X100 solution: L-Alanine 0.89 gram/liter; L-Asparagine·H2O 1.50 gram/liter; L-Aspartic Acid 1.33 gram/liter; L-Glutamic Acid 1.47 gram/liter; Glycine 0.75 gram/liter; L-Proline 1.15 gram/liter; and L-Serine 1.05 gram/liter], 50 μl of 50 mM stock Beta-mercaptoethanol (1 vile), 10 ml B27 supplement (Invitrogen 17504-044) or Xeno-free B27 (Invitrogen A14867-01), Insulin (Sigma I-1882; 12.5 μg/ml final concentration), Apo-transferrin (Sigma T-1147; 100 μg/ml final concentration), Progesterone (Sigma P8783, 0.02 μg/ml final concentration), Putrescine (Sigma P5780; 16 μg/ml final concentration), Sodium selenite (Sigma S5261; 5 μl of 3 mM stock solution per 500 ml medium, resulting in a final concentration of 3 nM), human serum albumin (10% solution from Biological Industries 05-720-1B, add 2 ml per 500 ml media bottle, resulting in a final concentration of 0.4% Human Serum Albumin) or bovine serum albumin (BSA) (100× Fraction V 7.5% Solution Gibco 15260-037, add 0.16 ml per 500 ml media bottle, resulting in a final concentration of 0.0024% BSA).

It is noted that the base medium according to some embodiments of the invention does not include ascorbic acid, and that ascorbic acid can be supplemented in some media as shown below.

FIG. 18 schematically illustrates the composition of the medium of some embodiments of the invention.

FIG. 19 provides non-limiting examples of culture media supplements (conditions 132-147 in FIG. 19) which are added to the base medium described hereinabove (in Example 6), as follows:

Supplements

Medium 132: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), L-ascorbic acid (50 μg/ml), SRCi (CGP77675, 0.5 μM), P38i (BIRB796, 0.25 μM), G9ai (BIX01294, 0.5 μM), and ROCKi (Y27632, 2 μM).

Medium 133: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), L-ascorbic acid (50 μg/ml), SRCi (CGP77675, 0.5 μM), P38i (BIRB796, 0.25 μM), and G9ai (BIX01294, 0.5 μM).

Medium 134: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), SRCi (CGP77675, 0.5 μM), P38i (BIRB796, 0.25 μM), G9ai (BIX01294, 0.5 μM), and ROCKi (Y27632, 2 μM).

Medium 135: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), L-ascorbic acid (50 μg/ml), SRCi (CGP77675, 0.5 μM), P38i (BIRB796, 0.25 μM), and ROCKi (Y27632, 2 μM).

Medium 136: LIF (20 ng/ml), ERK1/2i (PD0325901, 1 μM), AXINs (IWR1, 5 μM), PKCi (Go6983, 2 μM), JNKi (SP600125, 5 M), GSK3βi (CHIR99021, 1.5 μM), L-ascorbic acid (50 mg/ml), SRCi (CGP77675, 0.5 μM), G9ai (BIX01294, 0.5 μM), and ROCKi (Y27632, 2 μM)

Medium 137: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 M), L-ascorbic acid (50 μg/ml), SRCi (CGP77675, 0.5 μM), and G9ai (BIX01294, 0.5 μM).

Medium 138: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), SRCi (CGP77675, 0.5 M), G9ai (BIX01294, 0.5 μM), and ROCKi (Y27632, 2 μM).

Medium 139: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), L-ascorbic acid (50 μg/ml), SRCi (CGP77675, 0.5 μM), and ROCKi (Y27632, 2 μM).

Medium 140: LIF (20 ng/ml), ERK1/2i (PD0325901, 1 μM), AXINs (IWR1, 5 μM), PKCi (Go6983, 2 μM), JNKi (SP600125, 5 M), GSK3βi (CHIR99021, 1.5 μM), L-ascorbic acid (50 μg/ml), SRCi (CGP77675, 0.5 μM), P38i (BIRB796, 0.25 M), G9ai (BIX01294, 0.5 M), ROCKi (Y27632, 2 μM), and RAFi (SB590885, 0.25 μM).

Medium 141: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), L-ascorbic acid (50 μg/ml), SRCi (CGP77675, 0.5 μM), P38i (BIRB796, 0.25 μM), G9ai (BIX01294, 0.5 μM), and RAFi (SB590885, 0.25 μM), Medium 142: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), SRCi (CGP77675, 0.5 μM), P38i (BIRB796, 0.25 μM), G9ai (BIX01294, 0.5 μM), ROCKi (Y27632, 2 μM), and RAFi (SB590885, 0.25 μM)

Medium 143: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), L-ascorbic acid (50 μg/ml), SRCi (CGP77675, 0.5 μM), P38i (BIRB796, 0.25 μM), ROCKi (Y27632, 2 μM), and RAFi (SB590885, 0.25 μM.

Medium 144: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), L-ascorbic acid (50 μg/ml), SRCi (CGP77675, 0.5 μM), P38i (BIRB796, 0.25 μM), G9ai (BIX01294, 0.5 μM), ROCKi (Y27632, 2 μM), and SCF (20 ng/ml)

Medium 145: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), L-ascorbic acid (50 μg/ml), SRCi (CGP77675, 0.5 μM), P38i (BIRB796, 0.25 μM), G9ai (BIX01294, 0.5 μM), and SCF (10 ng/ml), Medium 146: LIF (20 ng/ml), ERK1/2i (PD0325901, 1 μM), AXINs (IWR1, 5 μM), PKCi (Go6983, 2 μM), JNKi (SP600125, 5 μM), GSK3βi (CHIR99021, 1.5 μM), SRCi (CGP77675, 0.5 μM), P38i (BIRB796, 0.25 μM), G9ai (BIX01294, 0.5 μM), ROCKi (Y27632, 2 μM), and SCF (10 ng/ml).

Medium 147: LIF (20 ng/ml), ERK1/2i (PD0325901, 1 μM), AXINs (IWR1, 5 μM), PKCi (Go6983, 2 μM), JNKi (SP600125, 5 M), GSK3βi (CHIR99021, 1.5 μM), L-ascorbic acid (50 μg/ml), SRCi (CGP77675, 0.5 μM), P38i (BIRB796, 0.25 μM), ROCKi (Y27632, 2 μM), and SCF (10 ng/ml).

Experimental Results

FIGS. 20-21 demonstrate that any of the culture media described hereinabove (Media 132-147) maintain human pluripotent stem cells in a naive undifferentiated and pluripotent state.

FIGS. 22A-C show examples of methylation assays of the XIST promoter (in the amplicon set forth in SEQ ID NO:70) for the naïve and primed pluripotent stem cells. These results of FIGS. 22A-B conclusively demonstrate that male and female Naive hESCs/iPSCs which are cultured on all of the tested culture media retain a unique pre-X inactivation state under various WIS-NHSM conditions.

In contrast, FIG. 22C shows an example of a non-naïve cell in which the XIST allele in the male cell is completely methylated (i.e., most of the CpG sites in the XIST promoter are methylated), and one allele of the promoter of the XIST gene is methylated in the female cell.

To test the ability of the culture medium of some embodiments of the invention to maintain a naïve PSC state, the level of TFE3 was measured in the nucleus and cytoplasm of the cells, and the relative ratio was determined. WIBR3 hESCs were expanded in the indicated conditions for 14 days on Matrigel coated plates in 5% O2 conditions at 37° C. All culture media included L-ascorbic acid (50 μg/ml).

Table 2 herein below, summarizes the Relative Nuclear/ Cytoplasmic TFE3 Enrichment (average value) in naïve PSCs cultured in the culture medium of some embodiments of the invention.

TABLE 2

| Naïve PSCs were expanded in the indicated culture media for 14 days on DR4 irradiate MEF cells and 0.2% gelatin coated plates in 5% O2 conditions at 37° C. All culture media included L-ascorbic acid (at a final concentration of 50 μg/ml). Key for small molecule abbreviation: LIF (20 ng/ml), ERK1/2i (PD0325901 1 μM), AXINs (IWR1 5 μM), PKCi (Go6983 2 μM), GSK3βi (CHIR99021 1.5 μM), P38i (BIRB796 0.25 μM), JNKi (SP600125 5 μM), SRCi (CGP77675 0.5 μM), and G9ai (BIX01294 0.5 μM). | |
|---|---|
| Relative Nuclear/ Cytoplasmic TFE3 Enrichment (average value) | Culture medium comprises: |
| 1.8 | AXINs 5 μM, ERK1/2i 1 μM, LIF 20 ng/ml, PKCi 2 μM, GSK3i 1.5 μM, P38i 0.25 μM, JNKi 5 μM, SRCi 0.5 μM |
| 1.9 | AXINs 5 μM, ERK1/2i 1 μM, LIF 20 ng/ml, PKCi 2 μM, GSK3i 1.5 μM, P38i 0.25 μM, JNKi 5 μM, SRCi 0.5 μM, G9ai 0.5 μM |
| 0.6 | Conditions for primed WIBR3 ESCs as Negative control: Primed cells expanded in mTESR™ (FGF2/TGFbeta1) Conditions (by Stem Cell Technologies) |

As shown in Table 2 above, Naive hESCs/iPSCs retain preferential TFE3 nuclear localizations. Thus, all of the tested culture media for naïve conditions were capable of maintaining the naïve PSCs in a naïve state which is characterized by a ratio higher than 1 between the nuclear and cytoplasmic TFE3 enrichment. In contrast, when conditions for primed PSCs were used (e.g., mTESR™ (FGF2/ TGFbeta1) Conditions (by Stem Cell Technologies)) the ration between the nuclear to cytoplasmic TFE3 was lower than 1.

Example 7

Previously described HUES64 cell line that lacks endogenous DNA methyltransferase 1 (DNMT1) alleles and retain an exogenous DNMT1 allele under a Tet-Off promoter (Liao J, et al. 2015. "Targeted disruption of DNMT1, DNMT3A and DNMT3B in human embryonic stem cells". Nat Genet. 2015 May; 47 (5): 469-78. doi: 10.1038/ng.3258. Epub 2015 Mar. 30; which is fully incorporated herein as reference) was used in the following experiment. Cells were expanded in the indicated conditions (Table 3 below), with or without Doxycycline for 10 passages (P10) on Gelatin/DR4 coated plates, and cultures were immunostained for OCT4 pluripotency marker in surviving cells. Primed cells, which were expanded in mTESR™ do not tolerate loss of DNMT1 expression induced by addition of DOX on these engineered cells. Cells expanded in the culture medium of some embodiments of the invention (Medium number 138 and 136 retain their pluripotency as is indicated by the high percentage of OCT4 positive cells (93% and 97%) despite the loss of DNMT1 expression in this engineered system (upper two examples). These results indicate how human naïve, but not primed, pluripotent cells can maintain their pluripotency in spite of DNMT1 loss of expression.

TABLE 3

| Key for small molecule abbreviation: LIF (20 ng/ml), ERK1/2i (PD0325901 1 μM), AXINs (IWR1 5 μM), PKCi (Go6983 2 μM), GSK3βi (CHIR99021 1.5 μM) P38i (BIRB796 0.25 μM), JNKi (SP600125 5 μM), SRCi (CGP77675 0.5 μM), G9ai (BIX01294 0.5 μM), ROCKi (Y27632 2 μM). | | |
|---|---|---|
| % OCT4+ cells at P10 | | |
| NO DOX | ++DOX (1 μg/ml) | Culture medium comprises: |
| 95 | 93 | Medium 138: AXINs 5 μM, ERK1/2i 1 μM, LIF 20 ng/ml, PKCi 2 μM, GSK3βi 1.5 μM, JNKi 5 μM, SRCi 0.5 μM, G9ai 0.5 μM, ROCKi 2 μM |
| 95 | 97 | Medium 136: AXINs 5 μM, ERK1/2i 1 μM, LIF 20 ng/ml PKCi 2 μM, GSK3βi 1.5 μM, P38i 0.25 μM, JNKi 5 μM, SRCi 0.5 μM, G9ai 0.5 μM, ROCKi 2 μM |
| 95 | 0 | Primed WIBR3 ESCs as Negative control: Primed cells expanded in mTESR™ (FGF2/TGFbeta1) Conditions (by Stem Cell Technologies) |

Example 8

The Naïve PSCS of the Invention can be Used for Generating Same or Cross-Species Chimeras Injecting naïve PSCs from one species into the early embryo of another species are likely to be outcompeted due to a variety of reasons including: difference in cell cycle progression, reduced reactivity to host morphogenesis, difference in gestation timing and the like. To increase the efficiency of chimerism in a host animal, the present inventors have uncovered that the principle of "Cell Cheating" or "Cell competition" can be employed in cross-species chimeric assays. For this purpose, the present inventors employed the isolated naïve human PSCs which maintain the "naïve state" and genetically engineered them to exhibit reduced levels of P53. The isolated genetically engineered naïve PSC, with reduced p53 expression were further injected into host mouse embryos, and the developing embryos were analyzed for chimerism levels. As shown below, while the wild type (WT) naïve PSCs were shown capable of contributing to developing mouse embryos, "cheater" P53 depleted naïve PSCs yielded remarkably higher contribution efficiency in chimerism levels.

Experimental Methods

Generation of the LIS38 tg-pTrip Ick EGFP p53 Crispr C2 Clone—

The present inventors have applied the CRISPR/CAS9 technology to generate mutants depleted for P53 protein. sgRNA (single stranded guide RNA) sequence targeting EXON3 of human P53 was designed, and naïve PSCs having a deletion in this region were established and validated for depletion in p53 protein levels. These cell lines were used as "super-competitors" in cross-species chimerism assays, as they were microinjected into E2.5 mouse embryos, and allowed to develop further to test for human (GFP+) cell detection in developing mouse embryos.

Experimental Results

Microinjection of LIS 38 EGFP hTP53 C2 Naive Human iPS Cells into Mouse Morulas Generates Cross-Species Chimaeric Humanized Mice FIGS. 23A-D depict the generation of the LIS38 tg-pTrip lck EGFP p53 crispr C2 clone, and the absence of p53 expression in PSC cells of this clone.

As is shown in FIGS. 24A-B, embryos injected with the LIS 38 EGFP hTP53 C2 naive human iPS cells into mouse morulas generates cross-species chimaeric humanized mice. Shown are representative images demonstrating widespread integration of GFP-labeled human naive iPS-derived cells into different locations of an E9.5 mouse embryo. Hoechst and CellTracker were used for counterstaining.

These results conclusively show that the naïve human or non-human primate iPSCs/ESCs that are depleted for P53 and/or overexpressing dominant negative P53 mutant, c-MYC, n-MYC, L-MYC, EDAR or ERAS (Dejosez M et al., 2013, See comment in PubMed Commons below Science. 2013 Sep. 27; 341 (6153): 1511-4; and Clavería C., et al., 2013, See comment in PubMed Commons below Nature. 500 (7460): 39-44) can be used as competitor cells when injected into host pre-implantation embryos (blastocyst, morula) of the same or a different species, to generate same-species or cross-species chimeras.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Additional References are Cited in Text

Ang, Y.-S., Tsai, S.-Y., Lee, D.-F., Monk, J., Su, J., Ratnakumar, K., Ding, J., Ge, Y., Darr, H., Chang, B., et al. (2011). Wdr5 mediates self-renewal and reprogramming via the embryonic stem cell core transcriptional network. Cell 145, 183-197.

De Los Angeles, A., Loh, Y.-H., Tesar, P. J., and Daley, G. Q. (2012). Accessing naive human pluripotency. Curr. Opin. Genet. Dev. 22, 272-282.

Durcova-Hills, G., Tang, F., Doody, G., Tooze, R., and Surani, M. A. (2008). Reprogramming primordial germ cells into pluripotent stem cells. PLOS ONE 3, e3531.

Fidalgo, M., Faiola, F., Pereira, C.-F., Ding, J., Saunders, A., Gingold, J., Schaniel, C., Lemischka, I. R., Silva, J. C. R., and Wang, J. (2012). Zfp281 mediates Nanog autorepression through recruitment of the NuRD complex and inhibits somatic cell reprogramming. Proc. Natl. Acad. Sci. U.S.a. 109, 16202-16207.

Hanna, J. H. (2010). The STATs on naive iPSC reprogramming. Cell Stem Cell 7, 274-276.

Hanna, J. H., Saha, K., and Jaenisch, R. (2010a). Pluripotency and cellular reprogramming: facts, hypotheses, unresolved issues. Cell 143, 508-525.

Hanna, J., Cheng, A. W., Saha, K., Kim, J., Lengner, C. J., Soldner, F., Cassady, J. P., Muffat, J., Carey, B. W., and Jaenisch, R. (2010b). Human embryonic stem cells with biological and epigenetic characteristics similar to those of mouse ESCs. Proc. Natl. Acad. Sci. U.S.a. 107, 9222-9227.

Hanna, J., Markoulaki, S., Mitalipova, M., Cheng, A. W., Cassady, J. P., Staerk, J., Carey, B. W., Lengner, C. J., Foreman, R., Love, J., et al. (2009a). Metastable pluripotent states in NOD-mouse-derived ESCs. Cell Stem Cell 4, 513-524.

Hanna, J., Saha, K., Pando, B., van Zon, J., Lengner, C. J., Creyghton, M. P., van Oudenaarden, A., and Jaenisch, R. (2009b). Direct cell reprogramming is a stochastic process amenable to acceleration. Nature 462, 595-601.

Hockemeyer, D., Wang, H., Kiani, S., Lai, C. S., Gao, Q., Cassady, J. P., Cost, G. J., Zhang, L., Santiago, Y., Miller, J. C., et al. (2011). Genetic engineering of human pluripotent cells using TALE nucleases. Nat Biotechnol 29, 731-734.

Kaji, K., Caballero, I. M., MacLeod, R., Nichols, J., Wilson, V. A., and Hendrich, B. (2006). The NuRD component Mbd3 is required for pluripotency of embryonic stem cells. Nat Cell Biol 8, 285-292.

Kaji, K., Nichols, J., and Hendrich, B. (2007). Mbd3, a component of the NuRD co-repressor complex, is required for development of pluripotent cells. Development 134, 1123-1132.

Lengner, C. J., Gimelbrant, A. A., Erwin, J. A., Cheng, A. W., Guenther, M. G., Welstead, G. G., Alagappan, R., Frampton, G. M., Xu, P., Muffat, J., et al. (2010). Derivation of pre-X inactivation human embryonic stem cells under physiological oxygen concentrations. Cell 141, 872-883.

Li, W., Wei, W., Zhu, S., Zhu, J., Shi, Y., Lin, T., Hao, E., Hayek, A., Deng, H., and Ding, S. (2009). Generation of rat and human induced pluripotent stem cells by combining genetic reprogramming and chemical inhibitors. Cell Stem Cell 4, 16-19.

Mansour, A. A., Gafni, O., Weinberger, L., Zviran, A., Ayyash, M., Rais, Y., Krupalnik, V., Zerbib, M., Amann-Zalcenstein, D., Maza, I., et al. (2012). The H3K27 demethylase Utx regulates somatic and germ cell epigenetic reprogramming. Nature 488, 409-413.

Marks, H., Kalkan, T., Menafra, R., Denissov, S., Jones, K., Hofemeister, H., Nichols, J., Kranz, A., Francis Stewart, A., Smith, A., et al. (2012). The transcriptional and epigenomic foundations of ground state pluripotency. Cell 149, 590-604.

Mikkelsen, T. S., Hanna, J., Zhang, X., Ku, M., Wernig, M., Schorderet, P., Bernstein, B. E., Jaenisch, R., Lander, E. S., and Meissner, A. (2008). Dissecting direct reprogramming through integrative genomic analysis. Nature 454, 49-55.

Nichols, J., and Smith, A. (2012). Pluripotency in the embryo and in culture. Cold Spring Harb Perspect Biol 4, a008128.

Okamoto, I., Patrat, C., Thépot, D., Peynot, N., Fauque, P., Daniel, N., Diabangouaya, P., Wolf, J.-P., Renard, J.-P., Duranthon, V., et al. (2011). Eutherian mammals use diverse strategies to initiate X-chromosome inactivation during development. Nature 1-7.

Onder, T. T., Kara, N., Cherry, A., Sinha, A. U., Zhu, N., Bernt, K. M., Cahan, P., Marcarci, B. O., Unternaehrer, J., Gupta, P. B., et al. (2012). Chromatin-modifying enzymes as modulators of reprogramming. Nature 483, 598-602.

Orkin, S. H., and Hochedlinger, K. (2011). Chromatin Connections to Pluripotency and Cellular Reprogramming. Cell 145, 835-850.

Polo, J. M., Anderssen, E., Walsh, R. M., Schwarz, B. A., Nefzger, C. M., Lim, S. M., Borkent, M., Apostolou, E., Alaei, S., Cloutier, J., et al. (2012). A Molecular Roadmap of Reprogramming Somatic Cells into iPS Cells. Cell 151, 1617-1632.

Pribluda, A., and Hanna, J. H. (2012). Tracing the genesis of human embryonic stem cells. Nat Biotechnol 30, 247-249.

Roode, M., Blair, K., Snell, P., Elder, K., Marchant, S., Smith, A., and Nichols, J. (2012). Human hypoblast formation is not dependent on FGF signalling. Dev. Biol. 361, 358-363.

Silva, J., Nichols, J., Theunissen, T. W., Guo, G., van Oosten, A. L., Barrandon, O., Wray, J., Yamanaka, S., Chambers, I., and Smith, A. (2009). Nanog is the gateway to the pluripotent ground state. Cell 138, 722-737.

Smith, Z. D., Nachman, I., Regev, A., and Meissner, A. (2010). Dynamic single-cell imaging of direct reprogramming reveals an early specifying event. Nat Biotechnol 28, 521-526.

Soufi, A., Donahue, G., and Zaret, K. S. (2012). Facilitators and Impediments of the Pluripotency Reprogramming Factors' Initial Engagement with the Genome. Cell 1-11.

Sridharan, R., Tchieu, J., Mason, M. J., and Yachechko, R. (2009). ScienceDirect(dot)com-Cell-Role of the Murine Reprogramming Factors in the Induction of Pluripotency. Cell.

Takahashi, K., and Yamanaka, S. (2006). Induction of pluripotent stem cells from mouse embryonic and adult fibroblast cultures by defined factors. Cell 126, 663-676.

Tesar, P. J., Chenoweth, J. G., Brook, F. A., Davies, T. J., Evans, E. P., Mack, D. L., Gardner, R. L., and Mckay, R. D. G. (2007). New cell lines from mouse epiblast share defining features with human embryonic stem cells. Nature 448, 196-199.

Tiwari, V. K., Stadler, M. B., Wirbelauer, C., Paro, R., Schübeler, D., and Beisel, C. (2011). A chromatin-modifying function of JNK during stem cell differentiation. Nat Genet.

Tomoda, K., Takahashi, K., Leung, K., Okada, A., Narita, M., Yamada, N. A., Eilertson, K. E., Tsang, P., Baba, S., White, M. P., et al. (2012). Derivation conditions impact x-inactivation status in female human induced pluripotent stem cells. Cell Stem Cell 11, 91-99.

Warren, L., Ebina, W., Mandal, P. K., Smith, Z. D., Meissner, A., and Daley, G. Q. (2010). ScienceDirect(dot)com-Cell Stem Cell-Highly Efficient Reprogramming to Pluripotency and Directed Differentiation of Human Cells with Synthetic Modified mRNA. Cell Stem Cell.

Wernig, M., Lengner, C. J., Hanna, J., Lodato, M. A., Steine, E., Foreman, R., Staerk, J., Markoulaki, S., and Jaenisch, R. (2008). A drug-inducible transgenic system for direct reprogramming of multiple somatic cell types. Nat Biotechnol 26, 916-924.

Ying, Q.-L., Wray, J., Nichols, J., Batlle-Morera, L., Doble, B., Woodgett, J., Cohen, P., and Smith, A. (2008). The ground state of embryonic stem cell self-renewal. Nature 453, 519-523.

Zhu, D., Fang, J., Li, Y., and Zhang, J. (2009). Mbd3, a Component of NuRD/Mi-2 Complex, Helps Maintain Pluripotency of Mouse Embryonic Stem Cells by Repressing Trophectoderm Differentiation. PLOS ONE 4, e7684.

What is claimed is:

1. A cell culture comprising human or rhesus monkey naive pluripotent stem cell (PSC) and a culture medium comprising a STAT3 activator at a concentration of 1-300 ng/ml, an ERK1/2 inhibitor at a concentration of 0.1-50 μM, a Tankyrase inhibitor at a concentration of 0.5-10 μM and at least one agent selected from the group consisting of a p38 inhibitor at a concentration of about 0.05-5 μM, an SRC inhibitor at a concentration of 0.2-10 μM, Activin A at a concentration of 1-40 ng/ml and a NOTCH inhibitor at a concentration of 0.05-50 μM, wherein the culture is capable of maintaining the human or rhesus monkey naive PSC in a naïve state for at least 5 passages, and wherein (i) when said naive PSC is a female PSC, then said naive female PSC has two unmethylated alleles of the promoter of the X-inactive specific transcript (XIST) gene; and (ii) when said naive PSC is a male PSC, then said naive male PSC has an unmethylated allele of said promoter of said XIST gene, and said naïve state is characterized by:

ability to maintain pluripotency the absence of DNA methyltransferase 1 (DNMT1) expression as determined by OCT4 expression in an immunostaining assay; and an expression level of transcription factor E3 (TFE3) in said naive PSC is characterized by a nucleus to cytoplasm expression ratio which is equal to or higher than 1 as determined by an immunostaining assay.

2. The cell culture of claim 1, wherein said STAT3 activator is selected from the group consisting of leukemia inhibitory factor (LIF), interleukin 6 (IL6) and epidermal growth factor (EGF), said ERK1/2 inhibitor is selected from the group consisting of PD0325901, PD98059 and PD184352, said Tankyrase inhibitor is selected from the group consisting of IWR-1 and XAV939, said p38 inhibitor is r selected from the group consisting of SB203580, SB 202190, LY 2228820, BIRB796 and PD169316, said SRC inhibitor is CGP77675, and said NOTCH inhibitor is a gamma secretase inhibitor selected from the group consisting of DAPT, LY2886721 hydrochloride and DBZ.

3. The cell culture of claim 1, wherein said culture medium further comprises at least one agent selected from the group consisting of a GSK3β inhibitor, a PKC inhibitor, a ROCK inhibitor, a JNK inhibitor, a PKA agonist, a YAP/TAZ inhibitor, an SHH inhibitor, a transforming growth factor receptor (TGFR) inhibitor, a BMP inhibitor, an FGFR inhibitor, an ERK5 inhibitor, a BRAF inhibitor, a CRAF inhibitor, a PI3K activator, basic fibroblast growth factor (bFGF), a SMAD activator, insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, BayK8644, an inhibitor of G9a and/or Glp, stem cell factor (SCF), YAP/TAZ inhibitor, L-Ascorbic Acid, an LSD1 inhibitor, a DOT1L inhibitor and a TGF inducer.

4. The cell culture of claim 1, wherein said culture medium further comprises a GSK3β inhibitor.

5. The cell culture of claim 4, wherein said GSK3b inhibitor is selected from the group consisting of CHIR99021, BIO and Kenpaullone.

6. The cell culture of claim 1, wherein said culture medium further comprises a PKC inhibitor.

7. The cell culture of claim 6, wherein said PKC inhibitor is Go6983.

8. The cell culture of claim 1, wherein said culture medium comprises said STAT3 activator, said ERK1/2 inhibitor, said Tankyrase inhibitor and said p38 inhibitor.

9. The cell culture medium of claim 8, wherein said culture medium further comprises a GSK3β inhibitor.

10. The cell culture of claim 9, wherein said culture medium further comprises a PKC inhibitor.

11. The cell culture of claim 1, wherein said culture medium being devoid of serum.

\*     \*     \*     \*     \*